(12) United States Patent
Chen et al.

(10) Patent No.: US 12,331,082 B2
(45) Date of Patent: **\*Jun. 17, 2025**

(54) CAPSID VARIANTS AND METHODS OF USING THE SAME

(71) Applicant: DYNO THERAPEUTICS, INC., Watertown, MA (US)

(72) Inventors: Ina Chen, Sommerville, MA (US); Jeff Gerold, Cambridge, MA (US); Jerrah Holth, Sudbury, MA (US); Sylvain Lapan, Brookline, MA (US); Kathy S. Lin, Sommerville, MA (US); Samuel Wolock, Cambridge, MA (US)

(73) Assignee: DYNO THERAPEUTICS, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/790,657

(22) Filed: Jul. 31, 2024

(65) Prior Publication Data
US 2024/0425552 A1    Dec. 26, 2024

Related U.S. Application Data

(60) Division of application No. 18/323,135, filed on May 24, 2023, now Pat. No. 12,116,385, which is a continuation of application No. PCT/US2022/077804, filed on Oct. 7, 2022.

(60) Provisional application No. 63/262,341, filed on Oct. 10, 2021, provisional application No. 63/262,330, filed on Oct. 8, 2021.

(51) Int. Cl.
C07H 21/02     (2006.01)
A61K 48/00     (2006.01)
C07K 14/015    (2006.01)
C12N 15/86     (2006.01)

(52) U.S. Cl.
CPC ........ C07K 14/015 (2013.01); A61K 48/0058 (2013.01); C12N 15/86 (2013.01); C12N 2750/14122 (2013.01); C12N 2750/14143 (2013.01); C12N 2750/14145 (2013.01)

(58) Field of Classification Search
None
See application file for complete search history.

(56) References Cited

U.S. PATENT DOCUMENTS 10,786,568 B2    9/2020  Limberis et al.
2015/0023924 A1  1/2015  High et al.
(Continued)

FOREIGN PATENT DOCUMENTS

WO    WO2005033321 A2    4/2005
WO    WO2009137006 A2    11/2009
WO    WO2010093784 A2    8/2010
(Continued)

OTHER PUBLICATIONS

Beharry et al., 2021, "The AAV9 Variant Capsid AAV-F Mediates Widespread Transgene Expression in Nonhuman Primate Spinal Cord After Intrathecal Administration," Human Gene Therapy 33(1-2): 61-75.
(Continued)

Primary Examiner — M Franco G Salvoza
(74) Attorney, Agent, or Firm — Biospark Intellectual Property Law

(57) ABSTRACT

The disclosure is directed in part to variant capsid polypeptides that can be used to deliver payloads.

30 Claims, 11 Drawing Sheets
Specification includes a Sequence Listing.

(56) References Cited

U.S. PATENT DOCUMENTS

| | | |
|---|---|---|
| 2017/0130245 A1 | 5/2017 | Kotin et al. |
| 2019/0300904 A1 | 10/2019 | Gao et al. |

FOREIGN PATENT DOCUMENTS

| | | |
|---|---|---|
| WO | WO2010138263 A2 | 12/2010 |
| WO | WO2012109570 A1 | 8/2012 |
| WO | WO2012145601 A2 | 10/2012 |
| WO | WO2013029030 A1 | 2/2013 |
| WO | WO2013170078 A1 | 11/2013 |
| WO | WO2015038958 A1 | 3/2015 |
| WO | WO2015048534 A1 | 4/2015 |
| WO | WO2015164757 A1 | 10/2015 |
| WO | WO2015191508 A1 | 12/2015 |
| WO | WO2017023724 A1 | 2/2017 |
| WO | WO2017058892 A2 | 4/2017 |
| WO | WO2017100671 A1 | 6/2017 |
| WO | WO2017189959 A1 | 11/2017 |
| WO | WO2017189963 A1 | 11/2017 |
| WO | WO2017189964 A2 | 11/2017 |
| WO | WO2017197355 A2 | 11/2017 |
| WO | WO2017201258 A1 | 11/2017 |
| WO | WO2018022905 A2 | 2/2018 |
| WO | WO2018075798 A1 | 4/2018 |
| WO | WO2018156654 A1 | 8/2018 |
| WO | WO2018174827 A1 | 9/2018 |
| WO | WO2018189244 A1 | 10/2018 |
| WO | WO2018204786 A1 | 11/2018 |
| WO | WO2018204797 A1 | 11/2018 |
| WO | WO2018204803 A1 | 11/2018 |
| WO | WO2018232055 A1 | 12/2018 |
| WO | WO2019006182 A1 | 1/2019 |
| WO | WO2019028306 A2 | 2/2019 |
| WO | WO2019060454 A2 | 3/2019 |
| WO | WO2019076856 A1 | 4/2019 |
| WO | WO2019104279 A1 | 5/2019 |
| WO | WO2019141765 A1 | 7/2019 |
| WO | WO2019158619 A1 | 8/2019 |
| WO | WO2019169132 A1 | 9/2019 |
| WO | WO2019191701 A1 | 10/2019 |
| WO | WO2019195423 A1 | 10/2019 |
| WO | WO2019195444 A1 | 10/2019 |
| WO | WO2019195449 A1 | 10/2019 |
| WO | WO2019207132 A1 | 10/2019 |
| WO | WO2019210267 A2 | 10/2019 |
| WO | WO2019217911 A1 | 11/2019 |
| WO | WO2019221992 A1 | 11/2019 |
| WO | WO2019222328 A1 | 11/2019 |
| WO | WO2019222329 A1 | 11/2019 |
| WO | WO2019222441 A1 | 11/2019 |
| WO | WO2019241324 A1 | 12/2019 |
| WO | WO2019246480 A1 | 12/2019 |
| WO | WO2020014471 A1 | 1/2020 |
| WO | WO2020028751 A2 | 2/2020 |
| WO | WO2020068990 A1 | 4/2020 |
| WO | WO2020069461 A1 | 4/2020 |
| WO | WO2020072683 A1 | 4/2020 |
| WO | WO2020077165 A1 | 4/2020 |
| WO | WO2020142714 A1 | 7/2020 |
| WO | WO2020150556 A1 | 7/2020 |
| WO | WO2020160337 A1 | 8/2020 |
| WO | WO2020168145 A1 | 8/2020 |
| WO | WO2020191300 A1 | 9/2020 |
| WO | WO2020193799 A1 | 10/2020 |
| WO | WO2020198737 A1 | 10/2020 |
| WO | WO2020205889 A1 | 10/2020 |
| WO | WO2020206189 A1 | 10/2020 |
| WO | WO2020210655 A1 | 10/2020 |
| WO | WO2020216861 A2 | 10/2020 |
| WO | WO2020219988 A1 | 10/2020 |
| WO | WO2020223276 A1 | 11/2020 |
| WO | WO2020223279 A1 | 11/2020 |
| WO | WO2020223280 A1 | 11/2020 |
| WO | WO2020227515 A1 | 11/2020 |
| WO | WO2021007382 A1 | 1/2021 |
| WO | WO2021009684 A1 | 1/2021 |
| WO | WO2021016505 A1 | 1/2021 |
| WO | WO2021025995 A1 | 2/2021 |
| WO | WO2021046155 A1 | 3/2021 |
| WO | WO2021050614 A2 | 3/2021 |
| WO | WO2021050974 A1 | 3/2021 |
| WO | WO2021072197 A1 | 4/2021 |
| WO | WO2021073568 A1 | 4/2021 |
| WO | WO2021077000 A1 | 4/2021 |
| WO | WO2021084133 A1 | 5/2021 |
| WO | WO2021102234 A1 | 5/2021 |
| WO | WO2021108468 A1 | 6/2021 |
| WO | WO2021113767 A1 | 6/2021 |
| WO | WO2021142300 A2 | 7/2021 |
| WO | WO2021150850 A1 | 7/2021 |
| WO | WO2021154923 A2 | 8/2021 |
| WO | WO2021155137 A1 | 8/2021 |
| WO | WO2021165544 A1 | 8/2021 |
| WO | WO2021168509 A1 | 9/2021 |
| WO | WO2021179861 A1 | 9/2021 |
| WO | WO2021183825 A1 | 9/2021 |
| WO | WO2021188993 A1 | 9/2021 |
| WO | WO2021202494 A1 | 10/2021 |
| WO | WO2021202651 A1 | 10/2021 |
| WO | WO2021207077 A1 | 10/2021 |
| WO | WO2021216456 A2 | 10/2021 |
| WO | WO2021219762 A1 | 11/2021 |
| WO | WO2021222148 A2 | 11/2021 |
| WO | WO2021222831 A2 | 11/2021 |
| WO | WO2021225921 A1 | 11/2021 |
| WO | WO2021226008 A1 | 11/2021 |
| WO | WO2021226267 A2 | 11/2021 |
| WO | WO2021230987 A1 | 11/2021 |
| WO | WO2021242909 A1 | 12/2021 |
| WO | WO2021243085 A2 | 12/2021 |
| WO | WO2021260204 A1 | 12/2021 |
| WO | WO2022003211 A1 | 1/2022 |
| WO | WO2022020616 A1 | 1/2022 |
| WO | WO2022040527 A2 | 2/2022 |
| WO | WO2022119871 A2 | 6/2022 |
| WO | WO2022126188 A1 | 6/2022 |
| WO | WO2022126189 A1 | 6/2022 |
| WO | WO2022150634 A2 | 7/2022 |
| WO | WO2022155482 A1 | 7/2022 |
| WO | WO2022173847 A2 | 8/2022 |
| WO | WO2022212928 A1 | 10/2022 |
| WO | WO2022221193 A1 | 10/2022 |
| WO | WO2022221400 A2 | 10/2022 |
| WO | WO2022221404 A2 | 10/2022 |
| WO | WO2022221420 A2 | 10/2022 |
| WO | WO2022221421 A2 | 10/2022 |
| WO | WO2022222869 A1 | 10/2022 |
| WO | WO2022226289 A2 | 10/2022 |
| WO | WO2022226294 A1 | 10/2022 |
| WO | WO2022226301 A1 | 10/2022 |
| WO | WO2022226374 A1 | 10/2022 |
| WO | WO2022226375 A1 | 10/2022 |
| WO | WO2022229702 A2 | 11/2022 |
| WO | WO2022229703 A2 | 11/2022 |
| WO | WO2022235970 A2 | 11/2022 |
| WO | WO2023283962 A1 | 1/2023 |
| WO | WO2023284879 A1 | 1/2023 |
| WO | WO2023010120 A2 | 2/2023 |
| WO | WO2023015297 A1 | 2/2023 |
| WO | WO2023023779 A1 | 3/2023 |
| WO | WO2023023781 A1 | 3/2023 |
| WO | WO2023039476 A1 | 3/2023 |
| WO | WO2023039480 A2 | 3/2023 |
| WO | WO2023060142 A2 | 4/2023 |

OTHER PUBLICATIONS

Bryant et al., 2021, "Deep diversification of an AAV capsid protein by machine learning," Nature Biotechnology 39(6): 691-696 https://doi.org/10.1038/s41587-020-00793-4 (13 pages).

Büning et al., 2019, "Capsid Modifications for Targeting and Improving the Efficacy of AAV Vectors," Molecular Therapy: Methods & Clinical Development 12: 248-265.r

(56) References Cited

OTHER PUBLICATIONS

Castle et al., 2016, "Controlling AAV Tropism in the Nervous System with Natural and Engineered Capsids," Methods Mol Biol. 1382: 133-149 doi: 10.1007/978-1-4939-3271-9_10 (17 pages).
Challis et al., 2019, "Systemic AAV vectors for widespread and targeted gene delivery in rodents," Nature Protocols 14: 379-414.
Chan et al., 2017, "Engineered AAVs for efficient noninvasive gene delivery to the central and peripheral nervous systems," Nat Neurosci. 20(8): 1172-1179 doi: 10.1038/nn.4593 (27 pages).
Chen et al., 2022, "Engineered AAVs for non-invasive gene delivery to rodent and non-human primate nervous systems," Neuron 110: 2242-2257 https://doi.org/10.1016/j.neuron.2022.05.003 (40 pages).
Choudhury et al., 2016, "In Vivo Selection Yields AAV-B1 Capsid for Central Nervous System and Muscle Gene Therapy," Molecular Therapy 24(7): 1247-1257.
Choudhury et al., 2016, "Widespread Central Nervous System Gene Transfer and Silencing After Systemic Delivery of Novel AAV-AS Vector," Molecular Therapy 24(4): 726-735.
Gao et al., 2004, "Clades of Adeno-Associated Viruses Are Widely Disseminated in Human Tissues," Journal of Virology 78(12): 6381-6388.
Gessler et al., 2019, "Intravenous Infusion of AAV for Widespread Gene Delivery to the Nervous System," Methods Mol Biol. 1950: 143-163 doi: 10.1007/978-1-4939-9139-6_8 (22 pages).
Goertsen et al., 2022, "AAV capsid variants with brain-wide transgene expression and decreased liver targeting after intravenous delivery in mouse and marmoset," Nature Neuroscience 25: 106-115 (26 pages).
Hsu et al., 2020, "Structural characterization of a novel human adeno-associated virus capsid with neurotropic properties," Nature Communications 11: 3279. https://doi.org/10.1038/s41467-020-17047-1 (14 pages).
Huang et al., 2019, "Delivering genes across the blood-brain barrier: LY6A, a novel cellular receptor for AAV-PHP.B capsids," PLoS One 14(11): e0225206 https://doi.org/10.1371/journal.pone.0225206 (17 pages).
Kondratov et al., 2021, "A comprehensive study of a 29-capsid AAV library in a non-human primate central nervous system," Molecular Therapy 29(9): 2806-2820.
Lin et al., 2020, "AAV9-Retro mediates efficient transduction with axon terminal absorption and blood-brain barrier transportation," Mol Brain 13: 138 https://doi.org/10.1186/s13041-020-00679-1 (12 pages).
Macdonald et al., 2021, "Capsid-Engineering for Central Nervous System-Directed Gene Therapy with Adeno-Associated Virus Vectors," Human Gene Therapy 32(19-20): 1096-1119 (25 pages).
NCBI Blast Alignment of instant SEQ ID No. 2 and SEQ ID No. 2 of U.S. Appl. No. 18/571,367 (Year: 2024) 10 pages.
Nonnenmacher et al., 2021, "Rapid evolution of blood-brain-barrier-penetrating AAV capsids by RNA-driven biopanning," Molecular Therapy: Methods & Clinical Development 20: 366-378.
Ogden et al., 2019, "Comprehensive AAV capsid fitness landscape reveals a viral gene and enables machine-guided design," Science 366(6469): 1139-1143 doi:10.1126/science.aaw2900 (9 pages).
Kumar et al., 2020, "Multiplexed Cre-dependent selection yields systemic AAVs for targeting distinct brain cell types," Nat Methods. 17(5): 541-550 doi: 10.1038/s41592-020-0799-7 (31 pages).
Saraiva et al., 2016, "Gene therapy for the CNS using AAVs: The impact of systemic delivery by AAV9," Journal of Control Release 241: 94-109.
Song et al., 2022, "Selection of rAAV vectors that cross the human blood-brain barrier and target the central nervous system using a transwell model," Molecular Therapy: Methods & Clinical Development 27: 73-88.
Stanton et al., 2023, "Systemic administration of novel engineered AAV capsids facilitates enhanced transgene expression in the macaque CNS," Med (NY) 4(1): 31-50 e8 doi: 10.1016/j.medj.2022.11.002 (38 pages).
Sullivan et al., 2018, "Rationally designed AAV2 and AAVrh8R capsids provide improved transduction in the retina and brain," Gene Therapy 25: 205-219 https://doi.org/10.1038/s41434-018-0017-8.
Tordo et al., 2018, "A novel adeno-associated virus capsid with enhanced neurotropism corrects a lysosomal transmembrane enzyme deficiency," Brain 141: 2014-2031.
Wu et al., 2000, "Mutational Analysis of the Adeno-Associated Virus Type 2 (AAV2) Capsid Gene and Construction of AAV2 Vectors with Altered Tropism," Journal of Virology 74(18): 8635-8647.
Yao et al., 2022, "Variants of the adeno-associated virus serotype 9 with enhanced penetration of the blood-brain barrier in rodents and primates," Nature Biomedical Engineering 6:1257-1271 https://doi.org/10.1038/s41551-022-00938-7 (29 pages).
International Search Report and Written Opinion issued in PCT/US22/77804 dated Feb. 14, 2023 (11 pages).

```
AAV5      MSFVDHPPDWLEE-VGEGLREFLGLEAGPPKPKPNQQHQDQARGLVLPGYNYLGPGNGLD   59
AAV2      MAADGYLPDWLEDTLSEGIRQWWKLKPGPPPPKPAERHKDDSRGLVLPGYKYLGPFNGLD   60
AAV9      MAADGYLPDWLEDNLSEGIREWWALKPGAPQPKANQQHQDNARGLVLPGYKYLGPGNGLD   60
AAV8      MAADGYLPDWLEDNLSEGIREWWALKPGAPKPKANQQKQDDGRGLVLPGYKYLGPFNGLD   60
AAVrh74   MAADGYLPDWLEDNLSEGIREWWDLKPGAPKPKANQQKQDNGRGLVLPGYKYLGPFNGLD   60

AAV5      RGEPVNRADEVAREHDISYNEQLEAGDNPYLKYNHADAEFQEKLADDTSFGGNLGKAVFQ   119
AAV2      KGEPVNEADAAALEHDKAYDRQLDSGDNPYLKYNHADAEFQERLKEDTSFGGNLGRAVFQ   120
AAV9      KGEPVNAADAAALEHDKAYDQQLKAGDNPYLKYNHADAEFQERLKEDTSFGGNLGRAVFQ   120
AAV8      KGEPVNAADAAALEHDKAYDQQLQAGDNPYLRYNHADAEFQERLQEDTSFGGNLGRAVFQ   120
AAVrh74   KGEPVNAADAAALEHDKAYDQQLQAGDNPYLRYNHADAEFQERLQEDTSFGGNLGRAVFQ   120

AAV5      AKKRVLEPFGLVEEGAKTAPTGKRIDDHFPKRKKARTEEDSK----PS--------TSSDA   168
AAV2      AKKRVLEPLGLVEEPVKTAPGKKRPVEHSPV-EPDSSSGTGKAGQQPARKRLNFGQTGDA   179
AAV9      AKKRLLEPLGLVEEAAKTAPGKKRPVEQSPQ-EPDSSAGIGKSGAQPAKKRLNFGQTGDT   179
AAV8      AKKRVLEPLGLVEEGAKTAPGKKRPVEPSPQRSPDSSTGIGKKGQQPARKRLNFGQTGDS   180
AAVrh74   AKKRVLEPLGLVESPVKTAPGKKRPVEPSPQRSPDSSTGIGKKGQQPAKKRLNFGQTGDS   180

AAV5      EAGPSGSQQLQIPAQPASSLGADTMSAGGGGPLGDNNQGADGVGNASGDWHCDSTWMGDR   228
AAV2      DS-VPDPQPLGQPPAAPSGLGTNTMATGSGAPMADNNEGADGVGNSSGNWHCDSTWMGDR   238
AAV9      ES-VPDPQPIGEPPAAPSGVGSLTMASGGGAPVADNNEGADGVGSSSGNWHCDSQWLGDR   238
AAV8      ES-VPDPQPLGEPPAAPSGVGPNTMAAGGGAPMADNNEGADGVGSSSGNWHCDSTWLGDR   239
AAVrh74   ES-VPDPQPIGEPPAGPSGLGSGTMAAGGGAPMADNNEGADGVGSSSGNWHCDSTWLGDR   239

AAV5      VVTKSTRTWVLPSYNNHQYREIKSGSVDG-SNANAYFGYSTPWGYFDFNRFHSHWSPRDW   287
AAV2      VITTSTRTWALPTYNNHLYKQISS--QSGASNDNHYFGYSTPWGYFDFNRFHCHFSPRDW   296
AAV9      VITTSTRTWALPTYNNHLYKQISNSTSGGSSNDNAYFGYSTPWGYFDFNRFHCHFSPRDW   298
AAV8      VITTSTRTWALPTYNNHLYKQISNGTSGGATNDNTYFGYSTPWGYFDFNRFHCHFSPRDW   299
AAVrh74   VITTSTRTWALPTYNNHLYKQISNGTSGGSTNDNTYFGYSTPWGYFDFNRFHCHFSPRDW   299

AAV5      QRLINNYWGFRPRSLRVKIFNIQVKEVTVQDSTTTIANNLTSTVQVFTDDDYQLPYVVGN   347
AAV2      QRLINNNWGFRPKRLNFKLFNIQVKEVTQNDGTTTIANNLTSTVQVFTDSEYQLPYVLGS   356
AAV9      QRLINNNWGFRPKRLNFKLFNIQVKEVTDNNGVKTIANNLTSTVQVFTDSDYQLPYVLGS   358
AAV8      QRLINNNWGFRPKRLSFKLFNIQVKEVTQNEGTKTIANNLTSTIQVFTDSEYQLPYVLGS   359
AAVrh74   QRLINNNWGFRPKRLNFKLFNIQVKEVTQNEGTKTIANNLTSTIQVFTDSEYQLPYVLGS   359
```

FIG. 1A

| | | |
|---|---|---|
| AAV5 | GTEGCLPAFPPQVFTLPQYGYATLNRDNTENPTERSSFFCLEYFPSKMLRTGNNFEFTYN | 407 |
| AAV2 | AHQGCLPPFPADVFMVPQYGYLTLNNG--SQAVGRSSFYCLEYFPSQMLRTGNNFTFSYT | 414 |
| AAV9 | AHEGCLPPFPADVFMIPQYGYLTLNDG--SQAVGRSSFYCLEYFPSQMLRTGNNFQFSYE | 416 |
| AAV8 | AHQGCLPPFPADVFMIPQYGYLTLNNG--SQAVGRSSFYCLEYFPSQMLRTGNNFQFTYT | 417 |
| AAVrh74 | AHQGCLPPFPADVFMIPQYGYLTLNNG--SQAVGRSSFYCLEYFPSQMLRTGNNFEFSYN | 417 |
| AAV5 | FEEVPFHSSFAPSQNLFKLANPLVDQYLYRFVSTNNTGGVQ------FNKNLAGRYANTY | 461 |
| AAV2 | FEDVPFHSSYAHSQSLDRLMNPLIDQYLYYLSRTNTPSGTTTQSRLQFSQAGASDIRDQS | 474 |
| AAV9 | FENVPFHSSYAHSQSLDRLMNPLIDQYLYYLSKTIN-GSGQNQQTLKFSVAGPSNMAVQG | 475 |
| AAV8 | FEDVPFHSSYAHSQSLDRLMNPLIDQYLYYLSRTQTTGGTANTQTLGFSQGGPNTMANQA | 477 |
| AAVrh74 | FEDVPFHSSYAHSQSLDRLMNPLIDQYLYYLSRTQSTGGTAGTQQLLFSQAGPNNMSAQA | 477 |
| AAV5 | KNWFPGPMGRTQGWNLGSGVNRASVSAFATTNRMELEGASYQVPPQPNGMTNNLQGSNTY | 521 |
| AAV2 | RNWLPGPCYRQQRVSKTSADNNNSEYSWTGATKYHLNGRDSLVNPGPAMASHKDDEEKFF | 534 |
| AAV9 | RNYIPGPSYRQQRVSTTVTQNNNSEFAWPGASSWALNGRNSLMNPGPAMASHKEGEDRFF | 535 |
| AAV8 | KNWLPGPCYRQQRVSTTTGQNNNSNFAWTAGTKYHLNGRNSLANPGIAMATHKDDEERFF | 537 |
| AAVrh74 | KNWLPGPCYRQQRVSTTLSQNNNSNFAWTGATKYHLNGRDSLVNPGVAMATHKDDEERFF | 537 |
| AAV5 | ALENTMIFNSQPANPGTTATYLEGNMLITSESETQPVNRVAYNVGGQMATNNQSSTTAPA | 581 |
| AAV2 | PQSGVLIFGKQGSEKTN---VDIEKVMITDEEEIRTTNPVATEQYGSVSTNLQRGNRQAA | 591 |
| AAV9 | PLSGSLIFGKQGTGRDN---VDADKVMITNEEEIKTTNPVATESYGQVATNHQSAQAQAQ | 592 |
| AAV8 | PSNGILIFGKQNAARDN---ADYSDVMLTSEEEIKTTNPVATEEYGIVADNLQQQNTAPQ | 594 |
| AAVrh74 | PSSGVLMFGKQGAGKDN---VDYSSVMLTSEEEIKTTNPVATEQYGVVADNLQQQNAAPI | 594 |

FIG. 1B

```
AAV5     TGTYNLQEIVPGSVWMERDVYLQGPIWAKIPETGAHFHPSPAMGGFGLKHPPPMMLIKNT  641
AAV2     TADVNTQGVLPGMVWQDRDVYLQGPIWAKIPHTDGHFHPSPLMGGFGLKHPPPQILIKNT  651
AAV9     TGWVQNQGILPGMVWQDRDVYLQGPIWAKIPHTDGNFHPSPLMGGFGMKHPPPQILIKNT  652
AAV8     IGTVNSQGALPGMVWQNRDVYLQGPIWAKIPHTDGNFHPSPLMGGEGLKHPPPQILIKNT  654
AAVrh74  VGAVNSQGALPGMVWQNRDVYLQGPIWAKIPHTDGNFHPSPLMGGFGLKHPPPQILIKNT  654

AAV5     PVPGNI-TSFSDVPVSSFITQYSTGQVTVEMEWELKKENSKRWNPEIQYTNNYNDPQFVD  700
AAV2     PVPANPSTTFSAAKFASFITQYSTGQVSVEIEWELQKENSKRWNPEIQYTSNYNKSVNVD  711
AAV9     PVPADPPTAFNKDKLNSFITQYSTGQVSVEIEWELQKENSKRWNPEIQYTSNYYKSNNVE  712
AAV8     PVPADPPTTFNQSKLNSFITQYSTGQVSVEIEWELQKENSKRWNPEIQYTSNYYKSTSVD  714
AAVrh74  PVPADPPTTFNQAKLASFITQYSTGQVSVEIEWELQKENSKRWNPEIQYTSNYYKSTNVD  714

AAV5     FAPDSTGEYRTTRPIGTRYLTRPL  724
AAV2     FTVDTNGVYSEPRPIGTRYLTRNL  735
AAV9     FAVNTEGVYSEPRPIGTRYLTRNL  736
AAV8     FAVNTEGVYSEPRPIGTRYLTRNL  738
AAVrh74  FAVNTEGTYSEPRPIGTRYLTRNL  738
```

FIG. 1C

CAPSID VARIANTS AND METHODS OF USING THE SAME

CROSS-REFERENCE TO RELATED APPLICATIONS

This application is a division application of U.S. patent application Ser. No. 18/323,135, filed May 24, 2023, which is a continuation application of International Application No. PCT/US2022/077804, filed Oct. 7, 2022, which claims priority to U.S. Provisional Application No. 63/262,341, filed Oct. 10, 2021, and U.S. Provisional Application No. 63/262,330, filed Oct. 8, 2021, the contents of each of which are hereby incorporated by reference in its entirety their entireties.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Jul. 18, 2024, is named "DYN-000D2 Sequence Listing.xml" and is 621,812 bytes in size.

BACKGROUND

Dependoparvoviruses, e.g. adeno-associated dependoparvoviruses, e.g. adeno-associated viruses (AAVs), are of interest as vectors for delivering various payloads to cells, including in human subjects.

SUMMARY

The present disclosure provides, in part, improved variant dependoparvovirus capsid proteins (e.g. AAV9 variant capsid polypeptides), such as VP1, VP2 and/or VP3 variant capsid polypeptides, methods of producing a dependoparvovirus, compositions for use in the same, as well as viral particles produced by the same. In some embodiments, the viral particles that are produced have increased central nervous system (CNS) biodistribution and/or transduction as compared to viral particles without the mutations in the capsid proteins.

In some embodiments, the disclosure is directed, in part, to a nucleic acid comprising a sequence encoding a variant capsid protein as provided for herein. In some embodiments, the dependoparvovirus is an adeno-associated dependoparvovirus (AAV). In some embodiments, the AAV is AAV9, e.g., a variant AAV9.

In some embodiments, the disclosure is directed, in part, to a variant capsid polypeptide described herein.

In some embodiments, the disclosure is directed, in part, to a variant capsid polypeptide comprising a polypeptide that has at least 70, 75, 80, 85, 90, 91, 92, 93, 94, 95, 96, 97, 98, 99% or 100% identity to a VP1, VP2, or VP3 sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally comprising, e.g., consisting of, SEQ ID NO: 2.

In some embodiments, the disclosure is directed, in part, to a dependoparvovirus particle comprising a nucleic acid described herein.

In some embodiments, the disclosure is directed, in part, to a vector, e.g., a plasmid, comprising a nucleic acid described herein.

In some embodiments, the disclosure is directed, in part, to a nucleic acid molecule comprising a sequence of SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265, a fragment thereof, or a variant thereof having at least 70, 75, 80, 85, 90, 91, 92, 93, 94, 95, 96, 97, 98, 99, or 100% sequence identity thereto.

In some embodiments, the disclosure is directed, in part, to a dependoparvovirus particle comprising a nucleic acid described herein (e.g., a nucleic acid comprising a sequence encoding a variant capsid polypeptide, such as VP1, wherein the encoding sequence comprises a change or mutation as provided herein.

In some embodiments, the disclosure is directed, in part, to a vector comprising a nucleic acid described herein, e.g., a nucleic acid comprising a sequence encoding a variant capsid polypeptide, e.g. a VP1 polypeptide, wherein the encoding sequence comprises a change or mutation as provided for herein.

In some embodiments, the disclosure is directed, in part, to a cell, cell-free system, or other translation system comprising a nucleic acid or vector described herein, e.g., comprising a sequence encoding a variant capsid polypeptide, such as VP1, wherein the variant capsid polypeptide encoding sequence comprises a change or mutation as provided for herein in the encoding sequence. In some embodiments, the cell, cell-free system, or other translation system comprises a dependoparvovirus particle described herein, e.g., wherein the particle comprises a nucleic acid comprising a sequence encoding a variant capsid polypeptide, such as a VP1 polypeptide, wherein the encoding sequence comprises a change or mutation as provided for herein.

In some embodiments, the disclosure is directed, in part, to a cell, cell-free system, or other translation system comprising a polypeptide described herein, wherein the polypeptide encoding sequence comprises a change or mutation as provided for herein. In some embodiments, the cell, cell-free system, or other translation system comprises a dependoparvovirus particle described herein, e.g., wherein the particle comprises a nucleic acid comprising a sequence encoding a VP1 polypeptide, wherein the VP1 encoding sequence comprises a change or mutation corresponding such as provided for herein.

In some embodiments, the disclosure is directed, in part, to a method of delivering a payload to a cell comprising contacting the cell with a dependoparvovirus particle comprising a nucleic acid described herein. In some embodiments, the disclosure is directed, in part, to a method of delivering a payload to a cell comprising contacting the cell with a dependoparvovirus particle comprising a variant capsid polypeptide described herein.

In some embodiments, the disclosure is directed, in part, to a method of making a dependoparvovirus particle, comprising providing a cell, cell-free system, or other translation system, comprising a nucleic acid described herein (e.g., a nucleic acid comprising a sequence encoding an capsid variant as provided for herein); and cultivating the cell, cell-free system, or other translation system, under conditions suitable for the production of the dependoparvovirus particle, thereby making the dependoparvovirus particle. In some embodiments, the disclosure is directed, in part, to a method of making a dependoparvovirus particle described herein.

In some embodiments, the disclosure is directed, in part, to a method of making a dependoparvovirus particle, comprising providing a cell, cell-free system, or other translation system, comprising a polypeptide described herein; and cultivating the cell, cell-free system, or other translation system, under conditions suitable for the production of the dependoparvovirus particle, thereby making the dependoparvovirus particle. In some embodiments, the disclosure is directed, in part, to a method of making a dependoparvovirus particle described herein.

In some embodiments, the disclosure is directed, in part, to a dependoparvovirus particle made in a cell, cell-free system, or other translation system, wherein the cell, cell-free system, or other translation system comprises a nucleic acid encoding a dependoparvovirus comprising an capsid variant as provided for herein.

In some embodiments, the disclosure is directed, in part, to a method of treating a disease or condition in a subject, comprising administering to the subject a dependoparvovirus particle described herein in an amount effective to treat the disease or condition.

The invention is further described with reference to the following numbered embodiments.

BRIEF DESCRIPTION OF THE DRAWINGS

FIG. 1A-1C. Illustration of exemplary AAV serotype alignments. Amino acids that are present only in VP1 polypeptides are in normal text; amino acids that are present only in VP1 and VP2 polypeptides are in bold; amino acids that are present in VP1, VP2 and VP3 polypeptides are underlined. FIGS. 1A-1C depict SEQ ID NOS: 7, 5, 1, 9 and 11, respectively, in order of appearance.

ENUMERATED EMBODIMENTS

Figure 2A:
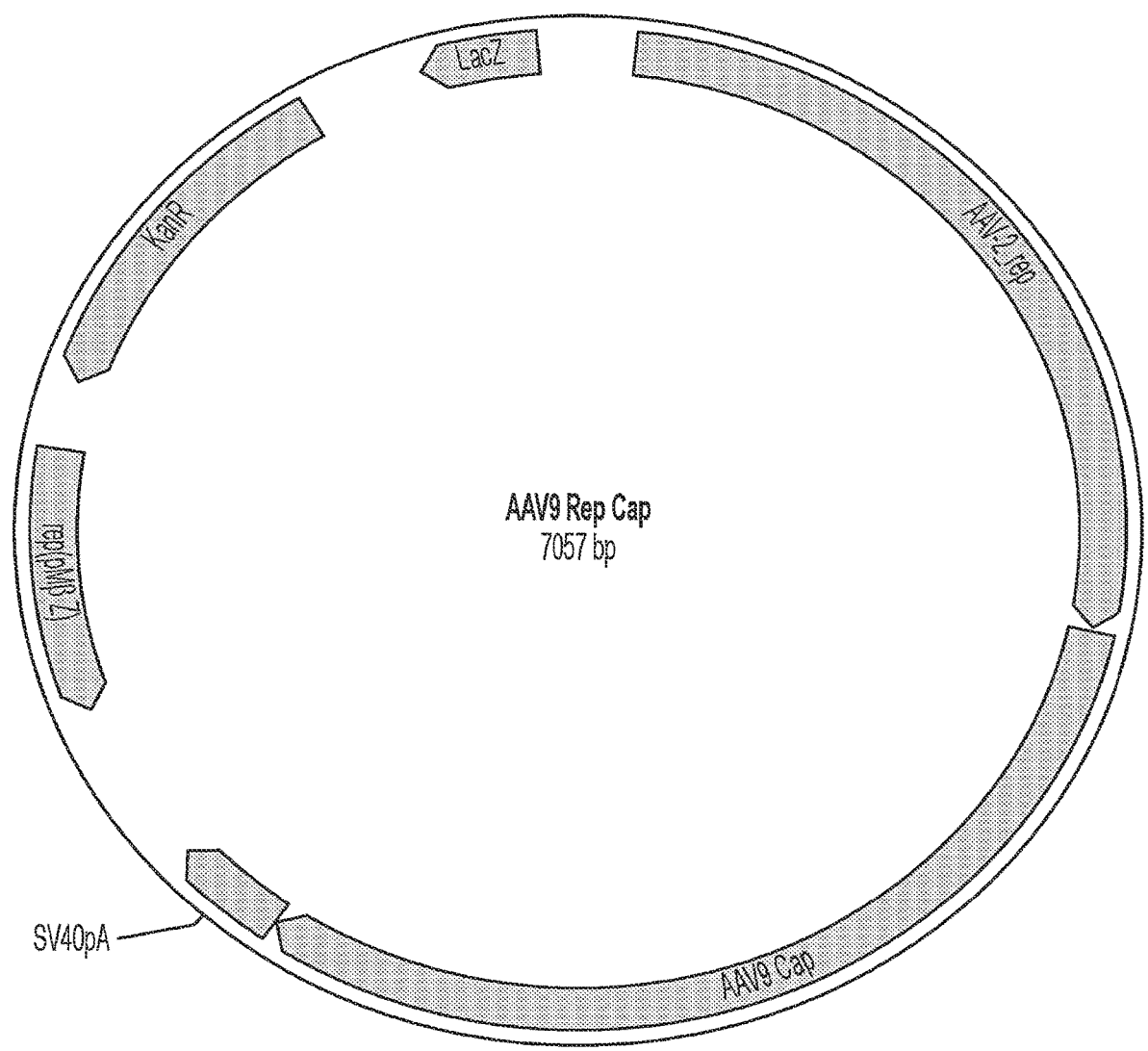
FIG. 2A-D. Genome maps of plasmids used in Example 2. A) Wild-type AAV9 rep cap plasmid. B) VAR-1 rep cap plasmid. C) Packaging plasmid pertaining to the heterologous nucleic acid sequence packaged in the VAR-1 capsid: ITR-containing plasmid encoding NLS-eGFP. D) Packaging plasmid pertaining to the heterologous nucleic acid sequence packaged in the wild-type AAV9 capsid: ITR-containing plasmid encoding NLS-mCherry.
Figure 2B:
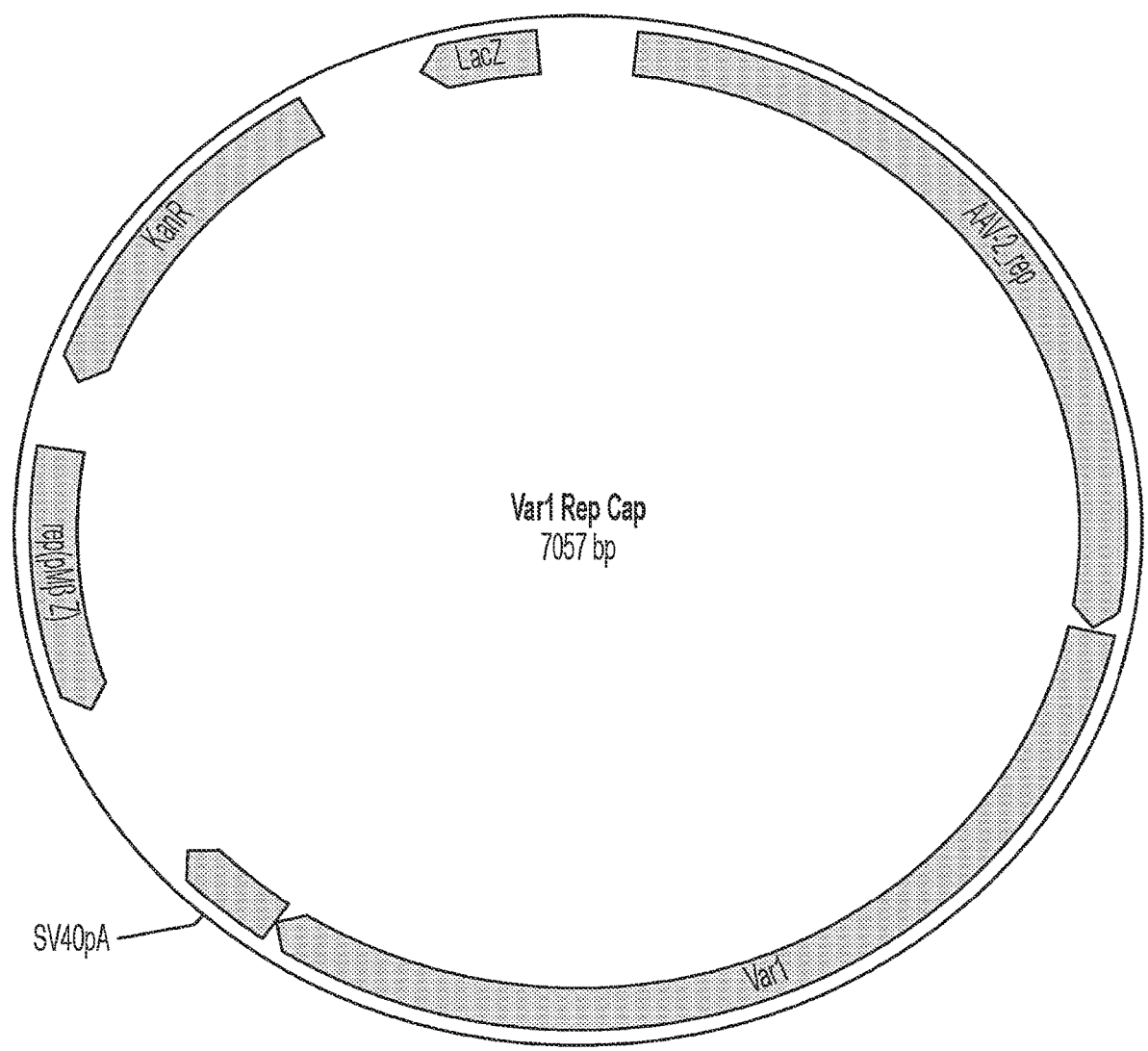
Figure 2C:
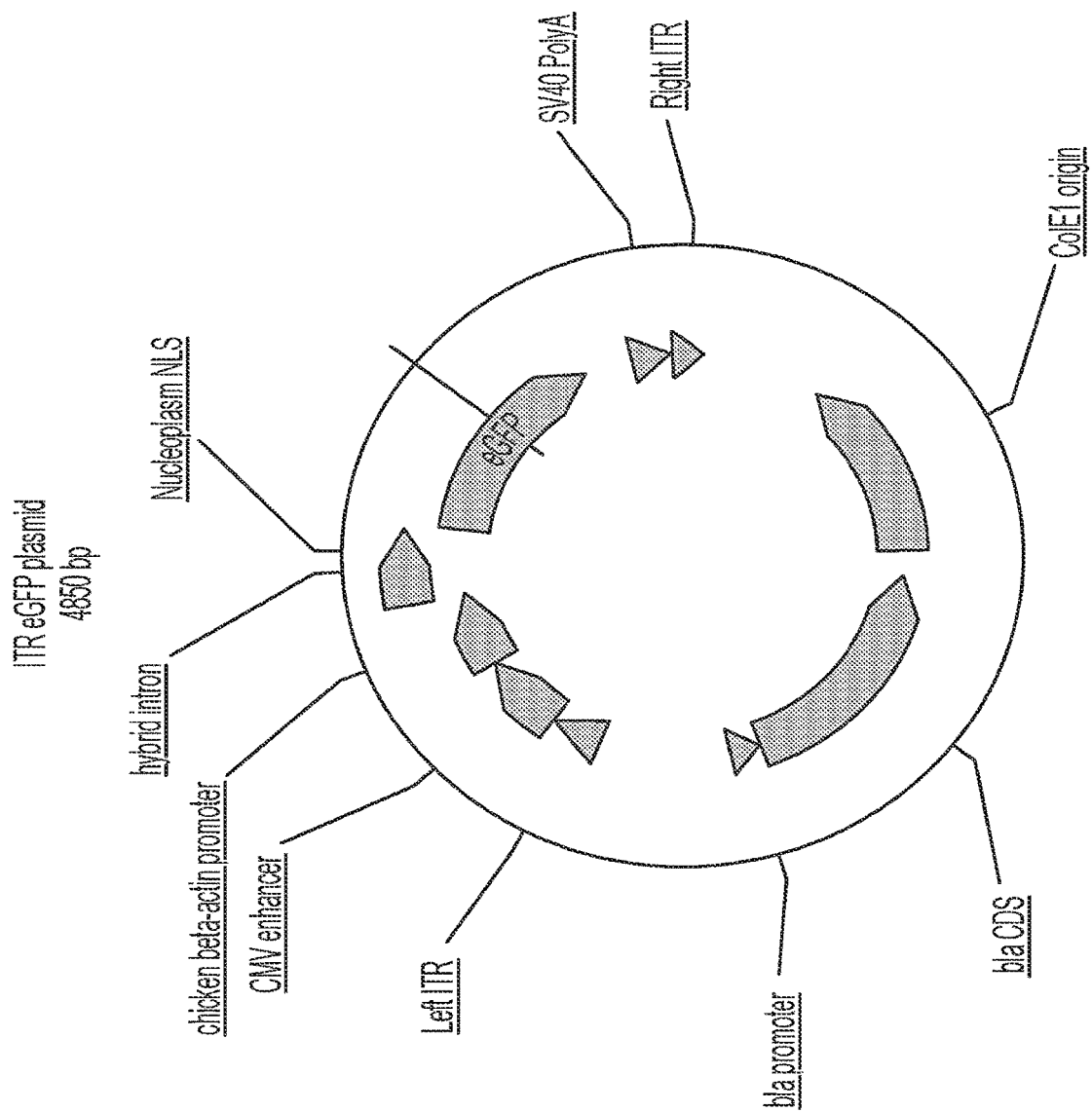
Figure 2D:
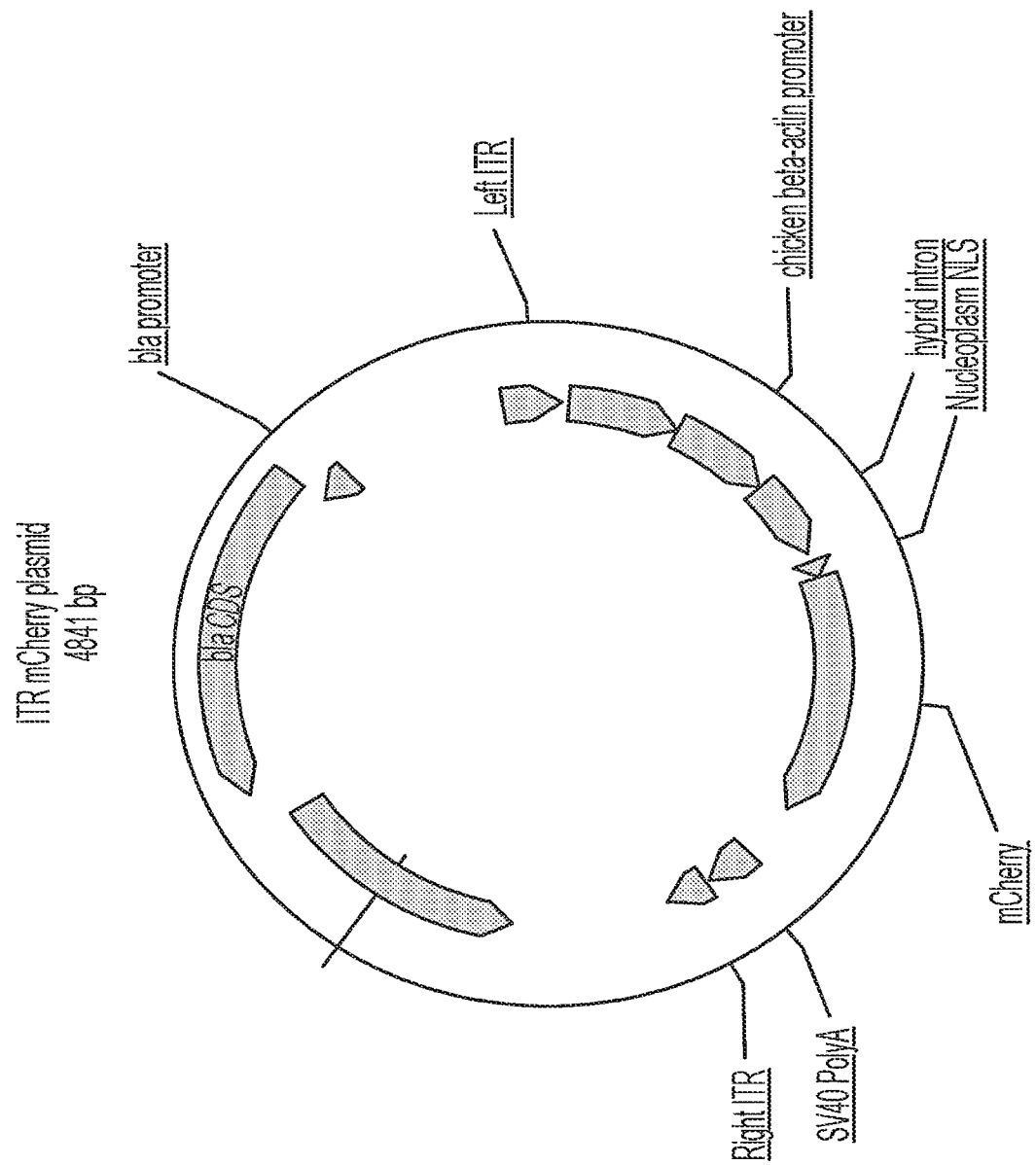

1. A variant capsid polypeptide comprising a polypeptide that has at least 70, 75, 80, 85, 90, 91, 92, 93, 94, 95, 96, 97, 98, 99% or 100% identity to a VP1, VP2, or VP3 sequence of SEQ ID NO: 2.

2. The variant capsid polypeptide of embodiment 1, wherein the variant capsid polypeptide is the same serotype as a polypeptide of SEQ ID NO: 2 (AAV9).

3. The variant capsid polypeptide of embodiment 1, wherein the variant capsid polypeptide is a different serotype as compared to a polypeptide of SEQ ID NO: 2 (AAV9).

4. The variant capsid polypeptide of any one of the preceding embodiments, wherein the variant capsid polypeptide comprises a mutation that corresponds to a mutation at one or more positions of 579, 592, 593, 595, 596, 598, 601, or any combination thereof, as compared to SEQ ID NO: 1, optionally wherein the mutation comprises an insertion, a deletion, or a substitution.

5. The variant capsid polypeptide of any of the preceding embodiments, wherein the variant capsid polypeptide comprises a mutation that corresponds to a mutation at position 579 as compared to SEQ ID NO: 1.

6. The variant capsid polypeptide of any of the preceding embodiments, wherein the variant capsid polypeptide comprises a mutation that corresponds to a mutation at position 592 as compared to SEQ ID NO: 1.

7. The variant capsid polypeptide of any of the preceding embodiments, wherein the variant capsid polypeptide comprises a mutation that corresponds to a mutation at position 593 as compared to SEQ ID NO: 1.

8. The variant capsid polypeptide of any of the preceding embodiments, wherein the variant capsid polypeptide comprises a mutation that corresponds to a mutation at position 595 as compared to SEQ ID NO: 1.

9. The variant capsid polypeptide of any of the preceding embodiments, wherein the variant capsid polypeptide comprises a mutation that corresponds to a mutation at position 596 as compared to SEQ ID NO: 1.

10. The variant capsid polypeptide of any of the preceding embodiments, wherein the variant capsid polypeptide comprises a mutation that corresponds to a mutation at position 598 as compared to SEQ ID NO: 1.

11. The variant capsid polypeptide of any of the preceding embodiments, wherein the variant capsid polypeptide comprises a mutation that corresponds to a mutation at position 601 as compared to SEQ ID NO: 1.

12. The variant capsid polypeptide of any of the preceding embodiments, wherein the variant capsid polypeptide comprises a mutation that corresponds to a mutation at position 579 and 592 as compared to SEQ ID NO: 1.

13. The variant capsid polypeptide of any of the preceding embodiments, wherein the variant capsid polypeptide comprises a mutation that corresponds to a mutation at position 579 and 593 as compared to SEQ ID NO: 1.

14. The variant capsid polypeptide of any of the preceding embodiments, wherein the variant capsid polypeptide comprises a mutation that corresponds to a mutation at position 579 and 595 as compared to SEQ ID NO: 1.

15. The variant capsid polypeptide of any of the preceding embodiments, wherein the variant capsid polypeptide comprises a mutation that corresponds to a mutation at position 579 and 596 as compared to SEQ ID NO: 1.

16. The variant capsid polypeptide of any of the preceding embodiments, wherein the variant capsid polypeptide comprises a mutation that corresponds to a mutation at position 579 and 598 as compared to SEQ ID NO: 1.

17. The variant capsid polypeptide of any of the preceding embodiments, wherein the variant capsid polypeptide comprises a mutation that corresponds to a mutation at position 579 and 601 as compared to SEQ ID NO: 1.

18. The variant capsid polypeptide of any of the preceding embodiments, wherein the variant capsid polypeptide comprises a mutation that corresponds to a mutation at position 592 and 593 as compared to SEQ ID NO: 1.

19. The variant capsid polypeptide of any of the preceding embodiments, wherein the variant capsid polypeptide comprises a mutation that corresponds to a mutation at position 592 and 595 as compared to SEQ ID NO: 1.

20. The variant capsid polypeptide of any of the preceding embodiments, wherein the variant capsid polypeptide comprises a mutation that corresponds to a mutation at position 592 and 596 as compared to SEQ ID NO: 1.

21. The variant capsid polypeptide of any of the preceding embodiments, wherein the variant capsid polypeptide comprises a mutation that corresponds to a mutation at position 592 and 598 as compared to SEQ ID NO: 1.

22. The variant capsid polypeptide of any of the preceding embodiments, wherein the variant capsid polypeptide comprises a mutation that corresponds to a mutation at position 592 and 601 as compared to SEQ ID NO: 1.

23. The variant capsid polypeptide of any of the preceding embodiments, wherein the variant capsid polypeptide comprises a mutation that corresponds to a mutation at position 593 and 595 as compared to SEQ ID NO: 1.

24. The variant capsid polypeptide of any of the preceding embodiments, wherein the variant capsid polypeptide comprises a mutation that corresponds to a mutation at position 593 and 596 as compared to SEQ ID NO: 1.

25. The variant capsid polypeptide of any of the preceding embodiments, wherein the variant capsid polypeptide comprises a mutation that corresponds to a mutation at position 593 and 598 as compared to SEQ ID NO: 1.

26. The variant capsid polypeptide of any of the preceding embodiments, wherein the variant capsid polypeptide comprises a mutation that corresponds to a mutation at position 593 and 601 as compared to SEQ ID NO: 1.

27. The variant capsid polypeptide of any of the preceding embodiments, wherein the variant capsid polypeptide comprises a mutation that corresponds to a mutation at position 595 and 596 as compared to SEQ ID NO: 1.

28. The variant capsid polypeptide of any of the preceding embodiments, wherein the variant capsid polypeptide comprises a mutation that corresponds to a mutation at position 595 and 598 as compared to SEQ ID NO: 1.

29. The variant capsid polypeptide of any of the preceding embodiments, wherein the variant capsid polypeptide comprises a mutation that corresponds to a mutation at position 595 and 601 as compared to SEQ ID NO: 1.

30. The variant capsid polypeptide of any of the preceding embodiments, wherein the variant capsid polypeptide comprises a mutation that corresponds to a mutation at position 596 and 598 as compared to SEQ ID NO: 1.

31. The variant capsid polypeptide of any of the preceding embodiments, wherein the variant capsid polypeptide comprises a mutation that corresponds to a mutation at position 596 and 601 as compared to SEQ ID NO: 1.

32. The variant capsid polypeptide of any of the preceding embodiments, wherein the variant capsid polypeptide comprises a mutation that corresponds to a mutation at position 598 and 601 as compared to SEQ ID NO: 1.

33. The variant capsid polypeptide of any of the preceding embodiments, wherein the variant capsid polypeptide comprises a mutation that corresponds to a mutation at position 579, 592, and 593 as compared to SEQ ID NO: 1.

34. The variant capsid polypeptide of any of the preceding embodiments, wherein the variant capsid polypeptide comprises a mutation that corresponds to a mutation at position 579, 592, and 595 as compared to SEQ ID NO: 1.

35. The variant capsid polypeptide of any of the preceding embodiments, wherein the variant capsid polypeptide comprises a mutation that corresponds to a mutation at position 579, 592, and 596 as compared to SEQ ID NO: 1.

36. The variant capsid polypeptide of any of the preceding embodiments, wherein the variant capsid polypeptide comprises a mutation that corresponds to a mutation at position 579, 592, and 598 as compared to SEQ ID NO: 1.

37. The variant capsid polypeptide of any of the preceding embodiments, wherein the variant capsid polypeptide comprises a mutation that corresponds to a mutation at position 579, 592, and 601 as compared to SEQ ID NO: 1.

38. The variant capsid polypeptide of any of the preceding embodiments, wherein the variant capsid polypeptide comprises a mutation that corresponds to a mutation at position 579, 593, and 595 as compared to SEQ ID NO: 1.

39. The variant capsid polypeptide of any of the preceding embodiments, wherein the variant capsid polypeptide comprises a mutation that corresponds to a mutation at position 579, 593, and 596 as compared to SEQ ID NO: 1.

40. The variant capsid polypeptide of any of the preceding embodiments, wherein the variant capsid polypeptide comprises a mutation that corresponds to a mutation at position 579, 593, and 598 as compared to SEQ ID NO: 1.

41. The variant capsid polypeptide of any of the preceding embodiments, wherein the variant capsid polypeptide comprises a mutation that corresponds to a mutation at position 579, 593, and 601 as compared to SEQ ID NO: 1.

42. The variant capsid polypeptide of any of the preceding embodiments, wherein the variant capsid polypeptide comprises a mutation that corresponds to a mutation at position 579, 595, and 596 as compared to SEQ ID NO: 1.

43. The variant capsid polypeptide of any of the preceding embodiments, wherein the variant capsid polypeptide comprises a mutation that corresponds to a mutation at position 579, 595, and 44. The variant capsid polypeptide of any of the preceding embodiments, wherein the variant capsid polypeptide comprises a mutation that corresponds to a mutation at position 579, 595, and 601 as compared to SEQ ID NO: 1.

45. The variant capsid polypeptide of any of the preceding embodiments, wherein the variant capsid polypeptide comprises a mutation that corresponds to a mutation at position 579, 596, and 598 as compared to SEQ ID NO: 1.

46. The variant capsid polypeptide of any of the preceding embodiments, wherein the variant capsid polypeptide comprises a mutation that corresponds to a mutation at position 579, 596, and 601 as compared to SEQ ID NO: 1.

47. The variant capsid polypeptide of any of the preceding embodiments, wherein the variant capsid polypeptide comprises a mutation that corresponds to a mutation at position 579, 598, and 601 as compared to SEQ ID NO: 1.

48. The variant capsid polypeptide of any of the preceding embodiments, wherein the variant capsid polypeptide comprises a mutation that corresponds to a mutation at position 592, 593, and 595 as compared to SEQ ID NO: 1.

49. The variant capsid polypeptide of any of the preceding embodiments, wherein the variant capsid polypeptide comprises a mutation that corresponds to a mutation at position 592, 593, and 596 as compared to SEQ ID NO: 1.

50. The variant capsid polypeptide of any of the preceding embodiments, wherein the variant capsid polypeptide comprises a mutation that corresponds to a mutation at position 592, 593, and 598 as compared to SEQ ID NO: 1.

51. The variant capsid polypeptide of any of the preceding embodiments, wherein the variant capsid polypeptide comprises a mutation that corresponds to a mutation at position 592, 593, and 601 as compared to SEQ ID NO: 1.

52. The variant capsid polypeptide of any of the preceding embodiments, wherein the variant capsid polypeptide comprises a mutation that corresponds to a mutation at position 592, 595, and 596 as compared to SEQ ID NO: 1.

53. The variant capsid polypeptide of any of the preceding embodiments, wherein the variant capsid polypeptide comprises a mutation that corresponds to a mutation at position 592, 595, and 54. The variant capsid polypeptide of any of the preceding embodiments, wherein the variant capsid polypeptide comprises a mutation that corresponds to a mutation at position 592, 595, and 601 as compared to SEQ ID NO: 1.

55. The variant capsid polypeptide of any of the preceding embodiments, wherein the variant capsid polypeptide comprises a mutation that corresponds to a mutation at position 592, 596, and 598 as compared to SEQ ID NO: 1.

56. The variant capsid polypeptide of any of the preceding embodiments, wherein the variant capsid polypeptide comprises a mutation that corresponds to a mutation at position 592, 596, and 601 as compared to SEQ ID NO: 1.

57. The variant capsid polypeptide of any of the preceding embodiments, wherein the variant capsid polypeptide comprises a mutation that corresponds to a mutation at position 592, 598, and 601 as compared to SEQ ID NO: 1.

58. The variant capsid polypeptide of any of the preceding embodiments, wherein the variant capsid polypeptide comprises a mutation that corresponds to a mutation at position 593, 595, and 596 as compared to SEQ ID NO: 1.

59. The variant capsid polypeptide of any of the preceding embodiments, wherein the variant capsid polypeptide comprises a mutation that corresponds to a mutation at position 593, 595, and 598 as compared to SEQ ID NO: 1.

60. The variant capsid polypeptide of any of the preceding embodiments, wherein the variant capsid polypeptide comprises a mutation that corresponds to a mutation at position 593, 595, and 601 as compared to SEQ ID NO: 1.

61. The variant capsid polypeptide of any of the preceding embodiments, wherein the variant capsid polypeptide comprises a mutation that corresponds to a mutation at position 593, 596, and 598 as compared to SEQ ID NO: 1.

62. The variant capsid polypeptide of any of the preceding embodiments, wherein the variant capsid polypeptide comprises a mutation that corresponds to a mutation at position 593, 596, and 601 as compared to SEQ ID NO: 1.

63. The variant capsid polypeptide of any of the preceding embodiments, wherein the variant capsid polypeptide comprises a mutation that corresponds to a mutation at position 593, 598, and 601 as compared to SEQ ID NO: 1.

64. The variant capsid polypeptide of any of the preceding embodiments, wherein the variant capsid polypeptide comprises a mutation that corresponds to a mutation at position 595, 596, and 598 as compared to SEQ ID NO: 1.

65. The variant capsid polypeptide of any of the preceding embodiments, wherein the variant capsid polypeptide comprises a mutation that corresponds to a mutation at position 595, 596, and 601 as compared to SEQ ID NO: 1.

66. The variant capsid polypeptide of any of the preceding embodiments, wherein the variant capsid polypeptide comprises a mutation that corresponds to a mutation at position 595, 598, and 601 as compared to SEQ ID NO: 1.

67. The variant capsid polypeptide of any of the preceding embodiments, wherein the variant capsid polypeptide comprises a mutation that corresponds to a mutation at position 596, 598, and 601 as compared to SEQ ID NO: 1.

68. The variant capsid polypeptide of any of the preceding embodiments, wherein the variant capsid polypeptide comprises a mutation that corresponds to a mutation at position 579, 592, 593, and 595 as compared to SEQ ID NO: 1.

69. The variant capsid polypeptide of any of the preceding embodiments, wherein the variant capsid polypeptide comprises a mutation that corresponds to a mutation at position 579, 592, 593, and 596 as compared to SEQ ID NO: 1.

70. The variant capsid polypeptide of any of the preceding embodiments, wherein the variant capsid polypeptide comprises a mutation that corresponds to a mutation at position 579, 592, 593, and 598 as compared to SEQ ID NO: 1.

71. The variant capsid polypeptide of any of the preceding embodiments, wherein the variant capsid polypeptide comprises a mutation that corresponds to a mutation at position 579, 592, 593, and 601 as compared to SEQ ID NO: 1.

72. The variant capsid polypeptide of any of the preceding embodiments, wherein the variant capsid polypeptide comprises a mutation that corresponds to a mutation at position 579, 593, 595, and 596 as compared to SEQ ID NO: 1.

73. The variant capsid polypeptide of any of the preceding embodiments, wherein the capsid polypeptide comprises a mutation that corresponds to a mutation at position 579, 593, 595, and 74. The variant capsid polypeptide of any of the preceding embodiments, wherein the variant capsid polypeptide comprises a mutation that corresponds to a mutation at position 579, 593, 595, and 601 as compared to SEQ ID NO: 1.

75. The variant capsid polypeptide of any of the preceding embodiments, wherein the variant capsid polypeptide comprises a mutation that corresponds to a mutation at position 579, 592, 595, and 596 as compared to SEQ ID NO: 1.

76. The variant capsid polypeptide of any of the preceding embodiments, wherein the variant capsid polypeptide comprises a mutation that corresponds to a mutation at position 579, 592, 595, and 598 as compared to SEQ ID NO: 1.

77. The variant capsid polypeptide of any of the preceding embodiments, wherein the variant capsid polypeptide comprises a mutation that corresponds to a mutation at position 579, 592, 595, and 601 as compared to SEQ ID NO: 1.

78. The variant capsid polypeptide of any of the preceding embodiments, wherein the variant capsid polypeptide comprises a mutation that corresponds to a mutation at position 579, 592, 593, and 596 as compared to SEQ ID NO: 1.

79. The variant capsid polypeptide of any of the preceding embodiments, wherein the variant capsid polypeptide comprises a mutation that corresponds to a mutation at position 579, 592, 593, and 598 as compared to SEQ ID NO: 1.

80. The variant capsid polypeptide of any of the preceding embodiments, wherein the variant capsid polypeptide comprises a mutation that corresponds to a mutation at position 579, 592, 593, and 601 as compared to SEQ ID NO: 1.

81. The variant capsid polypeptide of any of the preceding embodiments, wherein the variant capsid polypeptide comprises a mutation that corresponds to a mutation at position 592, 593, 595, and 596 as compared to SEQ ID NO: 1.

82. The variant capsid polypeptide of any of the preceding embodiments, wherein the variant capsid polypeptide comprises a mutation that corresponds to a mutation at position 592, 593, 595, and 598 as compared to SEQ ID NO: 1.

83. The variant capsid polypeptide of any of the preceding embodiments, wherein the variant capsid polypeptide comprises a mutation that corresponds to a mutation at position 592, 593, 595, and 601 as compared to SEQ ID NO: 1.

84. The variant capsid polypeptide of any of the preceding embodiments, wherein the variant capsid polypeptide comprises a mutation that corresponds to a mutation at position 593, 595, 596, and 598 as compared to SEQ ID NO: 1.

85. The variant capsid polypeptide of any of the preceding embodiments, wherein the variant capsid polypeptide comprises a mutation that corresponds to a mutation at position 593, 595, 596, and 601 as compared to SEQ ID NO: 1.

86. The variant capsid polypeptide of any of the preceding embodiments, wherein the variant capsid polypeptide comprises a mutation that corresponds to a mutation at position 595, 596, 598, and 601 as compared to SEQ ID NO: 1.

87. The variant capsid polypeptide of any of the preceding embodiments, wherein the variant capsid polypeptide comprises a mutation that corresponds to a mutation at position 579, 592, 593, 595, and 596 as compared to SEQ ID NO: 1.

88. The variant capsid polypeptide of any of the preceding embodiments, wherein the variant capsid polypeptide comprises a mutation that corresponds to a mutation at position 579, 592, 593, 595, and 598 as compared to SEQ ID NO: 1.

89. The variant capsid polypeptide of any of the preceding embodiments, wherein the variant capsid polypeptide comprises a mutation that corresponds to a mutation at position 579, 592, 593, 595, and 601 as compared to SEQ ID NO: 1.

90. The variant capsid polypeptide of any of the preceding embodiments, wherein the variant capsid polypeptide comprises a mutation that corresponds to a mutation at position 579, 593, 595, 596 and 598 as compared to SEQ ID NO: 1.

91. The variant capsid polypeptide of any of the preceding embodiments, wherein the variant capsid polypeptide comprises a mutation that corresponds to a mutation at position 579, 593, 595, 596 and 601 as compared to SEQ ID NO: 1.

92. The variant capsid polypeptide of any of the preceding embodiments, wherein the variant capsid polypeptide comprises a mutation that corresponds to a mutation at position 579, 592, 595, 596 and 598 as compared to SEQ ID NO: 1.

93. The variant capsid polypeptide of any of the preceding embodiments, wherein the variant capsid polypeptide comprises a mutation that corresponds to a mutation at position 579, 592, 595, 596 and 601 as compared to SEQ ID NO: 1.

94. The variant capsid polypeptide of any of the preceding embodiments, wherein the variant capsid polypeptide comprises a mutation that corresponds to a mutation at position 579, 592, 593, 596 and 598 as compared to SEQ ID NO: 1.

95. The variant capsid polypeptide of any of the preceding embodiments, wherein the variant capsid polypeptide comprises a mutation that corresponds to a mutation at position 579, 592, 593, 596 and 601 as compared to SEQ ID NO: 1.

96. The variant capsid polypeptide of any of the preceding embodiments, wherein the variant capsid polypeptide comprises a mutation that corresponds to a mutation at position 579, 592, 593, 595 and 598 as compared to SEQ ID NO: 1.

97. The variant capsid polypeptide of any of the preceding embodiments, wherein the variant capsid polypeptide comprises a mutation that corresponds to a mutation at position 579, 592, 593, 595 and 601 as compared to SEQ ID NO: 1.

98. The variant capsid polypeptide of any of the preceding embodiments, wherein the variant capsid polypeptide comprises a mutation that corresponds to a mutation at position 592, 593, 595, 596 and 598 as compared to SEQ ID NO: 1.

99. The variant capsid polypeptide of any of the preceding embodiments, wherein the variant capsid polypeptide comprises a mutation that corresponds to a mutation at position 592, 593, 595, 596 and 601 as compared to SEQ ID NO: 1.

100. The variant capsid polypeptide of any of the preceding embodiments, wherein the variant capsid polypeptide comprises a mutation that corresponds to a mutation at position 593, 595, 596, 598 and 601 as compared to SEQ ID NO: 1.

101. The variant capsid polypeptide of any of the preceding embodiments, wherein the variant capsid polypeptide comprises a mutation that corresponds to a mutation at position 579, 592, 593, 595, 596, and 598 as compared to SEQ ID NO: 1.

102. The variant capsid polypeptide of any of the preceding embodiments, wherein the variant capsid polypeptide comprises a mutation that corresponds to a mutation at position 579, 592, 593, 595, 596, and 601 as compared to SEQ ID NO: 1.

103. The variant capsid polypeptide of any of the preceding embodiments, wherein the variant capsid polypeptide comprises a mutation that corresponds to a mutation at position 592, 593, 595, 596, 598 and 601 as compared to SEQ ID NO: 1.

104. The variant capsid polypeptide of any of the preceding embodiments, wherein the variant capsid polypeptide comprises a mutation that corresponds to a mutation at position 579, 593, 595, 596, 598 and 601 as compared to SEQ ID NO: 1.

105. The variant capsid polypeptide of any of the preceding embodiments, wherein the variant capsid polypeptide comprises a mutation that corresponds to a mutation at position 579, 592, 595, 596, 598 and 601 as compared to SEQ ID NO: 1.

106. The variant capsid polypeptide of any of the preceding embodiments, wherein the variant capsid polypeptide comprises a mutation that corresponds to a mutation at position 579, 592, 593, 596, 598 and 601 as compared to SEQ ID NO: 1.

107. The variant capsid polypeptide of any of the preceding embodiments, wherein the variant capsid polypeptide comprises a mutation that corresponds to a mutation at position 579, 592, 593, 595, 598 and 601 as compared to SEQ ID NO: 1.

108. The variant capsid polypeptide of any of the preceding embodiments, wherein the variant capsid polypeptide comprises a mutation that corresponds to a mutation at position 579, 592, 593, 595, 596, 598 and 601 as compared to SEQ ID NO: 1.

109. The variant capsid polypeptide of any of the preceding embodiments, wherein the variant capsid polypeptide 110. The variant capsid polypeptide of any of the preceding embodiments, wherein the variant capsid polypeptide comprises a mutation that corresponds to a mutation at position 579, 592, 596, and 601 as compared to SEQ ID NO: 1.

111. The variant capsid polypeptide of any of the preceding embodiments, wherein the variant capsid polypeptide comprises a mutation that corresponds to a mutation at position 579, 592, 598, and 601 as compared to SEQ ID NO: 1.

112. The variant capsid polypeptide of any of the preceding embodiments, wherein the variant capsid polypeptide comprises a mutation that corresponds to a mutation at position 579, 593, 596, and 598 as compared to SEQ ID NO: 1.

113. The variant capsid polypeptide of any of the preceding embodiments, wherein the variant capsid polypeptide comprises a mutation that corresponds to a mutation at position 579, 593, 596, and 601 as compared to SEQ ID NO: 1.

114. The variant capsid polypeptide of any of the preceding embodiments, wherein the variant capsid polypeptide comprises a mutation that corresponds to a mutation at position 579, 593, 598, and 601 as compared to SEQ ID NO: 1.

115. The variant capsid polypeptide of any of the preceding embodiments, wherein the variant capsid polypeptide comprises a mutation that corresponds to a mutation at position 579, 595, 596, and 598 as compared to SEQ ID NO: 1.

116. The variant capsid polypeptide of any of the preceding embodiments, wherein the variant capsid polypeptide comprises a mutation that corresponds to a mutation at position 579, 595, 596, and 601 as compared to SEQ ID NO: 1.

117. The variant capsid polypeptide of any of the preceding embodiments, wherein the variant capsid polypeptide comprises a mutation that corresponds to a mutation at position 579, 595, 598, and 601 as compared to SEQ ID NO: 1.

118. The variant capsid polypeptide of any of the preceding embodiments, wherein the variant capsid polypeptide comprises a mutation that corresponds to a mutation at position 579, 596, 598, and 598 as compared to SEQ ID NO: 1.

119. The variant capsid polypeptide of any of the preceding embodiments, wherein the variant capsid polypeptide comprises a mutation that corresponds to a mutation at position 592, 593, 596, and 598 as compared to SEQ ID NO: 1.

120. The variant capsid polypeptide of any of the preceding embodiments, wherein the variant capsid polypeptide comprises a mutation that corresponds to a mutation at position 592, 593, 596, and 601 as compared to SEQ ID NO: 1.

121. The variant capsid polypeptide of any of the preceding embodiments, wherein the variant capsid polypeptide comprises a mutation that corresponds to a mutation at position 592, 593, 598, and 601 as compared to SEQ ID NO: 1.

122. The variant capsid polypeptide of any of the preceding embodiments, wherein the variant capsid polypeptide comprises a mutation that corresponds to a mutation at position 592, 595, 596, and 598 as compared to SEQ ID NO: 1.

123. The variant capsid polypeptide of any of the preceding embodiments, wherein the variant capsid polypeptide comprises a mutation that corresponds to a mutation at position 592, 595, 596, and 601 as compared to SEQ ID NO: 1.

124. The variant capsid polypeptide of any of the preceding embodiments, wherein the variant capsid polypeptide comprises a mutation that corresponds to a mutation at position 592, 595, 598, and 601 as compared to SEQ ID NO: 1.

125. The variant capsid polypeptide of any of the preceding embodiments, wherein the variant capsid polypeptide comprises a mutation that corresponds to a mutation at position 592, 596, 598, and 601 as compared to SEQ ID NO: 1.

126. The variant capsid polypeptide of any of the preceding embodiments, wherein the variant capsid polypeptide comprises a mutation that corresponds to a mutation at position 593, 595, 598, and 601 as compared to SEQ ID NO: 1.

127. The variant capsid polypeptide of any of the preceding embodiments, wherein the variant capsid polypeptide comprises a mutation that corresponds to a mutation at position 593, 596, 598, and 601 as compared to SEQ ID NO: 1.

128. The variant capsid polypeptide of any of the preceding embodiments, wherein the variant capsid polypeptide comprises a mutation that corresponds to a mutation at position 579, 593, 595, 598 and 601 as compared to SEQ ID NO: 1.

129. The variant capsid polypeptide of any of the preceding embodiments, wherein the variant capsid polypeptide comprises a mutation that corresponds to a mutation at position 579, 593, 596, 598 and 601 as compared to SEQ ID NO: 1.

130. The variant capsid polypeptide of any of the preceding embodiments, wherein the variant capsid polypeptide comprises a mutation that corresponds to a mutation at position 579, 595, 596, 598 and 601 as compared to SEQ ID NO: 1.

131. The variant capsid polypeptide of any of the preceding embodiments, wherein the variant capsid polypeptide comprises a mutation that corresponds to a mutation at position 579, 592, 595, 598 and 601 as compared to SEQ ID NO: 1.

132. The variant capsid polypeptide of any of the preceding embodiments, wherein the variant capsid polypeptide comprises a mutation that corresponds to a mutation at position 579, 592, 596, 598 and 601 as compared to SEQ ID NO: 1.

133. The variant capsid polypeptide of any of the preceding embodiments, wherein the variant capsid polypeptide comprises a mutation that corresponds to a mutation at position 579, 595, 596, 598 and 601 as compared to SEQ ID NO: 1.

134. The variant capsid polypeptide of any of the preceding embodiments, wherein the variant capsid polypeptide comprises a mutation that corresponds to a mutation at position 579, 592, 593, 598 and 601 as compared to SEQ ID NO: 1.

135. The variant capsid polypeptide of any of the preceding embodiments, wherein the variant capsid polypeptide comprises a mutation that corresponds to a mutation at position 592, 593, 595, 598 and 601 as compared to SEQ ID NO: 1.

136. The variant capsid polypeptide of any of the preceding embodiments, wherein the variant capsid polypeptide comprises a mutation that corresponds to a mutation at position 592, 593, 596, 598 and 601 as compared to SEQ ID NO: 1.

137. The variant capsid polypeptide of any of the preceding embodiments, wherein the variant capsid polypeptide comprises a mutation that corresponds to a mutation at position 592, 595, 596, 598 and 601 as compared to SEQ ID NO: 1.

138. A variant capsid polypeptide, comprising a polypeptide that has at least 70, 75, 80, 85, 90, 91, 92, 93, 94, 95, 96, 97, 98, or 99% identity to a VP1, VP2, or VP3 sequence of SEQ ID NO: 1 and comprises:
(a) A valine at a position corresponding to Q579 as compared to SEQ ID NO: 1;
(b) An isoleucine at a position corresponding to Q592 as compared to SEQ ID NO: 1;
(c) A valine at a position corresponding to T593 as compared to SEQ ID NO: 1;
(d) An alanine at a position corresponding to W595 as compared to SEQ ID NO: 1;
(e) A leucine at a position corresponding to V596 as compared to SEQ ID NO: 1;
(f) A serine at a position corresponding to N598 as compared to SEQ ID NO: 1;
(g) An alanine at a position corresponding to I601 as compared to SEQ ID NO: 1; or
(h) Combinations thereof, optionally wherein the variant capsid polypeptide comprises all of (a)-(g).

139. The variant capsid polypeptide of any of embodiments 1-138, wherein the variant capsid polypeptide comprises:
(a) A valine at a position corresponding to Q579 as compared to SEQ ID NO: 1;
(b) An isoleucine at a position corresponding to Q592 as compared to SEQ ID NO: 1;
(c) A valine at a position corresponding to T593 as compared to SEQ ID NO: 1;
(d) An alanine at a position corresponding to W595 as compared to SEQ ID NO: 1;
(e) A leucine at a position corresponding to V596 as compared to SEQ ID NO: 1;
(f) A serine at a position corresponding to N598 as compared to SEQ ID NO: 1;
(g) An alanine at a position corresponding to I601 as compared to SEQ ID NO: 1; or
(h) Combinations thereof, optionally wherein the variant capsid polypeptide comprises all of (a)-(g).

140. The variant capsid polypeptide of any of the preceding embodiments, wherein the variant capsid polypeptide comprises a valine at a position corresponding to Q579 as compared to SEQ ID NO: 1.

141. The variant capsid polypeptide of any of the preceding embodiments, wherein the variant capsid polypeptide comprises a isoleucine at a position corresponding to Q592 as compared to SEQ ID NO: 1.

142. The variant capsid polypeptide of any of the preceding embodiments, wherein variant capsid polypeptide comprises a valine at a position corresponding to T593 as compared to SEQ ID NO: 1.

143. The variant capsid polypeptide of any of the preceding embodiments, wherein the variant capsid polypeptide comprises an alanine at a position corresponding to W595 as compared to SEQ ID NO: 1.

144. The variant capsid polypeptide of any of the preceding embodiments, wherein the variant capsid polypeptide comprises a leucine at a position corresponding to V596 as compared to SEQ ID NO: 1.

145. The variant capsid polypeptide of any of the preceding embodiments, wherein the variant capsid polypeptide comprises a serine at a position corresponding to N598 as compared to SEQ ID NO: 1.

146. The variant capsid polypeptide of any of the preceding embodiments, wherein the variant capsid polypeptide comprises an alanine at a position corresponding to I601 as compared to SEQ ID NO: 1.

147. The variant capsid polypeptide of any of the preceding embodiments, wherein the variant capsid polypeptide comprises a valine at a position corresponding to Q579 and an isoleucine at a position corresponding to Q592 as compared to SEQ ID NO: 1.

148. The variant capsid polypeptide of any of the preceding embodiments, wherein the variant capsid polypeptide comprises a valine at a position corresponding to Q579 and a valine at a position corresponding to T593 as compared to SEQ ID NO: 1.

149. The variant capsid polypeptide of any of the preceding embodiments, wherein the variant capsid polypeptide comprises a valine at a position corresponding to Q579 and an alanine at a position corresponding to W595 as compared to SEQ ID NO: 1.

150. The variant capsid polypeptide of any of the preceding embodiments, wherein the variant capsid polypeptide comprises a valine at a position corresponding to Q579 and a leucine at a position corresponding to V596 as compared to SEQ ID NO: 1.

151. The variant capsid polypeptide of any of the preceding embodiments, wherein the variant capsid polypeptide comprises a valine at a position corresponding to Q579 and a serine at a position corresponding to N598 as compared to SEQ ID NO: 1.

152. The variant capsid polypeptide of any of the preceding embodiments, wherein the variant capsid polypeptide comprises a valine at a position corresponding to Q579 and an alanine at a position corresponding to I601 as compared to SEQ ID NO: 1.

153. The variant capsid polypeptide of any of the preceding embodiments, wherein the variant capsid polypeptide comprises an isoleucine at a position corresponding to Q592 and a valine at a position corresponding to T593 as compared to SEQ ID NO: 1.

154. The variant capsid polypeptide of any of the preceding embodiments, wherein the variant capsid polypeptide comprises an isoleucine at a position corresponding to Q592 and an alanine at a position corresponding to W595 as compared to SEQ ID NO: 1.

155. The variant capsid polypeptide of any of the preceding embodiments, wherein the variant capsid polypeptide comprises an isoleucine at a position corresponding to Q592 and a leucine at a position corresponding to V596 as compared to SEQ ID NO: 1.

156. The variant capsid polypeptide of any of the preceding embodiments, wherein the variant capsid polypeptide comprises an isoleucine at a position corresponding to Q592 and a serine at a position corresponding to N598 as compared to SEQ ID NO: 1.

157. The variant capsid polypeptide of any of the preceding embodiments, wherein the variant capsid polypeptide comprises an isoleucine at a position corresponding to Q592 and an alanine at a position corresponding to I601 as compared to SEQ ID NO: 1.

158. The variant capsid polypeptide of any of the preceding embodiments, wherein the variant capsid polypeptide comprises a valine at a position corresponding to T593 and an alanine at a position corresponding to W595 as compared to SEQ ID NO: 1.

159. The variant capsid polypeptide of any of the preceding embodiments, wherein the variant capsid polypeptide comprises a valine at a position corresponding to T593 and a leucine at a position corresponding to V596 as compared to SEQ ID NO: 1.

160. The variant capsid polypeptide of any of the preceding embodiments, wherein the variant capsid polypeptide comprises a valine at a position corresponding to T593 and a serine at a position corresponding to N598 as compared to SEQ ID NO: 1.

161. The variant capsid polypeptide of any of the preceding embodiments, wherein the variant capsid polypeptide comprises a valine at a position corresponding to T593 and an alanine at a position corresponding to I601 as compared to SEQ ID NO: 1.

162. The variant capsid polypeptide of any of the preceding embodiments, wherein the variant capsid polypeptide comprises an alanine at a position corresponding to W595 and a leucine at a position corresponding to V596 as compared to SEQ ID NO: 1.

163. The variant capsid polypeptide of any of the preceding embodiments, wherein the variant capsid polypeptide comprises an alanine at a position corresponding to W595 and a serine at a position corresponding to N598 as compared to SEQ ID NO: 1.

164. The variant capsid polypeptide of any of the preceding embodiments, wherein the variant capsid polypeptide comprises an alanine at a position corresponding to W595 and an alanine at a position corresponding to I601 as compared to SEQ ID NO: 1.

165. The variant capsid polypeptide of any of the preceding embodiments, wherein the variant capsid polypeptide comprises a leucine at a position corresponding to V596 and a serine at a position corresponding to N598 as compared to SEQ ID NO: 1.

166. The variant capsid polypeptide of any of the preceding embodiments, wherein the variant capsid polypeptide comprises a leucine at a position corresponding to V596 and an alanine at a position corresponding to I601 as compared to SEQ ID NO: 1.

167. The variant capsid polypeptide of any of the preceding embodiments, wherein the variant capsid polypeptide comprises a serine at a position corresponding to N598 and an alanine at a position corresponding to I601 as compared to SEQ ID NO: 1.

168. The variant capsid polypeptide of any of the preceding embodiments, wherein the variant capsid polypeptide comprises a valine at a position corresponding to Q579, an isoleucine at a position corresponding to Q592, and a valine at a position corresponding to T593 as compared to SEQ ID NO: 1.

169. The variant capsid polypeptide of any of the preceding embodiments, wherein the variant capsid polypeptide comprises a valine at a position corresponding to Q579, an isoleucine at a position corresponding to Q592, and an alanine at a position corresponding to W595 as compared to SEQ ID NO: 1.

170. The variant capsid polypeptide of any of the preceding embodiments, wherein the variant capsid polypeptide comprises a valine at a position corresponding to Q579, an isoleucine at a position corresponding to Q592, and a leucine at a position corresponding to V596 as compared to SEQ ID NO: 1.

171. The variant capsid polypeptide of any of the preceding embodiments, wherein the variant capsid polypeptide comprises a valine at a position corresponding to Q579, an isoleucine at a position corresponding to Q592, and a serine at a position corresponding to N598 as compared to SEQ ID NO: 1.

172. The variant capsid polypeptide of any of the preceding embodiments, wherein the variant capsid polypeptide comprises a valine at a position corresponding to Q579, an isoleucine at a position corresponding to Q592, and an alanine at a position corresponding to I601 as compared to SEQ ID NO: 1.

173. The variant capsid polypeptide of any of the preceding embodiments, wherein the variant capsid polypeptide comprises a valine at a position corresponding to Q579, a valine at a position corresponding to T593, and an alanine at a position corresponding to W595 as compared to SEQ ID NO: 1.

174. The variant capsid polypeptide of any of the preceding embodiments, wherein the variant capsid polypeptide comprises a valine at a position corresponding to Q579, a valine at a position corresponding to T593, and a leucine at a position corresponding to V596 as compared to SEQ ID NO: 1.

175. The variant capsid polypeptide of any of the preceding embodiments, wherein the variant capsid polypeptide comprises a valine at a position corresponding to Q579, a valine at a position corresponding to T593, and a serine at a position corresponding to N598 as compared to SEQ ID NO: 1.

176. The variant capsid polypeptide of any of the preceding embodiments, wherein the variant capsid polypeptide comprises a valine at a position corresponding to Q579, a valine at a position corresponding to T593, and an alanine at a position corresponding to I601 as compared to SEQ ID NO: 1.

177. The variant capsid polypeptide of any of the preceding embodiments, wherein the variant capsid polypeptide comprises a valine at a position corresponding to Q579, an alanine at a position corresponding to W595, and a leucine at a position corresponding to V596 as compared to SEQ ID NO: 1.

178. The variant capsid polypeptide of any of the preceding embodiments, wherein the variant capsid polypeptide comprises a valine at a position corresponding to Q579, an alanine at a position corresponding to W595, and a serine at a position corresponding to N598 as compared to SEQ ID NO: 1.

179. The variant capsid polypeptide of any of the preceding embodiments, wherein the variant capsid polypeptide comprises a valine at a position corresponding to Q579, an alanine at a position corresponding to W595, and an alanine at a position corresponding to I601 as compared to SEQ ID NO: 1.

180. The variant capsid polypeptide of any of the preceding embodiments, wherein the variant capsid polypeptide comprises a valine at a position corresponding to Q579, a leucine at a position corresponding to V596, and a serine at a position corresponding to N598 as compared to SEQ ID NO: 1.

181. The variant capsid polypeptide of any of the preceding embodiments, wherein the variant capsid polypeptide comprises a valine at a position corresponding to Q579, a leucine at a position corresponding to V596, and an alanine at a position corresponding to I601 as compared to SEQ ID NO: 1.

182. The variant capsid polypeptide of any of the preceding embodiments, wherein the variant capsid polypeptide comprises a valine at a position corresponding to Q579, a serine at a position corresponding to N598, and an alanine at a position corresponding to I601 as compared to SEQ ID NO: 1.

183. The variant capsid polypeptide of any of the preceding embodiments, wherein the variant capsid polypeptide comprises an isoleucine at a position corresponding to Q592, a valine at a position corresponding to T593, and an alanine at a position corresponding to W595 as compared to SEQ ID NO: 1.

184. The variant capsid polypeptide of any of the preceding embodiments, wherein the variant capsid polypeptide comprises an isoleucine at a position corresponding to Q592, a valine at a position corresponding to T593, and a leucine at a position corresponding to V596 as compared to SEQ ID NO: 1.

185. The variant capsid polypeptide of any of the preceding embodiments, wherein the variant capsid polypeptide comprises an isoleucine at a position corresponding to Q592, a valine at a position corresponding to T593, and a serine at a position corresponding to N598 as compared to SEQ ID NO: 1.

186. The variant capsid polypeptide of any of the preceding embodiments, wherein the variant capsid polypeptide comprises an isoleucine at a position corresponding to Q592, a valine at a position corresponding to T593, and an alanine at a position corresponding to I601 as compared to SEQ ID NO: 1.

187. The variant capsid polypeptide of any of the preceding embodiments, wherein the variant capsid polypeptide comprises an isoleucine at a position corresponding to Q592, an alanine at a position corresponding to W595, and a leucine at a position corresponding to V596 as compared to SEQ ID NO: 1.

188. The variant capsid polypeptide of any of the preceding embodiments, wherein the variant capsid polypeptide comprises an isoleucine at a position corresponding to Q592, an alanine at a position corresponding to W595, and a serine at a position corresponding to N598 as compared to SEQ ID NO: 1.

189. The variant capsid polypeptide of any of the preceding embodiments, wherein the variant capsid polypeptide comprises an isoleucine at a position corresponding to Q592, an alanine at a position corresponding to W595, and an alanine at a position corresponding to I601 as compared to SEQ ID NO: 1.

190. The variant capsid polypeptide of any of the preceding embodiments, wherein the variant capsid polypeptide comprises an isoleucine at a position corresponding to Q592, a leucine at a position corresponding to V596, and a serine at a position corresponding to N598 as compared to SEQ ID NO: 1.

191. The variant capsid polypeptide of any of the preceding embodiments, wherein the variant capsid polypeptide comprises an isoleucine at a position corresponding to Q592, a leucine at a position corresponding to V596, and an alanine at a position corresponding to I601 as compared to SEQ ID NO: 1.

192. The variant capsid polypeptide of any of the preceding embodiments, wherein the variant capsid polypeptide comprises an isoleucine at a position corresponding to Q592, a serine at a position corresponding to N598, and an alanine at a position corresponding to I601 as compared to SEQ ID NO: 1.

193. The variant capsid polypeptide of any of the preceding embodiments, wherein the variant capsid polypeptide comprises a valine at a position corresponding to T593, an alanine at a position corresponding to W595, and a leucine at a position corresponding to V596 as compared to SEQ ID NO: 1.

194. The variant capsid polypeptide of any of the preceding embodiments, wherein the variant capsid polypeptide comprises a valine at a position corresponding to T593, an alanine at a position corresponding to W595, and a serine at a position corresponding to N598 as compared to SEQ ID NO: 1.

195. The variant capsid polypeptide of any of the preceding embodiments, wherein the variant capsid polypeptide comprises a valine at a position corresponding to T593, an alanine at a position corresponding to W595, and an alanine at a position corresponding to I601 as compared to SEQ ID NO: 1.

196. The variant capsid polypeptide of any of the preceding embodiments, wherein the variant capsid polypeptide comprises a valine at a position corresponding to T593, a leucine at a position corresponding to V596, and a serine at a position corresponding to N598 as compared to SEQ ID NO: 1.

197. The variant capsid polypeptide of any of the preceding embodiments, wherein the variant capsid polypeptide comprises a valine at a position corresponding to T593, a leucine at a position corresponding to V596, and an alanine at a position corresponding to I601 as compared to SEQ ID NO: 1.

198. The variant capsid polypeptide of any of the preceding embodiments, wherein the variant capsid polypeptide comprises a valine at a position corresponding to T593, a serine at a position corresponding to N598, and an alanine at a position corresponding to I601 as compared to SEQ ID NO: 1.

199. The variant capsid polypeptide of any of the preceding embodiments, wherein the variant capsid polypeptide comprises an alanine at a position corresponding to W595, a leucine at a position corresponding to V596, and a serine at a position corresponding to N598 as compared to SEQ ID NO: 1.

200. The variant capsid polypeptide of any of the preceding embodiments, wherein the variant capsid polypeptide comprises an alanine at a position corresponding to W595, a leucine at a position corresponding to V596, and an alanine at a position corresponding to I601 as compared to SEQ ID NO: 1.

201. The variant capsid polypeptide of any of the preceding embodiments, wherein the variant capsid polypeptide comprises an alanine at a position corresponding to W595, a serine at a position corresponding to N598, and an alanine at a position corresponding to I601 as compared to SEQ ID NO: 1.

202. The variant capsid polypeptide of any of the preceding embodiments, wherein the variant capsid polypeptide comprises a leucine at a position corresponding to V596, a serine at a position corresponding to N598, and an alanine at a position corresponding to I601 as compared to SEQ ID NO: 1.

203. The variant capsid polypeptide of any of the preceding embodiments, wherein the variant capsid polypeptide comprises a valine at a position corresponding to Q579, an isoleucine at a position corresponding to Q592, a valine at a position corresponding to T593, and an alanine at a position corresponding to W595 as compared to SEQ ID NO: 1.

204. The variant capsid polypeptide of any of the preceding embodiments, wherein the variant capsid polypeptide comprises a valine at a position corresponding to Q579, an isoleucine at a position corresponding to Q592, a valine at a position corresponding to T593, and a leucine at a position corresponding to V596 as compared to SEQ ID NO: 1.

205. The variant capsid polypeptide of any of the preceding embodiments, wherein the variant capsid polypeptide comprises a valine at a position corresponding to Q579, an isoleucine at a position corresponding to Q592, a valine at a position corresponding to T593, and a serine at a position corresponding to N598 as compared to SEQ ID NO: 1.

206. The variant capsid polypeptide of any of the preceding embodiments, wherein the variant capsid polypeptide comprises a valine at a position corresponding to Q579, an isoleucine at a position corresponding to Q592, a valine at a position corresponding to T593, and an alanine at a position corresponding to I601 as compared to SEQ ID NO: 1.

207. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and a leucine at a position corresponding to V596 as compared to SEQ ID NO: 1.

208. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and a serine at a position corresponding to N598 as compared to SEQ ID NO: 1.

209. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and an alanine at a position corresponding to I601 as compared to SEQ ID NO: 1.

210. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and a leucine at a position corresponding to V596 as compared to SEQ ID NO: 1.

211. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and a serine at a position corresponding to N598 as compared to SEQ ID NO: 1.

212. The variant capsid polypeptide of any of the preceding embodiments, wherein the variant capsid polypeptide comprises a valine at a position corresponding to Q579, an isoleucine at a position corresponding to Q592, an alanine at a position corresponding to W595, and an alanine at a position corresponding to I601 as compared to SEQ ID NO: 1.

213. The variant capsid polypeptide of any of the preceding embodiments, wherein the variant capsid polypeptide comprises a valine at a position corresponding to Q579, an isoleucine at a position corresponding to Q592, a valine at a position corresponding to T593, and a leucine at a position corresponding to V596 as compared to SEQ ID NO: 1.

214. The variant capsid polypeptide of any of the preceding embodiments, wherein the variant capsid polypeptide comprises a valine at a position corresponding to Q579, an isoleucine at a position corresponding to Q592, a valine at a position corresponding to T593, and a serine at a position corresponding to N598 as compared to SEQ ID NO: 1.

215. The variant capsid polypeptide of any of the preceding embodiments, wherein the variant capsid polypeptide comprises a valine at a position corresponding to Q579, an isoleucine at a position corresponding to Q592, a valine at a position corresponding to T593, and an alanine at a position corresponding to I601 as compared to SEQ ID NO: 1.

216. The variant capsid polypeptide of any of the preceding embodiments, wherein the variant capsid polypeptide comprises an isoleucine at a position corresponding to Q592, a valine at a position corresponding to T593, an alanine at a position corresponding to W595, and n596s as compared to SEQ ID NO: 1.

217. The variant capsid polypeptide of any of the preceding embodiments, wherein the variant capsid polypeptide comprises an isoleucine at a position corresponding to Q592, a valine at a position corresponding to T593, an alanine at a position corresponding to W595, and a serine at a position corresponding to N598 as compared to SEQ ID NO: 1.

218. The variant capsid polypeptide of any of the preceding embodiments, wherein the variant capsid polypeptide comprises an isoleucine at a position corresponding to Q592, a valine at a position corresponding to T593, an alanine at a position corresponding to W595, and an alanine at a position corresponding to I601 as compared to SEQ ID NO: 1.

219. The variant capsid polypeptide of any of the preceding embodiments, wherein the variant capsid polypeptide comprises a valine at a position corresponding to T593, an alanine at a position corresponding to W595, a leucine at a position corresponding to V596, and a serine at a position corresponding to N598 as compared to SEQ ID NO: 1.

220. The variant capsid polypeptide of any of the preceding embodiments, wherein the variant capsid polypeptide comprises a valine at a position corresponding to T593, an alanine at a position corresponding to W595, a leucine at a position corresponding to V596, and an alanine at a position corresponding to I601 as compared to SEQ ID NO: 1.

221. The variant capsid polypeptide of any of the preceding embodiments, wherein the variant capsid polypeptide comprises an alanine at a position corresponding to W595, a leucine at a position corresponding to V596, a serine at a position corresponding to N598, and an alanine at a position corresponding to I601 as compared to SEQ ID NO: 1.

222. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, and a leucine at a position corresponding to V596 as compared to SEQ ID NO: 1.

223. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, and a serine at a position corresponding to N598 as compared to SEQ ID NO: 1.

224. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, and an alanine at a position corresponding to I601 as compared to SEQ ID NO: 1.

225. The variant capsid polypeptide of any of the preceding embodiments, wherein the variant capsid polypeptide comprises a valine at a position corresponding to Q579, a valine at a position corresponding to T593, an alanine at a position corresponding to W595, a leucine at a position corresponding to V596 and a serine at a position corresponding to N598 as compared to SEQ ID NO: 1.

226. The variant capsid polypeptide of any of the preceding embodiments, wherein the variant capsid polypeptide comprises a valine at a position corresponding to Q579, a valine at a position corresponding to T593, an alanine at a position corresponding to W595, a leucine at a position corresponding to V596 and an alanine at a position corresponding to I601 as compared to SEQ ID NO: 1.

227. The variant capsid polypeptide of any of the preceding embodiments, wherein the variant capsid polypeptide comprises a valine at a position corresponding to Q579, an isoleucine at a position corresponding to Q592, an alanine at a position corresponding to W595, a leucine at a position corresponding to V596 and a serine at a position corresponding to N598 as compared to SEQ ID NO: 1.

228. The variant capsid polypeptide of any of the preceding embodiments, wherein the variant capsid polypeptide comprises a valine at a position corresponding to Q579, an isoleucine at a position corresponding to Q592, an alanine at a position corresponding to W595, a leucine at a position corresponding to V596 and an alanine at a position corresponding to I601 as compared to SEQ ID NO: 1.

229. The variant capsid polypeptide of any of the preceding embodiments, wherein the variant capsid polypeptide comprises a valine at a position corresponding to Q579, an isoleucine at a position corresponding to Q592, a valine at a position corresponding to T593, a leucine at a position corresponding to V596 and a serine at a position corresponding to N598 as compared to SEQ ID NO: 1.

230. The variant capsid polypeptide of any of the preceding embodiments, wherein the variant capsid polypeptide comprises a valine at a position corresponding to Q579, an isoleucine at a position corresponding to Q592, a valine at a position corresponding to T593, a leucine at a position corresponding to V596 and an alanine at a position corresponding to I601 as compared to SEQ ID NO: 1.

231. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595 and a serine at a position corresponding to N598 as compared to SEQ ID NO: 1.

232. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595 and an alanine at a position corresponding to I601 as compared to SEQ ID NO: 1.

233. The variant capsid polypeptide of any of the preceding embodiments, wherein the variant capsid polypeptide comprises an isoleucine at a position corresponding to Q592, a valine at a position corresponding to T593, an alanine at a position corresponding to W595, a leucine at a position corresponding to V596 and a serine at a position corresponding to N598 as compared to SEQ ID NO: 1.

234. The variant capsid polypeptide of any of the preceding embodiments, wherein the variant capsid polypeptide comprises an isoleucine at a position corresponding to Q592, a valine at a position corresponding to T593, an alanine at a position corresponding to W595, a leucine at a position corresponding to V596 and an alanine at a position corresponding to I601 as compared to SEQ ID NO: 1.

235. The variant capsid polypeptide of any of the preceding embodiments, wherein the variant capsid polypeptide comprises a valine at a position corresponding to T593, an alanine at a position corresponding to W595, a leucine at a position corresponding to V596, a serine at a position corresponding to N598 and an alanine at a position corresponding to I601 as compared to SEQ ID NO: 1.

236. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, a leucine at a position corresponding to V596, and a serine at a position corresponding to N598 as compared to SEQ ID NO: 1.

237. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, a leucine at a position corresponding to V596, and an alanine at a position corresponding to I601 as compared to SEQ ID NO: 1.

238. The variant capsid polypeptide of any of the preceding embodiments, wherein the variant capsid polypeptide comprises a valine at a position corresponding to Q592, a valine at a position corresponding to T593, an alanine at a position corresponding to W595, a leucine at a position corresponding to V596, a serine at a position corresponding to N598 and an alanine at a position corresponding to I601 as compared to SEQ ID NO: 1.

239. The variant capsid polypeptide of any of the preceding embodiments, wherein the variant capsid polypeptide comprises a valine at a position corresponding to Q579, a valine at a position corresponding to T593, an alanine at a position corresponding to W595, a leucine at a position corresponding to V596, a serine at a position corresponding to N598 and an alanine at a position corresponding to I601 as compared to SEQ ID NO: 1.

240. The variant capsid polypeptide of any of the preceding embodiments, wherein the variant capsid polypeptide comprises a valine at a position corresponding to Q579, an isoleucine at a position corresponding to Q592, an alanine at a position corresponding to W595, a leucine at a position corresponding to V596, a serine at a position corresponding to N598 and an alanine at a position corresponding to I601 as compared to SEQ ID NO: 1.

241. The variant capsid polypeptide of any of the preceding embodiments, wherein the variant capsid polypeptide comprises a valine at a position corresponding to Q579, an isoleucine at a position corresponding to Q592, a valine at a position corresponding to T593, a leucine at a position corresponding to V596, a serine at a position corresponding to N598 and an alanine at a position corresponding to I601 as compared to SEQ ID NO: 1.

242. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, a serine at a position corresponding to N598 and an alanine at a position corresponding to I601 as compared to SEQ ID NO: 1.

243. The variant capsid polypeptide of any of the preceding embodiments, wherein the variant capsid polypeptide comprises a valine at a position corresponding to Q579, an isoleucine at a position corresponding to Q592, a valine at a position corresponding to T593, an alanine at a position corresponding to W595, a leucine at a position corresponding to V596, a serine at a position corresponding to N598 and an alanine at a position corresponding to I601 as compared to SEQ ID NO: 1.

244. The variant capsid polypeptide of any of the preceding embodiments, wherein the variant capsid polypeptide comprises a valine at a position corresponding to Q579, an isoleucine at a position corresponding to Q592, a leucine at a position corresponding to V596, and a serine at a position corresponding to N598 as compared to SEQ ID NO: 1.

245. The variant capsid polypeptide of any of the preceding embodiments, wherein the variant capsid polypeptide comprises a valine at a position corresponding to Q579, an isoleucine at a position corresponding to Q592, a leucine at a position corresponding to V596, and an alanine at a position corresponding to I601 as compared to SEQ ID NO: 1.

246. The variant capsid polypeptide of any of the preceding embodiments, wherein the variant capsid polypeptide comprises a valine at a position corresponding to Q579, an isoleucine at a position corresponding to Q592, a serine at a position corresponding to N598, and an alanine at a position corresponding to I601 as compared to SEQ ID NO: 1.

247. The variant capsid polypeptide of any of the preceding embodiments, wherein the variant capsid polypeptide comprises a valine at a position corresponding to Q579, a valine at a position corresponding to T593, a leucine at a position corresponding to V596, and a serine at a position corresponding to N598 as compared to SEQ ID NO: 1.

248. The variant capsid polypeptide of any of the preceding embodiments, wherein the variant capsid polypeptide comprises a valine at a position corresponding to Q579, a valine at a position corresponding to T593, a leucine at a position corresponding to V596, and an alanine at a position corresponding to I601 as compared to SEQ ID NO: 1.

249. The variant capsid polypeptide of any of the preceding embodiments, wherein the variant capsid polypeptide comprises a valine at a position corresponding to Q579, a valine at a position corresponding to T593, a serine at a position corresponding to N598, and an alanine at a position corresponding to I601 as compared to SEQ ID NO: 1.

250. The variant capsid polypeptide of any of the preceding embodiments, wherein the variant capsid polypeptide comprises a valine at a position corresponding to Q579, an alanine at a position corresponding to W595, a leucine at a position corresponding to V596, and a serine at a position corresponding to N598 as compared to SEQ ID NO: 1.

251. The variant capsid polypeptide of any of the preceding embodiments, wherein the variant capsid polypeptide comprises a valine at a position corresponding to Q579, an alanine at a position corresponding to W595, a leucine at a position corresponding to V596, and an alanine at a position corresponding to I601 as compared to SEQ ID NO: 1.

252. The variant capsid polypeptide of any of the preceding embodiments, wherein the variant capsid polypeptide comprises a valine at a position corresponding to Q579, an alanine at a position corresponding to W595, a serine at a position corresponding to N598, and an alanine at a position corresponding to I601 as compared to SEQ ID NO: 1.

253. The variant capsid polypeptide of any of the preceding embodiments, wherein the variant capsid polypeptide comprises an isoleucine at a position corresponding to Q592, a valine at a position corresponding to T593, a leucine at a position corresponding to V596, and a serine at a position corresponding to N598 as compared to SEQ ID NO: 1.

254. The variant capsid polypeptide of any of the preceding embodiments, wherein the variant capsid polypeptide comprises an isoleucine at a position corresponding to Q592, a valine at a position corresponding to T593, a leucine at a position corresponding to V596, and an alanine at a position corresponding to I601 as compared to SEQ ID NO: 1.

255. The variant capsid polypeptide of any of the preceding embodiments, wherein the variant capsid polypeptide comprises an isoleucine at a position corresponding to Q592, a valine at a position corresponding to T593, a serine at a position corresponding to N598, and an alanine at a position corresponding to I601 as compared to SEQ ID NO: 1.

256. The variant capsid polypeptide of any of the preceding embodiments, wherein the variant capsid polypeptide comprises an isoleucine at a position corresponding to Q592, an alanine at a position corresponding to W595, a leucine at a position corresponding to V596, and a serine at a position corresponding to N598 as compared to SEQ ID NO: 1.

257. The variant capsid polypeptide of any of the preceding embodiments, wherein the variant capsid polypeptide comprises an isoleucine at a position corresponding to Q592, an alanine at a position corresponding to W595, a leucine at a position corresponding to V596, and an alanine at a position corresponding to I601 as compared to SEQ ID NO: 1.

258. The variant capsid polypeptide of any of the preceding embodiments, wherein the variant capsid polypeptide comprises an isoleucine at a position corresponding to Q592, an alanine at a position corresponding to W595, a serine at a position corresponding to N598, and an alanine at a position corresponding to I601 as compared to SEQ ID NO: 1.

259. The variant capsid polypeptide of any of the preceding embodiments, wherein the variant capsid polypeptide comprises an isoleucine at a position corresponding to Q592, a leucine at a position corresponding to V596, a serine at a position corresponding to N598, and an alanine at a position corresponding to I601 as compared to SEQ ID NO: 1.

260. The variant capsid polypeptide of any of the preceding embodiments, wherein the variant capsid polypeptide comprises a valine at a position corresponding to T593, an alanine at a position corresponding to W595, a serine at a position corresponding to N598, and an alanine at a position corresponding to I601 as compared to SEQ ID NO: 1.

261. The variant capsid polypeptide of any of the preceding embodiments, wherein the variant capsid polypeptide comprises a valine at a position corresponding to T593, a leucine at a position corresponding to V596, a serine at a position corresponding to N598, and an alanine at a position corresponding to I601 as compared to SEQ ID NO: 1.

262. The variant capsid polypeptide of any of the preceding embodiments, wherein the variant capsid polypeptide comprises a valine at a position corresponding to Q579, a valine at a position corresponding to T593, an alanine at a position corresponding to W595, a serine at a position corresponding to N598 and an alanine at a position corresponding to I601 as compared to SEQ ID NO: 1.

263. The variant capsid polypeptide of any of the preceding embodiments, wherein the variant capsid polypeptide comprises a valine at a position corresponding to Q579, a valine at a position corresponding to T593, a leucine at a position corresponding to V596, a serine at a position corresponding to N598 and an alanine at a position corresponding to I601 as compared to SEQ ID NO: 1.

264. The variant capsid polypeptide of any of the preceding embodiments, wherein the variant capsid polypeptide comprises a valine at a position corresponding to Q579, an alanine at a position corresponding to W595, a leucine at a position corresponding to V596, a serine at a position corresponding to N598 and an alanine at a position corresponding to I601 as compared to SEQ ID NO: 1.

265. The variant capsid polypeptide of any of the preceding embodiments, wherein the variant capsid polypeptide comprises a valine at a position corresponding to Q579, an isoleucine at a position corresponding to Q592, an alanine at a position corresponding to W595, a serine at a position corresponding to N598 and an alanine at a position corresponding to I601 as compared to SEQ ID NO: 1.

266. The variant capsid polypeptide of any of the preceding embodiments, wherein the variant capsid polypeptide comprises a valine at a position corresponding to Q579, an isoleucine at a position corresponding to Q592, a leucine at a position corresponding to V596, a serine at a position corresponding to N598 and an alanine at a position corresponding to I601 as compared to SEQ ID NO: 1.

267. The variant capsid polypeptide of any of the preceding embodiments, wherein the variant capsid polypeptide comprises a valine at a position corresponding to Q579, an alanine at a position corresponding to W595, a leucine at a position corresponding to V596, a serine at a position corresponding to N598 and an alanine at a position corresponding to I601 as compared to SEQ ID NO: 1.

268. The variant capsid polypeptide of any of the preceding embodiments, wherein the variant capsid polypeptide comprises a valine at a position corresponding to Q579, an isoleucine at a position corresponding to Q592, a valine at a position corresponding to T593, a serine at a position corresponding to N598 and an alanine at a position corresponding to I601 as compared to SEQ ID NO: 1.

268. The variant capsid polypeptide of any of the preceding embodiments, wherein the variant capsid polypeptide comprises a valine at a position corresponding to Q592, a valine at a position corresponding to T593, an alanine at a position corresponding to W595, a serine at a position corresponding to N598 and an alanine at a position corresponding to I601 as compared to SEQ ID NO: 1.

269. The variant capsid polypeptide of any of the preceding embodiments, wherein the variant capsid polypeptide comprises a valine at a position corresponding to Q592, a valine at a position corresponding to T593, a leucine at a position corresponding to V596, a serine at a position corresponding to N598 and an alanine at a position corresponding to I601 as compared to SEQ ID NO: 1.

270. The variant capsid polypeptide of any of the preceding embodiments, wherein the variant capsid polypeptide comprises a valine at a position corresponding to Q592, an alanine at a position corresponding to W595, a leucine at a position corresponding to V596, a serine at a position corresponding to N598 and an alanine at a position corresponding to I601 as compared to SEQ ID NO: 1.

271. A variant capsid polypeptide (for example, a VP1, VP2, or VP3), that is at least, or about, 95, 96, 97, 98 or 99% identical to a capsid polypeptide of SEQ ID NO: 2 (for example, a VP1, VP2 or VP3 polypeptide SEQ ID NO: 2) and comprises at least 4, at least 5, at least 6, optionally all, the mutation differences of VAR-1.

272. A variant capsid polypeptide (for example, a VP1, VP2, or VP3), that has about 1 to about 20 mutations as compared to a capsid polypeptide (for example, a VP1, VP2 or VP3) of SEQ ID NO: 2 and comprises at least 4, at least 5, at least 6, optionally all, the mutation differences of VAR-1.

273. A variant capsid polypeptide of embodiment 215 that has about 1 to about 10 mutations as compared to a capsid polypeptide (for example, a VP1, VP2 or VP3).

274. A variant capsid polypeptide of embodiment 215, that has about 1 to about 5 mutations as compared to a capsid polypeptide (for example, a VP1, VP2 or VP3).

275. A variant capsid polypeptide (for example, a VP1, VP2, or VP3), that is at least, or about, 95, 96, 97, 98 or 99% identical to a polypeptide of SEQ ID NO: 2 and comprises a valine at a position corresponding to 596L according to SEQ ID NO: 1.

276. A variant capsid polypeptide (for example, a VP1, VP2, or VP3), that has about 1 to about 20 mutations as compared to a capsid polypeptide (for example, a VP1, VP2 or VP3) of SEQ ID NO: 2 and comprises a valine at a position corresponding to 596L according to SEQ ID NO: 1.

277. A variant capsid polypeptide of embodiment 219, that has about 1 to about 10 mutations as compared to a capsid polypeptide (for example a VP1, VP2, or VP3) of SEQ ID NO: 2.

278. A variant capsid polypeptide of embodiment 219, that has about 1 to about 5 mutations as compared to a capsid polypeptide (for example a VP1, VP2, or VP3) of SEQ ID NO: 2.

279. A variant capsid polypeptide comprising a VP1, VP2, or VP3 sequence of SEQ ID NO: 2.

280. A variant capsid polypeptide consisting of the VP1, VP2, or VP3 sequence of SEQ ID NO: 2.

281. The variant capsid polypeptide of any of the preceding embodiments, wherein the variant capsid polypeptide is a VP1 polypeptide, a VP2 polypeptide or a VP3 polypeptide.

282. A nucleic acid molecule encoding a capsid variant polypeptide of any one of the preceding embodiments.

283. The nucleic acid molecule of embodiment 282, wherein the nucleic acid molecule comprises a sequence of SEQ ID NO: 3, a fragment thereof (e.g., a VP1-encoding, a VP2-encoding or a VP3-encoding fragment thereof), or a sequence having at least 70, 75, 80, 85, 90, 91, 92, 93, 94, 95, 96, 97, 98, 99, or 100% sequence identity thereto.

284. The nucleic acid molecule of embodiment 282 or 283, wherein the fragment thereof encodes a VP2 capsid polypeptide or a VP3 capsid polypeptide.

285. The nucleic acid molecule of embodiment 282 or 283, wherein the nucleic acid molecule comprises a sequence of SEQ ID NO: 3.

286. A virus particle (e.g., adeno-associated virus ("AAV") particle) comprising a variant capsid polypeptide of any one of the preceding embodiments, or comprising a variant capsid polypeptide encoded by the nucleic acid molecule of any one of embodiments 282-285.

287. The virus particle of embodiment 286, comprising a nucleic acid comprising a payload (e.g., a heterologous transgene) and one or more regulatory elements.

288. A virus particle of any one of embodiments 286-287, wherein said virus particle exhibits increased central nervous system (CNS) biodistribution, e.g., as measured in a mammal, e.g., in mouse or in NHP, e.g., as described herein, relative to wild-type AAV9 (E.g., a virus particle comprising capsid polypeptides of SEQ ID NO: 1 or encoded by SEQ ID NO: 4), optionally wherein the biodistribution is at least 10-times, at least 20-times, at least 32-times, at least 45-times or greater than the biodistribution of a virus particle comprising capsid polypeptides of SEQ ID NO: 1.

289. The virus particle of embodiment 288, wherein the increased CNS biodistribution is exhibited upon systemic, e.g., intravenous, administration of said virus particle.

290. The virus particle of any of embodiments 286-289, wherein the virus particle exhibits higher CNS biodistribution than peripheral nervous system (PNS) biodistribution, optionally wherein the ratio of CNS biodistribution to PNS biodistribution is at least 10, at least 20 or at least 25 or greater, optionally where said CNS biodistribution and PNS biodistribution are as measured after systemic, e.g., intravenous, administration of the virus particle.

291. The virus particle of any of embodiments 286-290, wherein said virus particle exhibits increased transduction in CNS e.g., as measured in a mammal, e.g., in mouse or in NHP, e.g., as described herein, relative to wild-type AAV9 (E.g., a virus particle comprising capsid polypeptides of SEQ ID NO: 1 or encoded by SEQ ID NO: 4), optionally wherein the transduction is at least 10-times, at least 20-times, at least 50-times, at least 60-times, at least 65-times, at least 70-times, or at least 75-times or greater than the transduction of a virus particle comprising capsid polypeptides of SEQ ID NO: 1.

292. The virus particle of any of embodiments 286-291, wherein said virus particle exhibits one or more, e.g., all of:
Decreased liver biodistribution;
Decreased spleen biodistribution;
Decreased muscle biodistribution;
Decreased heart biodistribution;
Decreased liver transduction; or
Decreased heart transduction;
in each case, relative to wild-type AAV9 (e.g., a virus particle comprising capsid polypeptides of SEQ ID NO: 1 or encoded by SEQ ID NO: 4), optionally wherein the transduction or biodistribution is at least 1-times, at least 2-times, at least 3-times, at least 4-times, at least 5-times, or at least 10-times lower than the transduction or biodistribution of a virus particle comprising capsid polypeptides of SEQ ID NO: 1, e.g., as measured in a mammal, e.g., a mouse or NHP.

293. The nucleic acid molecule of any one of embodiments 282-285, wherein the nucleic acid molecule is double-stranded or single-stranded, and wherein the nucleic acid molecule is linear or circular, e.g., wherein the nucleic acid molecule is a plasmid.

294. A method of producing a virus particle comprising a variant capsid polypeptide, said method comprising introducing a nucleic acid molecule of any one of embodiments 282-285 or 293 into a cell (e.g., a HEK293 cell), and harvesting said virus particles therefrom.

295. A method of delivering a payload (e.g., a nucleic acid) to a cell comprising contacting the cell with a virus particle comprising the variant capsid polypeptide of any one of the preceding embodiments and a payload, or contacting the cell with the virus particle of any one of embodiments 286-292.

296. The method of embodiment 295, wherein the cell is a CNS cell.

297. The method of embodiment 296, wherein the CNS cell is a neuronal cell, a glial cell, an astrocyte, an oligodendrocyte, an endothelial cell, or any combination thereof.

298. A method of delivering a payload (e.g., a nucleic acid) to a subject comprising administering to the subject a virusparticle comprising the variant capsid polypeptide of any one of the preceding embodiments and the payload, or administering to the subject the virus particle of any one of embodiments 286-292.

299. The method of embodiment 298, wherein the virus particle delivers the payload to the CNS.

300. The variant capsid polypeptide of any one of the preceding embodiments, the virus particle of any one of embodiments 286-292, or the method of any one of embodiments 294-299, wherein the virus particle (e.g., the virus particle comprising the variant capsid polypeptide) delivers the payload to the CNS with increased biodistribution and/or transduction, e.g., biodistribution as compared to a virus particle comprising capsid polypeptides of SEQ ID NO: 1, optionally wherein the biodistribution is at least 10-times, at least 20-times, at least 32-times, at least 50-times, at least 75-times or greater than the biodistribution and/or transduction of a virus particle comprising capsid polypeptides of SEQ ID NO: 1.

301. The variant capsid polypeptide, virus particle or method of embodiment 300, wherein the one or more cell of the CNS is selected from a neuronal cell, a glial cell, an astrocyte, an oligodendrocyte, an endothelial cell, or any combination thereof.

302. A method of treating a disease or condition in a subject, comprising administering to the subject a virus particle or the composition of embodiment 312 in an amount effective to treat the disease or condition, wherein the virus particle is a particle comprising the variant capsid polypeptide of any one of the preceding embodiments, or comprises a variant capsid polypeptide encoded by the nucleic acid molecule of any one of embodiments 282-285 or 293, or the virus particle of any one of embodiments 286-292.

303. The method of embodiment 302, wherein the disease or condition is a disease or condition of the CNS.

304. The method of embodiment 303, wherein the disease or condition is Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS-Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Angleman syndrome, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Bechet's Disease, Bell's Palsy, Benign Essential Blepharospasm, Benign Focal Amyotrophy, Benign Intracranial Hypertension, Bernhardt- Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors (including, but not limited to those that have metastasized to the brain, for example, metastatic breast cancer), Brain Aneurysm, Brain Injury, Brown-Sequard Syndrome, Bulbar palsy, Bulbospinal Muscular Atrophy, Cerebral Autosomal Dominant Arteriopathy with Subcortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Concentric sclerosis (Baló's sclerosis), Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Chronic progressive external ophtalmoplegia, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia-Multi-Infarct, Dementia-Semantic, Dementia-Subcortical, Dementia With Lewy Bodies, Demyelination diseases, Dentate Cerebellar Ataxia, Dentatorubral Atrophy, Dermatomyositis, Developmental Dyspraxia, Devic's Syndrome, Diabetic Neuropathy, Diffuse Sclerosis, Distal hereditary motor neuronopathies, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalomyelitis, Encephalopathy, Encephalopathy (familial infantile), Encephalotrigeminal Angiomatosis, Epilepsy, Epileptic Hemiplegia, Episodic ataxia, Erb's Palsy, Erb-Duchenne and Dejerine-Klumpke Palsies, Essential Tremor, Extrapontine Myelinolysis, Faber's disease, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Fragile X disease, Friedreich's Ataxia, Frontotemporal Dementia, Gaucher Disease, Generalized Gangliosidoses (GM1, GM2), Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hurler syndrome, Hydranencephaly, Hydrocephalus, Hydrocephalus-Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lichtheim's disease, Lipid Storage Diseases, Lipoid Proteinosis, Lissencephaly, Locked-In Syndrome, Lou Gehrig's Disease, Lupus-Neurological Sequelae, Lyme Disease-Neurological Complications, Lysosomal storage disorders, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Mitochondrial DNA depletion syndromes, Moebius Syndrome, Monomelic Amyotrophy, Morvan Syndrome, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myelitis, Myoclonic Encephalopathy of Infants, Myoclonus, Myoclonus epilepsy, Myopathy, Myopathy-Congenital, Myopathy-Thyrotoxic, Myotonia, Myotonia Congenita, Narcolepsy, NARP (neuropathy, ataxia and retinitis pigmentosa), Neuroacanthocytosis, Neurodegeneration with Brain Iron Accumulation, Neurodegenerative disease, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathic pain, Neuropathy-Hereditary, Neuropathy, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain-Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Peroneal muscular atrophy, Periodic Paralyses, Peripheral Neuropathy, Periventricular Leukomalacia, Persistent Vegetative State, Pervasive Developmental Disorders, Phelan McDermid syndrome, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive bulbar palsy, Progressive Hemifacial Atrophy, Progressive Locomotor Ataxia, Progressive Multifocal Leukoencephalopathy, Progressive Muscular Atrophy, Progressive Sclerosing Poliodystrophy, Progressive Supranuclear Palsy, Prosopagnosia, Pseudobulbar palsy, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Ataxia, Spinocerebellar Atrophy, Spinocerebellar Degeneration, Sporadic ataxia, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Vitamin B12 deficiency, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, or X-Linked Spinal or Bulbar Muscular Atrophy.

305. The method of any of embodiments 302-304, wherein the subject is a mammal, e.g., a human.

306. A cell, cell-free system, or other translation system, comprising the capsid polypeptide, nucleic acid molecule, or virus particle of any one of the preceding embodiments.

307. A method of making a virus (e.g., an adeno-associated dependoparvovirus (AAV) particle), comprising:
providing a cell, cell-free system, or other translation system, comprising the nucleic acid of any of embodiments 282-285 or 293; and
cultivating the cell, cell-free system, or other translation system, under conditions suitable for the production of the virus particle,
thereby making the virus particle.

308. The method of embodiment 307, wherein the cell, cell-free system, or other translation system comprises a second nucleic acid molecule and at least a portion of said second nucleic acid molecule is packaged in the dependoparvovirus particle.

309. The method of embodiment 308, wherein the second nucleic acid comprises a payload, e.g., a heterologous nucleic acid sequence encoding a therapeutic product, e.g., as described herein.

310. The method of any one of embodiments 307-309, wherein the nucleic acid molecule of any of embodiments 282-285 or 293 mediates the production of a virus particle which does not include said nucleic acid of any of embodiments 282-285 or 293 or fragment thereof.

311. The method of any one of embodiments 307-310, wherein the nucleic acid molecule of any of embodiments 282-285 or 293 mediates the production of a virus particle at a level similar, or at least 10% greater than the production level mediated by a nucleic acid comprising SEQ ID NO: 4 in an otherwise similar production system.

312. A composition, e.g., a pharmaceutical composition, comprising a virus particle of any one of embodiments 286-292 or a virus particle produced by the method of any one of embodiments 307-311, and a pharmaceutically acceptable carrier.

313. The variant capsid polypeptide of any of the preceding embodiments, the nucleic acid molecule of any of embodiments 282-285 or 293, the virus particle of any of embodiments 286-292, or the composition of embodiment 312, for use in treating a disease or condition in a subject.

314. The variant capsid polypeptide of any of the preceding embodiments, the nucleic acid molecule of any of embodiments 282-285 or 293, or the virus particle of any of embodiments 286-292, or the composition of embodiment 312, for use in the manufacture of a medicament for use in treating a disease or condition in a subject.

315. A variant capsid polypeptide comprising a polypeptide that has at least 70, 75, 80, 85, 90, 91, 92, 93, 94, 95, 96, 97, 98, 99% or 100% identity to a VP1, VP2, or VP3 sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

316. The variant capsid polypeptide of embodiment 315, wherein the variant capsid polypeptide comprises a mutation that corresponds to a mutation at one or more positions of 579, 592, 593, 595, 596, 598, 601, or any combination thereof, as compared to SEQ ID NO: 1, optionally wherein the mutation comprises an insertion, a deletion, or a substitution.

317. The variant capsid polypeptide of embodiment 315, wherein the variant capsid polypeptide comprises at least 1, at least 2, at least 3, at least 4, at least 5, at least 6, but no more than 7 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution.

318. A variant capsid polypeptide, comprising a polypeptide that comprises:

(a) a valine at a position corresponding to Q579 as compared to SEQ ID NO: 1;

(b) an isoleucine at a position corresponding to Q592 as compared to SEQ ID NO: 1;

(c) a valine at a position corresponding to T593 as compared to SEQ ID NO: 1;

(d) an alanine at a position corresponding to W595 as compared to SEQ ID NO: 1;

(e) a leucine at a position corresponding to V596 as compared to SEQ ID NO: 1;

(f) a serine at a position corresponding to N598 as compared to SEQ ID NO: 1;

(g) an alanine at a position corresponding to I601 as compared to SEQ ID NO: 1; or (h) combinations thereof, optionally wherein the variant capsid polypeptide comprises all of (a)-(g);

optionally wherein the variant capsid polypeptide has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises combinations of (a)-(g), optionally wherein the variant capsid polypeptide comprises all of (a)-(g).

319. A variant capsid polypeptide, comprising a polypeptide that comprises:

(i) a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(ii) a valine at a position corresponding to Q579 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(iii) an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(iv) a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(v) an isoleucine at a position corresponding to Q592 as compared to SEQ ID NO: 1, a valine at a position corresponding to T593 as compared to SEQ ID NO: 1, and a leucine at a position corresponding to V596 as compared to SEQ ID NO: 1;

(vi) a valine at a position corresponding to T593 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(vii) a valine at a position corresponding to Q579 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(viii) a valine at a position corresponding to Q579 as compared to SEQ ID NO: 1; or (ix) a valine at a position corresponding to Q579 as compared to SEQ ID NO: 1, a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

optionally wherein the variant capsid polypeptide has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a mutation set of (i)-(ix).

320. A variant capsid polypeptide, comprising a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises:

(i) a mutation between positions 596 and 601 (numbering according to SEQ ID NO: 1), and wherein the mutation comprises a sequence:

L-n-S-n-n-A, wherein n is any amino acid, optionally wherein n is unmodified as set forth in SEQ ID NO: 1;

(ii) a mutation between positions 593 and 598 (numbering according to SEQ ID NO: 1), and wherein the mutation comprises a sequence:

n/V-n-A-L-n-S, wherein n is any amino acid, optionally wherein n is unmodified as set forth in SEQ ID NO: 1;

optionally wherein the amino acid residue at position 593 is valine;

(iii) a mutation between positions 579 and 601 (numbering according to SEQ ID NO: 1), and wherein the mutation comprises a sequence:

V-(n)11-n/I-n/V-n-n/A-L-n-S-n-n-A, wherein n is any amino acid, optionally wherein n is unmodified as set forth in SEQ ID NO: 1;

optionally wherein the amino acid residue at position 592 is isoleucine;

optionally wherein the amino acid residue at position 593 is valine; and optionally wherein the amino acid residue at position 595 is alanine; or (iv) a mutation between positions 579 and 601 (numbering according to SEQ ID NO: 1), and wherein the mutation comprises a sequence:

n/V-(n)11-n/I-n/V-n-n/A-L-n-S-n-n-A, wherein n is wile type reside as set forth in SEQ ID NO: 1;

optionally wherein the amino acid residue at position 579 is valine;

optionally wherein the amino acid residue at position 592 is isoleucine;

optionally wherein the amino acid residue at position 593 is valine; and optionally wherein the amino acid residue at position 595 is alanine.

321. A variant capsid polypeptide comprising a sequence VVATNHQSAQAQAIVGALQSQGA (SEQ ID NO: 266), or comprising a sequence IVGALQSQGA (SEQ ID NO: 267), or comprising the sequence VGALQS (SEQ ID NO: 268); optionally wherein said sequence is within a region corresponding to amino acids 550-620 according to SEQ ID NO: 1, of said variant capsid polypeptide.

322. The variant capsid polypeptide of embodiment 321, wherein the capsid polypeptide has greater than 95%, greater than 96%, greater than 97%, greater than 98%, or greater than 99% sequence identity to a capsid polypeptide of SEQ ID NO: 1.

323. The variant capsid polypeptide of embodiment 321, wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12.

324. The variant capsid polypeptide of any one of embodiments 321-323, wherein the sequence VVATNHQSAQAQAIVGALQSQGA (SEQ ID NO: 266) is present at a position corresponding to amino acids 579 to 601 according to SEQ ID NO: 1 or wherein the sequence IVGALQSQGA (SEQ ID NO: 267) is present at a position corresponding to amino acids 592 to 601 according to SEQ ID NO: 1, or wherein the sequence VGALQS (SEQ ID NO: 268).

325. A variant capsid polypeptide comprising a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprising the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

326. A variant capsid polypeptide comprising a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprising:
(a) 70% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes fewer than ten single amino acid mutations;
(b) 80% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes ten to nineteen single amino acid mutations; or
(c) 90% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes twenty or more single amino acid mutations.

327. A variant capsid polypeptide comprising, e.g., consisting of, a VP1, a VP2, or a VP3 sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally comprising, e.g., consisting of, SEQ ID NO: 2.

328. A variant capsid polypeptide comprising, e.g., consisting of, the sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

329. A nucleic acid molecule encoding a capsid variant polypeptide of any one of embodiments 315-328.

330. The nucleic acid molecule of embodiment 329, wherein the nucleic acid molecule comprises a sequence of SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265, or a fragment thereof (e.g., a VP1-encoding, a VP2-encoding or a VP3-encoding fragment thereof), or a sequence having at least 70, 75, 80, 85, 90, 91, 92, 93, 94, 95, 96, 97, 98, 99, or 100% sequence identity thereto.

331. The nucleic acid molecule of any one of embodiments 329 or 330, wherein the fragment thereof encodes a VP2 capsid polypeptide or a VP3 capsid polypeptide.

332. The nucleic acid molecule of any one of embodiments 329-331, wherein the nucleic acid molecule comprises a sequence of SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265.

333. A virus particle (e.g., adeno-associated virus ("AAV") particle) comprising a variant capsid polypeptide of any one of embodiments 315-328, or comprising a variant capsid polypeptide encoded by the nucleic acid molecule of any one of embodiments 329-332.

334. The virus particle of embodiment 19, comprising a nucleic acid comprising a payload (e.g., a heterologous transgene) and one or more regulatory elements.

335. A virus particle of any one of embodiments 19-20, wherein said virus particle exhibits increased central nervous system (CNS) biodistribution, e.g., as measured in a mammal, e.g., in mouse or in NHP, e.g., as described herein, relative to a virus particle comprising wild-type AAV9 (e.g., a virus particle comprising capsid polypeptides of SEQ ID NO: 1, or encoded by SEQ ID NO: 4), optionally wherein the biodistribution is at least 10-times, at least 20-times, at least 32-times, at least 45-times, at least 90-times, or greater than the biodistribution of a virus particle comprising wild-type AAV9 capsid polypeptides (e.g., comprising capsid polypeptides of SEQ ID NO: 1, or encoded by SEQ ID NO: 4), as measured by quantification of viral DNA in the target tissue (e.g., as described in Examples 1-2).

336. The virus particle of embodiment 335, wherein the increased CNS biodistribution is exhibited upon systemic, e.g., intravenous, administration of said virus particle.

337. The virus particle of any of embodiments 333-334, wherein the virus particle exhibits higher CNS biodistribution than peripheral nervous system (PNS) biodistribution, optionally wherein the ratio of CNS biodistribution to PNS biodistribution is at least 10, at least 20, at least 25, at least 50, at least 90, or greater, optionally where said CNS biodistribution and PNS biodistribution are as measured after systemic, e.g., intravenous, administration of the virus particle.

338. The virus particle of any of embodiments 333-334, wherein said virus particle exhibits increased transduction in CNS e.g., as measured in a mammal, e.g., in mouse, rat, or in NHP, e.g., as described herein, relative to a virus particle comprising wild-type AAV9 capsid polypeptides (e.g., a virus particle comprising capsid polypeptides of SEQ ID NO: 1 or encoded by SEQ ID NO: 4), optionally wherein the transduction is at least 10-times, at least 25-times, at least 50-times, at least 100-times, at least 150-times, at least 200-times, or at least 220-times or greater than the transduction of a virus particle comprising wild-type AAV9 capsid polypeptides (e.g., a virus particle comprising capsid polypeptides of SEQ ID NO: 1, or encoded by SEQ ID NO: 4), as measured by quantification of viral transcript mRNA present in target tissue (e.g., as described in Examples 1-3).

339. The virus particle of any of embodiments 333-334, wherein said virus particle exhibits one or more, e.g., all of:
(a) decreased liver biodistribution;
(b) decreased spleen biodistribution;
(c) decreased muscle biodistribution;
(d) decreased heart biodistribution;
(e) decreased liver transduction; or
(f) decreased heart transduction,
in each case, relative to a virus particle comprising wild-type AAV9 capsid polypeptides (e.g., a virus particle comprising capsid polypeptides of SEQ ID NO: 1, or encoded by SEQ ID NO: 4), optionally wherein the transduction or biodistribution is at least 1-times, at least 2-times, at least 3-times, at least 4-times, at least 5-times, or at least 10-times lower than the transduction or biodistribution of a virus particle comprising capsid polypeptides of SEQ ID NO: 1, e.g., as measured in a mammal, e.g., a mouse or NHP.

340. The nucleic acid molecule of any one of embodiments 329-332, wherein the nucleic acid molecule is double-stranded or single-stranded, and wherein the nucleic acid molecule is linear or circular, e.g., wherein the nucleic acid molecule is a plasmid.

341. A method of producing a virus particle comprising a variant capsid polypeptide, said method comprising introducing a nucleic acid molecule of any one of embodiments 329-332 or 340 into a cell (e.g., a HEK293 cell), and harvesting said virus particles therefrom.

342. A method of delivering a payload (e.g., a nucleic acid) to a cell comprising contacting the cell with a virus particle comprising the variant capsid polypeptide of any one of embodiments 315-328 and a payload, or contacting the cell with the virus particle of any one of embodiments 333-339.

343. The method of embodiment 342, wherein the cell is a CNS cell.

344. The method of embodiment 343, wherein the CNS cell is a neuronal cell, a glial cell, an astrocyte, an oligodendrocyte, an endothelial cell, or any combination thereof.

345. A method of delivering a payload (e.g., a nucleic acid) to a subject comprising administering to the subject a virus particle comprising the variant capsid polypeptide of any one of embodiments 315-328 and the payload, or administering to the subject the virus particle of any one of embodiments 333-339.

346. The method of embodiment 345, wherein the virus particle delivers the payload to the CNS.

347. The variant capsid polypeptide of any one of embodiments 315-328, the virus particle of any one of embodiments 333-339, or the method of any one of embodiments 341-346, wherein the virus particle (e.g., the virus particle comprising the variant capsid polypeptide) delivers the payload to the CNS with increased biodistribution and/or transduction, e.g., biodistribution as compared to a virus particle comprising capsid polypeptides of SEQ ID NO: 1, optionally wherein the biodistribution is at least 10, at least 20, at least 25, at least 50, at least 90, or greater than the biodistribution and/or transduction of a virus particle comprising capsid polypeptides of SEQ ID NO: 1.

348. The variant capsid polypeptide, virus particle or method of embodiment 347, wherein the one or more cell of the CNS is selected from a neuronal cell, a glial cell, an astrocyte, an oligodendrocyte, an endothelial cell, or any combination thereof.

349. A method of treating a disease or condition in a subject, comprising administering to the subject a virus particle of any one of embodiments 333-339 or 347, or the composition of embodiment 358, in an amount effective to treat the disease or condition.

350. The method of embodiment 349, wherein the disease or condition is a disease or condition of the CNS.

351. The method of embodiment 350, wherein the disease or condition is Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS-Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Angleman syndrome, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Bechet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors (including, but not limited to those that have metastasized to the brain, for example, metastatic breast cancer), Brain Aneurysm, Brain Injury, Brown-Sequard Syndrome, Bulbar palsy, Bulbospinal Muscular Atrophy, Cerebral Autosomal Dominant Arteriopathy with Subcortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Concentric sclerosis (Baló's sclerosis), Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Chronic progressive external ophtalmoplegia, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia-Multi-Infarct, Dementia-Semantic, Dementia-Subcortical, Dementia With Lewy Bodies, Demyelination diseases, Dentate Cerebellar Ataxia, Dentatorubral Atrophy, Dermatomyositis, Developmental Dyspraxia, Devic's Syndrome, Diabetic Neuropathy, Diffuse Sclerosis, Distal hereditary motor neuronopathies, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalomyelitis, Encephalopathy, Encephalopathy (familial infantile), Encephalotrigeminal Angiomatosis, Epilepsy, Epileptic Hemiplegia, Episodic ataxia, Erb's Palsy, Erb-Duchenne and Dejerine-Klumpke Palsies, Essential Tremor, Extrapontine Myelinolysis, Faber's disease, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Fragile X disease, Friedreich's Ataxia, Frontotemporal Dementia, Gaucher Disease, Generalized Gangliosidoses (GM1, GM2), Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hurler syndrome, Hydranencephaly, Hydrocephalus, Hydrocephalus-Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lichtheim's disease, Lipid Storage Diseases, Lipoid Proteinosis, Lissencephaly, Locked-In Syndrome, Lou Gehrig's Disease, Lupus-Neurological Sequelae, Lyme Disease-Neurological Complications, Lysosomal storage disorders, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Mitochondrial DNA depletion syndromes, Moebius Syndrome, Monomelic Amyotrophy, Morvan Syndrome, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myelitis, Myoclonic Encephalopathy of Infants, Myoclonus, Myoclonus epilepsy, Myopathy, Myopathy- Congenital, Myopathy-Thyrotoxic, Myotonia, Myotonia Congenita, Narcolepsy, NARP (neuropathy, ataxia and retinitis pigmentosa), Neuroacanthocytosis, Neurodegeneration with Brain Iron Accumulation, Neurodegenerative disease, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathic pain, Neuropathy-Hereditary, Neuropathy, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain-Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Peroneal muscular atrophy, Periodic Paralyses, Peripheral Neuropathy, Periventricular Leukomalacia, Persistent Vegetative State, Pervasive Developmental Disorders, Phelan McDermid syndrome, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive bulbar palsy, Progressive Hemifacial Atrophy, Progressive Locomotor Ataxia, Progressive Multifocal Leukoencephalopathy, Progressive Muscular Atrophy, Progressive Sclerosing Poliodystrophy, Progressive Supranuclear Palsy, Prosopagnosia, Pseudobulbar palsy, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Ataxia, Spinocerebellar Atrophy, Spinocerebellar Degeneration, Sporadic ataxia, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Vitamin B12 deficiency, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, or X-Linked Spinal or Bulbar Muscular Atrophy.

352. The method of any of embodiments 349-351, wherein the subject is a mammal, e.g., a human.

353. The method of any of embodiments 349-352, wherein the virus particle comprises a nucleic acid molecule encoding a therapeutic product effective to treat the disease or condition of the CNS and a promoter sufficient to drive expression of said therapeutic product.

354. A cell, cell-free system, or other translation system, comprising the capsid polypeptide, nucleic acid molecule, or virus particle of any one of the preceding embodiments.

355. A method of making a virus (e.g., an adeno-associated dependoparvovirus (AAV) particle), comprising:
   providing a cell, cell-free system, or other translation system, comprising the nucleic acid of any of embodiments 329-332 or 340; and
   cultivating the cell, cell-free system, or other translation system, under conditions suitable for the production of the virus particle,
   thereby making the virus particle.

356. The method of embodiment 355, wherein the cell, cell-free system, or other translation system comprises a second nucleic acid molecule comprising a payload, e.g., a heterologous nucleic acid sequence encoding a therapeutic product, e.g., as described herein, and at least a portion of said second nucleic acid molecule is packaged in the dependoparvovirus particle.

357. The method of any one of embodiments 355-356, wherein the nucleic acid molecule of any of embodiments 329-332 or 340 mediates the production of a virus particle which does not include said nucleic acid of any of embodiments 329-332 or 340, or fragment thereof; or wherein the nucleic acid molecule of any of embodiments 329-332 or 340 mediates the production of a virus particle at a level similar, or at least 10% greater than the production level mediated by a nucleic acid comprising SEQ ID NO: 4 in an otherwise similar production system.

358. A composition, e.g., a pharmaceutical composition, comprising a virus particle of any one of embodiments 333-339 or a virus particle produced by the method of any one of embodiments 355-357, and a pharmaceutically acceptable carrier.

359. The variant capsid polypeptide of any of embodiments 315-328, the nucleic acid molecule of any of embodiments 329-332 or 340, the virus particle of any of embodiments 333-339, or the composition of embodiment 358, for use in treating a disease or condition in a subject.

360. The variant capsid polypeptide of any of embodiments 315-328, the nucleic acid molecule of any of embodiments 329-332 or 340, or the virus particle of any of embodiments 333-339, or the composition of embodiment 358, for use in the manufacture of a medicament for use in treating a disease or condition in a subject.

361. A virus particle of any of embodiments 333-339, wherein the virus particle exhibits at least 50-time increased transduction of cells of the CNS in at least two different NHP species, optionally wherein the species are cynomolgus macaque and African green monkey.

362. A virus particle of any of embodiments 333-339, wherein the virus particle transduces Purkinje neurons of the cerebellum, e.g., at a level at least 10-fold or 100-fold greater than a virus particle comprising capsid polypeptides of SEQ ID NO: 1 (e.g., as measured by histology, e.g., according to Example 2).

363. A virus particle of any of embodiments 333-339, wherein the virus particle transduces CA3 Pyramidal neurons of the hippocampus, e.g., at a level at least 10-fold or 100-fold greater than a virus particle comprising capsid polypeptides of SEQ ID NO: 1 (e.g., as measured by histology, e.g., according to Example 2).

364. A composition of matter (e.g., a virus particle) comprising:
  (A) a capsid polypeptide comprising: (i) SEQ ID NO: 2 or 14-139, or (ii) a capsid polypeptide comprising a sequence having seventy percent (70%) or more of the mutation set of said SEQ ID NO: 2 or 14-139 and having an edit distance of 15 or fewer from said SEQ ID NO: 2 or 14-139; and
  (B) a heterologous nucleic acid for treating a disorder described herein.

365. A composition of matter (e.g., a virus particle) comprising:
  (A) a capsid polypeptide comprising: (i) SEQ ID NO: 2, or (ii) a capsid polypeptide comprising a sequence having seventy percent (70%) or more of the mutation set of SEQ ID NO: 2 and having an edit distance of 15 or fewer from SEQ ID NO: 2; and
  (B) a heterologous nucleic acid for treating a disorder described herein.

366. A method of treatment of a disorder described herein, comprising administering the composition of matter (e.g., virus particle) of embodiment 252 or 253 to a subject in need thereof wherein said disorder described herein is treated.

DETAILED DESCRIPTION

The present disclosure is directed, in part, to the variant capsid variants that can be used to generate dependoparvovirus particles. In some embodiments, the particles have increased CNS transduction that can be used to deliver a transgene or molecule of interest to the CNS with higher transduction efficiency in the CNS as compared to a dependoparvovirus particle without the variant capsid polypeptides. Accordingly, provided herein are variant capsid polypeptides, nucleic acid molecules encoding the same, viral particles comprising the variant capsid polypeptides, and methods of using the same.

Definitions

A, An, The: As used herein, the singular forms "a," "an" and "the" include plural referents unless the context clearly dictates otherwise.

About, Approximately: As used herein, the terms "about" and "approximately" shall generally mean an acceptable degree of error for the quantity measured given the nature or precision of the measurements. Exemplary degrees of error are within 15 percent (%), typically, within 10%, and more typically, within 5% of a given value or range of values.

Dependoparvovirus capsid: As used herein, the term "dependoparvovirus capsid" refers to an assembled viral capsid comprising dependoparvovirus polypeptides. In some embodiments, a dependoparvovirus capsid is a functional dependoparvovirus capsid, e.g., is fully folded and/or assembled, is competent to infect a target cell, or remains stable (e.g., folded/assembled and/or competent to infect a target cell) for at least a threshold time.

Dependoparvovirus particle: As used herein, the term "dependoparvovirus particle" refers to an assembled viral capsid comprising dependoparvovirus polypeptides and a packaged nucleic acid, e.g., comprising a payload, one or more components of a dependoparvovirus genome (e.g., a whole dependoparvovirus genome), or both. In some embodiments, a dependoparvovirus particle is a functional dependoparvovirus particle, e.g., comprises a desired payload, is fully folded and/or assembled, is competent to infect a target cell, or remains stable (e.g., folded/assembled and/or competent to infect a target cell) for at least a threshold time.

Dependoparvovirus X particle/capsid: As used herein, the term "dependoparvovirus X particle/capsid" refers to a dependoparvovirus particle/capsid comprising at least one polypeptide or polypeptide encoding nucleic acid sequence derived from a naturally occurring dependoparvovirus X species. For example, a dependoparvovirus B particle refers to a dependoparvovirus particle comprising at least one polypeptide or polypeptide encoding nucleic acid sequence derived from a naturally occurring dependoparvovirus B sequence. Derived from, as used in this context, means having at least 70, 75, 80, 85, 90, 91, 92, 93, 94, 95, 96, 97, 98, 99, or 100% identity to the sequence in question. Correspondingly, an AAVX particle/capsid, as used herein, refers to an AAV particle/caspid comprising at least one polypeptide or polypeptide encoding nucleic acid sequence derived from a naturally occurring AAV X serotype. For example, an AAV9 particle refers to an AAV particle comprising at least one polypeptide or polypeptide encoding nucleic acid sequence derived from a naturally occurring AAV9 sequence.

Exogenous: As used herein, the term "exogenous" refers to a feature, sequence, or component present in a circumstance (e.g., in a nucleic acid, polypeptide, or cell) that does not naturally occur in said circumstance. For example, a nucleic acid sequence comprising an ORF encoding a polypeptide may comprise an exogenous start codon or a new start codon (e.g., translation start codon), such as provided for herein. Use of the term exogenous in this fashion means that an ORF encoding a polypeptide comprising the start codon in question at this position does not occur naturally, e.g., is not present in AAV9, e.g., is not present in SEQ ID NO: 7. In some embodiments, the exogenous start codon may replace an endogenous start codon. In some embodiments, the exogenous start codon may replace a codon that is not recognized as a start codon by the host cell. A person of skill will readily understand that a sequence (e.g., a start codon) may be exogenous when provided in a first ORF (e.g., that does not naturally comprise a start codon at the site in question) but may not be exogenous in a second ORF (e.g., that does naturally comprise that particular start codon at the site in question).

Functional: As used herein in reference to a polypeptide component of a dependoparvovirus capsid (e.g., Cap (e.g., VP1, VP2, and/or VP3) or Rep), the term "functional" refers to a polypeptide which provides at least 50, 60, 70, 80, 90, or 100% of the activity of a naturally occurring version of that polypeptide component (e.g., when present in a host cell). For example, a functional VP1 polypeptide may stably fold and assemble into a dependoparvovirus capsid (e.g., that is competent for packaging and/or secretion). As used herein in reference to a dependoparvovirus capsid or particle, "functional" refers to a capsid or particle comprising one or more of the following production characteristics: comprises a desired payload, is fully folded and/or assembled, is competent to infect a target cell, or remains stable (e.g., folded/assembled and/or competent to infect a target cell) for at least a threshold time.

Nucleic acid: As used herein, in its broadest sense, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid monomer (e.g., a nucleotide and/or nucleoside); in some embodiments, "nucleic acid" refers to an oligonucleotide chain comprising individual nucleic acid monomers or a longer polynucleotide chain comprising many individual nucleic acid monomers. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid is, comprises, or consists of one or more modified, synthetic, or non-naturally occurring nucleotides. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid has a nucleotide sequence that encodes a functional gene product such as an RNA or protein. In some embodiments, a nucleic acid is partly or wholly single stranded; in some embodiments, a nucleic acid is partly or wholly double stranded.

Mutation Set: As used herein, the term "mutation set" refers to the complete set of single amino acid mutations (substitutions, deletions and/or insertions) in a variant capsid polypeptide sequence relative to a reference sequence (e.g., a wild-type reference sequence). In some embodiments, the reference sequence is wild-type AAV9 (SEQ ID NO: 1). In some cases, part of the mutation set (i.e., more than one single amino acid mutation) is notated collectively, however, it will be understood that even when referred to in this way, the mutation set is a collection of single amino acid mutations. For example, an insertion of amino acid 1, 2, and 3 between amino acid N at position nn and amino acid W at position ww of a reference sequence may be notated as "Nnn_3aa_Www_123," and it will be understood that each of amino acids 1, 2 and 3 represent separate single amino acid mutations within the mutation set. The mutation sets for certain variants described herein are found, for example, in the right-most column of Table 1.

Start codon: As used herein, the term "start codon" refers to any codon recognized by a host cell as a site to initiate translation (e.g., a site that mediates detectable translation initiation). Without wishing to be bound by theory, start codons vary in strength, with strong start codons more strongly promoting translation initiation and weak start codons less strongly promoting translation initiation. The canonical start codon is ATG, which encodes the amino acid methionine, but a number of non-canonical start codons are also recognized by host cells.

Variant: As used herein, a "variant" or "variant capsid polypeptide" refers to a polypeptide that differs from a reference sequence (e.g. SEQ ID NO: 1). The variant can, for example, comprise a mutation (e.g. substitution, deletion, or insertion). In some embodiments, the variant is about, or at least, 70%, 75%, 80%, 85%, 86%, 87%, 88%, 89%, 90%, 91%, 92%, 93%, 94%, 95%, 96%, 97%, 98%, or 99% identical to the reference sequence. In some embodiments, the reference sequence is a polypeptide comprising SEQ ID NO: 1. In some embodiments, the variant comprises at least 1, 2, 3, 4, 5, 6, 7, 8, 9, or 10 single amino acid mutations relative to a reference sequence (e.g., SEQ ID NO: 1), and optionally, further comprises no more than 70, 60, 50, 40, 30, 35, 30, 29, 28, 27, 26, 25, 24, 23, 22, 21, or 20 single amino acid mutations relative to said reference sequence (SEQ ID NO: 1).

CNS: as used herein, means one or more regions of the central nervous system. In some embodiments, the CNS includes one or more of: frontal cortex, temporal cortex, motor cortex, hippocampus, basal ganglia, midbrain, brainstem, cerebellum, and spinal cord.

PNS: as used herein, means one or more regions of the peripheral nervous system that does not include the CNS. In some embodiments, the PNS includes dorsal root ganglia. In some embodiments, the PNS includes sensory neurons and motor neurons.

Capsid Polypeptides and Nucleic Acids Encoding the Same

The disclosure is directed, in part, to a variant capsid polypeptide, and to a nucleic acid comprising a sequence encoding the variant capsid polypeptide, wherein the variant capsid polypeptide comprises a mutation (insertion, deletion, or substitution) as compared to the wild-type sequence. In some embodiments, the wild-type sequence is SEQ ID NO: 1. The disclosure is directed, in part, to a variant capsid polypeptide comprising SEQ ID NO: 1 with one or more mutations as compared to SEQ ID NO: 1, and nucleic acid molecules encoding the variant capsid polypeptide. The mutation can be, for example, an insertion, deletion, or substitution as compared to the wild-type sequence. In some embodiments, the wild-type sequence is SEQ ID NO: 1.

In some embodiments, the variant capsid polypeptide comprises a mutation that corresponds to a mutation at position 579, 592, 593, 595, 596, 598, 601, or any combination thereof as compared to SEQ ID NO: 1. In some embodiments, the variant capsid polypeptide comprises a mutation that corresponds to a mutation at position 579 as compared to SEQ ID NO: 1. In some embodiments, the variant capsid polypeptide comprises a mutation that corresponds to a mutation at position 592 as compared to SEQ ID NO: 1. In some embodiments, the variant capsid polypeptide comprises a mutation that corresponds to a mutation at position 593 as compared to SEQ ID NO: 1. In some embodiments, the variant capsid polypeptide comprises a mutation that corresponds to a mutation at position 595 as compared to SEQ ID NO: 1. In some embodiments, the variant capsid polypeptide comprises a mutation that corresponds to a mutation at position 596 as compared to SEQ ID NO: 1. In some embodiments, the variant capsid polypeptide comprises a mutation that corresponds to a mutation at position 598 as compared to SEQ ID NO: 1. In some embodiments, the variant capsid polypeptide comprises a mutation that corresponds to a mutation at position 601 as compared to SEQ ID NO: 1. In some embodiments, the variant capsid polypeptide comprises a mutation that corresponds to a mutation at position 579 and 592 as compared to SEQ ID NO: 1. In some embodiments, the variant capsid polypeptide comprises a mutation that corresponds to a mutation at position 579 and 593 as compared to SEQ ID NO: 1. In some embodiments, the variant capsid polypeptide comprises a mutation that corresponds to a mutation at position 579 and 595 as compared to SEQ ID NO: 1. In some embodiments, the variant capsid polypeptide comprises a mutation that corresponds to a mutation at position 579 and 596 as compared to SEQ ID NO: 1. In some embodiments, the variant capsid polypeptide comprises a mutation that corresponds to a mutation at position 579 and 598 as compared to SEQ ID NO: 1. In some embodiments, the variant capsid polypeptide comprises a mutation that corresponds to a mutation at position 579 and 601 as compared to SEQ ID NO: 1. In some embodiments, the variant capsid polypeptide comprises a mutation that corresponds to a mutation at position 592 and 593 as compared to SEQ ID NO: 1. In some embodiments, the variant capsid polypeptide comprises a mutation that corresponds to a mutation at position 592 and 595 as compared to SEQ ID NO: 1. In some embodiments, the variant capsid polypeptide comprises a mutation that corresponds to a mutation at position 592 and 596 as compared to SEQ ID NO: 1. In some embodiments, the variant capsid polypeptide comprises a mutation that corresponds to a mutation at position 592 and 598 as compared to SEQ ID NO: 1. In some embodiments, the variant capsid polypeptide comprises a mutation that corresponds to a mutation at position 592 and 601 as compared to SEQ ID NO: 1. In some embodiments, the variant capsid polypeptide comprises a mutation that corresponds to a mutation at position 593 and 595 as compared to SEQ ID NO: 1. In some embodiments, the variant capsid polypeptide comprises a mutation that corresponds to a mutation at position 593 and 596 as compared to SEQ ID NO: 1. In some embodiments, the variant capsid polypeptide comprises a mutation that corresponds to a mutation at position 593 and 598 as compared to SEQ ID NO: 1. In some embodiments, the variant capsid polypeptide comprises a mutation that corresponds to a mutation at position 593 and 601 as compared to SEQ ID NO: 1. In some embodiments, the variant capsid polypeptide comprises a mutation that corresponds to a mutation at position 595 and 596 as compared to SEQ ID NO: 1. In some embodiments, the variant capsid polypeptide comprises a mutation that corresponds to a mutation at position 595 and 598 as compared to SEQ ID NO: 1. In some embodiments, the variant capsid polypeptide comprises a mutation that corresponds to a mutation at position 595 and 601 as compared to SEQ ID NO: 1. In some embodiments, the variant capsid polypeptide comprises a mutation that corresponds to a mutation at position 596 and 598 as compared to SEQ ID NO: 1. In some embodiments, the variant capsid polypeptide comprises a mutation that corresponds to a mutation at position 596 and 601 as compared to SEQ ID NO: 1. In some embodiments, the variant capsid polypeptide comprises a mutation that corresponds to a mutation at position 598 and 601 as compared to SEQ ID NO: 1. In some embodiments, the variant capsid polypeptide comprises a mutation that corresponds to a mutation at position 579, 592, and 593 as compared to SEQ ID NO: 1. In some embodiments, the variant capsid polypeptide comprises a mutation that corresponds to a mutation at position 579, 592, and 595 as compared to SEQ ID NO: 1. In some embodiments, the variant capsid polypeptide comprises a mutation that corresponds to a mutation at position 579, 592, and 596 as compared to SEQ ID NO: 1. In some embodiments, the variant capsid polypeptide comprises a mutation that corresponds to a mutation at position 579, 592, and 598 as compared to SEQ ID NO: 1. In some embodiments, the variant capsid polypeptide comprises a mutation that corresponds to a mutation at position 579, 592, and 601 as compared to SEQ ID NO: 1. In some embodiments, the variant capsid polypeptide comprises a mutation that corresponds to a mutation at position 579, 593, and 595 as compared to SEQ ID NO: 1. In some embodiments, the variant capsid polypeptide comprises a mutation that corresponds to a mutation at position 579, 593, and 596 as compared to SEQ ID NO: 1. In some embodiments, the variant capsid polypeptide comprises a mutation that corresponds to a mutation at position 579, 593, and 598 as compared to SEQ ID NO: 1. In some embodiments, the variant capsid polypeptide comprises a mutation that corresponds to a mutation at position 579, 593, and 601 as compared to SEQ ID NO: 1. In some embodiments, the variant capsid polypeptide comprises a mutation that corresponds to a mutation at position 579, 595, and 596 as compared to SEQ ID NO: 1. In some embodiments, the variant capsid polypeptide comprises a mutation that corresponds to a mutation at position 579, 595, and 598 as compared to SEQ ID NO: 1. In some embodiments, the variant capsid polypeptide comprises a mutation that corresponds to a mutation at position 579, 595, and 601 as compared to SEQ ID NO: 1. In some embodiments, the variant capsid polypeptide comprises a mutation that corresponds to a mutation at position 579, 596, and 598 as compared to SEQ ID NO: 1. In some embodiments, the variant capsid polypeptide comprises a mutation that corresponds to a mutation at position 579, 596, and 601 as compared to SEQ ID NO: 1. In some embodiments, the variant capsid polypeptide comprises a mutation that corresponds to a mutation at position 579, 598, and 601 as compared to SEQ ID NO: 1. In some embodiments, the variant capsid polypeptide comprises a mutation that corresponds to a mutation at position 592, 593, and 595 as compared to SEQ ID NO: 1. In some embodiments, the variant capsid polypeptide comprises a mutation that corresponds to a mutation at position 592, 593, and 596 as compared to SEQ ID NO: 1. In some embodiments, the variant capsid polypeptide comprises a mutation that corresponds to a mutation at position 592, 593, and 598 as compared to SEQ ID NO: 1. In some embodiments, the variant capsid polypeptide comprises a mutation that corresponds to a mutation at position 592, 593, and 601 as compared to SEQ ID NO: 1. In some embodiments, the variant capsid polypeptide comprises a mutation that corresponds to a mutation at position 592, 595, and 596 as compared to SEQ ID NO: 1. In some embodiments, the variant capsid polypeptide comprises a mutation that corresponds to a mutation at position 592, 595, and 598 as compared to SEQ ID NO: 1. In some embodiments, the variant capsid polypeptide comprises a mutation that corresponds to a mutation at position 592, 595, and 601 as compared to SEQ ID NO: 1. In some embodiments, the variant capsid polypeptide comprises a mutation that corresponds to a mutation at position 592, 596, and 598 as compared to SEQ ID NO: 1. In some embodiments, the variant capsid polypeptide comprises a mutation that corresponds to a mutation at position 592, 596, and 601 as compared to SEQ ID NO: 1. In some embodiments, the variant capsid polypeptide comprises a mutation that corresponds to a mutation at position 592, 598, and 601 as compared to SEQ ID NO: 1. In some embodiments, the variant capsid polypeptide comprises a mutation that corresponds to a mutation at position 593, 595, and 596 as compared to SEQ ID NO: 1. In some embodiments, the variant capsid polypeptide comprises a mutation that corresponds to a mutation at position 593, 595, and 598 as compared to SEQ ID NO: 1. In some embodiments, the variant capsid polypeptide comprises a mutation that corresponds to a mutation at position 593, 595, and 601 as compared to SEQ ID NO: 1. In some embodiments, the variant capsid polypeptide comprises a mutation that corresponds to a mutation at position 593, 596, and 598 as compared to SEQ ID NO: 1. In some embodiments, the variant capsid polypeptide comprises a mutation that corresponds to a mutation at position 593, 596, and 601 as compared to SEQ ID NO: 1. In some embodiments, the variant capsid polypeptide comprises a mutation that corresponds to a mutation at position 593, 598, and 601 as compared to SEQ ID NO: 1. In some embodiments, the variant capsid polypeptide comprises a mutation that corresponds to a mutation at position 595, 596, and 598 as compared to SEQ ID NO: 1. In some embodiments, the variant capsid polypeptide comprises a mutation that corresponds to a mutation at position 595, 596, and 601 as compared to SEQ ID NO: 1. In some embodiments, the variant capsid polypeptide comprises a mutation that corresponds to a mutation at position 595, 598, and 601 as compared to SEQ ID NO: 1. In some embodiments, the variant capsid polypeptide comprises a mutation that corresponds to a mutation at position 596, 598, and 601 as compared to SEQ ID NO: 1. In some embodiments, the variant capsid polypeptide comprises a mutation that corresponds to a mutation at position 579, 592, 593, and 595 as compared to SEQ ID NO: 1. In some embodiments, the variant capsid polypeptide comprises a mutation that corresponds to a mutation at position 579, 592, 593, and 596 as compared to SEQ ID NO: 1. In some embodiments, the variant capsid polypeptide comprises a mutation that corresponds to a mutation at position 579, 592, 593, and 598 as compared to SEQ ID NO: 1. In some embodiments, the variant capsid polypeptide comprises a mutation that corresponds to a mutation at position 579, 592, 593, and 601 as compared to SEQ ID NO: 1. In some embodiments, the variant capsid polypeptide comprises a mutation that corresponds to a mutation at position 579, 592, 596, and 598 as compared to SEQ ID NO: 1. In some embodiments, the variant capsid polypeptide comprises a mutation that corresponds to a mutation at position 579, 592, 596, and 601 as compared to SEQ ID NO: 1. In some embodiments, the variant capsid polypeptide comprises a mutation that corresponds to a mutation at position 579, 592, 598, and 601 as compared to SEQ ID NO: 1. In some embodiments, the variant capsid polypeptide comprises a mutation that corresponds to a mutation at position 579, 593, 595, and 596 as compared to SEQ ID NO: 1. In some embodiments, the variant capsid polypeptide comprises a mutation that corresponds to a mutation at position 579, 593, 595, and 598 as compared to SEQ ID NO: 1. In some embodiments, the variant capsid polypeptide comprises a mutation that corresponds to a mutation at position 579, 593, 595, and 601 as compared to SEQ ID NO: 1. In some embodiments, the variant capsid polypeptide comprises a mutation that corresponds to a mutation at position 579, 593, 596, and 598 as compared to SEQ ID NO: 1. In some embodiments, the variant capsid polypeptide comprises a mutation that corresponds to a mutation at position 579, 593, 596, and 601 as compared to SEQ ID NO: 1. In some embodiments, the variant capsid polypeptide comprises a mutation that corresponds to a mutation at position 579, 593, 598, and 601 as compared to SEQ ID NO: 1. In some embodiments, the variant capsid polypeptide comprises a mutation that corresponds to a mutation at position 579, 592, 595, and 596 as compared to SEQ ID NO: 1. In some embodiments, the variant capsid polypeptide comprises a mutation that corresponds to a mutation at position 579, 592, 595, and 598 as compared to SEQ ID NO: 1. In some embodiments, the variant capsid polypeptide comprises a mutation that corresponds to a mutation at position 579, 592, 595, and 601 as compared to SEQ ID NO: 1. In some embodiments, the variant capsid polypeptide comprises a mutation that corresponds to a mutation at position 579, 592, 593, and 596 as compared to SEQ ID NO: 1. In some embodiments, the variant capsid polypeptide comprises a mutation that corresponds to a mutation at position 579, 592, 593, and 598 as compared to SEQ ID NO: 1. In some embodiments, the variant capsid polypeptide comprises a mutation that corresponds to a mutation at position 579, 592, 593, and 601 as compared to SEQ ID NO: 1. In some embodiments, the variant capsid polypeptide comprises a mutation that corresponds to a mutation at position 579, 595, 596, and 598 as compared to SEQ ID NO: 1. In some embodiments, the variant capsid polypeptide comprises a mutation that corresponds to a mutation at position 579, 595, 596, and 601 as compared to SEQ ID NO: 1. In some embodiments, the variant capsid polypeptide comprises a mutation that corresponds to a mutation at position 579, 595, 598, and 601 as compared to SEQ ID NO: 1. In some embodiments, the variant capsid polypeptide comprises a mutation that corresponds to a mutation at position 579, 596, 598, and 598 as compared to SEQ ID NO: 1. In some embodiments, the variant capsid polypeptide comprises a mutation that corresponds to a mutation at position 592, 593, 595, and 596 as compared to SEQ ID NO: 1. In some embodiments, the variant capsid polypeptide comprises a mutation that corresponds to a mutation at position 592, 593, 595, and 598 as compared to SEQ ID NO: 1. In some embodiments, the variant capsid polypeptide comprises a mutation that corresponds to a mutation at position 592, 593, 595, and 601 as compared to SEQ ID NO: 1. In some embodiments, the variant capsid polypeptide comprises a mutation that corresponds to a mutation at position 592, 593, 596, and 598 as compared to SEQ ID NO: 1. In some embodiments, the variant capsid polypeptide comprises a mutation that corresponds to a mutation at position 592, 593, 596, and 601 as compared to SEQ ID NO: 1. In some embodiments, the variant capsid polypeptide comprises a mutation that corresponds to a mutation at position 592, 593, 598, and 601 as compared to SEQ ID NO: 1. In some embodiments, the variant capsid polypeptide comprises a mutation that corresponds to a mutation at position 592, 595, 596, and 598 as compared to SEQ ID NO: 1. In some embodiments, the variant capsid polypeptide comprises a mutation that corresponds to a mutation at position 592, 595, 596, and 601 as compared to SEQ ID NO: 1. In some embodiments, the variant capsid polypeptide comprises a mutation that corresponds to a mutation at position 592, 595, 598, and 601 as compared to SEQ ID NO: 1. In some embodiments, the variant capsid polypeptide comprises a mutation that corresponds to a mutation at position 592, 596, 598, and 601 as compared to SEQ ID NO: 1. In some embodiments, the variant capsid polypeptide comprises a mutation that corresponds to a mutation at position 593, 595, 596, and 598 as compared to SEQ ID NO: 1. In some embodiments, the variant capsid polypeptide comprises a mutation that corresponds to a mutation at position 593, 595, 596, and 601 as compared to SEQ ID NO: 1. In some embodiments, the variant capsid polypeptide comprises a mutation that corresponds to a mutation at position 593, 595, 598, and 601 as compared to SEQ ID NO: 1. In some embodiments, the variant capsid polypeptide comprises a mutation that corresponds to a mutation at position 593, 596, 598, and 601 as compared to SEQ ID NO: 1. In some embodiments, the variant capsid polypeptide comprises a mutation that corresponds to a mutation at position 595, 596, 598, and 601 as compared to SEQ ID NO: 1. In some embodiments, the variant capsid polypeptide comprises a mutation that corresponds to a mutation at position 579, 592, 593, 595, and 596 as compared to SEQ ID NO: 1. In some embodiments, the variant capsid polypeptide comprises a mutation that corresponds to a mutation at position 579, 592, 593, 595, and 598 as compared to SEQ ID NO: 1. In some embodiments, the variant capsid polypeptide comprises a mutation that corresponds to a mutation at position 579, 592, 593, 595, and 601 as compared to SEQ ID NO: 1. In some embodiments, the variant capsid polypeptide comprises a mutation that corresponds to a mutation at position 579, 593, 595, 596 and 598 as compared to SEQ ID NO: 1. In some embodiments, the variant capsid polypeptide comprises a mutation that corresponds to a mutation at position 579, 593, 595, 596 and 601 as compared to SEQ ID NO: 1. In some embodiments, the variant capsid polypeptide comprises a mutation that corresponds to a mutation at position 579, 593, 595, 598 and 601 as compared to SEQ ID NO: 1. In some embodiments, the variant capsid polypeptide comprises a mutation that corresponds to a mutation at position 579, 593, 596, 598 and 601 as compared to SEQ ID NO: 1. In some embodiments, the variant capsid polypeptide comprises a mutation that corresponds to a mutation at position 579, 595, 596, 598 and 601 as compared to SEQ ID NO: 1. In some embodiments, the variant capsid polypeptide comprises a mutation that corresponds to a mutation at position 579, 592, 595, 596 and 598 as compared to SEQ ID NO: 1. In some embodiments, the variant capsid polypeptide comprises a mutation that corresponds to a mutation at position 579, 592, 595, 596 and 601 as compared to SEQ ID NO: 1. In some embodiments, the variant capsid polypeptide comprises a mutation that corresponds to a mutation at position 579, 592, 595, 598 and 601 as compared to SEQ ID NO: 1. In some embodiments, the variant capsid polypeptide comprises a mutation that corresponds to a mutation at position 579, 592, 596, 598 and 601 as compared to SEQ ID NO: 1. In some embodiments, the variant capsid polypeptide comprises a mutation that corresponds to a mutation at position 579, 595, 596, 598 and 601 as compared to SEQ ID NO: 1. In some embodiments, the variant capsid polypeptide comprises a mutation that corresponds to a mutation at position 579, 592, 593, 596 and 598 as compared to SEQ ID NO: 1. In some embodiments, the variant capsid polypeptide comprises a mutation that corresponds to a mutation at position 579, 592, 593, 596 and 601 as compared to SEQ ID NO: 1. In some embodiments, the variant capsid polypeptide comprises a mutation that corresponds to a mutation at position 579, 592, 593, 598 and 601 as compared to SEQ ID NO: 1. In some embodiments, the variant capsid polypeptide comprises a mutation that corresponds to a mutation at position 579, 592, 593, 595 and 598 as compared to SEQ ID NO: 1. In some embodiments, the variant capsid polypeptide comprises a mutation that corresponds to a mutation at position 579, 592, 593, 595 and 601 as compared to SEQ ID NO: 1. In some embodiments, the variant capsid polypeptide comprises a mutation that corresponds to a mutation at position 592, 593, 595, 596 and 598 as compared to SEQ ID NO: 1. In some embodiments, the variant capsid polypeptide comprises a mutation that corresponds to a mutation at position 592, 593, 595, 596 and 601 as compared to SEQ ID NO: 1. In some embodiments, the variant capsid polypeptide comprises a mutation that corresponds to a mutation at position 592, 593, 595, 598 and 601 as compared to SEQ ID NO: 1. In some embodiments, the variant capsid polypeptide comprises a mutation that corresponds to a mutation at position 592, 593, 596, 598 and 601 as compared to SEQ ID NO: 1. In some embodiments, the variant capsid polypeptide comprises a mutation that corresponds to a mutation at position 592, 595, 596, 598 and 601 as compared to SEQ ID NO: 1. In some embodiments, the variant capsid polypeptide comprises a mutation that corresponds to a mutation at position 593, 595, 596, 598 and 601 as compared to SEQ ID NO: 1. In some embodiments, the variant capsid polypeptide comprises a mutation that corresponds to a mutation at position 579, 592, 593, 595, 596, and 598 as compared to SEQ ID NO: 1. In some embodiments, the variant capsid polypeptide comprises a mutation that corresponds to a mutation at position 579, 592, 593, 595, 596, and 601 as compared to SEQ ID NO: 1. In some embodiments, the variant capsid polypeptide comprises a mutation that corresponds to a mutation at position 592, 593, 595, 596, 598 and 601 as compared to SEQ ID NO: 1. In some embodiments, the variant capsid polypeptide comprises a mutation that corresponds to a mutation at position 579, 593, 595, 596, 598 and 601 as compared to SEQ ID NO: 1. In some embodiments, the variant capsid polypeptide comprises a mutation that corresponds to a mutation at position 579, 592, 595, 596, 598 and 601 as compared to SEQ ID NO: 1. In some embodiments, the variant capsid polypeptide comprises a mutation that corresponds to a mutation at position 579, 592, 593, 596, 598 and 601 as compared to SEQ ID NO: 1. In some embodiments, the variant capsid polypeptide comprises a mutation that corresponds to a mutation at position 579, 592, 593, 595, 598 and 601 as compared to SEQ ID NO: 1. In some embodiments, the variant capsid polypeptide comprises a mutation that corresponds to a mutation at position 579, 592, 593, 595, 596, 598 and 601 as compared to SEQ ID NO: 1.

In some embodiments, the variant capsid polypeptide comprises at least 1, at least 2, at least 3, at least 4, at least 5, at least 6, but no more than 7 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 1 mutation that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 2 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 3 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 4 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 5 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises at least 6 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises 7 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises 7 or fewer mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution. In some embodiments, the variant capsid polypeptide comprises no more than 7 mutations that correspond to a mutation at one or more positions of 579, 592, 593, 595, 596, 598, 601, or any combination thereof, as compared to SEQ ID NO: 1, optionally wherein the mutation comprises an insertion, a deletion, or a substitution.

In some embodiments, the mutation that corresponds to position 529 is a substitution as compared to SEQ ID NO: 1. In some embodiments, the substitution is a naturally occurring amino acid. In some embodiments, the substitution is a valine. In some embodiments, the substitution at position 529 of SEQ ID NO: 1 is E529V. In some embodiments the substitution at a position corresponding to E529 of SEQ ID NO: 1 is a substitution of valine at the position corresponding to E529 of SEQ ID NO: 1 in a reference capsid sequence other than SEQ ID NO: 1, e.g., as described herein.

In some embodiments, the mutation that corresponds to position 530 is a substitution as compared to SEQ ID NO: 1. In some embodiments, the substitution is a naturally occurring amino acid. In some embodiments, the substitution is an alanine. In some embodiments, the substitution at position 530 is G530A according to SEQ ID NO: 1. In some embodiments the substitution at a position corresponding to G530 of SEQ ID NO: 1 is a substitution of alanine at the position corresponding to G530 of SEQ ID NO: 1 in a reference capsid sequence other than SEQ ID NO: 1, e.g., as described herein.

In some embodiments, the mutation that corresponds to position 579 is a substitution as compared to SEQ ID NO: 1. In some embodiments, the substitution is a naturally occurring amino acid. In some embodiments, the substitution is a valine. In some embodiments, the substitution at position 579 is Q579V according to SEQ ID NO: 1. In some embodiments the substitution at a position corresponding to Q579 of SEQ ID NO: 1 is a substitution of valine at the position corresponding to Q579 of SEQ ID NO: 1 in a reference capsid sequence other than SEQ ID NO: 1, e.g., as described herein.

In some embodiments, the mutation that corresponds to position 592 is a substitution as compared to SEQ ID NO: 1. In some embodiments, the substitution is a naturally occurring amino acid. In some embodiments, the substitution is an isoleucine. In some embodiments, the substitution at position 592 is Q592I according to SEQ ID NO: 1. In some embodiments the substitution at a position corresponding to Q592 of SEQ ID NO: 1 is a substitution of valine at the position corresponding to Q592 of SEQ ID NO: 1 in a reference capsid sequence other than SEQ ID NO: 1, e.g., as described herein.

In some embodiments, the mutation that corresponds to position 593 is a substitution as compared to SEQ ID NO: 1. In some embodiments, the substitution is a naturally occurring amino acid. In some embodiments, the substitution is a valine. In some embodiments, the substitution at position 593 is T593V according to SEQ ID NO: 1. In some embodiments the substitution at a position corresponding to T593 of SEQ ID NO: 1 is a substitution of valine at the position corresponding to T593 of SEQ ID NO: 1 in a reference capsid sequence other than SEQ ID NO: 1, e.g., as described herein.

In some embodiments, the mutation that corresponds to position 595 is a substitution as compared to SEQ ID NO: 1. In some embodiments, the substitution is a naturally occurring amino acid. In some embodiments, the substitution is an alanine. In some embodiments, the substitution at position 595 is W595A according to SEQ ID NO: 1. In some embodiments the substitution at a position corresponding to W595 of SEQ ID NO: 1 is a substitution of valine at the position corresponding to W595 of SEQ ID NO: 1 in a reference capsid sequence other than SEQ ID NO: 1, e.g., as described herein.

In some embodiments, the mutation that corresponds to position 596 is a substitution as compared to SEQ ID NO: 1. In some embodiments, the substitution is a naturally occurring amino acid. In some embodiments, the substitution is a leucine. In some embodiments, the substitution at position 596 is V596L according to SEQ ID NO: 1. In some embodiments the substitution at a position corresponding to V596 of SEQ ID NO: 1 is a substitution of valine at the position corresponding to V596 of SEQ ID NO: 1 in a reference capsid sequence other than SEQ ID NO: 1, e.g., as described herein.

In some embodiments, the mutation that corresponds to position 598 is a substitution as compared to SEQ ID NO: 1. In some embodiments, the substitution is a naturally occurring amino acid. In some embodiments, the substitution is a serine. In some embodiments, the substitution at position 598 is N598S according to SEQ ID NO: 1. In some embodiments the substitution at a position corresponding to N598 of SEQ ID NO: 1 is a substitution of valine at the position corresponding to N598 of SEQ ID NO: 1 in a reference capsid sequence other than SEQ ID NO: 1, e.g., as described herein.

In some embodiments, the mutation that corresponds to position 601 is a substitution as compared to SEQ ID NO: 1. In some embodiments, the substitution is a naturally occurring amino acid. In some embodiments, the substitution is an alanine. In some embodiments, the substitution at position 601 is I601A according to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises: (a) a valine at a position corresponding to Q579 as compared to SEQ ID NO: 1; (b) an isoleucine at a position corresponding to Q592 as compared to SEQ ID NO: 1; (c) a valine at a position corresponding to T593 as compared to SEQ ID NO: 1; (d) an alanine at a position corresponding to W595 as compared to SEQ ID NO: 1; (e) a leucine at a position corresponding to V596 as compared to SEQ ID NO: 1; (f) a serine at a position corresponding to N598 as compared to SEQ ID NO:

1; (g) an alanine at a position corresponding to I601 as compared to SEQ ID NO: 1; or (h) combinations thereof, optionally wherein the variant capsid polypeptide comprises all of (a)-(g).

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises:
 (i) a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(ii) a valine at a position corresponding to Q579 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(iii) an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(iv) a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(v) an isoleucine at a position corresponding to Q592 as compared to SEQ ID NO: 1, a valine at a position corresponding to T593 as compared to SEQ ID NO: 1, and a leucine at a position corresponding to V596 as compared to SEQ ID NO: 1;

(vi) a valine at a position corresponding to T593 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1;

(vii) a valine at a position corresponding to Q579 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1;

(viii) a valine at a position corresponding to Q579 as compared to SEQ ID NO: 1; or (ix) a valine at a position corresponding to Q579 as compared to SEQ ID NO: 1, a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to Q579 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises an isoleucine at a position corresponding to Q592 as compared to SEQ ID NO: 1, a valine at a position corresponding to T593 as compared to SEQ ID NO: 1, and a leucine at a position corresponding to V596 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to T593 as compared to SEQ ID NO: 1, a leucine at a position corresponding to V596 as compared to SEQ ID NO: 1, a serine at a position corresponding to N598 as compared to SEQ ID NO: 1, and an alanine at a position corresponding to I601 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to Q579 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to Q579 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 1, provided that the variant capsid polypeptide comprises a valine at a position corresponding to Q579 as compared to SEQ ID NO: 1, a valine at a position corresponding to T593 as compared to SEQ ID NO: 1, an alanine at a position corresponding to W595 as compared to SEQ ID NO: 1, a leucine at a position corresponding to V596 as compared to SEQ ID NO: 1, and a serine at a position corresponding to N598 as compared to SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises:

(i) a mutation between positions 596 and 601, and wherein the mutation comprises a sequence:
L-n-S-n-n-A,
wherein n is any amino acid, optionally wherein n is unmodified as set forth in SEQ ID NO: 1;

(ii) a mutation between positions 593 and 598, and wherein the mutation comprises a sequence:
n/V-n-A-L-n-S,
wherein n is any amino acid, optionally wherein n is unmodified as set forth in SEQ ID NO: 1;
optionally wherein the amino acid residue at position 593 is valine;

(iii) a mutation between positions 579 and 601, and wherein the mutation comprises a sequence:
V-(n)11-n/I-n/V-n-n/A-L-n-S-n-n-A,
wherein n is any amino acid, optionally wherein n is unmodified as set forth in SEQ ID NO: 1;
optionally wherein the amino acid residue at position 592 is isoleucine;
optionally wherein the amino acid residue at position 593 is valine; and
optionally wherein the amino acid residue at position 595 is alanine; or (iv) a mutation between positions 579 and 601, and wherein the mutation comprises a sequence:
n/V-(n)11-n/I-n/V-n-n/A-L-n-S-n-n-A,
wherein n is wile type reside as set forth in SEQ ID NO: 1;
optionally wherein the amino acid residue at position 579 is valine;
optionally wherein the amino acid residue at position 592 is isoleucine;
optionally wherein the amino acid residue at position 593 is valine; and
optionally wherein the amino acid residue at position 595 is alanine.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 596 and 601, and wherein the mutation comprises a sequence:
L-n-S-n-n-A,
wherein n is any amino acid, optionally wherein n is unmodified as set forth in SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 593 and 598, and wherein the mutation comprises a sequence:
n/V-n-A-L-n-S,
wherein n is any amino acid, optionally wherein n is unmodified as set forth in SEQ ID NO: 1; optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 593 and 598, and wherein the mutation comprises a sequence:
V-n-A-L-n-S,
wherein n is any amino acid, optionally wherein n is unmodified as set forth in SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:
V-(n)11-n/I-n/V-n-n/A-L-n-S-n-n-A,
wherein n is any amino acid, optionally wherein n is unmodified as set forth in SEQ ID NO: 1; optionally wherein the amino acid residue at position 592 is isoleucine; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:
V-(n)11-I-n/V-n-n/A-L-n-S-n-n-A,
wherein n is any amino acid, optionally wherein n is unmodified as set forth in SEQ ID NO: 1; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:
V-(n)11-n/I-V-n-n/A-L-n-S-n-n-A,
wherein n is any amino acid, optionally wherein n is unmodified as set forth in SEQ ID NO: 1; optionally wherein the amino acid residue at position 592 is isoleucine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:
V-(n)11-n/I-n/V-n-A-L-n-S-n-n-A,
wherein n is any amino acid, optionally wherein n is unmodified as set forth in SEQ ID NO: 1; optionally wherein the amino acid residue at position 592 is isoleucine; and optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-V-n-n/A-L-n-S-n-n-A, wherein n is any amino acid, optionally wherein n is unmodified as set forth in SEQ ID NO: 1; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-n/V-n-A-L-n-S-n-n-A, wherein n is any amino acid, optionally wherein n is unmodified as set forth in SEQ ID NO: 1; and optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-n/I-V-n-A-L-n-S-n-n-A, wherein n is any amino acid, optionally wherein n is unmodified as set forth in SEQ ID NO: 1; and optionally wherein the amino acid residue at position 592 is isoleucine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-V-n-A-L-n-S-n-n-A, wherein n is any amino acid, optionally wherein n is unmodified as set forth in SEQ ID NO: 1.

In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-n/I-n/V-n-n/A-L-n-S-n-n-A, wherein n is wile type reside as set forth in SEQ ID NO: 1; optionally wherein the amino acid residue at position 579 is valine; optionally wherein the amino acid residue at position 592 is isoleucine; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-n/I-n/V-n-n/A-L-n-S-n-n-A, wherein n is wile type reside as set forth in SEQ ID NO: 1; optionally wherein the amino acid residue at position 592 is isoleucine; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-I-n/V-n-n/A-L-n-S-n-n-A, wherein n is wile type reside as set forth in SEQ ID NO: 1; optionally wherein the amino acid residue at position 579 is valine; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-n/I-V-n-n/A-L-n-S-n-n-A, wherein n is wile type reside as set forth in SEQ ID NO: 1; optionally wherein the amino acid residue at position 579 is valine; optionally wherein the amino acid residue at position 592 is isoleucine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-n/I-n/V-n-A-L-n-S-n-n-A, wherein n is wile type reside as set forth in SEQ ID NO: 1; optionally wherein the amino acid residue at position 579 is valine; optionally wherein the amino acid residue at position 592 is isoleucine; and optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-n/V-n-n/A-L-n-S-n-n-A, wherein n is wile type reside as set forth in SEQ ID NO: 1; optionally wherein the amino acid residue at position 593 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-n/I-V-n-n/A-L-n-S-n-n-A, wherein n is wile type reside as set forth in SEQ ID NO: 1; optionally wherein the amino acid residue at position 592 is isoleucine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-n/I-n/V-n-A-L-n-S-n-n-A, wherein n is wile type reside as set forth in SEQ ID NO: 1; optionally wherein the amino acid residue at position 592 is isoleucine; and optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-I-V-n-n/A-L-n-S-n-n-A, wherein n is wile type reside as set forth in SEQ ID NO: 1; optionally wherein the amino acid residue at position 579 is valine; and optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-I-n/V-n-A-L-n-S-n-n-A, wherein n is wile type reside as set forth in SEQ ID NO: 1; optionally wherein the amino acid residue at position 579 is valine; and optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-n/I-V-n-A-L-n-S-n-n-A, wherein n is wile type reside as set forth in SEQ ID NO: 1; optionally wherein the amino acid residue at position 579 is valine; and optionally wherein the amino acid residue at position 592 is isoleucine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-V-n-n/A-L-n-S-n-n-A, wherein n is wile type reside as set forth in SEQ ID NO: 1; optionally wherein the amino acid residue at position 595 is alanine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-I-n/V-n-A-L-n-S-n-n-A, wherein n is wile type reside as set forth in SEQ ID NO: 1; optionally wherein the amino acid residue at position 593 is valine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

V-(n)11-n/I-V-n-A-L-n-S-n-n-A, wherein n is wile type reside as set forth in SEQ ID NO: 1; optionally wherein the amino acid residue at position 592 is isoleucine. In some embodiments, a variant capsid polypeptide comprises a polypeptide that has at least 70, 75, 80, 85, 90, 91, 92, 93, 94, 95, 96, 97, 98, or 99% identity to a VP1, VP2, or VP3 sequence of SEQ ID NO: 2, provided that the variant capsid polypeptide comprises a mutation between positions 579 and 601, and wherein the mutation comprises a sequence:

n/V-(n)11-I-V-n-A-L-n-S-n-n-A, wherein n is wile type reside as set forth in SEQ ID NO: 1; optionally wherein the amino acid residue at position 579 is valine.

In some embodiments, the variant capsid polypeptide comprises a mutation that corresponds to a Q579V mutation as compared to SEQ ID NO: 1. In some embodiments, the variant capsid polypeptide comprises a mutation that corresponds to a Q592I mutation as compared to SEQ ID NO: 1. In some embodiments, the variant capsid polypeptide comprises a mutation that corresponds to a T593V mutation as compared to SEQ ID NO: 1. In some embodiments, the variant capsid polypeptide comprises a mutation that corresponds to a W595A mutation as compared to SEQ ID NO: 1. In some embodiments, the variant capsid polypeptide comprises a mutation that corresponds to a V596L mutation as compared to SEQ ID NO: 1. In some embodiments, the variant capsid polypeptide comprises a mutation that corresponds to a N598S mutation as compared to SEQ ID NO: 1. In some embodiments, the variant capsid polypeptide comprises a mutation that corresponds to a I601A mutation as compared to SEQ ID NO: 1. In some embodiments, the variant capsid polypeptide comprises a mutation that corresponds to mutations of Q579V and Q592I as compared to SEQ ID NO: 1. In some embodiments, the variant capsid polypeptide comprises a mutation that corresponds to mutations of Q579V and T593V as compared to SEQ ID NO: 1. In some embodiments, the variant capsid polypeptide comprises a mutation that corresponds to mutations of Q579V and W595A as compared to SEQ ID NO: 1. In some embodiments, the variant capsid polypeptide comprises a mutation that corresponds to mutations of Q579V and V596L as compared to SEQ ID NO: 1. In some embodiments, the variant capsid polypeptide comprises a mutation that corresponds to mutations of Q579V and N598S as compared to SEQ ID NO: 1. In some embodiments, the variant capsid polypeptide comprises a mutation that corresponds to mutations of Q579V and I601A as compared to SEQ ID NO: 1. In some embodiments, the variant capsid polypeptide comprises a mutation that corresponds to mutations of Q592I and T593V as compared to SEQ ID NO: 1. In some embodiments, the variant capsid polypeptide comprises a mutation that corresponds to mutations of Q592I and W595A as compared to SEQ ID NO: 1. In some embodiments, the variant capsid polypeptide comprises a mutation that corresponds to mutations of Q592I and V596L as compared to SEQ ID NO: 1. In some embodiments, the variant capsid polypeptide comprises a mutation that corresponds to mutations of Q592I and N598S as compared to SEQ ID NO: 1. In some embodiments, the variant capsid polypeptide comprises a mutation that corresponds to mutations of Q592I and I601A as compared to SEQ ID NO: 1. In some embodiments, the variant capsid polypeptide comprises a mutation that corresponds to mutations of T593V and W595A as compared to SEQ ID NO: 1. In some embodiments, the variant capsid polypeptide comprises a mutation that corresponds to mutations of T593V and V596L as compared to SEQ ID NO: 1. In some embodiments, the variant capsid polypeptide comprises a mutation that corresponds to mutations of T593V and N598S as compared to SEQ ID NO: 1. In some embodiments, the variant capsid polypeptide comprises a mutation that corresponds to mutations of T593V and I601A as compared to SEQ ID NO: 1. In some embodiments, the variant capsid polypeptide comprises a mutation that corresponds to mutations of W595A and V596L as compared to SEQ ID NO: 1. In some embodiments, the variant capsid polypeptide comprises a mutation that corresponds to mutations of W595A and N598S as compared to SEQ ID NO: 1. In some embodiments, the variant capsid polypeptide comprises a mutation that corresponds to mutations of W595A and I601A as compared to SEQ ID NO: 1. In some embodiments, the variant capsid polypeptide comprises a mutation that corresponds to mutations of V596L and N598S as compared to SEQ ID NO: 1. In some embodiments, the variant capsid polypeptide comprises a mutation that corresponds to mutations of V596L and I601A as compared to SEQ ID NO: 1. In some embodiments, the variant capsid polypeptide comprises a mutation that corresponds to mutations of N598S and I601A as compared to SEQ ID NO: 1. In some embodiments, the variant capsid polypeptide comprises a mutation that corresponds to mutations of Q579V, Q592I, and T593V as compared to SEQ ID NO: 1. In some embodiments, the variant capsid polypeptide comprises a mutation that corresponds to mutations of Q579V, Q592I, and W595A as compared to SEQ ID NO: 1. In some embodiments, the variant capsid polypeptide comprises a mutation that corresponds to mutations of Q579V, Q592I, and V596L as compared to SEQ ID NO: 1. In some embodiments, the variant capsid polypeptide comprises a mutation that corresponds to mutations of Q579V, Q592I, and N598S as compared to SEQ ID NO: 1. In some embodiments, the variant capsid polypeptide comprises a mutation that corresponds to mutations of Q579V, Q592I, and I601A as compared to SEQ ID NO: 1. In some embodiments, the variant capsid polypeptide comprises a mutation that corresponds to mutations of Q579V, T593V, and W595A as compared to SEQ ID NO: 1. In some embodiments, the variant capsid polypeptide comprises a mutation that corresponds to mutations of Q579V, T593V, and V596L as compared to SEQ ID NO: 1. In some embodiments, the variant capsid polypeptide comprises a mutation that corresponds to mutations of Q579V, T593V, and N598S as compared to SEQ ID NO: 1. In some embodiments, the variant capsid polypeptide comprises a mutation that corresponds to mutations of Q579V, T593V, and I601A as compared to SEQ ID NO: 1. In some embodiments, the variant capsid polypeptide comprises a mutation that corresponds to mutations of Q579V, W595A, and V596L as compared to SEQ ID NO: 1. In some embodiments, the variant capsid polypeptide comprises a mutation that corresponds to mutations of Q579V, W595A, and N598S as compared to SEQ ID NO: 1. In some embodiments, the variant capsid polypeptide comprises a mutation that corresponds to mutations of Q579V, W595A, and I601A as compared to SEQ ID NO: 1. In some embodiments, the variant capsid polypeptide comprises a mutation that corresponds to mutations of Q579V, V596L, and N598S as compared to SEQ ID NO: 1. In some embodiments, the variant capsid polypeptide comprises a mutation that corresponds to mutations of Q579V, V596L, and I601A as compared to SEQ ID NO: 1. In some embodiments, the variant capsid polypeptide comprises a mutation that corresponds to mutations of Q579V, N598S, and I601A as compared to SEQ ID NO: 1. In some embodiments, the variant capsid polypeptide comprises a mutation that corresponds to mutations of Q592I, T593V, and W595A as compared to SEQ ID NO: 1. In some embodiments, the variant capsid polypeptide comprises a mutation that corresponds to mutations of Q592I, T593V, and V596L as compared to SEQ ID NO: 1. In some embodiments, the variant capsid polypeptide comprises a mutation that corresponds to mutations of Q592I, T593V, and N598S as compared to SEQ ID NO: 1. In some embodiments, the variant capsid polypeptide comprises a mutation that corresponds to mutations of Q592I, T593V, and I601A as compared to SEQ ID NO: 1. In some embodiments, the variant capsid polypeptide comprises a mutation that corresponds to mutations of Q592I, W595A, and V596L as compared to SEQ ID NO: 1. In some embodiments, the variant capsid polypeptide comprises a mutation that corresponds to mutations of Q592I, W595A, and N598S as compared to SEQ ID NO: 1. In some embodiments, the variant capsid polypeptide comprises a mutation that corresponds to mutations of Q592I, W595A, and I601A as compared to SEQ ID NO: 1. In some embodiments, the variant capsid polypeptide comprises a mutation that corresponds to mutations of Q592I, V596L, and N598S as compared to SEQ ID NO: 1. In some embodiments, the variant capsid polypeptide comprises a mutation that corresponds to mutations of Q592I, V596L, and I601A as compared to SEQ ID NO: 1. In some embodiments, the variant capsid polypeptide comprises a mutation that corresponds to mutations of Q592I, N598S, and I601A as compared to SEQ ID NO: 1. In some embodiments, the variant capsid polypeptide comprises a mutation that corresponds to mutations of T593V, W595A, and V596L as compared to SEQ ID NO: 1. In some embodiments, the variant capsid polypeptide comprises a mutation that corresponds to mutations of T593V, W595A, and N598S as compared to SEQ ID NO: 1. In some embodiments, the variant capsid polypeptide comprises a mutation that corresponds to mutations of T593V, W595A, and I601A as compared to SEQ ID NO: 1. In some embodiments, the variant capsid polypeptide comprises a mutation that corresponds to mutations of T593V, V596L, and N598S as compared to SEQ ID NO: 1. In some embodiments, the variant capsid polypeptide comprises a mutation that corresponds to mutations of T593V, V596L, and I601A as compared to SEQ ID NO: 1. In some embodiments, the variant capsid polypeptide comprises a mutation that corresponds to mutations of T593V, N598S, and I601A as compared to SEQ ID NO: 1. In some embodiments, the variant capsid polypeptide comprises a mutation that corresponds to mutations of W595A, V596L, and N598S as compared to SEQ ID NO: 1. In some embodiments, the variant capsid polypeptide comprises a mutation that corresponds to mutations of W595A, V596L, and I601A as compared to SEQ ID NO: 1. In some embodiments, the variant capsid polypeptide comprises a mutation that corresponds to mutations of W595A, N598S, and I601A as compared to SEQ ID NO: 1. In some embodiments, the variant capsid polypeptide comprises a mutation that corresponds to mutations of V596L, N598S, and I601A as compared to SEQ ID NO: 1. In some embodiments, the variant capsid polypeptide comprises a mutation that corresponds to mutations of Q579V, Q592I, T593V, and W595A as compared to SEQ ID NO: 1. In some embodiments, the variant capsid polypeptide comprises a mutation that corresponds to mutations of Q579V, Q592I, T593V, and V596L as compared to SEQ ID NO: 1. In some embodiments, the variant capsid polypeptide comprises a mutation that corresponds to mutations of Q579V, Q592I, T593V, and N598S as compared to SEQ ID NO: 1. In some embodiments, the variant capsid polypeptide comprises a mutation that corresponds to mutations of Q579V, Q592I, T593V, and I601A as compared to SEQ ID NO: 1. In some embodiments, the variant capsid polypeptide comprises a mutation that corresponds to mutations of Q579V, Q592I, W595A, and V596L as compared to SEQ ID NO: 1. In some embodiments, the variant capsid polypeptide comprises a mutation that corresponds to mutations of Q579V, Q592I, W595A, and N598S as compared to SEQ ID NO: 1. In some embodiments, the variant capsid polypeptide comprises a mutation that corresponds to mutations of Q579V, Q592I, W595A, and I601A as compared to SEQ ID NO: 1. In some embodiments, the variant capsid polypeptide comprises a mutation that corresponds to mutations of Q579V, Q592I, W595A, and V596L as compared to SEQ ID NO: 1. In some embodiments, the variant capsid polypeptide comprises a mutation that corresponds to mutations of Q579V, Q592I, W595A, and N598S as compared to SEQ ID NO: 1. In some embodiments, the variant capsid polypeptide comprises a mutation that corresponds to mutations of Q579V, Q592I, W595A, and I601A as compared to SEQ ID NO: 1. In some embodiments, the variant capsid polypeptide comprises a mutation that corresponds to mutations of Q579V, Q592I, T593V, and V596L as compared to SEQ ID NO: 1. In some embodiments, the variant capsid polypeptide comprises a mutation that corresponds to mutations of Q579V, Q592I, T593V, and N598S as compared to SEQ ID NO: 1. In some embodiments, the variant capsid polypeptide comprises a mutation that corresponds to mutations of Q579V, Q592I, T593V, and I601A as compared to SEQ ID NO: 1. In some embodiments, the variant capsid polypeptide comprises a mutation that corresponds to mutations of Q592I, T593V, W595A, and N596S as compared to SEQ ID NO: 1. In some embodiments, the variant capsid polypeptide comprises a mutation that corresponds to mutations of Q592I, T593V, W595A, and N598S as compared to SEQ ID NO: 1. In some embodiments, the variant capsid polypeptide comprises a mutation that corresponds to mutations of Q592I, T593V, W595A, and I601A as compared to SEQ ID NO: 1. In some embodiments, the variant capsid polypeptide comprises a mutation that corresponds to mutations of T593V, W595A, V596L, and N598S as compared to SEQ ID NO: 1. In some embodiments, the variant capsid polypeptide comprises a mutation that corresponds to mutations of T593V, W595A, V596L, and I601A as compared to SEQ ID NO: 1. In some embodiments, the variant capsid polypeptide comprises a mutation that corresponds to mutations of W595A, V596L, N598S, and I601A as compared to SEQ ID NO: 1. In some embodiments, the variant capsid polypeptide comprises a mutation that corresponds to mutations of Q579V, Q592I, V596L, and N598S as compared to SEQ ID NO: 1. In some embodiments, the variant capsid polypeptide comprises a mutation that corresponds to mutations of Q579V, Q592I, V596L, and I601A as compared to SEQ ID NO: 1. In some embodiments, the variant capsid polypeptide comprises a mutation that corresponds to mutations of Q579V, Q592I, N598S, and I601A as compared to SEQ ID NO: 1. In some embodiments, the variant capsid polypeptide comprises a mutation that corresponds to mutations of Q579V, T593V, V596L, and N598S as compared to SEQ ID NO: 1. In some embodiments, the variant capsid polypeptide comprises a mutation that corresponds to mutations of Q579V, T593V, V596L, and I601A as compared to SEQ ID NO: 1. In some embodiments, the variant capsid polypeptide comprises a mutation that corresponds to mutations of Q579V, T593V, N598S, and I601A as compared to SEQ ID NO: 1. In some embodiments, the variant capsid polypeptide comprises a mutation that corresponds to mutations of Q579V, W595A, V596L, and N598S as compared to SEQ ID NO: 1. In some embodiments, the variant capsid polypeptide comprises a mutation that corresponds to mutations of Q579V, W595A, V596L, and I601A as compared to SEQ ID NO: 1. In some embodiments, the variant capsid polypeptide comprises a mutation that corresponds to mutations of Q579V, W595A, N598S, and I601A as compared to SEQ ID NO: 1. In some embodiments, the variant capsid polypeptide comprises a mutation that corresponds to mutations of Q592I, T593V, V596L, and N598S as compared to SEQ ID NO: 1. In some embodiments, the variant capsid polypeptide comprises a mutation that corresponds to mutations of Q592I, T593V, V596L, and I601A as compared to SEQ ID NO: 1. In some embodiments, the variant capsid polypeptide comprises a mutation that corresponds to mutations of Q592I, T593V, N598S, and I601A as compared to SEQ ID NO: 1. In some embodiments, the variant capsid polypeptide comprises a mutation that corresponds to mutations of Q592I, W595A, V596L, and N598S as compared to SEQ ID NO: 1. In some embodiments, the variant capsid polypeptide comprises a mutation that corresponds to mutations of Q592I, W595A, V596L, and I601A as compared to SEQ ID NO: 1. In some embodiments, the variant capsid polypeptide comprises a mutation that corresponds to mutations of Q592I, W595A, N598S, and I601A as compared to SEQ ID NO: 1. In some embodiments, the variant capsid polypeptide comprises a mutation that corresponds to mutations of Q592I, V596L, N598S, and I601A as compared to SEQ ID NO: 1. In some embodiments, the variant capsid polypeptide comprises a mutation that corresponds to mutations of T593V, W595A, N598S, and I601A as compared to SEQ ID NO: 1. In some embodiments, the variant capsid polypeptide comprises a mutation that corresponds to mutations of T593V, V596L, N598S, and I601A as compared to SEQ ID NO: 1. In some embodiments, the variant capsid polypeptide comprises a mutation that corresponds to mutations of Q579V, Q592I, T593V, W595A, and V596L as compared to SEQ ID NO: 1. In some embodiments, the variant capsid polypeptide comprises a mutation that corresponds to mutations of Q579V, Q592I, T593V, W595A, and N598S as compared to SEQ ID NO: 1. In some embodiments, the variant capsid polypeptide comprises a mutation that corresponds to mutations of Q579V, Q592I, T593V, W595A, and I601A as compared to SEQ ID NO: 1. In some embodiments, the variant capsid polypeptide comprises a mutation that corresponds to mutations of Q579V, T593V, W595A, V596L and N598S as compared to SEQ ID NO: 1. In some embodiments, the variant capsid polypeptide comprises a mutation that corresponds to mutations of Q579V, T593V, W595A, V596L and I601A as compared to SEQ ID NO: 1. In some embodiments, the variant capsid polypeptide comprises a mutation that corresponds to mutations of Q579V, Q592I, W595A, V596L and N598S as compared to SEQ ID NO: 1. In some embodiments, the variant capsid polypeptide comprises a mutation that corresponds to mutations of Q579V, Q592I, W595A, V596L and I601A as compared to SEQ ID NO: 1. In some embodiments, the variant capsid polypeptide comprises a mutation that corresponds to mutations of Q579V, Q592I, T593V, V596L and N598S as compared to SEQ ID NO: 1. In some embodiments, the variant capsid polypeptide comprises a mutation that corresponds to mutations of Q579V, Q592I, T593V, V596L and I601A as compared to SEQ ID NO: 1. In some embodiments, the variant capsid polypeptide comprises a mutation that corresponds to mutations of Q579V, Q592I, T593V, W595A and N598S as compared to SEQ ID NO: 1. In some embodiments, the variant capsid polypeptide comprises a mutation that corresponds to mutations of Q579V, Q592I, T593V, W595A and I601A as compared to SEQ ID NO: 1. In some embodiments, the variant capsid polypeptide comprises a mutation that corresponds to mutations of Q592I, T593V, W595A, V596L and N598S as compared to SEQ ID NO: 1. In some embodiments, the variant capsid polypeptide comprises a mutation that corresponds to mutations of Q592I, T593V, W595A, V596L and I601A as compared to SEQ ID NO: 1. In some embodiments, the variant capsid polypeptide comprises a mutation that corresponds to mutations of T593V, W595A, V596L, N598S and I601A as compared to SEQ ID NO: 1. In some embodiments, the variant capsid polypeptide comprises a mutation that corresponds to mutations of Q579V, T593V, W595A, N598S and I601A as compared to SEQ ID NO: 1. In some embodiments, the variant capsid polypeptide comprises a mutation that corresponds to mutations of Q579V, T593V, V596L, N598S and I601A as compared to SEQ ID NO: 1. In some embodiments, the variant capsid polypeptide comprises a mutation that corresponds to mutations of Q579V, W595A, V596L, N598S and I601A as compared to SEQ ID NO: 1. In some embodiments, the variant capsid polypeptide comprises a mutation that corresponds to mutations of Q579V, Q592I, W595A, N598S and I601A as compared to SEQ ID NO: 1. In some embodiments, the variant capsid polypeptide comprises a mutation that corresponds to mutations of Q579V, Q592I, V596L, N598S and I601A as compared to SEQ ID NO: 1. In some embodiments, the variant capsid polypeptide comprises a mutation that corresponds to mutations of Q579V, W595A, V596L, N598S and I601A as compared to SEQ ID NO: 1. In some embodiments, the variant capsid polypeptide comprises a mutation that corresponds to mutations of Q579V, Q592I, T593V, N598S and I601A as compared to SEQ ID NO: 1. In some embodiments, the variant capsid polypeptide comprises a mutation that corresponds to mutations of Q592V, T593V, W595A, N598S and I601A as compared to SEQ ID NO: 1. In some embodiments, the variant capsid polypeptide comprises a mutation that corresponds to mutations of Q592V, T593V, V596L, N598S and I601A as compared to SEQ ID NO: 1. In some embodiments, the variant capsid polypeptide comprises a mutation that corresponds to mutations of Q592V, W595A, V596L, N598S and I601A as compared to SEQ ID NO: 1. In some embodiments, the variant capsid polypeptide comprises a mutation that corresponds to mutations of Q579V, Q592I, T593V, W595A, V596L, and N598S as compared to SEQ ID NO: 1. In some embodiments, the variant capsid polypeptide comprises a mutation that corresponds to mutations of Q579V, Q592I, T593V, W595A, V596L, and I601A as compared to SEQ ID NO: 1. In some embodiments, the variant capsid polypeptide comprises a mutation that corresponds to mutations of Q592V, T593V, W595A, V596L, N598S and I601A as compared to SEQ ID NO: 1. In some embodiments, the variant capsid polypeptide comprises a mutation that corresponds to mutations of Q579V, T593V, W595A, V596L, N598S and I601A as compared to SEQ ID NO: 1. In some embodiments, the variant capsid polypeptide comprises a mutation that corresponds to mutations of Q579V, Q592I, W595A, V596L, N598S and I601A as compared to SEQ ID NO: 1. In some embodiments, the variant capsid polypeptide comprises a mutation that corresponds to mutations of Q579V, Q592I, T593V, V596L, N598S and I601A as compared to SEQ ID NO: 1. In some embodiments, the variant capsid polypeptide comprises a mutation that corresponds to mutations of Q579V, Q592I, T593V, W595A, N598S and I601A as compared to SEQ ID NO: 1. In some embodiments, the variant capsid polypeptide comprises a mutation that corresponds to mutations of Q579V, Q592I, T593V, W595A, V596L, N598S and I601A as compared to SEQ ID NO: 1.

In some embodiments, the variant capsid polypeptide comprises: (a) a sequence comprising any one of SEQ ID NO: 2-139; (b) a sequence having at least 95%, at least 96%, at least 97%, at least 98% or at least 99% sequence identity to any one of SEQ ID NO: 2 or 14-139 and comprises the mutation set of said SEQ ID NO: 2 or 14-139; or (c) a sequence comprising the mutation set of any one of SEQ ID NO: 2 or 14-139 and having at least 1, 2, 3, 4, 5, 6, 7, 8, 9, or 10 single amino acid mutations relative to said any one of SEQ ID NO: 2 or 14-139, optionally having fewer than 70, 60, 50, 40, 35, 30 or 20 single amino acid mutations relative to said any one of SEQ ID NO: 2 or 14-139.

In some embodiments, the disclosure provides a variant capsid polypeptide (and nucleic acids encoding said variant capsid polypeptide) that comprises at least 1 of the mutation differences associated with any variant capsid polypeptide of Table 1 or comprises at least 1 mutation which corresponds to a mutation difference associated with any variant capsid polypeptide of Table 1. In some embodiments, the disclosure provides a variant capsid polypeptide (and nucleic acids encoding said capsid polypeptide) that comprises at least 2 mutation differences associated with any variant capsid polypeptide of Table 1 or comprises at least 2 mutations which corresponds to 2 mutation differences associated with any variant capsid polypeptide of Table 1. In some embodiments, the disclosure provides a variant capsid polypeptide (and nucleic acids encoding said capsid polypeptide) that comprises at least 3 mutation differences associated with any variant capsid polypeptide of Table 1 or comprises at least 3 mutations which corresponds to 3 mutation differences associated with any variant capsid polypeptide of Table 1. In some embodiments, the disclosure provides a variant capsid polypeptide (and nucleic acids encoding said capsid polypeptide) that comprises at least 4 mutation differences associated with any variant capsid polypeptide of Table 1 or comprises at least 4 mutations which corresponds to 4 mutation differences associated with any variant capsid polypeptide of Table 1. In some embodiments, the disclosure provides a variant capsid polypeptide (and nucleic acids encoding said capsid polypeptide) that comprises at least 5 mutation differences associated with any variant capsid polypeptide of Table 1 or comprises at least 5 mutations which corresponds to 5 mutation differences associated with any variant capsid polypeptide of Table 1. In some embodiments, the disclosure provides a variant capsid polypeptide (and nucleic acids encoding said capsid polypeptide) that comprises at least 6 mutation differences associated with any variant capsid polypeptide of Table 1 or comprises at least 6 mutations which corresponds to 6 mutation differences associated with any variant capsid polypeptide of Table 1. In some embodiments, the disclosure provides a variant capsid polypeptide (and nucleic acids encoding said capsid polypeptide) that comprises at least 7 mutation differences associated with any variant capsid polypeptide of Table 1 or comprises at least 7 mutations which corresponds to 7 mutation differences associated with any variant capsid polypeptide of Table 1.

In some embodiments, the disclosure provides a variant capsid polypeptide (and nucleic acids encoding said capsid polypeptide) that comprises all of the mutation differences associated with any variant capsid polypeptide of Table 1 or comprises mutations which corresponds to all of the mutation differences associated with any variant capsid polypeptide of Table 1.

In any of the above aspects it will be understood that in variant capsid polypeptides described above where a number of mutation differences associated with or corresponding to the mutation differences of any variant capsid polypeptide of Table 1 is specified, the mutations may be chosen from any of the mutation differences associated with that variant capsid polypeptide. Thus, for example, with respect to the mutation differences of VAR-1 (Q579V, Q592I, T593V, W595A, V596L, N598S, I601A), where a variant capsid comprises 1 of the mutation differences, it may be Q579V, Q592I, T593V, W595A, V596L, N598S or I601A; likewise, where a variant capsid comprises 2 of the mutation differences, those two may be Q579V and Q592I, Q579V and T593V, Q579V and W595A, Q579V and V596L, Q579V and N598S, Q579V and I601A, Q592I and T593V, Q592I and W595A, Q592I and V596L, Q592I and N598S, Q592I and I601A, T593V and W595A, T593V and V596L, T593V and N598S, T593V and I601A, W595A and V596L, W595A and N598S, W595A and I601A, V596L and N598S, V596L and I601A, N598S and I601A; likewise, where the variant comprises 3 of the mutation differences, those 3 may be Q579V and Q592I and T593V, Q579V and Q592I and W595A, Q579V and Q592I and V596L, Q579V and Q592I and N598S, Q579V and Q592I and I601A, Q592I and T593V and W595A, Q592I and T593V and V596L, Q592I and T593V and N598S, Q592I and T593V and I601A, T593V and W595A and V596L, T593V and W595A and N598S, T593V and W595A and I601A, W595A and V596L and N598S, W595A and V596L and I601A, V596L and N598S and I601A; likewise, where the variant comprises 4 of the mutation differences, those 4 may be Q579V and Q592I and T593V and W595A, Q579V and Q592I and T593V and V596L, Q579V and Q592I and T593V and N598S, Q579V and Q592I and T593V and I601A, Q592I and T593V and W595A and V596L, Q592I and T593V and W595A and N598S, Q592I and T593V and W595A and I601A, T593V and W595A and V596L and N598S, T593V and W595A and V596L and I601A, W595A and V596L and N598S and I601A; likewise, where the variant comprises 5 of the mutation differences, those 5 may be Q579V and Q592I and T593V and W595A and V596L, Q579V and Q592I and T593V and W595A and N598S, Q579V and Q592I and T593V and W595A and I601A, Q592I and T593V and W595A and V596L and N598S, Q592I and T593V and W595A and V596L and I601A, T593V and W595A and V596L and N598S and I601A; likewise, where the variant comprises 6 of the mutation differences, those 6 may be Q579V and Q592I and T593V and W595A and V596L and N598S, Q579V and Q592I and T593V and W595A and V596L and I601A, Q592I and T593V and W595A and V596L and N598S and I601A, Q579V and Q592I and W595A and V596L and N598S and I601A, Q579V and Q592I and T593V and V596L and N598S and I601A, Q579V and Q592I and T593V and W595A and N598S and I601A; likewise, where the variant comprises 7 of the mutation differences, those 7 may be Q579V and Q592I and T593V and W595A and V596L and N598S and I601A.

In some embodiments, the variant capsid polypeptide comprises one or more mutation differences, e.g., as described herein, e.g., as described in Table 1, and has at least 80%, at least 85%, at least 90%, at least 91%, at least 92%, at least 93%, at least 94%, at least 95%, at least 96%, at least 97%, at least 98%, or at least 99% sequence identity to a reference AAV serotype, e.g., as described herein, e.g., to SEQ ID NO: 1. In some embodiments, the variant capsid polypeptide comprises one or more mutation differences as described in Table 1 or which correspond to one or more mutation differences as described in Table 1. In some embodiments, the variant capsid polypeptide is, but for the mutation differences described in or corresponding to the mutation differences as described in Table 1, at least 90%, at least 95%, 96%, 97%, 98%, 99%, or 100% identical to a reference AAV serotype described herein. In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 1 (e.g., a VP1, VP2 or VP3 sequence of SEQ ID NO: 1). In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 5 (e.g., a VP1, VP2 or VP3 sequence of SEQ ID NO: 5). In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 7 (e.g., a VP1, VP2 or VP3 sequence of SEQ ID NO: 7). In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 9 (e.g., a VP1, VP2 or VP3 sequence of SEQ ID NO: 9). In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 11 (e.g., a VP1, VP2 or VP3 sequence of SEQ ID NO: 11). In some embodiments, the variant capsid polypeptide described herein is, but for the mutation differences of Table 1 or which correspond to the mutation differences of Table 1 comprised within such variant capsid polypeptide, at least 90%, at least 95%, 96%, 97%, 98%, 99%, or 100% identical to a capsid polypeptide of SEQ ID NO: 12 (e.g., a VP1, VP2 or VP3 sequence of SEQ ID NO: 12).

In some embodiments, a variant capsid polypeptide comprises a sequence VVATNHQSAQAQAIVGALQSQGA (SEQ ID NO: 266), or comprises a sequence IVGALQSQGA (SEQ ID NO: 267), or comprises the sequence VGALQS (SEQ ID NO: 268). In some embodiments, a variant capsid polypeptide comprises a sequence VVATNHQSAQAQAIVGALQSQGA (SEQ ID NO: 266), or comprises a sequence IVGALQSQGA (SEQ ID NO: 267), or comprises the sequence VGALQS (SEQ ID NO: 268); optionally wherein said sequence is within a region corresponding to amino acids 550-620 according to SEQ ID NO: 1, of said variant capsid polypeptide.

In some embodiments, a variant capsid polypeptide comprises a sequence VVATNHQSAQAQAIVGALQSQGA (SEQ ID NO: 266). In some embodiments, a variant capsid polypeptide comprises a sequence IVGALQSQGA (SEQ ID NO: 267). In some embodiments, a variant capsid polypeptide comprises a sequence VGALQS (SEQ ID NO: 268). In some embodiments, a variant capsid polypeptide comprises a sequence VVATNHQSAQAQAIVGALQSQGA (SEQ ID NO: 266), optionally wherein said sequence is within a region corresponding to amino acids 550-620 according to SEQ ID NO: 1, of said variant capsid polypeptide. In some embodiments, a variant capsid polypeptide comprises a sequence IVGALQSQGA (SEQ ID NO: 267), or comprises the sequence VGALQS (SEQ ID NO: 268); optionally wherein said sequence is within a region corresponding to amino acids 550-620 according to SEQ ID NO: 1, of said variant capsid polypeptide. In some embodiments, a variant capsid polypeptide comprises a sequence VGALQS (SEQ ID NO: 268); optionally wherein said sequence is within a region corresponding to amino acids 550-620 according to SEQ ID NO: 1, of said variant capsid polypeptide.

In some embodiments, a variant capsid polypeptide comprises a sequence VVATNHQSAQAQAIVGALQSQGA (SEQ ID NO: 266), wherein the capsid polypeptide has greater than 95%, greater than 96%, greater than 97%, greater than 98%, or greater than 99% sequence identity to a capsid polypeptide of SEQ ID NO: 1. In some embodiments, a variant capsid polypeptide comprises a sequence IVGALQSQGA (SEQ ID NO: 267), wherein the capsid polypeptide has greater than 95%, greater than 96%, greater than 97%, greater than 98%, or greater than 99% sequence identity to a capsid polypeptide of SEQ ID NO: 1. In some embodiments, a variant capsid polypeptide comprises a sequence VGALQS (SEQ ID NO: 268), wherein the capsid polypeptide has greater than 95%, greater than 96%, greater than 97%, greater than 98%, or greater than 99% sequence identity to a capsid polypeptide of SEQ ID NO: 1. In some embodiments, a variant capsid polypeptide comprises a sequence VVATNHQSAQAQAIVGALQSQGA (SEQ ID NO: 266), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12. In some embodiments, a variant capsid polypeptide comprises a sequence IVGALQSQGA (SEQ ID NO: 267), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12. In some embodiments, a variant capsid polypeptide comprises a sequence VGALQS (SEQ ID NO: 268), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12. In some embodiments, a variant capsid polypeptide comprises a sequence VVATNHQSAQAQAIVGALQSQGA (SEQ ID NO: 266), wherein the sequence VVATNHQSAQAQAIVGALQSQGA (SEQ ID NO: 266) is present at a position corresponding to amino acids 579 to 601 according to SEQ ID NO: 1. In some embodiments, a variant capsid polypeptide comprises a sequence IVGALQSQGA (SEQ ID NO: 267), wherein the sequence IVGALQSQGA (SEQ ID NO: 267) is present at a position corresponding to amino acids 592 to 601 according to SEQ ID NO: 1. In some embodiments, a variant capsid polypeptide comprises a sequence VGALQS (SEQ ID NO: 268), wherein the sequence VGALQS (SEQ ID NO: 268) is present at a position corresponding to amino acids 592 to 601 according to SEQ ID NO: 1. In some embodiments, a variant capsid polypeptide comprises a sequence VVATNHQSAQAQAIVGALQSQGA (SEQ ID NO: 266), wherein the capsid polypeptide has greater than 95%, greater than 96%, greater than 97%, greater than 98%, or greater than 99% sequence identity to a capsid polypeptide of SEQ ID NO: 1, and wherein the sequence VVATNHQSAQAQAIVGALQSQGA (SEQ ID NO: 266) is present at a position corresponding to amino acids 579 to 601 according to SEQ ID NO: 1. In some embodiments, a variant capsid polypeptide comprises a sequence IVGALQSQGA (SEQ ID NO: 267), wherein the capsid polypeptide has greater than 95%, greater than 96%, greater than 97%, greater than 98%, or greater than 99% sequence identity to a capsid polypeptide of SEQ ID NO: 1, and wherein the sequence IVGALQSQGA (SEQ ID NO: 267) is present at a position corresponding to amino acids 592 to 601 according to SEQ ID NO: 1. In some embodiments, a variant capsid polypeptide comprises a sequence VGALQS (SEQ ID NO: 268), wherein the capsid polypeptide has greater than 95%, greater than 96%, greater than 97%, greater than 98%, or greater than 99% sequence identity to a capsid polypeptide of SEQ ID NO: 1, and wherein the sequence VGALQS (SEQ ID NO: 268) is present at a position corresponding to amino acids 592 to 601 according to SEQ ID NO: 1. In some embodiments, a variant capsid polypeptide comprises a sequence VVATNHQSAQAQAIVGALQSQGA (SEQ ID NO: 266), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12, and wherein the sequence VVATNHQSAQAQAIVGALQSQGA (SEQ ID NO: 266) is present at a position corresponding to amino acids 579 to 601 according to SEQ ID NO: 1. In some embodiments, a variant capsid polypeptide comprises a sequence IVGALQSQGA (SEQ ID NO: 267), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12, and wherein the sequence IVGALQSQGA (SEQ ID NO: 267) is present at a position corresponding to amino acids 592 to 601 according to SEQ ID NO: 1. In some embodiments, a variant capsid polypeptide comprises a sequence VGALQS (SEQ ID NO: 268), wherein the capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12, and wherein the sequence VGALQS (SEQ ID NO: 268) is present at a position corresponding to amino acids 592 to 601 according to SEQ ID NO: 1.

In some embodiments, a variant capsid polypeptide comprises a sequence VGALQS (SEQ ID NO: 268), optionally wherein said variant capsid polypeptide has greater than 95%, greater than 96%, greater than 97%, greater than 98% or greater than 99% sequence identity to a capsid polypeptide of SEQ ID NO: 1. In some embodiments, a variant capsid polypeptide comprises a sequence VGALQS (SEQ ID NO: 268) and said variant capsid polypeptide has greater than 95%, greater than 96%, greater than 97%, greater than 98% or greater than 99% sequence identity to a capsid polypeptide of SEQ ID NO: 5, SEQ ID NO: 7, SEQ ID NO: 9, SEQ ID NO: 11 or SEQ ID NO: 12. In some embodiments, the sequence VGALQS (SEQ ID NO: 268) is present at a position corresponding to amino acids 593 to 598 according to SEQ ID NO: 1.

In some embodiments, described herein is a variant capsid polypeptide comprising a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprising the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In such embodiments, the reference sequence used to calculate the edit distance is the same as the sequence from which the mutation set present in the variant capsid polypeptide is derived. For example, in one embodiment, provided is a variant capsid polypeptide comprising a sequence with an edit distance of 15 or lower to SEQ ID NO: 2 and further comprising the mutation set of SEQ ID NO: 2 (i.e., a valine at position 579, an isoleucine at position 592, a valine at position 593, an alanine at position 595, a leucine at position 596, a serine at position 598 and an alanine at position 601, with numbering all with respect to SEQ ID NO: 1).

In some embodiments, a variant capsid polypeptide comprises a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, and further comprises the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, a variant capsid polypeptide comprises a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprises the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, a variant capsid polypeptide comprises a sequence with an edit distance of 15 or lower to SEQ ID NO: 2, and further comprises the mutation set of said any one of SEQ ID NO: 2. In some embodiments, a variant capsid polypeptide comprises a sequence with an edit distance of 15 or lower to SEQ ID NO: 14, and further comprises the mutation set of said any one of SEQ ID NO: 14. In some embodiments, a variant capsid polypeptide comprises a sequence with an edit distance of 15 or lower to SEQ ID NO: 15, and further comprises the mutation set of said any one of SEQ ID NO: 15. In some embodiments, a variant capsid polypeptide comprises a sequence with an edit distance of 15 or lower to SEQ ID NO: 16, and further comprises the mutation set of said any one of SEQ ID NO: 16. In some embodiments, a variant capsid polypeptide comprises a sequence with an edit distance of 15 or lower to SEQ ID NO: 17, and further comprises the mutation set of said any one of SEQ ID NO: 17. In some embodiments, a variant capsid polypeptide comprises a sequence with an edit distance of 15 or lower to SEQ ID NO: 18, and further comprises the mutation set of said any one of SEQ ID NO: 18. In some embodiments, a variant capsid polypeptide comprises a sequence with an edit distance of 15 or lower to SEQ ID NO: 19, and further comprises the mutation set of said any one of SEQ ID NO: 19. In some embodiments, a variant capsid polypeptide comprises a sequence with an edit distance of 15 or lower to SEQ ID NO: 20, and further comprises the mutation set of said any one of SEQ ID NO: 20. In some embodiments, a variant capsid polypeptide comprises a sequence with an edit distance of 15 or lower to SEQ ID NO: 21, and further comprises the mutation set of said any one of SEQ ID NO: 21. In some embodiments, a variant capsid polypeptide comprises a sequence with an edit distance of 15 or lower to SEQ ID NO: 22, and further comprises the mutation set of said any one of SEQ ID NO: 22. In some embodiments, a variant capsid polypeptide comprises a sequence with an edit distance of 15 or lower to SEQ ID NO: 23, and further comprises the mutation set of said any one of SEQ ID NO: 23. In some embodiments, a variant capsid polypeptide comprises a sequence with an edit distance of 15 or lower to SEQ ID NO: 24, and further comprises the mutation set of said any one of SEQ ID NO: 24. In some embodiments, a variant capsid polypeptide comprises a sequence with an edit distance of 15 or lower to SEQ ID NO: 25, and further comprises the mutation set of said any one of SEQ ID NO: 25. In some embodiments, a variant capsid polypeptide comprises a sequence with an edit distance of 15 or lower to SEQ ID NO: 26, and further comprises the mutation set of said any one of SEQ ID NO: 26. In some embodiments, a variant capsid polypeptide comprises a sequence with an edit distance of 15 or lower to SEQ ID NO: 27, and further comprises the mutation set of said any one of SEQ ID NO: 27. In some embodiments, a variant capsid polypeptide comprises a sequence with an edit distance of 15 or lower to SEQ ID NO: 28, and further comprises the mutation set of said any one of SEQ ID NO: 28. In some embodiments, a variant capsid polypeptide comprises a sequence with an edit distance of 15 or lower to SEQ ID NO: 29, and further comprises the mutation set of said any one of SEQ ID NO: 29. In some embodiments, a variant capsid polypeptide comprises a sequence with an edit distance of 15 or lower to SEQ ID NO: 30, and further comprises the mutation set of said any one of SEQ ID NO: 30. In some embodiments, a variant capsid polypeptide comprises a sequence with an edit distance of 15 or lower to SEQ ID NO: 31, and further comprises the mutation set of said any one of SEQ ID NO: 31. In some embodiments, a variant capsid polypeptide comprises a sequence with an edit distance of 15 or lower to SEQ ID NO: 32, and further comprises the mutation set of said any one of SEQ ID NO: 32. In some embodiments, a variant capsid polypeptide comprises a sequence with an edit distance of 15 or lower to SEQ ID NO: 33, and further comprises the mutation set of said any one of SEQ ID NO: 33. In some embodiments, a variant capsid polypeptide comprises a sequence with an edit distance of 15 or lower to SEQ ID NO: 34, and further comprises the mutation set of said any one of SEQ ID NO: 34. In some embodiments, a variant capsid polypeptide comprises a sequence with an edit distance of 15 or lower to SEQ ID NO: 35, and further comprises the mutation set of said any one of SEQ ID NO: 35. In some embodiments, a variant capsid polypeptide comprises a sequence with an edit distance of 15 or lower to SEQ ID NO: 36, and further comprises the mutation set of said any one of SEQ ID NO: 36. In some embodiments, a variant capsid polypeptide comprises a sequence with an edit distance of 15 or lower to SEQ ID NO: 37, and further comprises the mutation set of said any one of SEQ ID NO: 37. In some embodiments, a variant capsid polypeptide comprises a sequence with an edit distance of 15 or lower to SEQ ID NO: 38, and further comprises the mutation set of said any one of SEQ ID NO: 38. In some embodiments, a variant capsid polypeptide comprises a sequence with an edit distance of 15 or lower to SEQ ID NO: 39, and further comprises the mutation set of said any one of SEQ ID NO: 39. In some embodiments, a variant capsid polypeptide comprises a sequence with an edit distance of 15 or lower to SEQ ID NO: 40, and further comprises the mutation set of said any one of SEQ ID NO: 40. In some embodiments, a variant capsid polypeptide comprises a sequence with an edit distance of 15 or lower to SEQ ID NO: 41, and further comprises the mutation set of said any one of SEQ ID NO: 41. In some embodiments, a variant capsid polypeptide comprises a sequence with an edit distance of 15 or lower to SEQ ID NO: 42, and further comprises the mutation set of said any one of SEQ ID NO: 42. In some embodiments, a variant capsid polypeptide comprises a sequence with an edit distance of 15 or lower to SEQ ID NO: 43, and further comprises the mutation set of said any one of SEQ ID NO: 43. In some embodiments, a variant capsid polypeptide comprises a sequence with an edit distance of 15 or lower to SEQ ID NO: 44, and further comprises the mutation set of said any one of SEQ ID NO: 44. In some embodiments, a variant capsid polypeptide comprises a sequence with an edit distance of 15 or lower to SEQ ID NO: 45, and further comprises the mutation set of said any one of SEQ ID NO: 45. In some embodiments, a variant capsid polypeptide comprises a sequence with an edit distance of 15 or lower to SEQ ID NO: 46, and further comprises the mutation set of said any one of SEQ ID NO: 46. In some embodiments, a variant capsid polypeptide comprises a sequence with an edit distance of 15 or lower to SEQ ID NO: 47, and further comprises the mutation set of said any one of SEQ ID NO: 47. In some embodiments, a variant capsid polypeptide comprises a sequence with an edit distance of 15 or lower to SEQ ID NO: 48, and further comprises the mutation set of said any one of SEQ ID NO: 48. In some embodiments, a variant capsid polypeptide comprises a sequence with an edit distance of 15 or lower to SEQ ID NO: 49, and further comprises the mutation set of said any one of SEQ ID NO: 49. In some embodiments, a variant capsid polypeptide comprises a sequence with an edit distance of 15 or lower to SEQ ID NO: 50, and further comprises the mutation set of said any one of SEQ ID NO: 50. In some embodiments, a variant capsid polypeptide comprises a sequence with an edit distance of 15 or lower to SEQ ID NO: 51, and further comprises the mutation set of said any one of SEQ ID NO: 51. In some embodiments, a variant capsid polypeptide comprises a sequence with an edit distance of 15 or lower to SEQ ID NO: 52, and further comprises the mutation set of said any one of SEQ ID NO: 52. In some embodiments, a variant capsid polypeptide comprises a sequence with an edit distance of 15 or lower to SEQ ID NO: 53, and further comprises the mutation set of said any one of SEQ ID NO: 53. In some embodiments, a variant capsid polypeptide comprises a sequence with an edit distance of 15 or lower to SEQ ID NO: 54, and further comprises the mutation set of said any one of SEQ ID NO: 54. In some embodiments, a variant capsid polypeptide comprises a sequence with an edit distance of 15 or lower to SEQ ID NO: 55, and further comprises the mutation set of said any one of SEQ ID NO: 55. In some embodiments, a variant capsid polypeptide comprises a sequence with an edit distance of 15 or lower to SEQ ID NO: 56, and further comprises the mutation set of said any one of SEQ ID NO: 56. In some embodiments, a variant capsid polypeptide comprises a sequence with an edit distance of 15 or lower to SEQ ID NO: 57, and further comprises the mutation set of said any one of SEQ ID NO: 57. In some embodiments, a variant capsid polypeptide comprises a sequence with an edit distance of 15 or lower to SEQ ID NO: 58, and further comprises the mutation set of said any one of SEQ ID NO: 58. In some embodiments, a variant capsid polypeptide comprises a sequence with an edit distance of 15 or lower to SEQ ID NO: 59, and further comprises the mutation set of said any one of SEQ ID NO: 59. In some embodiments, a variant capsid polypeptide comprises a sequence with an edit distance of 15 or lower to SEQ ID NO: 60, and further comprises the mutation set of said any one of SEQ ID NO: 60. In some embodiments, a variant capsid polypeptide comprises a sequence with an edit distance of 15 or lower to SEQ ID NO: 61, and further comprises the mutation set of said any one of SEQ ID NO: 61. In some embodiments, a variant capsid polypeptide comprises a sequence with an edit distance of 15 or lower to SEQ ID NO: 62, and further comprises the mutation set of said any one of SEQ ID NO: 62. In some embodiments, a variant capsid polypeptide comprises a sequence with an edit distance of 15 or lower to SEQ ID NO: 63, and further comprises the mutation set of said any one of SEQ ID NO: 63. In some embodiments, a variant capsid polypeptide comprises a sequence with an edit distance of 15 or lower to SEQ ID NO: 64, and further comprises the mutation set of said any one of SEQ ID NO: 64. In some embodiments, a variant capsid polypeptide comprises a sequence with an edit distance of 15 or lower to SEQ ID NO: 65, and further comprises the mutation set of said any one of SEQ ID NO: 65. In some embodiments, a variant capsid polypeptide comprises a sequence with an edit distance of 15 or lower to SEQ ID NO: 66, and further comprises the mutation set of said any one of SEQ ID NO: 66. In some embodiments, a variant capsid polypeptide comprises a sequence with an edit distance of 15 or lower to SEQ ID NO: 67, and further comprises the mutation set of said any one of SEQ ID NO: 67. In some embodiments, a variant capsid polypeptide comprises a sequence with an edit distance of 15 or lower to SEQ ID NO: 68, and further comprises the mutation set of said any one of SEQ ID NO: 68. In some embodiments, a variant capsid polypeptide comprises a sequence with an edit distance of 15 or lower to SEQ ID NO: 69, and further comprises the mutation set of said any one of SEQ ID NO: 69. In some embodiments, a variant capsid polypeptide comprises a sequence with an edit distance of 15 or lower to SEQ ID NO: 70, and further comprises the mutation set of said any one of SEQ ID NO: 70. In some embodiments, a variant capsid polypeptide comprises a sequence with an edit distance of 15 or lower to SEQ ID NO: 71, and further comprises the mutation set of said any one of SEQ ID NO: 71. In some embodiments, a variant capsid polypeptide comprises a sequence with an edit distance of 15 or lower to SEQ ID NO: 72, and further comprises the mutation set of said any one of SEQ ID NO: 72. In some embodiments, a variant capsid polypeptide comprises a sequence with an edit distance of 15 or lower to SEQ ID NO: 73, and further comprises the mutation set of said any one of SEQ ID NO: 73. In some embodiments, a variant capsid polypeptide comprises a sequence with an edit distance of 15 or lower to SEQ ID NO: 74, and further comprises the mutation set of said any one of SEQ ID NO: 74. In some embodiments, a variant capsid polypeptide comprises a sequence with an edit distance of 15 or lower to SEQ ID NO: 75, and further comprises the mutation set of said any one of SEQ ID NO: 75. In some embodiments, a variant capsid polypeptide comprises a sequence with an edit distance of 15 or lower to SEQ ID NO: 76, and further comprises the mutation set of said any one of SEQ ID NO: 76. In some embodiments, a variant capsid polypeptide comprises a sequence with an edit distance of 15 or lower to SEQ ID NO: 77, and further comprises the mutation set of said any one of SEQ ID NO: 77. In some embodiments, a variant capsid polypeptide comprises a sequence with an edit distance of 15 or lower to SEQ ID NO: 78, and further comprises the mutation set of said any one of SEQ ID NO: 78. In some embodiments, a variant capsid polypeptide comprises a sequence with an edit distance of 15 or lower to SEQ ID NO: 79, and further comprises the mutation set of said any one of SEQ ID NO: 79. In some embodiments, a variant capsid polypeptide comprises a sequence with an edit distance of 15 or lower to SEQ ID NO: 80, and further comprises the mutation set of said any one of SEQ ID NO: 80. In some embodiments, a variant capsid polypeptide comprises a sequence with an edit distance of 15 or lower to SEQ ID NO: 81, and further comprises the mutation set of said any one of SEQ ID NO: 81. In some embodiments, a variant capsid polypeptide comprises a sequence with an edit distance of 15 or lower to SEQ ID NO: 82, and further comprises the mutation set of said any one of SEQ ID NO: 82. In some embodiments, a variant capsid polypeptide comprises a sequence with an edit distance of 15 or lower to SEQ ID NO: 83, and further comprises the mutation set of said any one of SEQ ID NO: 83. In some embodiments, a variant capsid polypeptide comprises a sequence with an edit distance of 15 or lower to SEQ ID NO: 84, and further comprises the mutation set of said any one of SEQ ID NO: 84. In some embodiments, a variant capsid polypeptide comprises a sequence with an edit distance of 15 or lower to SEQ ID NO: 85, and further comprises the mutation set of said any one of SEQ ID NO: 85. In some embodiments, a variant capsid polypeptide comprises a sequence with an edit distance of 15 or lower to SEQ ID NO: 86, and further comprises the mutation set of said any one of SEQ ID NO: 86. In some embodiments, a variant capsid polypeptide comprises a sequence with an edit distance of 15 or lower to SEQ ID NO: 87, and further comprises the mutation set of said any one of SEQ ID NO: 87. In some embodiments, a variant capsid polypeptide comprises a sequence with an edit distance of 15 or lower to SEQ ID NO: 88, and further comprises the mutation set of said any one of SEQ ID NO: 88. In some embodiments, a variant capsid polypeptide comprises a sequence with an edit distance of 15 or lower to SEQ ID NO: 89, and further comprises the mutation set of said any one of SEQ ID NO: 89. In some embodiments, a variant capsid polypeptide comprises a sequence with an edit distance of 15 or lower to SEQ ID NO: 90, and further comprises the mutation set of said any one of SEQ ID NO: 90. In some embodiments, a variant capsid polypeptide comprises a sequence with an edit distance of 15 or lower to SEQ ID NO: 91, and further comprises the mutation set of said any one of SEQ ID NO: 91. In some embodiments, a variant capsid polypeptide comprises a sequence with an edit distance of 15 or lower to SEQ ID NO: 92, and further comprises the mutation set of said any one of SEQ ID NO: 92. In some embodiments, a variant capsid polypeptide comprises a sequence with an edit distance of 15 or lower to SEQ ID NO: 93, and further comprises the mutation set of said any one of SEQ ID NO: 93. In some embodiments, a variant capsid polypeptide comprises a sequence with an edit distance of 15 or lower to SEQ ID NO: 94, and further comprises the mutation set of said any one of SEQ ID NO: 94. In some embodiments, a variant capsid polypeptide comprises a sequence with an edit distance of 15 or lower to SEQ ID NO: 95, and further comprises the mutation set of said any one of SEQ ID NO: 95. In some embodiments, a variant capsid polypeptide comprises a sequence with an edit distance of 15 or lower to SEQ ID NO: 96, and further comprises the mutation set of said any one of SEQ ID NO: 96. In some embodiments, a variant capsid polypeptide comprises a sequence with an edit distance of 15 or lower to SEQ ID NO: 97, and further comprises the mutation set of said any one of SEQ ID NO: 97. In some embodiments, a variant capsid polypeptide comprises a sequence with an edit distance of 15 or lower to SEQ ID NO: 98, and further comprises the mutation set of said any one of SEQ ID NO: 98. In some embodiments, a variant capsid polypeptide comprises a sequence with an edit distance of 15 or lower to SEQ ID NO: 99, and further comprises the mutation set of said any one of SEQ ID NO: 99. In some embodiments, a variant capsid polypeptide comprises a sequence with an edit distance of 15 or lower to SEQ ID NO: 100, and further comprises the mutation set of said any one of SEQ ID NO: 100. In some embodiments, a variant capsid polypeptide comprises a sequence with an edit distance of 15 or lower to SEQ ID NO: 101, and further comprises the mutation set of said any one of SEQ ID NO: 101. In some embodiments, a variant capsid polypeptide comprises a sequence with an edit distance of 15 or lower to SEQ ID NO: 102, and further comprises the mutation set of said any one of SEQ ID NO: 102. In some embodiments, a variant capsid polypeptide comprises a sequence with an edit distance of 15 or lower to SEQ ID NO: 103, and further comprises the mutation set of said any one of SEQ ID NO: 103. In some embodiments, a variant capsid polypeptide comprises a sequence with an edit distance of 15 or lower to SEQ ID NO: 104, and further comprises the mutation set of said any one of SEQ ID NO: 104. In some embodiments, a variant capsid polypeptide comprises a sequence with an edit distance of 15 or lower to SEQ ID NO: 105, and further comprises the mutation set of said any one of SEQ ID NO: 105. In some embodiments, a variant capsid polypeptide comprises a sequence with an edit distance of 15 or lower to SEQ ID NO: 106, and further comprises the mutation set of said any one of SEQ ID NO: 106. In some embodiments, a variant capsid polypeptide comprises a sequence with an edit distance of 15 or lower to SEQ ID NO: 107, and further comprises the mutation set of said any one of SEQ ID NO: 107. In some embodiments, a variant capsid polypeptide comprises a sequence with an edit distance of 15 or lower to SEQ ID NO: 108, and further comprises the mutation set of said any one of SEQ ID NO: 108. In some embodiments, a variant capsid polypeptide comprises a sequence with an edit distance of 15 or lower to SEQ ID NO: 109, and further comprises the mutation set of said any one of SEQ ID NO: 109. In some embodiments, a variant capsid polypeptide comprises a sequence with an edit distance of 15 or lower to SEQ ID NO: 110, and further comprises the mutation set of said any one of SEQ ID NO: 110. In some embodiments, a variant capsid polypeptide comprises a sequence with an edit distance of 15 or lower to SEQ ID NO: 111, and further comprises the mutation set of said any one of SEQ ID NO: 111. In some embodiments, a variant capsid polypeptide comprises a sequence with an edit distance of 15 or lower to SEQ ID NO: 112, and further comprises the mutation set of said any one of SEQ ID NO: 112. In some embodiments, a variant capsid polypeptide comprises a sequence with an edit distance of 15 or lower to SEQ ID NO: 113, and further comprises the mutation set of said any one of SEQ ID NO: 113. In some embodiments, a variant capsid polypeptide comprises a sequence with an edit distance of 15 or lower to SEQ ID NO: 114, and further comprises the mutation set of said any one of SEQ ID NO: 114. In some embodiments, a variant capsid polypeptide comprises a sequence with an edit distance of 15 or lower to SEQ ID NO: 115, and further comprises the mutation set of said any one of SEQ ID NO: 115. In some embodiments, a variant capsid polypeptide comprises a sequence with an edit distance of 15 or lower to SEQ ID NO: 116, and further comprises the mutation set of said any one of SEQ ID NO: 116. In some embodiments, a variant capsid polypeptide comprises a sequence with an edit distance of 15 or lower to SEQ ID NO: 117, and further comprises the mutation set of said any one of SEQ ID NO: 117. In some embodiments, a variant capsid polypeptide comprises a sequence with an edit distance of 15 or lower to SEQ ID NO: 118, and further comprises the mutation set of said any one of SEQ ID NO: 118. In some embodiments, a variant capsid polypeptide comprises a sequence with an edit distance of 15 or lower to SEQ ID NO: 119, and further comprises the mutation set of said any one of SEQ ID NO: 119. In some embodiments, a variant capsid polypeptide comprises a sequence with an edit distance of 15 or lower to SEQ ID NO: 120, and further comprises the mutation set of said any one of SEQ ID NO: 120. In some embodiments, a variant capsid polypeptide comprises a sequence with an edit distance of 15 or lower to SEQ ID NO: 121, and further comprises the mutation set of said any one of SEQ ID NO: 121. In some embodiments, a variant capsid polypeptide comprises a sequence with an edit distance of 15 or lower to SEQ ID NO: 122, and further comprises the mutation set of said any one of SEQ ID NO: 122. In some embodiments, a variant capsid polypeptide comprises a sequence with an edit distance of 15 or lower to SEQ ID NO: 123, and further comprises the mutation set of said any one of SEQ ID NO: 123. In some embodiments, a variant capsid polypeptide comprises a sequence with an edit distance of 15 or lower to SEQ ID NO: 124, and further comprises the mutation set of said any one of SEQ ID NO: 124. In some embodiments, a variant capsid polypeptide comprises a sequence with an edit distance of 15 or lower to SEQ ID NO: 125, and further comprises the mutation set of said any one of SEQ ID NO: 125. In some embodiments, a variant capsid polypeptide comprises a sequence with an edit distance of 15 or lower to SEQ ID NO: 126, and further comprises the mutation set of said any one of SEQ ID NO: 126. In some embodiments, a variant capsid polypeptide comprises a sequence with an edit distance of 15 or lower to SEQ ID NO: 127, and further comprises the mutation set of said any one of SEQ ID NO: 127. In some embodiments, a variant capsid polypeptide comprises a sequence with an edit distance of 15 or lower to SEQ ID NO: 128, and further comprises the mutation set of said any one of SEQ ID NO: 128. In some embodiments, a variant capsid polypeptide comprises a sequence with an edit distance of 15 or lower to SEQ ID NO: 129, and further comprises the mutation set of said any one of SEQ ID NO: 129. In some embodiments, a variant capsid polypeptide comprises a sequence with an edit distance of 15 or lower to SEQ ID NO: 130, and further comprises the mutation set of said any one of SEQ ID NO: 130. In some embodiments, a variant capsid polypeptide comprises a sequence with an edit distance of 15 or lower to SEQ ID NO: 131, and further comprises the mutation set of said any one of SEQ ID NO: 131. In some embodiments, a variant capsid polypeptide comprises a sequence with an edit distance of 15 or lower to SEQ ID NO: 132, and further comprises the mutation set of said any one of SEQ ID NO: 132. In some embodiments, a variant capsid polypeptide comprises a sequence with an edit distance of 15 or lower to SEQ ID NO: 133, and further comprises the mutation set of said any one of SEQ ID NO: 133. In some embodiments, a variant capsid polypeptide comprises a sequence with an edit distance of 15 or lower to SEQ ID NO: 134, and further comprises the mutation set of said any one of SEQ ID NO: 134. In some embodiments, a variant capsid polypeptide comprises a sequence with an edit distance of 15 or lower to SEQ ID NO: 135, and further comprises the mutation set of said any one of SEQ ID NO: 135. In some embodiments, a variant capsid polypeptide comprises a sequence with an edit distance of 15 or lower to SEQ ID NO: 136, and further comprises the mutation set of said any one of SEQ ID NO: 136. In some embodiments, a variant capsid polypeptide comprises a sequence with an edit distance of 15 or lower to SEQ ID NO: 137, and further comprises the mutation set of said any one of SEQ ID NO: 137. In some embodiments, a variant capsid polypeptide comprises a sequence with an edit distance of 15 or lower to SEQ ID NO: 138, and further comprises the mutation set of said any one of SEQ ID NO: 138. In some embodiments, a variant capsid polypeptide comprises a sequence with an edit distance of 15 or lower to SEQ ID NO: 139, and further comprises the mutation set of said any one of SEQ ID NO: 139.

In some embodiments, described herein is a variant capsid polypeptide comprising a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprising: (a) 70% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes fewer than ten single amino acid mutations; (b) 80% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes ten to nineteen single amino acid mutations; or (c) 90% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes twenty or more single amino acid mutations. In such embodiments, the reference sequence used to calculate the edit distance (e.g., SEQ ID NO: 2) is the same as the sequence from which the mutation set present in the variant capsid polypeptide is derived. For example, in one embodiment, provided is a variant capsid polypeptide comprising a sequence with an edit distance of 15 or lower to SEQ ID NO: 2 and further comprising at least 5 of the 7 single amino acid mutations of the mutation set of SEQ ID NO: 2 (i.e., at least 5 of a valine at position 579, an isoleucine at position 592, a valine at position 593, an alanine at position 595, a leucine at position 596, a serine at position 598 and an alanine at position 601, with numbering all with respect to SEQ ID NO: 1).

In some embodiments, a variant capsid polypeptide comprising a sequence with an edit distance of 15 or lower to any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, optionally SEQ ID NO: 2, and further comprising:
(a) 70% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes fewer than ten single amino acid mutations;
(b) 80% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes ten to nineteen single amino acid mutations; or
(c) 90% or more of the single amino acid mutations in the mutation set of said any one of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, if the mutation set includes twenty or more single amino acid mutations.

In some embodiments, a variant capsid polypeptide comprises a sequence with an edit distance of 15 or lower to SEQ ID NO: 2, optionally SEQ ID NO: 2, and further comprises 70% or more of the single amino acid mutations in the mutation set of SEQ ID NO: 2. In some embodiments, a variant capsid polypeptide comprises a sequence with an edit distance of 15 or lower to SEQ ID NO: 14, optionally SEQ ID NO: 2, and further comprises 70% or more of the single amino acid mutations in the mutation set of SEQ ID NO: 14. In some embodiments, a variant capsid polypeptide comprises a sequence with an edit distance of 15 or lower to SEQ ID NO: 15, optionally SEQ ID NO: 2, and further comprises 70% or more of the single amino acid mutations in the mutation set of SEQ ID NO: 15. In some embodiments, a variant capsid polypeptide comprises a sequence with an edit distance of 15 or lower to SEQ ID NO: 16, optionally SEQ ID NO: 2, and further comprises 70% or more of the single amino acid mutations in the mutation set of SEQ ID NO: 16. In some embodiments, a variant capsid polypeptide comprises a sequence with an edit distance of 15 or lower to SEQ ID NO: 17, optionally SEQ ID NO: 2, and further comprises 70% or more of the single amino acid mutations in the mutation set of SEQ ID NO: 17. In some embodiments, a variant capsid polypeptide comprises a sequence with an edit distance of 15 or lower to SEQ ID NO: 18, optionally SEQ ID NO: 2, and further comprises 70% or more of the single amino acid mutations in the mutation set of SEQ ID NO: 18. In some embodiments, a variant capsid polypeptide comprises a sequence with an edit distance of 15 or lower to SEQ ID NO: 19, optionally SEQ ID NO: 2, and further comprises 70% or more of the single amino acid mutations in the mutation set of SEQ ID NO: 19. In some embodiments, a variant capsid polypeptide comprises a sequence with an edit distance of 15 or lower to SEQ ID NO: 20, optionally SEQ ID NO: 2, and further comprises 70% or more of the single amino acid mutations in the mutation set of SEQ ID NO: 20. In some embodiments, a variant capsid polypeptide comprises a sequence with an edit distance of 15 or lower to SEQ ID NO: 21, optionally SEQ ID NO: 2, and further comprises 70% or more of the single amino acid mutations in the mutation set of SEQ ID NO: 21. In some embodiments, a variant capsid polypeptide comprises a sequence with an edit distance of 15 or lower to SEQ ID NO: 22, optionally SEQ ID NO: 2, and further comprises 70% or more of the single amino acid mutations in the mutation set of SEQ ID NO: 22. In some embodiments, a variant capsid polypeptide comprises a sequence with an edit distance of 15 or lower to SEQ ID NO: 23, optionally SEQ ID NO: 2, and further comprises 70% or more of the single amino acid mutations in the mutation set of SEQ ID NO: 23. In some embodiments, a variant capsid polypeptide comprises a sequence with an edit distance of 15 or lower to SEQ ID NO: 24, optionally SEQ ID NO: 2, and further comprises 70% or more of the single amino acid mutations in the mutation set of SEQ ID NO: 24. In some embodiments, a variant capsid polypeptide comprises a sequence with an edit distance of 15 or lower to SEQ ID NO: 25, optionally SEQ ID NO: 2, and further comprises 70% or more of the single amino acid mutations in the mutation set of SEQ ID NO: 25. In some embodiments, a variant capsid polypeptide comprises a sequence with an edit distance of 15 or lower to SEQ ID NO: 26, optionally SEQ ID NO: 2, and further comprises 70% or more of the single amino acid mutations in the mutation set of SEQ ID NO: 26. In some embodiments, a variant capsid polypeptide comprises a sequence with an edit distance of 15 or lower to SEQ ID NO: 27, optionally SEQ ID NO: 2, and further comprises 70% or more of the single amino acid mutations in the mutation set of SEQ ID NO: 27. In some embodiments, a variant capsid polypeptide comprises a sequence with an edit distance of 15 or lower to SEQ ID NO: 28, optionally SEQ ID NO: 2, and further comprises 70% or more of the single amino acid mutations in the mutation set of SEQ ID NO: 28. In some embodiments, a variant capsid polypeptide comprises a sequence with an edit distance of 15 or lower to SEQ ID NO: 29, optionally SEQ ID NO: 2, and further comprises 70% or more of the single amino acid mutations in the mutation set of SEQ ID NO: 29. In some embodiments, a variant capsid polypeptide comprises a sequence with an edit distance of 15 or lower to SEQ ID NO: 30, optionally SEQ ID NO: 2, and further comprises 70% or more of the single amino acid mutations in the mutation set of SEQ ID NO: 30. In some embodiments, a variant capsid polypeptide comprises a sequence with an edit distance of 15 or lower to SEQ ID NO: 31, optionally SEQ ID NO: 2, and further comprises 70% or more of the single amino acid mutations in the mutation set of SEQ ID NO: 31. In some embodiments, a variant capsid polypeptide comprises a sequence with an edit distance of 15 or lower to SEQ ID NO: 32, optionally SEQ ID NO: 2, and further comprises 70% or more of the single amino acid mutations in the mutation set of SEQ ID NO: 32. In some embodiments, a variant capsid polypeptide comprises a sequence with an edit distance of 15 or lower to SEQ ID NO: 33, optionally SEQ ID NO: 2, and further comprises 70% or more of the single amino acid mutations in the mutation set of SEQ ID NO: 33. In some embodiments, a variant capsid polypeptide comprises a sequence with an edit distance of 15 or lower to SEQ ID NO: 34, optionally SEQ ID NO: 2, and further comprises 70% or more of the single amino acid mutations in the mutation set of SEQ ID NO: 34. In some embodiments, a variant capsid polypeptide comprises a sequence with an edit distance of 15 or lower to SEQ ID NO: 35, optionally SEQ ID NO: 2, and further comprises 70% or more of the single amino acid mutations in the mutation set of SEQ ID NO: 35. In some embodiments, a variant capsid polypeptide comprises a sequence with an edit distance of 15 or lower to SEQ ID NO: 36, optionally SEQ ID NO: 2, and further comprises 70% or more of the single amino acid mutations in the mutation set of SEQ ID NO: 36. In some embodiments, a variant capsid polypeptide comprises a sequence with an edit distance of 15 or lower to SEQ ID NO: 37, optionally SEQ ID NO: 2, and further comprises 70% or more of the single amino acid mutations in the mutation set of SEQ ID NO: 37. In some embodiments, a variant capsid polypeptide comprises a sequence with an edit distance of 15 or lower to SEQ ID NO: 38, optionally SEQ ID NO: 2, and further comprises 70% or more of the single amino acid mutations in the mutation set of SEQ ID NO: 38. In some embodiments, a variant capsid polypeptide comprises a sequence with an edit distance of 15 or lower to SEQ ID NO: 39, optionally SEQ ID NO: 2, and further comprises 70% or more of the single amino acid mutations in the mutation set of SEQ ID NO: 39. In some embodiments, a variant capsid polypeptide comprises a sequence with an edit distance of 15 or lower to SEQ ID NO: 40, optionally SEQ ID NO: 2, and further comprises 70% or more of the single amino acid mutations in the mutation set of SEQ ID NO: 40. In some embodiments, a variant capsid polypeptide comprises a sequence with an edit distance of 15 or lower to SEQ ID NO: 41, optionally SEQ ID NO: 2, and further comprises 70% or more of the single amino acid mutations in the mutation set of SEQ ID NO: 41. In some embodiments, a variant capsid polypeptide comprises a sequence with an edit distance of 15 or lower to SEQ ID NO: 42, optionally SEQ ID NO: 2, and further comprises 70% or more of the single amino acid mutations in the mutation set of SEQ ID NO: 42. In some embodiments, a variant capsid polypeptide comprises a sequence with an edit distance of 15 or lower to SEQ ID NO: 43, optionally SEQ ID NO: 2, and further comprises 70% or more of the single amino acid mutations in the mutation set of SEQ ID NO: 43. In some embodiments, a variant capsid polypeptide comprises a sequence with an edit distance of 15 or lower to SEQ ID NO: 44, optionally SEQ ID NO: 2, and further comprises 70% or more of the single amino acid mutations in the mutation set of SEQ ID NO: 44. In some embodiments, a variant capsid polypeptide comprises a sequence with an edit distance of 15 or lower to SEQ ID NO: 45, optionally SEQ ID NO: 2, and further comprises 70% or more of the single amino acid mutations in the mutation set of SEQ ID NO: 45. In some embodiments, a variant capsid polypeptide comprises a sequence with an edit distance of 15 or lower to SEQ ID NO: 46, optionally SEQ ID NO: 2, and further comprises 70% or more of the single amino acid mutations in the mutation set of SEQ ID NO: 46. In some embodiments, a variant capsid polypeptide comprises a sequence with an edit distance of 15 or lower to SEQ ID NO: 47, optionally SEQ ID NO: 2, and further comprises 70% or more of the single amino acid mutations in the mutation set of SEQ ID NO: 47. In some embodiments, a variant capsid polypeptide comprises a sequence with an edit distance of 15 or lower to SEQ ID NO:

48, optionally SEQ ID NO: 2, and further comprises 70% or more of the single amino acid mutations in the mutation set of SEQ ID NO: 48. In some embodiments, a variant capsid polypeptide comprises a sequence with an edit distance of 15 or lower to SEQ ID NO: 49, optionally SEQ ID NO: 2, and further comprises 70% or more of the single amino acid mutations in the mutation set of SEQ ID NO: 49. In some embodiments, a variant capsid polypeptide comprises a sequence with an edit distance of 15 or lower to SEQ ID NO: 50, optionally SEQ ID NO: 2, and further comprises 70% or more of the single amino acid mutations in the mutation set of SEQ ID NO: 50. In some embodiments, a variant capsid polypeptide comprises a sequence with an edit distance of 15 or lower to SEQ ID NO: 51, optionally SEQ ID NO: 2, and further comprises 70% or more of the single amino acid mutations in the mutation set of SEQ ID NO: 51. In some embodiments, a variant capsid polypeptide comprises a sequence with an edit distance of 15 or lower to SEQ ID NO: 52, optionally SEQ ID NO: 2, and further comprises 70% or more of the single amino acid mutations in the mutation set of SEQ ID NO: 52. In some embodiments, a variant capsid polypeptide comprises a sequence with an edit distance of 15 or lower to SEQ ID NO: 53, optionally SEQ ID NO: 2, and further comprises 70% or more of the single amino acid mutations in the mutation set of SEQ ID NO: 53. In some embodiments, a variant capsid polypeptide comprises a sequence with an edit distance of 15 or lower to SEQ ID NO: 54, optionally SEQ ID NO: 2, and further comprises 70% or more of the single amino acid mutations in the mutation set of SEQ ID NO: 54. In some embodiments, a variant capsid polypeptide comprises a sequence with an edit distance of 15 or lower to SEQ ID NO: 55, optionally SEQ ID NO: 2, and further comprises 70% or more of the single amino acid mutations in the mutation set of SEQ ID NO: 55. In some embodiments, a variant capsid polypeptide comprises a sequence with an edit distance of 15 or lower to SEQ ID NO: 56, optionally SEQ ID NO: 2, and further comprises 70% or more of the single amino acid mutations in the mutation set of SEQ ID NO: 56. In some embodiments, a variant capsid polypeptide comprises a sequence with an edit distance of 15 or lower to SEQ ID NO: 57, optionally SEQ ID NO: 2, and further comprises 70% or more of the single amino acid mutations in the mutation set of SEQ ID NO: 57. In some embodiments, a variant capsid polypeptide comprises a sequence with an edit distance of 15 or lower to SEQ ID NO: 58, optionally SEQ ID NO: 2, and further comprises 70% or more of the single amino acid mutations in the mutation set of SEQ ID NO: 58. In some embodiments, a variant capsid polypeptide comprises a sequence with an edit distance of 15 or lower to SEQ ID NO: 59, optionally SEQ ID NO: 2, and further comprises 70% or more of the single amino acid mutations in the mutation set of SEQ ID NO: 59. In some embodiments, a variant capsid polypeptide comprises a sequence with an edit distance of 15 or lower to SEQ ID NO: 60, optionally SEQ ID NO: 2, and further comprises 70% or more of the single amino acid mutations in the mutation set of SEQ ID NO: 60. In some embodiments, a variant capsid polypeptide comprises a sequence with an edit distance of 15 or lower to SEQ ID NO: 61, optionally SEQ ID NO: 2, and further comprises 70% or more of the single amino acid mutations in the mutation set of SEQ ID NO: 61. In some embodiments, a variant capsid polypeptide comprises a sequence with an edit distance of 15 or lower to SEQ ID NO: 62, optionally SEQ ID NO: 2, and further comprises 70% or more of the single amino acid mutations in the mutation set of SEQ ID NO: 62. In some embodiments, a variant capsid polypeptide comprises a sequence with an edit distance of 15 or lower to SEQ ID NO: 63, optionally SEQ ID NO: 2, and further comprises 70% or more of the single amino acid mutations in the mutation set of SEQ ID NO: 63. In some embodiments, a variant capsid polypeptide comprises a sequence with an edit distance of 15 or lower to SEQ ID NO: 64, optionally SEQ ID NO: 2, and further comprises 70% or more of the single amino acid mutations in the mutation set of SEQ ID NO: 64. In some embodiments, a variant capsid polypeptide comprises a sequence with an edit distance of 15 or lower to SEQ ID NO: 65, optionally SEQ ID NO: 2, and further comprises 70% or more of the single amino acid mutations in the mutation set of SEQ ID NO: 65. In some embodiments, a variant capsid polypeptide comprises a sequence with an edit distance of 15 or lower to SEQ ID NO: 66, optionally SEQ ID NO: 2, and further comprises 70% or more of the single amino acid mutations in the mutation set of SEQ ID NO: 66. In some embodiments, a variant capsid polypeptide comprises a sequence with an edit distance of 15 or lower to SEQ ID NO: 67, optionally SEQ ID NO: 2, and further comprises 70% or more of the single amino acid mutations in the mutation set of SEQ ID NO: 67. In some embodiments, a variant capsid polypeptide comprises a sequence with an edit distance of 15 or lower to SEQ ID NO: 68, optionally SEQ ID NO: 2, and further comprises 70% or more of the single amino acid mutations in the mutation set of SEQ ID NO: 68. In some embodiments, a variant capsid polypeptide comprises a sequence with an edit distance of 15 or lower to SEQ ID NO: 69, optionally SEQ ID NO: 2, and further comprises 70% or more of the single amino acid mutations in the mutation set of SEQ ID NO: 69. In some embodiments, a variant capsid polypeptide comprises a sequence with an edit distance of 15 or lower to SEQ ID NO: 70, optionally SEQ ID NO: 2, and further comprises 70% or more of the single amino acid mutations in the mutation set of SEQ ID NO: 70. In some embodiments, a variant capsid polypeptide comprises a sequence with an edit distance of 15 or lower to SEQ ID NO: 71, optionally SEQ ID NO: 2, and further comprises 70% or more of the single amino acid mutations in the mutation set of SEQ ID NO: 71. In some embodiments, a variant capsid polypeptide comprises a sequence with an edit distance of 15 or lower to SEQ ID NO: 72, optionally SEQ ID NO: 2, and further comprises 70% or more of the single amino acid mutations in the mutation set of SEQ ID NO: 72. In some embodiments, a variant capsid polypeptide comprises a sequence with an edit distance of 15 or lower to SEQ ID NO: 73, optionally SEQ ID NO: 2, and further comprises 70% or more of the single amino acid mutations in the mutation set of SEQ ID NO: 73. In some embodiments, a variant capsid polypeptide comprises a sequence with an edit distance of 15 or lower to SEQ ID NO: 74, optionally SEQ ID NO: 2, and further comprises 70% or more of the single amino acid mutations in the mutation set of SEQ ID NO: 74. In some embodiments, a variant capsid polypeptide comprises a sequence with an edit distance of 15 or lower to SEQ ID NO: 75, optionally SEQ ID NO: 2, and further comprises 70% or more of the single amino acid mutations in the mutation set of SEQ ID NO: 75. In some embodiments, a variant capsid polypeptide comprises a sequence with an edit distance of 15 or lower to SEQ ID NO: 76, optionally SEQ ID NO: 2, and further comprises 70% or more of the single amino acid mutations in the mutation set of SEQ ID NO: 76. In some embodiments, a variant capsid polypeptide comprises a sequence with an edit distance of 15 or lower to SEQ ID NO: 77, optionally SEQ ID NO: 2, and further comprises 70% or more of the single amino acid mutations in the mutation set of SEQ ID NO: 77. In some embodiments, a variant capsid polypeptide comprises a sequence with an edit distance of 15 or lower to SEQ ID NO: 78, optionally SEQ ID NO: 2, and further comprises 70% or more of the single amino acid mutations in the mutation set of SEQ ID NO: 78. In some embodiments, a variant capsid polypeptide comprises a sequence with an edit distance of 15 or lower to SEQ ID NO: 79, optionally SEQ ID NO: 2, and further comprises 70% or more of the single amino acid mutations in the mutation set of SEQ ID NO: 79. In some embodiments, a variant capsid polypeptide comprises a sequence with an edit distance of 15 or lower to SEQ ID NO: 80, optionally SEQ ID NO: 2, and further comprises 70% or more of the single amino acid mutations in the mutation set of SEQ ID NO: 80. In some embodiments, a variant capsid polypeptide comprises a sequence with an edit distance of 15 or lower to SEQ ID NO: 81, optionally SEQ ID NO: 2, and further comprises 70% or more of the single amino acid mutations in the mutation set of SEQ ID NO: 81. In some embodiments, a variant capsid polypeptide comprises a sequence with an edit distance of 15 or lower to SEQ ID NO: 82, optionally SEQ ID NO: 2, and further comprises 70% or more of the single amino acid mutations in the mutation set of SEQ ID NO: 82. In some embodiments, a variant capsid polypeptide comprises a sequence with an edit distance of 15 or lower to SEQ ID NO: 83, optionally SEQ ID NO: 2, and further comprises 70% or more of the single amino acid mutations in the mutation set of SEQ ID NO: 83. In some embodiments, a variant capsid polypeptide comprises a sequence with an edit distance of 15 or lower to SEQ ID NO: 84, optionally SEQ ID NO: 2, and further comprises 70% or more of the single amino acid mutations in the mutation set of SEQ ID NO: 84. In some embodiments, a variant capsid polypeptide comprises a sequence with an edit distance of 15 or lower to SEQ ID NO: 85, optionally SEQ ID NO: 2, and further comprises 70% or more of the single amino acid mutations in the mutation set of SEQ ID NO: 85. In some embodiments, a variant capsid polypeptide comprises a sequence with an edit distance of 15 or lower to SEQ ID NO: 86, optionally SEQ ID NO: 2, and further comprises 70% or more of the single amino acid mutations in the mutation set of SEQ ID NO: 86. In some embodiments, a variant capsid polypeptide comprises a sequence with an edit distance of 15 or lower to SEQ ID NO: 87, optionally SEQ ID NO: 2, and further comprises 70% or more of the single amino acid mutations in the mutation set of SEQ ID NO: 87. In some embodiments, a variant capsid polypeptide comprises a sequence with an edit distance of 15 or lower to SEQ ID NO: 88, optionally SEQ ID NO: 2, and further comprises 70% or more of the single amino acid mutations in the mutation set of SEQ ID NO: 88. In some embodiments, a variant capsid polypeptide comprises a sequence with an edit distance of 15 or lower to SEQ ID NO: 89, optionally SEQ ID NO: 2, and further comprises 70% or more of the single amino acid mutations in the mutation set of SEQ ID NO: 89. In some embodiments, a variant capsid polypeptide comprises a sequence with an edit distance of 15 or lower to SEQ ID NO: 90, optionally SEQ ID NO: 2, and further comprises 70% or more of the single amino acid mutations in the mutation set of SEQ ID NO: 90. In some embodiments, a variant capsid polypeptide comprises a sequence with an edit distance of 15 or lower to SEQ ID NO: 91, optionally SEQ ID NO: 2, and further comprises 70% or more of the single amino acid mutations in the mutation set of SEQ ID NO: 91. In some embodiments, a variant capsid polypeptide comprises a sequence with an edit distance of 15 or lower to SEQ ID NO: 92, optionally SEQ ID NO: 2, and further comprises 70% or more of the single amino acid mutations in the mutation set of SEQ ID NO: 92. In some embodiments, a variant capsid polypeptide comprises a sequence with an edit distance of 15 or lower to SEQ ID NO: 93, optionally SEQ ID NO: 2, and further comprises 70% or more of the single amino acid mutations in the mutation set of SEQ ID NO: 93. In some embodiments, a variant capsid polypeptide comprises a sequence with an edit distance of 15 or lower to SEQ ID NO: 94, optionally SEQ ID NO: 2, and further comprises 70% or more of the single amino acid mutations in the mutation set of SEQ ID NO: 94. In some embodiments, a variant capsid polypeptide comprises a sequence with an edit distance of 15 or lower to SEQ ID NO: 95, optionally SEQ ID NO: 2, and further comprises 70% or more of the single amino acid mutations in the mutation set of SEQ ID NO: 95. In some embodiments, a variant capsid polypeptide comprises a sequence with an edit distance of 15 or lower to SEQ ID NO: 96, optionally SEQ ID NO: 2, and further comprises 70% or more of the single amino acid mutations in the mutation set of SEQ ID NO: 96. In some embodiments, a variant capsid polypeptide comprises a sequence with an edit distance of 15 or lower to SEQ ID NO: 97, optionally SEQ ID NO: 2, and further comprises 70% or more of the single amino acid mutations in the mutation set of SEQ ID NO: 97. In some embodiments, a variant capsid polypeptide comprises a sequence with an edit distance of 15 or lower to SEQ ID NO: 98, optionally SEQ ID NO: 2, and further comprises 70% or more of the single amino acid mutations in the mutation set of SEQ ID NO: 98. In some embodiments, a variant capsid polypeptide comprises a sequence with an edit distance of 15 or lower to SEQ ID NO: 99, optionally SEQ ID NO: 2, and further comprises 70% or more of the single amino acid mutations in the mutation set of SEQ ID NO: 99. In some embodiments, a variant capsid polypeptide comprises a sequence with an edit distance of 15 or lower to SEQ ID NO: 100, optionally SEQ ID NO: 2, and further comprises 70% or more of the single amino acid mutations in the mutation set of SEQ ID NO: 100. In some embodiments, a variant capsid polypeptide comprises a sequence with an edit distance of 15 or lower to SEQ ID NO: 101, optionally SEQ ID NO: 2, and further comprises 70% or more of the single amino acid mutations in the mutation set of SEQ ID NO: 101. In some embodiments, a variant capsid polypeptide comprises a sequence with an edit distance of 15 or lower to SEQ ID NO: 102, optionally SEQ ID NO: 2, and further comprises 70% or more of the single amino acid mutations in the mutation set of SEQ ID NO: 102. In some embodiments, a variant capsid polypeptide comprises a sequence with an edit distance of 15 or lower to SEQ ID NO: 103, optionally SEQ ID NO: 2, and further comprises 70% or more of the single amino acid mutations in the mutation set of SEQ ID NO: 103. In some embodiments, a variant capsid polypeptide comprises a sequence with an edit distance of 15 or lower to SEQ ID NO: 104, optionally SEQ ID NO: 2, and further comprises 70% or more of the single amino acid mutations in the mutation set of SEQ ID NO: 104. In some embodiments, a variant capsid polypeptide comprises a sequence with an edit distance of 15 or lower to SEQ ID NO: 105, optionally SEQ ID NO: 2, and further comprises 70% or more of the single amino acid mutations in the mutation set of SEQ ID NO: 105. In some embodiments, a variant capsid polypeptide comprises a sequence with an edit distance of 15 or lower to SEQ ID NO: 106, optionally SEQ ID NO: 2, and further comprises 70% or more of the single amino acid mutations in the mutation set of SEQ ID NO: 106. In some embodiments, a variant capsid polypeptide comprises a sequence with an edit distance of 15 or lower to SEQ ID NO: 107, optionally SEQ ID NO: 2, and further comprises 70% or more of the single amino acid mutations in the mutation set of SEQ ID NO: 107. In some embodiments, a variant capsid polypeptide comprises a sequence with an edit distance of 15 or lower to SEQ ID NO: 108, optionally SEQ ID NO: 2, and further comprises 70% or more of the single amino acid mutations in the mutation set of SEQ ID NO: 108. In some embodiments, a variant capsid polypeptide comprises a sequence with an edit distance of 15 or lower to SEQ ID NO: 109, optionally SEQ ID NO: 2, and further comprises 70% or more of the single amino acid mutations in the mutation set of SEQ ID NO: 109. In some embodiments, a variant capsid polypeptide comprises a sequence with an edit distance of 15 or lower to SEQ ID NO: 110, optionally SEQ ID NO: 2, and further comprises 70% or more of the single amino acid mutations in the mutation set of SEQ ID NO: 110. In some embodiments, a variant capsid polypeptide comprises a sequence with an edit distance of 15 or lower to SEQ ID NO: 111, optionally SEQ ID NO: 2, and further comprises 70% or more of the single amino acid mutations in the mutation set of SEQ ID NO: 111. In some embodiments, a variant capsid polypeptide comprises a sequence with an edit distance of 15 or lower to SEQ ID NO: 112, optionally SEQ ID NO: 2, and further comprises 70% or more of the single amino acid mutations in the mutation set of SEQ ID NO: 112. In some embodiments, a variant capsid polypeptide comprises a sequence with an edit distance of 15 or lower to SEQ ID NO: 113, optionally SEQ ID NO: 2, and further comprises 70% or more of the single amino acid mutations in the mutation set of SEQ ID NO: 113. In some embodiments, a variant capsid polypeptide comprises a sequence with an edit distance of 15 or lower to SEQ ID NO: 114, optionally SEQ ID NO: 2, and further comprises 70% or more of the single amino acid mutations in the mutation set of SEQ ID NO: 114. In some embodiments, a variant capsid polypeptide comprises a sequence with an edit distance of 15 or lower to SEQ ID NO: 115, optionally SEQ ID NO: 2, and further comprises 70% or more of the single amino acid mutations in the mutation set of SEQ ID NO: 115. In some embodiments, a variant capsid polypeptide comprises a sequence with an edit distance of 15 or lower to SEQ ID NO: 116, optionally SEQ ID NO: 2, and further comprises 70% or more of the single amino acid mutations in the mutation set of SEQ ID NO: 116. In some embodiments, a variant capsid polypeptide comprises a sequence with an edit distance of 15 or lower to SEQ ID NO: 117, optionally SEQ ID NO: 2, and further comprises 70% or more of the single amino acid mutations in the mutation set of SEQ ID NO: 117. In some embodiments, a variant capsid polypeptide comprises a sequence with an edit distance of 15 or lower to SEQ ID NO: 118, optionally SEQ ID NO: 2, and further comprises 70% or more of the single amino acid mutations in the mutation set of SEQ ID NO: 118. In some embodiments, a variant capsid polypeptide comprises a sequence with an edit distance of 15 or lower to SEQ ID NO: 119, optionally SEQ ID NO: 2, and further comprises 70% or more of the single amino acid mutations in the mutation set of SEQ ID NO: 119. In some embodiments, a variant capsid polypeptide comprises a sequence with an edit distance of 15 or lower to SEQ ID NO: 120, optionally SEQ ID NO: 2, and further comprises 70% or more of the single amino acid mutations in the mutation set of SEQ ID NO: 120. In some embodiments, a variant capsid polypeptide comprises a sequence with an edit distance of 15 or lower to SEQ ID NO: 121, optionally SEQ ID NO: 2, and further comprises 70% or more of the single amino acid mutations in the mutation set of SEQ ID NO: 121. In some embodiments, a variant capsid polypeptide comprises a sequence with an edit distance of 15 or lower to SEQ ID NO: 122, optionally SEQ ID NO: 2, and further comprises 70% or more of the single amino acid mutations in the mutation set of SEQ ID NO: 122. In some embodiments, a variant capsid polypeptide comprises a sequence with an edit distance of 15 or lower to SEQ ID NO: 123, optionally SEQ ID NO: 2, and further comprises 70% or more of the single amino acid mutations in the mutation set of SEQ ID NO: 123. In some embodiments, a variant capsid polypeptide comprises a sequence with an edit distance of 15 or lower to SEQ ID NO: 124, optionally SEQ ID NO: 2, and further comprises 70% or more of the single amino acid mutations in the mutation set of SEQ ID NO: 124. In some embodiments, a variant capsid polypeptide comprises a sequence with an edit distance of 15 or lower to SEQ ID NO: 125, optionally SEQ ID NO: 2, and further comprises 70% or more of the single amino acid mutations in the mutation set of SEQ ID NO: 125. In some embodiments, a variant capsid polypeptide comprises a sequence with an edit distance of 15 or lower to SEQ ID NO: 126, optionally SEQ ID NO: 2, and further comprises 70% or more of the single amino acid mutations in the mutation set of SEQ ID NO: 126. In some embodiments, a variant capsid polypeptide comprises a sequence with an edit distance of 15 or lower to SEQ ID NO: 127, optionally SEQ ID NO: 2, and further comprises 70% or more of the single amino acid mutations in the mutation set of SEQ ID NO: 127. In some embodiments, a variant capsid polypeptide comprises a sequence with an edit distance of 15 or lower to SEQ ID NO: 128, optionally SEQ ID NO: 2, and further comprises 70% or more of the single amino acid mutations in the mutation set of SEQ ID NO: 128. In some embodiments, a variant capsid polypeptide comprises a sequence with an edit distance of 15 or lower to SEQ ID NO: 129, optionally SEQ ID NO: 2, and further comprises 70% or more of the single amino acid mutations in the mutation set of SEQ ID NO: 129. In some embodiments, a variant capsid polypeptide comprises a sequence with an edit distance of 15 or lower to SEQ ID NO: 130, optionally SEQ ID NO: 2, and further comprises 70% or more of the single amino acid mutations in the mutation set of SEQ ID NO: 130. In some embodiments, a variant capsid polypeptide comprises a sequence with an edit distance of 15 or lower to SEQ ID NO: 131, optionally SEQ ID NO: 2, and further comprises 70% or more of the single amino acid mutations in the mutation set of SEQ ID NO: 131. In some embodiments, a variant capsid polypeptide comprises a sequence with an edit distance of 15 or lower to SEQ ID NO: 132, optionally SEQ ID NO: 2, and further comprises 70% or more of the single amino acid mutations in the mutation set of SEQ ID NO: 132. In some embodiments, a variant capsid polypeptide comprises a sequence with an edit distance of 15 or lower to SEQ ID NO: 133, optionally SEQ ID NO: 2, and further comprises 70% or more of the single amino acid mutations in the mutation set of SEQ ID NO: 133. In some embodiments, a variant capsid polypeptide comprises a sequence with an edit distance of 15 or lower to SEQ ID NO: 134, optionally SEQ ID NO: 2, and further comprises 70% or more of the single amino acid mutations in the mutation set of SEQ ID NO: 134. In some embodiments, a variant capsid polypeptide comprises a sequence with an edit distance of 15 or lower to SEQ ID NO: 135, optionally SEQ ID NO: 2, and further comprises 70% or more of the single amino acid mutations in the mutation set of SEQ ID NO: 135. In some embodiments, a variant capsid polypeptide comprises a sequence with an edit distance of 15 or lower to SEQ ID NO: 136, optionally SEQ ID NO: 2, and further comprises 70% or more of the single amino acid mutations in the mutation set of SEQ ID NO:

136. In some embodiments, a variant capsid polypeptide comprises a sequence with an edit distance of 15 or lower to SEQ ID NO: 137, optionally SEQ ID NO: 2, and further comprises 70% or more of the single amino acid mutations in the mutation set of SEQ ID NO: 137. In some embodiments, a variant capsid polypeptide comprises a sequence with an edit distance of 15 or lower to SEQ ID NO: 138, optionally SEQ ID NO: 2, and further comprises 70% or more of the single amino acid mutations in the mutation set of SEQ ID NO: 138. In some embodiments, a variant capsid polypeptide comprises a sequence with an edit distance of 15 or lower to SEQ ID NO: 139, optionally SEQ ID NO: 2, and further comprises 70% or more of the single amino acid mutations in the mutation set of SEQ ID NO: 139.

In some embodiments, the variant capsid polypeptide comprises the mutation set of SEQ ID NO: 2. In some embodiments, the variant capsid polypeptide comprises the mutation set of SEQ ID NO: 14. In some embodiments, the variant capsid polypeptide comprises the mutation set of SEQ ID NO: 15. In some embodiments, the variant capsid polypeptide comprises the mutation set of SEQ ID NO: 16. In some embodiments, the variant capsid polypeptide comprises the mutation set of SEQ ID NO: 17. In some embodiments, the variant capsid polypeptide comprises the mutation set of SEQ ID NO: 18. In some embodiments, the variant capsid polypeptide comprises the mutation set of SEQ ID NO: 19. In some embodiments, the variant capsid polypeptide comprises the mutation set of SEQ ID NO: 20. In some embodiments, the variant capsid polypeptide comprises the mutation set of SEQ ID NO: 21. In some embodiments, the variant capsid polypeptide comprises the mutation set of SEQ ID NO: 22. In some embodiments, the variant capsid polypeptide comprises the mutation set of SEQ ID NO: 23. In some embodiments, the variant capsid polypeptide comprises the mutation set of SEQ ID NO: 24. In some embodiments, the variant capsid polypeptide comprises the mutation set of SEQ ID NO: 25. In some embodiments, the variant capsid polypeptide comprises the mutation set of SEQ ID NO: 26. In some embodiments, the variant capsid polypeptide comprises the mutation set of SEQ ID NO: 27. In some embodiments, the variant capsid polypeptide comprises the mutation set of SEQ ID NO: 28. In some embodiments, the variant capsid polypeptide comprises the mutation set of SEQ ID NO: 29. In some embodiments, the variant capsid polypeptide comprises the mutation set of SEQ ID NO: 30. In some embodiments, the variant capsid polypeptide comprises the mutation set of SEQ ID NO: 31. In some embodiments, the variant capsid polypeptide comprises the mutation set of SEQ ID NO: 32. In some embodiments, the variant capsid polypeptide comprises the mutation set of SEQ ID NO: 33. In some embodiments, the variant capsid polypeptide comprises the mutation set of SEQ ID NO: 34. In some embodiments, the variant capsid polypeptide comprises the mutation set of SEQ ID NO: 35. In some embodiments, the variant capsid polypeptide comprises the mutation set of SEQ ID NO: 36. In some embodiments, the variant capsid polypeptide comprises the mutation set of SEQ ID NO: 37. In some embodiments, the variant capsid polypeptide comprises the mutation set of SEQ ID NO: 38. In some embodiments, the variant capsid polypeptide comprises the mutation set of SEQ ID NO: 39. In some embodiments, the variant capsid polypeptide comprises the mutation set of SEQ ID NO: 40. In some embodiments, the variant capsid polypeptide comprises the mutation set of SEQ ID NO: 41. In some embodiments, the variant capsid polypeptide comprises the mutation set of SEQ ID NO: 42. In some embodiments, the variant capsid polypeptide comprises the mutation set of SEQ ID NO: 43. In some embodiments, the variant capsid polypeptide comprises the mutation set of SEQ ID NO: 44. In some embodiments, the variant capsid polypeptide comprises the mutation set of SEQ ID NO: 45. In some embodiments, the variant capsid polypeptide comprises the mutation set of SEQ ID NO: 46. In some embodiments, the variant capsid polypeptide comprises the mutation set of SEQ ID NO: 47. In some embodiments, the variant capsid polypeptide comprises the mutation set of SEQ ID NO: 48. In some embodiments, the variant capsid polypeptide comprises the mutation set of SEQ ID NO: 49. In some embodiments, the variant capsid polypeptide comprises the mutation set of SEQ ID NO: 50. In some embodiments, the variant capsid polypeptide comprises the mutation set of SEQ ID NO: 51. In some embodiments, the variant capsid polypeptide comprises the mutation set of SEQ ID NO: 52. In some embodiments, the variant capsid polypeptide comprises the mutation set of SEQ ID NO: 53. In some embodiments, the variant capsid polypeptide comprises the mutation set of SEQ ID NO: 54. In some embodiments, the variant capsid polypeptide comprises the mutation set of SEQ ID NO: 55. In some embodiments, the variant capsid polypeptide comprises the mutation set of SEQ ID NO: 56. In some embodiments, the variant capsid polypeptide comprises the mutation set of SEQ ID NO: 57. In some embodiments, the variant capsid polypeptide comprises the mutation set of SEQ ID NO: 58. In some embodiments, the variant capsid polypeptide comprises the mutation set of SEQ ID NO: 59. In some embodiments, the variant capsid polypeptide comprises the mutation set of SEQ ID NO: 60. In some embodiments, the variant capsid polypeptide comprises the mutation set of SEQ ID NO: 61. In some embodiments, the variant capsid polypeptide comprises the mutation set of SEQ ID NO: 62. In some embodiments, the variant capsid polypeptide comprises the mutation set of SEQ ID NO: 63. In some embodiments, the variant capsid polypeptide comprises the mutation set of SEQ ID NO: 64. In some embodiments, the variant capsid polypeptide comprises the mutation set of SEQ ID NO: 65. In some embodiments, the variant capsid polypeptide comprises the mutation set of SEQ ID NO: 66. In some embodiments, the variant capsid polypeptide comprises the mutation set of SEQ ID NO: 67. In some embodiments, the variant capsid polypeptide comprises the mutation set of SEQ ID NO: 68. In some embodiments, the variant capsid polypeptide comprises the mutation set of SEQ ID NO: 69. In some embodiments, the variant capsid polypeptide comprises the mutation set of SEQ ID NO: 70. In some embodiments, the variant capsid polypeptide comprises the mutation set of SEQ ID NO: 71. In some embodiments, the variant capsid polypeptide comprises the mutation set of SEQ ID NO: 72. In some embodiments, the variant capsid polypeptide comprises the mutation set of SEQ ID NO: 73. In some embodiments, the variant capsid polypeptide comprises the mutation set of SEQ ID NO: 74. In some embodiments, the variant capsid polypeptide comprises the mutation set of SEQ ID NO: 75. In some embodiments, the variant capsid polypeptide comprises the mutation set of SEQ ID NO: 76. In some embodiments, the variant capsid polypeptide comprises the mutation set of SEQ ID NO: 77. In some embodiments, the variant capsid polypeptide comprises the mutation set of SEQ ID NO: 78. In some embodiments, the variant capsid polypeptide comprises the mutation set of SEQ ID NO: 79. In some embodiments, the variant capsid polypeptide comprises the mutation set of SEQ ID NO: 80. In some embodiments, the variant capsid polypeptide comprises the mutation set of SEQ ID NO: 81. In some embodiments, the variant capsid polypeptide comprises the mutation set of SEQ ID NO: 82. In some embodiments, the variant capsid polypeptide comprises the mutation set of SEQ ID NO: 83. In some embodiments, the variant capsid polypeptide comprises the mutation set of SEQ ID NO: 84. In some embodiments, the variant capsid polypeptide comprises the mutation set of SEQ ID NO: 85. In some embodiments, the variant capsid polypeptide comprises the mutation set of SEQ ID NO: 86. In some embodiments, the variant capsid polypeptide comprises the mutation set of SEQ ID NO: 87. In some embodiments, the variant capsid polypeptide comprises the mutation set of SEQ ID NO: 88. In some embodiments, the variant capsid polypeptide comprises the mutation set of SEQ ID NO: 89. In some embodiments, the variant capsid polypeptide comprises the mutation set of SEQ ID NO: 90. In some embodiments, the variant capsid polypeptide comprises the mutation set of SEQ ID NO: 91. In some embodiments, the variant capsid polypeptide comprises the mutation set of SEQ ID NO: 92. In some embodiments, the variant capsid polypeptide comprises the mutation set of SEQ ID NO: 93. In some embodiments, the variant capsid polypeptide comprises the mutation set of SEQ ID NO: 94. In some embodiments, the variant capsid polypeptide comprises the mutation set of SEQ ID NO: 95. In some embodiments, the variant capsid polypeptide comprises the mutation set of SEQ ID NO: 96. In some embodiments, the variant capsid polypeptide comprises the mutation set of SEQ ID NO: 97. In some embodiments, the variant capsid polypeptide comprises the mutation set of SEQ ID NO: 98. In some embodiments, the variant capsid polypeptide comprises the mutation set of SEQ ID NO: 99. In some embodiments, the variant capsid polypeptide comprises the mutation set of SEQ ID NO: 100. In some embodiments, the variant capsid polypeptide comprises the mutation set of SEQ ID NO: 101. In some embodiments, the variant capsid polypeptide comprises the mutation set of SEQ ID NO: 102. In some embodiments, the variant capsid polypeptide comprises the mutation set of SEQ ID NO: 103. In some embodiments, the variant capsid polypeptide comprises the mutation set of SEQ ID NO: 104. In some embodiments, the variant capsid polypeptide comprises the mutation set of SEQ ID NO: 105. In some embodiments, the variant capsid polypeptide comprises the mutation set of SEQ ID NO: 106. In some embodiments, the variant capsid polypeptide comprises the mutation set of SEQ ID NO: 107. In some embodiments, the variant capsid polypeptide comprises the mutation set of SEQ ID NO: 108. In some embodiments, the variant capsid polypeptide comprises the mutation set of SEQ ID NO: 109. In some embodiments, the variant capsid polypeptide comprises the mutation set of SEQ ID NO: 110. In some embodiments, the variant capsid polypeptide comprises the mutation set of SEQ ID NO: 111. In some embodiments, the variant capsid polypeptide comprises the mutation set of SEQ ID NO: 112. In some embodiments, the variant capsid polypeptide comprises the mutation set of SEQ ID NO: 113. In some embodiments, the variant capsid polypeptide comprises the mutation set of SEQ ID NO: 114. In some embodiments, the variant capsid polypeptide comprises the mutation set of SEQ ID NO: 115. In some embodiments, the variant capsid polypeptide comprises the mutation set of SEQ ID NO: 116. In some embodiments, the variant capsid polypeptide comprises the mutation set of SEQ ID NO: 117. In some embodiments, the variant capsid polypeptide comprises the mutation set of SEQ ID NO: 118. In some embodiments, the variant capsid polypeptide comprises the mutation set of SEQ ID NO: 119. In some embodiments, the variant capsid polypeptide comprises the mutation set of SEQ ID NO: 120. In some embodiments, the variant capsid polypeptide comprises the mutation set of SEQ ID NO: 121. In some embodiments, the variant capsid polypeptide comprises the mutation set of SEQ ID NO: 122. In some embodiments, the variant capsid polypeptide comprises the mutation set of SEQ ID NO: 123. In some embodiments, the variant capsid polypeptide comprises the mutation set of SEQ ID NO: 124. In some embodiments, the variant capsid polypeptide comprises the mutation set of SEQ ID NO: 125. In some embodiments, the variant capsid polypeptide comprises the mutation set of SEQ ID NO: 126. In some embodiments, the variant capsid polypeptide comprises the mutation set of SEQ ID NO: 127. In some embodiments, the variant capsid polypeptide comprises the mutation set of SEQ ID NO: 128. In some embodiments, the variant capsid polypeptide comprises the mutation set of SEQ ID NO: 129. In some embodiments, the variant capsid polypeptide comprises the mutation set of SEQ ID NO: 130. In some embodiments, the variant capsid polypeptide comprises the mutation set of SEQ ID NO: 131. In some embodiments, the variant capsid polypeptide comprises the mutation set of SEQ ID NO: 132. In some embodiments, the variant capsid polypeptide comprises the mutation set of SEQ ID NO: 133. In some embodiments, the variant capsid polypeptide comprises the mutation set of SEQ ID NO: 134. In some embodiments, the variant capsid polypeptide comprises the mutation set of SEQ ID NO: 135. In some embodiments, the variant capsid polypeptide comprises the mutation set of SEQ ID NO: 136. In some embodiments, the variant capsid polypeptide comprises the mutation set of SEQ ID NO: 137. In some embodiments, the variant capsid polypeptide comprises the mutation set of SEQ ID NO: 138. In some embodiments, the variant capsid polypeptide comprises the mutation set of SEQ ID NO: 139.

In some embodiments, the nucleic acid molecule encodes a variant capsid polypeptide as provided herein.

In some embodiments, the nucleic acid molecule encodes a variant capsid polypeptide that is at least 70%, 75%, 80%, 85%, 90%, 91%, 92%, 93%, 94%, 95%, 96%, 97%, 98%, 99%, or 100% identical to a variant capsid polypeptide as provided herein.

In some embodiments, a variant capsid polypeptide is provided that comprises a variant capsid polypeptide that is at least 70%, 75%, 80%, 85%, 90%, 91%, 92%, 93%, 94%, 95%, 96%, 97%, 98%, 99%, or 100% identical to a variant capsid polypeptide as provided herein.

In some embodiments where capsid polypeptides and variant capsid polypeptide sequences are concerned, it would be understood by one of ordinary skill in the art that when a VP1 sequence is disclosed, that sequence also discloses a VP2 sequence and a VP3 sequence as fragments thereof and as described herein. Thus, in some embodiments, variant capsid polypeptides disclosed herein are VP1 sequences, and in such cases, sequence identity or other comparison to reference sequences are with respect to the corresponding VP1 sequence. In other embodiments, variant capsid polypeptides disclosed herein are VP2 sequences, and in such cases sequence identity or other comparison to a reference sequence are with respect to the corresponding VP2 sequence. In other embodiments the variant capsid polypeptides disclosed herein are VP3 sequences, and in such cases, sequence identity or other comparisons to a reference sequence are made with respect to the corresponding VP3 sequence.

In some embodiments, the variant capsid polypeptide comprises a VP1, VP2, or VP3 sequence that is at least, or about, 95, 96, 97, 98 or 99% identical to a polypeptide of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the variant capsid polypeptide comprises a VP1, VP2, or VP3 sequence that has about 1 to about 20 mutations as compared to a polypeptide of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the variant capsid polypeptide comprises a VP1, VP2, or VP3 sequence that has about 1 to about 10 mutations as compared to a polypeptide of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the variant capsid polypeptide comprises a VP1, VP2, or VP3 sequence that has about 1 to about 5 mutations as compared to a polypeptide of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the variant capsid polypeptide comprising a VP1, VP2, or VP3, or any combination thereof, that is each at least, or about, 95, 96, 97, 98 or 99% identical to a polypeptide of SEQ ID NO: 2 and comprises the V596L mutation.

In some embodiments, the variant capsid polypeptide comprising a VP1, VP2, or VP3, or any combination thereof, that each has about 1 to about 20 mutations as compared to a polypeptide of SEQ ID NO: 2 and comprises the V596L mutation.

In some embodiments, the variant capsid polypeptide comprising a VP1, VP2, or VP3, or any combination thereof, that each has about 1 to about 10 mutations as compared to a polypeptide of SEQ ID NO: 2 and comprises the V596L mutation.

In some embodiments, the variant capsid polypeptide comprising a VP1, VP2, or VP3, or any combination thereof, that each has about 1 to about 5 mutations as compared to a polypeptide of SEQ ID NO: 2 and comprises the V596L mutation.

In some embodiments, the variant capsid polypeptide comprises a VP1, VP2 or VP3 sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, the variant capsid polypeptide comprises a VP1, VP2 or VP3 sequence of SEQ ID NO: 2. In some embodiments, the variant capsid polypeptide comprises a VP1, VP2 or VP3 sequence of SEQ ID NO: 14. In some embodiments, the variant capsid polypeptide comprises a VP1, VP2 or VP3 sequence of SEQ ID NO: 15. In some embodiments, the variant capsid polypeptide comprises a VP1, VP2 or VP3 sequence of SEQ ID NO: 16. In some embodiments, the variant capsid polypeptide comprises a VP1, VP2 or VP3 sequence of SEQ ID NO: 17. In some embodiments, the variant capsid polypeptide comprises a VP1, VP2 or VP3 sequence of SEQ ID NO: 18. In some embodiments, the variant capsid polypeptide comprises a VP1, VP2 or VP3 sequence of SEQ ID NO: 19. In some embodiments, the variant capsid polypeptide comprises a VP1, VP2 or VP3 sequence of SEQ ID NO: 20. In some embodiments, the variant capsid polypeptide comprises a VP1, VP2 or VP3 sequence of SEQ ID NO: 21. In some embodiments, the variant capsid polypeptide comprises a VP1, VP2 or VP3 sequence of SEQ ID NO: 22. In some embodiments, the variant capsid polypeptide comprises a VP1, VP2 or VP3 sequence of SEQ ID NO: 23. In some embodiments, the variant capsid polypeptide comprises a VP1, VP2 or VP3 sequence of SEQ ID NO: 24. In some embodiments, the variant capsid polypeptide comprises a VP1, VP2 or VP3 sequence of SEQ ID NO: 25. In some embodiments, the variant capsid polypeptide comprises a VP1, VP2 or VP3 sequence of SEQ ID NO: 26. In some embodiments, the variant capsid polypeptide comprises a VP1, VP2 or VP3 sequence of SEQ ID NO: 27. In some embodiments, the variant capsid polypeptide comprises a VP1, VP2 or VP3 sequence of SEQ ID NO: 28. In some embodiments, the variant capsid polypeptide comprises a VP1, VP2 or VP3 sequence of SEQ ID NO: 29. In some embodiments, the variant capsid polypeptide comprises a VP1, VP2 or VP3 sequence of SEQ ID NO: 30. In some embodiments, the variant capsid polypeptide comprises a VP1, VP2 or VP3 sequence of SEQ ID NO: 31. In some embodiments, the variant capsid polypeptide comprises a VP1, VP2 or VP3 sequence of SEQ ID NO: 32. In some embodiments, the variant capsid polypeptide comprises a VP1, VP2 or VP3 sequence of SEQ ID NO: 33. In some embodiments, the variant capsid polypeptide comprises a VP1, VP2 or VP3 sequence of SEQ ID NO: 34. In some embodiments, the variant capsid polypeptide comprises a VP1, VP2 or VP3 sequence of SEQ ID NO: 35. In some embodiments, the variant capsid polypeptide comprises a VP1, VP2 or VP3 sequence of SEQ ID NO: 36. In some embodiments, the variant capsid polypeptide comprises a VP1, VP2 or VP3 sequence of SEQ ID NO: 37. In some embodiments, the variant capsid polypeptide comprises a VP1, VP2 or VP3 sequence of SEQ ID NO: 38. In some embodiments, the variant capsid polypeptide comprises a VP1, VP2 or VP3 sequence of SEQ ID NO: 39. In some embodiments, the variant capsid polypeptide comprises a VP1, VP2 or VP3 sequence of SEQ ID NO: 40. In some embodiments, the variant capsid polypeptide comprises a VP1, VP2 or VP3 sequence of SEQ ID NO: 41. In some embodiments, the variant capsid polypeptide comprises a VP1, VP2 or VP3 sequence of SEQ ID NO: 42. In some embodiments, the variant capsid polypeptide comprises a VP1, VP2 or VP3 sequence of SEQ ID NO: 43. In some embodiments, the variant capsid polypeptide comprises a VP1, VP2 or VP3 sequence of SEQ ID NO: 44. In some embodiments, the variant capsid polypeptide comprises a VP1, VP2 or VP3 sequence of SEQ ID NO: 45. In some embodiments, the variant capsid polypeptide comprises a VP1, VP2 or VP3 sequence of SEQ ID NO: 46. In some embodiments, the variant capsid polypeptide comprises a VP1, VP2 or VP3 sequence of SEQ ID NO: 47. In some embodiments, the variant capsid polypeptide comprises a VP1, VP2 or VP3 sequence of SEQ ID NO: 48. In some embodiments, the variant capsid polypeptide comprises a VP1, VP2 or VP3 sequence of SEQ ID NO: 49. In some embodiments, the variant capsid polypeptide comprises a VP1, VP2 or VP3 sequence of SEQ ID NO: 50. In some embodiments, the variant capsid polypeptide comprises a VP1, VP2 or VP3 sequence of SEQ ID NO: 51. In some embodiments, the variant capsid polypeptide comprises a VP1, VP2 or VP3 sequence of SEQ ID NO: 52. In some embodiments, the variant capsid polypeptide comprises a VP1, VP2 or VP3 sequence of SEQ ID NO: 53. In some embodiments, the variant capsid polypeptide comprises a VP1, VP2 or VP3 sequence of SEQ ID NO: 54. In some embodiments, the variant capsid polypeptide comprises a VP1, VP2 or VP3 sequence of SEQ ID NO: 55. In some embodiments, the variant capsid polypeptide comprises a VP1, VP2 or VP3 sequence of SEQ ID NO: 56. In some embodiments, the variant capsid polypeptide comprises a VP1, VP2 or VP3 sequence of SEQ ID NO: 57. In some embodiments, the variant capsid polypeptide comprises a VP1, VP2 or VP3 sequence of SEQ ID NO: 58. In some embodiments, the variant capsid polypeptide comprises a VP1, VP2 or VP3 sequence of SEQ ID NO: 59. In some embodiments, the variant capsid polypeptide comprises a VP1, VP2 or VP3 sequence of SEQ ID NO: 60. In some embodiments, the variant capsid polypeptide comprises a VP1, VP2 or VP3 sequence of SEQ ID NO: 61. In some embodiments, the variant capsid polypeptide comprises a VP1, VP2 or VP3 sequence of SEQ ID NO: 62. In some embodiments, the variant capsid polypeptide comprises a VP1, VP2 or VP3 sequence of SEQ ID NO: 63. In some embodiments, the variant capsid polypeptide comprises a VP1, VP2 or VP3 sequence of SEQ ID NO: 64. In some embodiments, the variant capsid polypeptide comprises a VP1, VP2 or VP3 sequence of SEQ ID NO: 65. In some embodiments, the variant capsid polypeptide comprises a VP1, VP2 or VP3 sequence of SEQ ID NO: 66. In some embodiments, the variant capsid polypeptide comprises a VP1, VP2 or VP3 sequence of SEQ ID NO: 67. In some embodiments, the variant capsid polypeptide comprises a VP1, VP2 or VP3 sequence of SEQ ID NO: 68. In some embodiments, the variant capsid polypeptide comprises a VP1, VP2 or VP3 sequence of SEQ ID NO: 69. In some embodiments, the variant capsid polypeptide comprises a VP1, VP2 or VP3 sequence of SEQ ID NO: 70. In some embodiments, the variant capsid polypeptide comprises a VP1, VP2 or VP3 sequence of SEQ ID NO: 71. In some embodiments, the variant capsid polypeptide comprises a VP1, VP2 or VP3 sequence of SEQ ID NO: 72. In some embodiments, the variant capsid polypeptide comprises a VP1, VP2 or VP3 sequence of SEQ ID NO: 73. In some embodiments, the variant capsid polypeptide comprises a VP1, VP2 or VP3 sequence of SEQ ID NO: 74. In some embodiments, the variant capsid polypeptide comprises a VP1, VP2 or VP3 sequence of SEQ ID NO: 75. In some embodiments, the variant capsid polypeptide comprises a VP1, VP2 or VP3 sequence of SEQ ID NO: 76. In some embodiments, the variant capsid polypeptide comprises a VP1, VP2 or VP3 sequence of SEQ ID NO: 77. In some embodiments, the variant capsid polypeptide comprises a VP1, VP2 or VP3 sequence of SEQ ID NO: 78. In some embodiments, the variant capsid polypeptide comprises a VP1, VP2 or VP3 sequence of SEQ ID NO: 79. In some embodiments, the variant capsid polypeptide comprises a VP1, VP2 or VP3 sequence of SEQ ID NO: 80. In some embodiments, the variant capsid polypeptide comprises a VP1, VP2 or VP3 sequence of SEQ ID NO: 81. In some embodiments, the variant capsid polypeptide comprises a VP1, VP2 or VP3 sequence of SEQ ID NO: 82. In some embodiments, the variant capsid polypeptide comprises a VP1, VP2 or VP3 sequence of SEQ ID NO: 83. In some embodiments, the variant capsid polypeptide comprises a VP1, VP2 or VP3 sequence of SEQ ID NO: 84. In some embodiments, the variant capsid polypeptide comprises a VP1, VP2 or VP3 sequence of SEQ ID NO: 85. In some embodiments, the variant capsid polypeptide comprises a VP1, VP2 or VP3 sequence of SEQ ID NO: 86. In some embodiments, the variant capsid polypeptide comprises a VP1, VP2 or VP3 sequence of SEQ ID NO: 87. In some embodiments, the variant capsid polypeptide comprises a VP1, VP2 or VP3 sequence of SEQ ID NO: 88. In some embodiments, the variant capsid polypeptide comprises a VP1, VP2 or VP3 sequence of SEQ ID NO: 89. In some embodiments, the variant capsid polypeptide comprises a VP1, VP2 or VP3 sequence of SEQ ID NO: 90. In some embodiments, the variant capsid polypeptide comprises a VP1, VP2 or VP3 sequence of SEQ ID NO: 91. In some embodiments, the variant capsid polypeptide comprises a VP1, VP2 or VP3 sequence of SEQ ID NO: 92. In some embodiments, the variant capsid polypeptide comprises a VP1, VP2 or VP3 sequence of SEQ ID NO: 93. In some embodiments, the variant capsid polypeptide comprises a VP1, VP2 or VP3 sequence of SEQ ID NO: 94. In some embodiments, the variant capsid polypeptide comprises a VP1, VP2 or VP3 sequence of SEQ ID NO: 95. In some embodiments, the variant capsid polypeptide comprises a VP1, VP2 or VP3 sequence of SEQ ID NO: 96. In some embodiments, the variant capsid polypeptide comprises a VP1, VP2 or VP3 sequence of SEQ ID NO: 97. In some embodiments, the variant capsid polypeptide comprises a VP1, VP2 or VP3 sequence of SEQ ID NO: 98. In some embodiments, the variant capsid polypeptide comprises a VP1, VP2 or VP3 sequence of SEQ ID NO: 99. In some embodiments, the variant capsid polypeptide comprises a VP1, VP2 or VP3 sequence of SEQ ID NO: 100. In some embodiments, the variant capsid polypeptide comprises a VP1, VP2 or VP3 sequence of SEQ ID NO: 101. In some embodiments, the variant capsid polypeptide comprises a VP1, VP2 or VP3 sequence of SEQ ID NO: 102. In some embodiments, the variant capsid polypeptide comprises a VP1, VP2 or VP3 sequence of SEQ ID NO: 103. In some embodiments, the variant capsid polypeptide comprises a VP1, VP2 or VP3 sequence of SEQ ID NO: 104. In some embodiments, the variant capsid polypeptide comprises a VP1, VP2 or VP3 sequence of SEQ ID NO: 105. In some embodiments, the variant capsid polypeptide comprises a VP1, VP2 or VP3 sequence of SEQ ID NO: 106. In some embodiments, the variant capsid polypeptide comprises a VP1, VP2 or VP3 sequence of SEQ ID NO: 107. In some embodiments, the variant capsid polypeptide comprises a VP1, VP2 or VP3 sequence of SEQ ID NO: 108. In some embodiments, the variant capsid polypeptide comprises a VP1, VP2 or VP3 sequence of SEQ ID NO: 109. In some embodiments, the variant capsid polypeptide comprises a VP1, VP2 or VP3 sequence of SEQ ID NO: 110. In some embodiments, the variant capsid polypeptide comprises a VP1, VP2 or VP3 sequence of SEQ ID NO: 111. In some embodiments, the variant capsid polypeptide comprises a VP1, VP2 or VP3 sequence of SEQ ID NO: 112. In some embodiments, the variant capsid polypeptide comprises a VP1, VP2 or VP3 sequence of SEQ ID NO: 113. In some embodiments, the variant capsid polypeptide comprises a VP1, VP2 or VP3 sequence of SEQ ID NO: 114. In some embodiments, the variant capsid polypeptide comprises a VP1, VP2 or VP3 sequence of SEQ ID NO: 115. In some embodiments, the variant capsid polypeptide comprises a VP1, VP2 or VP3 sequence of SEQ ID NO: 116. In some embodiments, the variant capsid polypeptide comprises a VP1, VP2 or VP3 sequence of SEQ ID NO: 117. In some embodiments, the variant capsid polypeptide comprises a VP1, VP2 or VP3 sequence of SEQ ID NO: 118. In some embodiments, the variant capsid polypeptide comprises a VP1, VP2 or VP3 sequence of SEQ ID NO: 119. In some embodiments, the variant capsid polypeptide comprises a VP1, VP2 or VP3 sequence of SEQ ID NO: 120. In some embodiments, the variant capsid polypeptide comprises a VP1, VP2 or VP3 sequence of SEQ ID NO: 121. In some embodiments, the variant capsid polypeptide comprises a VP1, VP2 or VP3 sequence of SEQ ID NO: 122. In some embodiments, the variant capsid polypeptide comprises a VP1, VP2 or VP3 sequence of SEQ ID NO: 123. In some embodiments, the variant capsid polypeptide comprises a VP1, VP2 or VP3 sequence of SEQ ID NO: 124. In some embodiments, the variant capsid polypeptide comprises a VP1, VP2 or VP3 sequence of SEQ ID NO: 125. In some embodiments, the variant capsid polypeptide comprises a VP1, VP2 or VP3 sequence of SEQ ID NO: 126. In some embodiments, the variant capsid polypeptide comprises a VP1, VP2 or VP3 sequence of SEQ ID NO: 127. In some embodiments, the variant capsid polypeptide comprises a VP1, VP2 or VP3 sequence of SEQ ID NO: 128. In some embodiments, the variant capsid polypeptide comprises a VP1, VP2 or VP3 sequence of SEQ ID NO: 129. In some embodiments, the variant capsid polypeptide comprises a VP1, VP2 or VP3 sequence of SEQ ID NO: 130. In some embodiments, the variant capsid polypeptide comprises a VP1, VP2 or VP3 sequence of SEQ ID NO: 131. In some embodiments, the variant capsid polypeptide comprises a VP1, VP2 or VP3 sequence of SEQ ID NO: 132. In some embodiments, the variant capsid polypeptide comprises a VP1, VP2 or VP3 sequence of SEQ ID NO: 133. In some embodiments, the variant capsid polypeptide comprises a VP1, VP2 or VP3 sequence of SEQ ID NO: 134. In some embodiments, the variant capsid polypeptide comprises a VP1, VP2 or VP3 sequence of SEQ ID NO: 135. In some embodiments, the variant capsid polypeptide comprises a VP1, VP2 or VP3 sequence of SEQ ID NO: 136. In some embodiments, the variant capsid polypeptide comprises a VP1, VP2 or VP3 sequence of SEQ ID NO: 137. In some embodiments, the variant capsid polypeptide comprises a VP1, VP2 or VP3 sequence of SEQ ID NO: 138. In some embodiments, the variant capsid polypeptide comprises a VP1, VP2 or VP3 sequence of SEQ ID NO: 139.

In some embodiments, the variant capsid polypeptide consists of a VP1, VP2 or VP3 sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, the variant capsid polypeptide consists of a VP1, VP2 or VP3 sequence of SEQ ID NO: 2. In some embodiments, the variant capsid polypeptide consists of a VP1, VP2 or VP3 sequence of SEQ ID NO: 14. In some embodiments, the variant capsid polypeptide consists of a VP1, VP2 or VP3 sequence of SEQ ID NO: 15. In some embodiments, the variant capsid polypeptide consists of a VP1, VP2 or VP3 sequence of SEQ ID NO: 16. In some embodiments, the variant capsid polypeptide consists of a VP1, VP2 or VP3 sequence of SEQ ID NO: 17. In some embodiments, the variant capsid polypeptide consists of a VP1, VP2 or VP3 sequence of SEQ ID NO: 18. In some embodiments, the variant capsid polypeptide consists of a VP1, VP2 or VP3 sequence of SEQ ID NO: 19. In some embodiments, the variant capsid polypeptide consists of a VP1, VP2 or VP3 sequence of SEQ ID NO: 20. In some embodiments, the variant capsid polypeptide consists of a VP1, VP2 or VP3 sequence of SEQ ID NO: 21. In some embodiments, the variant capsid polypeptide consists of a VP1, VP2 or VP3 sequence of SEQ ID NO: 22. In some embodiments, the variant capsid polypeptide consists of a VP1, VP2 or VP3 sequence of SEQ ID NO: 23. In some embodiments, the variant capsid polypeptide consists of a VP1, VP2 or VP3 sequence of SEQ ID NO: 24. In some embodiments, the variant capsid polypeptide consists of a VP1, VP2 or VP3 sequence of SEQ ID NO: 25. In some embodiments, the variant capsid polypeptide consists of a VP1, VP2 or VP3 sequence of SEQ ID NO: 26. In some embodiments, the variant capsid polypeptide consists of a VP1, VP2 or VP3 sequence of SEQ ID NO: 27. In some embodiments, the variant capsid polypeptide consists of a VP1, VP2 or VP3 sequence of SEQ ID NO: 28. In some embodiments, the variant capsid polypeptide consists of a VP1, VP2 or VP3 sequence of SEQ ID NO: 29. In some embodiments, the variant capsid polypeptide consists of a VP1, VP2 or VP3 sequence of SEQ ID NO: 30. In some embodiments, the variant capsid polypeptide consists of a VP1, VP2 or VP3 sequence of SEQ ID NO: 31. In some embodiments, the variant capsid polypeptide consists of a VP1, VP2 or VP3 sequence of SEQ ID NO: 32. In some embodiments, the variant capsid polypeptide consists of a VP1, VP2 or VP3 sequence of SEQ ID NO: 33. In some embodiments, the variant capsid polypeptide consists of a VP1, VP2 or VP3 sequence of SEQ ID NO: 34. In some embodiments, the variant capsid polypeptide consists of a VP1, VP2 or VP3 sequence of SEQ ID NO: 35. In some embodiments, the variant capsid polypeptide consists of a VP1, VP2 or VP3 sequence of SEQ ID NO: 36. In some embodiments, the variant capsid polypeptide consists of a VP1, VP2 or VP3 sequence of SEQ ID NO: 37. In some embodiments, the variant capsid polypeptide consists of a VP1, VP2 or VP3 sequence of SEQ ID NO: 38. In some embodiments, the variant capsid polypeptide consists of a VP1, VP2 or VP3 sequence of SEQ ID NO: 39. In some embodiments, the variant capsid polypeptide consists of a VP1, VP2 or VP3 sequence of SEQ ID NO: 40. In some embodiments, the variant capsid polypeptide consists of a VP1, VP2 or VP3 sequence of SEQ ID NO: 41. In some embodiments, the variant capsid polypeptide consists of a VP1, VP2 or VP3 sequence of SEQ ID NO: 42. In some embodiments, the variant capsid polypeptide consists of a VP1, VP2 or VP3 sequence of SEQ ID NO: 43. In some embodiments, the variant capsid polypeptide consists of a VP1, VP2 or VP3 sequence of SEQ ID NO: 44. In some embodiments, the variant capsid polypeptide consists of a VP1, VP2 or VP3 sequence of SEQ ID NO: 45. In some embodiments, the variant capsid polypeptide consists of a VP1, VP2 or VP3 sequence of SEQ ID NO: 46. In some embodiments, the variant capsid polypeptide consists of a VP1, VP2 or VP3 sequence of SEQ ID NO: 47. In some embodiments, the variant capsid polypeptide consists of a VP1, VP2 or VP3 sequence of SEQ ID NO: 48. In some embodiments, the variant capsid polypeptide consists of a VP1, VP2 or VP3 sequence of SEQ ID NO: 49. In some embodiments, the variant capsid polypeptide consists of a VP1, VP2 or VP3 sequence of SEQ ID NO: 50. In some embodiments, the variant capsid polypeptide consists of a VP1, VP2 or VP3 sequence of SEQ ID NO: 51. In some embodiments, the variant capsid polypeptide consists of a VP1, VP2 or VP3 sequence of SEQ ID NO: 52. In some embodiments, the variant capsid polypeptide consists of a VP1, VP2 or VP3 sequence of SEQ ID NO: 53. In some embodiments, the variant capsid polypeptide consists of a VP1, VP2 or VP3 sequence of SEQ ID NO: 54. In some embodiments, the variant capsid polypeptide consists of a VP1, VP2 or VP3 sequence of SEQ ID NO: 55. In some embodiments, the variant capsid polypeptide consists of a VP1, VP2 or VP3 sequence of SEQ ID NO: 56. In some embodiments, the variant capsid polypeptide consists of a VP1, VP2 or VP3 sequence of SEQ ID NO: 57. In some embodiments, the variant capsid polypeptide consists of a VP1, VP2 or VP3 sequence of SEQ ID NO: 58. In some embodiments, the variant capsid polypeptide consists of a VP1, VP2 or VP3 sequence of SEQ ID NO: 59. In some embodiments, the variant capsid polypeptide consists of a VP1, VP2 or VP3 sequence of SEQ ID NO: 60. In some embodiments, the variant capsid polypeptide consists of a VP1, VP2 or VP3 sequence of SEQ ID NO: 61. In some embodiments, the variant capsid polypeptide consists of a VP1, VP2 or VP3 sequence of SEQ ID NO: 62. In some embodiments, the variant capsid polypeptide consists of a VP1, VP2 or VP3 sequence of SEQ ID NO: 63. In some embodiments, the variant capsid polypeptide consists of a VP1, VP2 or VP3 sequence of SEQ ID NO: 64. In some embodiments, the variant capsid polypeptide consists of a VP1, VP2 or VP3 sequence of SEQ ID NO: 65. In some embodiments, the variant capsid polypeptide consists of a VP1, VP2 or VP3 sequence of SEQ ID NO: 66. In some embodiments, the variant capsid polypeptide consists of a VP1, VP2 or VP3 sequence of SEQ ID NO: 67. In some embodiments, the variant capsid polypeptide consists of a VP1, VP2 or VP3 sequence of SEQ ID NO: 68. In some embodiments, the variant capsid polypeptide consists of a VP1, VP2 or VP3 sequence of SEQ ID NO: 69. In some embodiments, the variant capsid polypeptide consists of a VP1, VP2 or VP3 sequence of SEQ ID NO: 70. In some embodiments, the variant capsid polypeptide consists of a VP1, VP2 or VP3 sequence of SEQ ID NO: 71. In some embodiments, the variant capsid polypeptide consists of a VP1, VP2 or VP3 sequence of SEQ ID NO: 72. In some embodiments, the variant capsid polypeptide consists of a VP1, VP2 or VP3 sequence of SEQ ID NO: 73. In some embodiments, the variant capsid polypeptide consists of a VP1, VP2 or VP3 sequence of SEQ ID NO: 74. In some embodiments, the variant capsid polypeptide consists of a VP1, VP2 or VP3 sequence of SEQ ID NO: 75. In some embodiments, the variant capsid polypeptide consists of a VP1, VP2 or VP3 sequence of SEQ ID NO: 76. In some embodiments, the variant capsid polypeptide consists of a VP1, VP2 or VP3 sequence of SEQ ID NO: 77. In some embodiments, the variant capsid polypeptide consists of a VP1, VP2 or VP3 sequence of SEQ ID NO: 78. In some embodiments, the variant capsid polypeptide consists of a VP1, VP2 or VP3 sequence of SEQ ID NO: 79. In some embodiments, the variant capsid polypeptide consists of a VP1, VP2 or VP3 sequence of SEQ ID NO: 80. In some embodiments, the variant capsid polypeptide consists of a VP1, VP2 or VP3 sequence of SEQ ID NO: 81. In some embodiments, the variant capsid polypeptide consists of a VP1, VP2 or VP3 sequence of SEQ ID NO: 82. In some embodiments, the variant capsid polypeptide consists of a VP1, VP2 or VP3 sequence of SEQ ID NO: 83. In some embodiments, the variant capsid polypeptide consists of a VP1, VP2 or VP3 sequence of SEQ ID NO: 84. In some embodiments, the variant capsid polypeptide consists of a VP1, VP2 or VP3 sequence of SEQ ID NO: 85. In some embodiments, the variant capsid polypeptide consists of a VP1, VP2 or VP3 sequence of SEQ ID NO: 86. In some embodiments, the variant capsid polypeptide consists of a VP1, VP2 or VP3 sequence of SEQ ID NO: 87. In some embodiments, the variant capsid polypeptide consists of a VP1, VP2 or VP3 sequence of SEQ ID NO: 88. In some embodiments, the variant capsid polypeptide consists of a VP1, VP2 or VP3 sequence of SEQ ID NO: 89. In some embodiments, the variant capsid polypeptide consists of a VP1, VP2 or VP3 sequence of SEQ ID NO: 90. In some embodiments, the variant capsid polypeptide consists of a VP1, VP2 or VP3 sequence of SEQ ID NO: 91. In some embodiments, the variant capsid polypeptide consists of a VP1, VP2 or VP3 sequence of SEQ ID NO: 92. In some embodiments, the variant capsid polypeptide consists of a VP1, VP2 or VP3 sequence of SEQ ID NO: 93. In some embodiments, the variant capsid polypeptide consists of a VP1, VP2 or VP3 sequence of SEQ ID NO: 94. In some embodiments, the variant capsid polypeptide consists of a VP1, VP2 or VP3 sequence of SEQ ID NO: 95. In some embodiments, the variant capsid polypeptide consists of a VP1, VP2 or VP3 sequence of SEQ ID NO: 96. In some embodiments, the variant capsid polypeptide consists of a VP1, VP2 or VP3 sequence of SEQ ID NO: 97. In some embodiments, the variant capsid polypeptide consists of a VP1, VP2 or VP3 sequence of SEQ ID NO: 98. In some embodiments, the variant capsid polypeptide consists of a VP1, VP2 or VP3 sequence of SEQ ID NO: 99. In some embodiments, the variant capsid polypeptide consists of a VP1, VP2 or VP3 sequence of SEQ ID NO: 100. In some embodiments, the variant capsid polypeptide consists of a VP1, VP2 or VP3 sequence of SEQ ID NO: 101. In some embodiments, the variant capsid polypeptide consists of a VP1, VP2 or VP3 sequence of SEQ ID NO: 102. In some embodiments, the variant capsid polypeptide consists of a VP1, VP2 or VP3 sequence of SEQ ID NO: 103. In some embodiments, the variant capsid polypeptide consists of a VP1, VP2 or VP3 sequence of SEQ ID NO: 104. In some embodiments, the variant capsid polypeptide consists of a VP1, VP2 or VP3 sequence of SEQ ID NO: 105. In some embodiments, the variant capsid polypeptide consists of a VP1, VP2 or VP3 sequence of SEQ ID NO: 106. In some embodiments, the variant capsid polypeptide consists of a VP1, VP2 or VP3 sequence of SEQ ID NO: 107. In some embodiments, the variant capsid polypeptide consists of a VP1, VP2 or VP3 sequence of SEQ ID NO: 108. In some embodiments, the variant capsid polypeptide consists of a VP1, VP2 or VP3 sequence of SEQ ID NO: 109. In some embodiments, the variant capsid polypeptide consists of a VP1, VP2 or VP3 sequence of SEQ ID NO: 110. In some embodiments, the variant capsid polypeptide consists of a VP1, VP2 or VP3 sequence of SEQ ID NO: 111. In some embodiments, the variant capsid polypeptide consists of a VP1, VP2 or VP3 sequence of SEQ ID NO: 112. In some embodiments, the variant capsid polypeptide consists of a VP1, VP2 or VP3 sequence of SEQ ID NO: 113. In some embodiments, the variant capsid polypeptide consists of a VP1, VP2 or VP3 sequence of SEQ ID NO: 114. In some embodiments, the variant capsid polypeptide consists of a VP1, VP2 or VP3 sequence of SEQ ID NO: 115. In some embodiments, the variant capsid polypeptide consists of a VP1, VP2 or VP3 sequence of SEQ ID NO: 116. In some embodiments, the variant capsid polypeptide consists of a VP1, VP2 or VP3 sequence of SEQ ID NO: 117. In some embodiments, the variant capsid polypeptide consists of a VP1, VP2 or VP3 sequence of SEQ ID NO: 118. In some embodiments, the variant capsid polypeptide consists of a VP1, VP2 or VP3 sequence of SEQ ID NO: 119. In some embodiments, the variant capsid polypeptide consists of a VP1, VP2 or VP3 sequence of SEQ ID NO: 120. In some embodiments, the variant capsid polypeptide consists of a VP1, VP2 or VP3 sequence of SEQ ID NO: 121. In some embodiments, the variant capsid polypeptide consists of a VP1, VP2 or VP3 sequence of SEQ ID NO: 122. In some embodiments, the variant capsid polypeptide consists of a VP1, VP2 or VP3 sequence of SEQ ID NO: 123. In some embodiments, the variant capsid polypeptide consists of a VP1, VP2 or VP3 sequence of SEQ ID NO: 124. In some embodiments, the variant capsid polypeptide consists of a VP1, VP2 or VP3 sequence of SEQ ID NO: 125. In some embodiments, the variant capsid polypeptide consists of a VP1, VP2 or VP3 sequence of SEQ ID NO: 126. In some embodiments, the variant capsid polypeptide consists of a VP1, VP2 or VP3 sequence of SEQ ID NO: 127. In some embodiments, the variant capsid polypeptide consists of a VP1, VP2 or VP3 sequence of SEQ ID NO: 128. In some embodiments, the variant capsid polypeptide consists of a VP1, VP2 or VP3 sequence of SEQ ID NO: 129. In some embodiments, the variant capsid polypeptide consists of a VP1, VP2 or VP3 sequence of SEQ ID NO: 130. In some embodiments, the variant capsid polypeptide consists of a VP1, VP2 or VP3 sequence of SEQ ID NO: 131. In some embodiments, the variant capsid polypeptide consists of a VP1, VP2 or VP3 sequence of SEQ ID NO: 132. In some embodiments, the variant capsid polypeptide consists of a VP1, VP2 or VP3 sequence of SEQ ID NO: 133. In some embodiments, the variant capsid polypeptide consists of a VP1, VP2 or VP3 sequence of SEQ ID NO: 134. In some embodiments, the variant capsid polypeptide consists of a VP1, VP2 or VP3 sequence of SEQ ID NO: 135. In some embodiments, the variant capsid polypeptide consists of a VP1, VP2 or VP3 sequence of SEQ ID NO: 136. In some embodiments, the variant capsid polypeptide consists of a VP1, VP2 or VP3 sequence of SEQ ID NO: 137. In some embodiments, the variant capsid polypeptide consists of a VP1, VP2 or VP3 sequence of SEQ ID NO: 138. In some embodiments, the variant capsid polypeptide consists of a VP1, VP2 or VP3 sequence of SEQ ID NO: 139.

In some embodiments, the variant capsid polypeptide comprises a VP1 polypeptide, a VP2 polypeptide or a VP3 polypeptide. In some embodiments, the variant capsid polypeptide, or the reference polypeptide for purposes of % identity, comprises a sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the nucleic acid molecule or the nucleic acid molecule encoding the reference polypeptide for purposes of % identity, comprises a nucleotide sequence of SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265.

In some embodiments, the nucleic acid molecule or the nucleic acid molecule encoding the reference polypeptide for purposes of % identity, comprises a nucleotide sequence that encodes a sequence of a variant capsid polypeptide, e.g., as described herein, e.g., encodes a SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

In some embodiments, the variant capsid polypeptide, or the reference polypeptide for purposes of % identity, comprises a sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, that is encoded by a nucleotide sequence of SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265.

In some embodiments, the variant capsid polypeptide comprises a sequence that includes all of the mutation differences associated with any one of VAR-1 through VAR-127 (e.g., as indicated in Table 1), and further includes no more than 30, no more than 20, no more than 10, no more than 9, no more than 8, no more than 7, no more than 6, no more than 5, no more than 4, no more than 3, no more than 2 or no more than 1 additional mutations relative to a reference capsid sequence, e.g., relative to SEQ ID NO: 1.

In some embodiments, the variant capsid polypeptide is a VP1 capsid polypeptide. In some embodiments, the variant capsid polypeptide is a VP2 capsid polypeptide. In some embodiments, the variant capsid polypeptide is a VP3 capsid polypeptide. With respect to reference sequence SEQ ID NO: 1, a VP1 capsid polypeptide comprises amino acids 1-737 of SEQ ID NO: 1. With respect to reference sequence SEQ ID NO: 1, a VP2 capsid polypeptide comprises amino acids 138-737 of SEQ ID NO: 1. With respect to reference sequence SEQ ID NO: 1, a VP3 capsid polypeptide comprises amino acids 203-737 of SEQ ID NO: 1.

With respect to variant capsid polypeptide sequence SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, a VP1 capsid polypeptide comprises amino acids 1-737 of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

With respect to sequence SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, a VP2 capsid polypeptide comprises amino acids 138-737 of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

With respect to sequence SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139, a VP3 capsid polypeptide comprises amino acids 203-737 of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139.

Exemplary sequences of variant capsid polypeptides and nucleic acid molecules encoding the same are provided in Table 1 and the Sequence Listing submitted electronically in XML file format, which is hereby incorporated by reference in its entirety.

TABLE 1

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed) (SEQ ID NO) | Mutation Differences as compared to SEQ ID NO: 1. Collectively for each variant, the "mutation set" |
|---|---|---|---|
| VAR-1 | MAADGYLPDWLEDNLSEGIREWWALK<br>PGAPQPKANQQHQDNARGLVLPGYKY<br>LGPGNGLDKGEPVNAADAAALEHDKA<br>YDQQLKAGDNPYLKYNHADAEFQERL<br>KEDTSFGGNLGRAVFQAKKRLLEPLG<br>LVEEAAKTAPGKKRPVEQSPQEPDSS<br>AGIGKSGAQPAKKRLNFGQTGDTESV<br>PDPQPIGEPPAAPSGVGSLTMASGGG<br>APVADNNEGADGVGSSSGNWHCDSQW<br>LGDRVITTSTRTWALPTYNNHLYKQI<br>SNSTSGGSSNDNAYFGYSTPWGYFDF<br>NRFHCHFSPRDWQRLINNNWGFRPKR<br>LNFKLFNIQVKEVTDNNGVKTIANNL<br>TSTVQVFTDSDYQLPYVLGSAHEGCL<br>PPFPADVFMIPQYGYLTLNDGSQAVG<br>RSSFYCLEYFPSQMLRTGNNFQFSYE<br>FENVPFHSSYAHSQSLDRLMNPLIDQ<br>YLYYLSKTINGSGQNQQTLKFSVAGP<br>SNMAVQGRNYIPGPSYRQQRVSTTVT<br>QNNNSEFAWPGASSWALNGRNSLMNP | atggctgccgatggttatcttccagattg<br>gctcgaggacaaccttagtgaaggtattc<br>gcgagtggtgggctttgaaacctggagcc<br>cctcaacccaaggcaaatcaacaacatca<br>agacaacgctcgaggtcttgtgcttccgg<br>gttacaaataccttggacccggcaacgga<br>ctcgacaaggggggagccggtcaacgcagc<br>agacgcggcggccctcgagcacgacaagg<br>cctacgaccagcagctcaaggccggagac<br>aacccgtacctcaagtacaaccacgccga<br>cgccgagttccaggagcggctcaaagaag<br>atacgtcttttgggggcaacctcgggcga<br>gcagtcttccaggccaaaaagaggcttct<br>tgaacctcttggtctggttgaggaagcgg<br>ctaagacggctcctggaaagaagaggcct<br>gtagagcagtctcctcaggaaccggactc<br>ctccgcgggtattggcaaatcgggtgcac<br>agcccgctaaaaagagactcaatttcggt<br>cagactggcgacacagagtcagtcccaga<br>ccccctcaggtgtgggatctcttacaatg | ['Q579V', 'Q592I', 'T593V', 'W595A', 'V596L', 'N598S', 'I601A'] |

TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed) (SEQ ID NO) | Mutation Differences as compared to SEQ ID NO: 1. Collectively for each variant, the "mutation set" |
|---|---|---|---|
| VAR-100 | SEQ ID NO: 19 | SEQ ID NO: 145 | ["Q592I", "T593V", "W595A", "V596L", "N598S", "I601A"] |
| VAR-80 | SEQ ID NO: 20 | SEQ ID NO: 146 | ["T593V", "V596L", "N598S", "I601A"] |
| VAR-89 | SEQ ID NO: 21 | SEQ ID NO: 147 | ["T593V", "W595A", "V596L", "N598S", "I601A"] |
| VAR-102 | SEQ ID NO: 22 | SEQ ID NO: 148 | ["Q579V", "Q592I", "T593V", "V596L", "N598S", "I601A"] |
| VAR-122 | SEQ ID NO: 23 | SEQ ID NO: 149 | ["Q579V", "Q592I", "T593V", "W595A", "V596L", "N598S"] |
| VAR-75 | SEQ ID NO: 24 | SEQ ID NO: 150 | ["Q579V", "T593V", "W595A", "V596L", "N598S"] |
| VAR-96 | SEQ ID NO: 25 | SEQ ID NO: 151 | ["Q579V", "T593V", "V596L", "N598S"] |
| VAR-67 | SEQ ID NO: 26 | SEQ ID NO: 152 | ["Q579V", "V596L", "N598S", "I601A"] |
| VAR-57 | SEQ ID NO: 27 | SEQ ID NO: 153 | ["Q579V", "Q592I", "V596L", "N598S", "I601A"] |
| VAR-59 | SEQ ID NO: 28 | SEQ ID NO: 154 | ["Q592I", "T593V", "V596L", "N598S"] |
| VAR-35 | SEQ ID NO: 29 | SEQ ID NO: 155 | ["Q579V", "Q592I", "T593V", "W595A", "N598S", "I601A"] |
| VAR-110 | SEQ ID NO: 30 | SEQ ID NO: 156 | ["Q592I", "T593V", "V596L"] |
| VAR-93 | SEQ ID NO: 31 | SEQ ID NO: 157 | ["Q592I", "T593V", "W595A", "V596L", "N598S"] |
| VAR-76 | SEQ ID NO: 32 | SEQ ID NO: 158 | ["Q579V", "W595A", "I601A"] |
| VAR-119 | SEQ ID NO: 33 | SEQ ID NO: 159 | ["Q592I", "V596L", "N598S", "I601A"] |
| VAR-82 | SEQ ID NO: 34 | SEQ ID NO: 160 | ["Q579V", "W595A", "V596L", "N598S"] |
| VAR-83 | SEQ ID NO: 35 | SEQ ID NO: 161 | ["V596L", "N598S", "I601A"] |
| VAR-108 | SEQ ID NO: 36 | SEQ ID NO: 162 | ["Q579V", "Q592I", "T593V", "W595A", "I601A"] |
| VAR-71 | SEQ ID NO: 37 | SEQ ID NO: 163 | ["W595A", "V596L", "N598S", "I601A"] |
| VAR-90 | SEQ ID NO: 38 | SEQ ID NO: 164 | ["Q579V", "Q592I", "W595A", "V596L", "N598S"] |
| VAR-123 | SEQ ID NO: 39 | SEQ ID NO: 165 | ["Q579V", "T593V", "W595A", "V596L"] |
| VAR-44 | SEQ ID NO: 40 | SEQ ID NO: 166 | ["Q592I", "N598S"] |
| VAR-86 | SEQ ID NO: 41 | SEQ ID NO: 167 | ["Q579V", "V596L"] |
| VAR-81 | SEQ ID NO: 42 | SEQ ID NO: 168 | ["Q579V", "V596L", "N598S"] |
| VAR-43 | SEQ ID NO: 43 | SEQ ID NO: 169 | ["T593V", "N598S", "I601A"] |
| VAR-41 | SEQ ID NO: 44 | SEQ ID NO: 170 | ["Q579V", "Q592I", "W595A", "N598S"] |

TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed) (SEQ ID NO) | Mutation Differences as compared to SEQ ID NO: 1. Collectively for each variant, the "mutation set" |
|---|---|---|---|
| VAR-88 | SEQ ID NO: 45 | SEQ ID NO: 171 | ["Q579V", "T593V", "V596L"] |
| VAR-127 | SEQ ID NO: 46 | SEQ ID NO: 172 | ["Q592I", "W595A", "I601A"] |
| VAR-85 | SEQ ID NO: 47 | SEQ ID NO: 173 | |
| VAR-51 | SEQ ID NO: 48 | SEQ ID NO: 174 | ["Q592I", "T593V", "W595A"] |
| VAR-99 | SEQ ID NO: 49 | SEQ ID NO: 175 | ["Q579V", "Q592I", "V596L", "N598S"] |
| VAR-101 | SEQ ID NO: 50 | SEQ ID NO: 176 | ["Q592I", "V596L"] |
| VAR-107 | SEQ ID NO: 51 | SEQ ID NO: 177 | ["Q579V", "Q592I", "T593V", "W595A", "V596L"] |
| VAR-5 | SEQ ID NO: 52 | SEQ ID NO: 178 | ["Q579V", "T593V"] |
| VAR-33 | SEQ ID NO: 53 | SEQ ID NO: 179 | ["Q579V", "T593V", "W595A", "N598S"] |
| VAR-3 | SEQ ID NO: 54 | SEQ ID NO: 180 | ["I601A"] |
| VAR-25 | SEQ ID NO: 55 | SEQ ID NO: 181 | ["Q579V", "Q592I", "T593V", "W595A", "N598S"] |
| VAR-49 | SEQ ID NO: 56 | SEQ ID NO: 182 | ["Q579V", "Q592I", "T593V", "I601A"] |
| VAR-68 | SEQ ID NO: 57 | SEQ ID NO: 183 | ["Q579V", "W595A", "V596L"] |
| VAR-40 | SEQ ID NO: 58 | SEQ ID NO: 184 | ["T593V", "W595A", "N598S", "I601A"] |
| VAR-97 | SEQ ID NO: 59 | SEQ ID NO: 185 | ["Q579V", "W595A", "V596L", "I601A"] |
| VAR-10 | SEQ ID NO: 60 | SEQ ID NO: 186 | ["N598S"] |
| VAR-105 | SEQ ID NO: 61 | SEQ ID NO: 187 | ["Q579V", "T593V", "W595A", "N598S", "I601A"] |
| VAR-114 | SEQ ID NO: 62 | SEQ ID NO: 188 | ["T593V", "W595A", "V596L", "N598S"] |
| VAR-69 | SEQ ID NO: 63 | SEQ ID NO: 189 | ["Q579V", "Q592I", "W595A", "V596L", "I601A"] |
| VAR-14 | SEQ ID NO: 64 | SEQ ID NO: 190 | ["V596L"] |
| VAR-70 | SEQ ID NO: 65 | SEQ ID NO: 191 | ["V596L", "I601A"] |
| VAR-55 | SEQ ID NO: 66 | SEQ ID NO: 192 | ["T593V", "W595A", "V596L"] |
| VAR-78 | SEQ ID NO: 67 | SEQ ID NO: 193 | ["T593V", "W595A", "V596L", "I601A"] |
| VAR-50 | SEQ ID NO: 68 | SEQ ID NO: 194 | ["Q579V", "Q592I", "N598S"] |
| VAR-53 | SEQ ID NO: 69 | SEQ ID NO: 195 | ["Q592I", "T593V", "I601A"] |
| VAR-77 | SEQ ID NO: 70 | SEQ ID NO: 196 | ["Q579V", "T593V", "W595A", "V596L", "I601A"] |
| VAR-109 | SEQ ID NO: 71 | SEQ ID NO: 197 | ["Q579V", "W595A", "N598S", "I601A"] |
| VAR-112 | SEQ ID NO: 72 | SEQ ID NO: 198 | ["W595A", "V596L", "N598S"] |
| VAR-124 | SEQ ID NO: 73 | SEQ ID NO: 199 | ["Q579V", "N598S"] |

TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed) (S TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed)

TABLE 1-continued

| Capsid Variant | Amino Acid Sequence of VP1 capsid polypeptide (SEQ ID NO); starting amino acid of VP2 is underlined; starting amino acid of VP3 is in bold. | Exemplary nucleic acid sequence encoding a variant capsid VP1 polypeptide (includes TAA stop codon at 3' end which may optionally be removed) (SEQ ID NO) | Mutation Differences as compared to SEQ ID NO: 1. Collectively for each variant, the "mutation set" |
|---|---|---|---|
| VAR-106 | SEQ ID NO: 135 | SEQ ID NO: 261 | ["Q579V", "T593V", "I601A"] |
| VAR-111 | SEQ ID NO: 136 | SEQ ID NO: 262 | ["Q579V", "Q592I", "T593V", "V596L", "I601A"] |
| VAR-113 | SEQ ID NO: 137 | SEQ ID NO: 263 | ["Q592I", "T593V", "W595A", "N598S", "I601A"] |
| VAR-117 | SEQ ID NO: 138 | SEQ ID NO: 264 | ["Q592I", "V596L", "I601A"] |
| VAR-126 | SEQ ID NO: 139 | SEQ ID NO: 265 | ["Q592I", "T593V", "W595A", "I601A"] |

In some embodiments, disclosed herein is a nucleic acid molecule encoding a variant capsid polypeptide described herein. In some embodiments, the nucleic acid molecule encodes a variant capsid polypeptide that has at least 70, 75, 80, 85, 90, 91, 92, 93, 94, 95, 96, 97, 98, 99%, or 100% identity to a VP1, VP2, or VP3 sequence as provided in Table 1, or the Sequence Listing submitted electronically in XML file format, which is hereby incorporated by reference in its entirety. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 2. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 14. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 15. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 16. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 17. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 18. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 19. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 20. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 21. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 22. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 23. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 24. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 25. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 26. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 27. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 28. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 29. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 30. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 31. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 32. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 33. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 34. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 35. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 36. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 37. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 38. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 39. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 40. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 41. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 42. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 43. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 44. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 45. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 46. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 47. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 48. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 49. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 50. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 51. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 52. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 53. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 54. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 55. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 56. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 57. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 58. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 59. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 60. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 61. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 62. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 63. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 64. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 65. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 66. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 67. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 68. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 69. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 70. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 71. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 72. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 73. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 74. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 75. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 76. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 77. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 78. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 79. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 80. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 81. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 82. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 83. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 84. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 85. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 86. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 87. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 88. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 89. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 90. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 91. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 92. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 93. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 94. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 95. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 96. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 97. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 98. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 99. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 100. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 101. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 102. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 103. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 104. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 105. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 106. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 107. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 108. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 109. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 110. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 111. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 112. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 113. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 114. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 115. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 116. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 117. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 118. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 119. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 120. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 121. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 122. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 123. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 124. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 125. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 126. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 127. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 128. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 129. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 130. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 131. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 132. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 133. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 134. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 135. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 136. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 137. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 138. In some embodiments, the nucleic acid molecule encodes a variant capsid polypeptide that has at least 70, 75, 80, 85, 90, 91, 92, 93, 94, 95, 96, 97, 98, 99%, or 100% identity to a polypeptide of SEQ ID NO: 139.

Variant Capsids (Corresponding Positions)

The mutations to capsid polypeptide sequences described herein are described in relation to a position and/or amino acid at a position within a reference sequence, e.g., SEQ ID NO: 1. Thus, in some embodiments, the capsid polypeptides described herein are variant capsid polypeptides of the reference sequence, e.g., SEQ ID NO: 1, e.g., include capsid polypeptides comprising at least 80%, at least 85%, at least 90%, at least 91%, at least 92%, at least 93%, at least 94%, at least 95%, at least 96%, at least 97%, at least 98%, or at least 99% identity to the reference capsid polypeptide sequence (e.g., reference capsid polypeptide VP1, VP2 and/or VP3 sequence), e.g., SEQ ID NO: 1 (or VP2 or VP3 sequence comprised therein) and include one or more mutations described herein.

It will be understood by the skilled artisan, and without being bound by theory, that each amino acid position within a reference sequence corresponds to a position within the sequence of other reference capsid polypeptides such as capsid polypeptides derived from dependoparvoviruses with different serotypes. Such corresponding positions are identified using sequence alignment tools known in the art. A particularly preferred sequence alignment tool is Clustal Omega (Sievers F., et al., Mol. Syst. Biol. 7:359, 2011, DOI: 10.1038/msb.2011.75, incorporated herein by reference in its entirety). Other tools are described in Madeira F, et al., Nuc. Acids Res., 2019, 47 (W1): W636-W641 (DOI: 10.1093/nar/gkz268) (incorporated herein by reference in its entirety). An alignment of exemplary reference capsid polypeptides is shown in FIG. 1A-1C. Thus, in some embodiments, the variant capsid polypeptides of the invention include variants of reference capsid polypeptides that include one or more mutations described herein in such reference capsid polypeptides at positions corresponding to the position of the mutation described herein in relation to a different reference capsid polypeptide. Thus, for example, a mutation described as XnnnY relative to SEQ ID NO: 1 (where X is the amino acid present at position nnn in SEQ ID NO: 1 and Y is the amino acid mutation at that position, e.g., described herein), the disclosure provides variant capsid polypeptides comprising at least 70%, at least 75%, at least 80%, at least 85%, at least 90%, at least 91%, at least 92%, at least 93%, at least 94%, at least 95%, at least 96%, at least 97%, at least 98%, or at least 99% identity to a reference capsid polypeptide sequence (e.g., reference capsid polypeptide VP1, VP2 and/or VP3 sequence) other than SEQ ID NO: 1 (or VP2 or VP3 sequence comprised therein) and further comprising the disclosed mutation at a position corresponding to position nnn of SEQ ID NO: 1 (e.g., comprising Y at the position in the new variant capsid polypeptide sequence that corresponds to position nnn of SEQ ID NO: 1). As described above, such corresponding position is determined using a sequence alignment tool, such as, for example, the clustal omega tool described above. Examples of corresponding amino acid positions of exemplary known AAV serotypes is provided in FIG. 1A-1C. In some embodiments, the variant is a variant of the AAV9 capsid polypeptide, which can be referred to as a "AAV9 variant capsid polypeptide" or "variant AAV9 capsid polypeptide."

Thus, in some embodiments, the disclosure provides variant capsid polypeptide sequences that are variants of a reference sequence other than SEQ ID NO: 1, e.g., a reference sequence other than SEQ ID NO: 1 as described herein, which include one or more mutation corresponding to the mutations described herein. In some embodiments, such variants include mutations corresponding to all of the mutations associated with any one of VAR-1 through VAR-127 according to Table 1, and the Sequence Listing submitted electronically in the XML file format, which is hereby incorporated by reference in its entirety.

As used herein, the term "corresponds to" as used in reference to a position in a sequence, such as an amino acid or nucleic acid sequence, can be used in reference to an entire capsid polypeptide or polynucleotide sequence, such as the full length sequence of the capsid polypeptide that comprises a VP1, VP2, and VP3 polypeptide, or a nucleic acid molecule encoding the same. In some embodiments, the term "corresponds to" can be used in reference to a region or domain of the capsid polypeptide. For example, a position that corresponds to a position in the VP1 section of the reference capsid polypeptide can correspond to the VP1 portion of the polypeptide of the variant capsid polypeptide. Thus, when aligning the two sequences to determine whether a position corresponds to another position the full length polypeptide can be used or domains (regions) can be used to determine whether a position corresponds to a specific position. In some embodiments, the region is the VP1 polypeptide. In some embodiments, the region is the VP2 polypeptide. In some embodiments, the region is the VP3 polypeptide. In some embodiments, when the reference polypeptide is the wild-type sequence (e.g., full length or region) of a certain serotype of AAV, the variant polypeptide can be of the same serotype with a mutation made at such corresponding position as compared to the reference sequence (e.g., full length or region). In some embodiments, the variant capsid polypeptide is a different serotype as compared to the reference sequence.

The variant capsid polypeptides described herein are optionally variants of reference capsids serotypes known in the art. Non-limiting examples of such reference AAV serotypes include AAV1, AAVrh10, AAV-DJ, AAV-DJ8, AAV5, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP (3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.eB, AAVPHP.S/G2A12, AAVG2A15/G2A3 (G2A3), AAVG2B4 (G2B4), AAVG2B5 (G2B5), PHP.S, AAV2, AAV2G9, AAV3, AAV3a, AAV3b, AAV3-3, AAV4, AAV4-4, AAV6, AAV6.1, AAV6.2, AAV6.1.2, AAV7, AAV7.2, AAV8, AAV9.11, AAV9.13, AAV9, AAV9 K449R (or K449R AAV9), AAV9.16, AAV9.24, AAV9.45, AAbiodisV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAVF3, AAVF5, AAVH2, AAVrh.72, AAVhu.8, AAVrh.68, AAVrh.70, AAVpi. 1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVH-1/hu. 1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74 (also referred to as AAVrh74), AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV. VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9, 7m8, Spark 100, AAVMYO and variants thereof.

In some embodiments, the reference AAV capsid sequence comprises an AAV2 sequence. In some embodiments, the reference AAV capsid sequence comprises an AAV5 sequence. In some embodiments, the reference AAV capsid sequence comprises an AAV8 sequence. In some embodiments, the reference AAV capsid sequence comprises an AAV9 sequence. In some embodiments, the reference AAV capsid sequence comprises an AAVrh74 sequence. While not wishing to be bound by theory, it is understood that a reference AAV capsid sequence comprises a VP1 region. In certain some embodiments, a reference AAV capsid sequence comprises a VP1, VP2 and/or VP3 region, or any combination thereof. A reference VP1 sequence may be considered synonymous with a reference AAV capsid sequence.

The wild-type reference sequence of SEQ ID NO: 1 is as follows:

(SEQ ID NO: 1)
MAADGYLPDWLEDNLSEGIREWWALKPGAPQPKANQQQHQDNARGLVLPG

YKYLGPGNGLDKGEPVNAADAAALEIDKAYDQQLKAGDNPYLKYNHADAE

FQERLKEDTSFGGNLGRAVFQAKKRLLEPLGLVEEAAKTAPGKKRPVEQS

PQEPDSSAGIGKSGAQPAKKRLNFGQTGDTESVPDPQPIGEPPAAPSGVG

SLTMASGGGAPVADNNEGADGVGSSSGNWECDSsQWLGDRVITTSTRTWA

LPTYNNHLYKQQISNSTSGGSSNDNAYFGYSTPWCGYFDENRFHCHFSPR

DWQRLINNNWGERPKRLNFKLENIQVKEVTDNNGVKTIANNLTSTVQVFT

DSDYQLPYVLGSAREGCLPPFEPADVFMIPQYGYLTLNDGSQAVGRSSFY

CLEYFPSQQMLRTGNNFQFSYEFENVPFHSSYAHSQSLDRLMNPLIDQYL

YYLSKTINGSGQNQQTLKFSVAGPSNMAVQGRNYIPGPSYRQQRVSTTVT

QNNNSEFAWPGASSWALNGRNSLMNPGPAMASHKEGEDRFFPLSGSLIFG

KQQQGTGRDNVDADKVMITNEEEIKTTNPVATESYGQVATNHQQSAQAQQ

AQTGWVQNQGILPGMVWQDRDVYLQGPIWAKIPHTDGNEHPSPLMGGFGM

KHPPPQILIKNTPVPADPPTAFNKDKLNSFITQYSTGQVSVEIEWELQKE

NSKRWNPEIQYTSNYYKSNNVEFAVNTEGVYSEPRPIGTRYLTRNL.

Unless otherwise noted, SEQ ID NO: 1 is the reference sequence. In the sequence above, the sequence found in VP1, VP2 and VP3 is underlined (e.g., a VP3 capsid polypeptide includes, e.g., consists of, amino acids corresponding to amino acids 203-737 of SEQ ID NO: 1), the sequence found in both VP1 and VP2 is in bold (e.g., a VP2 capsid polypeptide includes, e.g., consists of, the sequence corresponding to amino acids 138-737 of SEQ ID NO: 1) and the sequence that is not underlined or bold is found only in VP1 (e.g., a VP1 capsid polypeptide includes, e.g., consists of, amino acids corresponding to amino acids 1-737 of SEQ ID NO: 1). The wild-type reference sequence of SEQ ID NO: 1 can be encoded by a reference nucleic acid molecule sequence of SEQ ID NO: 4:

```
                                              (SEQ ID NO: 4)
ATGGCTGCCGATGGTTATCTTCCAGATTGGCTCGAGGACAACCTTAGTGA

AGGTATTCGCGAGTGGTGGGCTTTGAAACCTGGAGCCCCTCAACCCAAGG

CAAATCAACAACATCAAGACAACGCTCGAGGTCTTGTGCTTCCGGGTTAC

AAATACCTTGGACCCGGCAACGGACTCGACAAGGGGGAGCCGGTCAACGC

AGCAGACGCGGCGGCCCTCGAGCACGACAAGGCCTACGACCAGCAGCTCA

AGGCCGGAGACAACCCGTACCTCAAGTACAACCACGCCGACGCCGAGTTC

CAGGAGCGGCTCAAAGAAGATACGTCTTTTGGGGGCAACCTCGGGCGAGC

AGTCTTCCAGGCCAAAAGAGGCTTCTTGAACCTCTTGGTCTGGTTGAGG

AAGCGGCTAAGACGGCTCCTGGAAAGAAGAGGCCTGTAGAGCAGTCTCCT

CAGGAACCGGACTCCTCCGCGGGTATTGGCAAATCGGGTGCACAGCCCGC

TAAAAAGAGACTCAATTTCGGTCAGACTGGCGACACAGAGTCAGTCCCAG

ACCCTCAACCAATCGGAGAACCTCCCGCAGCCCCCTCAGGTGTGGGATCT

CTTACAATGGCTTCAGGTGGTGGCGCACCAGTGGCAGACAATAACGAAGG

TGCCGATGGAGTGGGTAGTTCCTCGGGAAATTGGCATTGCGATTCCCAAT

GGCTGGGGACAGAGTCATCACCACCAGCACCCGAACCTGGGCCCTGCCC

ACCTACAACAATCACCTCTACAAGCAAATCTCCAACAGCACATCTGGAGG

ATCTTCAAATGACAACGCCTACTTCGGCTACAGCACCCCCTGGGGGTATT

TTGACTTCAACAGATTCCACTGCCACTTCTCACCACGTGACTGGCAGCGA

CTCATCAACAACAACTGGGGATTCCGCCTAAGCGACTCAACTTCAAGCT

CTTCAACATTCAGGTCAAAGAGGTTACGGACAACAATGGAGTCAAGACCA

TCGCCAATAACCTTACCAGCACGGTCCAGGTCTTCACGGACTCAGACTAT

CAGCTCCCGTACGTGCTCGGGTCGGCTCACGAGGGCTGCCTCCCGCCGTT

CCCAGCGGACGTTTTCATGATTCCTCAGTACGGGTATCTGACGCTTAATG

ATGGAAGCCAGGCCGTGGGTCGTTCGTCCTTTTACTGCCTGGAATATTTC

CCGTCGCAAATGCTAAGAACGGGTAACAACTTCCAGTTCAGCTACGAGTT

TTGAGAACGTACCTTTCCATAGCAGCTACGCTCACAGCCAAAGCCTGGAC

CGACTAATGAATCCACTCATCGACCAATACTTGTACTATCTCTCAAAGAC

TATTAACGGTTCTGGACAGAATCAACAAACGCTAAAATTCAGTGTGGCCG

GACCCAGCAACATGGCTGTCCAGGGAAGAAACTACATACCTGGACCCAGC

TACCGACAACAACGTGTCTCAACCACTGTGACTCAAAACAACAACAGCGA

ATTTTGCTTGGCCTGGAGCTTCTTCTTGGGCTCTCAATGGACGTAATAGC

TTGATGAATCCTGGACCTGCTATGGCCAGCCACAAGAAGGAGAGGACCG

TTTTTCTTTCCTTTGTCTGGATCTTTAATTTTTGGCAAACAAGGAACTGG

AAGAGACAACGTGGATGCGGACAAAGTCATGATAACCAACCGAAGAAGAA

ATTAAAACTACTAACCCGGTAGCAACGGAGTCCTATGGACAAGTGGCCAC

AAACCACCAGAGTGCCCAAGCACAGGCGCAGACCGGCTGGGTTCAAAACC

AAGGAATACTTCCGGGTATGGTTTGGCAGGACAGAGATGTGTACCTGCAA

GGACCCATTTGGGCCAAAATTCCTCACACGGACGGCAACTTTTTCACCCT

TCTCCGCTGATGGGAGGGTTTGGAATGAAGCACCCGCCTCCTCAGATCCT

CATCAAAAACACACCTGTACCTGCGGATCCTCCAACGGCCTTCAACAAGG

ACAAGCTGAACTCTTTCATCACCCAGTATTCTACTGGCCAAGTCAGCGTG

GAGATCGAGTGGGAGCTGCAGAAGGAAAACAGCAAGCGCTGGAACCCGGA

GATCCAGTACACTTCCAACTATTACAAGTCTAATAATGTTGAATTTTGCT

GTTAATACTGAAGGTGTATATAGTGAACCCCGCCCCATTGGCACCAGATA

CCTGACTCGTAATCTGTAA.
```

An exemplary reference sequence of wild-type AAV2, SEQ ID NO: 5 (wild-type AAV2) is as follows:

```
                                              (SEQ ID NO: 5)
MAADGYLPDWLEDTLSEGIRQQWWKLKPGPPPPKPAERKEKDDSRGLVLP

GYKYLGPFNGLDKGEPVNEADAAALEIDKAYDRQLDSGDNPYLKYNHADA

EFQERLKEDTSFGGNLGRAVFQAKKRVLEPLGLVEEPVKTAPGKKRPVEH

SPVEPDSSSGTGKAGQQPARKRLNFGQTGDADSVPDPQPLGQPPAAPSGL

GTNTMATGSGAPMADNNEGADGVGNSSGNWECDSTWMGDRVITTSTRTWA

LPTYNNHLYKQQISSQSGASNDNHYFGYSTPWGYFDFENRFHCHEFSPRD

WQRLINNNWGEFRPKRLNFKLENIQVKEVIQNDGTTTIANNLTSTVQVFT

DSEYQLPYVLGSAHQGCLPPFPADVEMVPQYGYLTLNNGSQQAVGRSSFY

CLEYFPSQQMLRTGNNFTFSYTFEDVPFHSSYAHSQSLDRLMNPLIDQQY

LYYLSRTNTPSGTTTQSRLQFSQQAGASDIRDQSRNWLPGPCYRQQRVSK

TSADNNNSEYSWTGATKYHLNGRDSLVNPGPAMASHKDDEEKFFPQSGVL

IFGKQGSEKTNVDIEKVMITDEEEIRTTINPVATEQYGSVSTNLQRGNRQ

AATADVNTQGVLPGMVWQDRDVYLQGPIWAKIPHETDGHFEHPSPLMGGF

GLKHPPPQILIKNTPVPANPSTTIFSAAKFASFITQYSTGQVSVEIEWEL

QKENSKRWNPEIQYTSNYNKSVNVDFTVDTNGVYSEPRPIGTRYLTRNL.
```

In the sequence above, the sequence found in VP1, VP2 and VP3 is underlined (e.g., a VP3 capsid polypeptide includes, e.g., consists of, amino acids corresponding to amino acids 203-735 of SEQ ID NO: 5), the sequence found in both VP1 and VP2 is in bold (e.g., a VP2 capsid polypeptide includes, e.g., consists of, the sequence corresponding to amino acids 138-735 of SEQ ID NO: 5) and the sequence that is not underlined or bold is found only in VP1 (e.g., a VP1 capsid polypeptide includes, e.g., consists of, amino acids corresponding to amino acids 1-735 of SEQ ID NO: 5).

An example nucleic acid sequence encoding SEQ ID NO: 5 is SEQ ID NO: 6:

(SEQ ID NO: 6)
ATGGCTGCCGATGGTTATCTTCCAGATTGGCTCGAGGACACTCTCTCTGA

AGGAATAAGACAGTGGTGGAAGCTCAAACCTGGCCCACCACCACCAAAGC

CCGCAGAGCGGCATAAGGACGACAGCAGGGGTCTTGTGCTTCCTGGGTAC

AAGTACCTCGGACCCTTCAACGGACTCGACAAGGGAGAGCCGGTCAACGA

GGCAGACGCCGCGGCCCTCGAGCACGACAAAGCCTACGACCGGCAGCTCG

ACAGCGGAGACAACCCGTACCTCAAGTACAACCACGCCGACGCGGAGTTT

CAGGAGCGCCTTAAAGAAGATACGTCTTTTGGGGGCAACCTCGGACGAGC

AGTCTTCCAGGCGAAAAAGAGGGTTCTTGAACCTCTGGGCCTGGTTGAGG

AACCTGTTAAGACGGCTCCGGGAAAAAAGAGGCCGGTAGAGCACTCTCCT

GTGGAGCCAGACTCCTCCTCGGGAACCGGAAAGGCGGGCCAGCAGCCTGC

AAGAAAAAGATTGAATTTIGGTCAGACTGGAGACGCAGACTCAGTACCTG

ACCCCCAGCCTCTCGGACAGCCACCAGCAGCCCCCTCTGGTCTGGGAACT

AATACGATGGCTACAGGCAGTGGCGCACCAATGGCAGACAATAACGAGGG

CGCCGACGGAGTGGGTAATTCCTCGGGAAATTGGCATTGCGATTCCACAT

GGATGGGCGACAGAGTCATCACCACCAGCACCCGAACCTGGGCCCTGCCC

ACCTACAACAACCACCTCTACAAACAAATTTCCAGCCAATCAGGAGCCTC

GAACGACAATCACTACTTTGGCTACAGCACCCCTTGGGGGTATTTTGACT

TCAACAGATTCCACTGCCACTTTTCACCACGTGACTGGCAAAGACTCATC

AACAACAACTGGGGATTCCGACCCAAGAGACTCAACTTCAAGCTCTTTAA

CATTCAAGTCAAAGAGGTCACGCAGAATGACGGTACGACGACGATTGCCA

ATAACCTTACCAGCACGGTTCAGGTGTTTACTGACTCGGAGTACCAGCTC

CCGTACGTCCTCGGCTCGGCGCATCAAGGATGCCTCCCGCCGTTCCCAGC

AGACGTCTTCATGGTGCCACAGTATGGATACCTCACCCTGAACAACGGGA

GTCAGGCAGTAGGACGCTCTTCATTTTACTGCCTGGAGTACTTTCCTTCT

CAGATGCTGCGTACCGGAAACAACTTTACCTTCAGCTACACTTTTGAGGA

CGTTCCTTTCCACAGCAGCTACGCTCACAGCCAGAGTCTGGACCGTCTCA

TGAATCCTCTCATCGACCAGTACCTGTATTACTTGAGCAGAACAAACACT

CCAAGTGGAACCACCACGCAGTCAAGGCTTCAGTTTTCTCAGGCCGGAGC

GAGTGACATTCGGGACCAGTCTAGGAACTGGCTTCCTGGACCCTGTTACC

GCCAGCAGCGAGTATCAAAGACATCTGCGGATAACAACAACAGTGAATAC

TCGTGGACTGGAGCTACCAAGTACCACCTCAATGGCAGAGACTCTCTGGT

GAATCCGGGCCCGGCCATGGCAAGCCACAAGGACGATGAAGAAAAGTTTT

TTCCTCAGAGCGGGGTTCTCATCTTTGGGAAGCAAGGCTCAGAGAAAACA

AATGTGGACATTGAAAAGGTCATGATTACAGACGAAGAGGAAATCAGGAC

AACCAATCCCGTGGCTACGGAGCAGTATGGTTCTGTATCTACCAACCTCC

AGAGAGGCAACAGACAAGCAGCTACCGCAGATGTCAACACACAAGGCGTT

CTTCCAGGCATGGTCTGGCAGGACAGAGATGTGTACCTTCAGGGGCCCAT

CTGGGCAAAGATTCCACACACGGACGGACATTTTCACCCCTCTCCCCTCA

-continued
TGGGTGGATTCGGACTTAAACACCCTCCTCCACAGATTCTCATCAAGAAC

ACCCCGGTACCTGCGAATCCTTCGACCACCTTCAGTGCGGCAAAGTTTGC

TTCCTTCATCACACAGTACTCCACGGGACAGGTCAGCGTGGAGATCGAGT

GGGAGCTGCAGAAGGAAAACAGCAAACGCTGGAATCCCGAAATTCAGTAC

ACTTCCAACTACAACAAGTCTGTTAATGTGGACTTTACTGTGGACACTAA

TGGCGTGTATTCAGAGCCTCGCCCCATTGGCACCAGATACCTGACTCGTA

ATCTGTAA.

An exemplary reference sequence of wild type AAV5, SEQ ID NO: 7 (wild-type AAV5), is as follows:

(SEQ ID NO: 7)
MSFVDHPPDWLEEVGEGLREFLGLEAGPPKPKPNQQHQDQARGLVLPGYN

YLGPGNGLDRGEPVNRADEVAREHDISYNEQLEAGDNPYLKYNHADAEFQ

EKLADDTSFGGNLGKAVFQQAKKRVLEPFGLVEEGAKTAPTGKRIDDHFP

KRKKARTEEDSKPSTSSDAEAGPSGSQQLQIPAQPASSLGADTMSAGGGG

PLGDNNQGADGVGNASGDWECDSTWMGDRVVTKSTRTWVLPSYNNHEQYR

EIKSGSVDGSNANAYFGYSTPWGYFDFNRFHSHWSPRDWQRLINNYWGFR

PRSLRVKIFNIQQVKEVTIVQQQDSTTTIANNLTSTVQQQVFTDDDYQLP

YVVGNGTEGCLPAFPPQVFTLPQQQYGYATLNRDNTENPTERSSEFCLEY

FPSKMLRTGNNFEFTYNFEEVPFHSSFAPSQNLFKLANPLVDQQYLYRFE

VSTNNTGGVQFNKNLAGRYANTYKNWEPGPMGRTQGWNLGSGVNRASVSA

FATTNRMELEGASYQVPPQPNGMTNNLQGSNTYALENTMIFNSQPANPGT

TATYLEGNMLITSESETQPVNRVAYNVGGQMATNNQSSTTAPATGTYNLQ

EIVPGSVWMERDVYLQGPIWAKIPETGAHFPHPSPAMGGFGLKHPPPMML

IKNTPVPGNITSFSDVPVSSFITQYSTGQVTVEMEWELKKENSKRWNPEI

QYTNNYNDPQFVDFAPDSTGEYRTTRPIGTRYLTRPL.

In the sequence above, the sequence found in VP1, VP2 and VP3 is underlined (e.g., a VP3 capsid polypeptide includes, e.g., consists of, amino acids corresponding to amino acids 193-725 of SEQ ID NO: 7), the sequence found in both VP1 and VP2 is in bold (e.g., a VP2 capsid polypeptide includes, e.g., consists of, the sequence corresponding to amino acids 137-725 of SEQ ID NO: 7) and the sequence that is not underlined or bold is found only in VP1 (e.g., a VP1 capsid polypeptide includes, e.g., consists of, amino acids corresponding to amino acids 1-725 of SEQ ID NO: 7).

An example nucleic acid sequence encoding SEQ ID NO: 7 is SEQ ID NO: 8:

(SEQ ID NO: 8)
ATGTCTTTTGTTGATCACCCTCCAGATTGGTTGGAAGAAGTTGGTGAAGG

TCTTCGCGAGTTTTTGGGCCTTGAAGCGGGCCCACCGAAACCAAAACCCA

ATCAGCAGCATCAAGATCAAGCCCGTGGTCTTGTGCTGCCTGGTTATAAC

TATCTCGGACCCGGAAACGGGCTCGATCGAGGAGAGCCTGTCAACAGGGC

AGACGAGGTCGCGCGAGAGCACGACATCTCGTACAACGAGCAGCTTGAGG

CGGGAGACAACCCCTACCTCAAGTACAACCACGCGGACGCCGAGTTTCAG

-continued

```
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATACAATGTCTGCGGGAGGTGGCGGCCCA
TTGGGCGACAATAACCAAGGTGCCGATGGAGTGGGCAATGCCTCGGGAGA
TTGGCATTGCGATTCCACGTGGATGGGGACAGAGTCGTCACCAAGTCCA
CCCGAACCTGGGTGCTGCCCAGCTACAACAACCACCAGTACCGAGAGATC
AAAAGCGGCTCCGTCGACGGAAGCAACGCCAACGCCTACTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTGTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTGCCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAACCACCAGACCTATCGGAAC
CCGATACCTTACCCGACCCCTTTAA.
```

An exemplary reference sequence of wild-type AAV8, SEQ ID NO: 9 (wild-type AAV8), is as follows:

(SEQ ID NO: 9)
MAADGYLPDWLEDNLSEGIREWWALKPGAPKPKANQQKQDDGRGLVLPGY

KYLGPFNGLDKGEPVNAADAAALEIDKAYDQQLQQAGDNPYLRYNHADAE

FQERLQEDTSFGGNLGRAVFQAKKRVLEPLGLVEEGAKTAPGKKRPVEPS

PQRSPDSSTGIGKKGQQPARKRLNFGQTGDSESVPDPQPLGEPPAAPSGV

GPNT<u>MAAGGGAPMADNNEGADGVGSSSGNWHECDSTWLGDRVITTSTRTW

ALPTYNNELYKQISNGTSGGATNDNTYFGYSTPWGYFDFNRFHECHEFSP

RDWQRLINNNWGFRPKRLSFKLENIQVKEVTQNEGTKTIANNLTSTIQVE

FTDSEYQLPYVLGSARQGCLPPFPADVFMIPQYGYLTLNNGSQAVGRSSF

YCLEYFPSQMLRTGNNFQFTYTFEDVPFHSSYAHSQQSLDRLMNPLIDQY

LYYLSRTQTTGGTANTQTLGFSQGGPNTMANQAKNWLPGPCYRQQRVSTT

TGQNNNSNFAWTAGTEKYHLNGRNSLANPGIAMATHKDDEERFFPSNGIL

IFGKQQNAARDNADYSDVMLTSEEEIKTTINPVATEEYGIVADNLQQQNT

APQIGTVNSQGALPGMVWQNRDVYLQGPIWAKIPHTDGNFHPSPLMGGFG

LKHPPPQILIKNTPVPADPPTTEFNQSKLNSFITQYSTGQVSVEIEWELQ

KENSKRWNPEIQYTSNYYKSTSVDFAVNTEGVYSEPRPIGTRYLTRNL.</u>

In the sequence above, the sequence found in VP1, VP2 and VP3 is underlined (e.g., a VP3 capsid polypeptide includes, e.g., consists of, amino acids corresponding to amino acids 204-739 of SEQ ID NO: 9), the sequence found in both VP1 and VP2 is in bold (e.g., a VP2 capsid polypeptide includes, e.g., consists of, the sequence corresponding to amino acids 138-735 of SEQ ID NO: 9) and the sequence that is not underlined or bold is found only in VP1 (e.g., a VP1 capsid polypeptide includes, e.g., consists of, amino acids corresponding to amino acids 1-739 of SEQ ID NO: 9).

An example nucleic acid sequence encoding SEQ ID NO: 9 is SEQ ID NO: 10:

(SEQ ID NO: 10)
```
ATGGCTGCCGATGGTTATCTTCCAGATTGGCTCGAGGACAACCTCTCTGA

GGGCATTCGCGAGTGGTGGGCGCTGAAACCTGGAGCCCCGAAGCCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGACGCAGCGGCCCTCGAGCACGACAAGGCCTACGACCAGCAGCTGC

AGGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAGAGACCGGTAGAGCCATCACCC

CAGCGTTCTCCAGACTCCTCTACGGGCATCGGCAAGAAAGGCCAACAGCC

CGCCAGAAAAGACTCAATTTTGGTCAGACTGGCGACTCAGAGTCAGTTC

CAGACCCTCAACCTCTCGGAGAACCTCCAGCAGCGCCCTCTGGTGTGGGA

CCTAATACAATGGCTGCAGGCGGTGGCGCACCAATGGCAGACAATAACGA

AGGCGCCGACGGAGTGGGTAGTTCCTCGGGAAATTGGCATTGCGATTCCA
```

```
CATGGCTGGGCGACAGAGTCATCACCACCAGCACCCGAACCTGGGCCCTG

CCCACCTACAACAACCACCTCTACAAGCAAATCTCCAACGGGACATCGG

AGGAGCCACCAACGACAACACCTACTTCGGCTACAGCACCCCCTGGGGT

ATTTTGACTTTAACAGATTCCACTGCCACTTTTCACCACGTGACTGGCAG

CGACTCATCAACAACAACTGGGGATTCCGGCCCAAGAGACTCAGCTTCAA

GCTCTTCAACATCCAGGTCAAGGAGGTCACGCAGAATGAAGGCACCAAGA

CCATCGCCAATAACCTCACCAGCACCATCCAGGTGTTTACGGACTCGGAG

TACCAGCTGCCGTACGTTCTCGGCTCTGCCCACCAGGGCTGCCTGCCTCC

GTTCCCGGCGGACGTGTTCATGATTCCCCAGTACGGCTACCTAACACTCA

ACAACGGTAGTCAGGCCGTGGGACGCTCCTCCTTCTACTGCCTGGAATAC

TTTCCTTCGCAGATGCTGAGAACCGGCAACAACTTCCAGTTTACTTACAC

CTTCGAGGACGTGCCTTTCCACAGCAGCTACGCCCACAGCCAGAGCTTGG

ACCGGCTGATGAATCCTCTGATTGACCAGTACCTGTACTACTTGTCTCGG

ACTCAAACAACAGGAGGCACGGCAAATACGCAGACTCTGGGCTTCAGCCA

AGGTGGGCCTAATACAATGGCCAATCAGGCAAAGAACTGGCTGCCAGGAC

CCTGTTACCGCCAACAACGCGTCTCAACGACAACCGGGCAAAACAACAAT

AGCAACTTTGCCTGGACTGCTGGGACCAAATACCATCTGAATGGAAGAAA

TTCATTGGCTAATCCTGGCATCGCTATGGCAACACACAAAGACGACGAGG

AGCGTTTTTTTCCCAGTAACGGGATCCTGATTTTTGGCAAACAAAATGCT

GCCAGAGACAATGCGGATTACAGCGATGTCATGCTCACCAGCGAGGAAGA

AATCAAAACCACTAACCCTGTGGCTACAGAGGAATACGGTATCGTGGCAG

ATAACTTGCAGCAGCAAAACACGGCTCCTCAAATTGGAACTGTCAACAGC

CAGGGGGCCTTACCCGGTATGGTCTGGCAGAACCGGGACGTGTACCTGCA

GGGTCCCATCTGGGCCAAGATTCCTCACACGGACGGCAACTTCCACCCGT

CTCCGCTGATGGGCGGCTTTGGCCTGAAACATCCTCCGCCTCAGATCCTG

ATCAAGAACACGCCTGTACCTGCGGATCCTCCGACCACCTTCAACCAGTC

AAAGCTGAACTCTTTCATCACGCAATACAGCACCGGACAGGTCAGCGTGG

AAATTGAATGGGAGCTGCAGAAGGAAAACAGCAAGCGCTGGAACCCCGAG

ATCCAGTACACCTCCAACTACTACAAATCTACAAGTGTGGACTTTGCTGT

TAATACAGAAGGCGTGTACTCTGAACCCCGCCCCATTGGCACCCGTTACC

TCACCCGTAATCTGTAA.
```

An exemplary reference sequence of wild-type AAVrh74, SEQ ID NO: 11 (wild-type AAVrh74), is as follows:

```
                                          (SEQ ID NO: 11)
MAADGYLPDWLEDNLSEGIREWWDLKPGAPKPKANQQKQDNGRGLVLPGY

KYLGPFNGLDKGEPVNAADAAALEIDKAYDQQLQQAGDNPYLRYNHADAE

FQERLQEDTSFGGNLGRAVFQAKKRVLEPLGLVESPVKTAPGKKRPVEPS

PQRSPDSSTGIGKKGQQPAKKRLNFGQTGDSESVPDPQPIGEPPAGPSGL

GSGTMAAGGGAPMADNNEGADGVGSSSGNWHECDSTWLGDRVITTSTRTW

ALPTYNNELYKQISNGTSGGSTNDNTYFGYSTPWGYFDFNRFHECHEFSP

RDWQRLINNNWGFRPKRLNFKLENIQVKEVTQNEGTKTIANNLTSTIQVE

FTDSEYQLPYVLGSARQGCLPPFPADVFMIPQQQYGYLTLNNGSQAVGRS

SFYCLEYFPSQMLRTGNNFEFSYNFEDVPFHSSYAHSQQSLDRLMNPLI

DQYLYYLSRTQSTGGTAGTQQQLLEFSQAGPNNMSAQAKNWLPGPCYRQQ

RVSTTLSQNNNSNFAWTGATEKYHELNGRDSLVNPGVAMATEKDDEERFF

PSSGVLMFGKQGAGKDNVDYSSVMLTSEEEIKTTINPVATEQQYGVVADN

LQQQNAAPIVGAVNSQQGALPGMVWQNRDVYLQGPIWAKIPHTDGNFHPS

PLMGGFGLKHPPPQILIKNTPVPADPPTTEFNQAKLASFITQYSTGQVSV

EIEWELQKENSKRWNPEIQYTSNYYKSTNVDFAVNTEGTYSEPRPIGTRY

LTRNL.
```

An alternative exemplary reference sequence of SEQ ID NO: 12 (alternate wild-type AAVrh74) is as follows:

```
                                          (SEQ ID NO: 12)
MAADGYLPDWLEDNLSEGIREWWDLKPGAPKPKANQQKQDNGRGLVLPGY

KYLGPFNGLDKGEPVNAADAAALEIDKAYDQQLQQAGDNPYLRYNHADAE

FQERLQEDTSFGGNLGRAVFQAKKRVLEPLGLVESPVKTAPGKKRPVEPS

PQRSPDSSTGIGKKGQQPAKKRLNFGQTGDSESVPDPQPIGEPPAGPSGL

GSGTMAAGGGAPMADNNEGADGVGSSSGNWHCDSTWLGDRVITTSTRTWA

LPTYNNELYKQISNGTSGGSTNDNTYFGYSTPWCGYFDFNRFHCHESPRD

WQRLINNNWGFRPKRLNFKLENIQVKEVTQNEGTKTIANNLTSTIQVEFT

DSEYQLPYVLGSARQGCLPPFPADVFMIPQQQYGYLTLNNGSQAVGRSSF

YCLEYFPSQMLRTGNNFEFSYNFEDVPFESSYAHSQQSLDRLMNPLIDQY

LYYLSRTQSTGGTAGTQQQLLFSQAGPNNMSAQAKNWLPGPCYRQQRVST

TLSQNNNSNFAWTGATKYHLNGRDSLVNPGVAMATEKDDEERFFPSSGVL

MFGKQGAGKDNVDYSSVMLTSEEEIKTTINPVATEQYGVVADNLQQQNAA

PIVGAVNSQGALPGMVWQNRDVYLQGPIWAKIPHTDGNFHPSPLMGGFGL

KHPPPQILIKNTPVPADPPTTFTKAKLASFITQYSTGQVSVEIEWELQKE

NSKRWNPEIQYTSNYYKSTNVDFAVNTEGTYSEPRPIGTRYLTRNL.
```

In the sequences above (SEQ ID NO: 11 or SEQ ID NO: 12), the sequence found in VP1, VP2 and VP3 is underlined (e.g., a VP3 capsid polypeptide includes, e.g., consists of, amino acids corresponding to amino acids 204-739 of SEQ ID NO: 11), the sequence found in both VP1 and VP2 is in bold (e.g., a VP2 capsid polypeptide includes, e.g., consists of, the sequence corresponding to amino acids 137-739 of SEQ ID NO: 11) and the sequence that is not underlined or bold is found only in VP1 (e.g., a VP1 capsid polypeptide includes, e.g., consists of, amino acids corresponding to amino acids 1-739 of SEQ ID NO: 11).

An example nucleic acid sequence encoding SEQ ID NO: 11 is SEQ ID NO: 13:

```
                                          (SEQ ID NO: 13)
ATGGCTGCCGATGGTTATCTTCCAGATTGGCTCGAGGACAACCTCTCTGA

GGGCATTCGCGAGTGGTGGGACCTGAAACCTGGAGCCCCGAAACCCAAAG

CCAACCAGCAAAAGCAGGACAACGGCCGGGGTCTGGTGCTTCCTGGCTAC
```

-continued

```
AAGTACCTCGGACCCTTCAACGGACTCGACAAGGGGGAGCCCGTCAACGC

GGCGGACGCAGCGGCCCTCGAGCACGACAAGGCCTACGACCAGCAGCTCC

AAGCGGGTGACAATCCGTACCTGCGGTATAATCACGCCGACGCCGAGTTT

CAGGAGCGTCTGCAAGAAGATACGTCTTTTGGGGGCAACCTCGGGCGCGC

AGTCTTCCAGGCCAAAAAGCGGGTTCTCGAACCTCTGGGCCTGGTTGAAT

CGCCGGTTAAGACGGCTCCTGGAAAGAAGAGGCCGGTAGAGCCATCACCC

CAGCGCTCTCCAGACTCCTCTACGGGCATCGGCAAGAAAGGCCAGCAGCC

CGCAAAAAAGAGACTCAATTTTGGGCAGACTGGCGACTCAGAGTCAGTCC

CCGACCCTCAACCAATCGGAGAACCACCAGCAGGCCCCTCTGGTCTGGGA

TCTGGTACAATGGCTGCAGGCGGTGGCGCTCCAATGGCAGACAATAACGA

AGGCGCCGACGGAGTGGGTAGTTCCTCAGGAAATTGGCATTGCGATTCCA

CATGGCTGGGCGACAGAGTCATCACCACCAGCACCCGCACCTGGGCCCTG

CCCACCTACAACAACCACCTCTACAAGCAAATCTCCAACGGGACCTCGGG

AGGAAGCACCAACGACAACACCTACTTCGGCTACAGCACCCCTGGGGGT

ATTTTGACTTCAACAGATTCCACTGCCACTTTTCACCACGTGACTGGCAG

CGACTCATCAACAACAACTGGGGATTCCGGCCCAAGAGGCTCAACTTCAA

GCTCTTCAACATCCAAGTCAAGGAGGTCACGCAGAATGAAGGCACCAAGA

CCATCGCCAATAACCTTACCAGCACGATTCAGGTCTTTACGGACTCGGAA

TACCAGCTCCCGTACGTGCTCGGCTCGGCGCACCAGGGCTGCCTGCCTCC

GTTCCCGGCGGACGTCTTCATGATTCCTCAGTACGGGTACCTGACTCTGA

ACAATGGCAGTCAGGCTGTGGGCCGGTCGTCCTTCTACTGCCTGGAGTAC

TTTCCTTCTCAAATGCTGAGAACGGGCAACAACTTTGAATTCAGCTACAA

CTTCGAGGACGTGCCCTTCCACAGCAGCTACGCGCACAGCCAGAGCCTGG

ACCGGCTGATGAACCCTCTCATCGACCAGTACTTGTACTACCTGTCCCGG

ACTCAAAGCACGGGCGGTACTGCAGGAACTCAGCAGTTGCTATTTTCTCA

GGCCGGGCCTAACAACATGTCGGCTCAGGCCAAGAACTGGCTACCCGGTC

CCTGCTACCGGCAGCAACGTGTCTCCACGACACTGTCGCAGAACAACAAC

AGCAACTTTGCCTGGACGGGTGCCACCAAGTATCATCTGAATGGCAGAGA

CTCTCTGGTGAATCCTGGCGTTGCCATGGCTACCCACAAGGACGACGAAG

AGCGATTTTTTCCATCCAGCGGAGTCTTAATGTTTGGGAAACAGGGAGCT

GGAAAAGACAACGTGGACTATAGCAGCGTGATGCTAACCAGCGAGGAAGA

AATAAAGACCACCAACCCAGTGGCCACAGAACAGTACGGCGTGGTGGCCG

ATAACCTGCAACAGCAAAACGCCGCTCCTATTGTAGGGGCCGTCAATAGT

CAAGGAGCCTTACCTGGCATGGTGTGGCAGAACCGGGACGTGTACCTGCA

GGGTCCCATCTGGGCCAAGATTCCTCATACGGACGGCAACTTTCATCCCT

CGCCGCTGATGGGAGGCTTTGGACTGAAGCATCCGCCTCCTCAGATCCTG

ATTAAAAACACACCTGTTCCCGCGGATCCTCCGACCACCTTCAATCAGGC

CAAGCTGGCTTCTTTCATCACGCAGTACAGTACCGGCCAGGTCAGCGTGG

AGATCGAGTGGGAGCTGCAGAAGGAGAACAGCAAACGCTGGAACCCAGAG

ATTCAGTACACTTCCAACTACTACAAATCTACAAATGTGGACTTTGCTGT

CAATACTGAGGGTACTTATTCCGAGCCTCGCCCCATTGGCACCCGTTACC

TCACCCGTAATCTGTAA.
```

The present disclosure refers to structural capsid proteins (including VP1, VP2 and VP3) which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins. Where the Met/AA-clipping is incomplete, a mixture of one or more (one, two or three) VP capsid proteins comprising the viral capsid can be produced, some of which include a Met1/AA1 amino acid (Met+/AA+) and some of which lack a Met1/AA1 amino acid as a result of Met/AA-clipping (Met–/AA–). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. Hum Gene Ther Methods. 2017 Oct. 28 (5): 255-267; Hwang, et al. N-Terminal Acetylation of Cellular Proteins Creates Specific Degradation Signals. Science. 2010 Feb. 19.327 (5968): 973-977; the contents of which are each incorporated herein by reference in its entirety. According to the present disclosure, references to capsid polypeptides is not limited to either clipped (Met–/AA–) or unclipped (Met+/AA+) and, in context, also refer to independent capsid polypeptides, viral capsids comprised of a mixture of capsid proteins, and/or polynucleotide sequences (or fragments thereof) which encode, describe, produce or result in capsid polypeptides of the present disclosure. A direct reference to a "capsid polypeptide" (such as VP1, VP2 or VP3) also comprise VP capsid proteins which include a Met1/AA1 amino acid (Met+/AA+) as well as corresponding VP capsid polypeptide which lack the Met1/AA1 amino acid as a result of Met/AA-clipping (Met–/AA–). Further according to the present disclosure, a reference to a specific SEQ ID NO: (whether a protein or nucleic acid) which comprises or encodes, respectively, one or more capsid polypeptides which include a Met1/AA1 amino acid (Met+/AA+) should be understood to teach the VP capsid polypeptides which lack the Met1/AA1 amino acid as upon review of the sequence, it is readily apparent any sequence which merely lacks the first listed amino acid (whether or not Met1/AA1). As a non-limiting example, reference to a VP1 polypeptide sequence which is 736 amino acids in length and which includes a "Met1" amino acid (Met+) encoded by the AUG/ATG start codon is also understood to teach a VP1 polypeptide sequence which is 735 amino acids in length and which does not include the "Met1" amino acid (Met–) of the 736 amino acid Met+ sequence. As a second non-limiting example, reference to a VP1 polypeptide sequence which is 736 amino acids in length and which includes an "AA1" amino acid (AA1+) encoded by any NNN initiator codon can also be understood to teach a VP1 polypeptide sequence which is 735 amino acids in length and which does not include the "AA1" amino acid (AA1−) of the 736 amino acid AA1+ sequence. References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met−/AA1−), and combinations thereof (Met+/AA1+ and Met−/AA1−). As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+) and VP3 (Met−/AA1−); and can also include similar optional combinations of VP2 (Met+/AA1) and VP2 (Met−/AA1−).

In some embodiments, the reference AAV capsid sequence comprises an amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

In some embodiments, the reference AAV capsid sequence is encoded by a nucleotide sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described above. In certain some embodiments, the reference sequence is not an AAV capsid sequence and is instead a different vector (e.g., lentivirus, plasmid, etc.).

In some embodiments, a nucleic acid of the disclosure (e.g., encoding an AAV9 variant capsid protein or a variant capsid polypeptide described herein) comprises conventional control elements or sequences which are operably linked to the nucleic acid molecule in a manner which permits transcription, translation and/or expression in a cell transfected with the nucleic acid (e.g., a plasmid vector comprising said nucleic acid) or infected with a virus comprising said nucleic acid. As used herein, "operably linked" sequences include both expression control sequences that are contiguous with the gene of interest and expression control sequences that act in trans or at a distance to control the gene of interest.

Expression control sequences include efficient RNA processing signals such as splicing and polyadenylation (polyA) signals; appropriate transcription initiation, termination, promoter and enhancer sequences; sequences that stabilize cytoplasmic mRNA; sequences that enhance protein stability; sequences that enhance translation efficiency (e.g., Kozak consensus sequence);

and in some embodiments, sequences that enhance secretion of the encoded transgene product. Expression control sequences, including promoters which are native, constitutive, inducible and/or tissue-specific, are known in the art and may be utilized with the compositions and methods disclosed herein.

In some embodiments, the native promoter for the transgene may be used. Without wishing to be bound by theory, the native promoter may mimic native expression of the transgene, or provide temporal, developmental, or tissue-specific expression, or expression in response to specific transcriptional stimuli. In some embodiment, the transgene may be operably linked to other native expression control elements, such as enhancer elements, polyadenylation sites or Kozak consensus sequences, e.g., to mimic the native expression.

In some embodiments, the transgene is operably linked to a tissue-specific promoter, e.g., a promoter active specifically in one or more CNS cell types. In some embodiments, the CNS cell is, for example, a neuronal cell, a glial cell, an astrocyte, an oligodendrocyte, an endothelia cell, and the like.

In some embodiments, a vector, e.g., a plasmid, carrying a transgene may also include a selectable marker or a reporter gene. Such selectable reporters or marker genes can be used to signal the presence of the vector, e.g., plasmid, in bacterial cells. Other components of the vector, e.g., plasmid, may include an origin of replication. Selection of these and other promoters and vector elements are conventional and many such sequences are available (see, e.g., Sambrook et al, and references cited therein).

In some embodiments, the viral particle comprising a variant capsid polypeptide, e.g., a variant capsid polypeptide described herein, exhibits increased CNS transduction as compared to a viral particle with the wild-type capsid polypeptide (SEQ ID NO: 1). In some embodiments, CNS transduction comprises brain, spinal cord, cortical, subcortical, midbrain and brainstem, and cerebellum transduction.

In some embodiments, the viral particle comprising a variant capsid polypeptide, e.g., a variant capsid polypeptide described herein, exhibits increased brain transduction as compared to a viral particle with the wild-type capsid polypeptide (SEQ ID NO: 1). In some embodiments, the viral particle comprising a variant capsid polypeptide, e.g., a variant capsid polypeptide described herein, exhibits increased brain transduction of at least 1-fold, e.g., as compared to a viral particle with a reference capsid polypeptide, for example, with the wild-type capsid polypeptide (SEQ ID NO: 1). In some embodiments, the variant capsid polypeptide present in a viral particle increases brain transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 64-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 70-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain transduction at least 100-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from tissue of one or more, e.g., 5 or more, brain regions, e.g., of an animal, e.g., of a non-human primate ("NHP") (e.g., as described in the examples).

In some embodiments, the viral particle comprising the variant capsid polypeptide, e.g., the variant capsid polypeptide described herein, exhibits increased cerebellum transduction as compared to a viral particle with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 64-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum transduction at least 90-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from cerebellum tissue, e.g., of an animal, e.g., of an NHP (e.g., as described in the examples).

In some embodiments, the viral particle comprising the variant capsid polypeptide, e.g., the variant capsid polypeptide described herein, exhibits increased cortical transduction as compared to a viral particle with the wild-type capsid polypeptide (SEQ ID NO: 1). In some embodiments, the viral particle comprising the variant capsid polypeptide, e.g., the variant capsid polypeptide described herein, exhibits increased cortical transduction at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 64-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical transduction at least 80-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from tissue of the cortex, e.g., of an animal, e.g., of a non-human primate ("NHP") (e.g., as described in the examples).

In some embodiments, the viral particle comprising the variant capsid polypeptide, e.g., the variant capsid polypeptide described herein, exhibits increased midbrain and brainstem transduction as compared to a viral particle with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem transduction at least 50-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from tissue of the midbrain and/or brainstem, e.g., of an animal, e.g., of a non-human primate ("NHP") (e.g., as described in the examples).

In some embodiments, the viral particle comprising the variant capsid polypeptide, e.g., the variant capsid polypeptide described herein, exhibits increased spinal cord transduction as compared to a viral particle with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord transduction at least 64-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from tissue of the spinal cord, e.g., of an animal, e.g., of a non-human primate ("NHP") (e.g., as described in the examples).

In some embodiments, the viral particle comprising the variant capsid polypeptide, e.g., the variant capsid polypeptide described herein, exhibits increased subcortical transduction as compared to a viral particle with the wild-type capsid polypeptide (SEQ ID NO: 1). In some embodiments, the viral particle comprising the variant capsid polypeptide, e.g., the variant capsid polypeptide described herein, exhibits increased subcortical transduction at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 64-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical transduction at least 90-fold, e.g., as compared to a viral particle with a reference capsid polypeptide, for example, with the wild-type capsid polypeptide (SEQ ID NO: 1). In some embodiments, the increased brain transduction is as measured by quantification of viral RNA isolated from tissue of the subcortex, e.g., of an animal, e.g., of a non-human primate ("NHP") (e.g., as described in the examples).

In some embodiments, the capsid polypeptide is an isolated or purified polypeptide (e.g., isolated or purified from a cell, other biological component, or contaminant). In some embodiments, the variant polypeptide is present in a dependoparvovirus particle, e.g., described herein. In some embodiments, the variant capsid polypeptide is present in a cell, cell-free system, or translation system, e.g., described herein.

In some embodiments, the capsid polypeptide is present in a dependoparvovirus B (e.g., AAV9) particle. In some embodiments, the capsid particle has increased CNS transduction.

In some embodiments, a dependoparvovirus particle comprises an amino acid sequence that has at least 80, 85, 90, 91, 92, 93, 94, 95, 96, 97, 98, 99, or 100% identity to the amino acid sequences provided for herein (e.g., SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139). In some embodiments, the variant capsid polypeptide comprises an amino acid sequence that differs by no more than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acids from the amino acid sequence of a variant capsid polypeptide provided for herein.

In some embodiments, the additional alteration improves a production characteristic of a dependoparvovirus particle or method of making the same. In some embodiments, the additional alteration improves or alters another characteristic of a dependoparvovirus particle, e.g., tropism.

Nucleic Acids and Polypeptides

The disclosure is further directed, in part, to a nucleic acid comprising a sequence encoding a variant capsid polypeptide as provided for herein. In some embodiments the nucleic acid encodes a VP1 variant capsid polypeptide, e.g., as described herein. In some embodiments, the nucleic acid encodes a VP2 variant capsid polypeptide, e.g., as described herein. In some embodiments, the nucleic acid encodes a VP3 variant capsid polypeptide, e.g., as described herein. In some embodiments, the nucleic acid encodes a VP1, VP2 and VP3 variant capsid polypeptide, e.g., as described herein. In some embodiments, the variant capsid polypeptide comprises a sequence of SEQ ID NO: 2, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, or 139. In some embodiments, the variant capsid polypeptide comprises a sequence of SEQ ID NO: 2.

In some embodiments, the nucleic acid comprises SEQ ID NO: 3, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, or 265; or comprises a VP2 or VP3-encoding fragment thereof. In some embodiments, the nucleic acid comprises SEQ ID NO: 3. In some embodiments, the nucleic acid comprises SEQ ID NO: 140. In some embodiments, the nucleic acid comprises SEQ ID NO: 141. In some embodiments, the nucleic acid comprises SEQ ID NO: 142. In some embodiments, the nucleic acid comprises SEQ ID NO: 143. In some embodiments, the nucleic acid comprises SEQ ID NO: 144. In some embodiments, the nucleic acid comprises SEQ ID NO: 145. In some embodiments, the nucleic acid comprises SEQ ID NO: 146. In some embodiments, the nucleic acid comprises SEQ ID NO: 147. In some embodiments, the nucleic acid comprises SEQ ID NO: 148. In some embodiments, the nucleic acid comprises SEQ ID NO: 149. In some embodiments, the nucleic acid comprises SEQ ID NO: 150. In some embodiments, the nucleic acid comprises SEQ ID NO: 151. In some embodiments, the nucleic acid comprises SEQ ID NO: 152. In some embodiments, the nucleic acid comprises SEQ ID NO: 153. In some embodiments, the nucleic acid comprises SEQ ID NO: 154. In some embodiments, the nucleic acid comprises SEQ ID NO: 155. In some embodiments, the nucleic acid comprises SEQ ID NO: 156. In some embodiments, the nucleic acid comprises SEQ ID NO: 157. In some embodiments, the nucleic acid comprises SEQ ID NO: 158. In some embodiments, the nucleic acid comprises SEQ ID NO: 159. In some embodiments, the nucleic acid comprises SEQ ID NO: 160. In some embodiments, the nucleic acid comprises SEQ ID NO: 161. In some embodiments, the nucleic acid comprises SEQ ID NO: 162. In some embodiments, the nucleic acid comprises SEQ ID NO: 163. In some embodiments, the nucleic acid comprises SEQ ID NO:164. In some embodiments, the nucleic acid comprises SEQ ID NO: 165. In some embodiments, the nucleic acid comprises SEQ ID NO: 166. In some embodiments, the nucleic acid comprises SEQ ID NO: 167. In some embodiments, the nucleic acid comprises SEQ ID NO: 168. In some embodiments, the nucleic acid comprises SEQ ID NO: 169. In some embodiments, the nucleic acid comprises SEQ ID NO: 170. In some embodiments, the nucleic acid comprises SEQ ID NO: 171. In some embodiments, the nucleic acid comprises SEQ ID NO: 172. In some embodiments, the nucleic acid comprises SEQ ID NO: 173. In some embodiments, the nucleic acid comprises SEQ ID NO: 174. In some embodiments, the nucleic acid comprises SEQ ID NO: 175. In some embodiments, the nucleic acid comprises SEQ ID NO: 176. In some embodiments, the nucleic acid comprises SEQ ID NO: 177. In some embodiments, the nucleic acid comprises SEQ ID NO: 178. In some embodiments, the nucleic acid comprises SEQ ID NO: 179. In some embodiments, the nucleic acid comprises SEQ ID NO: 180. In some embodiments, the nucleic acid comprises SEQ ID NO: 181. In some embodiments, the nucleic acid comprises SEQ ID NO: 182. In some embodiments, the nucleic acid comprises SEQ ID NO: 183. In some embodiments, the nucleic acid comprises SEQ ID NO: 184. In some embodiments, the nucleic acid comprises SEQ ID NO: 185. In some embodiments, the nucleic acid comprises SEQ ID NO: 186. In some embodiments, the nucleic acid comprises SEQ ID NO: 187. In some embodiments, the nucleic acid comprises SEQ ID NO: 188. In some embodiments, the nucleic acid comprises SEQ ID NO: 189. In some embodiments, the nucleic acid comprises SEQ ID NO: 190. In some embodiments, the nucleic acid comprises SEQ ID NO: 191. In some embodiments, the nucleic acid comprises SEQ ID NO: 192. In some embodiments, the nucleic acid comprises SEQ ID NO: 193. In some embodiments, the nucleic acid comprises SEQ ID NO: 194. In some embodiments, the nucleic acid comprises SEQ ID NO: 195. In some embodiments, the nucleic acid comprises SEQ ID NO: 196. In some embodiments, the nucleic acid comprises SEQ ID NO: 197. In some embodiments, the nucleic acid comprises SEQ ID NO: 198. In some embodiments, the nucleic acid comprises SEQ ID NO: 199. In some embodiments, the nucleic acid comprises SEQ ID NO: 200. In some embodiments, the nucleic acid comprises SEQ ID NO: 201. In some embodiments, the nucleic acid comprises SEQ ID NO: 202. In some embodiments, the nucleic acid comprises SEQ ID NO: 203. In some embodiments, the nucleic acid comprises SEQ ID NO: 204. In some embodiments, the nucleic acid comprises SEQ ID NO: 205. In some embodiments, the nucleic acid comprises SEQ ID NO: 206. In some embodiments, the nucleic acid comprises SEQ ID NO: 207. In some embodiments, the nucleic acid comprises SEQ ID NO: 208. In some embodiments, the nucleic acid comprises SEQ ID NO: 209. In some embodiments, the nucleic acid comprises SEQ ID NO: 210. In some embodiments, the nucleic acid comprises SEQ ID NO: 211. In some embodiments, the nucleic acid comprises SEQ ID NO: 212. In some embodiments, the nucleic acid comprises SEQ ID NO: 213. In some embodiments, the nucleic acid comprises SEQ ID NO: 214. In some embodiments, the nucleic acid comprises SEQ ID NO: 215. In some embodiments, the nucleic acid comprises SEQ ID NO: 216. In some embodiments, the nucleic acid comprises SEQ ID NO: 217. In some embodiments, the nucleic acid comprises SEQ ID NO: 218. In some embodiments, the nucleic acid comprises SEQ ID NO: 219. In some embodiments, the nucleic acid comprises SEQ ID NO: 220. In some embodiments, the nucleic acid comprises SEQ ID NO: 221. In some embodiments, the nucleic acid comprises SEQ ID NO: 222. In some embodiments, the nucleic acid comprises SEQ ID NO: 223. In some embodiments, the nucleic acid comprises SEQ ID NO: 224. In some embodiments, the nucleic acid comprises SEQ ID NO: 225. In some embodiments, the nucleic acid comprises SEQ ID NO: 226. In some embodiments, the nucleic acid comprises SEQ ID NO: 227. In some embodiments, the nucleic acid comprises SEQ ID NO: 228. In some embodiments, the nucleic acid comprises SEQ ID NO: 229. In some embodiments, the nucleic acid comprises SEQ ID NO: 230. In some embodiments, the nucleic acid comprises SEQ ID NO: 231. In some embodiments, the nucleic acid comprises SEQ ID NO: 232. In some embodiments, the nucleic acid comprises SEQ ID NO: 233. In some embodiments, the nucleic acid comprises SEQ ID NO: 234. In some embodiments, the nucleic acid comprises SEQ ID NO: 235. In some embodiments, the nucleic acid comprises SEQ ID NO: 236. In some embodiments, the nucleic acid comprises SEQ ID NO: 237. In some embodiments, the nucleic acid comprises SEQ ID NO: 238. In some embodiments, the nucleic acid comprises SEQ ID NO: 239. In some embodiments, the nucleic acid comprises SEQ ID NO: 240. In some embodiments, the nucleic acid comprises SEQ ID NO: 241. In some embodiments, the nucleic acid comprises SEQ ID NO: 242. In some embodiments, the nucleic acid comprises SEQ ID NO: 243. In some embodiments, the nucleic acid comprises SEQ ID NO: 244. In some embodiments, the nucleic acid comprises SEQ ID NO: 245. In some embodiments, the nucleic acid comprises SEQ ID NO: 246. In some embodiments, the nucleic acid comprises SEQ ID NO: 247. In some embodiments, the nucleic acid comprises SEQ ID NO: 248. In some embodiments, the nucleic acid comprises SEQ ID NO: 249. In some embodiments, the nucleic acid comprises SEQ ID NO: 250. In some embodiments, the nucleic acid comprises SEQ ID NO: 251. In some embodiments, the nucleic acid comprises SEQ ID NO: 252. In some embodiments, the nucleic acid comprises SEQ ID NO: 253. In some embodiments, the nucleic acid comprises SEQ ID NO: 254. In some embodiments, the nucleic acid comprises SEQ ID NO: 255. In some embodiments, the nucleic acid comprises SEQ ID NO: 256. In some embodiments, the nucleic acid comprises SEQ ID NO: 257. In some embodiments, the nucleic acid comprises SEQ ID NO: 258. In some embodiments, the nucleic acid comprises SEQ ID NO: 259. In some embodiments, the nucleic acid comprises SEQ ID NO: 260. In some embodiments, the nucleic acid comprises SEQ ID NO: 261. In some embodiments, the nucleic acid comprises SEQ ID NO: 262. In some embodiments, the nucleic acid comprises SEQ ID NO: 263. In some embodiments, the nucleic acid comprises SEQ ID NO: 264. In some embodiments, the nucleic acid comprises SEQ ID NO: 265.

Dependoparvovirus Particles

The disclosure is also directed, in part, to a dependoparvovirus particle (e.g., a functional dependoparvovirus particle) comprising a nucleic acid or polypeptide described herein or produced by a method described herein.

Dependoparvovirus is a single-stranded DNA parvovirus that grows only in cells in which certain functions are provided, e.g., by a co-infecting helper virus. Several species of dependoparvovirus are known, including dependoparvovirus A and dependoparvovirus B, which include serotypes known in the art as adeno-associated viruses (AAV). At least thirteen serotypes of AAV that have been characterized. General information and reviews of AAV can be found in, for example, Carter, *Handbook of Parvoviruses*, Vol. 1, pp. 169-228 (1989), and Berns, Virology, pp. 1743-1764, Raven Press, (New York, 1990). AAV serotypes, and to a degree, dependoparvovirus species, are significantly interrelated structurally and functionally. (See, for example, Blacklowe, pp. 165-174 of *Parvoviruses and Human Disease*, J. R. Pattison, ed. (1988); and Rose, *Comprehensive Virology* 3:1-61 (1974)). For example, all AAV serotypes apparently exhibit very similar replication properties mediated by homologous rep genes; and all bear three related capsid proteins. In addition, heteroduplex analysis reveals extensive cross-hybridization between serotypes along the length of the genome, further suggesting interrelatedness. Dependoparvoviruses genomes also comprise self-annealing segments at the termini that correspond to "inverted terminal repeat sequences" (ITRs).

The genomic organization of naturally occurring dependoparvoviruses, e.g., AAV serotypes, is very similar. For example, the genome of AAV is a linear, single-stranded DNA molecule that is approximately 5,000 nucleotides (nt) in length or less. Inverted terminal repeats (ITRs) flank the unique coding nucleotide sequences for the non-structural replication (Rep) proteins and the structural capsid (Cap) proteins. Three different viral particle (VP) proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins: Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a dependoparvovirus particle of the disclosure comprises a nucleic acid comprising a variant capsid polypeptide provided for herein. In some embodiments, the particle comprises a polypeptide as provided for herein.

In some embodiments, the dependoparvovirus particle of the disclosure may be an AAV9 particle. In some embodiments, the AAV9 particle comprises a variant capsid polypeptide as provided for herein or a nucleic acid molecule encoding the same.

In some embodiments the dependoparvovirus particle comprises a variant capsid comprising a variant capsid polypeptide described herein. In some embodiments, the dependoparvovirus particle comprises variant capsid polypeptide described herein and a nucleic acid molecule. In some embodiments, the dependoparvovirus particle comprises variant capsid polypeptide described herein and a nucleic acid molecule comprising one or more inverted terminal repeat sequences (ITRs), for example, ITRs derived from an AAV9 dependoparvovirus or an AAV2 dependoparvovirus, one or more regulatory elements (for example, a promoter), and a payload (e.g., as described herein, e.g., a heterologous transgene). In some embodiments, at least one of the ITRs is modified. In some embodiments, the nucleic acid molecule is single-stranded. In some embodiments, the nucleic acid molecule is double stranded, for example, self-complementary.

Increased ONS Biodistribution and Transduction Characteristics

The disclosure is directed, in part, to nucleic acids, polypeptides, cells, cell free systems, translation systems, viral particles, and methods associated with using and making the same to produce viral particles that have increased distribution to tissues and cells of the CNS and/or CNS transduction as compared to a viral particle comprising a variant capsid polypeptide comprising a reference sequence that does not otherwise comprise the mutations described herein (or mutations corresponding thereto), for example, as compared with a viral particle comprising a variant capsid polypeptide comprising a wild-type sequence of SEQ ID NO: 1. In some embodiments, a use of a viral particle comprising the variant capsid polypeptides leads to increased CNS biodistribution of the viral particle and/or increased transduction of a transgene virus particle in the cells of the CNS, and, therefore, increased expression of the payload (transgene) in the CNS of the transgene.

In some embodiments, the increase in CNS biodistribution and/or transduction is, on a log 2 scale, about or at least about 1-6 (for example, 2 times better, e.g., 4 times better, e.g., 8 times better, e.g., 16 times better, e.g., 32 times better, e.g., 64 times better, e.g., 128 times better) relative to a virus particle comprising a variant capsid polypeptide having a reference sequence, e.g., having the wild-type capsid protein, e.g., having capsid polypeptides of SEQ ID NO: 1. In some embodiments, biodistribution and transduction are measured as described herein. In some embodiments, the viral particle comprising the variant capsid polypeptide, e.g., the variant capsid polypeptide described herein, exhibits increased CNS biodistribution as compared to a viral particle with the wild-type capsid polypeptide (SEQ ID NO: 1). In some embodiments, CNS biodistribution comprises brain, spinal cord, cortical, subcortical, midbrain and brainstem, and cerebellum biodistribution.

In some embodiments, the viral particle comprising the variant capsid polypeptide, e.g., the variant capsid polypeptide described herein, exhibits increased brain biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased brain biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased brain biodistribution at least 40-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits increased cerebellum biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cerebellum biodistribution at least 60-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits increased cortical biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased cortical biodistribution at least 50-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits increased midbrain and brainstem biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased midbrain and brainstem biodistribution at least 40-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits increased spinal cord biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased spinal cord biodistribution at least 16-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits increased subcortical biodistribution as compared to a viral particle with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 1-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 4-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 6-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 8-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 10-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 15-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 16-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 32-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits increased subcortical biodistribution at least 40-fold, e.g., as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, does not exhibit increased dorsal root ganglia (DRG) biodistribution as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, does not exhibit increased peripheral nervous system (PNS) biodistribution as compared to a viral particle with a reference capsid polypeptide, for example, with the wild-type capsid polypeptide (SEQ ID NO: 1).

In some embodiments, the viral particle comprising the variant capsid polypeptide, e.g., the variant capsid polypeptide described herein, exhibits reduced liver biodistribution, e.g., of at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits reduced spleen biodistribution, e.g., of at least 2-fold, e.g., as compared to a viral particle with a reference capsid polypeptide, for example, with the wild-type capsid polypeptide (SEQ ID NO: 1). In some embodiments, the viral particle comprising the variant capsid polypeptide, e.g., the variant capsid polypeptide described herein, exhibits reduced spleen biodistribution, e.g., of at least 4-fold, e.g., as compared to a viral particle with a reference capsid polypeptide, for example, with the wild-type capsid polypeptide (SEQ ID NO: 1). In some embodiments the increased or decreased biodistribution and/or transduction is exhibited in a mammal, e.g., a primate, e.g., a human. In some embodiments, the increased or decreased biodistribution and/or transduction is exhibited upon administration of the virus particle or pharmaceutical composition comprising the virus particle, e.g., as described herein, by systemic administration, e.g., intravenous administration.

In some embodiments, the administration is intrathecal, intraventricular, or intravenous administration. In some embodiments, the administration is an intravenous administration. In some embodiments, the administration is an intraventricular administration. In some embodiments, the intraventricular administration is an administration into one or more brain ventricle. In some embodiments, the administration is an intrathecal administration. In some embodiments, the intrathecal administration is an intralumbar or intracisterna magna administration. In some embodiments, the intrathecal administration is an intralumbar administration. In some embodiments, the intrathecal administration is an intracisterna magna administration.

In some embodiments, the virus particle, e.g., as described herein, e.g., comprising a variant capsid polypeptide described herein, is capable of crossing the blood-brain barrier. In some embodiments the virus particle, e.g., as described herein, e.g., comprising a variant capsid polypeptide described herein, exhibits increased crossing of the blood-brain barrier relative to a virus particle comprising a reference capsid polypeptide, e.g., a reference capsid polypeptide of SEQ ID NO: 1. In some embodiments, the virus particle, e.g., as described herein, e.g., comprising a variant capsid polypeptide described herein, exhibits increased transduction of neurons, astrocytes, glial cells, or combinations thereof, relative to a virus particle comprising a reference capsid polypeptide, e.g., a reference capsid polypeptide of SEQ ID NO: 1.

In some embodiments, the virus particle, e.g., as described herein, e.g., comprising a variant capsid polypeptide described herein, exhibits at least 50-time increased transduction of cells of the CNS in at least two different NHP species, optionally wherein the species are cynomolgus macaque and African green monkey.

In some embodiments, the virus particle, e.g., as described herein, e.g., comprising a variant capsid polypeptide described herein, transduces Purkinje neurons of the cerebellum, e.g., at a level at least 10-fold or 100-fold greater than a virus particle comprising capsid polypeptides of SEQ ID NO: 1 (e.g., as measured by histology, e.g., according to Example 2).

In some embodiments, the virus particle, e.g., as described herein, e.g., comprising a variant capsid polypeptide described herein, transduces CA3 Pyramidal neurons of the hippocampus, e.g., at a level at least 10-fold or 100-fold greater than a virus particle comprising capsid polypeptides of SEQ ID NO: 1 (e.g., as measured by histology, e.g., according to Example 2).

Methods of Making Compositions Described Herein

The disclosure is directed, in part, to a method of making a dependoparvovirus particle, e.g., a dependoparvovirus particle described herein. In some embodiments, a method of making dependoparvovirus particle comprises providing a cell, cell-free system, or other translation system, comprising a nucleic acid described encoding a variant capsid polypeptide provided for herein, or a polypeptide provided for herein (e.g., a variant capsid polypeptide); and cultivating the cell, cell-free system, or other translation system under conditions suitable for the production of the dependoparvovirus particle, thereby making the dependoparvovirus particle.

In some embodiments, providing a cell comprising a nucleic acid described herein comprises introducing the nucleic acid to the cell, e.g., transfecting or transforming the cell with the nucleic acid. The nucleic acids of the disclosure may be situated as a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. Such a vector may be delivered by any suitable method, including transfection, liposome delivery, electroporation, membrane fusion techniques, viral infection, high velocity DNA-coated pellets, and protoplast fusion. A person of skill in the art possesses the knowledge and skill in nucleic acid manipulation to construct any embodiment of this invention and said skills include genetic engineering, recombinant engineering, and synthetic techniques. See, e.g., Sambrook et al, Molecular Cloning: A Laboratory Manual, Cold Spring Harbor Press, Cold Spring Harbor, NY.

In some embodiments, a vector of the disclosure comprises sequences encoding a dependoparvovirus variant capsid polypeptide as provided for herein or a fragment thereof. In some embodiments, a vectors of the disclosure comprises sequences encoding a dependoparvovirus rep protein or a fragment thereof. In some embodiments, such vectors may contain both dependoparvovirus cap and rep proteins. In vectors in which both AAV rep and cap are provided, the dependoparvovirus rep and dependoparvovirus cap sequences may both be of the same dependoparvovirus species or serotype origin, such as AAV9. Alternatively, the present embodiments also provides vectors in which the rep sequences are from a dependoparvovirus species or serotype which differs from that which is providing the cap sequences. In some embodiments, the rep and cap sequences are expressed from separate sources (e.g., separate vectors, or a host cell genome and a vector). In some embodiments, the rep sequences are fused in frame to cap sequences of a different dependoparvovirus species or serotype to form a chimeric dependoparvovirus vector. In some embodiments, the vectors of the invention further contain a payload, e.g., a minigene comprising a selected transgene, e.g., flanked by dependoparvovirus 5' ITR and dependoparvovirus 3' ITR.

The vectors described herein, e.g., a plasmid, are useful for a variety of purposes, but are particularly well suited for use in production of recombinant dependoparvovirus particles comprising dependoparvovirus sequences or a fragment thereof, and in some embodiments, a payload.

In one aspect, the disclosure provides a method of making a dependoparvovirus particle (e.g., a dependoparvovirus B particle, e.g., an AAV9 particle), or a portion thereof. In some embodiments, the method comprises culturing a host cell which contains a nucleic acid sequence encoding a dependoparvovirus variant capsid protein as provided for herein, or fragment thereof; a functional rep gene; a payload, e.g., a minigene comprising dependoparvovirus inverted terminal repeats (ITRs) and a transgene; and sufficient helper functions to promote packaging of the payload, e.g., minigene, into the dependoparvovirus capsid. The components necessary to be cultured in the host cell to package a payload, e.g., minigene, in a dependoparvovirus capsid may be provided to the host cell in trans. In some embodiments, any one or more of the required components (e.g., payload (e.g., minigene), rep sequences, cap sequences, and/or helper functions) may be provided by a host cell which has been engineered to stably comprise one or more of the required components using methods known to those of skill in the art. In some embodiments, a host cell which has been engineered to stably comprise the required component(s) comprises it under the control of an inducible promoter. In some embodiments, the required component may be under the control of a constitutive promoter. Examples of suitable inducible and constitutive promoters are provided herein and further examples are known to those of skill in the art. In some embodiments, a selected host cell which has been engineered to stably comprise one or more components may comprise a component under the control of a constitutive promoter and another component under the control of one or more inducible promoters. For example, a host cell which has been engineered to stably comprise the required components may be generated from 293 cells (e.g., which comprise helper functions under the control of a constitutive promoter), which comprises the rep and/or cap proteins under the control of one or more inducible promoters.

The payload (e.g., minigene), rep sequences, cap sequences, and helper functions required for producing a dependoparvovirus particle of the disclosure may be delivered to the packaging host cell in the form of any genetic element which transfers the sequences carried thereon (e.g., in a vector or combination of vectors). The genetic element may be delivered by any suitable method, including those described herein. Methods used to construct genetic elements, vectors, and other nucleic acids of the disclosure are known to those with skill and include genetic engineering, recombinant engineering, and synthetic techniques. See, e.g., Sambrook et al, Molecular Cloning: A Laboratory Manual, Cold Spring Harbor Press, Cold Spring Harbor, NY. Similarly, methods of generating rAAV virions are well known and the selection of a suitable method is not a limitation on the present invention. See, e.g., K. Fisher et al, J. Virol, 70:520-532 (1993) and U.S. Pat. No. 5,478,745. Unless otherwise specified, the dependoparvovirus ITRs, and other selected dependoparvovirus components described herein, may be readily selected from among any dependoparvovirus species and serotypes, e.g., AAV1, AAV2, AAV3, AAV4, AAV5, AAV6, AAV7, AAV9. ITRs or other dependoparvovirus components may be readily isolated using techniques available to those of skill in the art from a dependoparvovirus species or serotype. Dependoparvovirus species and serotypes may be isolated or obtained from academic, commercial, or public sources (e.g., the American Type Culture Collection, Manassas, VA). In some embodiments, the dependoparvovirus sequences may be obtained through synthetic or other suitable means by reference to published sequences such as are available in the literature or in databases such as, e.g., GenBank or PubMed.

The dependoparvovirus particles (e.g., including a variant capsid polypeptide and, for example, a payload) of the disclosure may be produced using any invertebrate cell type which allows for production of dependoparvovirus or biologic products and which can be maintained in culture. In some embodiments, an insect cell may be used in production of the compositions described herein or in the methods of making a dependoparvovirus particle described herein. For example, an insect cell line used can be from *Spodoptera frugiperda*, such as Sf9, SF21, SF900+, drosophila cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. In some embodiments, the insect cells are susceptible to baculovirus infection, including High Five, Sf9, Se301, SeIZD2109, SeUCR1, SP900+, Sf21, BTI-TN-5B1-4, MG-1, Tn368, HzAml, BM-N, Ha2302, Hz2E5 and A38.

In some embodiments, the methods of the disclosure can be carried out with any mammalian cell type which allows for replication of dependoparvovirus or production of biologic products, and which can be maintained in culture. In some embodiments, the mammalian cells used can be HEK293, HeLa, CHO, NS0, SP2/0, PER. C6, Vero, RD, BHK, HT 1080, A549, Cos-7, ARPE-19 or MRC-5 cells.

Methods of expressing proteins (e.g., recombinant or heterologous proteins, e.g., dependoparvovirus polypeptides) in insect cells are well documented, as are methods of introducing nucleic acids, such as vectors, e.g., insect-cell compatible vectors, into such cells and methods of maintaining such cells in culture. See, for example, *METHODS IN MOLECULAR BIOLOGY*, ed. Richard, Humana Press, N J (1995); O'Reilly et al., *BACULOVIRUS EXPRESSION VECTORS, A LABORATORY MANUAL*, Oxford Univ. Press (1994); Samulski et al., *J. Vir.* 63:3822-8 (1989); Kajigaya et al., *Proc. Nat'l. Acad. Sci. USA* 88:4646-50 (1991); Ruffing et al., *J. Vir.* 66:6922-30 (1992); Kirnbauer et al., *Vir.* 219:37-44 (1996); Zhao et al., *Vir.* 272:382-93 (2000); and Samulski et al., U.S. Pat. No. 6,204,059. In some embodiments, a nucleic acid construct encoding dependoparvovirus polypeptides (e.g., a dependoparvovirus genome) in insect cells is an insect cell-compatible vector. An "insect cell-compatible vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cell's genome or remain present extra-chromosomally. The vector may be present permanently or transiently, e.g., as an episomal vector. Vectors may be introduced by any means known in the art. Such means include but are not limited to chemical treatment of the cells, electroporation, or infection. In some embodiments, the vector is a baculovirus, a viral vector, or a plasmid.

In some embodiments, a nucleic acid sequence encoding an dependoparvovirus polypeptide is operably linked to regulatory expression control sequences for expression in a specific cell type, such as Sf9 or HEK cells. Techniques known to one skilled in the art for expressing foreign genes in insect host cells or mammalian host cells can be used with the compositions and methods of the disclosure. Methods for molecular engineering and expression of polypeptides in insect cells is described, for example, in Summers and Smith. *A Manual of Methods for Baculovirus Vectors and Insect Culture Procedures*, Texas Agricultural Experimental Station Bull. No. 7555, College Station, Tex. (1986); Luckow. 1991. In Prokop et al., *Cloning and Expression of Heterologous Genes in Insect Cells with Baculovirus Vectors' Recombinant DNA Technology and Applications*, 97-152 (1986); King, L. A. and R. D. Possee, *The baculovirus expression system*, Chapman and Hall, United Kingdom (1992); O'Reilly, D. R., L. K. Miller, V. A. Luckow, *Baculovirus Expression Vectors: A Laboratory Manual*, New York (1992); W. H. Freeman and Richardson, C. D., *Baculovirus Expression Protocols, Methods in Molecular Biology*, volume 39 (1995); U.S. Pat. No. 4,745,051; US2003148506; and WO 03/074714. Promoters suitable for transcription of a nucleotide sequence encoding a dependoparvovirus polypeptide include the polyhedron, p10, p35 or IE-1 promoters and further promoters described in the above references are also contemplated.

In some embodiments, providing a cell comprising a nucleic acid described herein comprises acquiring a cell comprising the nucleic acid.

Methods of cultivating cells, cell-free systems, and other translation systems are known to those of skill in the art. In some embodiments, cultivating a cell comprises providing the cell with suitable media and incubating the cell and media for a time suitable to achieve viral particle production.

In some embodiments, a method of making a dependoparvovirus particle further comprises a purification step comprising isolating the dependoparvovirus particle from one or more other components (e.g., from a cell or media component).

In some embodiments, production of the dependoparvovirus particle comprises one or more (e.g., all) of: expression of dependoparvovirus polypeptides, assembly of a dependoparvovirus capsid, expression (e.g., duplication) of a dependoparvovirus genome, and packaging of the dependoparvovirus genome into the dependoparvovirus capsid to produce a dependoparvovirus particle. In some embodiments, production of the dependoparvovirus particle further comprises secretion of the dependoparvovirus particle.

In some embodiments, and as described elsewhere herein, the nucleic acid molecule encoding the variant capsid polypeptide is disposed in a dependoparvovirus genome. In some embodiments, and as described elsewhere herein, the nucleic acid molecule encoding the variant capsid polypeptide is packaged into a dependoparvovirus particle along with the dependoparvovirus genome as part of a method of making a dependoparvovirus particle described herein. In other embodiments, the nucleic acid molecule encoding the variant capsid polypeptide is not packaged into a dependoparvovirus particle made by a method described herein.

In some embodiments, a method of making a dependoparvovirus particle described herein produces a dependoparvovirus particle comprising a payload (e.g., a payload described herein) and the variant capsid polypeptide. In some embodiments, the payload comprises a second nucleic acid (e.g., in addition to the dependoparvovirus genome), and production of the dependoparvovirus particle comprises packaging the second nucleic acid into the dependoparvovirus particle. In some embodiments, a cell, cell-free system, or other translation system for use in a method of making a dependoparvovirus particle comprises the second nucleic acid. In some embodiments, the second nucleic acid comprises an exogenous sequence (e.g., exogenous to the dependoparvovirus, the cell, or to a target cell or subject who will be administered the dependoparvovirus particle). In some embodiments, the exogenous sequence encodes an exogenous polypeptide. In some embodiments, the exogenous sequence encodes a therapeutic product.

In some embodiments, a nucleic acid or polypeptide described herein is produced by a method known to one of skill in the art. The nucleic acids, polypeptides, and fragments thereof of the disclosure may be produced by any suitable means, including recombinant production, chemical synthesis, or other synthetic means. Such production methods are within the knowledge of those of skill in the art and are not a limitation of the present invention.

Applications

The disclosure is directed, in part, to compositions comprising a nucleic acid, polypeptide, or particles described herein. The disclosure is further directed, in part, to methods utilizing a composition, nucleic acid, polypeptide, or particles described herein. As will be apparent based on the disclosure, nucleic acids, polypeptides, particles, and methods disclosed herein have a variety of utilities.

The disclosure is directed, in part, to a vector comprising a nucleic acid described herein, e.g., a nucleic acid encoding a variant capsid polypeptide. Many types of vectors are known to those of skill in the art. In some embodiments, a vector comprises a plasmid. In some embodiments, the vector is an isolated vector, e.g., removed from a cell or other biological components.

The disclosure is directed, in part to a cell, cell-free system, or other translation system, comprising a nucleic acid or vector described herein, e.g., a nucleic acid or vector comprising a nucleic acid molecule encoding a variant capsid polypeptide. In some embodiments, the cell, cell-free system, or other translation system is capable of producing dependoparvovirus particles comprising the variant capsid polypeptides. In some embodiments, the cell, cell-free system, or other translation system comprises a nucleic acid comprising a dependoparvovirus genome or components of a dependoparvovirus genome sufficient to promote production of dependoparvovirus particles comprising the variant capsid polypeptides.

In some embodiments, the cell, cell-free system, or other translation system further comprises one or more non-dependoparvovirus nucleic acid sequences that promote dependoparvovirus particle production and/or secretion. Said sequences are referred to herein as helper sequences. In some embodiments, a helper sequence comprises one or more genes from another virus, e.g., an adenovirus or herpes virus. In some embodiments, the presence of a helper sequence is necessary for production and/or secretion of a dependoparvovirus particle. In some embodiments, a cell, cell-free system, or other translation system comprises a vector, e.g., plasmid, comprising one or more helper sequences.

In some embodiments, a cell, cell-free system, or other translation system comprises a first nucleic acid and a second nucleic acid, wherein the first nucleic acid comprises a sequences encoding one or more dependoparvovirus genes (e.g., a Cap gene, a Rep gene, or a complete dependoparvovirus genome) and a helper sequence, and wherein the second nucleic acid comprises a payload. In some embodiments, a cell, cell-free system, or other translation system comprises a first nucleic acid and a second nucleic acid, wherein the first nucleic acid comprises a sequences encoding one or more dependoparvovirus genes (e.g., a Cap gene, a Rep gene, or a complete dependoparvovirus genome) and a payload, and wherein the second nucleic acid comprises a helper sequence. In some embodiments, a cell, cell-free system, or other translation system comprises a first nucleic acid and a second nucleic acid, wherein the first nucleic acid comprises a helper sequence and a payload, and wherein the second nucleic acid comprises a sequences encoding one or more dependoparvovirus genes (e.g., a Cap gene, a Rep gene, or a complete dependoparvovirus genome). In some embodiments, a cell, cell-free system, or other translation system comprises a first nucleic acid, a second nucleic acid, and a third nucleic acid, wherein the first nucleic acid comprises a sequences encoding one or more dependoparvovirus genes (e.g., a Cap gene, a Rep gene, or a complete dependoparvovirus genome), the second nucleic acid comprises a helper sequence, and the third nucleic acid comprises a payload.

In some embodiments, the first nucleic acid, second nucleic acid, and optionally third nucleic acid are situated in separate molecules, e.g., separate vectors or a vector and genomic DNA. In some embodiments, one, two, or all of the first nucleic acid, second nucleic acid, and optionally third nucleic acid are integrated (e.g., stably integrated) into the genome of a cell.

A cell of the disclosure may be generated by transfecting a suitable cell with a nucleic acid described herein. In some embodiments, a method of making a dependoparvovirus particle comprising a variant capsid polypeptide as provided for herein or improving a method of making a dependoparvovirus particle comprises providing a cell described herein. In some embodiments, providing a cell comprises transfecting a suitable cell with one or more nucleic acids described herein.

Many types and kinds of cells suitable for use with the nucleic acids and vectors described herein are known in the art. In some embodiments, the cell is a human cell. In some embodiments, the cell is an immortalized cell or a cell from a cell line known in the art. In some embodiments, the cell is an HEK293 cell. In some embodiments, the cell is an HEK293T cell.

Methods of Delivering a Payload

The disclosure is directed, in part, to a method of delivering a payload to a cell, e.g., a cell in a subject or in a sample. In some embodiments, a method of delivering a payload to a cell comprises contacting the cell with a dependoparvovirus particle comprising a variant capsid polypeptide (e.g., described herein) comprising the payload. In some embodiments, the dependoparvovirus particle is a dependoparvovirus particle described herein and comprises a payload described herein. In some embodiments, the cell is a CNS cell. In some embodiments, the CNS cell is, for example, a neuronal cell, a glial cell, an astrocyte, an oligodendrocyte, an endothelia cell, and the like.

In some embodiments, the payload comprises a transgene. In some embodiments, the transgene is a nucleic acid sequence heterologous to the vector sequences flanking the transgene which encodes a polypeptide, RNA (e.g., a miRNA or siRNA) or other product of interest. The nucleic acid of the transgene may be operatively linked to a regulatory component in a manner sufficient to promote transgene transcription, translation, and/or expression in a host cell.

A transgene may be any polypeptide or RNA encoding sequence and the transgene selected will depend upon the use envisioned. In some embodiments, a transgene comprises a reporter sequence, which upon expression produces a detectable signal. Such reporter sequences include, without limitation, DNA sequences encoding colorimetric reporters (e.g., β-lactamase, β-galactosidase (LacZ), alkaline phosphatase), cell division reporters (e.g., thymidine kinase), fluorescent or luminescence reporters (e.g., green fluorescent protein (GFP) or luciferase), resistance conveying sequences (e.g., chloramphenicol acetyltransferase (CAT)), or membrane bound proteins including to which high affinity antibodies directed thereto exist or can be produced by conventional means, e.g., comprising an antigen tag, e.g., hemagglutinin or Myc.

In some embodiments, a reporter sequence operably linked with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. In some embodiments, the transgene encodes a product which is useful in biology and medicine, such as RNA, proteins, peptides, enzymes, dominant negative mutants. In some embodiments, the RNA comprises a tRNA, ribosomal RNA, dsRNA, catalytic RNAs, small hairpin RNA, siRNA, trans-splicing RNA, and antisense RNAs. In some embodiments, the RNA inhibits or abolishes expression of a targeted nucleic acid sequence in a treated subject (e.g., a human or animal subject).

In some embodiments, the transgene may be used to correct or ameliorate gene deficiencies. In some embodiments, gene deficiencies include deficiencies in which normal genes are expressed at less than normal levels or deficiencies in which the functional gene product is not expressed. In some embodiments, the transgene encodes a therapeutic protein or polypeptide which is expressed in a host cell. In some embodiments, a dependoparvovirus particle may comprise or deliver multiple transgenes, e.g., to correct or ameliorate a gene defect caused by a multi-subunit protein. In some embodiments, a different transgene (e.g., each situated/delivered in a different dependoparvovirus particle, or in a single dependoparvovirus particle) may be used to encode each subunit of a protein, or to encode different peptides or proteins, e.g., when the size of the DNA encoding the protein subunit is large, e.g., for immunoglobulin, platelet-derived growth factor, or dystrophin protein. In some embodiments, different subunits of a protein may be encoded by the same transgene, e.g., a single transgene encoding each of the subunits with the DNA for each subunit separated by an internal ribozyme entry site (IRES). In some embodiments, the DNA may be separated by sequences encoding a 2A peptide, which self-cleaves in a post-translational event. See, e.g., Donnelly et al, *J. Gen. Virol.*, 78 (Pt 1): 13-21 (January 1997); Furler, et al, *Gene Ther.*, 8 (11): 864-873 (June 2001); Klump et al., *Gene Ther* 8 (10): 811-817 (May 2001).

In some embodiments, virus particles comprising a genome are provided, wherein the genome includes a nucleic acid expression construct. The nucleic acid expression construct can include a heterologous transgene and one or more regulatory elements.

In some embodiments, the regulatory elements include a promoter. In some embodiments, the promoter is a ubiquitous or constitutive promoter active in a mammalian cell, for example a human cell, for example, in a human cell type of interest. In some embodiments, the cell type is a CNS cell such as, for example, a neuronal cell, a glial cell, an astrocyte, an oligodendrocyte, an endothelia cell, and the like. Examples of ubiquitous promoters include, but are not limited, to a CAG promoter (hybrid from a cytomegalovirus early enhancer element, a chicken-beta actin promoter, e.g., the first exon and the first intron of the chicken beta actin gene, and the splice acceptor of the rabbit beta globin gene), chicken-beta actin promoter, CBA promoter, CBh promoter, CB6 promoter, CMV promoter, human EF1-alpha promoter, PGK promoter, ubiquitin C (UBC) promoter and fragments thereof. In some embodiments, the promoter is a tissue-specific promoter, for example, a promoter specific in CNS tissue or cells of the CNS. Examples of CNS-specific promoters include but are not limited to a synapsin (SYN or SYN1) promoter, a neuron-specific enolase (NSE) promoter, a Ca2/calmodulin-dependent kinase subunit a (CaMKII) promoter, a synapsin I with a minimal CMV sequence (SynI-minCMV) promoter, a glial fibrillary acidic protein (GFAP) promoter, a internexin neuronal intermediate filament protein alpha (INA) promoter, a nestin (NES) promoter, a neurofilament light chain (NfL) promoter, a neurofilament heavy chain (NfH) promoter, a myelin-associated oligodendrocyte basic protein (MOBP) promoter, a myelin basic protein (MBP) promoter, a tyrosine hydroxylase (TH) promoter, a forkhead box A2 (FOXA2) promoter, a aldehyde dehydrogenase 1 family member L1 (ALDH1L1) promoter, a glutamate decarboxylase 2 (GAD2) promoter, a riken gene A930098C07Rik (A93) promoter, a somatostatin (SST) promoter, a platelet derived growth factor receptor alpha (PDGFRA) promoter, a glutamate receptor metabotropic 1 (GRM1) promoter, a C-type natriuretic peptide precursor (NPPC) promoter, a adrenomedullin (ADM) promoter, a type 2 lactosamine alpha-2,3-sialyltransferase (ST3GAL6) promoter, a ras responsive element binding protein 1 (RREB1) promoter, a deiodinase iodothyronine type II (DIO2) promoter, an excitatory amino acid transporter 2 (EAAT2) promoter, a nuclear receptor subfamily 2 group F member 2 (NR2F2) promoter, a platelet-derived growth factor (PDGF) promoter, a methyl-CpG binding protein 2 (MeCP2) promoter, and mouse, primate or human homologs of any of the forgoing, and fragments (e.g., active fragments) of any of the foregoing. In some embodiments, the CNS-specific promoter is a neuron specific promoter. In some embodiments, the CNS-specific promoter is a astrocyte-specific promoter.

In some embodiments, the nucleic acid expression construct comprises an intron. The intron may be disposed between the promoter and the heterologous transgene. In some aspects, the intron is disposed 5' to the heterologous transgene on the expression construct, for example immediately 5' to the heterologous transgene or 100 nucleotides or less 5' to the heterologous transgene. In some aspects, the intron is a chimeric intron derived from human b-globin and Ig heavy chain (also known as b-globin splice donor/immunoglobulin heavy chain splice acceptor intron, or b-globin/IgG chimeric intron; Reed, R., et al. Genes and Development, 1989, incorporated herein by reference in its entirety). In other aspects, the intron is a VH4 intron or a SV40 intron.

As provided herein, in some embodiments, virus particles comprising a payload, wherein the payload includes a nucleic acid that includes a heterologous transgene are provided. In some embodiments, the heterologous transgene encodes an RNA interference agent, for example a siRNA, shRNA or other interfering nucleic acid.

In some embodiments, the payload includes a heterologous transgene that encodes a therapeutic polypeptide. In some aspects, the heterologous transgene is a human gene or fragment thereof. In some aspects, the therapeutic polypeptide is a human protein. In some embodiments, the heterologous transgene of the virus particle encodes a molecule useful in treating a disease, and the virus particle is administered to a patient in need thereof to treat said disease. In some aspects the payload comprises a molecule that is effective in treating chronic CNS disease, such as, for example, an RNA interference nucleotide (e.g., shRNA, siRNA or miRNA that inhibits APOL-1). Examples of diseases (and heterologous transgenes or molecules encoded by said heterologous transgenes) according to the present disclosure include: MPSI (alpha-L-iduronidase (IDUA)); MPS II-Hunter syndrome (iduronate-2-sulfatase (IDS)); Ceroid lipofuscinosis-Batten disease (CLN1, CLN2, CLN10, CLN13, CLN5, CLN11, CLN4, CNL14, CLN3, CLN6, CLN7, CLN8, CLN12); MPS IIIa—Sanfilippo Type A syndrome (heparin sulfate sulfatase (also called N-sulfoglucosamine sulfohydrolase (SGSH)); MPS IIIB—Sanfilippo Type b syndrome (N-acetyl-alpha-D-glucosaminidase (NAGLU)); MPS VI—Maroteaux-Lamy syndrome (arylsulfatase B); MPS IV A—Morquio syndrome type A (GALNS); MPS IV B—Morquio syndrome type B (GLB1); chronic or neuropathic pain; Osteogenesis Imperfecgta Type I, II, III or IV (COL1A1 and/or COL1A2); hereditary angioedema (SERPING1, CINH); Osteogenesis Imperfecta Type V (IFITM5); Osteogenesis Imperfecta Type VI (SERPINF1); Osteogenesis Imperfecta Type VII (CRTAP); Osteogenesis Imperfecta Type VIII (LEPRE1 and/or P3H1); Osteogenesis Imperfecta Type IX (PPIB); Gaucher disease type I, II and III (Glucocerebrosidase; GBA1); Parkinson's Disease (Glucocerebrosidase; GBA1 and/or dopamine decarboxylase); Pompe (acid maltase; GAA; hGAA); Metachromatic leukodystrophy (Aryl sulfatase A); MPS VII-Sly syndrome (beta-glucuronidase); MPS VIII (glucosamine-6-sulfate sulfatase); MPS IX (Hyaluronidase); maple syrup urine disease (BCKDHA, BCKDHB, and/or DBT); Niemann-Pick disease (Sphingomyelinase); Parkinson's disease (anti-alpha synuclein RNAi); Alzheimer's disease (anti-mutant APP RNAi); Niemann-Pick disease without sphingomyelinase deficiency (NPC1 or NPC gene encoding a cholesterol metabolizing enzyme); Tay-Sachs disease (alpha subunit of beta-hexosaminidase); Sandhoff disease (both alpha and beta subunit of beta-hexosaminidase); Fabry Disease (alpha-galactosidase); Fucosidosis (fucosidase (FUCA1)); Alpha-mannosidosis (alpha-mannosidase); Beta-mannosidosis (beta-mannosidase); Wolman disease (cholesterol ester hydrolase); Dravet syndrome (SCN1A, SCN1B, SCN2A, GABRG2); Parkinson's disease (Neurturin); Parkinson's disease (glial derived growth factor (GDGF)); Parkinson's disease (tyrosine hydroxylase); frontotemporal dementia (progranulin); Angleman syndrome (ubiquitin protein ligase 3A (UBE3A), gene editing systems targeting a UBE3A inhibitory RNA (UBE3A-anitsense transcript)); Parkinson's disease (glutamic acid decarboxylase; FGF-2; BDGF); Spinal Muscular Atrophy (SMN, including SMN1 or SMN2); Friedreich's ataxia (Frataxin); Amyotrophic lateral sclerosis (ALS) (SOD1 inhibitor, e.g., anti-SOD1 RNAi); Glycogen Storage Disease 1a (Glucose-6-phosphatase); XLMTM (MTM1); Crigler Najjar (UGT1A1); CPVT (CASQ2); spinocerebellar ataxia (ATXN2; ATXN3 or other ATXN gene; anti-mutant Machado-Joseph disease/SCA3 allele RNAi); Rett syndrome (MECP2 or fragment thereof); Achromatopsia (CNGB3, CNGA3, GNAT2, PDE6C); Choroidermia (CDM); Danon Disease (LAMP2); Cystic Fibrosis (CFTR or fragment thereof); Duchenne Muscular Dystrophy (Mini-/Micro-Dystrophin Gene); SARS-Cov-2 infection (anti-SARS-Cov-2 RNAi, SARS-Cov-2 genome fragments or S protein (including variants)); Limb Girdle Muscular Dystrophy Type 2C-Gamma-sarcoglycanopathy (human-alpha-sarcoglycan); Advanced Heart Failure (SERCA2a); Rheumatoid Arthritis (TNFR: Fc Fusion; anti-TNF antibody or fragment thereof); Leber Congenital Amaurosis (GAA); X-linked adrenoleukodystrophy (ABCD1); Limb Girdle Muscular Dystrophy Type 2C-Gamma-sarcoglycanopathy (gamma-sarcoglycan); Angelman syndrome (UBE3A); Retinitis Pigmentosa (hMERTK); Age-Related Macular Degeneration (sFLT01); Phelan-McDermid syndrome (SHANK3; 22q13.3 replacement); Becker Muscular Dystrophy and Sporadic Inclusion Body Myositis (huFollistatin344); Parkinson's Disease (GDNF); Metachromatic Leukodystrophy-MLD (cuARSA); Hepatitis C (anti-HCV RNAi); Limb Girdle Muscular Dystrophy Type 2D (hSGCA); Human Immunodeficiency Virus Infections; (PG9DP); Acute Intermittant Porphyria (PBGD); Leber's Hereditary Optical Neuropathy (PIND4v2); Alpha-1 Antitrypsin Deficiency (alphaIAT); X-linked Retinoschisis (RS1); Choroideremia (hCHM); Giant Axonal Neuropathy (GAN); Hemophilia B (Factor IX); Homozygous FH (hLDLR); Dysferlinopathies (DYSF); Achromatopsia (CNGA3 or CNGB3); Progressive supranuclear palsy (MAPT; anti-Tau; anti-MAPT RNAi); Omithine Transcarbamylase deficiency (OTC); Hemophilia A (Factor VIII); Age-related macular degeneration (AMD), including wetAMD (anti-VEGF antibody or RNAi); X-Linked Retinitis Pigmentosa (RPGR); Myotonic dystrophy Type 1 (DMPK; anti-DMPK RNAi, including anti-CTG trinucleotide repeat RNAi); Myotonic dystrophy Type 2 (CNBP); Facioscapulohumeral muscular dystrophy (D4Z4 DNA); oculopharynggeal muscular dystrophy (PABPN1; mutated PABPN1 inhibitor (e.g., RNAi)); Mucopolysaccharidosis Type VI (hARSB); Leber Hereditary Optic Neuropathy (ND4); X-Linked myotubular Myopathy (MTM1); Crigler-Najjar Syndrome (UGT1A1); Retinitis Pigmentosa (hPDE6B); Mucopolysaccharidosis Type 3B (hNAGLU); Duchenne Muscular Dystrophy (GALGT2); Alzheimer's Disease (NGF; ApoE4; ApoE2; ApoE3; Anti-ApoE RNAi, MAPT, anti-Tau antibody, anti-amyloid beta antibody (e.g., aducanumab)); multiple system atrophy; Familial Lipoprotein Lipase Deficiency (LPL); Alpha-1 Antitrypsin Deficiency (hAAT); Leber Congenital Amaurosis 2 (hRPE65v2); Batten Disease; Late Infantile Neuronal Lipofuscinosis (CLN2); Huntington's disease (HTT; anti-HTT RNAi); Fragile X syndrome (FMR1); Leber's Hereditary Optical Neuropathy (PIND4v2); Aromatic Amino Acid Decarboxylase Deficiency (hAADC); Retinitis Pigmentosa (hMERKTK); and Retinitis Pigmentosa (RLBP1).

In some embodiments, the heterologous transgene encodes a therapeutic polypeptide. In some aspects, the heterologous transgene is a human gene or fragment thereof. In some aspects, the therapeutic polypeptide is a human protein. In some aspects, the heterologous transgene encodes an antibody or fragment thereof (for example an antibody light chain, an antibody heavy chain, a Fab or an scFv). Examples of antibodies or fragments thereof that are encoded by the heterologous transgene include but are not limited to; and an anti-Ab antibody (e.g. solanezumab, GSK933776, and lecanemab), anti-sortilin (e.g. AL-001), anti-Tau (e.g. ABBV-8E12, UCB-0107, and NI-105), anti-SEMA4D (e.g. VX15/2503), anti-alpha synuclein (e.g. prasinezumab, NI-202, and MED-1341), anti-SOD1 (e.g. NI-204), anti-CGRP receptor (e.g. eptinezumab, fremanezumab, or galcanezumab), anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab, ravulizumab, and eculizumab), anti-CD105 (e.g., carotuximab), anti-CCIQ (e.g., ANX-007), anti-TNFa (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab, tocilizumab, and sarilumab), anti-IL6 (e.g. siltuximab, clazakizumab, sirukumab, olokizumab, and gerilimzumab), anti-IL4R (e.g., dupilumab), anti-IL17A (e.g., ixekizumab and secukinumab), anti-IL5R (e.g. reslizumab), anti-IL-5 (e.g., benralizumab and mepolizumab), anti-IL13 (e.g. tralokinumab), anti-IL 12/IL23 (e.g., ustekinumab), anti-CD 19 (e.g., inebilizumab), anti-IL31RA (e.g. nemolizumab), anti-ITGF7 mAb (e.g., etrolizumab), anti-SOST mAb (e.g., romosozumab), anti-IgE (e.g. omalizumab), anti-TSLP (e.g. nemolizumab), anti-pKa1 mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., denosumab), anti-PCSK9 (e.g., alirocumab and evolocumab), anti-ANGPTL3 (e.g., evinacumab*), anti-OxPL (e.g., E06), anti-fD (e.g., lampalizumab), or anti-MMP9 (e.g., andecaliximab), optionally wherein the heavy chain (Fab and Fc region) and the light chain are separated by a self-cleaving furin (F)/F2A or furin (F)/T2A, IRES site, or flexible linker, for example, ensuring expression of equal amounts of the heavy and the light chain polypeptides.

In some embodiments, the virus particle comprises a heterologous transgene encoding a genome editing system. Examples include a CRISPR genome editing system (e.g., one or more components of a CRISPR genome editing system such as, for example, a guide RNA molecule and/or a RNA-guided nuclease such as a Cas enzyme such as Cas9, Cpf1 and the like), a zinc finger nuclease genome editing system, a TALEN genome editing system or a meganuclease genome editing system. In some embodiments, the genome editing system targets a mammalian, e.g., human, genomic target sequence. In some embodiments, the virus particle includes a heterologous transgene encoding a targetable transcription regulator. Examples include a CRISPR-based transcription regulator (for example, one or more components of a CRISPR-based transcription regulator, for example, a guide RNA molecule and/or a enzymatically-inactive RNA-guided nuclease/transcription factor ("TF") fusion protein such as a dCas9-TF fusion, dCpf1-TF fusion and the like), a zinc finger transcription factor fusion protein, a TALEN transcription regulator or a meganuclease transcription regulator.

In some embodiments, components of a therapeutic molecule or system are delivered by more than one unique virus particle (e.g., a population that includes more than one unique virus particles). In other embodiments, the therapeutic molecule or components of a therapeutic molecule or system are delivered by a single unique virus particle (e.g., a population that includes a single unique virus particle).

The transgene may also encode any biologically active product or other product, e.g., a product desirable for study. Suitable transgenes may be readily selected by persons of skill in the art, such as those, but not limited to, those described herein.

Other examples of proteins encoded for by the transgene include, but are not limited to, colony stimulating factors (CSF); blood factors, such as B-globin, hemoglobin, tissue plasminogen activator, and coagulation factors; interleukins; soluble receptors, such as soluble TNF-α. receptors, soluble VEGF receptors, soluble interleukin receptors (e.g., soluble IL-1 receptors and soluble type II IL-1 receptors), or ligand-binding fragments of a soluble receptor; growth factors, such as keratinocyte growth factor (KGF), stem cell factor (SCF), or fibroblast growth factor (FGF, such as basic FGF and acidic FGF); enzymes; chemokines; enzyme activators, such as tissue plasminogen activator; angiogenic agents, such as vascular endothelial growth factors, glioma-derived growth factor, angiogenin, or angiogenin-2; anti-angiogenic agents, such as a soluble VEGF receptor; a protein vaccine; neuroactive peptides, such as nerve growth factor (NGF) or oxytocin; thrombolytic agents; tissue factors; macrophage activating factors; tissue inhibitors of metalloproteinases; or IL-1 receptor antagonists.

Accordingly, provided herein is a virus particle comprising a capsid polypeptide comprising (a) a VP1, VP2 or VP3 sequence of SEQ ID NO: 2, (b) a VP1, VP2 or VP3 sequence comprising the mutation set of VAR-1 and having greater than 80% (for example, greater than 85%, greater than 90%, greater than 91%, greater than 92%, greater than 93%, greater than 94%, greater than 95%, greater than 96%, greater than 97%, greater than 98%, greater than 99%) identity to SEQ ID NO: 2, or (c) a VP1, VP2 or VP3 sequence comprising the mutation set of VAR-1 and having at least 1, 2, 3, 4, 5, 6, 7, 8, 9 or 10 additional mutations, but fewer than 16 additional mutations, relative to SEQ ID NO: 1. In embodiments, the capsid polypeptide comprises VP1, VP2 and VP3 sequences of SEQ ID NO: 2. In embodiments, the virus particle comprises a nucleic acid molecule comprising a transgene, for example a transgene encoding a molecule for the treatment of a CNS disorder (for example as described herein).

In embodiments, the transgene encodes a molecule for the treatment of Alzheimer's disease. In embodiments, the molecule for the treatment of Alzheimer's disease comprises an inhibitory nucleic acid molecule (e.g., an antisense oligonucleotide or inhibitory RNA (e.g., siRNA, miRNA or shRNA molecule). In embodiments, the molecule for the treatment of Alzheimer's disease comprises an inhibitory nucleic acid molecule (e.g., an antisense oligonucleotide or inhibitory RNA (e.g., siRNA, miRNA or shRNA molecule) targeting beta-amyloid, alpha-synuclein, Tau, TREM, e.g., TREM2, or an apolipoprotein (APO) E protein, e.g. APOE1, APOE2, APOE3 or APOE4.

In embodiments, the molecule for the treatment of Alzheimer's disease comprises a genome editing system (for example a zinc finger nuclease, a meganuclease, a TALEN, or an RNA-guided genome editing system (e.g. a Cas polypeptide and a guide RNA molecule). In embodiments the genome editing system targets a genetic region encoding a beta-amyloid protein or a Tau protein. In embodiments, the genome editing system targets MSA4. In embodiments, the molecule for the treatment of Alzheimer's disease is an antibody or antigen-binding fragment thereof (e.g., as scFV). In embodiments, the molecule for the treatment of Alzheimer's disease is a human protein or fragment or variant thereof. In embodiments, the molecule for the treatment of Alzheimer's disease is an inhibitor of beta-amyloid aggregation. In embodiments, the molecule for the treatment of Alzheimer's disease is an inhibitor of alpha-synuclein. In embodiments, the molecule for the treatment of Alzheimer's disease is an anti-beta amyloid antibody, e.g., gantenerumab, crenezumab, aducanumab or lecanemab. In embodiments, the molecule for the treatment of Alzheimer's disease is a Tau inhibitor, e.g., an anti-tau antibody (e.g., semorinemab). In embodiments, the molecule for the treatment of Alzheimer's disease is an anti-TREM antibody or antigen-binding fragment thereof. In embodiments, the molecule for the treatment of Alzheimer's disease is human nerve growth factor or a fragment or variant thereof. In embodiments, the molecule for the treatment of Alzheimer's disease is human brain-derived neurotrophic factor or a fragment or variant thereof. In embodiments, the molecule for the treatment of Alzheimer's disease is human synapsin-caveolin-1 (Syn-Cav1) or a fragment or variant thereof.

Accordingly, in embodiments, described herein is a virus particle comprising (a) a capsid polypeptide described herein, e.g., a capsid polypeptide comprising SEQ ID NO: 2 and (b) a heterologous nucleic acid comprising (i) a transgene encoding a molecule for the treatment of Alzheimer's disease, for example as described herein, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence. In embodiments, provided herein is a virus particle comprising (a) a capsid polypeptide comprising a VP1, VP2 or VP3 sequence of SEQ ID NO: 2; and (b) a heterologous nucleic acid comprising (i) a transgene encoding a molecule for the treatment of Alzheimer's disease, for example as described herein, and (ii) a promoter operably linked to said transgene.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Alzheimer's disease, for example gantenerumab or an antigen binding fragment thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Alzheimer's disease, for example crenezumab or an antigen binding fragment thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of myasthenia Gravis disease, for example an anti-IL-6 antibody (e.g., satralizumab) or antigen-binding fragment thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Parkinson's disease, for example an anti-alpha synuclein antibody (e.g., prasinezumab or BIIB054) or antigen-binding fragment thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene (e.g., a human GBA gene) encoding a molecule for the treatment of Parkinson's disease, for example human beta-glucocerebrosidase or a fragment thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Parkinson's disease, for example an inhibitor of LRRK2, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Parkinson's disease, for example a trophic factor (e.g., glial cell line-derived neurotrophic factor (GDNF) or cerebral dopamine neurotrophic factor (CDNF)) or a fragment thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene (e.g., a human GBA gene, e.g., a human GBA-1 gene) encoding a molecule for the treatment of Gaucher's disease, for example a human glucocerebrosidase (GCase, e.g. beta-glucosylceramidase-1) or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of multiple sclerosis, for example an anti-CD-20 antibody (e.g., ocrelizumab, rituximab or ofatumumab) or antigen-binding fragment thereof, and (ii) a promoter operably linked to said transgene. In embodiments the multiple sclerosis is relapsing remitting multiple sclerosis. In embodiments the multiple sclerosis is primary progressing multiple sclerosis. In embodiments the multiple sclerosis is secondary progressive multiple sclerosis. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Huntington's disease, for example an inhibitory nucleic acid directed to mutated huntingtin protein (HTT) (e.g., tominersen), and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Phelan McDermid syndrome, for example human SHANK3 or fragment or variant thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Phelan McDermid syndrome, for example a human growth hormone, e.g., human insulin like growth factor 1 (IGF-1), or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of frontotemporal dementia, for example human progranulin or granulin, or fragment or variant thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of frontotemporal dementia, for example an anti-tau antibody (e.g., semorinemab), or fragment or variant thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of frontotemporal dementia, for example an inhibitory nucleic acid which targets SOD-1 (e.g., tofersen). In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of amyotrophic lateral sclerosis (ALS), for example an inhibitory nucleic acid which targets SOD-1 (e.g., tofersen), and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of ALS, for example an inhibitory nucleic acid which targets C9orf72 (e.g., BIIB078), and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of ALS, for example an inhibitory nucleic acid which targets ATXN2 (e.g., BIIB105), and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of ALS, for example an inhibitory nucleic acid which targets FUS, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of multiple system atrophy, for example an anti-alpha synuclein antibody (e.g., prasinezumab), and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of multiple system atrophy, for example human glial cell-derived neurotrophic factor (GDNF) or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of progressive supranuclear palsy (PSP), for example an anti-Tau antibody (e.g., semorinemab), and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of progressive supranuclear palsy (PSP), for example an anti-alpha-synuclein antibody (e.g., prasinezumab), and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Freidrich's ataxia, for example human frataxin (FRXN) or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Angelman syndrome, for example an inhibitor of a UBE3A antisense nucleic acid (e.g., rugonersen) or a human UBE3A or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Fragile X syndrome, for example human fragile X mental retardation protein (FMRP) or fragment or variant thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Fragile X syndrome, for example an inhibitor of transcriptional silencing of FMRP, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Fragile X syndrome, for example human diacylglycerol kinase (DGKk) or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Rett syndrome, for example a human MECP2 or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Dravet syndrome, for example human sodium channel, voltage gated, type 1-alpha (SCN1A or Nav1.1) or fragment or variant thereof, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Dravet syndrome, for example an inhibitory nucleic acid targeting a mutant SCN1A transcript, and (ii) a promoter operably linked to said transgene. In embodiments, described herein is a virus particle comprising (a) a capsid polypeptide described herein, for example, a capsid polypeptide comprising SEQ ID NO: 2 and (b) a heterologous nucleic acid comprising (i) a transgene encoding a molecule for the treatment of Dravet syndrome, for example an anti-tau antibody (e.g., semorinemab), or fragment or variant thereof, and (ii) a promoter operably linked to said transgene. In embodiments, the heterologous nucleic acid molecule of the virus particle further comprises one or more of (a) a dependoparvovirus ITR, (b) an intron, (c) an enhancer or repressor sequence, (d) a stuffer sequence, and (e) a polyA sequence.

The disclosure is further directed, in part, to a method of delivering a payload to a subject, e.g., an animal or human subject. In some embodiments, a method of delivering a payload to a subject comprises administering to the subject a dependoparvovirus particle comprising a variant polypeptide (e.g., described herein) comprising the payload, e.g., in a quantity and for a time sufficient to deliver the payload. In some embodiments, the dependoparvovirus particle is a dependoparvovirus particle described herein and comprises a payload described herein. In some embodiments, the particle delivers the payload to the CNS. In some embodiments, the delivery to the CNS is increased as compared to a particle without the variant capsid polypeptide or as compared to a wild-type capsid polypeptide.

In some embodiments, administration of the virus particle, e.g., a virus particle described herein, is by systemic, e.g., intravenous, administration. In some embodiments, administration of the virus particle, e.g., a virus particle described herein, is by intrathecal administration, e.g., by intracisternal magna administration or by intralumbar administration. In some embodiments, administration of the virus particle, e.g., a virus particle described herein, is by direct injection into a CNS region, e.g., intra cerebral ventricular administration. In some embodiments, administration of the virus particle, e.g., a virus particle described herein, is by intramuscular administration.

Methods of Treatment

The disclosure is directed, in part, to a method of treating a disease or condition in a subject, e.g., an animal or human subject. As used herein, the term "treating a disease or condition" refers to treating a manifest disease or condition, for example, where the subject is already suffering from one or more symptoms of the disease or condition, or refers to treating a pre-manifest disease or condition, for example, where the subject is identified as having a disease or condition but is not yet exhibiting one or more symptoms of the disease or condition. Pre-manifest conditions may be identified by, for example, genetic testing. In some embodiments, a method of treating a disease or condition in a subject comprises administering to the subject a dependoparvovirus particle comprising a variant polypeptide described herein, e.g., comprising a payload described herein. In some embodiments, the dependoparvovirus particle, which comprises a variant polypeptide, comprising a payload described herein is administered in an amount and/or time effective to treat the disease or condition. In some embodiments, the payload is a therapeutic product. In some embodiments, the payload is a nucleic acid, e.g., encoding an exogenous polypeptide.

The dependoparvovirus particles comprising a variant polypeptide described herein or produced by the methods described herein can be used to express one or more therapeutic proteins to treat various diseases or disorders. In some embodiments, the disease or disorder is a cancer, e.g., a cancer such as carcinoma, sarcoma, leukemia, lymphoma; or an autoimmune disease, e.g., multiple sclerosis. Non-limiting examples of carcinomas include esophageal carcinoma; bronchogenic carcinoma; colon carcinoma; colorectal carcinoma; gastric carcinoma; hepatocellular carcinoma; basal cell carcinoma, squamous cell carcinoma (various tissues); bladder carcinoma, including transitional cell carcinoma; lung carcinoma, including small cell carcinoma and non-small cell carcinoma of the lung; adrenocortical carcinoma; sweat gland carcinoma; sebaceous gland carcinoma; thyroid carcinoma; pancreatic carcinoma; breast carcinoma; ovarian carcinoma; prostate carcinoma; adenocarcinoma; papillary carcinoma; papillary adenocarcinoma; cystadenocarcinoma; medullary carcinoma; renal cell carcinoma; uterine carcinoma; testicular carcinoma; osteogenic carcinoma; ductal carcinoma in situ or bile duct carcinoma; choriocarcinoma; seminoma; embryonal carcinoma; Wilm's tumor; cervical carcinoma; epithelial carcinoma; and nasopharyngeal carcinoma. Non-limiting examples of sarcomas include fibrosarcoma, myxosarcoma, liposarcoma, angiosarcoma, endotheliosarcoma, lymphangiosarcoma, chondrosarcoma, chordoma, osteogenic sarcoma, osteosarcoma, lymphangioendotheliosarcoma, synovioma, mesothelioma, Ewing's sarcoma, leiomyosarcoma, rhabdomyosarcoma, and other soft tissue sarcomas. Non-limiting examples of solid tumors include ependymoma, pinealoma, hemangioblastoma, acoustic neuroma, oligodendroglioma, glioma, astrocytoma, medulloblastoma, craniopharyngioma, menangioma, melanoma, neuroblastoma, and retinoblastoma. Non-limiting examples of leukemias include chronic myeloproliferative syndromes; T-cell CLL prolymphocytic leukemia, acute myelogenous leukemias; chronic lymphocytic leukemias, including B-cell CLL, hairy cell leukemia; and acute lymphoblastic leukemias. Examples of lymphomas include, but are not limited to, B-cell lymphomas, such as Burkitt's lymphoma; and Hodgkin's lymphoma. In some embodiments, the disease or disorder is a genetic disorder. In some embodiments, the genetic disorder is sickle cell anemia, Glycogen storage diseases (GSD, e.g., GSD types I, II, III, IV, V, VI, VII, VIII, IX, X, XI, XII, XIII, and XIV), cystic fibrosis, lysosomal acid lipase (LAL) deficiency 1, Tay-Sachs disease, Phenylketonuria, Mucopolysaccharidoses, Galactosemia, muscular dystrophy (e.g., Duchenne muscular dystrophy), hemophilia such as hemophilia A (classic hemophilia) or hemophilia B (Christmas Disease), Wilson's disease, Fabry Disease, Gaucher Disease hereditary angioedema (HAE), and alpha 1 antitrypsin deficiency. Examples of other diseases or disorders are provided above in the "Methods of delivering a payload" section.

In aspects, the disease or condition is a disease of the CNS. Exemplary diseases of the CNS include, Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS-Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Angleman syndrome, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Bechet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors (including, but not limited to those that have metastasized to the brain, for example, metastatic breast cancer), Brain Aneurysm, Brain Injury, Brown-Sequard Syndrome, Bulbar palsy, Bulbospinal Muscular Atrophy, Cerebral Autosomal Dominant Arteriopathy with Sub-cortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Concentric sclerosis (Baló's sclerosis), Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Chronic progressive external ophtalmoplegia, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia-Multi-Infarct, Dementia-Semantic, Dementia-Subcortical, Dementia With Lewy Bodies, Demyelination diseases, Dentate Cerebellar Ataxia, Dentatorubral Atrophy, Dermatomyositis, Developmental Dyspraxia, Devic's Syndrome, Diabetic Neuropathy, Diffuse Sclerosis, Distal hereditary motor neuronopathies, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalomyelitis, Encephalopathy, Encephalopathy (familial infantile), Encephalotrigeminal Angiomatosis, Epilepsy, Epileptic Hemiplegia, Episodic ataxia, Erb's Palsy, Erb-Duchenne and Dejerine-Klumpke Palsies, Essential Tremor, Extrapontine Myelinolysis, Faber's disease, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Fragile X disease, Friedreich's Ataxia, Frontotemporal Dementia, Gaucher Disease, Generalized Gangliosidoses (GM1, GM2), Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hurler syndrome, Hydranencephaly, Hydrocephalus, Hydrocephalus-Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lichtheim's disease, Lipid Storage Diseases, Lipoid Proteinosis, Lissencephaly, Locked-In Syndrome, Lou Gehrig's Disease, Lupus-Neurological Sequelae, Lyme Disease-Neurological Complications, Lysosomal storage disorders, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Mitochondrial DNA depletion syndromes, Moebius Syndrome, Monomelic Amyotrophy, Morvan Syndrome, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myelitis, Myoclonic Encephalopathy of Infants, Myoclonus, Myoclonus epilepsy, Myopathy, Myopathy-Congenital, Myopathy-Thyrotoxic, Myotonia, Myotonia Congenita, Narcolepsy, NARP (neuropathy, ataxia and retinitis pigmentosa), Neuroacanthocytosis, Neurodegeneration with Brain Iron Accumulation, Neurodegenerative disease, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathic pain, Neuropathy-Hereditary, Neuropathy, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain-Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Peroneal muscular atrophy, Periodic Paralyses, Peripheral Neuropathy, Periventricular Leukomalacia, Persistent Vegetative State, Pervasive Developmental Disorders, Phelan McDermid syndrome, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive bulbar palsy, Progressive Hemifacial Atrophy, Progressive Locomotor Ataxia, Progressive Multifocal Leukoencephalopathy, Progressive Muscular Atrophy, Progressive Sclerosing Poliodystrophy, Progressive Supranuclear Palsy, Prosopagnosia, Pseudobulbar palsy, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Ataxia, Spinocerebellar Atrophy, Spinocerebellar Degeneration, Sporadic ataxia, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Vitamin B12 deficiency, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, or X-Linked Spinal or Bulbar Muscular Atrophy. Examples of other diseases or disorders are provided above in the "Methods of delivering a payload" section.

In some embodiments, administration of a dependoparvovirus particle comprising a variant polypeptide and comprising a payload (e.g., a transgene) to a subject induces expression of the payload (e.g., transgene) in a subject. In some embodiments, the expression is induced in the CNS. In some embodiments, the production is similar in the CNS as compared to a similar particle with the wild-type capsid protein. In some embodiments, the production is increased in the CNS as compared to a similar particle with the wild-type capsid protein. The amount of a payload, e.g., transgene, e.g., heterologous protein, e.g., therapeutic polypeptide, expressed in a subject (e.g., the serum of the subject) can vary. For example, in some embodiments the payload, e.g., protein or RNA product of a transgene, can be expressed in the serum of the subject in the amount of at least about 9 µg/ml, at least about 10 µg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml. In some embodiments, the payload, e.g., protein or RNA product of a transgene, is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500 µg/ml, about 2000 µg/ml, about 2500 µg/ml, or a range between any two of these values.

In some embodiments, administration of the virus particle, e.g., a virus particle described herein, is by systemic, e.g., intravenous, administration. In some embodiments, administration of the virus particle, e.g., a virus particle described herein, is by intrathecal administration, e.g., by intracisternal magna administration or by intralumbar administration. In some embodiments, administration of the virus particle, e.g., a virus particle described herein, is by direct injection into a CNS region, e.g., intra cerebral ventricular administration. In embodiments, administration of the virus particle, e.g., a virus particle described herein, is by intramuscular administration.

Sequences disclosed herein may be described in terms of percent identity. A person of skill will understand that such characteristics involve alignment of two or more sequences. Alignments may be performed using any of a variety of publicly or commercially available Multiple Sequence Alignment Programs, such as "Clustal W", accessible via the Internet. As another example, nucleic acid sequences may be compared using FASTA, a program in GCG Version 6.1. FASTA provides alignments and percent sequence identity of the regions of the best overlap between the query and search sequences. For instance, percent identity between nucleic acid sequences may be determined using FASTA with its default parameters as provided in GCG Version 6.1, herein incorporated by reference. Similar programs are available for amino acid sequences, e.g., the "Clustal X" program. Additional sequence alignment tools that may be used are provided by (protein sequence alignment; (http://www.ebi.ac.uk/Tools/psa/emboss_needle/)) and (nucleic acid alignment; http://www.ebi.ac.uk/Tools/psa/emboss_needle/nucleotide.html)). Generally, any of these programs may be used at default settings, although one of skill in the art can alter these settings as needed. Alternatively, one of skill in the art can utilize another algorithm or computer program which provides at least the level of identity or alignment as that provided by the referenced algorithms and programs. Sequences disclosed herein may further be described in terms of edit distance. As used herein, the term "Edit Distance" shall mean with respect to any two amino acid sequences being compared, the minimum number of single amino acid substitutions, insertions or deletions that are sufficient to change one amino acid sequence into another amino acid sequence. The minimum number of sequence edits (i.e., additions, substitutions, or deletions of a single amino acid residue or a nucleotide residue) which change one sequence into another sequence is the edit distance between the two sequences. In some embodiments, the distance between two sequences is calculated as the Levenshtein distance.

All publications, patent applications, patents, and other publications and references (e.g., sequence database reference numbers) cited herein are incorporated by reference in their entirety. For example, all GenBank, Unigene, and Entrez sequences referred to herein, e.g., in any Table herein, are incorporated by reference. Unless otherwise specified, the sequence accession numbers specified herein, including in any Table herein, refer to the database entries current as of Aug. 21, 2020. When one gene or protein references a plurality of sequence accession numbers, all of the sequence variants are encompassed.

The invention is further illustrated by the following examples. The examples are provided for illustrative purposes only and are not to be construed as limiting the scope or content of the invention in any way.

EXAMPLES

Example 1

High Throughput AAV9 Library Evaluation in the CNS
Library Creation

Using machine learning algorithms trained on data from hundreds of thousands of capsid variants across multiple serotypes, including AAV particle production efficiency, and transduction and biodistribution across multiple tissues, a library of 1E5 capsid variants of wild-type AAV9 was designed with the goals of producing a capsid that would package into AAV particles, transduce central nervous system tissues after intravenous injection with high efficiency, and detarget the liver and other tissue types. The designed capsid polypeptides were cloned into plasmids to create a library of plasmids encoding the capsid variants. A library of AAV variant genomes encoding each variant's capsid and a unique capsid variant barcode identifier was cloned into two ITR plasmid backbones as described previously (Ogden et al. Science, Nov. 19, 2019, 366, (6469): 1139-1143; doi: 10.1126/science.aaw2900, hereby incorporated by reference in its entirety), one with expression of the capsid gene under the control of a human EF1-alpha promoter (hEF1-alpha) and the other with expression of the capsid gene under the control of a CBh promoter. Both hEF1-alpha and CBh are ubiquitous promoters that express in CNS and other tissues. Each plasmid backbone contained a unique genomic identifier ("backbone tag") enabling analysis of biodistribution and transduction efficiencies via each of the two promoters. Each capsid polypeptide variant was included in combination with between 1-500 unique genomic identifiers ("barcodes") to enable measurement of biological replicates for each virus comprising a unique capsid polypeptide. A library of AAV capsid variants, each comprising a genome encoding that variant's capsid polypeptides, was produced via transient triple transfection of adherent HEK293T. Transfections were completed at a 1:1:1 ratio of Helper, Rep, and Cap-inside-ITR plasmid. which has been optimized with these plasmids to limit cross packaging. Cells were harvested, lysed, and purified by a sequence of steps: (1) diafiltration, (2) tangential flow filtration (TFF), (3) iodixanol gradient purification, and (4) buffer exchange. The produced virus was tested for suitable sterility and endotoxin, and titer performed by ddPCR.

In Vitro Evaluation of Library

Data was prepared as described below. To measure each variant's packaging efficiency (or "production"), barcodes from vector genomes in the plasmid library and produced AAV library were prepared for Illumina sequencing using two rounds of PCR. Production efficiency for each of the produced AAV particle variants was normalized for its abundance in the input plasmid library, and was expressed by comparing barcode sequencing levels for each variant in the produced AAV particle vector pool to the barcode sequence levels for each variant in the input plasmid library used to create the AAV vector pool. The measurements of variant frequency in the AAV vector library also enable downstream normalization of biodistribution and transduction measurements by variant frequency in the input vector library.

In Vivo Evaluation of Library in Non-Human Primate

All NHP experiments were conducted in accordance with institutional policies and NIH guidelines. Two female African Green Monkeys (Chlorocebus sabaeus) weighing 3.04 and 3.33 kg and seronegative for anti-AAV9 neutralizing antibodies (serum NAb titers <1:4 based on in vitro NAb assay) were selected for the study. Prior to test article administrations, samples of blood were collected. The animals were anesthetized with ketamine and zylazine and received an intravenous injection of a mixture of the vector libraries having the different promoters (doses: 8.5e13 vg/kg and 9.5e13 vg/kg). During the in-life period the animals were monitored for signs of inflammation and were treated with weekly IM injections of steroids (methylprednisolone, 8 mg/kg), and dexamethasone as needed according to the animal facility's SOPs and recommendations from the veterinarian. Serum samples were collected at 1 h, 4 h and 24 h, and weekly after the injections. The animals were sacrificed 4 weeks after the injections and tissues were collected for biodistribution and transduction analyses. The tissues collected are shown in Table 2. All samples were collected into RNAlater® RNA preservation solution (Sigma-Aldrich) and incubated overnight at 4° C., after which the RNAlater® RNA preservation solution was drained and samples were frozen at −80° C. or maintained at 4° C. in RNAlater® RNA preservation solution (small subset of samples). In addition, samples of serum and cerebrospinal fluid were collected at necropsy and stored at −80° C.

TABLE 2

List of tissues collected.

Tissue

Adrenal gland
Artery (carotid)
Aorta
brain (full brain except cerebellum) coronal axis slices
cerebellum sagittal axis slices
dorsal root ganglion (cervical)
dorsal root ganglion (thoracic)
dorsal root ganglion (lumbar)
gonad (ovaries)
heart, basal
heart, apex
kidney
liver
Lung
lymph nodes, cervical
Neural Retinal
Sciatic nerve
skeletal muscle, gastrocnemius
skeletal muscle, quadriceps
spinal cord (cervical)
spinal cord (thoracic)
spinal cord (lumbar)
spleen Brain slices were dissected to isolate regions including, but not limited to, frontal cortex, temporal cortex, motor cortex, hippocampus, basal ganglia, midbrain, brainstem, and cerebellum. For all biodistribution and transduction analyses, total DNA and RNA was extracted from tissue samples with Trizol/chloroform and isopropanol precipitation. Reverse transcription was done with Protoscript II Reverse Transcriptase (NEB) utilizing primers that were specific to the vector transgene and included unique molecular identifiers (UMIs). Control reactions lacking the reverse transcriptase enzyme (−RT control) were also prepared. Quantification of biodistribution (based on viral DNA quantification) and transduction (based on viral transcript RNA quantification) was done with Luna Universal Probe qPCR Master Mix (NEB) using primers and probes specific to the transgene construct. Finally, samples were prepared for next-generation sequencing by amplifying the transgene barcode regions with primers compatible with Illumina NGS platform and sequenced with NextSeq 550 (Illumina).

After sequencing, the barcode tags were extracted from reads with the expected amplicon structure, and the abundance (number of reads or number of UMIs) of each barcode was recorded. Analyses were restricted to the set of barcodes that were present in the input plasmid sample, as measured by a separate sequencing assay that targeted the variant regions of the input plasmid sample.

To aggregate packaging replicates, the read counts from replicate virus production samples were summed. To aggregate biodistribution samples, read counts from samples from the same tissue were summed. To aggregate transduction samples, the number of transduction events (measured by unique id tags detected) from samples from the same tissue were summed.

Virus packaging and transduction of tissue were calculated using a Bayesian model with aggregated production and/or transduction samples as the input. Briefly, probabilistic programming and stochastic variational inference were used to model the measurement process and sources of decoupling (e.g., cross-packaging, template switching, and errors in DNA synthesis) between the actual test virus particles and their designed sequences, and to calculate virus production and transduction (in various tissue samples), and error rates. Biodistribution of tissue was calculated by normalizing aggregated biodistribution samples with input virus abundance. The output was the log 2-transformed mean of the calculated distribution or normalized rate relative to the wild-type (WT) AAV9. Thus, positive values indicate higher performance than WT for the measured property, and negative values indicate lower-than-WT performance. Unless otherwise noted, all results are reported from aggregated values from the library comprising the CBh promoter.

Results

One variant capsid (VAR-1) was identified that showed a more than 75-fold increase in transduction and biodistribution across multiple brain regions relative to wild-type AAV9. This variant additionally packaged/produced AAV virus particles efficiently from the HEK293T cell production system. Property measurements for VAR-1, averaged across all tissue pieces for the indicated tissue type and across both NHPs, are reported in Table 3. Assessment of off-target tissues showed that VAR-1 exhibits reduced biodistribution to liver (approximately 2-fold lower than wild-type AAV9), reduced transduction of liver tissue (approximately 6-fold lower than AAV9), and reduced biodistribution to spleen, muscle and heart (approximately 4-fold lower, 2-fold lower and 2-fold lower, respectively, relative to wild-type AAV9), indicating that this AAV variant capsid is specific for the brain regions of interest after intravenous administration. In addition, relative transduction of dorsal root ganglia to overall brain transduction for VAR-1 was substantially lower than for AAV9 (0.023 for VAR-1 vs. 1.0 for wtAAV9), indicating a substantial (over 40-fold) specificity for brain regions of interest relative to the DRG. In addition, measurements of biodistribution and transduction for VAR-1 were well-correlated across the two primates. Taken together, these findings indicate that capsid polypeptides such as VAR-1 and as described herein are suitable for gene therapies where targeting the brain is important, for example, as described herein. Without being bound by theory, such gene therapies are preferred over existing alternatives, such as those using wild-type AAV9, due to their enhanced specificity for the brain regions of interest and substantial increase in transduction efficiency.

TABLE 3

Mean production, biodistribution and transduction of VAR-1.

| Property | Log2 relative to wtAAV9 (fold-change) |
|---|---|
| Production - HEK293T cells | −0.6675 (0.63) |
| Brain transduction | 6.2845 (77.95) |
| Brain biodistribution | 5.5945 (48.31) |
| Cerebellum transduction | 6.5867 (96.11) |
| Cerebellum biodistribution | 5.9750 (62.90) |
| Cortex transduction | 6.4616 (88.13) |
| Cortex biodistribution | 5.8256 (56.71) |
| Midbrain/Brainstem transduction | 5.9003 (59.72) |
| Midbrain/Brainstem biodistribution | 5.3450 (40.65) |
| Spinal cord transduction | 6.0535 (66.42) |
| Spinal cord biodistribution | 4.0654 (16.74) |
| Subcortex transduction | 6.5805 (95.70) |
| Subcortex biodistribution | 5.4570 (43.93) |
| Liver transduction | −2.6841 (0.16) |
| Liver biodistribution | −1.0338 (0.49) |
| Heart transduction | −0.9601 (0.51) |

TABLE 3-continued

Mean production, biodistribution and transduction of VAR-1.

| Property | Log2 relative to wtAAV9 (fold-change) |
|---|---|
| Heart biodistribution | −0.8876 (0.54) |
| Muscle transduction | 0.1441 (1.10) |
| Muscle biodistribution | −0.8026 (0.57) |
| DRG biodistribution | 0.8356 (1.78) |
| Spleen biodistribution | −2.0366 (0.24) |

All values reported as log2 relative to wtAAV9.
All values are calculated from aggregating across all tissue samples collected from both NHP animals in the study.

Example 2

Low Throughput In Vivo Evaluation of VAR-1 in NHP

In order to confirm the performance of virus particles comprising the capsid polypeptide of VAR-1 and further investigate its properties, virus particle comprising the VAR-1 capsid polypeptide and carrying a transgene encoding a fluorescent protein was synthesized and tested in in vivo and in vitro studies alongside virus particle comprising a wild-type AAV9 capsid polypeptide and different fluorescent protein, as described below.

Virus Design and Production

Virus particles comprising the VAR-1 and wild-type AAV9 capsids were produced individually via transient triple transfection of adherent HEK293T cells (pRepCap (VAR-1), pHELP (pALD X-80, Aldevron), pITR.Cbh.GFP; and pRepCap (wtAAV9), pHELP (pALD X-80, Aldevron), pITR.CBh.mCherry) (See FIG. 2) followed by purification as described in Example 1. Each variant capsid was produced with a self-complementary (scAAV) genome containing 5 distinct regions: One, the ubiquitous CBh promoter (CMV enhancer, Cba promoter, CBA/MVM hybrid intron); two, a fluorescent reporter unique to each virus with a nuclear localization signal (NLS) tag (GFP in the case of VAR-1 virus particles and mCherry in the case of wild-type AAV9 virus particles); three, a unique barcode. Each genome was produced with 8 unique barcodes per florescent reporter, which were included to provide technical replicates for each capsid within the single study. Four, the SV40 PolyA termination signal; and five, left and right ITRs capable of enabling self-complementary genome packaging in the virus particles (See FIG. 2A-2D). After individual purification of each virus, concentrations and amounts were quantified using ddPCR and a final test article was formulated at 50% VAR-1: 50% AAV9.

In Vivo Study Design

All NHP experiments were conducted in accordance with institutional policies and NIH guidelines. Two female Cynomolgus macaque NHPs weighing 3 kg and seronegative for anti-AAV9 neutralizing antibodies (serum NAb titers <1:4 based on in vitro NAb assay) were selected for the study. Animals were treated with Kenalog (10 mg/mL, 0.8 mg/kg) on Day-8 and 2× weekly for the duration of the study. Prior to test article administration, samples of blood were collected. The animals received an intravenous injection of final test article virus containing VAR-1 and AAV9 (total combined doses: 9e12 vg/kg (low dose) and 1.9e13 vg/kg (high dose)). During the in-life period the animals were monitored according to the animal facility's SOPs. Serum samples were collected at 1 day, 2 days, 4 days, and weekly post injection. The animals were sacrificed 4 weeks after the injections, perfused with cold saline, and tissues were collected for biodistribution, transduction, and histology analyses. The tissues and collection methods are shown in Table 4. For brain, the left hemisphere was dissected, and flash froze in 4 mm slices (stored at −80° C.) and the right hemisphere was sliced at 4 mm and fixed in 10% naturally buffered formalin at room temperature for 48 hours before being moved to cold PBS. Other samples were collected and either flash frozen, formalin fixed, or collected into RNAlater® RNA preservation solution (Sigma-Aldrich), as indicated in Table 4. Samples collected in RNAlater® RNA preservation solution were incubated overnight at 4° C., after which the RNAlater® RNA preservation solution was drained and samples were frozen at −80° C. In addition, serum samples were collected at necropsy and stored at −80° C.

TABLE 4

List of tissues collected

| Tissue | Collection Method |
|---|---|
| Left brain coronal axis slices | Flash Frozen |
| Right brain coronal axis slices | Formalin Fixed |
| Brainstem | Flash Frozen, Formalin Fixed |
| dorsal root ganglion (cervical) | Flash Frozen, Formalin Fixed |
| dorsal root ganglion (thoracic) | Flash Frozen, Formalin Fixed |
| dorsal root ganglion (lumbar) | Flash Frozen, Formalin Fixed |
| dorsal root ganglion (sacral) | Flash Frozen, Formalin Fixed |
| gonad (ovaries) | RNALATER ® |
| heart, basal | RNALATER ® |
| heart, apex | RNALATER ® |
| kidney | RNALATER ®, Formalin Fixed |
| liver | RNALATER ®, Formalin Fixed, Flash Frozen |
| lymph nodes, cervical | RNALATER ® |
| Neural Retinal | Flash Frozen, Formalin Fixed |
| skeletal muscle, gastrocnemius | RNALATER ® |
| skeletal muscle, quadriceps | RNALATER ® |
| spinal cord (cervical) | Flash Frozen, Formalin Fixed |
| spinal cord (thoracic) | Flash Frozen, Formalin Fixed |
| spinal cord (lumbar) | Flash Frozen, Formalin Fixed |
| spinal cord (sacral) | Flash Frozen, Formalin Fixed |
| spleen | RNALATER ® |
| carotid artery | RNALATER ® |

Tissue Biodistribution and Transduction Analysis

Left Hemisphere Flash Frozen brain slices were dissected to isolate regions including, but not limited to, frontal cortex, temporal cortex, motor cortex, hippocampus, basal ganglia, midbrain, brainstem, and cerebellum. Liver, Spleen, and DRG samples were also analyzed. For biodistribution and transduction analyses, total DNA and RNA was extracted from tissue samples with Trizol/chloroform and isopropanol precipitation. Reverse transcription was done with Protoscript II Reverse Transcriptase (NEB) with primers that were specific to the vector transgene and transcripts included the unique molecular identifiers (UMIs). Control reactions lacking the reverse transcriptase enzyme (−RT control) were also prepared. Quantification of biodistribution and transduction was done with Luna Universal Probe qPCR Master Mix (NEB) using primers and probes specific to the transgene construct. Finally, samples were prepared for next-generation sequencing by amplifying the transgene barcode regions with primers compatible with Illumina NGS platform and sequenced with NextSeq 550 (Illumina).

After sequencing, the barcode tags were extracted from reads with the expected amplicon structure, and the abundance (number of reads or number of UMIs) of each barcode was recorded. Analyses were restricted to the set of barcodes that were present in the input plasmid sample, as measured by a separate sequencing assay that targeted the variant regions of the input plasmid sample.

To aggregate packaging replicates, the read counts from replicate virus production samples were summed. To aggregate biodistribution samples, read counts from samples from the same tissue were summed. To aggregate transduction samples, the UMI counts from samples from the same tissue were summed.

NHP Tissue Immunofluorescence

Formalin fixed right hemisphere brain slices, as well as DRG and spinal cord, were paraffin embedded, sliced at 5 uM, and stained for NeuN (neuronal marker), mCherry, and GFP. The NeuN/GFP/mCherry staining was performed on the Leica BOND RX Autostainer. The primary antibodies used include GFP (PA5-34974, Thermo-Fisher), mCherry (Ab6556, Abcam), and NeuN (Ab177487, Abcam). Immunofluorescence-stained tissue 1"×3" glass slides were scanned using an Akoya Vectra Polaris Fluorescent scanner to produce whole-slide digital images. The number of total cells staining for GFP (VAR-1) and mCherry (AAV9), as well as the number of VAR-1 and AAV9 positive cells co-staining with NeuN (to ascertain transduction and expression in neurons), were manually counted in the high dose animal using QuPath software. Regions of interest (ROI) analyzed included the hippocampus, frontal cortex, caudate, cerebellum, and spinal cord. All areas were analyzed in duplicate (2 slides each), except spinal cord which was analyzed in triplicate. All ROIs were counted in their entirely on the slide except the cerebellum where 2 cortical folds were analyzed per slice.

Results

Bulk Tissue Analysis by NGS Sequencing of Viral RNA (Transduction) and Viral DNA (Biodistribution)

Figure 3A:
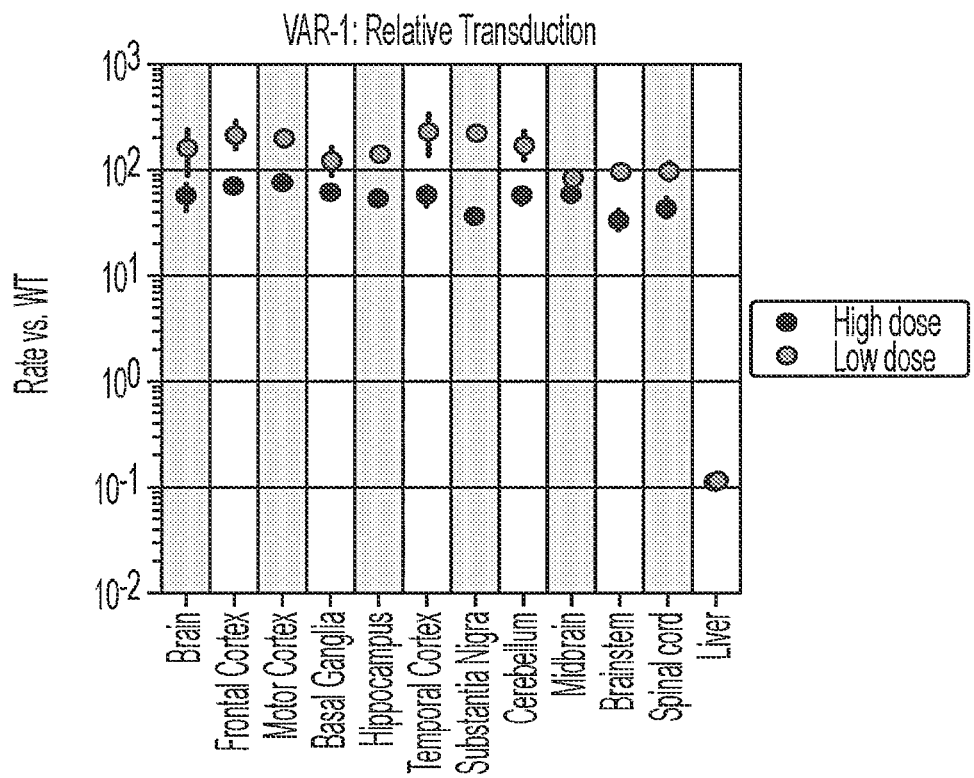
FIG. 3A-3B Relative transduction (A) and biodistribution (B) for VAR-1 (relative to wild-type AAV9) from the 2-capsid NHP experiment described in Example 2.
Figure 3B:
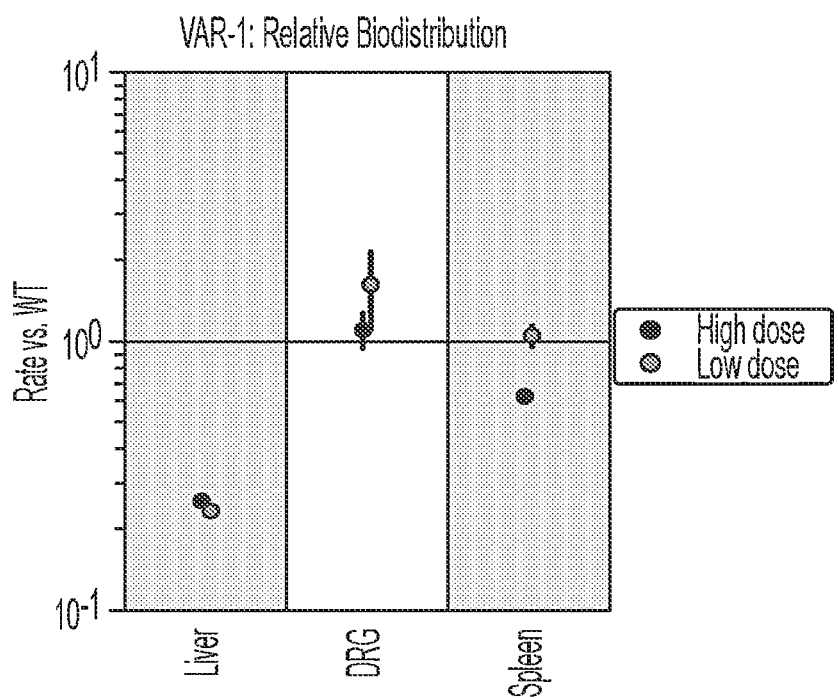

VAR-1 shows increased transduction across multiple brain regions compared to WT AAV9 in this two-capsid, direct comparison study. The number of samples analyzed by NGS in each animal and brain region is listed in Tables 5 and 6 and the property measurements for VAR-1, averaged across all tissue pieces for the indicated tissue type for each NHP, are reported in Table 7 and in FIG. 3A (transduction relative to wild-type AAV9) and FIG. 3B (biodistribution relative to wild-type AAV9). In FIG. 3A and Table 7, "brain transduction" represents an aggregated measurement of relative transduction averaged across all collected tissue samples. The high dose resulted in a 56.73 fold increase in brain transduction overall with a range of 34 to 76 fold increase in different regions (Table 7 and FIG. 3A). The low dose resulted in a relative increase to WT AAV9 of 161-fold for total brain transduction, ranging from 82 to 213 fold increase in different brain regions (Table 7 and FIG. 3A). Assessment of off-target tissues showed that VAR-1 exhibits reduced liver biodistribution at 0.26 and 0.23 fold AAV9 in high and low doses respectively, and liver transduction was 0.11 fold WT AAV9 for both doses (Table 7 and FIGS. 3A and 3B). Biodistribution of VAR-1 in the DRG was largely unchanged from WT AAV9 with a 1.1 and 1.6 fold increase to AAV9 observed in high and low doses, respectively (Table 7 and FIG. 3B). Spleen biodistribution was unchanged at the low dose but decreased to 0.63 fold AAV9 at the high dose (FIG. 3B). These results confirm the improved properties of VAR-1 exhibited in the high-throughput library experiment reported in Example 1. These results suggest that, without being bound by theory, gene therapies that include the capsid variant described herein is useful for the treatment of CNS disorders, for example as described herein, for example, neurodegenerative disorders such as, but not limited to, Parkinson's Disease, Hunting- ton's disease, Alzheimer's disease, Fragile X, Rett Syndrome, Angelman Syndrome, ataxias and frontotemporal dementia.

TABLE 5

RNA transduction tissue sample number

| Tissue | High Dose | Low Dose |
|---|---|---|
| Frontal Cortex | 1 | 5 |
| Motor Cortex | 5 | 2 |
| Basal Ganglia | 8 | 9 |
| Hippocampus | 3 | 4 |
| Temporal Cortex | 7 | 7 |
| Substantia Nigra | 1 | 1 |
| Cerebellum | 5 | 6 |
| Midbrain | 3 | 2 |
| Brainstem | 6 | 5 |
| Spinal Cord | 5 | 5 |
| Liver | 2 | 2 |

TABLE 6 vDNA biodistribution sample number

| Tissue | High Dose | Low Dose |
|---|---|---|
| Liver | 4 | 4 |
| DRG | 4 | 4 |
| Spleen | 4 | 4 |

TABLE 7

Biodistribution and transduction of VAR-1.

| | Fold Change from WT AAV9 | |
| Property | High Dose | Low Dose |
|---|---|---|
| Brain transduction | 56.7314 | 160.8062 |
| Frontal Cortex transduction | 70.7492 | 213.4124 |
| Motor Cortex Transduction | 76.7434 | 196.2372 |
| Basal Ganglia transduction | 61.8081 | 120.7397 |
| Hippocampus transduction | 54.2627 | 139.2863 |
| Temporal Cortex transduction | 57.2538 | 228.6310 |
| Substantia Nigra transduction | 36.3738 | 220.6999 |
| Cerebellum transduction | 57.3525 | 170.9359 |
| Midbrain transduction | 58.4986 | 82.2261 |
| Brainstem transduction | 33.5664 | 95.7057 |
| Spinal cord transduction | 43.7355 | 97.4933 |
| Liver transduction | 0.111524 | 0.112531 |
| Liver biodistribution | 0.255386 | 0.234775 |
| DRG biodistribution | 1.102479 | 1.621922 |
| Spleen biodistribution | 0.625651 | 1.046902 |

All values reported fold change relative to WT AAV9.
All values are an aggregate across all tissue samples collected from each NHP animal in the study.
"Brain transduction" is an aggregate across all brain samples analyzed from each NHP animal in the study.

Histology: Immunofluorescence

Figure 4A:
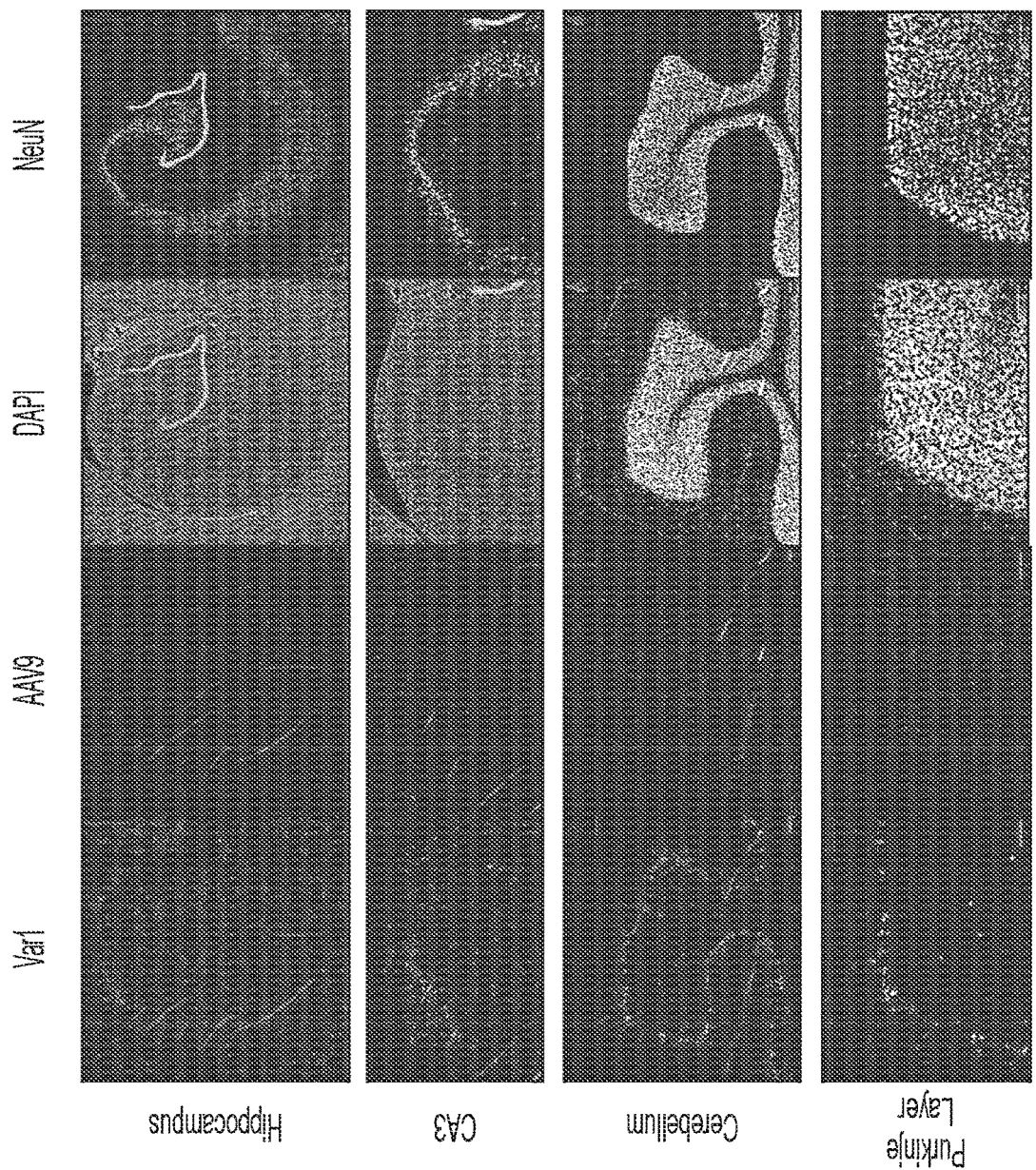
FIG. 4A-B. A) Representative images of VAR-1 and wild-type AAV9 immunofluorescence in the hippocampus and cerebellum. In the hippocampus, the number of cells with VAR-1 GFP expression is ~25 fold those with AAV9 mCherry expression. This was also found in the CA3 layer, where VAR-1 GFP is visible in the CA3 pyramidal neurons showing co-staining with the neuronal marker NeuN. In the cerebellum, VAR-1 GFP is expressed in more cells than AAV9 mCherry and has highest expression in the purkinje cell layer. B) Representative images of VAR-1 and wild-type AAV9 immunofluorescence in the cervical spinal cord, frontal cortex, and caudate. The number of cells with VAR-1 GFP expression in the spinal cord is 9.4 fold AAV9 mCherry. VAR-1-expressed GFP is also detected in some neurons (co-stain with NeuN), unlike AAV9 mCherry. In the frontal cortex and caudate, the total number of cells expressing VAR-1 GFP is increased compared to AAV9 mCherry (15.9 and 4.6 fold increase) and this increases to 25 and 37-fold for neurons specifically (co-stain with NeuN).
Figure 4B:
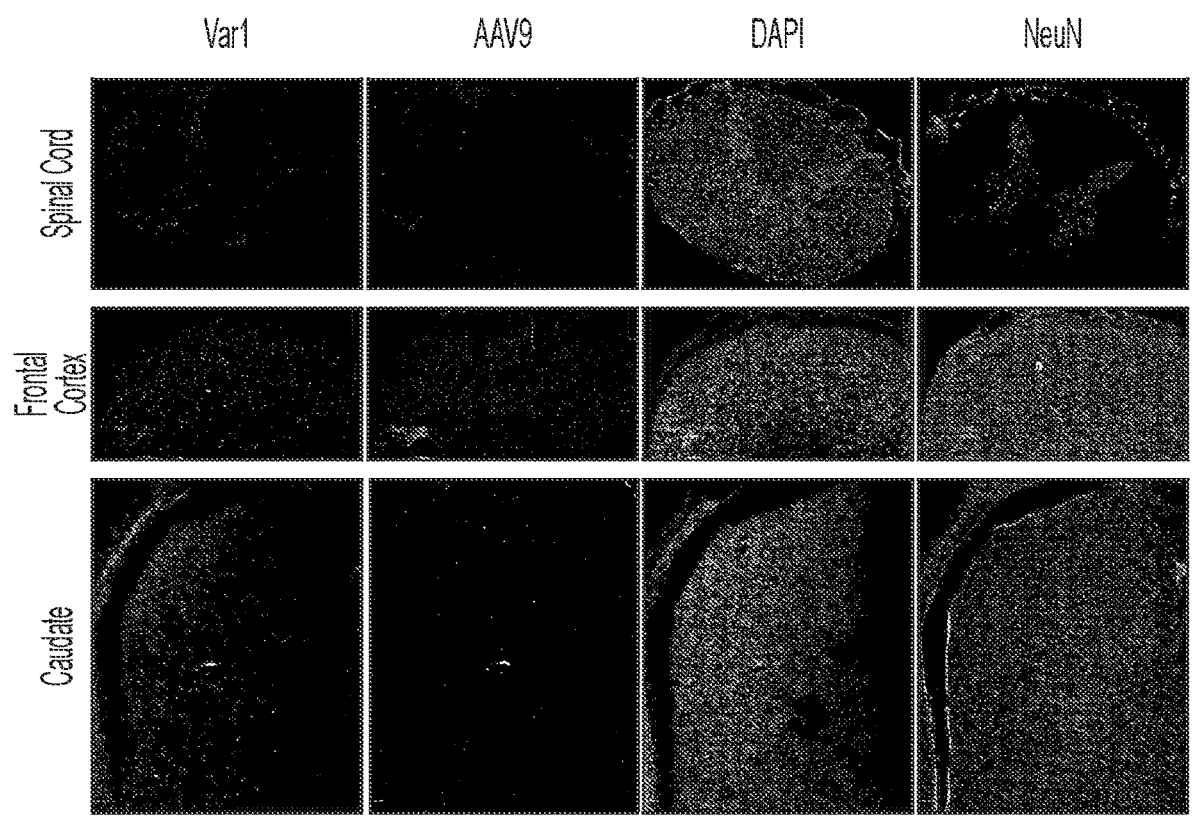

Histological analysis of cell numbers expressing GFP from the VAR-1 virus particles and mCherry from the wild-type AAV9 virus particles demonstrates that VAR-1 virus particles have increased transgene expression relative to wild-type AAV9 virus particles throughout the brain areas analyzed from the high dose animal. The fold increase in number of cells stained for VAR-1 compared to WT AAV9 virus particles transgene expression varies by region, with highest increases in the hippocampus and cerebellar cortex (Table 8, FIGS. 4A and 4B). A consistent increase in the number of neurons stained was also observed for VAR-1 compared to AAV9, although also varying by area. Large increases in neuronal staining are observed in the frontal cortex and caudate (Table 8, FIG. 4B). The hippocampal CA3 also shows distinct staining by transduction from VAR-1 in the pyramidal neuron layer, with 16.6% of neurons in this region expressing GFP whereas no neurons express mCherry (Table 8, FIG. 4A). Additionally, 5% of the total counted CA3 neurons expressed the VAR-1 virus particle transgene (GFP). The Purkinje cell layer of the cerebellar cortex also had very high levels of VAR-1 GFP staining compared to AAV9 mCherry. However, despite having visual appearance of large neurons, Purkinje neurons do not stain with the NeuN antibody used, so neuronal staining cannot be determined (FIG. 4A). The high transduction and cell staining patterns exhibited in the cerebellum suggest that, without being bound by theory, gene therapies that include the capsid variant described herein are particularly useful for the treatment of Spinocerebellar ataxias. The full brain histology staining results suggest that, without being bound by theory, gene therapies that include the capsid variant described herein are useful for the treatment of CNS disorders, e.g., as described herein, e.g., neurodegenerative disorders such as Parkinson's Disease, Huntington's disease, and Alzheimer's disease.

TABLE 8

Cell counts for VAR-1 virus particle transgene expression (GFP) normalized to wild-type AAV9 virus particle transgene expression (mCherry) for total cells and neurons.

| Brain Region | Total Cells Fold change from AAV9 in VAR-1 positive cells | Neuron Fold change from AAV9 in VAR-1 positive cells |
|---|---|---|
| Hippocampus Total | 25.0 | 4.3 |
| Hippocampus CA3 | 24.7 | Not determinable: no AAV9 staining |
| Frontal Cortex | 15.9 | 25.2 |
| Cerebellum Purkinje Layer | 36.4 | N/A* |
| Cerebellum Granule Layer | 25.3 | 11 |
| Caudate | 4.6 | 37.2 |
| Spinal Cord | 9.4 | Not determinable: no AAV9 staining |

All values are the reported fold change relative to AAV9 and are the average of counts in 2 slices for all regions except the cerebellar cortex (average of 4 cortical folds (2/slice) and spinal cord (3 slices).
Not determinable: fold change not able to be determined due to 0 neurons detected with AAV9 mCherry.
N/A*: Purkinje neurons in the Purkinje layer do not stain with NeuN.

Example 3

In Vitro Evaluation of VAR-1 and AAV9

In vitro transduction was used to evaluate the ability of WT AAV9 and VAR-1 virus particles to infect and transduce human neurons. Sh-sy5y and primary neuron cultures were used for this analysis and analyzed for the expression of GFP from the VAR-1 virus particles and mCherry from the WT AAV9 virus particles produced in Example 2.

Sh-sy5y In Vitro Transduction Assay

The assays were performed in 12 well plates with poly-l-lysine coated coverslips. Sh-sy5y (human glioblastoma cell line, Sigma, 94030304-1VL) cells were plated at a density of 300,000 cells per well. 24 hours post plating the virus particles were added to the cells at MOIs of 100,000, 50,000, and 10,000 vg/cell in media lacking FBS and incubated on ice for 1 hour. After one hour, complete media was added to the cells. Four days post transduction the cells were fixed with 4% paraformaldehyde and stained by immunofluorescence for MAP2 (1:1000 Abcam ab5392) and NeuN (1:500, Sigma Aldrich ABN78), utilizing Alexa 595 and 405 conjugated (1:1000) secondary antibodies. GFP was visualized using the native fluorescence from the capsid transgene.

Primary Human Neurons In Vitro Transduction Assay

The assays were performed in 12 well plates with poly-l-lysine coated coverslips. Primary Human Neurons (Sciencell #1530) were plated at 8.3e4 cells per well. The cells were grown for 7 days in a 37° C. incubator with media changes every two days. At 7 days in vitro the virus particles were added to the cells at MOIs of 10,000, 25,000, or 50,000 vg/cell and incubated at 37° C. for 1 hour. After one hour incubation complete media was added, including all the required supplements. Seven days post-transduction the cells were fixed with 4% paraformaldehyde and stained/visualized using MAP2 (1:1000 Abcam ab5392), native GFP or mCherry fluorescence, and DAPI (Vectashield NCI601055).

Image Acquisition

Images were acquired on an EVOS M5000 with a 20× objective. The images were quantified using ImageJ plugin cell count. The counts were averaged across 5-7 fields of view from two different coverslips.

Results

Figure 5:
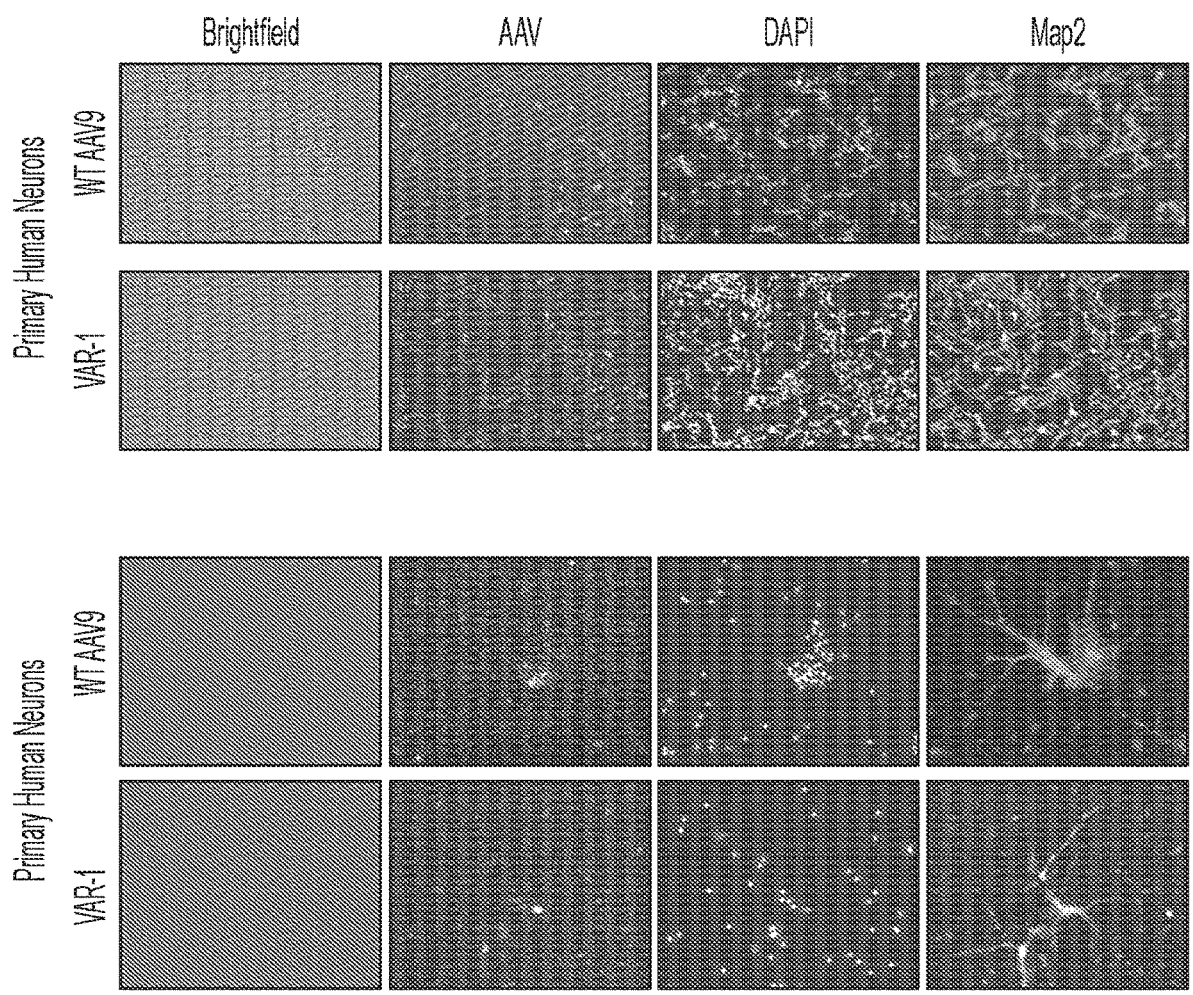
FIG. 5. Representative images from in vitro cell transduction experiments showing transduction of VAR-1and WT AAV9 in both Primary Human Neurons and the Sh-sy5y cell line. Primary human neurons were treated with virus at 50K MOI and Sh-sy5y cells with virus at 100K MOI for both VAR-1 and WT AAV9. Images were taken from fixed samples using a 20× objective on an EVOS M5000.

The in vitro transduction results are summarized in Table 9. VAR-1 virus particles transduce Primary Human Neurons at a rate of 8.65% (50K MOI) and Sh-sy5y glioblastoma neurons at 37.65% (100K MOI). VAR-1 also transduces human neurons at a greater abundance than WT AAV9 in both cell types with a 3.7 fold increased compared to WT in Sh-sy5y (100K MOI) and 1.6 fold increase in primary human neurons (50K MOI). Representative images (brightfield, transgene expression, and cell markers) from sh-sy5y and primary human neurons treated with VAR-1 and WT AAV9 virus particles are shown in FIG. 5. These results demonstrate that VAR-1 has the ability to transduce human neurons in vitro, supporting a translational and clinical application of this capsid in gene therapies targeting CNS disorders, for example as described herein.

TABLE 9

Cell transduction of Var1 and WT AAV9 quantification in Sh-sy5y and Primary Human Neurons

| Cell Type | Test Article | MOI Transduced | Cells Counted | % Cells Transduced | Standard Error |
|---|---|---|---|---|---|
| Primary Human Neurons | WT AAV9 | 10K MOI | 403 | 1.74 | 1.1 |
| | | 25K MOI | 284 | 3.26 | 0.95 |
| | | 50K MOI | 1033 | 5.5 | 2.26 |
| | VAR-1 | 10K MOI | 551 | 1.42 | 0.61 |
| | | 25K MOI | 590 | 3.8 | 1.7 |
| | | 50K MOI | 577 | 8.65 | 2.9 |
| Sh-sy5y | WT AAV9 | 10K MOI | 1201 | 1.74 | 2.5 |
| | | 50K MOI | 1955 | 11.19 | 5.1 |
| | | 100K MOI | 940 | 10.14 | 3.7 |
| | VAR-1 | 10K MOI | 2552 | 6.63 | 0.65 |
| | | 50K MOI | 1581 | 28.64 | 2.216 |
| | | 100K MOI | 2868 | 37.69 | 1.66 |

Example 4

High-Through Evaluation of VAR-1 Additional Capsid Variants

Library Creation

A library of 1E5 capsid variants of wild-type AAV9 was designed with the goals of producing a capsid that would package into AAV particles, transduce central nervous system tissues after intravenous injection with high efficiency, and de-target the liver and other tissue types. This library was designed and synthesized according to Example 1, with the following variations. First, a subset of these variants included in this library is 126 capsid polypeptide variants that are identical to the sequence of wild-type AAV9, but contain various subcombinations of the amino acid mutations in the mutation set of VAR-1. The capsid polypeptide VP1 sequences are provided as SEQ ID NOS: 14 to 139 (corresponding representative nucleic acid sequences are provided in SEQ ID NOS: 140-256) as shown in Table 1) ("subcombination variant set"). The mutation set associated with each of these variants is provided below in Table 1. Without being bound by theory, these variants were designed to specifically characterize the minimally active set of mutations responsible for the enhanced activity of VAR-1. In addition, the library contained a selection of variants which, relative to wild-type AAV9, included between 1 and 3 amino acid mutations in addition to the mutations of the mutation set of VAR-1. Without being bound by theory, these additional variants were designed to provide evidence confirming the enhanced performance of virus particles comprising the mutation sets described herein, for example, of VAR-1, in different sequence contexts. Second, the library was cloned twice using two different versions of the viral genome, one with expression of the capsid gene under the control of a ubiquitous CBh promoter and the other with expression of the capsid gene under the control of a neuronal specific hSyn promoter. Each plasmid backbone contained a unique genomic identifier enabling analysis of biodistribution and transduction efficiencies of each capsid variant via each of the two promoters.

In Vitro Evaluation of Library

In vitro evaluation of the library was completed as outlined in Example 1.

In Vivo Evaluation of Library in Non-Human Primate

All NHP experiments were conducted in accordance with institutional policies and NIH guidelines. Two female Cynomolgus Macaque primates weighing 2.5 and 2.6 kg and seronegative for anti-AAV9 neutralizing antibodies (serum NAb titers <1:4 based on in vitro NAb assay) were selected for the study. Animals were treated with Methylprednisolone (40 or 80 mg IM) on Day-8 and weekly for the duration of the study. Prior to test article administration, samples of blood were collected. The animals received an intravenous injection of a mixture of the promoter vector libraries (total combined dose for each animal: 8.64 e13 vg/kg). During the in-life period the animals were monitored according to the animal facility's SOPs. Serum samples were collected at 2 days, 4 days, 7 days, and weekly after the injections. The animals were sacrificed 4 weeks after the injections and tissues were collected and analyzed as described in Example 1 for biodistribution and transduction. The tissues collected are shown in Table 11.

TABLE 11

| List of tissue collected |
|---|
| Tissue |
| Adrenal gland |
| Adipose Tissue |
| Aorta |
| Brain coronal axis slices |
| Carotid artery |
| dorsal root ganglion (cervical) |
| dorsal root ganglion (thoracic) |
| dorsal root ganglion (lumbar) |
| dorsal root ganglion (sacral) |
| gonad (ovaries) |
| heart, basal |
| heart, apex |
| Heart, ventricle |
| kidney |
| liver |
| Lung |
| lymph nodes, cervical |
| Optic nerve |
| Sciatic nerve |
| skeletal muscle, gastrocnemius |
| skeletal muscle, quadriceps |
| Skeletal muscle, diaphragm |
| spinal cord (cervical) |
| spinal cord (cranial thoracic) |
| spinal cord (caudal thoracic) |
| Spinal cord (lumbar) |
| spleen |

After sequencing, the barcode tags were extracted from reads with the expected amplicon structure, and the abundance (number of reads or number of UMIs) of each barcode was recorded. Analyses were restricted to the set of barcodes that were present in the input plasmid sample, as measured by a separate sequencing assay that targeted the variant regions of the input plasmid sample.

To aggregate packaging replicates, the read counts from replicate virus production samples were summed. To aggregate biodistribution samples, read counts from samples from the same tissue were summed. To aggregate transduction samples, the number of transduction events (measured by unique id tags detected) from samples from the same tissue were summed.

Virus packaging was calculated by normalizing aggregated production replicates with input plasmid abundance. Biodistribution and transduction of tissue were calculated by normalizing aggregated biodistribution or transduction samples with input virus abundance. The output was reported as fold change relative to the WT AAV9.

Results

The production, biodistribution and transduction results for VAR-1 and the subcombination variant set from this library experiment are summarized in Table 13 (production), Table 14 (CNS biodistribution), Table 15 (periphery biodistribution), Table 16 (CNS transduction) and Table 17 (periphery transduction). As was the case in the library experiment described in Example 1 and the single capsid experiment described in Example 2, VAR-1 displays increased transduction and biodistribution across the brain regions sampled compared to AAV9. This was observed for both promoters with brain transduction having a 138 fold and 129 fold increase compared to WT AAV9 with the CBh and hSyn promoters, respectively. Additionally, periphery VAR-1 biodistribution and transduction in the liver is decreased to 0.3 fold AAV9 and biodistribution was also decreased in the spleen, again confirming the results of the previous experiments. HEK293 virus production was also suitable in this study. Taken together, these findings further indicate that VAR-1 is suitable for gene therapies where targeting the brain is important, for example, as described herein.

In addition to VAR-1, other VAR-1-like capsid polypeptides (e.g., containing subcombinations of the mutation set of VAR-1) exhibited similar transduction profiles to VAR-1 with elevated transduction across the brain. As shown in Table 16, of the 93 variants where brain transduction data could be captured, 77 of the variants with subcombinations of the VAR-1 mutation set exhibited better than WT AAV9 transduction in aggregated brain regions assessed when transgene expression was under the control of the neuronal specific hSyn promoter, and 79 of the 93 variants measured showed better than WT AAV9 transduction in aggregated brain regions when expression was under the control of the ubiquitous CBh promoter.

Assessment of the set of variants with subcombinations of the VAR-1 mutation set revealed several sequences which represent minimal sets of mutations conferring enhanced brain transduction of variant capsid polypeptides. In particular, VAR-80 (having 4 mutations in its mutation set: ["T593V", "V596L", "N598S", and "I601A"]) exhibited 22.4 and 32.2 fold increases in aggregated brain transduction relative to wild-type AAV9 from the CBh and hSyn promoters, respectively. In addition, the mutations V596L, N598S and I601A are entirely conserved in the top 10 subcombination set variants when ranked by aggregated brain expression from the hSyn promoter, and the variant comprising only these three mutations (VAR-83) exhibits greater than 5-fold increased transduction in aggregated brain relative to wild-type AAV9. Another highly conserved motif in the top aggregated brain transducers is the combination of W595A, V596L, and N598S. The variant containing only these three mutations in its mutation set (VAR-112) exhibited nearly 2-fold increased transduction relative to wild-type AAV9 in aggregated brain tissue. Interestingly, the variant which also includes the Q579V mutation to this mutation set (VAR-82) exhibited a 6.5-fold increase in aggregated brain transduction relative to AAV9 from the hSyn promoter, indicating that the combination of valine at 579, alanine at position 595, leucine at position 596 and serine at position 589 confers enhanced brain transduction properties on virus particles. Another motif which emerged was the combination of Q592I, T593V and V596L. The variant having only these mutations in its mutation set (VAR-110) was the strongest transducing variant with only 3 mutations relative to wtAAV9, exhibiting 8.2-fold increase in aggregated brain transduction from the hSyn promoter relative to wild-type AAV9. Another motif which emerged was the combination of T593V, W595A, V596L, and N598S. 5 of the 10 ten variants ranked according to fold improvement over wild-type AAV9 in aggregated brain transduction from the hSyn promoter included this mutation set and the variant with only these 4 mutations (VAR-114) exhibited 2.18-fold aggregate brain transduction over wild-type AAV9 from the hSyn promoter and 1.06-fold aggregate brain transduction from the CBh promoter. Again, the results show an improved effect when combining the mutation sets: for example, when these 4 mutations (T593V, W595A, V596L, and N598S) are included with the Q579V mutation (VAR-75), virus particles show 17.07-fold and 18.85-fold aggregated brain transduction relative to wild-type AAV9 from the CBh and hSyn promoters, respectively. Since these minimal motifs independently lead to increased brain transduction, without being bound by theory, these motifs are additive and/or synergistic, and can lead to enhanced effects when combined.

Of the variants exhibiting greater than 5-fold aggregated brain transduction from the hSyn promoter, 6 variants had 6 of the 7 mutations of the VAR-1 mutation set; 9 variants had 5 of the 7 mutations of the VAR-1 mutation set; 7 variants had 4 of the 7 mutations of the VAR-1 mutation set; and 3 variants had 3 of the 7 mutations of the VAR-1 mutation set. This indicates that variants which contain 3, 4, 5, 6 or 7 of the mutations in the mutation set of VAR-1 are capable of transducing cells of the CNS upon intravenous injection, indicating the potential to cross the blood brain barrier and reach cells of interest to treat CNS disorders for example as described herein.

Finally, an additional set of variants were designed which included the mutation set of VAR-1 and which included between 1 and 3 additional mutations. Of the variants from this set, all but one of the designed variants (18 of 19 designed variants) which were detected in at least one brain region exhibited transduction levels of at least 1.75-fold over wild-type AAV9 in aggregated brain regions from the hSyn promoter. Fold increases in these 19 variants in aggregated brain samples ranged from a 1.75-fold improvement to an over 134-fold improvement. Without being bound by theory, these results indicate that the mutation set of VAR-1 is active in providing increased brain transduction when present in diverse sequence contexts.

When assessing the data by individual brain region, 3 variants other than VAR-1; VAR-54, VAR-74, and VAR-87, exhibit high transduction in the temporal cortex. Additionally, VAR-61 exhibits consistent increased transduction for the hSyn neuronal promoter compared to the CBh promoter (relative to AVV9). This result suggests that this variant could have more neuronal-specific characteristics and without being bound by theory, gene therapies that include the capsid variants described herein are useful for the treatment of neuronal specific disorder such as Rett Syndrome, Angelman syndrome, Fragile-X, or Tay-Sachs disease, as well as broader neurodegenerative diseases.

Another important finding is based on the fact the experiments described in Example 1 and Example 4 were completed in AGM and Cynomolgus macaque non-human primates, respectively, thereby enabling comparison of VAR-1 across 2 different genus of NHP. VAR-1 transduction compared to AAV9 in AGM (Exp 1) and Cyno (Exp 4) are shown in Table 12. Similar levels of brain transduction were observed in both species. In the experiment described in Example 4, in Cynos, VAR-1 did show slightly increased transduction across the brain (with the exception of spinal cord) compared to the results in AGM. However, differences between species/experiment are minor and suggest that the method by which VAR-1 increases brain transduction is conserved across NHP species of 2 different genus. These findings further indicate that VAR-1 is suitable for gene therapies where targeting the brain is important, and in particular in other related species such as humans, for example, as described herein.

TABLE 12

Aggregated brain transduction of VAR-1 in two separate high-throughput library experiments, one in AGM (Example 1) and one in Cynomolgus macaque (Example 4).

| | Fold Transduction for VAR-1 relative to AAV9 | |
|---|---|---|
| Brain region | Results from Example, 1: AGM | Results from Example 4: Cyno |
| Whole brain | 78x (63-96x) | 139x (75-300x) |
| Cerebellum | 96x | 122x |
| Cortex | 88x | 129x |
| Spinal cord | 66x | 46x |

Relative fold transduction increase to AAV9 is conserved across species for multiple regions.

TABLE 13

Production efficiency in HEK293 cells in vitro, relative to production efficiency of WT AAV9, ranked from highest to lowest.

| Variant Name | CBh Fold Change Relative to wtAAV9 | hSyn Fold Change Relative to wtAAV9 |
| --- | --- | --- |
| VAR-10 | 1.19 | 1.41 |
| VAR-14 | 1.26 | 1.17 |
| VAR-114 | 1.35 | 0.99 |
| VAR-124 | 1.16 | 0.97 |
| VAR-9 | 1.21 | 0.96 |
| VAR-15 | 0.93 | 0.94 |
| VAR-67 | 0.66 | 0.91 |
| VAR-82 | 1.32 | 0.91 |
| VAR-121 | 1.18 | 0.89 |
| VAR-13 | 1.22 | 0.88 |
| VAR-93 | 1.11 | 0.87 |
| VAR-81 | 1.8 | 0.87 |
| VAR-104 | 0.92 | 0.87 |
| VAR-7 | 1.16 | 0.87 |
| VAR-63 | 0.55 | 0.87 |
| VAR-87 | 0.54 | 0.83 |
| VAR-68 | 1.2 | 0.83 |
| VAR-24 | 1.22 | 0.83 |
| VAR-38 | 0.44 | 0.83 |
| VAR-83 | 0.7 | 0.82 |
| VAR-85 | 1.63 | 0.82 |
| VAR-112 | 1.32 | 0.81 |
| VAR-120 | 1.2 | 0.81 |
| VAR-32 | 0.89 | 0.78 |
| VAR-79 | 1.09 | 0.77 |
| VAR-101 | 0.91 | 0.76 |
| VAR-98 | 0.51 | 0.76 |
| VAR-6 | 0.94 | 0.76 |
| VAR-21 | 1.07 | 0.76 |
| VAR-75 | 1.16 | 0.75 |
| VAR-116 | 0.53 | 0.74 |
| VAR-28 | 0.94 | 0.74 |
| VAR-27 | 1.18 | 0.74 |
| VAR-57 | 0.76 | 0.73 |
| VAR-96 | 1.44 | 0.72 |
| VAR-90 | 1.21 | 0.72 |
| VAR-58 | 1.05 | 0.72 |
| VAR-42 | 0.93 | 0.72 |
| VAR-48 | 0.65 | 0.72 |
| VAR-4 | 0.55 | 0.71 |
| VAR-33 | 0.77 | 0.7 |
| VAR-95 | 0.77 | 0.7 |
| VAR-71 | 0.78 | 0.69 |
| VAR-50 | 1.03 | 0.69 |
| VAR-44 | 0.91 | 0.68 |
| VAR-118 | 0.5 | 0.68 |
| VAR-25 | 0.74 | 0.67 |
| VAR-70 | 0.55 | 0.67 |
| VAR-55 | 1.31 | 0.67 |
| VAR-29 | 0.72 | 0.67 |
| VAR-89 | 0.51 | 0.66 |
| VAR-8 | 0.46 | 0.66 |
| VAR-12 | 0.87 | 0.66 |
| VAR-56 | 0.83 | 0.66 |
| VAR-54 | 0.52 | 0.65 |
| VAR-94 | 0.67 | 0.65 |
| VAR-119 | 0.54 | 0.64 |
| VAR-51 | 0.74 | 0.64 |
| VAR-34 | 0.81 | 0.64 |
| VAR-88 | 0.73 | 0.62 |
| VAR-17 | 0.79 | 0.62 |
| VAR-47 | 0.6 | 0.62 |
| VAR-2 | 0.41 | 0.62 |
| VAR-31 | 0.9 | 0.61 |
| VAR-74 | 0.53 | 0.6 |
| VAR-123 | 0.95 | 0.58 |
| VAR-86 | 1.07 | 0.58 |
| VAR-11 | 0.52 | 0.58 |
| VAR-22 | 0.24 | 0.58 |
| VAR-99 | 1.2 | 0.57 |
| VAR-3 | 0.32 | 0.57 |
| VAR-109 | 0.28 | 0.57 |
| VAR-122 | 0.87 | 0.56 |
| VAR-107 | 0.72 | 0.55 |
| VAR-115 | 0.41 | 0.55 |
| VAR-80 | 0.41 | 0.54 |
| VAR-69 | 0.41 | 0.54 |
| VAR-77 | 0.4 | 0.54 |
| VAR-45 | 0.38 | 0.54 |
| VAR-97 | 0.82 | 0.53 |
| VAR-78 | 0.33 | 0.53 |
| VAR-26 | 1.14 | 0.52 |
| VAR-36 | 0.95 | 0.52 |
| VAR-41 | 0.84 | 0.5 |
| VAR-23 | 0.66 | 0.5 |
| VAR-60 | 0.41 | 0.5 |
| VAR-84 | 0.42 | 0.5 |
| VAR-5 | 0.95 | 0.49 |
| VAR-19 | 0.31 | 0.48 |
| VAR-106 | 0.28 | 0.48 |
| VAR-65 | 0.31 | 0.47 |
| VAR-1 | 0.43 | 0.46 |
| VAR-66 | 0.39 | 0.46 |
| VAR-100 | 0.36 | 0.45 |
| VAR-52 | 0.33 | 0.45 |
| VAR-61 | 0.29 | 0.44 |
| VAR-105 | 0.3 | 0.44 |
| VAR-73 | 0.11 | 0.44 |
| VAR-117 | 0.46 | 0.44 |
| VAR-62 | 0.35 | 0.43 |
| VAR-59 | 0.39 | 0.42 |
| VAR-43 | 0.36 | 0.42 |
| VAR-103 | 0.35 | 0.42 |
| VAR-39 | 0.37 | 0.42 |
| VAR-125 | 0.39 | 0.41 |
| VAR-53 | 0.24 | 0.39 |
| VAR-30 | 0.28 | 0.39 |
| VAR-102 | 0.37 | 0.38 |
| VAR-40 | 0.29 | 0.38 |
| VAR-110 | 0.26 | 0.37 |
| VAR-20 | 0.39 | 0.36 |
| VAR-49 | 0.31 | 0.35 |
| VAR-46 | 0.32 | 0.34 |
| VAR-113 | 0.37 | 0.33 |
| VAR-72 | 0.54 | 0.31 |
| VAR-111 | 0.34 | 0.31 |
| VAR-35 | 0.4 | 0.29 |
| VAR-76 | 0.26 | 0.29 |
| VAR-18 | 0.22 | 0.28 |
| VAR-108 | 0.19 | 0.26 |
| VAR-91 | 0.34 | 0.26 |
| VAR-16 | 0.19 | 0.25 |
| VAR-37 | 0.29 | 0.25 |
| VAR-92 | 0.24 | 0.25 |
| VAR-126 | 0.27 | 0.25 |
| VAR-64 | 0.15 | 0.23 |
| VAR-127 | 0.21 | 0.22 |

CBh indicates virus particles comprising genomes with the cap gene under the control of the CBh promoter.
hSyn indicates virus particles comprising genomes with the cap gene under the control of the hSyn promoter.
Variants are ranked in order of highest fold change to lowest fold change from the hSyn-containing virus particles.

TABLE 14

Fold change in biodistribution of virus particles comprising the indicated variant capsid polypeptid, relative to the biodistribtuion of virus particles comprising WT AAV9 for brain regions. "Aggregated" is an average across all other measured areas. CBh indicated measurements from virus particles comprising genomes with the cap gene under the contol of CBh promoter. hSyn indicated virus particles comprising genomes with cap gene under the control of the hSyn promoter. Values of "0" indicated variant was not detected in the indicated samples.

| | organ | | | | | | | | |
|---|---|---|---|---|---|---|---|---|---|
| | brain | brain | brain | brain | brain tissue | brain | brain | brain | brain |
| Variant Name | aggregated | aggregated | basal_ganglia | basal_ganglia | brainstem promoter | brainstem | cerebellum | cerebellum | forebrain |
| | CBh | hSyn | CBh | hSyn | CBh | hSyn | CBh | hSyn | CBh |
| VAR-1 | 28.15 | 31.96 | 34.04 | 41.13 | 20.84 | 21.8 | 37.28 | 40.29 | 27.68 |
| VAR-54 | 41.9 | 42.98 | 54.79 | 54.69 | 27.25 | 27.63 | 50.55 | 51.82 | 33.14 |
| VAR-74 | 18.31 | 19.67 | 18.5 | 36.45 | 14.63 | 9.84 | 24.14 | 26.96 | 15.74 |
| VAR-87 | 31.11 | 30.01 | 54.19 | 28.27 | 13.15 | 28.54 | 30.87 | 30.98 | 29.47 |
| VAR-61 | 16.22 | 17.31 | 23.2 | 17.81 | 9.95 | 19.35 | 23.46 | 19.65 | 16.94 |
| VAR-116 | 13.39 | 18.5 | 11.92 | 22.24 | 5.24 | 12.7 | 19.31 | 18.45 | 13.25 |
| VAR-100 | 22.35 | 28.52 | 18.86 | 37.94 | 16.17 | 17.72 | 36.64 | 31.52 | 26.50 |
| VAR-80 | 14.9 | 18.21 | 15.91 | 23.83 | 8.31 | 14.79 | 12.5 | 16.89 | 7.83 |
| VAR-89 | 27.05 | 18.9 | 35.73 | 19.18 | 14 | 20.82 | 32.21 | 18.95 | 23.38 |
| VAR-102 | 4.75 | 7.98 | 1.95 | 13.5 | 3.22 | 3.79 | 0.45 | 11.36 | 7.78 |
| VAR-122 | 3.01 | 2.73 | 2.18 | 2.05 | 2.96 | 1.38 | 6.27 | 4.42 | 1.69 |
| VAR-75 | 5.22 | 6.29 | 6.92 | 12.33 | 2.92 | 3.15 | 6.76 | 5.24 | 5.94 |
| VAR-96 | 2.76 | 2.75 | 4.34 | 2.09 | 1.28 | 4.08 | 3.58 | 4.18 | 3.05 |
| VAR-67 | 9.64 | 10.69 | 12.72 | 10.68 | 5.82 | 8.54 | 12.26 | 14.46 | 6.99 |
| VAR-57 | 6.25 | 7.12 | 6.49 | 7.66 | 6.29 | 6.35 | 8.35 | 5.61 | 5.45 |
| VAR-59 | 3.25 | 3.74 | 0.53 | 4.34 | 3.73 | 2.48 | 1.71 | 6.89 | 5.25 |
| VAR-35 | 2.16 | 0.52 | 0 | 0 | 0.13 | 0 | 5.91 | 0 | 0.59 |
| VAR-110 | 0.9 | 0 | 0.76 | 0 | 0.02 | 0 | 0 | 0 | 0 |
| VAR-93 | 1.64 | 2.5 | 1.39 | 2.096 | 1.29 | 1.4 | 0.97 | 1.56 | 2.32 |
| VAR-76 | 0.23 | 1.16 | 0 | 1.18 | 1.26 | 0.21 | 0 | 1.27 | 0 |
| VAR-119 | 1.82 | 1.89 | 5.62 | 4.35 | 1.5 | 2.2 | 1.35 | 1.11 | 0.8 |
| VAR-82 | 3.33 | 3.87 | 2.46 | 3.63 | 3.61 | 3.76 | 3.02 | 4.2 | 3.25 |
| VAR-83 | 2.59 | 3.31 | 2.49 | 6.21 | 2.42 | 3.03 | 0.43 | 0.41 | 3.21 |
| VAR-108 | 0.27 | 1.72 | 0.01 | 4.88 | 0.12 | 1.17 | 0.92 | 0.09 | 0.01 |
| VAR-71 | 2.82 | 2.6 | 3.8 | 1.29 | 2.04 | 1.37 | 1.79 | 0.57 | 4.11 |
| VAR-90 | 1.69 | 1.79 | 1.25 | 0.68 | 0.74 | 0.49 | 3.7 | 1.88 | 1.22 |
| VAR-123 | 0.91 | 1.15 | 1.1 | 0 | 0.37 | 0.45 | 1.35 | 0 | 0.62 |
| VAR-44 | 0.73 | 0.41 | 0.15 | 0 | 0.42 | 0 | 1.15 | 0 | 1.9 |
| VAR-86 | 1.01 | 1.44 | 0.68 | 0.02 | 2.72 | 2.98 | 0.7 | 0.25 | 0.31 |
| VAR-81 | 0.99 | 1.92 | 0.93 | 0.79 | 0.76 | 1.34 | 0.89 | 1.46 | 0.61 |
| VAR-43 | 0.94 | 1.26 | 1.36 | 1.78 | 0.18 | 0 | 2.8 | 1.68 | 0.14 |
| VAR-41 | 0.8 | 0.71 | 0.22 | 0.15 | 0.64 | 0.82 | 1.77 | 0.02 | 0.6 |
| VAR-88 | 0.99 | 1.04 | 0.57 | 0.83 | 0.88 | 0.76 | 0.12 | 1.12 | 4.12 |
| VAR-127 | 0.82 | 0.93 | 1.77 | 0.01 | 0 | 0.84 | 1.67 | 0.08 | 0.69 |
| VAR-85 | 1.13 | 1.18 | 0.46 | 1.84 | 1.72 | 0.97 | 1.6 | 0.84 | 0.93 |
| VAR-51 | 0.38 | 0.16 | 0 | 0 | 0.54 | 0.11 | 0 | 0 | 0.63 |
| VAR-99 | 0.7 | 2.4 | 0.51 | 0.35 | 0.83 | 0.1 | 0.47 | 11.07 | 0.66 |
| VAR-101 | 0.61 | 0.6 | 1.17 | 0.72 | 0.64 | 0.34 | 0 | 0 | 0.42 |
| VAR-107 | 1.01 | 0.59 | 0.77 | 2.18 | 0.63 | 0.59 | 0.5 | 0 | 0.3 |
| VAR-5 | 0.25 | 0.39 | 0.22 | 0 | 0.13 | 0.6 | 0 | 0.75 | 0.56 |
| VAR-33 | 1 | 0.66 | 0.61 | 1.43 | 0.52 | 0.77 | 1.99 | 0.19 | 1.19 |
| VAR-3 | 0.74 | 0.33 | 1.24 | 0 | 0.55 | 0.19 | 0 | 0 | 0 |
| VAR-25 | 0.62 | 0.8 | 0.67 | 0.7 | 0.16 | 1.21 | 0.84 | 0 | 0.43 |
| VAR-49 | 0.42 | 0.37 | 0 | 0.24 | 0.2 | 0 | 0 | 0.92 | 2.45 |
| VAR-68 | 0.85 | 1.31 | 0.56 | 0.12 | 0.88 | 1.31 | 0.64 | 2.54 | 0.63 |
| VAR-40 | 0.71 | 0.88 | 1.76 | 0.64 | 0.37 | 0.72 | 0.49 | 0.97 | 0.88 |
| VAR-97 | 0.93 | 1.74 | 2.12 | 0.49 | 0.69 | 0.4 | 0 | 6.24 | 0 |
| VAR-10 | 0.95 | 0.71 | 0.65 | 1.1 | 1.32 | 0.47 | 0.61 | 0.18 | 1.57 |
| VAR-105 | 0.78 | 0.92 | 1.67 | 2 | 1.26 | 2.64 | 4.74 | 0.41 | 2.89 |
| VAR-114 | 2.49 | 1.92 | 1.67 | 2 | 1.26 | 2.64 | 4.74 | 0.41 | 2.89 |
| VAR-69 | 0.75 | 1.96 | 0.82 | 0.04 | 0.86 | 0.51 | 1.52 | 0.39 | 0.32 |
| VAR-14 | 0.97 | 0.24 | 0.37 | 0.61 | 0.97 | 0.77 | 0.49 | 0 | 0.32 |
| VAR-70 | 0.92 | 1.17 | 0.04 | 0.66 | 0 | 0.19 | 4.58 | 3.33 | 0.1 |
| VAR-55 | 1.03 | 0.28 | 0.25 | 0 | 0.36 | 0 | 2.57 | 0.01 | 0.13 |
| VAR-78 | 1.2 | 0.33 | 0.15 | 0 | 1.36 | 0.09 | 0 | 0 | 0.81 |
| VAR-50 | 0.88 | 0.53 | 0.71 | 0.65 | 0.29 | 0.91 | 0.93 | 0.27 | 0.16 |
| VAR-53 | 0.6 | 0.49 | 0.14 | 0.07 | 0.11 | 2.45 | 0 | 0 | 2.91 |
| VAR-77 | 0.57 | 0.24 | 0.01 | 0.01 | 0 | 0.25 | 0 | 0.68 | 2.98 |
| VAR-109 | 0.46 | 0.92 | 0.65 | 1.76 | 0 | 0.58 | 0 | 1.64 | 1.17 |
| VAR-112 | 0.89 | 0.67 | 0.77 | 0.03 | 0.85 | 0.54 | 0.29 | 0.23 | 1.01 |
| VAR-124 | 1 | 1.21 | 2.43 | 1.26 | 0.82 | 0.53 | 0.45 | 2.15 | 0.75 |
| VAR-46 | 0.42 | 0.44 | 1.66 | 0.36 | 0.16 | 0.87 | 0 | 1.03 | 0.3 |
| VAR-28 | 1.28 | 1.17 | 0.64 | 0.81 | 1.29 | 2.04 | 1.61 | 0.11 | 0.47 |
| VAR-17 | 0.56 | 1.46 | 0.14 | 1.02 | 0.42 | 0.77 | 0.77 | 1.26 | 0.89 |

TABLE 14-continued

Fold change in biodistribution of virus particles comprising the indicated variant capsid polypeptid, relative to the biodistribtuion of virus particles comprising WT AAV9 for brain regions. "Aggregated" is an average across all other measured areas. CBh indicated measurements from virus particles comprising genomes with the cap gene under the contol of CBh promoter. hSyn indicated virus particles comprising genomes with cap gene under the control of the hSyn promoter. Values of "0" indicated variant was not detected in the indicated samples.

| | | | | | | | | | |
|---|---|---|---|---|---|---|---|---|---|
| VAR-47 | 0.34 | 0.44 | 0.04 | 0.12 | 1.29 | 0.56 | 0 | 0.68 | 0.16 |
| VAR-62 | 0.89 | 0.93 | 1.04 | 0.29 | 1.12 | 0.77 | 0.06 | 1.31 | 0.7 |
| VAR-2 | 0.84 | 0.73 | 1.86 | 0 | 0.18 | 1.72 | 0.01 | 1.52 | 2.31 |
| VAR-30 | 0.26 | 0.14 | 0.66 | 0 | 0.08 | 0.39 | 0.37 | 0 | 0.06 |
| VAR-103 | 0.49 | 0.23 | 1.34 | 0 | 0 | 0.55 | 0 | 0 | 1.6 |
| VAR-72 | 0.37 | 0.62 | 0 | 0 | 0.4 | 0.85 | 0 | 0 | 0.41 |
| VAR-23 | 0.12 | 0.54 | 0.18 | 0.11 | 0 | 0.07 | 0.29 | 1.85 | 0 |
| VAR-95 | 3.71 | 2.86 | 4.02 | 2.1 | 2.26 | 2.94 | 2.79 | 1.4 | 3.28 |
| VAR-73 | 0.41 | 0.97 | 2.11 | 1.02 | 0 | 1.83 | 0 | 0.81 | 0.24 |
| VAR-79 | 0.21 | 1.21 | 0 | 3.89 | 0.6 | 0.05 | 0 | 0 | 0.27 |
| VAR-115 | 1.35 | 1.1 | 0.55 | 0.27 | 1.11 | 1.55 | 3.89 | 1.25 | 0.51 |
| VAR-98 | 1.14 | 1.37 | 0.28 | 1.44 | 0.64 | 1.42 | 1.33 | 2.3 | 0.27 |
| VAR-125 | 0.8 | 0.57 | 0.9 | 2.94 | 0.68 | 0.02 | 0 | 0.02 | 0.98 |
| VAR-104 | 1.79 | 0.58 | 1.94 | 0 | 1.35 | 2.41 | 2.75 | 0 | 1.8 |
| VAR-31 | 0.59 | 0.23 | 0.33 | 0.07 | 0.44 | 0.38 | 0 | 0.23 | 0.45 |
| VAR-24 | 0.87 | 0.83 | 0.38 | 0.6 | 0.64 | 0.2 | 1.86 | 1.13 | 1.06 |
| VAR-39 | 0.16 | 0.06 | 0 | 0 | 0.25 | 0 | 0 | 0.01 | 0 |
| VAR-8 | 1.12 | 0.53 | 0.53 | 1.91 | 0.11 | 0.39 | 1.04 | 0.01 | 1.46 |
| VAR-11 | 0.87 | 0.84 | 0.65 | 0.01 | 1.3 | 4.13 | 0.89 | 0 | 0.66 |
| VAR-32 | 0.99 | 0.63 | 1.19 | 0.79 | 0.54 | 0.67 | 1.48 | 0 | 0.97 |
| VAR-6 | 1.37 | 0.83 | 2.61 | 0.31 | 0.65 | 0.75 | 1.28 | 0.29 | 1.87 |
| VAR-121 | 0.97 | 0.78 | 0.78 | 0.8 | 0.65 | 0.77 | 1.75 | 0.76 | 0.26 |
| VAR-9 | 1 | 0.26 | 1.28 | 0.1 | 2.02 | 0.17 | 0.06 | 0.07 | 0.6 |
| VAR-65 | 0.96 | 0.55 | 0.37 | 1.29 | 0.17 | 0.48 | 3.63 | 0.23 | 0.41 |
| VAR-21 | 1.28 | 0.72 | 0.32 | 0.03 | 1.67 | 0.15 | 2.93 | 2.15 | 0.57 |
| VAR-58 | 0.76 | 0.89 | 0.8 | 0.56 | 0.88 | 1.03 | 0.45 | 0.39 | 1.58 |
| VAR-34 | 0.52 | 1.24 | 0.5 | 3.57 | 0.77 | 0.61 | 0.12 | 0.93 | 1.23 |
| VAR-120 | 1.01 | 0.85 | 1.35 | 0.87 | 0.53 | 0.45 | 1.27 | 0.87 | 1.39 |
| VAR-118 | 0.73 | 1.31 | 0.3 | 1.23 | 0.47 | 2.11 | 0.39 | 1.31 | 0.01 |
| VAR-27 | 0.59 | 0.55 | 0.17 | 0.18 | 1.38 | 0.37 | 0.77 | 0.22 | 0.55 |
| VAR-29 | 0.45 | 0.47 | 0.61 | 0.85 | 0.58 | 0.5 | 0.32 | 0.11 | 0.34 |
| VAR-4 | 0.34 | 0.67 | 0 | 0.01 | 0.31 | 0.05 | 0 | 0.8 | 1.22 |
| VAR-7 | 1.69 | 1.12 | 3.28 | 2.53 | 1.95 | 0.24 | 1.88 | 0.13 | 0.15 |
| VAR-12 | 1.12 | 0.81 | 0.43 | 0.85 | 2.58 | 0.47 | 0.01 | 0.83 | 1.15 |
| VAR-13 | 0.55 | 0.07 | 0.46 | 0 | 0.32 | 0 | 0.49 | 0 | 0.98 |
| VAR-15 | 1.58 | 2.11 | 0.99 | 6.46 | 1.62 | 1.69 | 1.75 | 0.47 | 1.73 |
| VAR-16 | 0.97 | 0.96 | 0.61 | 0.66 | 3 | 0 | 1.41 | 3.2 | 0.1 |
| VAR-18 | 1.09 | 0.19 | 0 | 0 | 5.84 | 0.36 | 0 | 0 | 0.01 |
| VAR-19 | 1.07 | 0.98 | 1.61 | 0 | 1.87 | 1.59 | 0 | 0 | 0 |
| VAR-20 | 1.77 | 1.2 | 0.85 | 3.09 | 1.76 | 0.58 | 0.81 | 0.55 | 0.97 |
| VAR-22 | 0.63 | 1.3 | 0 | 2.65 | 0.34 | 0.22 | 1.66 | 0 | 0.98 |
| VAR-26 | 1.1 | 1.3 | 1.73 | 1.94 | 0.9 | 0.63 | 0 | 0 | 0.39 |
| VAR-36 | 0.16 | 0.24 | 0 | 0 | 0 | 0 | 0.02 | 0 | 0.93 |
| VAR-37 | 0.85 | 1.8 | 0 | 0.26 | 1.19 | 0.77 | 0.81 | 0 | 0.01 |
| VAR-38 | 0.49 | 0.13 | 0.14 | 0 | 1.2 | 0.18 | 0.61 | 0 | 0 |
| VAR-42 | 0.77 | 0.99 | 0.47 | 3.37 | 0.98 | 0.69 | 0.35 | 0 | 0.86 |
| VAR-45 | 0.25 | 0.62 | 0 | 0.36 | 0.04 | 0.11 | 0 | 0 | 0.34 |
| VAR-48 | 1.15 | 1.35 | 0.24 | 1.29 | 1.36 | 1.03 | 1.35 | 0.66 | 1.1 |
| VAR-52 | 0.18 | 0.44 | 0.03 | 0.9 | 0.17 | 0.08 | 0 | 0 | 0.8 |
| VAR-56 | 1.04 | 1.46 | 1.57 | 0.53 | 0.36 | 0.94 | 0.01 | 3.87 | 1.32 |
| VAR-60 | 1.5 | 0.73 | 3.11 | 0.08 | 0 | 3.48 | 4.86 | 0.01 | 0.05 |
| VAR-63 | 3.19 | 1.18 | 2.62 | 0.71 | 2.92 | 0.59 | 8.08 | 2.76 | 0.68 |
| VAR-64 | 0.55 | 0.18 | 0 | 0 | 0 | 0 | 0 | 0 | 0 |
| VAR-66 | 0.37 | 1.03 | 0.8 | 0.02 | 0.88 | 0.05 | 0 | 3.97 | 0.33 |
| VAR-84 | 0.56 | 1.62 | 1.9 | 0 | 0.19 | 0.04 | 0 | 0 | 0.83 |
| VAR-91 | 0.23 | 0 | 0.56 | 0 | 0 | 0 | 0 | 0 | 0.54 |
| VAR-92 | 0.3 | 1.41 | 0.54 | 3.65 | 0.84 | 4.05 | 0 | 0 | 0.05 |
| VAR-94 | 1.05 | 0.29 | 0.44 | 1.19 | 4.27 | 0 | 0 | 0.11 | 0.11 |
| VAR-106 | 0.47 | 1.13 | 0 | 0.19 | 0.99 | 0.87 | 0.8 | 2.15 | 0.53 |
| VAR-111 | 1.37 | 0.47 | 0 | 0.54 | 0 | 0.57 | 4.69 | 0 | 0.88 |
| VAR-113 | 1.4 | 1.05 | 0 | 1.68 | 0.43 | 1 | 0 | 0 | 6.18 |
| VAR-117 | 1.62 | 0.82 | 1.35 | 1.07 | 3.85 | 1.05 | 2.5 | 0.06 | 0.2 |
| VAR-126 | 0.87 | 0.97 | 0 | 0.1 | 2.4 | 3.67 | 0 | 0.33 | 2 |

TABLE 14-continued

Fold change in biodistribution of virus particles comprising the indicated variant capsid polypeptid, relative to the biodistribtuion of virus particles comprising WT AAV9 for brain regions. "Aggregated" is an average across all other measured areas. CBh indicated measurements from virus particles comprising genomes with the cap gene under the contol of CBh promoter. hSyn indicated virus particles comprising genomes with cap gene under the control of the hSyn promoter. Values of "0" indicated variant was not detected in the indicated samples.

| Variant Name | organ | | | | | | |
|---|---|---|---|---|---|---|---|
| | brain | brain | brain | brain | brain | brain | brain |
| | tissue | | | | | | |
| | forebrain | hippocampus | hippocampus | midbrain | midbrain | temporal_cortex | temporal_cortex |
| | promoter | | | | | | |
| | hSyn | CBh | hSyn | CBh | hSyn | CBh | hSyn |
| VAR-1 | 30.34 | 25.39 | 23.62 | 22.52 | 30.62 | 23.08 | 25.87 |
| VAR-54 | 35.06 | 47.9 | 21.3 | 50.73 | 47.03 | 37.04 | 35.02 |
| VAR-74 | 13.48 | 26.34 | 8.29 | 10.11 | 15.58 | 18.98 | 12.4 |
| VAR-87 | 35.51 | 67.62 | 27.49 | 16.53 | 33.56 | 24.58 | 26.22 |
| VAR-61 | 12.65 | 13.65 | 13.48 | 11.63 | 18.46 | 9.54 | 16.8 |
| VAR-116 | 17.11 | 2.42 | 10.82 | 14.41 | 24.2 | 19.12 | 21.38 |
| VAR-100 | 24.09 | 30.57 | 24.09 | 20.27 | 49.99 | 11.93 | 21.08 |
| VAR-80 | 13.81 | 27.7 | 19.72 | 26 | 26.44 | 21.71 | 17.08 |
| VAR-89 | 23.91 | 43.42 | 18.9 | 23.03 | 11.71 | 26.64 | 14.95 |
| VAR-102 | 5.59 | 0 | 0 | 10.46 | 4.19 | 10.03 | 8 |
| VAR-122 | 2.91 | 1.1 | 0.68 | 3.05 | 4.22 | 1.95 | 2.51 |
| VAR-75 | 8.63 | 3.41 | 0 | 6.69 | 5.89 | 3.38 | 3.9 |
| VAR-96 | 0.96 | 2.76 | 2.41 | 4.26 | 1.36 | 0.95 | 2.76 |
| VAR-67 | 7.15 | 18.4 | 14.52 | 15.86 | 13.05 | 5.16 | 9.16 |
| VAR-57 | 6.65 | 3.64 | 4.27 | 7.13 | 13.28 | 4.67 | 7.85 |
| VAR-59 | 2.15 | 1.49 | 0.18 | 9.12 | 5.81 | 3.47 | 1.99 |
| VAR-35 | 3.35 | 20.05 | 0 | 0 | 0 | 0 | 0 |
| VAR-110 | 0 | 10.53 | 0 | 2.78 | 0 | 0.52 | 0 |
| VAR-93 | 1.35 | 1.4 | 5.71 | 3.61 | 8.75 | 1.64 | 2.63 |
| VAR-76 | 0.04 | 0 | 0 | 0 | 0 | 0 | 3.89 |
| VAR-119 | 0.96 | 0.11 | 2.03 | 0.54 | 0.52 | 0.71 | 1.23 |
| VAR-82 | 1.94 | 6.53 | 3.03 | 2.24 | 6.84 | 3.97 | 4.59 |
| VAR-83 | 3.7 | 4.94 | 0.61 | 4.74 | 8.42 | 3.2 | 2.27 |
| VAR-108 | 2.48 | 1.16 | 3.8 | 0.04 | 0.02 | 0.08 | 0.17 |
| VAR-71 | 3.74 | 1.96 | 7.78 | 3.99 | 5.95 | 2.35 | 3.76 |
| VAR-90 | 1.88 | 3.5 | 9.98 | 0.83 | 0.32 | 1.22 | 2.22 |
| VAR-123 | 0.9 | 0.01 | 12.37 | 0.24 | 1.14 | 1.01 | 1.4 |
| VAR-44 | 2.25 | 0 | 0 | 0.4 | 0 | 0.43 | 0.39 |
| VAR-86 | 4.96 | 0.14 | 0 | 2.18 | 0 | 0.32 | 0.74 |
| VAR-81 | 2.4 | 3.32 | 0.01 | 1.17 | 8.14 | 1.06 | 1.81 |
| VAR-43 | 0.82 | 0 | 3.81 | 0.35 | 2.22 | 0.42 | 0.58 |
| VAR-41 | 1.17 | 0 | 1.58 | 0.48 | 1.26 | 0.99 | 1.17 |
| VAR-88 | 0.78 | 0 | 0.21 | 0.2 | 1.21 | 0.26 | 1.87 |
| VAR-127 | 2.11 | 0 | 0 | 0 | 5.73 | 0.4 | 0.25 |
| VAR-85 | 1.62 | 0.75 | 0 | 1.26 | 0.01 | 0.93 | 1.55 |
| VAR-51 | 0.85 | 1.96 | 0 | 0 | 0 | 0.43 | 0.05 |
| VAR-99 | 0.04 | 0.75 | 0 | 1.02 | 0 | 0.93 | 0 |
| VAR-101 | 0.84 | 1.16 | 0 | 0.89 | 1.13 | 0.58 | 1.23 |
| VAR-107 | 0.13 | 7.69 | 0 | 1.76 | 0 | 0.81 | 0.4 |
| VAR-5 | 0 | 1.44 | 0.42 | 0.24 | 0 | 0.11 | 0.69 |
| VAR-33 | 0.71 | 0.37 | 0 | 0.6 | 0.75 | 0.97 | 0.41 |
| VAR-3 | 0.02 | 0 | 0 | 2.7 | 3.95 | 1.3 | 0.07 |
| VAR-25 | 2.19 | 1.79 | 0.02 | 0.59 | 0 | 0.65 | 0.79 |
| VAR-49 | 0.1 | 0 | 0 | 0 | 0 | 0 | 0.74 |
| VAR-68 | 2.02 | 0.78 | 1.03 | 1.27 | 0.83 | 1.39 | 0.71 |
| VAR-40 | 1.95 | 0 | 0 | 1.42 | 0 | 0 | 0.85 |
| VAR-97 | 0.1 | 5.92 | 2.03 | 1.14 | 0.94 | 0.49 | 0.55 |
| VAR-10 | 0.77 | 0 | 0.62 | 0.39 | 0 | 1.16 | 1.5 |
| VAR-105 | 3.26 | 0.82 | 2.11 | 2.29 | 2.54 | 2.25 | 1.45 |
| VAR-114 | 3.26 | 0.82 | 2.11 | 2.29 | 2.54 | 2.25 | 1.45 |
| VAR-69 | 4.16 | 1.58 | 0 | 0.01 | 12.62 | 0.18 | 1.48 |
| VAR-14 | 0.02 | 11.5 | 0 | 0 | 0 | 0.38 | 0 |
| VAR-70 | 0.63 | 0 | 0 | 0 | 0.55 | 0.09 | 1.1 |
| VAR-55 | 0.16 | 3.55 | 0 | 0.6 | 1.69 | 1.15 | 0.81 |
| VAR-78 | 0.9 | 6.2 | 0 | 2.29 | 0.92 | 2.03 | 0.65 |
| VAR-50 | 0.56 | 0 | 0.08 | 1.5 | 0 | 2.22 | 0.7 |
| VAR-53 | 0.44 | 0 | 0 | 0.2 | 0 | 0.47 | 0.04 |
| VAR-77 | 0.31 | 0 | 0.07 | 0.6 | 0.03 | 0.32 | 0.01 |
| VAR-109 | 0.09 | 0.77 | 0 | 0 | 0.75 | 0.74 | 0.53 |
| VAR-112 | 0.68 | 0 | 5.5 | 1.21 | 0 | 1.68 | 0.86 |
| VAR-124 | 1.38 | 2.7 | 1.39 | 0.46 | 0 | 0.37 | 0.93 |
| VAR-46 | 0.11 | 0 | 0 | 0 | 0 | 0.27 | 0 |
| VAR-28 | 1.71 | 4.99 | 1.42 | 2.39 | 1.77 | 0.88 | 1.2 |
| VAR-17 | 4.01 | 0 | 0 | 0.43 | 0.98 | 0.8 | 1.19 |

TABLE 14-continued

Fold change in biodistribution of virus particles comprising the indicated variant capsid polypeptid, relative to the biodistribtuion of virus particles comprising WT AAV9 for brain regions. "Aggregated" is an average across all other measured areas. CBh indicated measurements from virus particles comprising genomes with the cap gene under the contol of CBh promoter. hSyn indicated virus particles comprising genomes with cap gene under the control of the hSyn promoter. Values of "0" indicated variant was not detected in the indicated samples.

| | | | | | | | |
|---|---|---|---|---|---|---|---|
| VAR-47 | 0.34 | 0 | 0 | 0.59 | 0.02 | 0.18 | 0.8 |
| VAR-62 | 0.65 | 1.67 | 0 | 0.67 | 0.42 | 1.44 | 2.09 |
| VAR-2 | 0.77 | 0 | 0 | 0.01 | 0.17 | 0.65 | 0 |
| VAR-30 | 0.31 | 0 | 0 | 0 | 0 | 0.27 | 0.18 |
| VAR-103 | 0 | 0 | 0 | 0 | 0.16 | 0.01 | 0.8 |
| VAR-72 | 1.12 | 0 | 0 | 0.02 | 0 | 1.34 | 1.87 |
| VAR-23 | 0.46 | 0 | 0 | 0.17 | 0.19 | 0.14 | 0.18 |
| VAR-95 | 5.18 | 17 | 1.81 | 4.39 | 6.21 | 2.6 | 2.15 |
| VAR-73 | 0.44 | 0 | 0 | 0 | 1.16 | 0 | 0.94 |
| VAR-79 | 0 | 0 | 0 | 0 | 0 | 0.35 | 2.96 |
| VAR-115 | 0.17 | 0.44 | 6.4 | 0.01 | 0.12 | 1.15 | 1.02 |
| VAR-98 | 0.5 | 8.06 | 1.86 | 3.56 | 0.35 | 0.3 | 1.13 |
| VAR-125 | 0.1 | 0 | 0 | 3.96 | 0 | 0.47 | 0 |
| VAR-104 | 0.7 | 1.7 | 0 | 2.81 | 0.17 | 0.64 | 0.36 |
| VAR-31 | 0.61 | 0.06 | 0 | 0.01 | 0 | 2.17 | 0.07 |
| VAR-24 | 1.39 | 0 | 1.73 | 0.28 | 0 | 0.81 | 0.88 |
| VAR-39 | 0.02 | 0 | 0 | 0 | 0.3 | 0.66 | 0.19 |
| VAR-8 | 0.28 | 8.29 | 0 | 2.73 | 0.11 | 0.05 | 0.33 |
| VAR-11 | 0.46 | 0.65 | 0 | 1.32 | 0 | 0.7 | 0.52 |
| VAR-32 | 1.06 | 0.14 | 0.05 | 0.33 | 0.14 | 1.22 | 1.2 |
| VAR-6 | 2.21 | 1.75 | 1.47 | 0.02 | 0.84 | 0.96 | 0.66 |
| VAR-121 | 1.41 | 0.74 | 0.96 | 1.55 | 0.03 | 1.06 | 0.51 |
| VAR-9 | 0.45 | 1.9 | 1.84 | 1.99 | 0.01 | 0.47 | 0.19 |
| VAR-65 | 0.23 | 0.02 | 1.21 | 0.3 | 0.75 | 0.42 | 0.22 |
| VAR-21 | 0.33 | 0 | 0.29 | 2.18 | 0.08 | 0.7 | 1.03 |
| VAR-58 | 0.18 | 0.37 | 3.98 | 0.17 | 0.24 | 0.56 | 1.75 |
| VAR-34 | 0.43 | 0 | 0.41 | 0 | 2.28 | 0.42 | 0.17 |
| VAR-120 | 1.25 | 0.49 | 1 | 1.44 | 0.21 | 0.51 | 1.08 |
| VAR-118 | 0.84 | 0 | 0 | 4.41 | 0.01 | 1.16 | 2.02 |
| VAR-27 | 0.58 | 0.01 | 2.82 | 0.22 | 0 | 0.37 | 1.08 |
| VAR-29 | 0.24 | 0.88 | 1.54 | 0.29 | 0.36 | 0.38 | 0.4 |
| VAR-4 | 0.32 | 0 | 0 | 0 | 1.58 | 0.51 | 2.02 |
| VAR-7 | 3.39 | 0 | 0 | 3.42 | 0.08 | 0.7 | 0.35 |
| VAR-12 | 0.65 | 0 | 0 | 1.58 | 0.9 | 1.61 | 1.46 |
| VAR-13 | 0.03 | 0 | 0 | 1.32 | 0 | 0.39 | 0.4 |
| VAR-15 | 0.28 | 0 | 0 | 6.08 | 0.24 | 0.42 | 2.88 |
| VAR-16 | 0.27 | 0 | 0 | 0 | 0 | 0.18 | 0.76 |
| VAR-18 | 0.54 | 0 | 0 | 0 | 0 | 0.25 | 0.31 |
| VAR-19 | 0 | 0 | 14.06 | 0 | 0 | 2.56 | 0 |
| VAR-20 | 0.02 | 5.75 | 0 | 0.3 | 4.91 | 4.05 | 0.36 |
| VAR-22 | 0.58 | 0 | 0 | 0.97 | 4.13 | 0.14 | 2.35 |
| VAR-26 | 0.01 | 0 | 10.33 | 4.51 | 0 | 1.39 | 1.86 |
| VAR-36 | 1.58 | 0 | 0 | 0 | 0 | 0.04 | 0 |
| VAR-37 | 7.43 | 0 | 8.3 | 2.59 | 0 | 1.68 | 0.3 |
| VAR-38 | 0.64 | 2.75 | 0 | 0 | 0 | 0.05 | 0 |
| VAR-42 | 0.64 | 5.87 | 1.77 | 0 | 0.06 | 0.24 | 0.38 |
| VAR-45 | 1.99 | 0 | 3.69 | 0 | 0 | 1.08 | 0.22 |
| VAR-48 | 3.48 | 2.37 | 0.03 | 1.7 | 0.49 | 1.15 | 1.41 |
| VAR-52 | 1.54 | 0 | 0 | 0 | 0 | 0.11 | 0.12 |
| VAR-56 | 0.62 | 0.02 | 3.25 | 2.95 | 0.01 | 1.58 | 0.84 |
| VAR-60 | 0.23 | 0 | 0 | 0 | 0 | 0.01 | 0.65 |
| VAR-63 | 0.83 | 0 | 0.15 | 3.47 | 1.22 | 1.6 | 0.92 |
| VAR-64 | 0 | 0 | 0 | 7.66 | 0 | 0 | 1.09 |
| VAR-66 | 0.29 | 0 | 0 | 0 | 1.42 | 0.08 | 0.26 |
| VAR-84 | 3.16 | 0 | 18.49 | 0.66 | 0 | 0.07 | 1.09 |
| VAR-91 | 0 | 0.03 | 0 | 0 | 0 | 0.26 | 0 |
| VAR-92 | 0.44 | 0 | 0 | 0.48 | 0 | 0.04 | 0 |
| VAR-94 | 0 | 0 | 0 | 0 | 0 | 1.04 | 0.27 |
| VAR-106 | 1.08 | 0 | 0 | 0 | 1.07 | 0.33 | 1.58 |
| VAR-111 | 0.35 | 0 | 0 | 1.13 | 0.01 | 1.37 | 1.34 |
| VAR-113 | 2.23 | 0.05 | 2.09 | 0 | 0.45 | 1.98 | 0.56 |
| VAR-117 | 1.31 | 0 | 0 | 0 | 1.45 | 1 | 0.83 |
| VAR-126 | 1.71 | 0 | 0 | 0 | 0 | 0.74 | 0.09 |

TABLE 15

Fold change in biodistribution of virus particles comprising the indicated variant capsid polypeptide, relative to the biodistribution of virus particles comprising WT AAV9 for non-brain regions. CBh indicated measurements from virus particles comprising genomes with the cap gene under the control of the CBh promoter. hSyn indicates virus particles comprsing genomes with the cap gene under the control of the hSyn promoter. Values of "0" indicate variant was not detected in the indicated sample.

| | organ | | | | |
|---|---|---|---|---|---|
| | dorsal_root_ganglion | dorsal_root_ganglion tissue | liver | liver | skeletal_muscle |
| Variant Name | aggregated CBh | aggregated promoter hSyn | aggregated CBh | aggregated hSyn | aggregated CBh |
| VAR-1 | 5.37 | 8.11 | 0.32 | 0.3 | 4.22 |
| VAR-54 | 3.94 | 6.71 | 0.37 | 0.32 | 5.07 |
| VAR-74 | 10.37 | 10.08 | 0.27 | 0.26 | 3.33 |
| VAR-87 | 5.85 | 2.93 | 0.68 | 0.6 | 3.57 |
| VAR-61 | 6.39 | 8.33 | 0.42 | 0.31 | 4.57 |
| VAR-116 | 3.14 | 2.36 | 0.65 | 0.69 | 2.24 |
| VAR-100 | 1.25 | 1.31 | 0.68 | 0.77 | 2.72 |
| VAR-80 | 3.83 | 13.9 | 0.44 | 0.39 | 2.56 |
| VAR-89 | 3.4 | 1.15 | 0.71 | 0.69 | 1.88 |
| VAR-102 | 27.04 | 3.8 | 0.12 | 0.15 | 1.98 |
| VAR-122 | 1.52 | 0.71 | 0.33 | 0.35 | 0.5 |
| VAR-75 | 1.3 | 0.12 | 0.51 | 0.46 | 0.79 |
| VAR-96 | 1.83 | 0.6 | 0.23 | 0.23 | 0.88 |
| VAR-67 | 1.01 | 3.17 | 0.71 | 0.71 | 1.73 |
| VAR-57 | 2.4 | 1.71 | 0.61 | 0.61 | 1.08 |
| VAR-59 | 1.73 | 1.6 | 0.49 | 0.5 | 0.54 |
| VAR-35 | 0.08 | 0 | 0.23 | 0.37 | 0 |
| VAR-110 | 1.98 | 0 | 0.64 | 0.67 | 1.74 |
| VAR-93 | 0.95 | 1.45 | 0.89 | 0.78 | 1.37 |
| VAR-76 | 0.06 | 2.24 | 0.63 | 0.78 | 0.4 |
| VAR-119 | 1.39 | 0.83 | 0.83 | 0.79 | 1.15 |
| VAR-82 | 1.35 | 0.16 | 0.84 | 0.83 | 0.34 |
| VAR-83 | 0.37 | 0.81 | 0.95 | 0.97 | 2.71 |
| VAR-108 | 0.17 | 0.06 | 0.34 | 0.45 | 0 |
| VAR-71 | 0.62 | 1.01 | 0.93 | 1.02 | 1.07 |
| VAR-90 | 0.59 | 0.8 | 0.65 | 0.76 | 1.31 |
| VAR-123 | 0.1 | 1.09 | 0.65 | 0.63 | 0.74 |
| VAR-44 | 0.38 | 0 | 1 | 1.11 | 0.34 |
| VAR-86 | 2.4 | 0.99 | 1.01 | 1.06 | 2.3 |
| VAR-81 | 0.73 | 1.76 | 0.73 | 0.67 | 0.75 |
| VAR-43 | 0 | 1.03 | 0.73 | 0.86 | 2.04 |
| VAR-41 | 0.75 | 0.14 | 0.61 | 0.67 | 0.74 |
| VAR-88 | 0.79 | 1.11 | 0.38 | 0.35 | 0.73 |
| VAR-127 | 0.06 | 0 | 0.75 | 0.78 | 0 |
| VAR-85 | 0.42 | 0.71 | 0.92 | 1.04 | 1.29 |
| VAR-51 | 0.24 | 2.24 | 0.84 | 0.78 | 1.29 |
| VAR-99 | 2.53 | 0.34 | 0.62 | 0.73 | 1.2 |
| VAR-101 | 1.07 | 0.09 | 0.98 | 0.91 | 0.39 |
| VAR-107 | 0.6 | 0.43 | 0.45 | 0.45 | 0.74 |
| VAR-5 | 1.28 | 0.13 | 0.32 | 0.36 | 0.52 |
| VAR-33 | 1.09 | 0.7 | 0.5 | 0.44 | 0.63 |
| VAR-3 | 2.26 | 0.86 | 0.96 | 1.03 | 1.06 |
| VAR-25 | 0.43 | 0.45 | 0.36 | 0.39 | 2.38 |
| VAR-49 | 0 | 0.26 | 0.24 | 0.22 | 0 |
| VAR-68 | 0.94 | 0.29 | 1.03 | 0.94 | 1.3 |
| VAR-40 | 0.23 | 1.21 | 0.81 | 0.66 | 1.54 |
| VAR-97 | 0 | 1.02 | 0.79 | 0.88 | 2.17 |
| VAR-10 | 1.52 | 0.99 | 0.88 | 0.96 | 0.55 |
| VAR-105 | 2.94 | 0.75 | 0.43 | 0.44 | 0.46 |
| VAR-114 | 1.49 | 1.3 | 0.85 | 0.73 | 1.02 |
| VAR-69 | 0.84 | 1.77 | 0.79 | 0.89 | 1.53 |
| VAR-14 | 0.09 | 1.3 | 0.97 | 0.99 | 0.01 |
| VAR-70 | 0.5 | 0.31 | 1.07 | 1.03 | 0.23 |
| VAR-55 | 0.53 | 0.1 | 0.91 | 0.73 | 0.39 |
| VAR-78 | 1.27 | 0.7 | 1.17 | 1.06 | 0 |
| VAR-50 | 0.66 | 1.77 | 0.54 | 0.53 | 1.67 |
| VAR-53 | 0.79 | 0.83 | 0.6 | 0.57 | 1.24 |
| VAR-77 | 0.48 | 0.54 | 0.6 | 0.52 | 1.7 |
| VAR-109 | 0.25 | 0.04 | 0.67 | 0.72 | 0.54 |
| VAR-112 | 1.36 | 1.46 | 1.01 | 0.96 | 2.2 |
| VAR-124 | 0.46 | 0.19 | 0.79 | 0.86 | 0.96 |
| VAR-46 | 0.42 | 0 | 0.63 | 0.6 | 3.5 |
| VAR-28 | 0.31 | 0.45 | 0.53 | 0.49 | 0.33 |

TABLE 15-continued

Fold change in biodistribution of virus particles comprising the indicated variant capsid polypeptide, relative to the biodistribution of virus particles comprising WT AAV9 for non-brain regions. CBh indicated measurements from virus particles comprising genomes with the cap gene under the control of the CBh promoter. hSyn indicates virus particles comprsing genomes with the cap gene under the control of the hSyn promoter. Values of "0" indicate variant was not detected in the indicated sample.

| | | | | | |
|---|---|---|---|---|---|
| VAR-17 | 0.36 | 0.15 | 0.89 | 0.97 | 0.59 |
| VAR-47 | 1.35 | 0.3 | 0.59 | 0.54 | 0.92 |
| VAR-62 | 2.24 | 0.99 | 0.59 | 0.55 | 0.75 |
| VAR-2 | 0.47 | 1.53 | 0.95 | 0.85 | 0.45 |
| VAR-30 | 0.43 | 0.23 | 0.66 | 0.63 | 0 |
| VAR-103 | 0.29 | 18.77 | 0.77 | 0.78 | 0.72 |
| VAR-72 | 0 | 0.18 | 0.27 | 0.24 | 0.42 |
| VAR-23 | 0.99 | 0.38 | 0.22 | 0.17 | 0.81 |
| VAR-95 | 2.77 | 1.43 | 0.66 | 0.64 | 1.6 |
| VAR-73 | 1.8 | 1.88 | 1.23 | 0.79 | 3.95 |
| VAR-79 | 0.76 | 2.01 | 0.89 | 1 | 0.94 |
| VAR-115 | 0.93 | 1.51 | 0.73 | 0.71 | 0 |
| VAR-98 | 2.7 | 2.31 | 0.87 | 0.89 | 0.98 |
| VAR-125 | 0.74 | 3.48 | 1.04 | 0.89 | 0.66 |
| VAR-104 | 1.32 | 1.07 | 0.85 | 0.69 | 2.83 |
| VAR-31 | 0.54 | 0.17 | 0.37 | 0.33 | 0.11 |
| VAR-24 | 1.56 | 1.51 | 0.85 | 0.95 | 0.99 |
| VAR-39 | 0 | 0.34 | 0.19 | 0.21 | 1.66 |
| VAR-8 | 1.72 | 0.69 | 0.72 | 0.68 | 0.93 |
| VAR-11 | 2.01 | 0.73 | 0.78 | 0.81 | 0 |
| VAR-32 | 0.28 | 0.11 | 0.75 | 0.81 | 1.05 |
| VAR-6 | 0.88 | 0.53 | 0.89 | 0.93 | 1.06 |
| VAR-121 | 0.61 | 0.21 | 0.91 | 0.86 | 1.04 |
| VAR-9 | 0.54 | 1.19 | 1.23 | 1.01 | 0.95 |
| VAR-65 | 0.93 | 0.74 | 0.89 | 0.89 | 0.72 |
| VAR-21 | 0.8 | 0.48 | 0.63 | 0.6 | 0.31 |
| VAR-58 | 0.7 | 0.28 | 1.07 | 1.1 | 1.04 |
| VAR-34 | 1.14 | 0.3 | 0.31 | 0.32 | 0.87 |
| VAR-120 | 0.4 | 1 | 1.05 | 0.93 | 0.59 |
| VAR-118 | 0.98 | 0.17 | 0.99 | 1.07 | 0.03 |
| VAR-27 | 0.22 | 0.43 | 0.78 | 0.75 | 0.42 |
| VAR-29 | 1.04 | 0.6 | 0.73 | 0.88 | 0.71 |
| VAR-4 | 0.16 | 0.8 | 0.89 | 0.94 | 0.39 |
| VAR-7 | 0.62 | 0.04 | 0.78 | 0.99 | 1.08 |
| VAR-12 | 0.23 | 0.18 | 0.9 | 1.06 | 1.53 |
| VAR-13 | 0.74 | 4.06 | 0.77 | 0.92 | 0.16 |
| VAR-15 | 1.05 | 0.91 | 0.97 | 0.88 | 2.52 |
| VAR-16 | 0.14 | 0 | 0.9 | 0.78 | 1.29 |
| VAR-18 | 0.02 | 0.26 | 0.85 | 0.74 | 0.68 |
| VAR-19 | 1.41 | 0 | 0.64 | 0.83 | 0.71 |
| VAR-20 | 0 | 1.67 | 0.8 | 0.88 | 1.31 |
| VAR-22 | 1.66 | 5.74 | 0.88 | 0.85 | 0.08 |
| VAR-26 | 0.46 | 0.8 | 0.83 | 1.01 | 1.28 |
| VAR-36 | 0.67 | 0 | 0.17 | 0.17 | 0.02 |
| VAR-37 | 1.27 | 0.01 | 0.55 | 0.51 | 0.23 |
| VAR-38 | 0.18 | 0 | 0.44 | 0.42 | 1.3 |
| VAR-42 | 0.72 | 0.84 | 0.73 | 0.78 | 1.53 |
| VAR-45 | 1.87 | 0.09 | 0.25 | 0.3 | 0.83 |
| VAR-48 | 0.32 | 0.65 | 0.68 | 0.55 | 0.96 |
| VAR-52 | 0.94 | 0 | 0.64 | 0.79 | 0.38 |
| VAR-56 | 1.04 | 0.76 | 0.75 | 0.8 | 0.97 |
| VAR-60 | 0.04 | 1.66 | 0.78 | 0.63 | 1.7 |
| VAR-63 | 0.88 | 0.48 | 0.59 | 0.51 | 0.2 |
| VAR-64 | 0 | 0 | 0.68 | 0.77 | 0 |
| VAR-66 | 1 | 2.79 | 0.5 | 0.44 | 2.14 |
| VAR-84 | 0.38 | 5.7 | 0.33 | 0.39 | 0.01 |
| VAR-91 | 0.3 | 0.62 | 0.17 | 0.16 | 0 |
| VAR-92 | 0.6 | 3.53 | 0.4 | 0.53 | 0.21 |
| VAR-94 | 0.9 | 1.29 | 0.79 | 0.76 | 4.55 |
| VAR-106 | 0.06 | 0.22 | 0.43 | 0.36 | 0.25 |
| VAR-111 | 0 | 0 | 0.29 | 0.221 | 1.66 |
| VAR-113 | 0.73 | 1.98 | 0.75 | 0.76 | 0.07 |
| VAR-117 | 0.69 | 0.46 | 0.91 | 0.92 | 0.31 |
| VAR-126 | 1.29 | 0 | 0.71 | 0.76 | 1.08 |

TABLE 15-continued

Fold change in biodistribution of virus particles comprising the indicated variant capsid polypeptide, relative to the biodistribution of virus particles comprising WT AAV9 for non-brain regions. CBh indicated measurements from virus particles comprising genomes with the cap gene under the control of the CBh promoter. hSyn indicates virus particles comprsing genomes with the cap gene under the control of the hSyn promoter. Values of "0" indicate variant was not detected in the indicated sample.

| | organ | | | | |
|---|---|---|---|---|---|
| | skeletal_muscle | spinal_cord | spinal_cord tissue | spleen | spleen |
| Variant Name | aggregated | aggregated | aggregated prometer | aggregated | aggregated |
| | hSyn | CBh | hSyn | CBh | hSyn |
| VAR-1 | 4.62 | 18.01 | 11.81 | 0.85 | 0.9 |
| VAR-54 | 5.37 | 22.73 | 21.66 | 0.7 | 0.85 |
| VAR-74 | 5.22 | 16.29 | 15.2 | 0.76 | 0.73 |
| VAR-87 | 2.9 | 24.18 | 18.85 | 0.84 | 0.65 |
| VAR-61 | 1.14 | 9.96 | 1.39 | 0.72 | 0.56 |
| VAR-116 | 2.51 | 11.11 | 5.18 | 1.22 | 1.09 |
| VAR-100 | 2.42 | 14.08 | 8.55 | 0.56 | 1.19 |
| VAR-80 | 4.26 | 20.78 | 15.31 | 0.81 | 0.67 |
| VAR-89 | 5.63 | 11.21 | 19.88 | 1.68 | 0.86 |
| VAR-102 | 1.11 | 17.77 | 4.6 | 0.32 | 0.11 |
| VAR-122 | 0.89 | 4.98 | 1.14 | 0.74 | 1.01 |
| VAR-75 | 1.7 | 5.53 | 0.92 | 1.13 | 1.07 |
| VAR-96 | 0.8 | 2.8 | 0.99 | 0.71 | 0.6 |
| VAR-67 | 2.16 | 4.44 | 7.29 | 0.94 | 0.86 |
| VAR-57 | 2.41 | 2.99 | 3.31 | 0.46 | 0.66 |
| VAR-59 | 1.99 | 0.88 | 3.25 | 0.51 | 0.8 |
| VAR-35 | 0 | 0 | 0 | 0.44 | 1.11 |
| VAR-110 | 2.05 | 0.09 | 0.31 | 1.14 | 0.77 |
| VAR-93 | 0.46 | 0.52 | 0.48 | 0.81 | 0.73 |
| VAR-76 | 0.05 | 0.52 | 0.26 | 0.97 | 1.14 |
| VAR-119 | 0.78 | 0.93 | 1.3 | 0.59 | 0.6 |
| VAR-82 | 1.35 | 0.65 | 0.55 | 0.73 | 1.05 |
| VAR-83 | 1.87 | 1.19 | 0.55 | 0.8 | 0.84 |
| VAR-108 | 0.49 | 11.04 | 0.9 | 1.52 | 1.17 |
| VAR-71 | 2.19 | 2.36 | 1.7 | 1.03 | 1.06 |
| VAR-90 | 0 | 0.57 | 0.04 | 1 | 1.15 |
| VAR-123 | 0.96 | 1.77 | 1.47 | 0.79 | 0.74 |
| VAR-44 | 1.04 | 4.07 | 0.07 | 0.65 | 0.86 |
| VAR-86 | 0.38 | 0.39 | 0 | 1.03 | 0.99 |
| VAR-81 | 1.88 | 2.33 | 0.04 | 0.92 | 0.62 |
| VAR-43 | 0.36 | 0 | 1.44 | 0.77 | 1.26 |
| VAR-41 | 1.48 | 0.55 | 0.69 | 0.96 | 1.05 |
| VAR-88 | 1.21 | 1.71 | 0.54 | 0.54 | 0.76 |
| VAR-127 | 0 | 5.7 | 0 | 1.16 | 1.3 |
| VAR-85 | 0.74 | 0.67 | 7.03 | 0.78 | 1.09 |
| VAR-51 | 0.62 | 0.18 | 0 | 1.23 | 0.5 |
| VAR-99 | 0 | 0.04 | 0 | 0.84 | 1.37 |
| VAR-101 | 0.96 | 0.33 | 0.48 | 1 | 0.94 |
| VAR-107 | 0.44 | 0.04 | 0.62 | 0.84 | 0.95 |
| VAR-5 | 0.74 | 0.09 | 0.03 | 0.57 | 0.84 |
| VAR-33 | 0.98 | 1.37 | 2.06 | 1.15 | 1.52 |
| VAR-3 | 0 | 0.33 | 0 | 1.18 | 0.75 |
| VAR-25 | 0.46 | 0 | 0.68 | 1.08 | 1.07 |
| VAR-49 | 0.78 | 0 | 0 | 0.55 | 1.16 |
| VAR-68 | 1.28 | 0.12 | 0.09 | 0.81 | 1.01 |
| VAR-40 | 0.01 | 0.85 | 0 | 0.69 | 0.67 |
| VAR-97 | 0.61 | 0.64 | 0.31 | 0.57 | 1.18 |
| VAR-10 | 1.19 | 0.97 | 0.86 | 0.94 | 0.78 |
| VAR-105 | 0.27 | 0.37 | 0.41 | 0.88 | 0.82 |
| VAR-114 | 1.48 | 0.44 | 1.22 | 1.22 | 0.98 |
| VAR-69 | 0.75 | 4.14 | 0.32 | 0.98 | 1.06 |
| VAR-14 | 0 | 1.17 | 0.22 | 0.88 | 0.85 |
| VAR-70 | 0.78 | 0.01 | 2.31 | 0.96 | 1.28 |
| VAR-55 | 0.41 | 0.58 | 0 | 1.23 | 0.85 |
| VAR-78 | 0.59 | 0.13 | 0.29 | 0.88 | 2.23 |
| VAR-50 | 0 | 0.47 | 0 | 0.55 | 1.01 |
| VAR-53 | 1.32 | 0.01 | 7.93 | 0.52 | 0.63 |
| VAR-77 | 0.96 | 1.24 | 0.03 | 1.17 | 0.88 |
| VAR-109 | 0.07 | 0.76 | 0.49 | 0.68 | 0.78 |
| VAR-112 | 1.31 | 0.52 | 2.24 | 1.05 | 1.14 |
| VAR-124 | 0.78 | 0.45 | 1.04 | 0.82 | 1.06 |
| VAR-46 | 0.65 | 3.47 | 0 | 0.78 | 1.64 |
| VAR-28 | 0.43 | 0.14 | 1.62 | 0.87 | 1.3 |

TABLE 15-continued

Fold change in biodistribution of virus particles comprising the indicated variant capsid polypeptide, relative to the biodistribution of virus particles comprising WT A

TABLE 16

Fold change in transduction of virus particles comprising the indicated variant capsid polypeptide, relative to the transduction of virus particles comprising wild-type AAV9 in brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | property | | | | | | | | |
|---|---|---|---|---|---|---|---|---|---|
| | transduction | transduction | transduction | transduction | transduction organ | transduction | transduction | transduction | transduction |
| | brain | brain | brain | brain | brain tissue | brain | brain | brain | brain |
| Variant Name | aggregated CBh | aggregated hSyn | basal_ganglia CBh | basal_ganglia hSyn | brainstem promoter CBh | brainstem hSyn | cerebellum CBh | cerebellum hSyn | forebrain CBh |
| VAR-1 | 138.56 | 129.23 | 328.84 | 311.32 | 83.55 | 64.71 | 122.43 | 103.86 | 183.47 |
| VAR-54 | 139.39 | 102.71 | 188.54 | 271.6 | 94.53 | 52.68 | 64.49 | 115.27 | 244.29 |
| VAR-74 | 82.23 | 97.04 | 110.69 | 288.47 | 86.17 | 56.91 | 82.03 | 16.8 | 92.2 |
| VAR-87 | 55.93 | 67.84 | 144.33 | 82.43 | 33.68 | 62.46 | 57.58 | 14.93 | 50.08 |
| VAR-61 | 33.03 | 67.11 | 19.17 | 149.46 | 9.94 | 37.17 | 76.5 | 130.59 | 66.54 |
| VAR-116 | 24.32 | 41.56 | 34.75 | 111.65 | 9.01 | 21.38 | 29.71 | 29.27 | 36.18 |
| VAR-100 | 28.65 | 34.95 | 0 | 46.95 | 30.19 | 24.52 | 28.44 | 41.03 | 57.71 |
| VAR-80 | 22.41 | 32.16 | 9.91 | 62.2 | 20.57 | 16.24 | 22.6 | 27.17 | 41.29 |
| VAR-89 | 37.41 | 29.26 | 69.5 | 41.97 | 24.03 | 25.05 | 48.42 | 26.2 | 42.88 |
| VAR-102 | 25.95 | 24.83 | 0 | 30.02 | 7.81 | 26.13 | 17.17 | 0 | 104.55 |
| VAR-122 | 9.87 | 20.49 | 11.83 | 10.44 | 5.37 | 10.56 | 3.37 | 8.83 | 24.64 |
| VAR-75 | 17.07 | 18.85 | 38.75 | 52.16 | 10.05 | 13.22 | 8.03 | 18.1 | 26.9 |
| VAR-96 | 12.64 | 17.45 | 34.52 | 43.65 | 7.15 | 2.53 | 5.9 | 25.43 | 28.75 |
| VAR-67 | 20.97 | 17.3 | 33.26 | 23.24 | 16.02 | 11.56 | 13.54 | 26.11 | 42.87 |
| VAR-57 | 22.54 | 16.12 | 23.79 | 16.24 | 16.04 | 12.25 | 21.7 | 23.65 | 46.24 |
| VAR-59 | 13.83 | 9.08 | 10.7 | 14.96 | 11.1 | 6.95 | 24.41 | 4.36 | 14.86 |
| VAR-35 | 0 | 8.63 | 0 | 0 | 0 | 18.17 | 0 | 0 | 0 |
| VAR-110 | 2.81 | 8.22 | 0 | 0 | 5.77 | 8.65 | 0 | 0 | 0 |
| VAR-93 | 2.42 | 7.48 | 0 | 0 | 2.5 | 6.3 | 1.83 | 7.9 | 2.23 |
| VAR-76 | 2.3 | 6.88 | 0 | 0 | 5.54 | 9.55 | 0 | 0 | 0 |
| VAR-119 | 1.25 | 6.74 | 0 | 0 | 3 | 10.85 | 0 | 4.19 | 0 |
| VAR-82 | 4.54 | 6.43 | 6.02 | 26.14 | 4.68 | 4.55 | 6.87 | 5.71 | 2.09 |
| VAR-83 | 3.03 | 5.69 | 9.37 | 0 | 2.43 | 6.84 | 5.34 | 8.59 | 0 |
| VAR-108 | 2.35 | 5.64 | 0 | 45.49 | 5.66 | 3.96 | 0 | 0 | 0 |
| VAR-71 | 5.97 | 5.47 | 9.24 | 33.08 | 4.79 | 3.84 | 0 | 0 | 5.41 |
| VAR-90 | 2.46 | 5.26 | 5.71 | 10.59 | 0 | 1.84 | 0 | 0 | 3.96 |
| VAR-123 | 1.99 | 4.96 | 4.62 | 20.01 | 1.2 | 3.48 | 2.64 | 0 | 3.21 |
| VAR-44 | 1.89 | 4.62 | 0 | 0 | 0 | 0 | 5.66 | 0 | 4.06 |
| VAR-86 | 1.71 | 4.49 | 0 | 0 | 4.12 | 0 | 0 | 11.86 | 0 |
| VAR-81 | 3.17 | 4 | 3.68 | 0 | 0.95 | 4.21 | 6.29 | 10.57 | 5.1 |
| VAR-43 | 0 | 3.88 | 0 | 0 | 0 | 2.72 | 0 | 13.67 | 0 |
| VAR-41 | 1.44 | 3.86 | 0 | 0 | 3.48 | 8.13 | 0 | 0 | 0 |
| VAR-88 | 4.36 | 3.61 | 11.58 | 0 | 3 | 3.37 | 3.3 | 0 | 8.04 |
| VAR-127 | 0 | 3.41 | 0 | 0 | 0 | 0 | 0 | 0 | 0 |
| VAR-85 | 0.81 | 3.36 | 0 | 0 | 1.95 | 4.71 | 0 | 0 | 0 |
| VAR-51 | 0 | 3.28 | 0 | 0 | 0 | 0 | 0 | 0 | 0 |
| VAR-99 | 2.43 | 3.16 | 0 | 0 | 1.46 | 0 | 3.21 | 0 | 1.91 |
| VAR-101 | 1.01 | 3.15 | 0 | 0 | 1.22 | 4.97 | 0 | 0 | 3.27 |
| VAR-107 | 3.81 | 2.91 | 0 | 0 | 4.59 | 4.08 | 10.09 | 0 | 0 |
| VAR-5 | 2.7 | 2.86 | 0 | 0 | 2.17 | 2 | 4.76 | 0 | 0 |
| VAR-33 | 0.57 | 2.82 | 5.29 | 0 | 0 | 4.45 | 0 | 0 | 0 |
| VAR-3 | 0 | 2.62 | 0 | 0 | 0 | 5.51 | 0 | 0 | 0 |
| VAR-25 | 1.5 | 2.58 | 0 | 20.8 | 1.8 | 1.81 | 0 | 0 | 0 |
| VAR-49 | 0 | 2.56 | 0 | 0 | 0 | 2.7 | 0 | 0 | 0 |
| VAR-68 | 0.98 | 2.33 | 0 | 0 | 0 | 2.8 | 3.47 | 0 | 2.11 |
| VAR-40 | 0 | 2.51 | 0 | 15.94 | 0 | 2.43 | 0 | 0 | 0 |
| VAR-97 | 0 | 2.31 | 0 | 0 | 0 | 2.43 | 0 | 0 | 0 |
| VAR-10 | 0.88 | 2.3 | 0 | 13.93 | 1.06 | 0 | 0 | 6.09 | 0 |
| VAR-105 | 5.03 | 2.26 | 0 | 0 | 8.08 | 1.9 | 0 | 0 | 5.41 |
| VAR-114 | 1.06 | 2.18 | 0 | 0 | 1.28 | 0 | 0 | 0 | 3.42 |
| VAR-69 | 0 | 2.16 | 0 | 8.69 | 0 | 1.51 | 0 | 0 | 0 |
| VAR-14 | 1.72 | 2.14 | 0 | 0 | 4.13 | 0 | 0 | 0 | 0 |
| VAR-70 | 0.86 | 2.07 | 8.01 | 0 | 0 | 4.37 | 0 | 0 | 0 |
| VAR-55 | 1.78 | 1.95 | 0 | 0 | 4.28 | 0 | 0 | 0 | 0 |
| VAR-78 | 2.32 | 1.91 | 0 | 0 | 0 | 0 | 0 | 0 | 0 |
| VAR-50 | 0.83 | 1.88 | 0 | 0 | 1 | 1.32 | 2.19 | 0 | 0 |
| VAR-53 | 0 | 1.87 | 0 | 0 | 0 | 3.93 | 0 | 0 | 0 |
| VAR-77 | 7.02 | 1.86 | 0 | 0 | 16.91 | 3.92 | 0 | 0 | 0 |
| VAR-109 | 7.4 | 1.84 | 34.35 | 0 | 8.91 | 3.86 | 0 | 0 | 0 |
| VAR-112 | 0.37 | 1.84 | 0 | 0 | 0.89 | 3.86 | 0 | 0 | 0 |
| VAR-124 | 3.02 | 1.81 | 2.55 | 8.73 | 3.31 | 0.76 | 2.91 | 0 | 3.54 |

TABLE 16-continued

Fold change in transduction of virus particles comprising the indicated variant capsid polypeptide, relative to the transduction of virus particles comprising wild-type AAV9 in brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | | | | | | | | | |
|---|---|---|---|---|---|---|---|---|---|
| VAR-46 | 0 | 1.77 | 0 | 21.43 | 0 | 0 | 0 | 0 | 0 |
| VAR-28 | 1 | 1.7 | 4.66 | 0 | 1.21 | 2.68 | 0 | 0 | 0 |
| VAR-17 | 1.62 | 1.62 | 0 | 0 | 1.3 | 1.71 | 2.86 | 0 | 3.49 |
| VAR-47 | 2.06 | 1.62 | 0 | 0 | 1.65 | 0 | 0 | 0 | 8.86 |
| VAR-62 | 0.99 | 1.57 | 9.21 | 0 | 0 | 0 | 0 | 0 | 0 |
| VAR-2 | 1.09 | 1.52 | 0 | 0 | 2.62 | 3.2 | 0 | 0 | 0 |
| VAR-30 | 3.13 | 1.51 | 0 | 0 | 3.77 | 3.17 | 0 | 0 | 10.1 |
| VAR-103 | 0 | 1.45 | 0 | 0 | 0 | 0 | 0 | 0 | 0 |
| VAR-72 | 3.26 | 1.35 | 0 | 0 | 2.62 | 2.84 | 5.76 | 0 | 0 |
| VAR-23 | 1.16 | 1.34 | 0 | 0 | 1.4 | 0 | 0 | 7.1 | 3.75 |
| VAR-95 | 6.92 | 1.34 | 12.85 | 0 | 3.33 | 0 | 7.33 | 14.11 | 8.92 |
| VAR-73 | 0 | 1.27 | 0 | 0 | 0 | 2.66 | 0 | 0 | 0 |
| VAR-79 | 1.8 | 1.21 | 8.34 | 14.63 | 2.16 | 0 | 0 | 0 | 0 |
| VAR-115 | 2.63 | 1.16 | 6.1 | 0 | 0 | 1.22 | 3.48 | 0 | 0 |
| VAR-98 | 0.98 | 1.15 | 0 | 0 | 2.36 | 2.41 | 0 | 0 | 0 |
| VAR-125 | 1.39 | 1.05 | 0 | 0 | 3.35 | 0 | 0 | 0 | 0 |
| VAR-104 | 0 | 1.03 | 0 | 0 | 0 | 2.16 | 0 | 0 | 0 |
| VAR-31 | 1.34 | 0.99 | 0 | 0 | 1.08 | 2.08 | 2.36 | 0 | 0 |
| VAR-24 | 1.43 | 0.97 | 0 | 0 | 0 | 0 | 0 | 0 | 9.2 |
| VAR-39 | 0 | 0.96 | 0 | 0 | 0 | 0 | 0 | 0 | 0 |
| VAR-8 | 1.5 | 0.94 | 0 | 0 | 0 | 1.97 | 0 | 0 | 0 |
| VAR-11 | 2.94 | 0.91 | 0 | 0 | 0 | 0 | 0 | 0 | 18.96 |
| VAR-32 | 0.91 | 0.8 | 4.21 | 0 | 0 | 1.68 | 0 | 0 | 0 |
| VAR-6 | 0.37 | 0.75 | 0 | 0 | 0 | 1.59 | 1.98 | 0 | 0 |
| VAR-121 | 0.51 | 0.76 | 0 | 0 | 0.62 | 0.53 | 1.36 | 2.66 | 0 |
| VAR-9 | 1.02 | 0.73 | 4.75 | 0 | 1.23 | 1.54 | 0 | 0 | 0 |
| VAR-65 | 1.29 | 0.65 | 0 | 0 | 3.11 | 0 | 0 | 0 | 0 |
| VAR-21 | 1.03 | 0.62 | 0 | 0 | 1.24 | 1.3 | 2.73 | 0 | 0 |
| VAR-58 | 1 | 0.59 | 5.1 | 0 | 0.8 | 0 | 0 | 0 | 2.15 |
| VAR-34 | 1.04 | 0.58 | 0 | 0 | 0 | 1.22 | 0 | 0 | 5.69 |
| VAR-120 | 0.57 | 0.54 | 0 | 0 | 0.68 | 0 | 0 | 0 | 1.83 |
| VAR-118 | 0 | 0.53 | 0 | 0 | 0 | 0 | 0 | 0 | 0 |
| VAR-27 | 0 | 0.51 | 0 | 0 | 0 | 0 | 0 | 0 | 0 |
| VAR-29 | 1.45 | 0.46 | 8.98 | 0 | 0 | 0 | 2.56 | 0 | 0 |
| VAR-4 | 0 | 0 | 0 | 0 | 0 | 0 | 0 | 0 | 0 |
| VAR-7 | 2.87 | 0 | 0 | 0 | 3.45 | 0 | 3.79 | 0 | 0 |
| VAR-12 | 1.89 | 0 | 0 | 0 | 2.28 | 0 | 0 | 0 | 6.1 |
| VAR-13 | 4.84 | 0 | 0 | 0 | 9.33 | 0 | 5.13 | 0 | 0 |
| VAR-15 | 0 | 0 | 0 | 0 | 0 | 0 | 0 | 0 | 0 |
| VAR-16 | 0 | 0 | 0 | 0 | 0 | 0 | 0 | 0 | 0 |
| VAR-18 | 11.04 | 0 | 0 | 0 | 26.5 | 0 | 0 | 0 | 0 |
| VAR-19 | 0 | 0 | 0 | 0 | 0 | 0 | 0 | 0 | 0 |
| VAR-20 | 1.54 | 0 | 0 | 0 | 0 | 0 | 8.71 | 0 | 0 |
| VAR-22 | 0 | 0 | 0 | 0 | 0 | 0 | 0 | 0 | 0 |
| VAR-26 | 2.33 | 0 | 7.2 | 0 | 0 | 0 | 8.21 | 0 | 0 |
| VAR-36 | 1.42 | 0 | 0 | 0 | 3.42 | 0 | 0 | 0 | 0 |
| VAR-37 | 0 | 0 | 0 | 0 | 0 | 0 | 0 | 0 | 0 |
| VAR-38 | 1.4 | 0 | 13.04 | 0 | 0 | 0 | 0 | 0 | 0 |
| VAR-42 | 2.93 | 0 | 5.45 | 0 | 4.24 | 0 | 3.11 | 0 | 0 |
| VAR-45 | 0 | 0 | 0 | 0 | 0 | 0 | 0 | 0 | 0 |
| VAR-48 | 0.57 | 0 | 0 | 0 | 0 | 0 | 0 | 0 | 3.67 |
| VAR-52 | 0 | 0 | 0 | 0 | 0 | 0 | 0 | 0 | 0 |
| VAR-56 | 1.19 | 0 | 0 | 0 | 1.43 | 0 | 3.14 | 0 | 0 |
| VAR-60 | 0 | 0 | 0 | 0 | 0 | 0 | 0 | 0 | 0 |
| VAR-63 | 0 | 0 | 0 | 0 | 0 | 0 | 0 | 0 | 0 |
| VAR-64 | 6.27 | 0 | 0 | 0 | 0 | 0 | 0 | 0 | 40.4 |
| VAR-66 | 4.98 | 0 | 0 | 0 | 4.8 | 0 | 5.27 | 0 | 6.42 |
| VAR-84 | 0 | 0 | 0 | 0 | 0 | 0 | 0 | 0 | 0 |
| VAR-91 | 0 | 0 | 0 | 0 | 0 | 0 | 0 | 0 | 0 |
| VAR-92 | 0 | 0 | 0 | 0 | 0 | 0 | 0 | 0 | 0 |
| VAR-94 | 0 | 0 | 0 | 0 | 0 | 0 | 0 | 0 | 0 |
| VAR-106 | 4.24 | 0 | 19.71 | 0 | 5.11 | 0 | 0 | 0 | 0 |
| VAR-111 | 2.28 | 0 | 0 | 0 | 5.44 | 0 | 0 | 0 | 0 |
| VAR-113 | 2.13 | 0 | 0 | 0 | 5.13 | 0 | 0 | 0 | 0 |
| VAR-117 | 0 | 0 | 0 | 0 | 0 | 0 | 0 | 0 | 0 |
| VAR-126 | 0 | 0 | 0 | 0 | 0 | 0 | 0 | 0 | 0 |

TABLE 16-continued

Fold change in transduction of virus particles comprising the indicated variant capsid polypeptide, relative to the transduction of virus particles comprising wild-type AAV9 in brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | property | | | | | | |
|---|---|---|---|---|---|---|---|
| | transduction | transduction | transduction | transduction organ | transduction | transduction | transduction |
| | brain | brain | brain | brain tissue | brain | brain | brain |
| Variant Name | forebrain hSyn | hippocampus CBh | hippocampus hSyn | midbrain CBh | midbrain promoter hSyn | temporal_cortex CBh | temporal_cortex hSyn |
| VAR-1 | 179.59 | 0 | 339.62 | 159.13 | 186.76 | 129.25 | 155.4 |
| VAR-54 | 106.34 | 0 | 0 | 121.07 | 335.24 | 290.19 | 72.56 |
| VAR-74 | 135.33 | 0 | 0 | 79.97 | 173.08 | 14.2 | 89.91 |
| VAR-87 | 56.95 | 340.56 | 0 | 34.75 | 215.28 | 55.53 | 99.85 |
| VAR-61 | 71.17 | 0 | 0 | 46.17 | 76.86 | 0 | 74.87 |
| VAR-116 | 70.3 | 0 | 0 | 125.51 | 40.19 | 0 | 26.1 |
| VAR-100 | 60.86 | 0 | 0 | 0 | 42.26 | 21.33 | 0 |
| VAR-80 | 48.95 | 0 | 0 | 47.75 | 69.98 | 0 | 36.35 |
| VAR-89 | 31.09 | 0 | 0 | 37.19 | 32.38 | 29.71 | 42.05 |
| VAR-102 | 33.35 | 0 | 0 | 72.55 | 0 | 0 | 35.09 |
| VAR-122 | 26.21 | 0 | 0 | 7.12 | 18.2 | 18.97 | 65 |
| VAR-75 | 25.58 | 0 | 0 | 25.45 | 0 | 22.59 | 0 |
| VAR-96 | 29.64 | 0 | 0 | 8.31 | 26.19 | 0 | 34.01 |
| VAR-67 | 17.21 | 0 | 0 | 34.32 | 17.93 | 0 | 38.8 |
| VAR-57 | 20.05 | 0 | 0 | 34.38 | 48.72 | 6.1 | 0 |
| VAR-59 | 11.09 | 0 | 0 | 0 | 17.96 | 13.73 | 11.66 |
| VAR-35 | 0 | 0 | 0 | 0 | 0 | 0 | 0 |
| VAR-110 | 0 | 0 | 0 | 0 | 89.39 | 0 | 0 |
| VAR-93 | 0 | 0 | 0 | 7.73 | 65.13 | 4.12 | 10.57 |
| VAR-76 | 10.27 | 0 | 0 | 0 | 0 | 0 | 0 |
| VAR-119 | 5.33 | 0 | 0 | 0 | 0 | 0 | 0 |
| VAR-82 | 4.84 | 0 | 0 | 0 | 11.76 | 3.86 | 0 |
| VAR-83 | 3.54 | 0 | 0 | 0 | 0 | 0 | 11.49 |
| VAR-108 | 0 | 0 | 0 | 0 | 0 | 0 | 0 |
| VAR-71 | 0 | 0 | 0 | 0 | 19.85 | 23.69 | 0 |
| VAR-90 | 11.77 | 0 | 119.18 | 13.75 | 0 | 7.32 | 0 |
| VAR-123 | 7.41 | 0 | 0 | 0 | 0 | 0 | 0 |
| VAR-44 | 20.67 | 0 | 0 | 0 | 0 | 0 | 0 |
| VAR-86 | 10.06 | 0 | 0 | 0 | 0 | 0 | 1587 |
| VAR-81 | 4.48 | 0 | 0 | 0 | 0 | 4.71 | 0 |
| VAR-43 | 5.79 | 0 | 0 | 0 | 0 | 0 | 0 |
| VAR-41 | 0 | 0 | 0 | 0 | 0 | 0 | 0 |
| VAR-88 | 7.17 | 0 | 0 | 0 | 8.72 | 0 | 0 |
| VAR-127 | 0 | 0 | 0 | 0 | 0 | 0 | 48.18 |
| VAR-85 | 0 | 0 | 0 | 0 | 0 | 0 | 15.81 |
| VAR-51 | 14.7 | 0 | 0 | 0 | 0 | 0 | 0 |
| VAR-99 | 0 | 0 | 0 | 13.57 | 68.69 | 0 | 0 |
| VAR-101 | 3.52 | 0 | 0 | 0 | 0 | 0 | 0 |
| VAR-107 | 4.34 | 0 | 0 | 0 | 0 | 0 | 0 |
| VAR-5 | 4.26 | 98.59 | 0 | 0 | 0 | 5.36 | 13.45 |
| VAR-33 | 3.15 | 0 | 0 | 0 | 0 | 0 | 0 |
| VAR-3 | 0 | 0 | 0 | 0 | 0 | 0 | 0 |
| VAR-25 | 0 | 0 | 0 | 0 | 0 | 8.92 | 0 |
| VAR-49 | 0 | 0 | 0 | 0 | 0 | 0 | 18.1 |
| VAR-68 | 1.49 | 0 | 0 | 0 | 0 | 0 | 9.4 |
| VAR-40 | 0 | 0 | 0 | 0 | 0 | 0 | 0 |
| VAR-97 | 5.17 | 0 | 0 | 0 | 0 | 0 | 0 |
| VAR-10 | 0 | 0 | 0 | 0 | 0 | 5.23 | 8.14 |
| VAR-105 | 6.07 | 0 | 0 | 18.79 | 0 | 0 | 0 |
| VAR-114 | 6.5 | 0 | 0 | 0 | 15.8 | 0 | 0 |
| VAR-69 | 3.22 | 0 | 0 | 0 | 0 | 0 | 0 |
| VAR-14 | 9.57 | 0 | 0 | 0 | 0 | 0 | 0 |
| VAR-70 | 0 | 0 | 0 | 0 | 0 | 0 | 0 |
| VAR-55 | 8.72 | 0 | 0 | 0 | 0 | 0 | 0 |
| VAR-78 | 0 | 0 | 0 | 0 | 41.55 | 27.59 | 0 |
| VAR-50 | 5.62 | 0 | 0 | 0 | 0 | 0 | 0 |
| VAR-53 | 0 | 0 | 0 | 0 | 0 | 0 | 0 |
| VAR-77 | 0 | 0 | 0 | 0 | 0 | 0 | 0 |
| VAR-109 | 0 | 0 | 0 | 0 | 0 | 0 | 0 |
| VAR-112 | 0 | 0 | 0 | 0 | 0 | 0 | 0 |
| VAR-124 | 1.62 | 60.19 | 0 | 0 | 7.86 | 0 | 0 |

TABLE 16-continued

Fold change in transduction of virus particles comprising the indicated variant capsid polypeptide, relative to the transduction of virus particles comprising wild-type AAV9 in brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | | | | | | | |
|---|---|---|---|---|---|---|---|
| VAR-46 | 0 | 0 | 0 | 0 | 0 | 0 | 0 |
| VAR-28 | 1.9 | 0 | 0 | 0 | 0 | 0 | 0 |
| VAR-17 | 3.64 | 0 | 0 | 0 | 0 | 0 | 0 |
| VAR-47 | 2.42 | 0 | 0 | 0 | 11.78 | 0 | 7.65 |
| VAR-62 | 7.02 | 0 | 0 | 0 | 0 | 0 | 0 |
| VAR-2 | 0 | 0 | 0 | 0 | 0 | 0 | 0 |
| VAR-30 | 0 | 0 | 0 | 0 | 0 | 0 | 0 |
| VAR-103 | 6.46 | 0 | 0 | 0 | 0 | 0 | 0 |
| VAR-72 | 0 | 0 | 0 | 0 | 0 | 12.95 | 0 |
| VAR-23 | 0 | 0 | 0 | 0 | 14.63 | 0 | 0 |
| VAR-95 | 0 | 0 | 0 | 15.47 | 0 | 8.24 | 0 |
| VAR-73 | 0 | 0 | 0 | 0 | 0 | 0 | 0 |
| VAR-79 | 0 | 0 | 0 | 0 | 0 | 0 | 0 |
| VAR-115 | 2.6 | 0 | 0 | 29.37 | 0 | 0 | 0 |
| VAR-98 | 0 | 0 | 0 | 0 | 0 | 0 | 0 |
| VAR-125 | 4.68 | 0 | 0 | 0 | 0 | 0 | 0 |
| VAR-104 | 0 | 0 | 0 | 0 | 0 | 0 | 0 |
| VAR-31 | 0 | 97.9 | 0 | 0 | 0 | 0 | 0 |
| VAR-24 | 4.33 | 0 | 0 | 0 | 0 | 0 | 0 |
| VAR-39 | 0 | 0 | 0 | 0 | 0 | 0 | 13.53 |
| VAR-8 | 0 | 0 | 0 | 33.59 | 0 | 0 | 0 |
| VAR-11 | 4.08 | 0 | 0 | 0 | 0 | 0 | 0 |
| VAR-32 | 0 | 0 | 0 | 0 | 0 | 5.4 | 0 |
| VAR-6 | 0 | 0 | 0 | 0 | 0 | 0 | 0 |
| VAR-121 | 1.13 | 0 | 0 | 0 | 0 | 0 | 0 |
| VAR-9 | 0 | 0 | 0 | 0 | 0 | 0 | 0 |
| VAR-65 | 2.91 | 0 | 0 | 0 | 0 | 0 | 0 |
| VAR-21 | 0 | 0 | 0 | 0 | 0 | 0 | 0 |
| VAR-58 | 2.65 | 0 | 0 | 0 | 0 | 0 | 0 |
| VAR-34 | 0 | 0 | 0 | 0 | 0 | 0 | 0 |
| VAR-120 | 0 | 0 | 0 | 0 | 0 | 0 | 7.63 |
| VAR-118 | 2.36 | 0 | 0 | 0 | 0 | 0 | 0 |
| VAR-27 | 2.27 | 0 | 0 | 0 | 0 | 0 | 0 |
| VAR-29 | 2.07 | 0 | 0 | 0 | 0 | 0 | 0 |
| VAR-4 | 0 | 0 | 0 | 0 | 0 | 0 | 0 |
| VAR-7 | 0 | 0 | 0 | 16.03 | 0 | 0 | 0 |
| VAR-12 | 0 | 0 | 0 | 0 | 0 | 0 | 0 |
| VAR-13 | 0 | 0 | 0 | 0 | 0 | 0 | 0 |
| VAR-15 | 0 | 0 | 0 | 0 | 0 | 0 | 0 |
| VAR-16 | 0 | 0 | 0 | 0 | 0 | 0 | 0 |
| VAR-18 | 0 | 0 | 0 | 0 | 0 | 0 | 0 |
| VAR-19 | 0 | 0 | 0 | 0 | 0 | 0 | 0 |
| VAR-20 | 0 | 0 | 0 | 0 | 0 | 0 | 0 |
| VAR-22 | 0 | 0 | 0 | 0 | 0 | 0 | 0 |
| VAR-26 | 0 | 0 | 0 | 0 | 0 | 0 | 0 |
| VAR-36 | 0 | 0 | 0 | 0 | 0 | 0 | 0 |
| VAR-37 | 0 | 0 | 0 | 0 | 0 | 0 | 0 |
| VAR-38 | 0 | 0 | 0 | 0 | 0 | 0 | 0 |
| VAR-42 | 0 | 0 | 0 | 0 | 0 | 0 | 0 |
| VAR-45 | 0 | 0 | 0 | 0 | 0 | 0 | 0 |
| VAR-48 | 0 | 0 | 0 | 0 | 0 | 0 | 0 |
| VAR-52 | 0 | 0 | 0 | 0 | 0 | 0 | 0 |
| VAR-56 | 0 | 0 | 0 | 0 | 0 | 0 | 0 |
| VAR-60 | 0 | 0 | 0 | 0 | 0 | 0 | 0 |
| VAR-63 | 0 | 0 | 0 | 0 | 0 | 0 | 0 |
| VAR-64 | 0 | 0 | 0 | 0 | 0 | 0 | 0 |
| VAR-66 | 0 | 0 | 0 | 22.28 | 0 | 0 | 0 |
| VAR-84 | 0 | 0 | 0 | 0 | 0 | 0 | 0 |
| VAR-91 | 0 | 0 | 0 | 0 | 0 | 0 | 0 |
| VAR-92 | 0 | 0 | 0 | 0 | 0 | 0 | 0 |
| VAR-94 | 0 | 0 | 0 | 0 | 0 | 0 | 0 |
| VAR-106 | 0 | 0 | 0 | 0 | 0 | 0 | 0 |
| VAR-111 | 0 | 0 | 0 | 0 | 0 | 0 | 0 |
| VAR-113 | 0 | 0 | 0 | 0 | 0 | 0 | 0 |
| VAR-117 | 0 | 0 | 0 | 0 | 0 | 0 | 0 |
| VAR-126 | 0 | 0 | 0 | 0 | 0 | 0 | 0 |

TABLE 17

Fold change in transduction of virus particles conspiring the indicated variant capsid polypeptide, relative to the transduction of virus particles comprising wild-type AAV9 in non-brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | property | | | | |
|---|---|---|---|---|---|
| | transduction | transduction | transduction | transduction | transduction |
| | | | organ | | |
| | dorsal_root_ganglion | dorsal_root_ganglion | liver | liver | skeletal_muscle |
| | | | tissue | | |
| | aggregated | aggregated | aggregated | aggregated | aggregated |
| Variant | | | promoter | | |
| Name | CBh | hSyn | CBh | hSyn | CBh |
| VAR-1 | 1.76 | 1.78 | 0.32 | 0.52 | 1.19 |
| VAR-54 | 0 | 2.43 | 0.3 | 0.4 | 2.65 |
| VAR-74 | 5.88 | 0 | 0.17 | 0.5 | 1.33 |
| VAR-87 | 0 | 0 | 1.02 | 1.03 | 1.3 |
| VAR-61 | 0 | 0 | 0.45 | 0.18 | 2.89 |
| VAR-116 | 0 | 3.5 | 1.09 | 0.86 | 2.61 |
| VAR-100 | 0 | 14.72 | 1.04 | 0.81 | 1.5 |
| VAR-80 | 0 | 0 | 0.23 | 0.47 | 1.79 |
| VAR-89 | 0 | 0 | 0.61 | 0.52 | 1.16 |
| VAR-102 | 16.01 | 0 | 0.24 | 0.26 | 0 |
| VAR-122 | 3.14 | 3.17 | 0.28 | 0.3 | 0.8 |
| VAR-75 | 0 | 0 | 0.36 | 0.71 | 1.8 |
| VAR-96 | 3.67 | 4.56 | 0.16 | 0.19 | 1.45 |
| VAR-67 | 0 | 0 | 1.04 | 1.11 | 1.57 |
| VAR-57 | 0 | 0 | 0.45 | 1.07 | 1.72 |
| VAR-59 | 0 | 1.56 | 0.84 | 0.6 | 0.97 |
| VAR-35 | 0 | 0 | 0 | 1.79 | 0 |
| VAR-110 | 0 | 0 | 0.41 | 0.85 | 0 |
| VAR-93 | 5.12 | 0 | 0.68 | 1.4 | 1.64 |
| VAR-76 | 0 | 0 | 1.51 | 1.43 | 1.93 |
| VAR-119 | 4.1 | 0 | 0.61 | 0.7 | 0.81 |
| VAR-82 | 0 | 2.05 | 1.04 | 1.52 | 1.09 |
| VAR-83 | 0 | 0 | 1.1 | 1.27 | 0.56 |
| VAR-108 | 0 | 0 | 0.34 | 1.17 | 2.63 |
| VAR-71 | 0 | 3.46 | 0.94 | 2.27 | 0.56 |
| VAR-90 | 0 | 0 | 0.72 | 0.55 | 1.03 |
| VAR-123 | 2.46 | 0 | 0.8 | 0.86 | 0.97 |
| VAR-44 | 0 | 0 | 1.29 | 0.64 | 0.35 |
| VAR-86 | 0 | 4.26 | 0.83 | 1.75 | 1.28 |
| VAR-81 | 1.95 | 0 | 0.81 | 0.31 | 1.22 |
| VAR-43 | 0 | 0 | 0.4 | 1.88 | 0.77 |
| VAR-41 | 0 | 0 | 0.46 | 0.48 | 0.54 |
| VAR-88 | 3.08 | 0 | 0.5 | 0.29 | 0.52 |
| VAR-127 | 0 | 0 | 1.04 | 1.06 | 0 |
| VAR-85 | 2 | 0 | 0.86 | 0.81 | 1.36 |
| VAR-51 | 0 | 12.44 | 1.06 | 1.02 | 0.51 |
| VAR-99 | 3 | 11.97 | 0.58 | 1.31 | 2.04 |
| VAR-101 | 0 | 0 | 0.55 | 0.74 | 0.71 |
| VAR-107 | 0 | 0 | 0.19 | 0.71 | 0.53 |
| VAR-5 | 0 | 10.83 | 0.56 | 0.3 | 0.75 |
| VAR-33 | 8.44 | 5.34 | 0.71 | 0.37 | 1.12 |
| VAR-3 | 0 | 0 | 1.4 | 1.22 | 0.54 |
| VAR-25 | 0 | 0 | 0.38 | 0.54 | 1.05 |
| VAR-49 | 0 | 0 | 0.5 | 0.8 | 0 |
| VAR-68 | 1.62 | 2.52 | 0.86 | 1.21 | 1.1 |
| VAR-40 | 8.14 | 0 | 0.12 | 0.6 | 0.46 |
| VAR-97 | 0 | 0 | 1.04 | 1.2 | 0 |
| VAR-10 | 0 | 0 | 0.77 | 0.54 | 0.86 |
| VAR-105 | 0 | 1.71 | 0.24 | 0.52 | 0.94 |
| VAR-114 | 2.62 | 0 | 0.77 | 0.75 | 0.74 |
| VAR-69 | 4.62 | 2.73 | 1.23 | 1.57 | 0.79 |
| VAR-14 | 0 | 0 | 1.38 | 0.44 | 1.44 |
| VAR-70 | 0 | 1.97 | 0.76 | 1.08 | 1.45 |
| VAR-55 | 0 | 0 | 0.84 | 0.4 | 0.5 |
| VAR-78 | 0 | 0 | 1.35 | 1.59 | 1.94 |
| VAR-50 | 4.09 | 0 | 0.33 | 0.72 | 1.04 |
| VAR-53 | 0 | 0 | 0.39 | 0.58 | 1.5 |
| VAR-77 | 0 | 0 | 0.34 | 0.19 | 0 |
| VAR-109 | 0 | 0 | 0.4 | 1.05 | 0.52 |

TABLE 17-continued

Fold change in transduction of virus particles conspiring the indicated variant capsid polypeptide, relative to the transduction of virus particles comprising wild-type AAV9 in non-brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| VAR-112 | 0 | 0 | 1.08 | 0.95 | 1.04 |
| VAR-124 | 2.71 | 2.74 | 1.42 | 1.54 | 1.23 |
| VAR-46 | 0 | 0 | 0.39 | 0.37 | 0.99 |
| VAR-28 | 0 | 0 | 0.29 | 0.62 | 0 |
| VAR-17 | 0 | 0 | 0.47 | 1.18 | 1.81 |
| VAR-47 | 0 | 0 | 0.8 | 1.07 | 1.54 |
| VAR-62 | 0 | 2.97 | 0.43 | 0.57 | 0.28 |
| VAR-2 | 0 | 5.77 | 1.03 | 0.63 | 1.22 |
| VAR-30 | 7.74 | 5.71 | 0.69 | 0.78 | 0 |
| VAR-103 | 0 | 0 | 0.93 | 1.05 | 0 |
| VAR-72 | 0 | 0 | 0.4 | 0.28 | 0.3 |
| VAR-23 | 0 | 2.55 | 0.13 | 0.35 | 1.45 |
| VAR-95 | 0 | 0 | 0.3 | 0.28 | 2.13 |
| VAR-73 | 0 | 4.8 | 1.91 | 0.53 | 0 |
| VAR-79 | 4.43 | 4.59 | 0.26 | 0.5 | 0.5 |
| VAR-115 | 0 | 0 | 0.53 | 0.84 | 1.29 |
| VAR-98 | 0 | 2.17 | 0.79 | 1.13 | 0.55 |
| VAR-125 | 0 | 0 | 0.81 | 0.76 | 2.34 |
| VAR-104 | 0 | 3.9 | 1.07 | 0.96 | 0.27 |
| VAR-31 | 4.41 | 1.87 | 0.85 | 0.51 | 1 |
| VAR-24 | 0 | 0 | 0.68 | 1 | 0 |
| VAR-39 | 0 | 0 | 0 | 0.5 | 0.44 |
| VAR-8 | 0 | 0 | 0.66 | 0.78 | 1.26 |
| VAR-11 | 0 | 0 | 0.64 | 0.66 | 0.82 |
| VAR-32 | 0 | 0 | 0.43 | 1.08 | 1.27 |
| VAR-6 | 1.85 | 0 | 0.79 | 0.91 | 1.26 |
| VAR-121 | 1.27 | 0 | 0.86 | 0.63 | 1.22 |
| VAR-9 | 2.53 | 0 | 1.19 | 0.76 | 01.29 |
| VAR-65 | 0 | 2.46 | 0.66 | 0.74 | 1.81 |
| VAR-21 | 0 | 4.68 | 0.34 | 1.03 | 1.73 |
| VAR-58 | 1.65 | 4.48 | 1.1 | 0.98 | 1.03 |
| VAR-34 | 0 | 0 | 0.19 | 0.48 | 0.43 |
| VAR-120 | 1.4 | 0 | 0.68 | 1.23 | 1.43 |
| VAR-118 | 0 | 0 | 0.09 | 1.15 | 1.44 |
| VAR-27 | 2.61 | 0 | 0.77 | 0.74 | 1.03 |
| VAR-29 | 4.77 | 0 | 1.27 | 1.35 | 1.76 |
| VAR-4 | 4.92 | 0 | 0.44 | 1.11 | 0.28 |
| VAR-7 | 0 | 0 | 1.15 | 1.34 | 0.8 |
| VAR-12 | 0 | 0 | 0.62 | 0.64 | 0.53 |
| VAR-13 | 0 | 0 | 0.71 | 1.69 | 2.44 |
| VAR-15 | 0 | 0 | 1.95 | 1.02 | 0.85 |
| VAR-16 | 0 | 6.06 | 0.63 | 0.66 | 0.8 |
| VAR-18 | 0 | 0 | 0.54 | 0 | 2.06 |
| VAR-19 | 0 | 0 | 0.78 | 0.93 | 0.99 |
| VAR-20 | 8.12 | 0 | 0.48 | 1.1 | 1.84 |
| VAR-22 | 0 | 0 | 0.36 | 0.33 | 0.68 |
| VAR-26 | 0 | 0 | .850 | 0.86 | 0.43 |
| VAR-36 | 0 | 0 | 0.1 | 0 | 0.79 |
| VAR-37 | 0 | 10.25 | 1.66 | 1.69 | 0.64 |
| VAR-38 | 0 | 0 | 0.31 | 0.16 | 1.18 |
| VAR-42 | 2.9 | 2.47 | 0.56 | 0.68 | 2.63 |
| VAR-45 | 6.29 | 0 | 0.74 | 0.21 | 1.07 |
| VAR-48 | 0 | 1.48 | 0.5 | 0.69 | 1.11 |
| VAR-52 | 0 | 0 | 0.51 | 0.99 | 1.18 |
| VAR-56 | 2.93 | 0 | 1.04 | 0.74 | 0.56 |
| VAR-60 | 0 | 0 | 1.69 | 0.94 | 5.18 |
| VAR-63 | 0 | 0 | 0.67 | 0.83 | 051 |
| VAR-64 | 0 | 0 | 1.37 | 0 | 1.75 |
| VAR-66 | 0 | 2.63 | 0.22 | 0.58 | 1.11 |
| VAR-84 | 0 | 0 | 0.26 | 0 | 0 |
| VAR-91 | 0 | 0 | 0.18 | 0 | 0.67 |
| VAR-92 | 0 | 0 | 0.51 | 0.81 | 0.65 |
| VAR-94 | 0 | 0 | 0.66 | 0.38 | 0 |
| VAR-106 | 0 | 0 | 0.15 | 0.13 | 1.78 |
| VAR-111 | 0 | 0 | 0 | 0.5 | 1.26 |
| VAR-113 | 0 | 0 | 1.24 | 0.26 | 0.59 |
| VAR-117 | 0 | 0 | 0.5 | 1.53 | 1.6 |
| VAR-126 | 0 | 0 | 0.38 | 0.84 | 0 |

TABLE 17-continued

Fold change in transduction of virus particles conspiring the indicated variant capsid polypeptide, relative to the transduction of virus particles comprising wild-type AAV9 in non-brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | property | | | | |
|---|---|---|---|---|---|
| | transduction | transduction | transduction organ | transduction | transduction |
| | skeletal_muscle | spinal_cord | spinal_cord tissue | spleen | spleen |
| Variant Name | aggregated hSyn | aggregated CBh | aggregated promoter hSyn | aggregated CBh | aggregated hSyn |
| VAR-1 | 1.47 | 46.06 | 63.23 | 0 | 2.36 |
| VAR-54 | 1.73 | 89.64 | 48.29 | 0 | 0 |
| VAR-74 | 0 | 50.24 | 18.41 | 0 | 0 |
| VAR-87 | 0 | 9.36 | 8.18 | 0 | 0 |
| VAR-61 | 0 | 12.43 | 10.22 | 0 | 0 |
| VAR-116 | 0 | 11.26 | 32.07 | 0 | 0 |
| VAR-100 | 0 | 21.56 | 33.71 | 0 | 0 |
| VAR-80 | 3.47 | 6.43 | 11.17 | 0 | 0 |
| VAR-89 | 0.67 | 10.01 | 17.22 | 0 | 0 |
| VAR-102 | 0 | 19.53 | 28.74 | 0 | 0 |
| VAR-122 | 0.56 | 7.67 | 2.42 | 0 | 0 |
| VAR-75 | 0 | 2.28 | 6.61 | 0 | 0 |
| VAR-96 | 0 | 6.71 | 3.48 | 0 | 0 |
| VAR-67 | 0.37 | 12.32 | 9.54 | 0 | 0 |
| VAR-57 | 1.21 | 15.43 | 2.59 | 4.8 | 6.77 |
| VAR-59 | 0 | 6.94 | 7.16 | 10.8 | 6.24 |
| VAR-35 | 0 | 0 | 0 | 0 | 0 |
| VAR-110 | 5.54 | 0 | 0 | 0 | 0 |
| VAR-93 | 1.01 | 4.16 | 0 | 0 | 0 |
| VAR-76 | 3.09 | 0 | 0 | 0 | 0 |
| VAR-119 | 3.74 | 2.5 | 4.59 | 0 | 0 |
| VAR-82 | 0 | 3.9 | 3.13 | 0 | 0 |
| VAR-83 | 2.19 | 0 | 4.7 | 0 | 0 |
| VAR-108 | 0 | 0 | 10.89 | 0 | 0 |
| VAR-71 | 1.23 | 5.99 | 0 | 0 | 0 |
| VAR-90 | 1.18 | 0 | 0 | 0 | 0 |
| VAR-123 | 4.46 | 9 | 9.58 | 0 | 25.01 |
| VAR-44 | 2.07 | 0 | 0 | 0 | 0 |
| VAR-86 | 1.51 | 0 | 0 | 10.69 | 0 |
| VAR-81 | 0 | 2.38 | 0 | 0 | 0 |
| VAR-43 | 1.74 | 0 | 0 | 0 | 0 |
| VAR-41 | 0 | 2.9 | 0 | 0 | 0 |
| VAR-88 | 1.08 | 3.75 | 2.32 | 0 | 0 |
| VAR-127 | 0 | 0 | 0 | 0 | 0 |
| VAR-85 | 4.52 | 0 | 0 | 0 | 0 |
| VAR-51 | 0 | 10.91 | 19 | 0 | 0 |
| VAR-99 | 0 | 7.31 | 0 | 0 | 0 |
| VAR-101 | 2.12 | 3.05 | 0 | 0 | 0 |
| VAR-107 | 0 | 0 | 11.22 | 0 | 0 |
| VAR-5 | 0 | 2.71 | 0 | 0 | 0 |
| VAR-33 | 1.9 | 0 | 8.15 | 0 | 0 |
| VAR-3 | 0 | 0 | 7.57 | 0 | 0 |
| VAR-25 | 0 | 0 | 4.98 | 0 | 0 |
| VAR-49 | 0 | 0 | 0 | 0 | 0 |
| VAR-68 | 0.9 | 0 | 1.92 | 3.07 | 0 |
| VAR-40 | 0 | 0 | 0 | 0 | 0 |
| VAR-97 | 0 | 0 | 0 | 0 | 0 |
| VAR-10 | 0.78 | 0 | 0 | 0 | 0 |
| VAR-105 | 3.05 | 0 | 0 | 0 | 0 |
| VAR-114 | 1.96 | 3.19 | 4.2 | 0 | 0 |
| VAR-69 | 0.97 | 0 | 0 | 0 | 0 |
| VAR-14 | 2.88 | 0 | 0 | 0 | 0 |
| VAR-70 | 2.1 | 0 | 0 | 0 | 7.84 |
| VAR-55 | 0 | 0 | 0 | 0 | 0 |
| VAR-78 | 2.58 | 0 | 0 | 0 | 0 |
| VAR-50 | 0.85 | 0 | 0 | 0 | 0 |
| VAR-53 | 0 | 0 | 0 | 0 | 0 |
| VAR-77 | 0 | 0 | 0 | 0 | 0 |
| VAR-109 | 0 | 0 | 0 | 0 | 0 |

TABLE 17-continued

Fold change in transduction of virus particles conspiring the indicated variant capsid polypeptide, relative to the transduction of virus particles comprising wild-type AAV9 in non-brain tissues. CBh indicates measurements from virus particles comprising genomes with the cap gene under the control of the CBh promoter. hSyn indicates virus particles comprising genomes with the cap gene under the control of the hSyn promoter. Values of "0" indicate variant transduction was not detected in the indicated sample. Variants are ranked in order of fold improvement over WT AAV9 in aggregated brain from the hSyn promoter.

| | | | | | |
|---|---|---|---|---|---|
| VAR-112 | 1.25 | 0 | 0 | 0 | 0 |
| VAR-124 | 0.97 | 0 | 0 | 2.57 | 0 |
| VAR-46 | 0 | 0 | 0 | 0 | 0 |
| VAR-28 | 0.57 | 0 | 4.97 | 0 | 0 |
| VAR-17 | 2.19 | 0 | 0 | 0 | 0 |
| VAR-47 | 1.46 | 0 | 0 | 0 | 0 |
| VAR-62 | 0 | 0 | 0 | 0 | 0 |
| VAR-2 | 0 | 0 | 0 | 0 | 0 |
| VAR-30 | 0 | 0 | 0 | 0 | 0 |
| VAR-103 | 1.95 | 0 | 0 | 0 | 0 |
| VAR-72 | 0 | 0 | 7.8 | 0 | 0 |
| VAR-23 | 0 | 3.5 | 3.89 | 0 | 0 |
| VAR-95 | 3.6 | 0 | 0 | 0 | 0 |
| VAR-73 | 1.71 | 0 | 0 | 0 | 0 |
| VAR-79 | 0 | 0 | 0 | 0 | 0 |
| VAR-115 | 2.35 | 0 | 0 | 0 | 0 |
| VAR-98 | 0.77 | 5.91 | 0 | 0 | 0 |
| VAR-125 | 1.41 | 0 | 0 | 13.04 | 15.81 |
| VAR-104 | 1.39 | 0 | 0 | 0 | 0 |
| VAR-31 | 3.32 | 2.69 | 2.85 | 0 | 0 |
| VAR-24 | 0 | 0 | 0 | 0 | 0 |
| VAR-39 | 0 | 0 | 0 | 0 | 0 |
| VAR-8 | 0 | 0 | 5.43 | 0 | 0 |
| VAR-11 | 0 | 0 | 0 | 0 | 0 |
| VAR-32 | 0 | 0 | 0 | 0 | 0 |
| VAR-6 | 0 | 2.25 | 0 | 0 | 5.73 |
| VAR-121 | 1.36 | 1.55 | 0 | 0 | 3.81 |
| VAR-9 | 0 | 3.08 | 0 | 0 | 11.07 |
| VAR-65 | 0 | 0 | 0 | 0 | 0 |
| VAR-21 | 0 | 0 | 3.57 | 0 | 9.33 |
| VAR-58 | 1.59 | 0 | 0 | 0 | 0 |
| VAR-34 | 0.78 | 3.12 | 0 | 0 | 0 |
| VAR-120 | 2.18 | 0 | 0 | 2.66 | 0 |
| VAR-118 | 0.71 | 0 | 0 | 0 | 7.96 |
| VAR-27 | 0.68 | 0 | 0 | 9.89 | 0 |
| VAR-29 | 0.62 | 0 | 2.68 | 0 | 0 |
| VAR-4 | 1.2 | 12 | 5.15 | 0 | 0 |
| VAR-7 | 1.93 | 0 | 0 | 0 | 0 |
| VAR-12 | 1.38 | 0 | 5.93 | 0 | 0 |
| VAR-13 | 0 | 0 | 0 | 0 | 0 |
| VAR-15 | 0 | 0 | 0 | 0 | 0 |
| VAR-16 | 0 | 0 | 0 | 0 | 0 |
| VAR-18 | 0 | 0 | 0 | 0 | 0 |
| VAR-19 | 0 | 0 | 0 | 0 | 0 |
| VAR-20 | 3.57 | 0 | 0 | 0 | 0 |
| VAR-22 | 0 | 0 | 0 | 0 | 0 |
| VAR-26 | 0 | 0 | 0 | 0 | 0 |
| VAR-36 | 2.79 | 0 | 0 | 0 | 0 |
| VAR-37 | 0 | 0 | 0 | 0 | 0 |
| VAR-38 | 2.1 | 0 | 0 | 0 | 0 |
| VAR-42 | 2.63 | 0 | 0 | 0 | 9.83 |
| VAR-45 | 0 | 0 | 0 | 0 | 0 |
| VAR-48 | 0 | 0 | 6.78 | 0 | 0 |
| VAR-52 | 0 | 0 | 0 | 0 | 0 |
| VAR-56 | 0 | 0 | 5.16 | 0 | 0 |
| VAR-60 | 0 | 0 | 0 | 0 | 0 |
| VAR-63 | 1.2 | 0 | 5.14 | 0 | 0 |
| VAR-64 | 0 | 0 | 0 | 0 | 0 |
| VAR-66 | 0 | 0 | 4.02 | 0 | 0 |
| VAR-84 | 0 | 0 | 18.3 | 0 | 0 |
| VAR-91 | 12.41 | 0 | 0 | 0 | 0 |
| VAR-92 | 0 | 0 | 0 | 0 | 0 |
| VAR-94 | 4.99 | 0 | 0 | 0 | 0 |
| VAR-106 | 5.05 | 12.78 | 7.23 | 19.87 | 0 |
| VAR-111 | 2.16 | 0 | 0 | 0 | 0 |
| VAR-113 | 0 | 0 | 0 | 0 | 0 |
| VAR-117 | 0 | 0 | 0 | 0 | 0 |
| VAR-126 | 0 | 0 | 0 | 0 | 0 |

SEQUENCE LISTING

```
Sequence total quantity: 268
SEQ ID NO: 1            moltype = AA   length = 736
FEATURE                 Location/Qualifiers
source                  1..736
                        mol_type = protein
                        organism = Adeno-associated dependoparvovirus
SEQUENCE: 1
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 2            moltype = AA   length = 736
FEATURE                 Location/Qualifiers
source                  1..736
                        mol_type = protein
                        organism = synthetic construct
SEQUENCE: 2
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AIVGALQSQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 3            moltype = DNA   length = 2211
FEATURE                 Location/Qualifiers
source                  1..2211
                        mol_type = other DNA
                        organism = synthetic construct
SEQUENCE: 3
atggctgccg atggttatct tccagattgg ctcgaggaca accttagtga aggtattcgc   60
gagtggtggg cttttgaaacc tggagcccct caacccaagg caaatcaaca acatcaagac  120
aacgctcgag gtcttgtgct tccgggttac aaataccttg acccggcaa cggactcgac  180
aagggggagc cggtcaacgc agcagacgcg gcggccctcg agcacgacaa ggcctacgac  240
cagcagctca aggccggaga caacccgtac ctcaagtaca accacgcga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcggtg cacagcccgc taaaaagaga ctcaatttcg gtcagactgg cgacacagag  540
tcagtcccag accctcaacc aatcggagaa cctcccgcag cccctccagg tgtgggatct  600
cttacaatgg cttcaggtgg tggcgcacca gtgcagaca ataacgaagg tgccgatgga  660
gtgggtagtt cctcgggaaa ttggcattgc gattccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcacccc  840
tgggggtatt ttgacttcaa cagattccac tgccactct caccacgtga ctggcagcga  900
ctcatcaaca caactgggg attccggcct aagcgactca cttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg ctcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcagagccaa agcctgacc gactaatgaa tcccactcat 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttcctt gtctggatct 1620
ttaatttttg gcaaacaagg aactggaaga gacaacgtgg atgcggacaa agtcatgata 1680
accaacgaag aagaaattaa aactactaac ccggtagcaa cggagtccta tggagtagtg 1740
gccacaaaacc accagagtgc ccaagcacag gcgattgttg cgctcttca atctcaagga 1800
gcgcttccgg gtatggtttg caggacaga gatgtgtacc tgcaaggacc catttgggcc 1860
```

```
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 4           moltype = DNA   length = 2211
FEATURE                Location/Qualifiers
source                 1..2211
                       mol_type = genomic DNA
                       organism = Adeno-associated dependoparvovirus
SEQUENCE: 4
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccggggtac aaataccttg gacccggcaa cggactcgac   180
aaggggagc cggtcaacgc agcagacgcg gcggccctcg agcacgacaa ggcctacgac   240
cagcagctca aggccggaga caaccgtac ctcaagtaca accacgccga cgccgagttc   300
caggagcggc tcaaagaaga tacgtctttt ggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcggtg cacagcccgc taaaaagaga ctcaatttcg gtcagactgg cgacacagag   540
tcagtcccag accctcaacc aatcggagaa cctccgcag cccctcagg tgtgggatct   600
cttacaatgg cttcaggtgg tggcgcacca gtggcagaca taacgaagg tgccgatgga   660
gtgggtagtt cctcggaaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcc acttcggcta cagcacccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga tcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctactgagt tgaaaccgta   1260
ccttccata gcagctacgc tcacagccaa agcctggacc gactagtgaa tccactcatc   1320
gaccaatact tgtactatct ctcaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttcctttt gtctggatct   1620
ttaatttttg gcaaacaagg aactggaaga gacaacgtgg atgcggacaa agtcatgata   1680
accaacgaag aagaaatta aactactaac ccggtagcaa cggagtccta tggacaagtg   1740
gccacacaac cagagtgc caagcacag gcgcaagccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 5           moltype = AA   length = 735
FEATURE                Location/Qualifiers
source                 1..735
                       mol_type = protein
                       organism = Adeno-associated dependoparvovirus
SEQUENCE: 5
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNRQA ATADVNTQGV   600
LPGMVWQDRD VYLQGPIWAK IPHTDGHFHP SPLMGGFGLK HPPPQILIKN TPVPANPSTT   660
FSAAKFASFI TQYSTGQVSV EIEWELQKEN SKRWNPEIQY TSNYNKSVNV DFTVDTNGVY   720
SEPRPIGTRY LTRNL                                                    735

SEQ ID NO: 6           moltype = DNA   length = 2208
FEATURE                Location/Qualifiers
source                 1..2208
                       mol_type = genomic DNA
                       organism = Adeno-associated dependoparvovirus
SEQUENCE: 6
atggctgccg atggttatct tccagattgg ctcgaggaca ctctctctga aggaataaga   60
cagtggtgga agctcaaacc tggcccacca ccaccaaagc ccgcagagcg gcataaggac   120
```

```
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca ccacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg tcagactgga gacgcagac  540
tcagtacctg accccagcc tctcggacag ccaccagcag cccctctgg tctgggaact  600
aatacgatgg ctacaggcag tggcgcacca atggcagaca ataaccaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg ctacagcac ccttgggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataacttac cagcacggtt 1020
caggtgttta ctgactcgga gtaccagctc ccgtacgtcc tcggctcgg gcatcaagga 1080
tgcctcccgc cgttcccagc agacgtcttc atggtgccac agtatggata cctcacccctg 1140
aacaacggaa gtcaggcagt aggacgctct tcatttttact gcctggagta cttccttcct 1200
cagatgctgc gtaccggaaa caactttacc ttcagctaca ctttgagga cgttcctttc 1260
cacagcagct acgctcacag ccagagtctg gaccgtctca tgaatcctct catcgaccag 1320
tacctgtatt acttgagcag aacaaacact ccaagtggaa ccaccacgca gtcaaggctt 1380
cagttttctc aggccggagc gagtgacatt cgggaccagt ctaggaactg gcttcctgga 1440
ccctgttacc gccagcagcg agtatcaaag acatctgcgg ataacaacaa cagtgaatac 1500
tcgtggactg gagctaccaa gtaccacctc aatggcagag actctctggt gaatccgggc 1560
ccggccatgg caagccacaa ggacgatgaa gaaaagtttt ttcctcagag cgggggttctc 1620
atctttggga agcaaggctc agagaaaaca aatgtgaaaa aggttcatga ttaca 1680
gacgaagagg aaatcaggac aaccaatccc gtgctacgag agcagtatgg ttctgtatct 1740
accaacctcc agagaggcaa cagacaagca gctaccgcag atgtcaacac acaaggcgtt 1800
cttccaggca tggtctggca ggacagagat gtgtaccttc aggggcccat ctgggcaaag 1860
attccacaca cggacgaca ttttcacccc ctccccctca tgggtggatt cggacttaaa 1920
caccctcctc cacagattct catcaagaac acccccggtac ctgcgaatcc ttcgaccacc 1980
ttcagtgcgg caaagtttgc ttccttcatc acacagtact ccacgggaca ggtcagcgtg 2040
gagatcgagt gggagctgca aaggaaaac agcaaacgct ggaatcccga aattcagtac 2100
acttccaact acaacaagtc tgttaatgtg gactttactg tggacactaa tggcgtgtat 2160
tcagagcctc gccccattgg caccagatac ctgactcgta atctgtaa       2208

SEQ ID NO: 7          moltype = AA  length = 724
FEATURE               Location/Qualifiers
source                1..724
                      mol_type = protein
                      organism = Adeno-associated dependoparvovirus
SEQUENCE: 7
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                              724

SEQ ID NO: 8          moltype = DNA  length = 2175
FEATURE               Location/Qualifiers
source                1..2175
                      mol_type = genomic DNA
                      organism = Adeno-associated dependoparvovirus
SEQUENCE: 8
atgtcttttg ttgatcaccc tccagattgg ttggaagaag ttggtgaagg tcttcgcgag   60
ttttggggcc ttgaagcggg cccaccgaaa ccaaaaccca atcagcagca tcaagatcaa  120
gcccgtggtc ttgtgctgcc tggttataac tatctcggac ccggaaacgg gctcgatcga  180
ggagagcctg tcaacagggc agacgaggtc gcgcgagagc acgacatctc gtacaacgag  240
cagcttgagc gggagacaa ccctacctc aagtacaacc acgcggacgc cgagtttcag  300
gagaagctcg ccgacgacac atcctccggg gaaacctcg gaaaggcagt ctttcaggcc  360
aagaaaaggg ttctcgaacc tttttggcctg gttgaagagg gtgctaagac ggcccctacc  420
ggaaagcgga tagacgacca ctttcccaaa agaaagaagg ctcggaccga agaggactcc  480
aagccttcca cctcgtcaga cgccgaagct ggacccagcg gatcccagca gctgcaaatc  540
ccagcccaac cagcctcaag tttgggagct gatacaatgt ctgcggggag tggcggccca  600
ttgggcgaca ataaccaagg tgccgatgga gtgggcaatg cctcgggaga ttggcattgc  660
gattccacgt ggatggggga cagagtcgtc accaagtcca cgagaacctg ggtgctgccc  720
agctacaaca accaccagta ccgagagatc aaaagcggct ccgtcgacgg aagcaacgca  780
aacgcctact ttgatacag caccccctgg gggtactttg actttaaccg cttccacagc  840
cactggagcc ccgagactgg caaagactac atcaacaact actgggggcttt cagacccggg  900
tccctcgagag tcaaaatctt caacattcaa gtcaagagg tcacggtgca ggactccacc  960
accaccatcg ccaacaacct cacctccacc gtccaagtgt ttacggacga cgactaccag 1020
```

-continued

```
ctgccctacg tcgtcggcaa cgggaccgag ggatgcctgc cggccttccc tccgcaggtc      1080
tttacgctgc cgcagtacgg ttacgcgacg ctgaaccgcg acaacacaga aaatcccacc      1140
gagaggagca gcttcttctg cctagagtac tttcccagca agatgctgag aacgggcaac      1200
aactttgagt ttacctacaa ctttgaggag gtgcccttcc actccagctt cgctcccagt      1260
cagaacctgt tcaagctggc caacccgctg gtggaccagt acttgtaccg cttcgtgagc      1320
acaaataaca ctggcggagt ccagttcaac aagaacctgg ccgggagata cgccaacacc      1380
tacaaaaact ggttcccggg gcccatgggc cgaacccagg gctggaacct gggctccggg      1440
gtcaaccgcg ccagtgtcag cgccttcgcc acgaccaata ggatggagct cgagggcgcg      1500
agttaccagg tgccccgca gccgaacggc atgaccaaca acctccaggg cagcaacacc      1560
tatgccctgg agaacactat gatcttcaac agccagccgg cgaacccggg caccaccgtc      1620
acgtacctcg agggcaacat gctcatcacc agcgagagcg agacgcagcc ggtgaaccgc      1680
gtggcgtaca acgtcggcgg gcagatggcc accaacaacc agagctccac cactgccccc      1740
gcgaccggca cgtacaacct ccaggaaatc gtgcccggac gcgtgtggat ggagagggac      1800
gtgtacctcc aaggacccat ctgggcaaag atcccagaga cgggggcgca ctttcaccct      1860
tctccggcca tgggcggatt cggactcaaa cacccaccgc ccatgatgct catcaagaac      1920
acgcctgtgc ccgaaaatat caccagcttc tcggacgtgc ccgtcagcag cttcatcacc      1980
cagtacagca ccgggcaggt caccgtggag atggagtggg agctcaagaa ggaaaactcc      2040
aagaggtgga acccagagat ccagtacaca aacaactaca acgaccccca gtttgtggac      2100
tttgccccgg acagcaccgg ggaatacaga accaccgagc tatccggaac ccgataccttt    2160
acccgacccc tttaa                                                      2175

SEQ ID NO: 9              moltype = AA   length = 738
FEATURE                   Location/Qualifiers
source                    1..738
                          mol_type = protein
                          organism = Adeno-associated dependoparvovirus
SEQUENCE: 9
MAADGYLPDW LEDNLSEGIR EWWALKPGAP KPKANQQKQD DGRGLVLPGY KYLGPFNGLD      60
KGEPVNAADA AALEHDKAYD QQLQAGDNPY LRYNHADAEF QERLQEDTSF GGNLGRAVFQ     120
AKKRVLEPLG LVEEGAKTAP GKKRPVEPSP QRSPDSSTGI GKKGQQPARK RLNFGQTGDS     180
ESVPDPQPLG EPPAAPSGVG PNTMAAGGGA PMADNNEGAD GVGSSSGNWH CDSTWLGDRV     240
ITTSTRTWAL PTYNNHLYKQ ISNGTSGGAT NDNTYFGYST PWGYFDFNRF HCHFSPRDWQ     300
RLINNNWGFR PKRLSFKLFN IQVKEVTQNE GTKTIANNLT STIQVFTDSE YQLPYVLGSA     360
HQGCLPPFPA DVFMIPQYGY LTLNNGSQAV GRSSFYCLEY FPSQMLRTGN NFQFTYTFED     420
VPFHSSYAHS QSLDRLMNPL IDQYLYYLSR TQTTGGTANT QTLGFSQGGP NTMANQAKNW     480
LPGPCYRQQR VSTTTGQNNN SNFAWTAGTK YHLNGRNSLA NPGIAMATHK DDEERFFPSN     540
GILIFGKQNA ARDNADYSDV MLTSEEEIKT TNPVATEEYG IVADNLQQQN TAPQIGTVNS     600
QGALPGMVWQ NRDVYLQGPI WAKIPHTDGN FHPSPLMGGF GLKHPPPQIL IKNTPVPADP     660
PTTFNQSKLN SFITQYSTGQ VSVEIEWELQ KENSKRWNPE IQYTSNYYKS TSVDFAVNTE     720
GVYSEPRPIG TRYLTRNL                                                  738

SEQ ID NO: 10             moltype = DNA   length = 2217
FEATURE                   Location/Qualifiers
source                    1..2217
                          mol_type = genomic DNA
                          organism = Adeno-associated dependoparvovirus
SEQUENCE: 10
atggctgccg atggttatct tccagattgg ctcgaggaca acctctctga gggcattcgc       60
gagtggtggg cgctgaaacc tggagccccg aagcccaaag ccaaccagca aaagcaggac     120
gacggccggg gtctggtgct tcctggctac aagtacctcg gacccttcaa cggactcgac     180
aaggggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc agcgttctc cagactcctc tacgggcatc     480
ggcaagaaag gccaacagcc cgccagaaaa agactcaatt ttggtcagac tggcgactca     540
gagtcagttc cagaccctca acctctcgga gaacctccag cagcgccctc tggtgtggga     600
cctaatacaa tggctgcagg cggtggcgca ccaatggcag acaataacga aggcgccgac     660
ggagtgggta gttcctcggg aaattggcat tgcgattcca catgctgggc tcgacagagtc     720
atcaccacca gcacccgaac ctgggcctg cccacctaca caaccacacct ctacaagcaa     780
atctccaacg gaacatcggg aggagccacc aacgacaaca cctacttcgg ctacagcacc     840
ccctgggggt attttgactt taacagattc cactgccact tttccaccacg tgactggcag     900
cgactcatca acaacaactg gggattccgg cccaagagac tcagcttcaa gctcttcaac     960
atccaggtca aggaggtcac gcagaatgaa gccaccaaaa tcatcgccaa taacctcacc    1020
agcaccatcc aggtgtttac ggactcggag taccagctgc cgtacgttct cggctctgcc    1080
caccagggct gcctgcctcc gttccgcgcg gacgtgttca tgattcccca gtacggctac    1140
ctaacactca acaacggtag tcaggccgtg ggacgctcct ccttctactg cctggaatac    1200
ttccctcgc agatgctgag aaccggcaac aacttccagt ttacttacac cttcgaggac    1260
gtgccttttc acagcagcta cgcccacagc cagagcctgg accgcctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga tggaagaaa ttcattggct    1560
aatcctggca tcgctatggc aacacacaaa gacgacgagg agcgtttttt tccagtaac    1620
gggatcctga tttttggcaa acaaaatgct gccagagaca atgcggatta cagcgatgtc    1680
atgctcacca gcgaggaaga aatcaaaaacc actaaccctg tggctacaga ggaatacggt    1740
atcgtggcag ataacttgca gcagcaaaac acggctcctc aaattggaac tgtcaacagc    1800
cagggggcct acccggtat ggtctggcag aaccgggacg tgtacctgca gggtccatc    1860
tgggccaaga ttcctcacac ggacggcaac ttccacccgt ctccgctgat gggcggcttt    1920
```

```
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacgaaa   2160
ggcgtgtact ctgaaccccg ccccattggc acccgttacc tcacccgtaa tctgtaa     2217

SEQ ID NO: 11         moltype = AA   length = 738
FEATURE               Location/Qualifiers
source                1..738
                      mol_type = protein
                      organism = Adeno-associated dependoparvovirus
SEQUENCE: 11
MAADGYLPDW LEDNLSEGIR EWWDLKPGAP KPKANQQKQD NGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVESPVKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYNFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFNQAKLA SFITQYSTGQ VSVEIEWELQ KENSKRWNPE IQYTSNYYKS TNVDFAVNTE   720
GTYSEPRPIG TRYLTRNL                                                738

SEQ ID NO: 12         moltype = AA   length = 738
FEATURE               Location/Qualifiers
source                1..738
                      mol_type = protein
                      organism = Adeno-associated dependoparvovirus
SEQUENCE: 12
MAADGYLPDW LEDNLSEGIR EWWDLKPGAP KPKANQQKQD NGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVESPVKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYNFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFTKAKLA SFITQYSTGQ VSVEIEWELQ KENSKRWNPE IQYTSNYYKS TNVDFAVNTE   720
GTYSEPRPIG TRYLTRNL                                                738

SEQ ID NO: 13         moltype = DNA   length = 2217
FEATURE               Location/Qualifiers
source                1..2217
                      mol_type = genomic DNA
                      organism = Adeno-associated dependoparvovirus
SEQUENCE: 13
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtcttgtgct tcctggctac aagtacctcg gacccttcaa cggactcgac   180
aagggggagc ccgtcaacgc ggcggacgca gcggccctcg agcacgacaa ggcctacgac   240
cagcagctcc aagcgggtga caatccgtac ctgcggtata atcacgccga cgccgagttt   300
caggagcgtc tgcaagaaga tacgtctttt ggggggcaacc tcgggcgcgc agtcttccag   360
gccaaaaagc gggttctcga acctctgggc ctggttgaat cgccggttaa gacggctcct   420
ggaaagaaga ggccggtaga gccatcaccc cagcgctctc cagactcctc tacgggcatc   480
ggcaagaaag gccagcagcc cgcaaaaaag agactcaatt ttgggcagac tggcgactca   540
gagtcagtcc ccgacccttca accaatcgga gaaccaccag caggcccttc tggtctggga   600
tctggtacaa tggctgcagg cggtggcgct ccaatggcag acaataacga aggcgccgac   660
ggagtgggta gttcctcagg aaattggcat tgcgattcca catggctggg cgacagagtc   720
atcaccacca gcacccgcac ctgggccctg cccacctaca caaccacct ctacaagcaa   780
atctccaacg gaacctcggg aggaagcacc aacgacaaca cctacttcgg ctacagcacc   840
ccctgggggt attttgactt caacagattc cactgccact tttcaccacg tgactggcag   900
cgactcatca caacaactg gggattccgc ccaagaggc tcaactttaa gctcttcaac   960
atccaagtca aggaggtcac gcagaatgaa ggcaccaaga ccatcgccaa taaccttacc  1020
agcacgattc aggtctttac ggactcggaa taccagctcc cgtacgtgct cggctcggcg  1080
caccagggct gcctgcctcc gttcccggcg gacgtcttca tgattcctca gtacgggtac  1140
ctgactctga acaatggcag tcaggctgtg ggccggtcgt ccttctactg cctggagtac  1200
tttccttctc aaatgctgag aacgggcaac aactttgaat tcagctacaa cttcgaggac  1260
gtgccctcc acagcagcta cgcccacagc cagtcgctcg atcgtctcat gaaccccctc  1320
atcgaccagt acttgtacta cctgtcccgg actcaaagca cgggcggtac tgcaggaact  1380
cagcagttgc tattttctca ggccgggcct aacaacatgt cggctcaggc caagaactgg  1440
ctacccggtc cctgctaccg gcagcaacgt gtctccacga cactgtcgca gaacaacaac  1500
agcaactttg cctggacggg tgccaccaag tatcatctga atggcagaga ctctctggtg  1560
aatcctggcg ttgccatggc tacccacaag gacgacgaag agcgatttt tccatccagc  1620
```

```
ggagtcttaa tgtttgggaa acagggagct ggaaaagaca acgtggacta tagcagcgtg    1680
atgctaacca gcgaggaaga aataaagacc accaacccag tggccacaga acagtacggc    1740
gtggtggccg ataacctgca acagcaaaac gccgctccta ttgtaggggc cgtcaatagt    1800
caaggagcct acctggcat ggtgtggcag aaccgggacg tgtacctgca gggtcccatc     1860
tgggccaaga ttcctcatac ggacggcaac tttcatcct cgccgcgtgat ggaggcttt     1920
ggactgaagc atccgcctcc tcagatcctg attaaaaaca cacctgttcc cgcgatcct    1980
ccgaccacct tcaatcaggc caagctggct ctttttcatca cgcagtacag taccggccag   2040
gtcagcgtgg agatcgagtg ggagctgcag aaggagaaca gcaaacgctg gaacccagag   2100
attcagtaca cttccaacta ctacaaatct acaaatgtgg actttgctgt caatactgag   2160
ggtacttatt ccgagcctcg ccccattggc accgttacc tcacccgtaa tctgtaa       2217

SEQ ID NO: 14          moltype = AA   length = 736
FEATURE                Location/Qualifiers
source                 1..736
                       mol_type = protein
                       organism = synthetic construct
SEQUENCE: 14
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGALQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 15          moltype = AA   length = 736
FEATURE                Location/Qualifiers
source                 1..736
                       mol_type = protein
                       organism = synthetic construct
SEQUENCE: 15
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 16          moltype = AA   length = 736
FEATURE                Location/Qualifiers
source                 1..736
                       mol_type = protein
                       organism = synthetic construct
SEQUENCE: 16
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGALQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 17          moltype = AA   length = 736
FEATURE                Location/Qualifiers
source                 1..736
                       mol_type = protein
                       organism = synthetic construct
SEQUENCE: 17
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ   120
```

```
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AIVGWLQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 18           moltype = AA   length = 736
FEATURE                 Location/Qualifiers
source                  1..736
                        mol_type = protein
                        organism = synthetic construct
SEQUENCE: 18
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGALQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 19           moltype = AA   length = 736
FEATURE                 Location/Qualifiers
source                  1..736
                        mol_type = protein
                        organism = synthetic construct
SEQUENCE: 19
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AIVGALQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 20           moltype = AA   length = 736
FEATURE                 Location/Qualifiers
source                  1..736
                        mol_type = protein
                        organism = synthetic construct
SEQUENCE: 20
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGWLQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 21           moltype = AA   length = 736
FEATURE                 Location/Qualifiers
source                  1..736
                        mol_type = protein
                        organism = synthetic construct
```

```
SEQUENCE: 21
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQVGALQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 22          moltype = AA  length = 736
FEATURE                Location/Qualifiers
source                 1..736
                       mol_type = protein
                       organism = synthetic construct
SEQUENCE: 22
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 23          moltype = AA  length = 736
FEATURE                Location/Qualifiers
source                 1..736
                       mol_type = protein
                       organism = synthetic construct
SEQUENCE: 23
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 24          moltype = AA  length = 736
FEATURE                Location/Qualifiers
source                 1..736
                       mol_type = protein
                       organism = synthetic construct
SEQUENCE: 24
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 25          moltype = AA  length = 736
FEATURE                Location/Qualifiers
```

```
                                       -continued source                   1..736
                         mol_type = protein
                         organism = synthetic construct
SEQUENCE: 25
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGWLQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 26            moltype = AA  length = 736
FEATURE                  Location/Qualifiers
source                   1..736
                         mol_type = protein
                         organism = synthetic construct
SEQUENCE: 26
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 27            moltype = AA  length = 736
FEATURE                  Location/Qualifiers
source                   1..736
                         mol_type = protein
                         organism = synthetic construct
SEQUENCE: 27
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 28            moltype = AA  length = 736
FEATURE                  Location/Qualifiers
source                   1..736
                         mol_type = protein
                         organism = synthetic construct
SEQUENCE: 28
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AIVGWLQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 29            moltype = AA  length = 736
```

```
FEATURE                 Location/Qualifiers
source                  1..736
                        mol_type = protein
                        organism = synthetic construct
SEQUENCE: 29
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVADKVMI TNEEEIKTTN PVATESYGVV ATNHQSAQAQ AIVGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 30           moltype = AA  length = 736
FEATURE                 Location/Qualifiers
source                  1..736
                        mol_type = protein
                        organism = synthetic construct
SEQUENCE: 30
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVADKVMI TNEEEIKTTN PVATESYGQV ATNHQSAQAQ AIVGWLQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 31           moltype = AA  length = 736
FEATURE                 Location/Qualifiers
source                  1..736
                        mol_type = protein
                        organism = synthetic construct
SEQUENCE: 31
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVADKVMI TNEEEIKTTN PVATESYGVV ATNHQSAQAQ AIVGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 32           moltype = AA  length = 736
FEATURE                 Location/Qualifiers
source                  1..736
                        mol_type = protein
                        organism = synthetic construct
SEQUENCE: 32
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVADKVMI TNEEEIKTTN PVATESYGVV ATNHQSAQAQ AQTGAVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736
```

```
SEQ ID NO: 33             moltype = AA   length = 736
FEATURE                   Location/Qualifiers
source                    1..736
                          mol_type = protein
                          organism = synthetic construct
SEQUENCE: 33
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 34             moltype = AA   length = 736
FEATURE                   Location/Qualifiers
source                    1..736
                          mol_type = protein
                          organism = synthetic construct
SEQUENCE: 34
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 35             moltype = AA   length = 736
FEATURE                   Location/Qualifiers
source                    1..736
                          mol_type = protein
                          organism = synthetic construct
SEQUENCE: 35
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWLQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 36             moltype = AA   length = 736
FEATURE                   Location/Qualifiers
source                    1..736
                          mol_type = protein
                          organism = synthetic construct
SEQUENCE: 36
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGAVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736
```

```
SEQ ID NO: 37           moltype = AA  length = 736
FEATURE                 Location/Qualifiers
source                  1..736
                        mol_type = protein
                        organism = synthetic construct
SEQUENCE: 37
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGALQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 38           moltype = AA  length = 736
FEATURE                 Location/Qualifiers
source                  1..736
                        mol_type = protein
                        organism = synthetic construct
SEQUENCE: 38
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 39           moltype = AA  length = 736
FEATURE                 Location/Qualifiers
source                  1..736
                        mol_type = protein
                        organism = synthetic construct
SEQUENCE: 39
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGALQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 40           moltype = AA  length = 736
FEATURE                 Location/Qualifiers
source                  1..736
                        mol_type = protein
                        organism = synthetic construct
SEQUENCE: 40
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGWVQSQG   600
```

```
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 41           moltype = AA   length = 736
FEATURE                 Location/Qualifiers
source                  1..736
                        mol_type = protein
                        organism = synthetic construct
SEQUENCE: 41
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWLQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 42           moltype = AA   length = 736
FEATURE                 Location/Qualifiers
source                  1..736
                        mol_type = protein
                        organism = synthetic construct
SEQUENCE: 42
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWLQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 43           moltype = AA   length = 736
FEATURE                 Location/Qualifiers
source                  1..736
                        mol_type = protein
                        organism = synthetic construct
SEQUENCE: 43
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGWVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 44           moltype = AA   length = 736
FEATURE                 Location/Qualifiers
source                  1..736
                        mol_type = protein
                        organism = synthetic construct
SEQUENCE: 44
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
```

```
LIFGKQGTGR DNVDADKVMI TNEEEIKTTN PVATESYGVV ATNHQSAQAQ AITGAVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 45            moltype = AA  length = 736
FEATURE                  Location/Qualifiers
source                   1..736
                         mol_type = protein
                         organism = synthetic construct
SEQUENCE: 45
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGWLQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 46            moltype = AA  length = 736
FEATURE                  Location/Qualifiers
source                   1..736
                         mol_type = protein
                         organism = synthetic construct
SEQUENCE: 46
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGV ATNHQSAQAQ AITGAVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 47            moltype = AA  length = 736
FEATURE                  Location/Qualifiers
source                   1..736
                         mol_type = protein
                         organism = synthetic construct
SEQUENCE: 47
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWLQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 48            moltype = AA  length = 736
FEATURE                  Location/Qualifiers
source                   1..736
                         mol_type = protein
                         organism = synthetic construct
SEQUENCE: 48
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
```

```
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AIVGAVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 49           moltype = AA   length = 736
FEATURE                 Location/Qualifiers
source                  1..736
                        mol_type = protein
                        organism = synthetic construct
SEQUENCE: 49
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AITGWLQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 50           moltype = AA   length = 736
FEATURE                 Location/Qualifiers
source                  1..736
                        mol_type = protein
                        organism = synthetic construct
SEQUENCE: 50
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AITGWLQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 51           moltype = AA   length = 736
FEATURE                 Location/Qualifiers
source                  1..736
                        mol_type = protein
                        organism = synthetic construct
SEQUENCE: 51
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 52           moltype = AA   length = 736
FEATURE                 Location/Qualifiers
source                  1..736
                        mol_type = protein
                        organism = synthetic construct
SEQUENCE: 52
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
```

```
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 53           moltype = AA  length = 736
FEATURE                 Location/Qualifiers
source                  1..736
                        mol_type = protein
                        organism = synthetic construct
SEQUENCE: 53
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGAVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 54           moltype = AA  length = 736
FEATURE                 Location/Qualifiers
source                  1..736
                        mol_type = protein
                        organism = synthetic construct
SEQUENCE: 54
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 55           moltype = AA  length = 736
FEATURE                 Location/Qualifiers
source                  1..736
                        mol_type = protein
                        organism = synthetic construct
SEQUENCE: 55
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGAVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 56           moltype = AA  length = 736
FEATURE                 Location/Qualifiers
source                  1..736
                        mol_type = protein
                        organism = synthetic construct
SEQUENCE: 56
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
```

```
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGWVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 57             moltype = AA   length = 736
FEATURE                   Location/Qualifiers
source                    1..736
                          mol_type = protein
                          organism = synthetic construct
SEQUENCE: 57
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 58             moltype = AA   length = 736
FEATURE                   Location/Qualifiers
source                    1..736
                          mol_type = protein
                          organism = synthetic construct
SEQUENCE: 58
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGAVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 59             moltype = AA   length = 736
FEATURE                   Location/Qualifiers
source                    1..736
                          mol_type = protein
                          organism = synthetic construct
SEQUENCE: 59
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGALQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 60             moltype = AA   length = 736
FEATURE                   Location/Qualifiers
source                    1..736
                          mol_type = protein
                          organism = synthetic construct
SEQUENCE: 60
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
```

```
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGWVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 61           moltype = AA   length = 736
FEATURE                 Location/Qualifiers
source                  1..736
                        mol_type = protein
                        organism = synthetic construct
SEQUENCE: 61
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 62           moltype = AA   length = 736
FEATURE                 Location/Qualifiers
source                  1..736
                        mol_type = protein
                        organism = synthetic construct
SEQUENCE: 62
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQVGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 63           moltype = AA   length = 736
FEATURE                 Location/Qualifiers
source                  1..736
                        mol_type = protein
                        organism = synthetic construct
SEQUENCE: 63
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGALQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 64           moltype = AA   length = 736
FEATURE                 Location/Qualifiers
source                  1..736
                        mol_type = protein
                        organism = synthetic construct
SEQUENCE: 64
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
```

```
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWLQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 65           moltype = AA  length = 736
FEATURE                 Location/Qualifiers
source                  1..736
                        mol_type = protein
                        organism = synthetic construct
SEQUENCE: 65
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWLQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 66           moltype = AA  length = 736
FEATURE                 Location/Qualifiers
source                  1..736
                        mol_type = protein
                        organism = synthetic construct
SEQUENCE: 66
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 67           moltype = AA  length = 736
FEATURE                 Location/Qualifiers
source                  1..736
                        mol_type = protein
                        organism = synthetic construct
SEQUENCE: 67
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGALQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 68           moltype = AA  length = 736
FEATURE                 Location/Qualifiers
source                  1..736
                        mol_type = protein
                        organism = synthetic construct
SEQUENCE: 68
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGWVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 69          moltype = AA  length = 736
FEATURE                Location/Qualifiers
source                 1..736
                       mol_type = protein
                       organism = synthetic construct
SEQUENCE: 69
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AIVGWVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 70          moltype = AA  length = 736
FEATURE                Location/Qualifiers
source                 1..736
                       mol_type = protein
                       organism = synthetic construct
SEQUENCE: 70
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGALQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 71          moltype = AA  length = 736
FEATURE                Location/Qualifiers
source                 1..736
                       mol_type = protein
                       organism = synthetic construct
SEQUENCE: 71
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGAVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 72          moltype = AA  length = 736
FEATURE                Location/Qualifiers
source                 1..736
                       mol_type = protein
                       organism = synthetic construct
SEQUENCE: 72
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
```

```
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGALQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 73           moltype = AA   length = 736
FEATURE                 Location/Qualifiers
source                  1..736
                        mol_type = protein
                        organism = synthetic construct
SEQUENCE: 73
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 74           moltype = AA   length = 736
FEATURE                 Location/Qualifiers
source                  1..736
                        mol_type = protein
                        organism = synthetic construct
SEQUENCE: 74
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGAVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 75           moltype = AA   length = 736
FEATURE                 Location/Qualifiers
source                  1..736
                        mol_type = protein
                        organism = synthetic construct
SEQUENCE: 75
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGAVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 76           moltype = AA   length = 736
FEATURE                 Location/Qualifiers
source                  1..736
                        mol_type = protein
                        organism = synthetic construct
```

```
SEQUENCE: 76
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQVGAVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 77            moltype = AA  length = 736
FEATURE                  Location/Qualifiers
source                   1..736
                         mol_type = protein
                         organism = synthetic construct
SEQUENCE: 77
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AIVGWVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 78            moltype = AA  length = 736
FEATURE                  Location/Qualifiers
source                   1..736
                         mol_type = protein
                         organism = synthetic construct
SEQUENCE: 78
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGWVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 79            moltype = AA  length = 736
FEATURE                  Location/Qualifiers
source                   1..736
                         mol_type = protein
                         organism = synthetic construct
SEQUENCE: 79
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736
```

```
SEQ ID NO: 80            moltype = AA  length = 736
FEATURE                  Location/Qualifiers
source                   1..736
                         mol_type = protein
                         organism = synthetic construct
SEQUENCE: 80
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AIVGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 81            moltype = AA  length = 736
FEATURE                  Location/Qualifiers
source                   1..736
                         mol_type = protein
                         organism = synthetic construct
SEQUENCE: 81
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 82            moltype = AA  length = 736
FEATURE                  Location/Qualifiers
source                   1..736
                         mol_type = protein
                         organism = synthetic construct
SEQUENCE: 82
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGWLQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 83            moltype = AA  length = 736
FEATURE                  Location/Qualifiers
source                   1..736
                         mol_type = protein
                         organism = synthetic construct
SEQUENCE: 83
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGWVQNQG   600
```

```
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 84           moltype = AA   length = 736
FEATURE                 Location/Qualifiers
source                  1..736
                        mol_type = protein
                        organism = synthetic construct
SEQUENCE: 84
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVADKVMI TNEEEIKTTN PVATESYGQV ATNHQSAQAQ AQVGWLQSQG     600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 85           moltype = AA   length = 736
FEATURE                 Location/Qualifiers
source                  1..736
                        mol_type = protein
                        organism = synthetic construct
SEQUENCE: 85
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVADKVMI TNEEEIKTTN PVATESYGQV ATNHQSAQAQ AQVGWLQNQG     600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 86           moltype = AA   length = 736
FEATURE                 Location/Qualifiers
source                  1..736
                        mol_type = protein
                        organism = synthetic construct
SEQUENCE: 86
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVADKVMI TNEEEIKTTN PVATESYGQV ATNHQSAQAQ AITGWLQSQG     600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 87           moltype = AA   length = 736
FEATURE                 Location/Qualifiers
source                  1..736
                        mol_type = protein
                        organism = synthetic construct
SEQUENCE: 87
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
```

```
LIFGKQGTGR DNVDADKVMI TNEEEIKTTN PVATESYGVV ATNHQSAQAQ AITGWLQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 88           moltype = AA   length = 736
FEATURE                 Location/Qualifiers
source                  1..736
                        mol_type = protein
                        organism = synthetic construct
SEQUENCE: 88
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWLQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 89           moltype = AA   length = 736
FEATURE                 Location/Qualifiers
source                  1..736
                        mol_type = protein
                        organism = synthetic construct
SEQUENCE: 89
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGALQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 90           moltype = AA   length = 736
FEATURE                 Location/Qualifiers
source                  1..736
                        mol_type = protein
                        organism = synthetic construct
SEQUENCE: 90
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 91           moltype = AA   length = 736
FEATURE                 Location/Qualifiers
source                  1..736
                        mol_type = protein
                        organism = synthetic construct
SEQUENCE: 91
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
```

```
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQVGWVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 92           moltype = AA  length = 736
FEATURE                 Location/Qualifiers
source                  1..736
                        mol_type = protein
                        organism = synthetic construct
SEQUENCE: 92
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV AITGAVQNQG                600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 93           moltype = AA  length = 736
FEATURE                 Location/Qualifiers
source                  1..736
                        mol_type = protein
                        organism = synthetic construct
SEQUENCE: 93
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGWVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 94           moltype = AA  length = 736
FEATURE                 Location/Qualifiers
source                  1..736
                        mol_type = protein
                        organism = synthetic construct
SEQUENCE: 94
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 95           moltype = AA  length = 736
FEATURE                 Location/Qualifiers
source                  1..736
                        mol_type = protein
                        organism = synthetic construct
SEQUENCE: 95
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
```

-continued

```
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AIVGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 96           moltype = AA  length = 736
FEATURE                 Location/Qualifiers
source                  1..736
                        mol_type = protein
                        organism = synthetic construct
SEQUENCE: 96
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGAVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 97           moltype = AA  length = 736
FEATURE                 Location/Qualifiers
source                  1..736
                        mol_type = protein
                        organism = synthetic construct
SEQUENCE: 97
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGAVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 98           moltype = AA  length = 736
FEATURE                 Location/Qualifiers
source                  1..736
                        mol_type = protein
                        organism = synthetic construct
SEQUENCE: 98
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGALQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 99           moltype = AA  length = 736
FEATURE                 Location/Qualifiers
source                  1..736
                        mol_type = protein
                        organism = synthetic construct
SEQUENCE: 99
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
```

```
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 100          moltype = AA  length = 736
FEATURE                 Location/Qualifiers
source                  1..736
                        mol_type = protein
                        organism = synthetic construct
SEQUENCE: 100
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AIVGALQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 101          moltype = AA  length = 736
FEATURE                 Location/Qualifiers
source                  1..736
                        mol_type = protein
                        organism = synthetic construct
SEQUENCE: 101
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 102          moltype = AA  length = 736
FEATURE                 Location/Qualifiers
source                  1..736
                        mol_type = protein
                        organism = synthetic construct
SEQUENCE: 102
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AITGALQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 103          moltype = AA  length = 736
FEATURE                 Location/Qualifiers
source                  1..736
                        mol_type = protein
                        organism = synthetic construct
SEQUENCE: 103
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
```

```
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AIVGAVQNGG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 104          moltype = AA   length = 736
FEATURE                 Location/Qualifiers
source                  1..736
                        mol_type = protein
                        organism = synthetic construct
SEQUENCE: 104
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTDTE     180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AITGALQNG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 105          moltype = AA   length = 736
FEATURE                 Location/Qualifiers
source                  1..736
                        mol_type = protein
                        organism = synthetic construct
SEQUENCE: 105
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTDTE     180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGALQNG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 106          moltype = AA   length = 736
FEATURE                 Location/Qualifiers
source                  1..736
                        mol_type = protein
                        organism = synthetic construct
SEQUENCE: 106
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTDTE     180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AITGAVQSG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 107          moltype = AA   length = 736
FEATURE                 Location/Qualifiers
source                  1..736
                        mol_type = protein
                        organism = synthetic construct
SEQUENCE: 107
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTDTE     180
SVPDPQPIGE PPAAPSGVGS LTMASGGGAP VADNNEGADG VGSSSGNWHC DSQWLGDRVI    240
```

```
TTSTRTWALP  TYNNHLYKQI  SNSTSGGSSN  DNAYFGYSTP  WGYFDFNRFH  CHFSPRDWQR   300
LINNNWGFRP  KRLNFKLFNI  QVKEVTDNNG  VKTIANNLTS  TVQVFTDSDY  QLPYVLGSAH   360
EGCLPPPPAD  VFMIPQYGYL  TLNDGSQAVG  RSSFYCLEYF  PSQMLRTGNN  FQFSYEFENV   420
PFHSSYAHSQ  SLDRLMNPLI  DQYLYYLSKT  INGSGQNQQT  LKFSVAGPSN  MAVQGRNYIP   480
GPSYRQQRVS  TTVTQNNNSE  FAWPGASSWA  LNGRNSLMNP  GPAMASHKEG  EDRFFPLSGS   540
LIFGKQGTGR  DNVDADKVMI  TNEEEIKTTN  PVATESYGQV  ATNHQSAQAQ  AQVGWVQSQG   600
ILPGMVWQDR  DVYLQGPIWA  KIPHTDGNFH  PSPLMGGFGM  KHPPPQILIK  NTPVPADPPT   660
AFNKDKLNSF  ITQYSTGQVS  VEIEWELQKE  NSKRWNPEIQ  YTSNYYKSNN  VEFAVNTEGV   720
YSEPRPIGTR  YLTRNL                                                      736

SEQ ID NO: 108          moltype = AA  length = 736
FEATURE                 Location/Qualifiers
source                  1..736
                        mol_type = protein
                        organism = synthetic construct
SEQUENCE: 108
MAADGYLPDW  LEDNLSEGIR  EWWALKPGAP  QPKANQQHQD  NARGLVLPGY  KYLGPGNGLD    60
KGEPVNAADA  AALEHDKAYD  QQLKAGDNPY  LKYNHADAEF  QERLKEDTSF  GGNLGRAVFQ   120
AKKRLLEPLG  LVEEAAKTAP  GKKRPVEQSP  QEPDSSAGIG  KSGAQPAKKR  LNFGQTGDTE   180
SVPDPQPIGE  PPAAPSGVGS  LTMASGGGAP  VADNNEGADG  VGSSSGNWHC  DSQWLGDRVI   240
TTSTRTWALP  TYNNHLYKQI  SNSTSGGSSN  DNAYFGYSTP  WGYFDFNRFH  CHFSPRDWQR   300
LINNNWGFRP  KRLNFKLFNI  QVKEVTDNNG  VKTIANNLTS  TVQVFTDSDY  QLPYVLGSAH   360
EGCLPPPPAD  VFMIPQYGYL  TLNDGSQAVG  RSSFYCLEYF  PSQMLRTGNN  FQFSYEFENV   420
PFHSSYAHSQ  SLDRLMNPLI  DQYLYYLSKT  INGSGQNQQT  LKFSVAGPSN  MAVQGRNYIP   480
GPSYRQQRVS  TTVTQNNNSE  FAWPGASSWA  LNGRNSLMNP  GPAMASHKEG  EDRFFPLSGS   540
LIFGKQGTGR  DNVDADKVMI  TNEEEIKTTN  PVATESYGQV  ATNHQSAQAQ  AQVGWVQNQG   600
ILPGMVWQDR  DVYLQGPIWA  KIPHTDGNFH  PSPLMGGFGM  KHPPPQILIK  NTPVPADPPT   660
AFNKDKLNSF  ITQYSTGQVS  VEIEWELQKE  NSKRWNPEIQ  YTSNYYKSNN  VEFAVNTEGV   720
YSEPRPIGTR  YLTRNL                                                      736

SEQ ID NO: 109          moltype = AA  length = 736
FEATURE                 Location/Qualifiers
source                  1..736
                        mol_type = protein
                        organism = synthetic construct
SEQUENCE: 109
MAADGYLPDW  LEDNLSEGIR  EWWALKPGAP  QPKANQQHQD  NARGLVLPGY  KYLGPGNGLD    60
KGEPVNAADA  AALEHDKAYD  QQLKAGDNPY  LKYNHADAEF  QERLKEDTSF  GGNLGRAVFQ   120
AKKRLLEPLG  LVEEAAKTAP  GKKRPVEQSP  QEPDSSAGIG  KSGAQPAKKR  LNFGQTGDTE   180
SVPDPQPIGE  PPAAPSGVGS  LTMASGGGAP  VADNNEGADG  VGSSSGNWHC  DSQWLGDRVI   240
TTSTRTWALP  TYNNHLYKQI  SNSTSGGSSN  DNAYFGYSTP  WGYFDFNRFH  CHFSPRDWQR   300
LINNNWGFRP  KRLNFKLFNI  QVKEVTDNNG  VKTIANNLTS  TVQVFTDSDY  QLPYVLGSAH   360
EGCLPPPPAD  VFMIPQYGYL  TLNDGSQAVG  RSSFYCLEYF  PSQMLRTGNN  FQFSYEFENV   420
PFHSSYAHSQ  SLDRLMNPLI  DQYLYYLSKT  INGSGQNQQT  LKFSVAGPSN  MAVQGRNYIP   480
GPSYRQQRVS  TTVTQNNNSE  FAWPGASSWA  LNGRNSLMNP  GPAMASHKEG  EDRFFPLSGS   540
LIFGKQGTGR  DNVDADKVMI  TNEEEIKTTN  PVATESYGVV  ATNHQSAQAQ  AQTGAVQNQG   600
ILPGMVWQDR  DVYLQGPIWA  KIPHTDGNFH  PSPLMGGFGM  KHPPPQILIK  NTPVPADPPT   660
AFNKDKLNSF  ITQYSTGQVS  VEIEWELQKE  NSKRWNPEIQ  YTSNYYKSNN  VEFAVNTEGV   720
YSEPRPIGTR  YLTRNL                                                      736

SEQ ID NO: 110          moltype = AA  length = 736
FEATURE                 Location/Qualifiers
source                  1..736
                        mol_type = protein
                        organism = synthetic construct
SEQUENCE: 110
MAADGYLPDW  LEDNLSEGIR  EWWALKPGAP  QPKANQQHQD  NARGLVLPGY  KYLGPGNGLD    60
KGEPVNAADA  AALEHDKAYD  QQLKAGDNPY  LKYNHADAEF  QERLKEDTSF  GGNLGRAVFQ   120
AKKRLLEPLG  LVEEAAKTAP  GKKRPVEQSP  QEPDSSAGIG  KSGAQPAKKR  LNFGQTGDTE   180
SVPDPQPIGE  PPAAPSGVGS  LTMASGGGAP  VADNNEGADG  VGSSSGNWHC  DSQWLGDRVI   240
TTSTRTWALP  TYNNHLYKQI  SNSTSGGSSN  DNAYFGYSTP  WGYFDFNRFH  CHFSPRDWQR   300
LINNNWGFRP  KRLNFKLFNI  QVKEVTDNNG  VKTIANNLTS  TVQVFTDSDY  QLPYVLGSAH   360
EGCLPPPPAD  VFMIPQYGYL  TLNDGSQAVG  RSSFYCLEYF  PSQMLRTGNN  FQFSYEFENV   420
PFHSSYAHSQ  SLDRLMNPLI  DQYLYYLSKT  INGSGQNQQT  LKFSVAGPSN  MAVQGRNYIP   480
GPSYRQQRVS  TTVTQNNNSE  FAWPGASSWA  LNGRNSLMNP  GPAMASHKEG  EDRFFPLSGS   540
LIFGKQGTGR  DNVDADKVMI  TNEEEIKTTN  PVATESYGQV  ATNHQSAQAQ  AITGWVQNQG   600
ILPGMVWQDR  DVYLQGPIWA  KIPHTDGNFH  PSPLMGGFGM  KHPPPQILIK  NTPVPADPPT   660
AFNKDKLNSF  ITQYSTGQVS  VEIEWELQKE  NSKRWNPEIQ  YTSNYYKSNN  VEFAVNTEGV   720
YSEPRPIGTR  YLTRNL                                                      736

SEQ ID NO: 111          moltype = AA  length = 736
FEATURE                 Location/Qualifiers
source                  1..736
                        mol_type = protein
                        organism = synthetic construct
SEQUENCE: 111
MAADGYLPDW  LEDNLSEGIR  EWWALKPGAP  QPKANQQHQD  NARGLVLPGY  KYLGPGNGLD    60
KGEPVNAADA  AALEHDKAYD  QQLKAGDNPY  LKYNHADAEF  QERLKEDTSF  GGNLGRAVFQ   120
AKKRLLEPLG  LVEEAAKTAP  GKKRPVEQSP  QEPDSSAGIG  KSGAQPAKKR  LNFGQTGDTE   180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGVV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 112        moltype = AA  length = 736
FEATURE               Location/Qualifiers
source                1..736
                      mol_type = protein
                      organism = synthetic construct
SEQUENCE: 112
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGAVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 113        moltype = AA  length = 736
FEATURE               Location/Qualifiers
source                1..736
                      mol_type = protein
                      organism = synthetic construct
SEQUENCE: 113
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGAVQSQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 114        moltype = AA  length = 736
FEATURE               Location/Qualifiers
source                1..736
                      mol_type = protein
                      organism = synthetic construct
SEQUENCE: 114
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQVGAVQNQG    600
ALPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 115        moltype = AA  length = 736
FEATURE               Location/Qualifiers
source                1..736
                      mol_type = protein
                      organism = synthetic construct
SEQUENCE: 115
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
```

```
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQVGWVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 116          moltype = AA   length = 736
FEATURE                 Location/Qualifiers
source                  1..736
                        mol_type = protein
                        organism = synthetic construct
SEQUENCE: 116
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 117          moltype = AA   length = 736
FEATURE                 Location/Qualifiers
source                  1..736
                        mol_type = protein
                        organism = synthetic construct
SEQUENCE: 117
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 118          moltype = AA   length = 736
FEATURE                 Location/Qualifiers
source                  1..736
                        mol_type = protein
                        organism = synthetic construct
SEQUENCE: 118
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGAVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 119          moltype = AA   length = 736
FEATURE                 Location/Qualifiers
source                  1..736
                        mol_type = protein
                        organism = synthetic construct
```

```
SEQUENCE: 119
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGWVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 120          moltype = AA  length = 736
FEATURE                 Location/Qualifiers
source                  1..736
                        mol_type = protein
                        organism = synthetic construct
SEQUENCE: 120
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGAVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 121          moltype = AA  length = 736
FEATURE                 Location/Qualifiers
source                  1..736
                        mol_type = protein
                        organism = synthetic construct
SEQUENCE: 121
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AITGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 122          moltype = AA  length = 736
FEATURE                 Location/Qualifiers
source                  1..736
                        mol_type = protein
                        organism = synthetic construct
SEQUENCE: 122
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGAVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 123          moltype = AA  length = 736
FEATURE                 Location/Qualifiers
```

```
source                    1..736
                          mol_type = protein
                          organism = synthetic construct
SEQUENCE: 123
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 124          moltype = AA  length = 736
FEATURE                 Location/Qualifiers
source                  1..736
                        mol_type = protein
                        organism = synthetic construct
SEQUENCE: 124
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQTGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 125          moltype = AA  length = 736
FEATURE                 Location/Qualifiers
source                  1..736
                        mol_type = protein
                        organism = synthetic construct
SEQUENCE: 125
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGWVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 126          moltype = AA  length = 736
FEATURE                 Location/Qualifiers
source                  1..736
                        mol_type = protein
                        organism = synthetic construct
SEQUENCE: 126
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPPPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQVGAVQSQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 127          moltype = AA  length = 736
```

```
FEATURE               Location/Qualifiers
source                1..736
                      mol_type = protein
                      organism = synthetic construct
SEQUENCE: 127
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQVGWLQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 128        moltype = AA  length = 736
FEATURE               Location/Qualifiers
source                1..736
                      mol_type = protein
                      organism = synthetic construct
SEQUENCE: 128
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AITGALQSQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 129        moltype = AA  length = 736
FEATURE               Location/Qualifiers
source                1..736
                      mol_type = protein
                      organism = synthetic construct
SEQUENCE: 129
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AIVGWLQNQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 130        moltype = AA  length = 736
FEATURE               Location/Qualifiers
source                1..736
                      mol_type = protein
                      organism = synthetic construct
SEQUENCE: 130
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AIVGALQNQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

```
SEQ ID NO: 131          moltype = AA  length = 736
FEATURE                 Location/Qualifiers
source                  1..736
                        mol_type = protein
                        organism = synthetic construct
SEQUENCE: 131
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AQVGWLQNQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 132          moltype = AA  length = 736
FEATURE                 Location/Qualifiers
source                  1..736
                        mol_type = protein
                        organism = synthetic construct
SEQUENCE: 132
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AIVGWLSQG   600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 133          moltype = AA  length = 736
FEATURE                 Location/Qualifiers
source                  1..736
                        mol_type = protein
                        organism = synthetic construct
SEQUENCE: 133
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AQVGAVQNQG  600
ALPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 134          moltype = AA  length = 736
FEATURE                 Location/Qualifiers
source                  1..736
                        mol_type = protein
                        organism = synthetic construct
SEQUENCE: 134
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGVV ATNHQSAQAQ AITGWLQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736
```

```
SEQ ID NO: 135          moltype = AA  length = 736
FEATURE                 Location/Qualifiers
source                  1..736
                        mol_type = protein
                        organism = synthetic construct
SEQUENCE: 135
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AQVGWVQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 136          moltype = AA  length = 736
FEATURE                 Location/Qualifiers
source                  1..736
                        mol_type = protein
                        organism = synthetic construct
SEQUENCE: 136
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGVV ATNHQSAQAQ AIVGWLQNQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 137          moltype = AA  length = 736
FEATURE                 Location/Qualifiers
source                  1..736
                        mol_type = protein
                        organism = synthetic construct
SEQUENCE: 137
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AIVGAVQSQG   600
ALPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 138          moltype = AA  length = 736
FEATURE                 Location/Qualifiers
source                  1..736
                        mol_type = protein
                        organism = synthetic construct
SEQUENCE: 138
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSN  DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AITGWLQNQG   600
```

```
ALPGMVWQDR DVYLQGPIWA KIPHTDGNFH PSPLMGGFGM KHPPPQILIK NTPVPADPPT      660
AFNKDKLNSF ITQYSTGQVS VEIEWELQKE NSKRWNPEIQ YTSNYYKSNN VEFAVNTEGV      720
YSEPRPIGTR YLTRNL                                                     736

SEQ ID NO: 139          moltype = AA   length = 736
FEATURE                 Location/Qualifiers
source                  1..736
                        mol_type = protein
                        organism = synthetic construct
SEQUENCE: 139
MAADGYLPDW LEDNLSEGIR EWWALKPGAP QPKANQQHQD NARGLVLPGY KYLGPGNGLD       60
KGEPVNAADA AALEHDKAYD QQLKAGDNPY LKYNHADAEF QERLKEDTSF GGNLGRAVFQ      120
AKKRLLEPLG LVEEAAKTAP GKKRPVEQSP QEPDSSAGIG KSGAQPAKKR LNFGQTGDTE      180
SVPDPQPIGE PPAAPSGVGS LTMASGGGAP VADNNEGADG VGSSSGNWHC DSQWLGDRVI      240
TTSTRTWALP TYNNHLYKQI SNSTSGGSSN DNAYFGYSTP WGYFDFNRFH CHFSPRDWQR      300
LINNNWGFRP KRLNFKLFNI QVKEVTDNNG VKTIANNLTS TVQVFTDSDY QLPYVLGSAH      360
EGCLPPFPAD VFMIPQYGYL TLNDGSQAVG RSSFYCLEYF PSQMLRTGNN FQFSYEFENV      420
PFHSSYAHSQ SLDRLMNPLI DQYLYYLSKT INGSGQNQQT LKFSVAGPSN MAVQGRNYIP      480
GPSYRQQRVS TTVTQNNNSE FAWPGASSWA LNGRNSLMNP GPAMASHKEG EDRFFPLSGS      540
LIFGKQGTGR DNVDADKVMI TNEEEIKTTN PVATESYGQV ATNHQSAQAQ AIVGAVQNQG      600
ALPGMVWQDR DVYLQGPIWA KIPHTDGNFH PSPLMGGFGM KHPPPQILIK NTPVPADPPT      660
AFNKDKLNSF ITQYSTGQVS VEIEWELQKE NSKRWNPEIQ YTSNYYKSNN VEFAVNTEGV      720
YSEPRPIGTR YLTRNL                                                     736

SEQ ID NO: 140          moltype = DNA   length = 2211
FEATURE                 Location/Qualifiers
source                  1..2211
                        mol_type = other DNA
                        organism = synthetic construct
SEQUENCE: 140
atggctgccg atggttatct tccagattgg ctcgaggaca accttagtga aggtattcgc       60
gagtggtggg ctttgaaacc tggagcccct caacccaagg caaatcaaca acatcaagac      120
aacgctcgag tcttgtgct tccgggttac aaataccttg acccggcaa cggactcgac        180
aaggggggagc cggtcaacgc agcagacgcg gcggccctcg agcacgacaa ggcctacgac     240
cagcagctca aggccggaga caacccgtac ctcaagtaca accgcccga cgccgagttc       300
caggagcggc tcaaagaaga tacgtctttt ggggcaacc tcgggcgagc agtcttccag       360
gccaaaaaga ggcttcttga acctcttggt ctggttgagg aagcggctaa gacggctcct      420
ggaaagaaga ggcctgtaga gcagtctcct caggaaccgg actcctccgc gggtattggc      480
aaatcgggtg cacagcccgc taaaaagaga ctcaatttcg gtcagactgg cgacacagag     540
tcagtcccag accctcaacc aatcggagaa cctcccgcag cccctcagg tgtgggatct       600
cttacaatgg cttcaggtgg tggcgcacca gtggcagaca taacgaagg tgccgatgga       660
gtgggtagtt cctcggaaaa ttggcattgc gattcccaat ggctggggga cagagtcatc      720
accaccagca cccgaacctg ggccctgccc acctacaaca ataccctcta caagcaaatc      780
tccaacagca catctggagg atcttcaaat gacaacgcct acttcggcta cagcaccccc      840
tgggggtatt ttgacttcaa cagattccac tgccactct caccacgtga ctggcagcga      900
ctcatcaaca acaactgggg attccggcct aagcgactca acttcaagct cttcaacatt      960
caggtcaaag aggttacgga caacaatgga gtcaagacca tcgccaataa ccttaccagc     1020
acgtccagg tcttcacgga ctcagactat cagctcccgt acgtgctcgg gtcggctcac     1080
gagggctgcc tcccgccgtt cccagcggac gttttcatga ttcctcagta cgggtatctg    1140
acgcttaatg atggaagcca ggccgtgggt cgttcgtccc tttactgcct ggaatatttc    1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact gtactatct ctcaaagact attaacggtt ctggacagaa tcaacaaacg    1380
ctaaaattca gtgtggccgg acccagcaac atggctgtcc agggaagaaa ctacatacct   1440
ggaccagct accgacaaca acgtgtctca accactgtga ctcaaaacaa caacagcgaa    1500
tttgcttggc ctggagcttc ttcttgggct ctcaatggac gtaatagctt gatgaatcct   1560
ggacctgcta tggccagcca caagaagga ggaccgtt tctttccttt gtctggatct       1620
taattttgt gcaaacaagg aactggaaga gacaacgtgg atgcggacaa agtcatgata    1680
accaacgaag aagaaattaa aactactaac ccggtagcaa cggagtccta tggagtcgtg    1740
gccacaaacc accagagtgc ccaagcacag gcgcaggtag gcgcattgca aagccaagga    1800
gctcttccgg gtatggtttg gcaggacaga gatgtgtacc tgcaaggacc catttgggcc    1860
aaaattcctc acacggacgg caactttcac ccttctccgc tgatgggagg gtttggaatg   1920
aagcaccgc tcctcagat cctcatcaaa acacacctg tacctgcgga tcctccaacg      1980
gccttcaaca aggacaagct gaactctttc atcacccagt attctactgg ccaagtcagt   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac ccgcccccat ggcaccagat acctgactc gtaatctgta a              2211

SEQ ID NO: 141          moltype = DNA   length = 2211
FEATURE                 Location/Qualifiers
source                  1..2211
                        mol_type = other DNA
                        organism = synthetic construct
SEQUENCE: 141
atggctgccg atggttatct tccagattgg ctcgaggaca accttagtga aggtattcgc       60
gagtggtggg ctttgaaacc tggagcccct caacccaagg caaatcaaca acatcaagac      120
aacgctcgag tcttgtgct tccgggttac aaataccttg acccggcaa cggactcgac        180
aaggggggagc cggtcaacgc agcagacgcg gcggccctcg agcacgacaa ggcctacgac     240
cagcagctca aggccggaga caacccgtac ctcaagtaca accgcccga cgccgagttc       300
```

```
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga ggaccgtt tctttccttt gtctggatct      1620
ttaattttg gcaaacaagg aactggaaga gacaacgtgg atgcggacaa agtcatgata   1680
accaacgaag aagaaattaa aactactaac ccggtagcaa cggagtccta tggagtcgtg  1740
gccacaaacc accagagtgc ccaagcacag gcgcaggtcg gctggctgca atcacaagga  1800
gcgcttccgg gtatggtttg gcaggacaga gatgtgtacc tgcaaggacc catttgggcc  1860
aaaattcctc acacgacgg caactttcac ccttctccgc tgatgggagg gtttggaatg   1920
aagcaccgc ctcctcagat cctcatcaaa acacacctg tacctgcgga tcctccaacg    1980
gccttcaaca aggacaagct gaactctttc atcacccagt attctactgg ccaagtcagc  2040
gtggagatcg agtgggagct gcagaaggaa aacagcaagc gctgaaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 142         moltype = DNA   length = 2211
FEATURE                Location/Qualifiers
source                 1..2211
                       mol_type = other DNA
                       organism = synthetic construct
SEQUENCE: 142
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggggtac aaataccttg acccggcaa cggactcgac   180
aaggggagc cggtcaacgc agcagacgcg gcggccctcg agcacgacaa ggcctacgac  240
cagcagctca aggccggaga caaccccgtac ctcaagtaca ccacgccga cgccgagttc  300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga ggaccgtt tctttccttt gtctggatct      1620
ttaattttg gcaaacaagg aactggaaga gacaacgtgg atgcggacaa agtcatgata   1680
accaacgaag aagaaattaa aactactaac ccggtagcaa cggagtccta tggagtggtg  1740
gccacaaacc accagagtgc ccaagcacag gcgcaggaccg ctcca aagtcaagga      1800
gcgcttccgg gtatggtttg gcaggacaga gatgtgtacc tgcaaggacc catttgggcc  1860
aaaattcctc acacgacgg caactttcac ccttctccgc tgatgggagg gtttggaatg   1920
aagcaccgc ctcctcagat cctcatcaaa acacacctg tacctgcgga tcctccaacg    1980
gccttcaaca aggacaagct gaactctttc atcacccagt attctactgg ccaagtcagc  2040
gtggagatcg agtgggagct gcagaaggaa aacagcaagc gctgaaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 143         moltype = DNA   length = 2211
FEATURE                Location/Qualifiers
```

```
source                  1..2211
                        mol_type = other DNA
                        organism = synthetic construct
SEQUENCE: 143
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttcctt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgatagtcg gctggctgca atcccaagga  1800
gcgcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctgaaccc gagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 144          moltype = DNA   length = 2211
FEATURE                 Location/Qualifiers
source                  1..2211
                        mol_type = other DNA
                        organism = synthetic construct
SEQUENCE: 144
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttcctt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgataaccg cgctctcca atcacaagga  1800
gcccttccgg gtatggtttg gcaggacaga gatgtgtacc tgcaaggacc catttgggcc  1860
```

```
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 145            moltype = DNA   length = 2211
FEATURE                   Location/Qualifiers
source                    1..2211
                          mol_type = other DNA
                          organism = synthetic construct
SEQUENCE: 145
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggggtatt ttgacttcaa cagattccac tgccactct caccacgtga ctggcagcga    900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg tcggctcac    1080
gagggctgcc tcccgcgctt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttcctttt gtctggatct   1620
ttaattttg caaacaagg aactggaaga gacaacgtgg atgcggacaa agtcatgata    1680
accaacgaag aagaaattaa aactactaac ccggtagcaa cggagtccta tggacaagtg   1740
gccacaaacc accagagtgc ccaagcacag gcgatcgctg gcgcgctcca aagccaagga   1800
gcccttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 146            moltype = DNA   length = 2211
FEATURE                   Location/Qualifiers
source                    1..2211
                          mol_type = other DNA
                          organism = synthetic construct
SEQUENCE: 146
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggggtatt ttgacttcaa cagattccac tgccactct caccacgtga ctggcagcga    900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg tcggctcac    1080
gagggctgcc tcccgcgctt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
```

```
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcaggtcg gctggttgca atcgcaagga  1800
gcccttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 147           moltype = DNA   length = 2211
FEATURE                  Location/Qualifiers
source                   1..2211
                         mol_type = other DNA
                         organism = synthetic construct
SEQUENCE: 147
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aaggggagc cggtcaacgc agcagacgcg gcggcccctcg agcacgacaa ggcctacgac  240
cagcagctca aggccggaga caacccgtac ctcaagtaca ccacgccga cgccgagttc  300
caggagcggc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct  600
cttacaatgc cttcaggtgg tggcgcacca gtggcagaca taacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atctcaaat gacaacgcct acttcggcta cagcaccccc  840
tgggggtatt ttgactcaa cagattccca tgccactcct caccacgtga ctggcagcga  900
ctcatcaaca acaactgggg attccggct aagcgactca acttcaagct cttcaacatt  960
caggtcaaag aggttacgga caacaatgga gtcaagacca tcgccaataa ccttaccagc 1020
acgtccagg tcttcacgga ctcagactat cagctcccgt acgtgctcgg tcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tcccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag gcgcaggtgg gcgccttaca atctcaagga 1800
gctcttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a           2211

SEQ ID NO: 148           moltype = DNA   length = 2211
FEATURE                  Location/Qualifiers
source                   1..2211
                         mol_type = other DNA
                         organism = synthetic construct
SEQUENCE: 148
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aaggggagc cggtcaacgc agcagacgcg gcggcccctcg agcacgacaa ggcctacgac  240
cagcagctca aggccggaga caacccgtac ctcaagtaca ccacgccga cgccgagttc  300
caggagcggc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct  600
cttacaatgc cttcaggtgg tggcgcacca gtggcagaca taacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
```

```
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggagttgtg   1740
gccacaaacc accagagtgc caagcacag gcgattgtcg gctggttgca atcacaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 149          moltype = DNA  length = 2211
FEATURE                 Location/Qualifiers
source                  1..2211
                        mol_type = other DNA
                        organism = synthetic construct
SEQUENCE: 149
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca ccacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc ggtgattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgc ttcaggtgg tggcgcacca gtggcagaca taacgaagg tgccgatgga   660
gtgggtagtt cctcgggaaa ttggcattgc gattccaat ggctggggga cagagtcatt   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggagttgtg   1740
gccacaaacc accagagtgc caagcacag gcgatagtgg gcgcactgca atcacaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 150          moltype = DNA  length = 2211
FEATURE                 Location/Qualifiers
source                  1..2211
                        mol_type = other DNA
                        organism = synthetic construct
SEQUENCE: 150
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
```

-continued

```
cagcagctca aggccggaga caacccgtac ctcaagtaca accacgccga cgccgagttc  300
caggagcggc tcaaagaaga tacgtctttt ggggcaacc tcgggcgagc agtcttccag   360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct   600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc   720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccct 1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct   1620
ttaattttg gcaaacaagg aactggaaga gacaacgtgg atgcggacaa agtcatgata  1680
accaacgaag aagaaattaa aactactaac ccggtagcaa cggagtccta tggagtagtg   1740
gccacaaacc accagagtgc ccaagcacag gcgcaggtcg gcgcactaca aagtcaagga   1800
atacttccgg gtatggtttg gcaggacaga gatgtgtacc tgcaaggacc catttgggcc   1860
aaaaattcctc acacggacgg caactttcac ccttctccgc tgatgggagg gtttggaatg  1920
aagcaccgc ctcctcagat cctcatcaaa acacacctg tacctgcgga tcctccaacg    1980
gccttcaaca aggacaagct gaactctttc atcacccagt attctactgg ccaagtcgac  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 151           moltype = DNA  length = 2211
FEATURE                  Location/Qualifiers
source                   1..2211
                         mol_type = other DNA
                         organism = synthetic construct
SEQUENCE: 151
atggctgccg atggttatct tccagattgg ctcgaggaca accttagtga aggtattcgc  60
gagtggtggg ctttgaaacc tggagcccct caacccaagg caaatcaaca acatcaagac 120
aacgctcgag gtcttgtgct tccggttac aaataccttg gacccggcaa cggactggac  180
aaggggagc cggtcaacgc agcagacgcg gcgccctcg agcacgacaa ggcctacgac  240
cagcagctca aggccggaga caacccgtac ctcaagtaca accacgccga cgccgagttc  300
caggagcggc tcaaagaaga tacgtctttt ggggcaacc tcgggcgagc agtcttccag   360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct   600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc   720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccct 1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct   1620
ttaattttg gcaaacaagg aactggaaga gacaacgtgg atgcggacaa agtcatgata  1680
accaacgaag aagaaattaa aactactaac ccggtagcaa cggagtccta tggagtagtg   1740
gccacaaacc accagagtgc ccaagcacag gcgcaggttg ctggttaca atcgcaagga   1800
atacttccgg gtatggtttg gcaggacaga gatgtgtacc tgcaaggacc catttgggcc   1860
aaaaattcctc acacggacgg caactttcac ccttctccgc tgatgggagg gtttggaatg  1920
aagcaccgc ctcctcagat cctcatcaaa acacacctg tacctgcgga tcctccaacg    1980
gccttcaaca aggacaagct gaactctttc atcacccagt attctactgg ccaagtcgac  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 152           moltype = DNA  length = 2211
```

```
FEATURE                 Location/Qualifiers
source                  1..2211
                        mol_type = other DNA
                        organism = synthetic construct
SEQUENCE: 152
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct   600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt  960
caggtcaaag aggttacgga caacaatgga gtcaagacca cgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaacaagg aactggaaga gacaacgtgg atgcggacaa agtcatgata  1680
accaacgaag aagaaattaa aactactaac ccggtagcaa cggagtccta tggagtcgtg  1740
gccacaaaacc accagagtgc ccaagcacag gcgcaggaa gctggctcca atcccgggcc  1800
gctcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctcccaag  1980
gccttcaaca aggacaagct gaactctttc atcacccagt attctactgg ccaagtcgg  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 153          moltype = DNA   length = 2211
FEATURE                 Location/Qualifiers
source                  1..2211
                        mol_type = other DNA
                        organism = synthetic construct
SEQUENCE: 153
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag cccctcagg tgtgggatct   600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt  960
caggtcaaag aggttacgga caacaatgga gtcaagacca cgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaacaagg aactggaaga gacaacgtgg atgcggacaa agtcatgata  1680
accaacgaag aagaaattaa aactactaac ccggtagcaa cggagtccta tggagtcgtg  1740
gccacaaaacc accagagtgc ccaagcacag gcgataaccg ctggctgca atcccaagga  1800
```

```
gcccttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgcccat tggcaccaga tacctgactc gtaatctgta a              2211

SEQ ID NO: 154          moltype = DNA   length = 2211
FEATURE                 Location/Qualifiers
source                  1..2211
                        mol_type = other DNA
                        organism = synthetic construct
SEQUENCE: 154
atggctgccg atggttatct tccagattgg ctcgaggaca accttagtga aggtattcgc      60
gagtggtggg ctttgaaacc tggagcccct caacccaagg caaatcaaca acatcaagac     120
aacgctcgag gtcttgtgct tccgggttac aaataccttg gacccggcaa cggactcgac     180
aaggggagc cggtcaacgc agcagacgcg gcggcccctg agcacgacaa ggcctacgac     240
cagcagctca aggccggaga caacccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgc cttcaggtgg tggcgcacca gtggcagaca taacgaagg tgccgatgga    660
gtgggtagtt cctcgggaaa ttggcattgc gattcccaat ggctgggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac    1080
gagggctgcc tcccgccgtt cccagcgac gttttcatga ttcctcagta cgggtatctg    1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtca ctcaaaacaa cacagcgaa    1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga cacaacgtgg atgcggacaa agtcatgata   1680
accaacgaag aagaaattaa aactactaac ccggtagcaa cggagtccta tggacaagtg   1740
gccacaaacc accagagtgc ccaagcacag cgcgattgttg gctggctcca atcacaagga   1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgcccat tggcaccaga tacctgactc gtaatctgta a              2211

SEQ ID NO: 155          moltype = DNA   length = 2211
FEATURE                 Location/Qualifiers
source                  1..2211
                        mol_type = other DNA
                        organism = synthetic construct
SEQUENCE: 155
atggctgccg atggttatct tccagattgg ctcgaggaca accttagtga aggtattcgc      60
gagtggtggg ctttgaaacc tggagcccct caacccaagg caaatcaaca acatcaagac     120
aacgctcgag gtcttgtgct tccgggttac aaataccttg gacccggcaa cggactcgac     180
aaggggagc cggtcaacgc agcagacgcg gcggcccctg agcacgacaa ggcctacgac     240
cagcagctca aggccggaga caacccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgc cttcaggtgg tggcgcacca gtggcagaca taacgaagg tgccgatgga    660
gtgggtagtt cctcgggaaa ttggcattgc gattcccaat ggctgggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac    1080
gagggctgcc tcccgccgtt cccagcgac gttttcatga ttcctcagta cgggtatctg    1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
```

```
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct     1620
ttaattttg gcaaacaagg aactggaaga gacaacgtgg atgcggacaa agtcatgata    1680
accaacgaag aagaaattaa aactactaac ccggtagcaa cggagtccta tggagtagtg   1740
gccacaaacc accagagtgc caagcacaag gcgatagtag gcgcggttca atcgcaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 156          moltype = DNA  length = 2211
FEATURE                 Location/Qualifiers
source                  1..2211
                        mol_type = other DNA
                        organism = synthetic construct
SEQUENCE: 156
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcgccctcg agcacgacaa ggcctacgac     240
cagcagctca aggccggaga caaccgtac ctcaagtaca accacgccga cgccgagttc     300
caggagcggc tcaaagaaga tacgtctttt ggggcaacc tcgggcgagc agtcttccag      360
gccaaaaaga ggcttcttga acctcttggt ctggttgaag aagcggctaa gacggctcct   420
ggaaagaaga ggcctgtaga gcagtctcct caggaaccgg actcctcgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct     600
cttacaatgg cttcaggtgg tggcgcacca gtggcagaca taacgaagg tgccgatgga     660
gtgggtagtt cctcggggaaa ttggcattgc gattccaat ggctggggga cagagtcatc    720
accaccagca cccgaacctg ggccctgccc acctacaaca atcacctcta caagcaaatc   780
tccaacagca catctggagg atcttcaat gacaacgcct acttcggcta cagcaccccc     840
tgggggtatt ttgacttcaa cagattccac tgccactct caccacgtga ctggcagcga     900
ctcatcaaca acaactgggg attccgcct aagcgactca acttcaagct cttcaacatt     960
caggtcaaag aggttacgga caacaatgga gtcaagacca tcgccaataa cccttaccagc 1020
acgtccaagg tcttcacgga ctcagactat cagctcccgt acgtgctcgg gtcggctcac  1080
gagggctgcc tcccgccgtt cccagcggac gttttcatga ttcctcagta cgggtatctg   1140
acgcttaatg atggaagcca ggccgtgggt cgttcgtct tttactgcct ggaatattc    1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct    1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc caagcacag gcgatcgtag gctggctaca aaaccaagga    1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 157          moltype = DNA  length = 2211
FEATURE                 Location/Qualifiers
source                  1..2211
                        mol_type = other DNA
                        organism = synthetic construct
SEQUENCE: 157
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcgccctcg agcacgacaa ggcctacgac    240
cagcagctca aggccggaga caaccgtac ctcaagtaca accacgccga cgccgagttc    300
caggagcggc tcaaagaaga tacgtctttt ggggcaacc tcgggcgagc agtcttccag     360
gccaaaaaga ggcttcttga acctcttggt ctggttgaag aagcggctaa gacggctcct   420
ggaaagaaga ggcctgtaga gcagtctcct caggaaccgg actcctcgc gggtattggc    480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcggggaaa ttggcattgc gattccaat ggctggggga cagagtcatc   720
```

```
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgatagtag gcgcgctgca aagtcaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa acacacctg tacctgcgga tcctccaacg   1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 158          moltype = DNA   length = 2211
FEATURE                 Location/Qualifiers
source                  1..2211
                        mol_type = other DNA
                        organism = synthetic construct
SEQUENCE: 158
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggaaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgcagaccg gcgcagttca aaaccaagga  1800
gcccttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa acacacctg tacctgcgga tcctccaacg   1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 159          moltype = DNA   length = 2211
FEATURE                 Location/Qualifiers
source                  1..2211
                        mol_type = other DNA
                        organism = synthetic construct
SEQUENCE: 159
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
```

```
aaggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgataaccg gctggcttca atcgcaagga   1800
gcacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccggc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac ccgccccat tggcaccaga tacctgactc gtaatctgta a             2211

SEQ ID NO: 160          moltype = DNA  length = 2211
FEATURE                 Location/Qualifiers
source                  1..2211
                        mol_type = other DNA
                        organism = synthetic construct
SEQUENCE: 160
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggagtggtg   1740
gccacaaacc accagagtgc ccaagcacag gcgcagaccg cgccttaca atctcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccggc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac ccgccccat tggcaccaga tacctgactc gtaatctgta a             2211
```

```
SEQ ID NO: 161         moltype = DNA   length = 2211
FEATURE                Location/Qualifiers
source                 1..2211
                       mol_type = other DNA
                       organism = synthetic construct
SEQUENCE: 161
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gtttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccy  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tcttcctttt gtctggatct  1620
taatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctggcttca atcccaagga  1800
gcacttccgg gtatggttg gcaggacaga gatgtgtacc tgcaaggacc catttgggcc  1860
aaaattccc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa acagcaagc gctggaaccc ggagatccag  2100
tacacttcca actattacaa gtctaataat gttgaatttg ctgttaatac tgaaggtgta  2160
tatagtgaac ccgccccat ggcaccaga tacctgactc gtaatctgta a            2211

SEQ ID NO: 162         moltype = DNA   length = 2211
FEATURE                Location/Qualifiers
source                 1..2211
                       mol_type = other DNA
                       organism = synthetic construct
SEQUENCE: 162
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gtttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccy  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tcttcctttt gtctggatct  1620
taatttttg gcaaacaagg aactggaaga gacaacgtgg atgcggacaa agtcatgata  1680
accaacgaag aagaaattaa aactactaac ccggtagcaa cggagtccta tggagttgtg  1740
```

```
gccacaaacc accagagtgc ccaagcacag gcgatagtcg gcgcggttca aaaccaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa acacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 163          moltype = DNA  length = 2211
FEATURE                 Location/Qualifiers
source                  1..2211
                        mol_type = other DNA
                        organism = synthetic construct
SEQUENCE: 163
atggctgccg atggttatct tccagattgg ctcgaggaca accttagtga aggtattcgc    60
gagtggtggg ctttgaaacc tggagcccct caacccaagg caaatcaaca acatcaagac   120
aacgctgag gtcttgtgct tccgggttac aaataccttg gacccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt tgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttctgggct caatggac gtaatagctt gatgaatcct     1560
ggacctgcta tggccagcca caaagaagga gaggaccgtt tctttcctt gtctggatct    1620
ttaattttg gcaaacaagg aactggaaga gacaacgtgg atgcgacaa agtcatgata    1680
accaacgaag aagaaattaa aactactaac ccggtagcaa cggagtccta tggacaagtg   1740
gccacaaacc accagagtgc ccaagcacag gcgcagaccg gcgccctgca aagccaagga   1800
gcacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa acacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 164          moltype = DNA  length = 2211
FEATURE                 Location/Qualifiers
source                  1..2211
                        mol_type = other DNA
                        organism = synthetic construct
SEQUENCE: 164
atggctgccg atggttatct tccagattgg ctcgaggaca accttagtga aggtattcgc    60
gagtggtggg ctttgaaacc tggagcccct caacccaagg caaatcaaca acatcaagac   120
aacgctgag gtcttgtgct tccgggttac aaataccttg gacccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt tgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
```

```
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttccttt gtctggatct 1620
ttaatttttg gcaaacaagg aactggaaga gacaacgtgg atgcggacaa agtcatgata 1680
accaacgaag aagaaattaa aactactaac ccggtagcaa cggagtccta tggagtcgtg 1740
gccacaaacc accagagtgc ccaagcacag gcgattaccg gcgctctaca aagtcaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 165        moltype = DNA   length = 2211
FEATURE               Location/Qualifiers
source                1..2211
                      mol_type = other DNA
                      organism = synthetic construct
SEQUENCE: 165
atggctgccg atggttatct tccagattgg ctcgaggaca accttagtga aggtattcgc 60
gagtggtggg ctttgaaacc tggagccccct caacccaagg caaatcaaca acatcaagac 120
aacgctcgag gtcttgtgct tccgggttac aaataccttg acccggcaa cggactcgac 180
aagggggagc cggtcaacgc agcagacgcg gcggccctcg agcacgacaa ggcctacgac 240
cagcagctca aggccggaga caacccgtac ctcaagtaca ccacgccga cgccgagttc 300
caggagcgc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacaatgg cttcaggtgg tggcgcacca gtggcagaca ataacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca acaactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg tcggctcac 1080
gagggctgcc tcccgccgtt cccagcgacc gttttcatga ttcctcagta cggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttccttt gtctggatct 1620
ttaatttttg gcaaacaagg aactggaaga gacaacgtgg atgcggacaa agtcatgata 1680
accaacgaag aagaaattaa aactactaac ccggtagcaa cggagtccta tggagtggtg 1740
gccacaaacc accagagtgc caagcacag gcgcaggttg gcgcgttaca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 166        moltype = DNA   length = 2211
FEATURE               Location/Qualifiers
source                1..2211
                      mol_type = other DNA
                      organism = synthetic construct
SEQUENCE: 166
atggctgccg atggttatct tccagattgg ctcgaggaca accttagtga aggtattcgc 60
gagtggtggg ctttgaaacc tggagccccct caacccaagg caaatcaaca acatcaagac 120
aacgctcgag gtcttgtgct tccgggttac aaataccttg acccggcaa cggactcgac 180
aagggggagc cggtcaacgc agcagacgcg gcggccctcg agcacgacaa ggcctacgac 240
cagcagctca aggccggaga caacccgtac ctcaagtaca ccacgccga cgccgagttc 300
caggagcgc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacaatgg cttcaggtgg tggcgcacca gtggcagaca ataacgaagg tgccgatgga 660
```

```
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tcttttcctttg tctggatct  1620
ttaatttttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag gcgcagaccg gctgggttca atctcaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 167           moltype = DNA   length = 2211
FEATURE                  Location/Qualifiers
source                   1..2211
                         mol_type = other DNA
                         organism = synthetic construct
SEQUENCE: 167
atggctgccg atggttatct tccagattgg ctcgaggaca accttagtga aggtattcgc   60
gagtggtggg cttttgaaacc tggagcccct caacccaagg caaatcaaca acatcaagac  120
aacgctcgag gtcttgtgct tccgggttac aaataccttg acccggcaa cggactcgac  180
aagggggagc cggtcaacgc agcagacgcg gcggccctcg agcacgacaa ggcctacgac  240
cagcagctca aggccggaga caacccgtac ctcaagtaca ccacgccga cgccgagttc  300
caggagcgcc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaagagac tcaatttcg gtcagactgg cgacacagag  540
tcagtcccag accctcaacc aatcggagaa cctcccgcag cccctcagg tgtgggatcc  600
cttacaatgg cttcaggtgg tggcgcacca gtgcagcaa ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tcttttccttt gtctggatct 1620
ttaatttttg gcaaacaagg aactggaaga gacaacgtgg atgcggacaa agtcatgata 1680
accaacgaag aagaaattaa aactactaac ccggtagcaa cggagtccta tggagtagtg 1740
gccacaaacc accagagtgc ccaagcacag gcgcagaccg gctggttgca aaatcaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 168           moltype = DNA   length = 2211
FEATURE                  Location/Qualifiers
source                   1..2211
                         mol_type = other DNA
                         organism = synthetic construct
SEQUENCE: 168
atggctgccg atggttatct tccagattgg ctcgaggaca accttagtga aggtattcgc   60
gagtggtggg cttttgaaacc tggagcccct caacccaagg caaatcaaca acatcaagac  120
```

```
aacgctcgag gtcttgtgct tccgggttac aaataccttg gacccggcaa cggactcgac    180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagtagtg   1740
gccacaaacc accagagtgc ccaagcacag gcgcagaccg gctggctgca atctcaagga   1800
atacttccgg gtatggtttg gcaggacaga gatgtgtacc tgcaaggacc catttgggcc   1860
aaaattcctc acacggacgg caacttttcac ccttctccgc tgatgggagg gttttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 169          moltype = DNA   length = 2211
FEATURE                 Location/Qualifiers
source                  1..2211
                        mol_type = other DNA
                        organism = synthetic construct
SEQUENCE: 169
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg gacccggcaa cggactcgac    180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcaggtcg gctgggttca atcacaagga   1800
gcacttccgg gtatggtttg gcaggacaga gatgtgtacc tgcaaggacc catttgggcc   1860
aaaattcctc acacggacgg caacttttcac ccttctccgc tgatgggagg gttttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

| SEQ ID NO: 170 | moltype = DNA length = 2211 |
| --- | --- |
| FEATURE | Location/Qualifiers |
| source | 1..2211 |
| | mol_type = other DNA |
| | organism = synthetic construct |

SEQUENCE: 170

```
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctgggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt ttgacttcaa cagattccac tgccacttct caccacgtga ctggcagcga    900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacgctc tggacagaa tcaacaaacg   1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttctgggct ctcaatggac gtaatagctt gatgaatcct   1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgattaccg gcgcggttca atctcaagga  1800
atacttccgg gtatggtttg gcaggacaga gatgtgtacc tgcaaggacc catttgggcc  1860
aaaattcctc acacggacgg caacttccac ccttctccgc tgatgggagg gtttggaatg  1920
aagcaccccgc ctcctcagat cctcatcaaa aacacacctg tacctgcgga tcctccaacg  1980
gccttcaaca aggacaagct gaactctttc atcacccagt atagtactgg ccaagtcagc  2040
gtggagatcg agtgggagct gcagaaggaa acagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211
```

| SEQ ID NO: 171 | moltype = DNA length = 2211 |
| --- | --- |
| FEATURE | Location/Qualifiers |
| source | 1..2211 |
| | mol_type = other DNA |
| | organism = synthetic construct |

SEQUENCE: 171

```
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctgggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt ttgacttcaa cagattccac tgccacttct caccacgtga ctggcagcga    900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacgctc tggacagaa tcaacaaacg   1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttctgggct ctcaatggac gtaatagctt gatgaatcct   1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
```

```
accaacgaag aagaaattaa aactactaac ccggtagcaa cggagtccta tggagtagtg   1740
gccacaaacc accagagtgc ccaagcacag gcgcaggttg gctggctgca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 172        moltype = DNA  length = 2211
FEATURE               Location/Qualifiers
source                1..2211
                      mol_type = other DNA
                      organism = synthetic construct
SEQUENCE: 172
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtgcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacgtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatgac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgatcaccg cgccgttca aaaccaagga  1800
gcccttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 173        moltype = DNA  length = 2211
FEATURE               Location/Qualifiers
source                1..2211
                      mol_type = other DNA
                      organism = synthetic construct
SEQUENCE: 173
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtgcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
```

```
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacataccc   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctggcttca atcccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcaccgc ctcctcagat cctcatcaaa aacacacctg tacctgcgga tcctccaacg      1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 174           moltype = DNA   length = 2211
FEATURE                  Location/Qualifiers
source                   1..2211
                         mol_type = other DNA
                         organism = synthetic construct
SEQUENCE: 174
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccgc   840
tgggggtatt ttgacttcaa cagattccgt tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc   1020
acggtcagg tcttcacgga ctcagactat cagctccccg acgtgctcgg tcggctcac     1080
gagggctgcc tccgccgtt cccagcggac gttttcatga ttcctcagta cgggtatctg    1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacataccc   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgatagtag gcgccgttca aaaccaagga   1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcaccgc ctcctcagat cctcatcaaa aacacacctg tacctgcgga tcctccaacg      1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 175           moltype = DNA   length = 2211
FEATURE                  Location/Qualifiers
source                   1..2211
                         mol_type = other DNA
                         organism = synthetic construct
SEQUENCE: 175
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
```

```
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagtggtg   1740
gccacaaacc accagagtgc ccaagcacag gcgataaccg gctggttgca atcccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211

SEQ ID NO: 176          moltype = DNA   length = 2211
FEATURE                 Location/Qualifiers
source                  1..2211
                        mol_type = other DNA
                        organism = synthetic construct SEQUENCE: 176
atggctgccg atggttatct tccagattgg ctcgaggaca accttagtga aggtattcgc     60
gagtggtggg cttttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg cggccctcg agcacgacaa ggcctacgac    240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctctc    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgataccg gctggctaca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211

SEQ ID NO: 177          moltype = DNA   length = 2211
FEATURE                 Location/Qualifiers
source                  1..2211
                        mol_type = other DNA
                        organism = synthetic construct
```

```
SEQUENCE: 177
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa dacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaattttttg gcaaacaagg aactggaaga dacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgatagtcg gcgcactaca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gttggaatgt  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a          2211

SEQ ID NO: 178        moltype = DNA  length = 2211
FEATURE               Location/Qualifiers
source                1..2211
                      mol_type = other DNA
                      organism = synthetic construct
SEQUENCE: 178
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaattttttg gcaaacaagg aactggaaga dacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgcaggtcg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gttggaatgt  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
```

```
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 179          moltype = DNA   length = 2211
FEATURE                 Location/Qualifiers
source                  1..2211
                        mol_type = other DNA
                        organism = synthetic construct
SEQUENCE: 179
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccggggtac aaataccttg acccggcaa cggactcgac     180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggggcaacc tcgggcgagc agtcttccag   360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgc ttcaggtgg tggcgcacca gtggcagaca ataacgaagg tgccgatgga    660
gtgggtagtt cctcgggaaa ttggcattgc gattcccaat ggctgggga cagagtcatc    720
accaccagca cccgaacctg ggccctgccc acctacaaca atcacctcta caagcaaatc    780
tccaacagca catctggagg atcttcaaat gacaacgcct acttcggcta cagcacccc    840
tggggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact gtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctgagcttc ttcttgggct ctcaatggac gtaatagctt gatgaatcct    1560
ggacctgcta tggccagcca caagaagga gaggaccgtt tctttcctt gtctggatct    1620
ttaatttttg gcaaacaagg aactggaaga caacgtgg atgcggacaa agtcatgata    1680
accaacgaag aagaaattaa aactactaac ccggtagcaa cggagtccta tggagtcgtg    1740
gccacaaacc accagagtgc ccaagcacag gcgcaggtgg gcgctgttca atctcaagga    1800
atacttccgg gtatggttg gcaggacaga gatgtgtacc tgcaaggacc catttgggcc    1860
aaaattcctc acacggacgg caactttcac ccttctccgc tgatgggagg gtttggaatg    1920
aagcaccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 180          moltype = DNA   length = 2211
FEATURE                 Location/Qualifiers
source                  1..2211
                        mol_type = other DNA
                        organism = synthetic construct
SEQUENCE: 180
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccggggtac aaataccttg acccggcaa cggactcgac     180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggggcaacc tcgggcgagc agtcttccag   360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctgggga cagagtcatc    720
accaccagca cccgaacctg ggccctgccc acctacaaca atcacctcta caagcaaatc    780
tccaacagca catctggagg atcttcaaat gacaacgcct acttcggcta cagcacccc    840
tggggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact gtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
```

```
tttgcttggc ctggagcttc ttccttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
gcacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa acacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaattg ctgttaatac tgaaggtgta  2160
tatagtgaac cccgccccat tggcaccaga tacctgactc gtaatctgta a            2211

SEQ ID NO: 181           moltype = DNA   length = 2211
FEATURE                  Location/Qualifiers
source                   1..2211
                         mol_type = other DNA
                         organism = synthetic construct
SEQUENCE: 181
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggttac aaataccttg gacccggcaa cggactcgac  180
aaggggagc cggtcaacgc agcagacgcg gcgccctcg agcacgacaa ggcctacgac  240
cagcagctca aggccggaga caacccgtac ctcaagtaca accacgccga cgccgagttc  300
caggagcggc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatattc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccaacaac atggctgctc agggaagaa ctacatacct 1440
ggacccagct accgacaaca acgtgtctca accactgtga ctcaaaacaa caacagcgaa 1500
tttgcttggc ctggagcttc ttccttgggct ctcaatggac gtaatagctt gatgaatcct 1560
ggacctgcta tggccagcca caaagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagttgtg 1740
gccacaaacc accagagtgc ccaagcacag gcgatagtag gcgcagttca aagccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa acacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaattg ctgttaatac tgaaggtgta 2160
tatagtgaac cccgccccat tggcaccaga tacctgactc gtaatctgta a           2211

SEQ ID NO: 182           moltype = DNA   length = 2211
FEATURE                  Location/Qualifiers
source                   1..2211
                         mol_type = other DNA
                         organism = synthetic construct
SEQUENCE: 182
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggttac aaataccttg gacccggcaa cggactcgac  180
aaggggagc cggtcaacgc agcagacgcg gcgccctcg agcacgacaa ggcctacgac  240
cagcagctca aggccggaga caacccgtac ctcaagtaca accacgccga cgccgagttc  300
caggagcggc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
```

```
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atgaagcca ggccgtgggt cgttcgtcct tttactgcct ggaatatttc    1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggagtcgtg   1740
gccacaaacc accagagtgc ccaagcacag gcgattgtgg gctgggttca aaaccaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 183          moltype = DNA  length = 2211
FEATURE                 Location/Qualifiers
source                  1..2211
                        mol_type = other DNA
                        organism = synthetic construct
SEQUENCE: 183
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tggggggtatt ttgacttcaa cagattccac tgccactttt caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atgaagcca ggccgtgggt cgttcgtcct tttactgcct ggaatatttc    1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggagtcgtg   1740
gccacaaacc accagagtgc ccaagcacag gcgcagaccg cgcacttca aaaccaagga    1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 184          moltype = DNA  length = 2211
FEATURE                 Location/Qualifiers
source                  1..2211
                        mol_type = other DNA
                        organism = synthetic construct
SEQUENCE: 184
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
```

```
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaattaa aactactaac ccggtagcaa cggagtccta tggacaagtg  1740
gccacaaacc accagagtgc ccaagcacag cgcagaccg cgcgctgttca aagccaagga   1800
gcacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacactccca actattacaa gtctaataat gttgaatttg ctgttaatac tgaaggtgta  2160
tatagtgaac cccgccccat tggcaccaga tacctgactc gtaatctgta a           2211

SEQ ID NO: 185           moltype = DNA  length = 2211
FEATURE                  Location/Qualifiers
source                   1..2211
                         mol_type = other DNA
                         organism = synthetic construct
SEQUENCE: 185
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggggtac aaataccttg gacccggcaa cggactcgac  180
aaggggggagc cggtcaacgc agcagacgcg gcggccctcg agcagcgacaa ggcctacgac  240
cagcagctca aggccggaga caaccccgtac ctcaagtaca accacgccga cgccgagttc  300
caggagcggc tcaaagaaga tacgtctttt ggggcaacc tcgggcgagc agtcttccag   360
gccaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgcagaccg cgcgctgca aaccaagga    1800
gcacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacactccca actattacaa gtctaataat gttgaatttg ctgttaatac tgaaggtgta  2160
tatagtgaac cccgccccat tggcaccaga tacctgactc gtaatctgta a           2211

SEQ ID NO: 186           moltype = DNA  length = 2211
FEATURE                  Location/Qualifiers
```

```
source                  1..2211
                        mol_type = other DNA
                        organism = synthetic construct
SEQUENCE: 186
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacataccct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaaggga ggagaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag gcgcaggtgg cgcggttcaa atcgcaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccccg ctcctcagat cctcatcaaa acacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaggc gctgaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 187           moltype = DNA  length = 2211
FEATURE                  Location/Qualifiers
source                   1..2211
                         mol_type = other DNA
                         organism = synthetic construct
SEQUENCE: 187
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccggggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacataccct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaaggga ggagaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagtcgtg 1740
gccacaaacc accagagtgc ccaagcacag gcgcaggtgg cgcggttcaa atcacaagga 1800
gctcttccgg gtatggtttg gcaggacaga gatgtgtacc tgcaaggacc catttgggcc 1860
```

```
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211

SEQ ID NO: 188          moltype = DNA   length = 2211
FEATURE                 Location/Qualifiers
source                  1..2211
                        mol_type = other DNA
                        organism = synthetic construct
SEQUENCE: 188
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccggggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca accacgcga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaattttg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccactcct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctcg accactgtga ctcaaaacaa caacagcgaa   1500
tttgcttggc ctggagcttc ttcttggctc tcaatggacg gtaatagctt gatgaatcct   1560
ggacctgcta tggccagcca caagaaggga ggaaccgtt tctttcctt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag cgcagggta gcgccctaca atcgcaagga   1800
atacttccgg gtatggtttg caggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211

SEQ ID NO: 189          moltype = DNA   length = 2211
FEATURE                 Location/Qualifiers
source                  1..2211
                        mol_type = other DNA
                        organism = synthetic construct
SEQUENCE: 189
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccggggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
```

```
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggagttgtg   1740
gccacaaacc accagagtgc caagcacag gcgataaccg cgctctgca aaaccaagga     1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 190        moltype = DNA   length = 2211
FEATURE               Location/Qualifiers
source                1..2211
                      mol_type = other DNA
                      organism = synthetic construct
SEQUENCE: 190
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggcccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgc cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atctcaaat gacaacgcct acttcggcta cagcaccccc   840
tgggggtatt ttgacttcaa cagattccac tgccactct caccacgtga ctggcagcga    900
ctcatcaaca acaactgggg attccggcct aagcgactca acttcaagct cttcaacatt   960
caggtcaaag aggttacgga caacaatgga gtcaagacca tcgccaataa ccttaccagc   1020
acgtccagg tcttcacgga ctcagactat cagctcccgt acgtgctcgg tcgggctcac   1080
gagggctgcc tcccgccgtt cccagccgac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagtca gctgctgagt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggagttgtg   1740
gccacaaacc accagagtgc caagcacag gcgcagaccg gctggctaca aaaccaagga    1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 191        moltype = DNA   length = 2211
FEATURE               Location/Qualifiers
source                1..2211
                      mol_type = other DNA
                      organism = synthetic construct
SEQUENCE: 191
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggcccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgc cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
```

```
tccaacagca catctggagg atcttcaaat gacaacgcct acttcggcta cagcacccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag cgcagaccg ctggctcca aaaccaagga 1800
gctcttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc tcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagc gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a         2211

SEQ ID NO: 192          moltype = DNA  length = 2211
FEATURE                 Location/Qualifiers
source                  1..2211
                        mol_type = other DNA
                        organism = synthetic construct
SEQUENCE: 192
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac  180
aaggggagc cggtcaacgc agcagacgcg gcggccctcg agcacgacaa ggcctacgac  240
cagcagctca aggccggaga caacccgtac ctcaagtaca ccacgccga cgccgagttc  300
caggagcggc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggctgtaga gcagtctcct caggaaccgg actcctccgc cggtgattgc  480
aaatcgggtg cacagcccgc taaaaagaga ctcaatttcg gtcagactgg cgacacagag  540
tcagtcccag accctcaacc aatcggaaaa cctcccgcag ccccctcagg tgtgggatct  600
cttacaatgc ttcaggtgg tggcgcacca gtggcagaca taacgaagg tgccgatgga  660
gtgggtagtt cctcgggaaa ttggcattgc gattcccaat ggctggggga cagagtcagc  720
accaccagca cccgaacctg ggccctgccc acctacaaca atcacctcta caagcaaatc  780
tccaacagca catctggagg atcttcaaat gacaacgcct acttcggcta cagcacccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caaagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag cgcaggtcg gcgcgcttca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc tcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagc gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a         2211

SEQ ID NO: 193          moltype = DNA  length = 2211
FEATURE                 Location/Qualifiers
source                  1..2211
                        mol_type = other DNA
                        organism = synthetic construct
SEQUENCE: 193
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac  180
aaggggagc cggtcaacgc agcagacgcg gcggccctcg agcacgacaa ggcctacgac  240
```

```
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcacccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacataccct   1440
ggacccagct accgacaaca acgtgtctca accactgtga ctcaaaacaa caacagcgaa    1500
tttgcttggc ctgagcttc ttcttgggct ctcaatggac gtaatagctt gatgaatcct     1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc caagcacag gcgcaggtag gcgcttaca aaaccaagga     1800
gctcttccgg gtatggtttg gcaggacaga gatgtgtacc tgcaaggacc catttgggcc    1860
aaaaattcctc acacggacgg caactttcac ccttctccgc tgatgggagg gtttggaatg    1920
aagcaccgc ctcctcagat cctcatcaaa aacacacctg tacctgcgga tcctccaacg     1980
gccttcaaca aggacaagct gaactctttc atcacccagt attctactgg ccaagtcgga    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 194        moltype = DNA  length = 2211
FEATURE               Location/Qualifiers
source                1..2211
                      mol_type = other DNA
                      organism = synthetic construct
SEQUENCE: 194
atggctgccg atggttatct tccagattgg ctcgaggaca accttagtga aggtattcgc      60
gagtggtggg ctttgaaacc tggagcccct caacccaagg caaatcaaca acatcaagac     120
aacgctcgag gtcttgtgct tccggttac aaataccttg gacccggcaa cggactcgac      180
aaggggagc cggtcaacgc agcagacgcg gcgccctcg agcacgacaa ggcctacgac       240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcacccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacataccct   1440
ggacccagct accgacaaca acgtgtctca accactgtga ctcaaaacaa caacagcgaa    1500
tttgcttggc ctgagcttc ttcttgggct ctcaatggac gtaatagctt gatgaatcct     1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggagtagtg    1740
gccacaaacc accagagtgc caagcacag gcgataaccg gctgggttca agccaagga     1800
atacttccgg gtatggtttg gcaggacaga gatgtgtacc tgcaaggacc catttgggcc    1860
aaaaattcctc acacggacgg caactttcac ccttctccgc tgatgggagg gtttggaatg    1920
aagcaccgc ctcctcagat cctcatcaaa aacacacctg tacctgcgga tcctccaacg     1980
gccttcaaca aggacaagct gaactctttc atcacccagt attctactgg ccaagtcgga    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

SEQ ID NO: 195        moltype = DNA  length = 2211
```

```
FEATURE              Location/Qualifiers
source               1..2211
                     mol_type = other DNA
                     organism = synthetic construct
SEQUENCE: 195
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca ccacgccga cgccgagttc    300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttcctt gtctggatct   1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgattgttg gctgggttca aaaccaagga  1800
gctcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg   1980
gccttcaaca aggacaagct gaactctttc atcacccagt attctactgg ccaagtccgt  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 196       moltype = DNA  length = 2211
FEATURE              Location/Qualifiers
source               1..2211
                     mol_type = other DNA
                     organism = synthetic construct
SEQUENCE: 196
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca ccacgccga cgccgagttc    300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttcctt gtctggatct   1620
ttaatttttg gcaaacaagg aactggaaga gacaacgtgg atgcggacaa agtcatgata  1680
accaacgaag aagaaattaa aactactaac ccggtagcaa cggagtccta tggagttgtg  1740
gccacaaacc accagagtgc ccaagcacag gcgcaggtgg gcgcgctgca aaaccaagga  1800
```

```
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 197          moltype = DNA   length = 2211
FEATURE                 Location/Qualifiers
source                  1..2211
                        mol_type = other DNA
                        organism = synthetic construct
SEQUENCE: 197
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac     180
aaggggagc cggtcaacgc agcagacgcg gcggccctcg agcacgacaa ggcctacgac     240
cagcagctca aggccggaga caacccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca taacgaaggg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggtatt ttgacttcaa cagattccac tgccacttct caccacgtga ctggcagcga    900
ctcatcaaca caactgggg atttccggct aagcgactca cttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tcctctcatc   1320
gaccaatact gtactatct ctcaaagact attaacggt ctggacagaa tcaacaaacg   1380
ctaaaattca gtgtggccgg acccagcaac atggctgtcc agggaagaaa ctacatacct   1440
ggacccagct accgacaaca acgtgtctca accactgtca ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagttgta   1740
gccacaaacc accagagtgc ccaagcacag gcgcagaccg gcgctgttca aagtcaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 198          moltype = DNA   length = 2211
FEATURE                 Location/Qualifiers
source                  1..2211
                        mol_type = other DNA
                        organism = synthetic construct
SEQUENCE: 198
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac     180
aaggggagc cggtcaacgc agcagacgcg gcggccctcg agcacgacaa ggcctacgac     240
cagcagctca aggccggaga caacccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca taacgaaggg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggtatt ttgacttcaa cagattccac tgccacttct caccacgtga ctggcagcga    900
ctcatcaaca caactgggg atttccggct aagcgactca cttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
```

```
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc caagcacag cgcagaccg cgctctcca atcgcaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 199          moltype = DNA   length = 2211
FEATURE                 Location/Qualifiers
source                  1..2211
                        mol_type = other DNA
                        organism = synthetic construct
SEQUENCE: 199
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaatacttg gacccggcaa cggactcgac  180
aaggggagc cggtcaacgc agcagacgcg gcgccctcg agcacgacaa ggcctacgac   240
cagcagctca aggccggaga caaccgtac ctcaagtaca accacgccga cgccgagttc   300
caggagcggc tcaaagaaga tacgtctttt ggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctcgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct  600
cttacaatgg cttcaggtgg tggcgcacca gtggcagaca ataacgaagg tgccgatgga  660
gtgggtagtt cctcgggaaa ttggcattgc gattccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt ttgacttcaa cagattccac tgccactct caccacgtga ctggcagcga   900
ctcatcaaca acaactgggg attccgcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatattc  1200
ccgtcgcaaa tgctaagaac gggtaacaac ttccagttca gctacgagtt tgagaacgta  1260
cctttccata gcagctacgc tcacagccaa agccgggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagttgtg  1740
gccacaaacc accagagtgc caagcacag cgcagaccg ctgggttca atcgcaagga   1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 200          moltype = DNA   length = 2211
FEATURE                 Location/Qualifiers
source                  1..2211
                        mol_type = other DNA
                        organism = synthetic construct
SEQUENCE: 200
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaatacttg gacccggcaa cggactcgac  180
aaggggagc cggtcaacgc agcagacgcg gcgccctcg agcacgacaa ggcctacgac   240
cagcagctca aggccggaga caaccgtac ctcaagtaca accacgccga cgccgagttc   300
caggagcggc tcaaagaaga tacgtctttt ggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctcgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct  600
cttacaatgg cttcaggtgg tggcgcacca gtggcagaca ataacgaagg tgccgatgga  660
gtgggtagtt cctcgggaaa ttggcattgc gattccaat ggctggggga cagagtcatc   720
```

```
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagtggtg   1740
gccacaaacc accagagtgc ccaagcacag gcgatcaccg gcgcagttca atcccaagga   1800
gcgcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 201         moltype = DNA  length = 2211
FEATURE                Location/Qualifiers
source                 1..2211
                       mol_type = other DNA
                       organism = synthetic construct
SEQUENCE: 201
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccggggttac aaataccttg acccggcaa cggactcgac    180
aagggggagc cggtcaacgc agcagacgcg gcgcccctcg agcacgacaa ggcctacgac    240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagtggtg   1740
gccacaaacc accagagtgc ccaagcacag gcgcaggtgg gcgccgttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 202         moltype = DNA  length = 2211
FEATURE                Location/Qualifiers
source                 1..2211
                       mol_type = other DNA
                       organism = synthetic construct
SEQUENCE: 202
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccggggttac aaataccttg acccggcaa cggactcgac    180
```

```
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaaattaa aactactaac ccggtagcaa cggagtccta tggacaagtg   1740
gccacaaacc accagagtgc ccaagcacag gcgcaggtag gcgccgttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 203              moltype = DNA   length = 2211
FEATURE                     Location/Qualifiers
source                      1..2211
                            mol_type = other DNA
                            organism = synthetic construct
SEQUENCE: 203
atggctgccg atggttatct tccagattgg ctcgaggaca accttagtga aggtattcgc    60
gagtggtggg cctttgaaacc tggagccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaatttttg gcaaacaagg aactggaaga gacaacgtgg atgcggacaa agtcatgata   1680
accaacgaag aagaaaattaa aactactaac ccggtagcaa cggagtccta tggacaagtg   1740
gccacaaacc accagagtgc ccaagcacag gcgatcgtgg ctgggttca atcgcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

| SEQ ID NO: 204 | moltype = DNA length = 2211 |
| --- | --- |
| FEATURE | Location/Qualifiers |
| source | 1..2211 |
| | mol_type = other DNA |
| | organism = synthetic construct |

SEQUENCE: 204

```
atggctgccg atggttatct tccagattgg ctcgaggaca accttagtga aggtattcgc  60
gagtggtggg ctttgaaacc tggagcccct caacccaagg caaatcaaca acatcaagac 120
aacgctcgag gtcttgtgct tccggggttac aaataccttg gacccggcaa cggactcgac 180
aaggggggagc cggtcaacgc agcagacgcg gcggccctcg agcacgacaa ggcctacgac 240
cagcagctca aggccggaga caacccgtac ctcaagtaca accacgccga cgccgagttc 300
caggagcggc tcaaagaaga tacgtctttt ggggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacaatgg cttcaggtgg tggcgcacca gtggcagaca taacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca caactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacataccct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagtggtg 1740
gccacaaacc accagagtgc ccaagcacag gcgatcaccg gctgggttca aaaccaagga 1800
gctcttccgg gtatggtttg gcaggacaga gatgtgtacc tgcaaggacc catttgggcc 1860
aaaattcctc acacggacgg caacttcac ccttctccgc tgatgggagg gtttggaatg 1920
aagcacccgc ctccctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac ccgcccccat tggcaccaga tacctgactc gtaatctgta a         2211
```

| SEQ ID NO: 205 | moltype = DNA length = 2211 |
| --- | --- |
| FEATURE | Location/Qualifiers |
| source | 1..2211 |
| | mol_type = other DNA |
| | organism = synthetic construct |

SEQUENCE: 205

```
atggctgccg atggttatct tccagattgg ctcgaggaca accttagtga aggtattcgc  60
gagtggtggg ctttgaaacc tggagcccct caacccaagg caaatcaaca acatcaagac 120
aacgctcgag gtcttgtgct tccggggttac aaataccttg gacccggcaa cggactcgac 180
aaggggggagc cggtcaacgc agcagacgcg gcggccctcg agcacgacaa ggcctacgac 240
cagcagctca aggccggaga caacccgtac ctcaagtaca accacgccga cgccgagttc 300
caggagcggc tcaaagaaga tacgtctttt ggggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacaatgg cttcaggtgg tggcgcacca gtggcagaca taacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca caactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacataccct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
```

| | | | |
|---|---|---|---|
| gccacaaacc | accagagtgc | ccaagcacag | gcgcagaccg gctgggttca atctcaagga | 1800 |
| gcccttccgg | gtatggtttg | gcaggacaga | gatgtgtacc tgcaaggacc catttgggcc | 1860 |
| aaaattcctc | acacggacgg | caactttcac | ccttctccgc tgatgggagg gtttggaatg | 1920 |
| aagcaccgc | ctcctcagat | cctcatcaaa | acacacctg tacctgcgga tcctccaacg | 1980 |
| gccttcaaca | aggacaagct | gaactctttc | atcacccagt attctactgg ccaagtcagc | 2040 |
| gtggagatcg | agtgggagct | gcagaaggaa | aacagcaagc gctggaaccc ggagatccag | 2100 |
| tacacttcca | actattacaa | gtctaataat | gttgaatttg ctgttaatac tgaaggtgta | 2160 |
| tatagtgaac | cccgccccat | tggcaccaga | tacctgactc gtaatctgta a | 2211 |

```
SEQ ID NO: 206        moltype = DNA   length = 2211
FEATURE               Location/Qualifiers
source                1..2211
                      mol_type = other DNA
                      organism = synthetic construct
SEQUENCE: 206
```

| | | | |
|---|---|---|---|
| atggctgccg | atggttatct | tccagattgg | ctcgaggaca accttagtga aggtattcgc | 60 |
| gagtggtggg | ctttgaaacc | tggagcccct | caacccaagg caaatcaaca acatcaagac | 120 |
| aacgctcgag | gtcttgtgct | tccgggttac | aaataccttg gacccggcaa cggactcgac | 180 |
| aaggggagc | cggtcaacgc | agcagacgcg | gcggccctcg agcacgacaa ggcctacgac | 240 |
| cagcagctca | aggccggaga | caacccgtac | ctcaagtaca accacgccga cgccgagttc | 300 |
| caggagcggc | tcaaagaaga | tacgtctttt | ggggcaacc tcgggcgagc agtcttccag | 360 |
| gccaaaaaga | ggcttcttga | acctcttggt | ctggttgagg aagcggctaa gacggctcct | 420 |
| ggaaagaaga | ggcctgtaga | gcagtctcct | caggaaccgg actcctccgc gggtattggc | 480 |
| aaatcgggtg | cacagcccgc | taaaaagaga | ctcaatttcg gtcagactgg cgacacagag | 540 |
| tcagtcccag | accctcaacc | aatcggagaa | cctcccgcag cccctcagg tgtgggatct | 600 |
| cttacaatgg | cttcaggtgg | tggcgcacca | gtggcagaca ataacgaagg tgccgatgga | 660 |
| gtgggtagtt | cctcgggaaa | ttggcattgc | gattcccaat ggctggggga cagagtcatc | 720 |
| accaccagca | cccgaacctg | ggccctgccc | acctacaaca atcacctcta caagcaaatc | 780 |
| tccaacagca | catctggagg | atcttcaaat | gacaacgcct acttcggcta cagcaccccc | 840 |
| tgggggtatt | ttgacttcaa | cagattccac | tgccactcct caccacgtga ctggcagcga | 900 |
| ctcatcaaca | acaactgggg | attccggcct | aagcgactca acttcaagct cttcaacatt | 960 |
| caggtcaaag | aggttacgga | caacaatgga | gtcaagacca tcgccaataa ccttaccagc | 1020 |
| acggtccagg | tcttcacgga | ctcagactat | cagctcccgt acgtgctcgg gtcggctcac | 1080 |
| gagggctgcc | tcccgccgtt | cccagcggac | gttttcatga ttcctcagta cgggtatctg | 1140 |
| acgcttaatg | atggaagcca | ggccgtgggt | cgttcgtcct tttactgcct ggaatatttc | 1200 |
| ccgtcgcaaa | tgctaagaac | gggtaacaac | ttccagttca gctacgagtt tgagaacgta | 1260 |
| cctttccata | gcagctacgc | tcacagccaa | agcctggacc gactaatgaa tccactcatc | 1320 |
| gaccaatact | tgtactatct | ctcaaagact | attaacggtt ctggacagaa tcaacaaacg | 1380 |
| ctaaaattca | gtgtggccgg | acccgacaac | atggctgtcc agggaagaaa ctacatacct | 1440 |
| ggacccagct | accgacaaca | acgtgtctca | accactgtga ctcaaaacaa caacagcgaa | 1500 |
| tttgcttggc | ctgagcttc | ttctgggct | ctcaatggac gtaatagctt gatgaatcct | 1560 |
| ggacctgcta | tggccagcca | caagaagga | gaggaccgtt tctttcctttt gtctggatct | 1620 |
| ttaattttg | gcaaacaagg | aactggaaga | gacaacgtga atgcggacaa agtcatgata | 1680 |
| accaacgaag | aagaaattaa | aactactaac | ccggtagcaa cggagtccta tggacaagtg | 1740 |
| gccacaaacc | accagagtgc | ccaagcacag | gcgattgttg gctgggttca atcacaagga | 1800 |
| gcgcttccgg | gtatggtttg | gcaggacaga | gatgtgtacc tgcaaggacc catttgggcc | 1860 |
| aaaattcctc | acacggacgg | caactttcac | ccttctccgc tgatgggagg gtttggaatg | 1920 |
| aagcaccgc | ctcctcagat | cctcatcaaa | acacacctg tacctgcgga tcctccaacg | 1980 |
| gccttcaaca | aggacaagct | gaactctttc | atcacccagt attctactgg ccaagtcagc | 2040 |
| gtggagatcg | agtgggagct | gcagaaggaa | aacagcaagc gctggaaccc ggagatccag | 2100 |
| tacacttcca | actattacaa | gtctaataat | gttgaatttg ctgttaatac tgaaggtgta | 2160 |
| tatagtgaac | cccgccccat | tggcaccaga | tacctgactc gtaatctgta a | 2211 |

```
SEQ ID NO: 207        moltype = DNA   length = 2211
FEATURE               Location/Qualifiers
source                1..2211
                      mol_type = other DNA
                      organism = synthetic construct
SEQUENCE: 207
```

| | | | |
|---|---|---|---|
| atggctgccg | atggttatct | tccagattgg | ctcgaggaca accttagtga aggtattcgc | 60 |
| gagtggtggg | ctttgaaacc | tggagcccct | caacccaagg caaatcaaca acatcaagac | 120 |
| aacgctcgag | gtcttgtgct | tccgggttac | aaataccttg gacccggcaa cggactcgac | 180 |
| aaggggagc | cggtcaacgc | agcagacgcg | gcggccctcg agcacgacaa ggcctacgac | 240 |
| cagcagctca | aggccggaga | caacccgtac | ctcaagtaca accacgccga cgccgagttc | 300 |
| caggagcggc | tcaaagaaga | tacgtctttt | ggggcaacc tcgggcgagc agtcttccag | 360 |
| gccaaaaaga | ggcttcttga | acctcttggt | ctggttgagg aagcggctaa gacggctcct | 420 |
| ggaaagaaga | ggcctgtaga | gcagtctcct | caggaaccgg actcctccgc gggtattggc | 480 |
| aaatcgggtg | cacagcccgc | taaaaagaga | ctcaatttcg gtcagactgg cgacacagag | 540 |
| tcagtcccag | accctcaacc | aatcggagaa | cctcccgcag cccctcagg tgtgggatct | 600 |
| cttacaatgg | cttcaggtgg | tggcgcacca | gtggcagaca ataacgaagg tgccgatgga | 660 |
| gtgggtagtt | cctcgggaaa | ttggcattgc | gattcccaat ggctggggga cagagtcatc | 720 |
| accaccagca | cccgaacctg | ggccctgccc | acctacaaca atcacctcta caagcaaatc | 780 |
| tccaacagca | catctggagg | atcttcaaat | gacaacgcct acttcggcta cagcaccccc | 840 |
| tgggggtatt | ttgacttcaa | cagattccac | tgccactcct caccacgtga ctggcagcga | 900 |
| ctcatcaaca | acaactgggg | attccggcct | aagcgactca acttcaagct cttcaacatt | 960 |
| caggtcaaag | aggttacgga | caacaatgga | gtcaagacca tcgccaataa ccttaccagc | 1020 |
| acggtccagg | tcttcacgga | ctcagactat | cagctcccgt acgtgctcgg gtcggctcac | 1080 |
| gagggctgcc | tcccgccgtt | cccagcggac | gttttcatga ttcctcagta cgggtatctg | 1140 |
| acgcttaatg | atggaagcca | ggccgtgggt | cgttcgtcct tttactgcct ggaatatttc | 1200 |

```
cgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcaagaca gcgctgttca atcgcaagga   1800
gcacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 208           moltype = DNA  length = 2211
FEATURE                  Location/Qualifiers
source                   1..2211
                         mol_type = other DNA
                         organism = synthetic construct
SEQUENCE: 208
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcgc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcaccccc   840
tgggggtatt ttgacttcaa cagattccac tgccactct caccacgtga ctggcagcga   900
ctcatcaaca caactggggg attccgcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcgacc gttttcatga ttcctcagta cgggtatctg  1140
acgcttaatg atggaagcca ggccgtgggt cgttcgtcct tttactgct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgattgttg gctggttgca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 209           moltype = DNA  length = 2211
FEATURE                  Location/Qualifiers
source                   1..2211
                         mol_type = other DNA
                         organism = synthetic construct
SEQUENCE: 209
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcgc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
```

```
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccactcct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttccata gcagctacgc tcacagccaa agcctggacc gactaatgaa tccactcatc    1320
gaccaatact tgtactatct ctcaaagact attaacggtt ctggacagaa tcaacaaacg   1380
ctaaaattca gtgtggccgg acccagcaac atggctgtcc agggagaaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttcctt gtctggatct    1620
ttaattttg gcaaacaagg aactggaaga gacaacgtgg atgcggacaa agtcatgata   1680
accaacgaag aagaaattaa aactactaac ccggtagcaa cggagtccta tggagtagtg   1740
gccacaaacc accagagtgc ccaagcacag cgcgattgtcg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgcccccat tggcaccaga tacctgactc gtaatctgta a            2211

SEQ ID NO: 210          moltype = DNA   length = 2211
FEATURE                 Location/Qualifiers
source                  1..2211
                        mol_type = other DNA
                        organism = synthetic construct
SEQUENCE: 210
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac     180
aagggggagc cggtcaacgc agcagacgcg gcggccctcg agcacgacaa ggcctacgac    240
cagcagctca aggccggaga caacccgtac ctcaagtaca ccacgccga cgccgagttc    300
caggagcgc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggtg cacagcccgc taaaagaga ctcaatttcg gtcagactgg cgacacagag    540
tcagtcccag accctcaacc aatcggagaa cctccccgcag ccccctcagg tgtgggatct   600
cttacaatgg cttcaggtgg tggcgcacca gtgcagacaa ataacgaagg tgccgatgga   660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccactcct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttccata gcagctacgc tcacagccaa agcctggacc gactaatgaa tccactcatc    1320
gaccaatact tgtactatct ctcaaagact attaacggtt ctggacagaa tcaacaaacg   1380
ctaaaattca gtgtggccgg acccagcaac atggctgtcc agggagaaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag cgcaggtgg gctggctcca atcgcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgcccccat tggcaccaga tacctgactc gtaatctgta a            2211

SEQ ID NO: 211          moltype = DNA   length = 2211
FEATURE                 Location/Qualifiers
source                  1..2211
                        mol_type = other DNA
                        organism = synthetic construct
SEQUENCE: 211
atggctgccg atggttatct tccagattgg ctcgaggaca accttagtga aggtattcgc     60
gagtggtggg ctttgaaacc tggagcccct caacccaagg caaatcaaca acatcaagac    120
```

```
aacgctcgag gtcttgtgct tccgggttac aaataccttg gacccggcaa cggactcgac    180
aagggggagc cggtcaacgc agcagacgcg gcggcccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcaggttg gctggctcca aaaccaagga    1800
gcccttccgg gtatggtttg gcaggacaga gatgtgtacc tgcaaggacc catttgggcc    1860
aaaattcctc acacggacgg caacttttcac ccttctccgc tgatggaagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa acagcaagc gctggaaccc ggagatccag    2100
tacacttcca actattacaa gtctaataat gttgaatttg ctgttaatac tgaaggtgta    2160
tatagtgaac ccgccccat tggcaccaga tacctgactc gtaatctgta a              2211

SEQ ID NO: 212       moltype = DNA   length = 2211
FEATURE              Location/Qualifiers
source               1..2211
                     mol_type = other DNA
                     organism = synthetic construct
SEQUENCE: 212
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg gacccggcaa cggactcgac    180
aagggggagc cggtcaacgc agcagacgcg gcggcccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgataaccg gctggctcca atcacaagga    1800
atacttccgg gtatggtttg gcaggacaga gatgtgtacc tgcaaggacc catttgggcc    1860
aaaattcctc acacggacgg caacttttcac ccttctccgc tgatggaagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa acagcaagc gctggaaccc ggagatccag    2100
tacacttcca actattacaa gtctaataat gttgaatttg ctgttaatac tgaaggtgta    2160
tatagtgaac ccgccccat tggcaccaga tacctgactc gtaatctgta a              2211
```

| SEQ ID NO: 213 | moltype = DNA  length = 2211 |
| --- | --- |
| FEATURE | Location/Qualifiers |
| source | 1..2211 |
| | mol_type = other DNA |
| | organism = synthetic construct |

SEQUENCE: 213

```
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aaggggagc cggtcaacgc agcagacgcg gcggccctcg agcacgacaa ggcctacgac   240
cagcagctca aggccggaga caacccgtac ctcaagtaca accacgccga cgccgagttc  300
caggagcggc tcaaagaaga tacgtctttt ggggcaacc tcgggcgagc agtcttccag   360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttcc accacgtga ctggcagcga   900
ctcatcaaca caactggggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctgagcttc ttctgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagttgtg 1740
gccacaaacc accagagtgc ccaagcacag gcgataccg ctggttgca aaaccaagga  1800
gcccttccgg gtatggttg gcaggacaga gatgtgtacc tgcaaggacc catttgggcg 1860
aaaattcctc acacggacgg caactttcac ccttctccgg tgggagg gtttggaatg   1920
aagcaccgc ctcctcagat cctcatcaaa aacacctg tacctgcga tcctccaacg    1980
gccttcaaca aggacaagct gaactctttc atcacccagt attctactgg ccaagtcagc 2040
gtggagatcg agtgggagct gcagaaggaa acagcaagc gctggaaccc ggagatccag 2100
tacacttcca actattacaa gtctaataat gttgaattg ctgttaatac tgaaggtgta   2160
tatagtgaac cccgcccat tggcaccaga tacctgactc gtaatctgta a             2211
```

| SEQ ID NO: 214 | moltype = DNA  length = 2211 |
| --- | --- |
| FEATURE | Location/Qualifiers |
| source | 1..2211 |
| | mol_type = other DNA |
| | organism = synthetic construct |

SEQUENCE: 214

```
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aaggggagc cggtcaacgc agcagacgcg gcggccctcg agcacgacaa ggcctacgac   240
cagcagctca aggccggaga caacccgtac ctcaagtaca accacgccga cgccgagttc  300
caggagcggc tcaaagaaga tacgtctttt ggggcaacc tcgggcgagc agtcttccag   360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactggggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctgagcttc ttctgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
```

```
accaacgaag aagaaattaa aactactaac ccggtagcaa cggagtccta tggagtggtg   1740
gccacaaacc accagagtgc ccaagcacag gcgcagaccg gctggctaca aaaccaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 215          moltype = DNA   length = 2211
FEATURE                 Location/Qualifiers
source                  1..2211
                        mol_type = other DNA
                        organism = synthetic construct
SEQUENCE: 215
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcgg tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtgcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tcccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggacctt tctttcctt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgataaccg cgctctaca aaaccaagga  1800
gcccttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 216          moltype = DNA   length = 2211
FEATURE                 Location/Qualifiers
source                  1..2211
                        mol_type = other DNA
                        organism = synthetic construct
SEQUENCE: 216
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caaccccgtac ctcaagtaca ccacgccga cgccgagttc   300
caggagcggt caaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtgcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
```

```
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgctc agggaagaaa ctacataccct   1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct      1620
ttaattttg gcaaacaagg aactggaaga gacaacgtgg atgcggacaa agtcatgata      1680
accaacgaag aagaaattaa aactactaac ccggtagcaa cggagtccta tggacaagtg    1740
gccacaaacc accagagtgc ccaagcacag cgcatcgttg gcgcgttaca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcaccgc ctcctcagat cctcatcaaa aacacacctg tacctgcgga tcctccaacg     1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta     2160
tatagtgaac cccgccccat tggcaccaga tacctgactc gtaatctgta a             2211

SEQ ID NO: 217        moltype = DNA   length = 2211
FEATURE               Location/Qualifiers
source                1..2211
                      mol_type = other DNA
                      organism = synthetic construct
SEQUENCE: 217
atggctgccg atggttatct tccagattgg ctcgaggaca accttagtga aggtattcgc      60
gagtggtggg ctttgaaacc tggagcccct caacccaagg caaatcaaca acatcaagac    120
aacgctcgag gtcttgtgct tccgggttac aaataccttg acccggcaa cggactcgac     180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggtg cacagcccgc taaaaagaga ctcaatttcg gtcagactgg cgacacagag     540
tcagtcccag accctcaacc aatcggagaa cctcccgcag cccctcagg tgtgggatct      600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacataccct   1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct      1620
ttaattttg gcaaacaagg aactggaaga gacaacgtgg atgcggacaa agtcatgata      1680
accaacgaag aagaaattaa aactactaac ccggtagcaa cggagtccta tggagtagtg    1740
gccacaaacc accagagtgc ccaagcacag cgcagggtca gctgggttca atctcaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcaccgc ctcctcagat cctcatcaaa aacacacctg tacctgcgga tcctccaacg     1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta     2160
tatagtgaac cccgccccat tggcaccaga tacctgactc gtaatctgta a             2211

SEQ ID NO: 218        moltype = DNA   length = 2211
FEATURE               Location/Qualifiers
source                1..2211
                      mol_type = other DNA
                      organism = synthetic construct
SEQUENCE: 218
atggctgccg atggttatct tccagattgg ctcgaggaca accttagtga aggtattcgc      60
gagtggtggg ctttgaaacc tggagcccct caacccaagg caaatcaaca acatcaagac    120
aacgctcgag gtcttgtgct tccgggttac aaataccttg acccggcaa cggactcgac     180
aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggtg cacagcccgc taaaaagaga ctcaatttcg gtcagactgg cgacacagag     540
tcagtcccag accctcaacc aatcggagaa cctcccgcag cccctcagg tgtgggatct      600
```

```
cttacaatgg cttcaggtgg tggcgcacca gtggcagaca ataacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca acaactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc caagcacag gcgataaccg gcgcagttca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 219          moltype = DNA   length = 2211
FEATURE                 Location/Qualifiers
source                  1..2211
                        mol_type = other DNA
                        organism = synthetic construct
SEQUENCE: 219
atggctgccg atggttatct tccagattgg ctcgaggaca accttagtga aggtattcgc 60
gagtggtggg cttttgaaacc tggagcccct caacccaagg caaatcaaca acatcaagac 120
aacgctcgag gtcttgtgct tccgggttac aaataccttg acccggcaa cggactcgac 180
aagggggagc cggtcaacgc agcagacgcg cggccctcg agcacgacaa ggcctacgac 240
cagcagctca aggccggaga caacccgtac ctcaagtaca ccacgccga cgccgagttc 300
caggagcggc tcaaagaaga tacgtctttt ggggcaacc tcgggcgagc agtcttccag 360
gccaaaaaga ggcttcttga acctcttggt ctggttgagg aagcggctaa gacggctcgc 420
ggaaagaaga ggcctgtaga gcagtctcct caggaaccgg actcctccgc gggtattggc 480
aaatcgggtg cacagcccgc taaaagagac ctcaatttcg gtcagactgg cgacacagag 540
tcagtcccag accctcaacc aatcggagaa cctcccgcag cccctcagg tgtgggatct 600
cttacaatgg cttcaggtgg tggcgcacca gtggcagaca ataacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca acaactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagttgtg 1740
gccacaaacc accagagtgc caagcacag gcgatagtcg gctgggttca atcccaagga 1800
gcgcttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 220          moltype = DNA   length = 2211
FEATURE                 Location/Qualifiers
source                  1..2211
                        mol_type = other DNA
                        organism = synthetic construct
```

```
SEQUENCE: 220
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggagtagtg  1740
gccacaaacc accagagtgc ccaagcacag gcgcagaccg gctgggttca aaaccaagga  1800
gcacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 221    moltype = DNA  length = 2211
FEATURE           Location/Qualifiers
source            1..2211
                  mol_type = other DNA
                  organism = synthetic construct
SEQUENCE: 221
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggagtagtg  1740
gccacaaacc accagagtgc ccaagcacag gcgatcgtag ctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
```

```
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 222          moltype = DNA   length = 2211
FEATURE                 Location/Qualifiers
source                  1..2211
                        mol_type = other DNA
                        organism = synthetic construct
SEQUENCE: 222
atggctgccg atggttatct tccagattgg ctcgaggaca accttagtga aggtattcgc 60
gagtggtggg ctttgaaacc tggagcccct caacccaagg caaatcaaca acatcaagac 120
aacgctcgag gtcttgtgct tccggggttac aaataccttg acccggcaa cggactcgac 180
aaggggggagc cggtcaacgc agcagacgcg gcggccctcg agcacgacaa ggcctacgac 240
cagcagctca aggccggaga caacccgtac ctcaagtaca accacgccga cgccgagttc 300
caggagcggc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaagagaa ctcaatttcg gtcagactgg cgacacagag 540
tcagtcccag accctcaacc aatcggagaa cctcccgcag cccctcagg tgtgggatct 600
cttacaatgc ttcaggtgg tggcgcacca gtggcagaca taacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca caactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctgagcttc ttcttgggct ctcaatggac gtaatagctt gatgaatcct 1560
ggacctgcta tggccagcca caagaagga gaggaccgtt tctttcctt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagtggtg 1740
gccacaaacc accagagtgc caagcacacg gcgatcaccg gcgcggttca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 223          moltype = DNA   length = 2211
FEATURE                 Location/Qualifiers
source                  1..2211
                        mol_type = other DNA
                        organism = synthetic construct
SEQUENCE: 223
atggctgccg atggttatct tccagattgg ctcgaggaca accttagtga aggtattcgc 60
gagtggtggg ctttgaaacc tggagcccct caacccaagg caaatcaaca acatcaagac 120
aacgctcgag gtcttgtgct tccggggttac aaataccttg acccggcaa cggactcgac 180
aaggggggagc cggtcaacgc agcagacgcg gcggccctcg agcacgacaa ggcctacgac 240
cagcagctca aggccggaga caacccgtac ctcaagtaca accacgccga cgccgagttc 300
caggagcggc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaagagaa ctcaatttcg gtcagactgg cgacacagag 540
tcagtcccag accctcaacc aatcggagaa cctcccgcag cccctcagg tgtgggatct 600
cttacaatgc ttcaggtgg tggcgcacca gtggcagaca taacgaagg tgccgatgga 660
gtgggtagtt cctcgggaaa ttggcattgc gattcccaat ggctggggga cagagtcatc 720
accaccagca cccgaacctg ggccctgccc acctacaaca atcacctcta caagcaaatc 780
tccaacagca catctggagg atcttcaaat gacaacgcct acttcggcta cagcaccccc 840
tgggggtatt ttgacttcaa cagattccac tgccacttct caccacgtga ctggcagcga 900
ctcatcaaca caactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
```

```
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gcgctgttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa acacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 224          moltype = DNA  length = 2211
FEATURE                 Location/Qualifiers
source                  1..2211
                        mol_type = other DNA
                        organism = synthetic construct
SEQUENCE: 224
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggttac aaataccttg gacccggcaa cggactcgac   180
aaggggagc cggtcaacgc agcagacgcg gcggccctcg agcacgacaa ggcctacgac   240
cagcagctca aggccggaga caacccgtac ctcaagtaca ccacgccga cgccgagttc   300
caggagcggc tcaaagaaga tacgtctttt ggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaattcg gtcagactgg cgacacagag    540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atgaagcca ggccgtgggt cgttcgtcct tttactgcct ggaatattc   1200
ccgtcgcaaa tgctaagaac gggtaacaac ttccagttca gctacgagtt tgagaacgta   1260
cctttccata gcagctacgc tcacagccaa agctcggacc gactaatgaa tccactcatc   1320
gaccaatact tgtactatct ctcaaagact attaacggt ctggacagaa tcaacaaacg   1380
ctaaaattca gtgtggccgg acccagcaac atggctgctc aggaggaaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgataaccg gcgcgttaca aagtcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa acacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 225          moltype = DNA  length = 2211
FEATURE                 Location/Qualifiers
source                  1..2211
                        mol_type = other DNA
                        organism = synthetic construct
SEQUENCE: 225
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggttac aaataccttg gacccggcaa cggactcgac   180
aaggggagc cggtcaacgc agcagacgcg gcggccctcg agcacgacaa ggcctacgac   240
cagcagctca aggccggaga caacccgtac ctcaagtaca ccacgccga cgccgagttc   300
caggagcggc tcaaagaaga tacgtctttt ggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaattcg gtcagactgg cgacacagag    540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca tcacctcta caagcaaatc   780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca acaactgggg attccggcct aagcgactca acttcaagct cttcaacatt   960
```

```
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcagc 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag gcgcaaggca gcgccttaca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc tcctcagat cctcatcaaa acacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 226          moltype = DNA   length = 2211
FEATURE                 Location/Qualifiers
source                  1..2211
                        mol_type = other DNA
                        organism = synthetic construct
SEQUENCE: 226
atggctgccg atggttatct tccagattgg ctcgaggaca accttagtga aggtattcgc 60
gagtggtggg ctttgaaacc tggagcccct caacccaagg caaatcaaca acatcaagac 120
aacgctcgag gtcttgtgct tccgggttac aaataccttg acccggcaa cggactcgac 180
aaggggagc cggtcaacgc agcagacgcg cggccctcg agcacgacaa ggcctacgac 240
cagcagctca aggccggaga caacccgtac ctcaagtaca accacgccga cgccgagttc 300
caggagcggc tcaaagaaga tacgtctttt ggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag cccctcagg tgtgggatct 600
cttacaatgg cttcaggtgg tggcgcacca gtggcagaca ataacgaagg tgccgatgga 660
gtgggtagtt cctcgggaaa ttggcattgc gattccaat ggctggggga cagagtcatc 720
accaccagca cccgaacctg ggccctgccc acctacaaca tcacctcta caagcaaatc 780
tccaacagca catctggagg atcttcaaat gacaacgcct acttcggcta cagcaccccc 840
tggggtatt ttgacttcaa cagattccac tgccactttc caccacgtga ctggcagcga 900
ctcatcaaca acaactgggg attccgcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atgggagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag gcgatagtcg gcgcgttaca aaaccaagga 1800
gctcttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc tcctcagat cctcatcaaa acacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 227          moltype = DNA   length = 2211
FEATURE                 Location/Qualifiers
source                  1..2211
                        mol_type = other DNA
                        organism = synthetic construct
SEQUENCE: 227
atggctgccg atggttatct tccagattgg ctcgaggaca accttagtga aggtattcgc 60
gagtggtggg ctttgaaacc tggagcccct caacccaagg caaatcaaca acatcaagac 120
aacgctcgag gtcttgtgct tccgggttac aaataccttg acccggcaa cggactcgac 180
aaggggagc cggtcaacgc agcagacgcg cggccctcg agcacgacaa ggcctacgac 240
cagcagctca aggccggaga caacccgtac ctcaagtaca accacgccga cgccgagttc 300
caggagcggc tcaaagaaga tacgtctttt ggggcaacc tcgggcgagc agtcttccag 360
gccaaaaaga ggcttcttga acctcttggt ctggttgagg aagcggctaa gacggctcct 420
```

```
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgattaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 228        moltype = DNA   length = 2211
FEATURE               Location/Qualifiers
source                1..2211
                      mol_type = other DNA
                      organism = synthetic construct
SEQUENCE: 228
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggggtac aaataccttg gacccggcaa cggactcgac   180
aaggggagc cggtcaacgc agcagacgcg gcggccctcg agcacgacaa ggcctacgac   240
cagcagctca aggccggaga caaccccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgttgca aaaccaagga              1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 229        moltype = DNA   length = 2211
FEATURE               Location/Qualifiers
```

| source | 1..2211 |
| | mol_type = other DNA |
| | organism = synthetic construct |

SEQUENCE: 229

```
atggctgccg atggttatct tccagattgg ctcgaggaca accttagtga aggtattcgc    60
gagtggtggg cttttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaaggga ggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtggtg  1740
gccacaaacc accagagtgc ccaagcacag gcgataggtg gcgcagttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211
```

| SEQ ID NO: 230 | moltype = DNA   length = 2211 |
| FEATURE | Location/Qualifiers |
| source | 1..2211 |
| | mol_type = other DNA |
| | organism = synthetic construct |

SEQUENCE: 230

```
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaaggga ggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgatcaccg cgctttaca aaaccaagga  1800
atacttccgg gtatggtttg gcaggacaga gatgtgtacc tgcaaggacc catttgggcc  1860
```

```
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

SEQ ID NO: 231          moltype = DNA   length = 2211
FEATURE                 Location/Qualifiers
source                  1..2211
                        mol_type = other DNA
                        organism = synthetic construct
SEQUENCE: 231

```
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccactct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttggggct ctcaatggac gtaatagctt gatgaatcct  1560
ggacctgcta tggccagcca caagaaagga gaggacgtt tctttcctt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagacgg gcgccttca aaaccaagga  1800
gcgcttccgg gtatggtttg caggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211
```

SEQ ID NO: 232          moltype = DNA   length = 2211
FEATURE                 Location/Qualifiers
source                  1..2211
                        mol_type = other DNA
                        organism = synthetic construct
SEQUENCE: 232

```
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccactct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
```

-continued

```
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg  gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgataaccg gcgcggttca aagtcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 233         moltype = DNA   length = 2211
FEATURE                Location/Qualifiers
source                 1..2211
                       mol_type = other DNA
                       organism = synthetic construct SEQUENCE: 233
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggggttac aaataccttg gacccggcaa cggactcgac   180
aaggggagc cggtcaacgc agcagacgcg gcggcccctcg agcacgacaa ggcctacgac   240
cagcagctca aggccggaga caaccccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattgcc   480
aaatcgggtg cacagcccgc taaaagaga  ctcaatttcg gtcagactgg cgacacagag   540
tcagtcccag accctcaacc aatcggagaa cctcccgcag cccccctcagg tgtgggatct   600
cttacaatgc cttcaggtgg tggcgcacca gtggcagaca taacgaagg  tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggggtat ttgacttcaa cagattccac tgccactttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acgtccagg  tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca cctacgagtt tgagaacgta  1260
ccttttccata gcagctacgc tcacagccaa agcctggacc gactaatgaa tcccactcatc 1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg  gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcaggttg gctgggttca aagccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 234         moltype = DNA   length = 2211
FEATURE                Location/Qualifiers
source                 1..2211
                       mol_type = other DNA
                       organism = synthetic construct SEQUENCE: 234
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccggggttac aaataccttg gacccggcaa cggactcgac   180
aaggggagc cggtcaacgc agcagacgcg gcggcccctcg agcacgacaa ggcctacgac   240
cagcagctca aggccggaga caaccccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattgcc   480
aaatcgggtg cacagcccgc taaaagaga  ctcaatttcg gtcagactgg cgacacagag   540
tcagtcccag accctcaacc aatcggagaa cctcccgcag cccccctcagg tgtgggatct   600
cttacaatgc cttcaggtgg tggcgcacca gtggcagaca taacgaagg  tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
```

```
tccaacagca catctggagg atcttcaaat gacaacgcct acttcggcta cagcacccec  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga ggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaagcacag cgcaggtcg gctgggttca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a         2211

SEQ ID NO: 235       moltype = DNA   length = 2211
FEATURE              Location/Qualifiers
source               1..2211
                     mol_type = other DNA
                     organism = synthetic construct
SEQUENCE: 235
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag tcttgtgct tccgggttac aaataccttg acccggcaa cggactcgac   180
aagggggagc cggtcaacgc agcagacgcg gcggccctcg agcacgacaa ggcctacgac  240
cagcagctca aggccggaga caacccgtac ctcaagtaca ccacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc cgtgtattgc  480
aaatcgggtg cacagcccgc taaaaagaga ctcaatttcg gtcagactgg cgacacagag  540
tcagtcccag accctcaacc aatcggagaa cctcccgcag cccccctcagg tgtgggatct  600
cttacaatgc ttcaggtgg tggcgcacca gtggcagaca taacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga ggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagtcgtg 1740
gccacaaacc accagagtgc ccaagcacag cgcagaccg cgccgttca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcacccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a         2211

SEQ ID NO: 236       moltype = DNA   length = 2211
FEATURE              Location/Qualifiers
source               1..2211
                     mol_type = other DNA
                     organism = synthetic construct
SEQUENCE: 236
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag tcttgtgct tccgggttac aaataccttg acccggcaa cggactcgac   180
aagggggagc cggtcaacgc agcagacgcg gcggccctcg agcacgacaa ggcctacgac  240
```

```
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atgggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttccttt gtctggatct    1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc caagcacag gcgataaccg gctgggttca aaaccaagga   1800
atacttccgg gtatggttttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg   1980
gccttcaaca aggacaagct gaactctttc atcacccagt attctactgg ccaagtcgag   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 237         moltype = DNA  length = 2211
FEATURE                Location/Qualifiers
source                 1..2211
                       mol_type = other DNA
                       organism = synthetic construct
SEQUENCE: 237
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccggttac aaataccttg gacccggcaa cggactggac    180
aagggggagc cggtcaacgc agcagacgcg gcgccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atgggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttccttt gtctggatct    1620
ttaattttg gcaaacaagg aactggaaga gacaacgtgg atgcggacaa agtcatgata   1680
accaacgaag aagaaattaa aactactaac ccggtagcaa cggagtccta tggagtcgtg   1740
gccacaaacc accagagtgc caagcacag gcgcagaccg gctgggttca aaaccaagga   1800
atacttccgg gtatggttttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg   1980
gccttcaaca aggacaagct gaactctttc atcacccagt attctactgg ccaagtcgag   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 238         moltype = DNA  length = 2211
```

```
FEATURE                 Location/Qualifiers
source                  1..2211
                        mol_type = other DNA
                        organism = synthetic construct
SEQUENCE: 238
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaaacc accagagtgc ccaagcacag gcgcagaccg gcgctgttca atcccaagga  1800
atacttccgg gtatggttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcgg  2040
gtggagatcg agtgggagct gcagaaggaa aacagcaagc gctggaaccc ggagatccag  2100
tacacttcca actattacaa gtctaataat gttgaattg ctgttaatac tgaaggtgta   2160
tatagtgaac cccgccccat tggcaccaga tacctgactc gtaatctgta a            2211

SEQ ID NO: 239           moltype = DNA  length = 2211
FEATURE                  Location/Qualifiers
source                   1..2211
                         mol_type = other DNA
                         organism = synthetic construct
SEQUENCE: 239
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggggtatt ttgacttcaa cagattccac tgccacttct caccacgtga ctggcggcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaaacc accagagtgc ccaagcacag gcgcagaccg gcgctgttca aaaccaagga  1800
```

```
gcacttccgg gtatggtttg gcaggacaga gatgtgtacc tgcaaggacc catttgggcc  1860
aaaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 240          moltype = DNA   length = 2211
FEATURE                 Location/Qualifiers
source                  1..2211
                        mol_type = other DNA
                        organism = synthetic construct
SEQUENCE: 240
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggcccctcg agcacgacaa ggcctacgac  240
cagcagctca aggccggaga caacccgtac ctcaagtaca ccacgccga cgccgagttc  300
caggagcggc tcaaagaaga tacgtctttt ggggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaagaga ctcaatttcg gtcagactgg cgacacagag  540
tcagtcccag accctcaacc aatcggagaa cctcccgcag cccctcagg tgtgggatct  600
cttacaatgc cttcaggtgg tggcgcacca gtggcagaca taacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tggggggtatt ttgacttcaa cagattccac tgccacttct caccacgtga ctggcagcga  900
ctcatcaaca caactgggg attccggcct aagcgactca cttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcgac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtca ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcaggtcg gcgcggttca aaaccaagga  1800
gcgcttccgg gtatggtttg gcaggacaga gatgtgtacc tgcaaggacc catttgggcc  1860
aaaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgcccat tggcaccaga tacctgactc gtaatctgta a            2211

SEQ ID NO: 241          moltype = DNA   length = 2211
FEATURE                 Location/Qualifiers
source                  1..2211
                        mol_type = other DNA
                        organism = synthetic construct
SEQUENCE: 241
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggcccctcg agcacgacaa ggcctacgac  240
cagcagctca aggccggaga caacccgtac ctcaagtaca ccacgccga cgccgagttc  300
caggagcggc tcaaagaaga tacgtctttt ggggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaagaga ctcaatttcg gtcagactgg cgacacagag  540
tcagtcccag accctcaacc aatcggagaa cctcccgcag cccctcagg tgtgggatct  600
cttacaatgc cttcaggtgg tggcgcacca gtggcagaca taacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tggggggtatt ttgacttcaa cagattccac tgccacttct caccacgtga ctggcagcga  900
ctcatcaaca caactgggg attccggcct aagcgactca cttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcgac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
```

-continued

```
ccttteccata gcagctacge tcacagccaa agcctggace gactaatgaa tccactcatc     1320
gaccaatact tgtactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcca caaagaagga gaggaccgtt tctttccttt gtctggatct     1620
ttaattttg gcaaacaagg aactggaaga gacaacgtgg atgcggacaa agtcatgata     1680
accaacgaag aagaaattaa aactactaac ccggtagcaa cggagtccta tggacaagtg     1740
gccacaaacc accagagtgc ccaagcacag cgcaggtagg gctgggttca aaaccaagga     1800
gctcttccgg gtatggttg gcaggacaga gatgtgtacc tgcaaggacc catttgggcc      1860
aaaattcctc acacggacgg caactttcac ccttctccgc tgatgggagg gtttggaatg     1920
aagcacccgc tcctcagat cctcatcaaa aacacacctg tacctgcgga tcctccaacg      1980
gccttcaaca aggacaagct gaactctttc atcacccagt attctactgg ccaagtcagc     2040
gtggagatcg agtgggagct gcagaaggaa aacagcaagc gctggaaccc ggagatccag     2100
tacacttcca actattacaa gtctaataat gttgaatttg ctgttaatac tgaaggtgta     2160
tatagtgaac cccgccccat tggcaccaga tacctgactc gtaatctgta a              2211

SEQ ID NO: 242          moltype = DNA   length = 2211
FEATURE                 Location/Qualifiers
source                  1..2211
                        mol_type = other DNA
                        organism = synthetic construct
SEQUENCE: 242
atggctgccg atggttatct tccagattgg ctcgaggaca accttagtga aggtattcgc     60
gagtggtggg ctttgaaacc tggagcccct caacccaagg caaatcaaca acatcaagac     120
aacgctcgag gtcttgtgct tccgggttac aaataccttg gacccggcaa cggactcgac     180
aagggggagc cggtcaacgc agcagacgcg gcgccctcg agcacgacaa ggcctacgac      240
cagcagctca aggccggaga caacccgtac ctcaagtaca ccacgccga cgccgagttc      300
caggagcggc tcaaagaaga tacgtctttt ggggcaacc tcgggcgagc agtcttccag      360
gccaaaaaga ggcttcttga acctcttggt ctggttgagg aagcggctaa gacggctcct     420
ggaaagaaga ggcctgtaga gcagtctcct caggaaccgg actcctcgc gggtattggc      480
aaatcgggtg cacagcccgc taaaaagaga ctcaatttcg gtcagactgg cgacacagag     540
tcagtcccag accctcaacc aatcggagaa cctcccgcag ccccctcagg tgtgggatct     600
cttacaatgg cttcaggtgg tggcgcacca gtggcagaca ataacgaagg tgccgatgga     660
gtgggtagtt cctcgggaaa ttggcattgc gattccaat ggctggggga cagagtcatc      720
accaccagca cccgaacctg gccctgccc acctacaaca atcacctcta caagcaaatc     780
tccaacagca catctggagg atcttcaaat gacaacgcct acttcggcta cagcaccccc     840
tgggggtatt ttgacttcaa cagattccac tgccactct caccacgtga ctggcagcga      900
ctcatcaaca acaactgggg attccggcct aagcgactca acttcaagct cttcaacatt     960
caggtcaaag aggttacgga caacaatgga gtcaagacca tcgccaataa ccttaccagc     1020
acggtccagg tcttcacgga ctcagactat cagctcccgt acgtgctcgg gtcggctcac     1080
gagggctgcc tcccgccgtt cccagcggac gttttcatga ttcctcagta cgggtatctg     1140
acgcttaatg atggaagcca ggccgtgggt cgttcgtctt tttactgcct ggaatattg     1200
ccgtcgcaaa tgctaagaac gggtaacaac ttccagttca gctacgagtt tgagaacgta     1260
ccttteccata gcagctacge tcacagccaa agcctggace gactaatgaa tccactcatc     1320
gaccaatact tgtactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcca caaagaagga gaggaccgtt tctttccttt gtctggatct     1620
ttaattttg gcaaacaagg aactggaaga gacaacgtgg atgcggacaa agtcatgata     1680
accaacgaag aagaaattaa aactactaac ccggtagcaa cggagtccta tggacaagtg     1740
gccacaaacc accagagtgc ccaagcacag cgataaccg gcgcagttca atcccaagga      1800
gcccttccgg gtatggttg gcaggacaga gatgtgtacc tgcaaggacc catttgggcc      1860
aaaattcctc acacggacgg caactttcac ccttctccgc tgatgggagg gtttggaatg     1920
aagcacccgc tcctcagat cctcatcaaa aacacacctg tacctgcgga tcctccaacg      1980
gccttcaaca aggacaagct gaactctttc atcacccagt attctactgg ccaagtcagc     2040
gtggagatcg agtgggagct gcagaaggaa aacagcaagc gctggaaccc ggagatccag     2100
tacacttcca actattacaa gtctaataat gttgaatttg ctgttaatac tgaaggtgta     2160
tatagtgaac cccgccccat tggcaccaga tacctgactc gtaatctgta a              2211

SEQ ID NO: 243          moltype = DNA   length = 2211
FEATURE                 Location/Qualifiers
source                  1..2211
                        mol_type = other DNA
                        organism = synthetic construct
SEQUENCE: 243
atggctgccg atggttatct tccagattgg ctcgaggaca accttagtga aggtattcgc     60
gagtggtggg ctttgaaacc tggagcccct caacccaagg caaatcaaca acatcaagac     120
aacgctcgag gtcttgtgct tccgggttac aaataccttg gacccggcaa cggactcgac     180
aagggggagc cggtcaacgc agcagacgcg gcgccctcg agcacgacaa ggcctacgac      240
cagcagctca aggccggaga caacccgtac ctcaagtaca ccacgccga cgccgagttc      300
caggagcggc tcaaagaaga tacgtctttt ggggcaacc tcgggcgagc agtcttccag      360
gccaaaaaga ggcttcttga acctcttggt ctggttgagg aagcggctaa gacggctcct     420
ggaaagaaga ggcctgtaga gcagtctcct caggaaccgg actcctcgc gggtattggc      480
aaatcgggtg cacagcccgc taaaaagaga ctcaatttcg gtcagactgg cgacacagag     540
tcagtcccag accctcaacc aatcggagaa cctcccgcag ccccctcagg tgtgggatct     600
cttacaatgg cttcaggtgg tggcgcacca gtggcagaca ataacgaagg tgccgatgga     660
gtgggtagtt cctcgggaaa ttggcattgc gattccaat ggctggggga cagagtcatc      720
```

```
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgataaccg gctgggttca aaaccaagga  1800
gcgcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaattg ctgttaatac tgaaggtgta  2160
tatagtgaac cccgccccat tggcaccaga tacctgactc gtaatctgta a           2211

SEQ ID NO: 244            moltype = DNA   length = 2211
FEATURE                   Location/Qualifiers
source                    1..2211
                          mol_type = other DNA
                          organism = synthetic construct
SEQUENCE: 244
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca ccacgccga cgccgagttc   300
caggagcggc tcaaagaaga tacgtctttt ggggcaacc tcgggcgagc agtcttccag   360
gccaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggaaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccc    840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtagtg  1740
gccacaaacc accagagtgc ccaagcacag gcgcagaccg gcgcggttca aagtcaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaattg ctgttaatac tgaaggtgta  2160
tatagtgaac cccgccccat tggcaccaga tacctgactc gtaatctgta a           2211

SEQ ID NO: 245            moltype = DNA   length = 2211
FEATURE                   Location/Qualifiers
source                    1..2211
                          mol_type = other DNA
                          organism = synthetic construct
SEQUENCE: 245
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
```

```
aaggggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcgggaaa ttggcattgc gattccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagttgtg   1740
gccacaaacc accagagtgc ccaagcacag gcgatcgttg gctgggttca aagccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgccga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac ccgcccat tggcaccaga tacctgactc gtaatctgta a             2211

SEQ ID NO: 246         moltype = DNA   length = 2211
FEATURE                Location/Qualifiers
source                 1..2211
                       mol_type = other DNA
                       organism = synthetic construct
SEQUENCE: 246
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgattaccg cgcagttca aaaccaagga  1800
gcgcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgccga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac ccgcccat tggcaccaga tacctgactc gtaatctgta a             2211
```

```
SEQ ID NO: 247          moltype = DNA  length = 2211
FEATURE                 Location/Qualifiers
source                  1..2211
                        mol_type = other DNA
                        organism = synthetic construct
SEQUENCE: 247
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgaaacgta   1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct   1620
ttaattttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgataaccg gctgggttca atcccaagga  1800
gctcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg   1980
gccttcaaca aggacaagct gaactctttc atcacccagt attctactgg ccaagtcagc  2040
gtggagatcg agtgggagct gcagaaggaa acagcaagc gctggaaccc ggagatccag  2100
tacacttcca actattacaa gtctaataat gttgaatttg ctgttaatac tgaaggtgta  2160
tatagtgaac ccgccccat ggcaccaga tacctgactc gtaatctgta a               2211

SEQ ID NO: 248          moltype = DNA  length = 2211
FEATURE                 Location/Qualifiers
source                  1..2211
                        mol_type = other DNA
                        organism = synthetic construct
SEQUENCE: 248
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgaaacgta   1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct   1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
```

```
gccacaaacc accagagtgc ccaagcacag gcgatcgttg gcgcggttca atcccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa acacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 249           moltype = DNA   length = 2211
FEATURE                  Location/Qualifiers
source                   1..2211
                         mol_type = other DNA
                         organism = synthetic construct
SEQUENCE: 249
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcgccctcg agcacgacaa ggcctacgac     240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa dacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggaaa cctcccgcag ccccctcagg tgtgggatct    600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgggagcttc ttctgggct caatggac gtaatagctt gatgaatcct   1560
ggacctgcta tggccagcca caagaagga gaggaccgtt tctttcctt gtctggatct    1620
ttaattttg gcaaacaagg aactggaaga gacaacgtga atgcggacaa agtcatgata   1680
accaacgaag aagaaattaa aactactaac ccggtagcaa cggagtccta tggagtcgtg   1740
gccacaaacc accagagtgc ccaagcacag gcgcaggtag gctgggttca aagtcaagga   1800
gcgcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa acacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 250           moltype = DNA   length = 2211
FEATURE                  Location/Qualifiers
source                   1..2211
                         mol_type = other DNA
                         organism = synthetic construct
SEQUENCE: 250
atggctgccg atggttatct tccagattgg ctcgaggaca accttagtga aggtattcgc   60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcgccctcg agcacgacaa ggcctacgac     240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa dacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggaaa cctcccgcag ccccctcagg tgtgggatct    600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
```

```
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggagtagtg   1740
gccacaaacc accagagtgc ccaagcacag gcgcaggacg gctgggttca aagccaagga   1800
gctcttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcaccgc ctcctcagat cctcatcaaa aacacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 251         moltype = DNA  length = 2211
FEATURE                Location/Qualifiers
source                 1..2211
                       mol_type = other DNA
                       organism = synthetic construct
SEQUENCE: 251
atggctgccg atggttatct tccagattgg ctcgaggaca accttagtga aggtattcgc     60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca ccacgccga cgccgagttc    300
caggagcggc tcaaagaaga tacgtctttt gggggcaact cgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattccaat ggctggggga cagagtcatc    720
accaccagca cccgaacctg ggccctgccc acctacaaca tcacctcta caagcaaatc    780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcgacc gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggacaagtg   1740
gccacaaacc accagagtgc ccaagcacag gcgatcaccg gctgggttca atctcaagga   1800
gccttccgg gtatggtttg gcaggacaga gatgtgtacc tgcaaggacc catttgggcc    1860
aaaattcctc acacggacgg caactttcac ccttctccgc tgatgggagg gtttggaatg   1920
aagcaccgc ctcctcagat cctcatcaaa aacacacctg tacctgcgga tcctccaacg    1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 252         moltype = DNA  length = 2211
FEATURE                Location/Qualifiers
source                 1..2211
                       mol_type = other DNA
                       organism = synthetic construct
SEQUENCE: 252
atggctgccg atggttatct tccagattgg ctcgaggaca accttagtga aggtattcgc     60
gagtggtggg ctttgaaacc tggagcccct caacccaagg caaatcaaca acatcaagac   120
aacgctcgag gtcttgtgct tccgggttac aaataccttg acccggcaa cggactcgac    180
aagggggagc cggtcaacgc agcagacgcg gcggccctcg agcacgacaa ggcctacgac   240
cagcagctca aggccggaga caacccgtac ctcaagtaca ccacgccga cgccgagttc    300
caggagcggc tcaaagaaga tacgtctttt gggggcaact cgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
```

```
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcacccccc   840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct    1620
ttaattttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcaggttg gcgccgttca atcacaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211

SEQ ID NO: 253          moltype = DNA   length = 2211
FEATURE                 Location/Qualifiers
source                  1..2211
                        mol_type = other DNA
                        organism = synthetic construct
SEQUENCE: 253
atggctgccg atggttatct tccagattgg ctcgaggaca accttagtga aggtattcgc     60
gagtggtggg cttttgaaacc tggagcccct caacccaagg caaatcaaca acatcaagac   120
aacgctcgag gtcttgtgct tccgggttac aaataccttg acccggcaa cggactcgac     180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcgg tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggggtg cacagcccgc taaaagaga ctcaatttcg gtcagactgg cgacacagag    540
tcagtcccag accctcaacc aatcggaaga cctcccgcag cccctcagg tgtgggatcc    600
cttacaatgg cttcaggtgg tggcgcacca gtgcagacaa ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcacccccc  840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct   1620
ttaattttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcaggtag gctggctaca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 254          moltype = DNA   length = 2211
FEATURE                 Location/Qualifiers
source                  1..2211
                        mol_type = other DNA
                        organism = synthetic construct
SEQUENCE: 254
atggctgccg atggttatct tccagattgg ctcgaggaca accttagtga aggtattcgc     60
gagtggtggg cttttgaaacc tggagcccct caacccaagg caaatcaaca acatcaagac   120
```

```
aacgctcgag gtcttgtgct tccgggttac aaataccttg acccggcaa cggactcgac      180
aagggggagc cggtcaacgc agcagacgcg gcggccctcg agcacgacaa ggcctacgac      240
cagcagctca aggccggaga caacccgtac ctcaagtaca accacgccga cgccgagttc      300
caggagcggc tcaaagaaga tacgtctttt gggggcaacc tcgggcgagc agtcttccag      360
gccaaaaaga ggcttcttga acctcttggt ctggttgagg aagcggctaa gacggctcct      420
ggaaagaaga ggcctgtaga gcagtctcct caggaaccgg actcctccgc gggtattggc      480
aaatcgggtg cacagcccgc taaaaagaga ctcaatttcg gtcagactgg cgacacagag      540
tcagtcccag accctcaacc aatcggagaa cctcccgcag cccctcagg tgtgggatct       600
cttacaatgg cttcaggtgg tggcgcacca gtggcagaca ataacgaagg tgccgatgga      660
gtgggtagtt cctcgggaaa ttggcattgc gattcccaat ggctggggga cagagtcatc      720
accaccagca cccgaacctg ggccctgccc acctacaaca atcacctcta caagcaaatc      780
tccaacagca catctggagg atcttcaaat gacaacgcct acttcggcta cagcacccc       840
tgggggtatt ttgacttcaa cagattccac tgccacttct caccacgtga ctggcagcga      900
ctcatcaaca acaactgggg attccggcct aagcgactca acttcaagct cttcaacatt      960
caggtcaaag aggttacgga caacaatgga gtcaagacca tcgccaataa ccttaccagc     1020
acggtccagg tcttcacgga ctcagactat cagctcccgt acgtgctcgg gtcggctcac     1080
gagggctgcc tcccgccgtt cccagcggac gttttcatga ttcctcagta cgggtatctg     1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta     1260
cctttccata gcagctacgc tcacagccaa agcctggacc gactaatgaa tccactcatc     1320
gaccaatact tgtactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcca caagaagga gaggaccgtt tctttccttt gtctggatct      1620
ttaattttg gcaaacaagg aactggaaga gacaacgtgg atgcggacaa agtcatgata      1680
accaacgaag aagaaattaa aactactaac ccggtagcaa cggagtccta tggacaagtg     1740
gccacaaacc accagagtgc ccaagcacag gcgataaccg gcgcactcca atcacaagga     1800
gcgcttccgg gtatggtttg gcaggacaga gatgtgtacc tgcaaggacc catttgggcc     1860
aaaattcctc acacggacgg caacttttcac ccttctccgc tgatgggagg gttggaatg     1920
aagcacccgc ctcctcagat cctcatcaaa acacacctg tacctgcgga tcctccaacg      1980
gccttcaaca aggacaagct gaactctttc atcacccagt attctactgg ccaagtcagc     2040
gtggagatcg agtgggagct gcagaaggaa acagcaagc gctggaaccc ggagatccag      2100
tacacttcca actattacaa gtctaataat gttgaatttg ctgttaatac tgaaggtgta     2160
tatagtgaac cccgccccat tggcaccaga tacctgactc gtaatctgta a              2211

SEQ ID NO: 255            moltype = DNA  length = 2211
FEATURE                   Location/Qualifiers
source                    1..2211
                          mol_type = other DNA
                          organism = synthetic construct
SEQUENCE: 255
atggctgccg atggttatct tccagattgg ctcgaggaca accttagtga aggtattcgc       60
gagtggtggg ctttgaaacc tggagcccct caacccaagg caaatcaaca acatcaagac      120
aacgctcgag gtcttgtgct tccgggttac aaataccttg acccggcaa cggactcgac       180
aagggggagc cggtcaacgc agcagacgcg gcggccctcg agcacgacaa ggcctacgac      240
cagcagctca aggccggaga caacccgtac ctcaagtaca accacgccga cgccgagttc      300
caggagcggc tcaaagaaga tacgtctttt gggggcaacc tcgggcgagc agtcttccag      360
gccaaaaaga ggcttcttga acctcttggt ctggttgagg aagcggctaa gacggctcct      420
ggaaagaaga ggcctgtaga gcagtctcct caggaaccgg actcctccgc gggtattggc      480
aaatcgggtg cacagcccgc taaaaagaga ctcaatttcg gtcagactgg cgacacagag      540
tcagtcccag accctcaacc aatcggagaa cctcccgcag cccctcagg tgtgggatct       600
cttacaatgg cttcaggtgg tggcgcacca gtggcagaca ataacgaagg tgccgatgga      660
gtgggtagtt cctcgggaaa ttggcattgc gattcccaat ggctggggga cagagtcatc      720
accaccagca cccgaacctg ggccctgccc acctacaaca atcacctcta caagcaaatc      780
tccaacagca catctggagg atcttcaaat gacaacgcct acttcggcta cagcacccc       840
tgggggtatt ttgacttcaa cagattccac tgccacttct caccacgtga ctggcagcga      900
ctcatcaaca acaactgggg attccggcct aagcgactca acttcaagct cttcaacatt      960
caggtcaaag aggttacgga caacaatgga gtcaagacca tcgccaataa ccttaccagc     1020
acggtccagg tcttcacgga ctcagactat cagctcccgt acgtgctcgg gtcggctcac     1080
gagggctgcc tcccgccgtt cccagcggac gttttcatga ttcctcagta cgggtatctg     1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta     1260
cctttccata gcagctacgc tcacagccaa agcctggacc gactaatgaa tccactcatc     1320
gaccaatact tgtactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcca caagaagga gaggaccgtt tctttccttt gtctggatct      1620
ttaattttg gcaaacaagg aactggaaga gacaacgtgg atgcggacaa agtcatgata      1680
accaacgaag aagaaattaa aactactaac ccggtagcaa cggagtccta tggacaagtg     1740
gccacaaacc accagagtgc ccaagcacag gcgattgtcg gctggctgca aaaccaagga     1800
gcccttccgg gtatggtttg gcaggacaga gatgtgtacc tgcaaggacc catttgggcc     1860
aaaattcctc acacggacgg caacttttcac ccttctccgc tgatgggagg gttggaatg     1920
aagcacccgc ctcctcagat cctcatcaaa acacacctg tacctgcgga tcctccaacg      1980
gccttcaaca aggacaagct gaactctttc atcacccagt attctactgg ccaagtcagc     2040
gtggagatcg agtgggagct gcagaaggaa acagcaagc gctggaaccc ggagatccag      2100
tacacttcca actattacaa gtctaataat gttgaatttg ctgttaatac tgaaggtgta     2160
tatagtgaac cccgccccat tggcaccaga tacctgactc gtaatctgta a              2211
```

| SEQ ID NO: 256 | moltype = DNA length = 2211 |
|---|---|
| FEATURE | Location/Qualifiers |
| source | 1..2211 |
| | mol_type = other DNA |
| | organism = synthetic construct |

SEQUENCE: 256
```
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttcc accacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagtagtg   1740
gccacaaacc accagagtgc ccaagcacag gcgatcgtcg gcgcactcca aaaccaagga   1800
gcccttccgg gtatggtttg gcaggacaga gatgtgtacc tgcaaggacc catttgggcg   1860
aaaattcctc acacggacgg caactttcac ccttctccgg tgatggggag gtttggaatg   1920
aagcacccgc ctcctcagat cctcatcaaa aacacacctg tacctgcgga tcctccaacg   1980
gccttcaaca aggacaagct gaactctttc atcacccagt atctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgcccat tggcaccaga tacctgactc gtaatctgta a              2211
```

| SEQ ID NO: 257 | moltype = DNA length = 2211 |
|---|---|
| FEATURE | Location/Qualifiers |
| source | 1..2211 |
| | mol_type = other DNA |
| | organism = synthetic construct |

SEQUENCE: 257
```
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
```

```
accaacgaag aagaaattaa aactactaac ccggtagcaa cggagtccta tggagtggtg   1740
gccacaaacc accagagtgc ccaagcacag gcgcaggttg gctggctgca aaaccaagga   1800
gcccttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

```
SEQ ID NO: 258          moltype = DNA  length = 2211
FEATURE                 Location/Qualifiers
source                  1..2211
                        mol_type = other DNA
                        organism = synthetic construct
SEQUENCE: 258
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac    180
aagggggagc cggtcaacgc agcagacgcg gcggccctcg agcacgacaa ggcctacgac    240
cagcagctca aggccggaga caaccccgtac ctcaagtaca ccacgccga cgccgagttc    300
caggagcggc tcaaagaaga tacgtctttt ggggggcaacc tcgggcgagc agtcttccag    360
gccaaaaaga ggcttcttga acctcttggt ctggttgagg aagcggctaa dacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tgcgcacca gtgcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcacccgc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc    1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggc cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct   1560
ggacctgcta tggccagcca caaagaagga gaggacctct tctttccttt gtctggatct   1620
ttaattttttg gcaaacaagg aactggaaga dacaacgtgg atgcggacaa agtcatgata   1680
accaacgaag aagaaattaa aactactaac ccggtagcaa cggagtccta tggagtcgtg   1740
gccacaaacc accagagtgc ccaagcacag gcgatagtgg gctggttaca atcgcaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211
```

```
SEQ ID NO: 259          moltype = DNA  length = 2211
FEATURE                 Location/Qualifiers
source                  1..2211
                        mol_type = other DNA
                        organism = synthetic construct
SEQUENCE: 259
atggctgccg atggttatct tccagattgg ctcgaggaca accttagtga aggtattcgc     60
gagtggtggg ctttgaaacc tggagcccct caacccaagg caaatcaaca acatcaagac    120
aacgctcgag gtcttgtgct tccgggttac aaataccttg acccggcaa cggactcgac    180
aagggggagc cggtcaacgc agcagacgcg gcggccctcg agcacgacaa ggcctacgac    240
cagcagctca aggccggaga caaccccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa dacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tgcgcacca gtgcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcacccgc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
```

```
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccT  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggagtcgtg  1740
gccacaaacc accagagtgc ccaagcacag gcgcaggttg gcgcggttca aaaccaagga  1800
gctcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcaccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a  2211

SEQ ID NO: 260           moltype = DNA   length = 2211
FEATURE                  Location/Qualifiers
source                   1..2211
                         mol_type = other DNA
                         organism = synthetic construct
SEQUENCE: 260
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga ccgcgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcggggtg cacagcccgc taaaaagaga ctcaatttcg gtcagactgg cgacacagag  540
tcagtcccag accctcaacc aatcggagaa cctcccgcag cccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggcctgtgcc acctacaaca atcacctcta caagcaaatc  780
tccaacagca catctggagg atcttcaaat gacaacgcct acttcggcta cagcacccgc  840
tgggggtatt ttgacttcaa cagattccat tgccacttct caccacgtga ctggcagcga  900
ctcatcaaca caactggggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg atcgcctcac 1080
gagggctgcc tccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacataccT 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggagtcgtg 1740
gccacaaacc accagagtgc ccaagcacag gcgataaccg gctggctgca aaaccaagga 1800
atacttccgg gtatggtttg gcaggacaga gatgtgtacc tgcaaggacc catttgggcc 1860
aaaattcctc acacggacgg caactttcac ccttctccgc tgatgggagg gtttggaatg 1920
aagcaccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a 2211

SEQ ID NO: 261           moltype = DNA   length = 2211
FEATURE                  Location/Qualifiers
source                   1..2211
                         mol_type = other DNA
                         organism = synthetic construct
SEQUENCE: 261
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga ccgcgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcggggtg cacagcccgc taaaaagaga ctcaatttcg gtcagactgg cgacacagag  540
tcagtcccag accctcaacc aatcggagaa cctcccgcag cccctcagg tgtgggatct  600
```

```
cttacaatgg cttcaggtgg tggcgcacca gtggcagaca ataacgaagg tgccgatgga    660
gtgggtagtt cctcgggaaa ttggcattgc gattccaat ggctggggga cagagtcatc     720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct    1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagttgtg   1740
gccacaaacc accagagtgc ccaagcacag gcgcaggtgg gctgggttca aaaccaagga   1800
gcgcttccgg gtatgtttg cagggacaga gatgtgtacc tgcaaggacc catttgggcc    1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acacagcaag gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 262         moltype = DNA   length = 2211
FEATURE                Location/Qualifiers
source                 1..2211
                       mol_type = other DNA
                       organism = synthetic construct SEQUENCE: 262
atggctgccg atggttatct tccagattgg ctcgaggaca accttagtga aggtattcgc     60
gagtggtggg cttgaaacc tggagccct caacccaagg caaatcaaca acatcaagac     120
aacgctcgag gtcttgtgct tccgggttac aaataccttg acccggcaa cggactcgac    180
aaggggagc cggtcaacgc agcagacgcg cggccctcg agcacgacaa ggcctacgac     240
cagcagctca aggccggaga caaccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctctc    420
ggaaagaaga ggcctgtaga gcagtctcct caggaaccgg actcctcgc gggtattggc    480
aaatcgggtg cacagcccgc taaaagaga ctcaatttcg gtcagactgg cgacacagag    540
tcagtcccag accctcaacc aatcggagaa cctcccgcag ccccctcagg tgtgggatct    600
cttacaatgg cttcaggtgg tggcgcacca gtggcagaca ataacgaagg tgccgatgga    660
gtgggtagtt cctcgggaaa ttggcattgc gattccaat ggctggggga cagagtcatc     720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctgagcttc ttcttgggct ctcaatggac gtaatagctt gatgaatcct    1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggagttgtg   1740
gccacaaacc accagagtgc ccaagcacag gcgatagtcg gctggcttca aaaccaagga   1800
gcacttccgg gtatgtttg cagggacaga gatgtgtacc tgcaaggacc catttgggcc    1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acacagcaag gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211

SEQ ID NO: 263         moltype = DNA   length = 2211
FEATURE                Location/Qualifiers
source                 1..2211
                       mol_type = other DNA
                       organism = synthetic construct
```

```
SEQUENCE: 263
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac   1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaattttg gcaacaagg aactggaaga dacaacgtgg atgcggacaa agtcatgata   1680
accaacgaag aagaaattaa aactactaac ccggtagcaa cggagtccta tggacaagtg  1740
gccacaaacc accagagtgc ccaagcacag cgcgattgtgg gcgcggttca atcacaagga  1800
gcacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a            2211

SEQ ID NO: 264      moltype = DNA   length = 2211
FEATURE             Location/Qualifiers
source              1..2211
                    mol_type = other DNA
                    organism = synthetic construct
SEQUENCE: 264
atggctgccg atggttatct tccagattgg ctcgaggaca accttagtga aggtattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac   1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttctttgggct ctcaatggac gtaatagctt gatgaatcct  1560
ggacctgcta tggccagcca caagaagga gaggaccgtt tctttccttt gtctggatct  1620
ttaattttg gcaacaagg aactggaaga dacaacgtgg atgcggacaa agtcatgata   1680
accaacgaag aagaaattaa aactactaac ccggtagcaa cggagtccta tggacaagtg  1740
gccacaaacc accagagtgc ccaagcacag cgcgataacg gctggttaca aaaccaagga  1800
gcgcttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
```

```
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 265          moltype = DNA  length = 2211
FEATURE                 Location/Qualifiers
source                  1..2211
                        mol_type = other DNA
                        organism = synthetic construct
SEQUENCE: 265
atggctgccg atggttatct tccagattgg ctcgaggaca accttagtga aggtattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aagggggagc cggtcaacgc agcagacgcg cggccctcg agcacgacaa ggcctacgac   240
cagcagctca aggccggaga caacccgtac ctcaagtaca ccacgccga cgccgagttc   300
caggagcggc tcaaagaaga tacgtctttt ggggcaaccc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaagagac tcaatttcg gtcagactgg cgacacagag   540
tcagtcccag accctcaacc aatcggagaa cctcccgcag cccctcagg tgtgggatct   600
cttacaatgc ttcaggtgg tggcgcacca gtggcagaca ataacgaagg tgccgatgga   660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca caactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atgggagcca ggccgtgggt cgttcgtttc tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ccaaagact attaacggtt ctggacagaa tcaacaaacg 1380
ctaaaattca gtgtggccgg acccagcaac atggctgtcc agggaagaaa ctacataccc 1440
ggacccagct accgacaaca acgtgtctca accactgtga ctcaaaacaa caacagcgaa 1500
tttgcttggc ctggagcttc ttcttgggct ctcaatggac gtaatagctt gatgaatcct 1560
ggacctgcta tggccagcca caagaggga ggagccgtt tctttccttt gtctggatct 1620
ttaattttg gcaaacaagg aactctctaa ctgcggacaa agtcatgata 1680
accaacgaag aagaaattaa aactactaac ccggtagcaa cggagtccta tggacaagtg 1740
gccacaaacc accagagtgc ccaagcacag gcgatcgtag gcgcggttca aaaccaagga 1800
gcgcttccgg gtatggttg gcaggacaga gatgtgtacc tgcaaggacc catttgggcc 1860
aaaattcctc acacggacgg caactttcac ccttctccgc tgatgggagg gtttggaatg 1920
aagcaccgc ctcctcagat cctcatcaaa aacacacctg tacctgcgga tcctccaacg 1980
gccttcaaca aggacaagct gaactctttc atcacccagt attctactgg ccaagtcagc 2040
gtggagatcg agtgggagct gcagaaggaa aacagcaagc gctggaaccc ggagatccag 2100
tacacttcca actattacaa gtctaataat gttgaatttg ctgttaatac tgaaggtgta 2160
tatagtgaac cccgccccat tggcaccaga tacctgactc gtaatctgta a          2211

SEQ ID NO: 266          moltype = AA  length = 23
FEATURE                 Location/Qualifiers
source                  1..23
                        mol_type = protein
                        organism = synthetic construct
SEQUENCE: 266
VVATNHQSAQ AQAIVGALQS QGA                                           23

SEQ ID NO: 267          moltype = AA  length = 10
FEATURE                 Location/Qualifiers
source                  1..10
                        mol_type = protein
                        organism = synthetic construct
SEQUENCE: 267
IVGALQSQGA                                                          10

SEQ ID NO: 268          moltype = AA  length = 6
FEATURE                 Location/Qualifiers
source                  1..6
                        mol_type = protein
                        organism = synthetic construct
SEQUENCE: 268
VGALQS                                                               6
```

The invention claimed is:

1. A nucleic acid molecule encoding a variant adeno-associated virus (AAV) capsid polypeptide having at least 95% sequence identity to SEQ ID NO: 2 and comprising:
   (a) an alanine at a position corresponding to W595 as compared to SEQ ID NO: 1
   (b) a leucine at a position corresponding to V596 as compared to SEQ ID NO: 1; and
   (c) a serine at a position corresponding to N598 as compared to SEQ ID NO: 1.

2. The nucleic acid molecule of claim 1, which encodes a variant AAV capsid polypeptide having at least 96% sequence identity to SEQ ID NO: 2.

3. The nucleic acid molecule of claim 1, which encodes a variant AAV capsid polypeptide having at least 98% sequence identity to SEQ ID NO: 2.

4. The nucleic acid molecule of claim 1, which encodes a variant AAV capsid polypeptide having at least 99% sequence identity to SEQ ID NO: 2.

5. The nucleic acid molecule of claim 1, which encodes a variant AAV capsid polypeptide further comprising an alanine at a position corresponding to I601 as compared to SEQ ID NO: 1.

6. The nucleic acid molecule of claim 5, which encodes a variant AAV capsid polypeptide having at least 96% sequence identity to SEQ ID NO: 2.

7. The nucleic acid molecule of claim 5, which encodes a variant AAV capsid polypeptide having at least 98% sequence identity to SEQ ID NO: 2.

8. The nucleic acid molecule of claim 5, which encodes a variant AAV capsid polypeptide having at least 99% sequence identity to SEQ ID NO: 2.

9. The nucleic acid molecule of claim 1, which encodes a variant AAV capsid polypeptide further comprising a valine at a position corresponding to T593 as compared to SEQ ID NO: 1.

10. The nucleic acid molecule of claim 1, which encodes a variant AAV capsid polypeptide further comprising a valine at a position corresponding to Q579 as compared to SEQ ID NO: 1.

11. The nucleic acid molecule of claim 1, which encodes a variant AAV capsid polypeptide further comprising:
   (a) a valine at a position corresponding to Q579 as compared to SEQ ID NO: 1;
   (b) an isoleucine at a position corresponding to Q592 as compared to SEQ ID NO: 1;
   (c) a valine at a position corresponding to T593 as compared to SEQ ID NO: 1; and
   (d) an alanine at a position corresponding to I601 as compared to SEQ ID NO: 1.

12. The nucleic acid molecule of claim 11, which encodes a variant AAV capsid polypeptide having at least 96% sequence identity to SEQ ID NO: 2.

13. The nucleic acid molecule of claim 11, which encodes a variant AAV capsid polypeptide having at least 98% sequence identity to SEQ ID NO: 2.

14. The nucleic acid molecule of claim 11, which encodes a variant AAV capsid polypeptide having at least 99% sequence identity to SEQ ID NO: 2.

15. The nucleic acid molecule of claim 1, which encodes a variant AAV capsid polypeptide comprising the mutation set of any one of SEQ ID NOs: 2, 14, 16, 18, 19, 21, 23, 24, 31, 34, 37, 38, 62, 98 and 128.

16. The nucleic acid molecule of claim 15, which encodes a variant AAV capsid polypeptide having at least 98% sequence identity to SEQ ID NO: 2.

17. The nucleic acid molecule of claim 1, which encodes a variant AAV capsid polypeptide comprising the amino acid sequence of any one of SEQ ID NOs: 2, 14, 16, 18, 19, 21, 23, 24, 31, 34, 37, 38, 62, 72, 98 and 128.

18. A nucleic acid molecule encoding a variant AAV capsid polypeptide comprising the amino acid sequence of SEQ ID NO: 2.

19. An isolated host cell comprising a nucleic acid molecule encoding a variant AAV capsid polypeptide having at least 95% sequence identity to SEQ ID NO: 2 and comprising:
   (a) an alanine at a position corresponding to W595 as compared to SEQ ID NO: 1
   (b) a leucine at a position corresponding to V596 as compared to SEQ ID NO: 1; and
   (c) a serine at a position corresponding to N598 as compared to SEQ ID NO: 1.

20. The isolated host cell of claim 19, which comprises a nucleic acid molecule encoding a variant AAV capsid polypeptide having at least 96% sequence identity to SEQ ID NO: 2.

21. The isolated host cell of claim 19, which comprises a nucleic acid molecule encoding a variant AAV capsid polypeptide having at least 98% sequence identity to SEQ ID NO: 2.

22. The isolated host cell of claim 19, which comprises a nucleic acid molecule encoding a variant AAV capsid polypeptide having at least 99% sequence identity to SEQ ID NO: 2.

23. The isolated host cell of claim 19, which comprises a nucleic acid molecule encoding a variant AAV capsid polypeptide further comprising an alanine at a position corresponding to I601 as compared to SEQ ID NO: 1.

24. The isolated host cell of claim 19, which comprises a nucleic acid molecule encoding a variant AAV capsid polypeptide further comprising a valine at a position corresponding to Q579 as compared to SEQ ID NO: 1.

25. The isolated host cell of claim 24, which comprises a nucleic acid molecule encoding a variant AAV capsid polypeptide further comprising a valine at a position corresponding to T593 as compared to SEQ ID NO: 1.

26. The isolated host cell of claim 19, which comprises a nucleic acid molecule encoding a variant AAV capsid polypeptide further comprising:
   (a) a valine at a position corresponding to Q579 as compared to SEQ ID NO: 1;
   (b) an isoleucine at a position corresponding to Q592 as compared to SEQ ID NO: 1;
   (c) a valine at a position corresponding to T593 as compared to SEQ ID NO: 1; and
   (d) an alanine at a position corresponding to I601 as compared to SEQ ID NO: 1.

27. The isolated host cell of claim 26, which comprises a nucleic acid molecule encoding a variant AAV capsid polypeptide having at least 96% sequence identity to SEQ ID NO: 2.

28. The isolated host cell of claim 26, which comprises a nucleic acid molecule encoding a variant AAV capsid polypeptide having at least 98% sequence identity to SEQ ID NO: 2.

29. The isolated host cell of claim 26, which comprises a nucleic acid molecule encoding a variant AAV capsid polypeptide having at least 99% sequence identity to SEQ ID NO: 2.

30. An isolated host cell comprising a nucleic acid molecule encoding a variant AAV capsid polypeptide comprising the amino acid sequence of SEQ ID NO: 2.

* * * * *

UNITED STATES PATENT AND TRADEMARK OFFICE
CERTIFICATE OF CORRECTION

PATENT NO. : 12,331,082 B2
APPLICATION NO. : 18/790657
DATED : June 17, 2025
INVENTOR(S) : Ina Chen et al.

Page 1 of 1

It is certified that error appears in the above-identified patent and that said Letters Patent is hereby corrected as shown below:

In the Claims

Claim 11, Column 445, Lines 50-51, the phrase "an alanine at a position corresponding to 1601 as compared to SEQ ID NO: 1." should read --an alanine at a position corresponding to I601 as compared to SEQ ID NO: 1.--

Claim 26, Column 446, Lines 53-54, the phrase "an alanine at a position corresponding to 1601 as compared to SEQ ID NO: 1." should read --an alanine at a position corresponding to I601 as compared to SEQ ID NO: 1.--

Signed and Sealed this
Twenty-ninth Day of July, 2025

Coke Morgan Stewart
*Acting Director of the United States Patent and Trademark Office*